US011007184B2

(12) United States Patent
Saha et al.

(10) Patent No.: US 11,007,184 B2
(45) Date of Patent: May 18, 2021

(54) CANCER TREATMENTS USING COMBINATIONS OF TYPE 2 MEK AND ERK INHIBITORS

(71) Applicant: BIOMED VALLEY DISCOVERIES, INC., Kansas City, MO (US)

(72) Inventors: Saurabh Saha, Wellesley Hills, MA (US); Dean Welsch, Parkville, MO (US); Gary DeCrescenzo, Parkville, MO (US); Jeffrey James Roix, Boston, MA (US)

(73) Assignee: BIOMED VALLEY DISCOVERIES, INC., Kansas City, MO (US)

( * ) Notice: Subject to any disclaimer, the term of this patent is extended or adjusted under 35 U.S.C. 154(b) by 0 days.

(21) Appl. No.: 15/105,871

(22) PCT Filed: Dec. 19, 2014

(86) PCT No.: PCT/US2014/071724

§ 371 (c)(1),
(2) Date: Jun. 17, 2016

(87) PCT Pub. No.: WO2015/095825

PCT Pub. Date: Jun. 25, 2015

(65) Prior Publication Data

US 2016/0367539 A1 Dec. 22, 2016

Related U.S. Application Data

(60) Provisional application No. 61/919,625, filed on Dec. 20, 2013.

(51) Int. Cl.

| | |
|---|---|
| *A61K 31/4439* | (2006.01) |
| *A61K 31/506* | (2006.01) |
| *A61K 31/437* | (2006.01) |
| *A61K 31/519* | (2006.01) |
| *A61K 45/06* | (2006.01) |
| *A61K 31/4184* | (2006.01) |
| *A61K 31/337* | (2006.01) |

(52) U.S. Cl.

CPC ........ *A61K 31/4439* (2013.01); *A61K 31/337* (2013.01); *A61K 31/4184* (2013.01); *A61K 31/437* (2013.01); *A61K 31/506* (2013.01); *A61K 31/519* (2013.01); *A61K 45/06* (2013.01)

(58) Field of Classification Search

None

See application file for complete search history.

(56) References Cited

U.S. PATENT DOCUMENTS

| | | | |
|---|---|---|---|
| 5,034,506 A | 7/1991 | Summerton et al. | |
| 5,235,033 A | 8/1993 | Summerton et al. | |
| 5,622,824 A | 4/1997 | Köster | |
| 6,140,053 A | 10/2000 | Köster | |
| 7,354,939 B2 * | 4/2008 | Martinez-Botella ......................... | C07D 401/04 514/343 |
| 8,288,520 B2 | 10/2012 | Eder et al. | |
| 8,389,219 B2 | 3/2013 | Anthony et al. | |
| 2006/0106069 A1 | 5/2006 | Martinez-Botella et al. | |
| 2011/0152230 A1 | 6/2011 | Mascharak | |
| 2012/0264632 A1 | 10/2012 | Leamon et al. | |
| 2013/0023531 A1 | 1/2013 | Mantoulidis et al. | |
| 2013/0203632 A1 | 8/2013 | Nazarenko et al. | |

FOREIGN PATENT DOCUMENTS

| | | | |
|---|---|---|---|
| WO | 2005021786 A1 | 3/2005 | |
| WO | 2012046981 A2 | 4/2012 | |
| WO | WO-2012068562 A2 * | 5/2012 | ......... C12Q 1/16886 |
| WO | 2012125848 A2 | 9/2012 | |
| WO | 2013187983 A1 | 12/2013 | |

OTHER PUBLICATIONS

Falchook, Gerald S., et al. "Activity of the oral MEK inhibitor trametinib in patients with advanced melanoma: a phase 1 dose-escalation trial." The lancet oncology 13.8 (2012): 782-789.*

Shapiro, G., et al. "Clinical combination of the MEK inhibitor GDC-0973 and the PI3K inhibitor GDC-0941: A first-in-human phase Ib study testing daily and intermittent dosing schedules in patients with advanced solid tumors."Journal of Clinical Oncology 29.15_suppl (2011): 3005-3005.*

Jing, Junping, et al. "Comprehensive predictive biomarker analysis for MEK inhibitor GSK1120212." Molecular cancer therapeutics 11.3 (2012): 720-729.*

Hatzivassiliou, Georgia, et al. "ERK inhibition overcomes acquired resistance to MEK inhibitors." Molecular cancer therapeutics 11.5 (2012): 1143-1154.*

Markman B., et al., Targeting the PI3K/Akt/mTOR Pathway—Beyond Rapalogs, Oncotarget, Oct. 22, 2010, vol. 1, No. 7., pp. 530-543.

Falchook, Gerald S., et al., Activity of the oral MEK inhibitor trametinib in patients with advanced melanoma; a phase 1 dose-escalation trial, The Lancet/Oncology, Aug. 2012, vol. 13, pp. 782-789.

Shapiro, G., et al., Clinical combination of the MEK inhibitors GDC-0973 and the PI3K inhibitor GDC-0941: A first-In-human phas Ib study testing daily and intermittent dosing schedules in patients with advanced solid tumors, Journal of Clinical Oncology, (2011), 29, 15_suppl., 3005, Abstract only.

(Continued)

*Primary Examiner* — Nissa M Westerberg

(74) *Attorney, Agent, or Firm* — Bryan Cave Leighton Paisner LLP

(57) ABSTRACT

The present invention provides, inter alia, methods, kits, and pharmaceutical compositions for treating or ameliorating the effects of a cancer in a subject in need thereof. The method includes administering to the subject an effective amount of (i) a first anti-cancer agent, which is BVD 523 or a pharmaceutically acceptable salt thereof and (ii) a second anti-cancer agent, which is a type 2 MEK inhibitor, or other MEK inhibitors, or pharmaceutically acceptable salts thereof, to treat or ameliorate the effects of the cancer. Additional methods for effecting cancer cell death are also provided.

33 Claims, 196 Drawing Sheets

Specification includes a Sequence Listing.

(56) References Cited

OTHER PUBLICATIONS

International Search Report and Written Opinion Issued by International Searching Authority, dated Apr. 20, 2015.
Absalan, F., et al., Molecular Inversion Probe Assay, Methods in Molecular Biology, vol. 396: Comparative Genomics, vol. 2, pp. 315-330 (2008).
Greger, J.G., et al., Combinations of BRAF, MEK, and PI3K/mTOR Inhibitors Overcome Acquired Resistance to the BRAF Inhibitor GSK2118436 Dabrafenib, Mediated by NRAS or MEK Mutations, Molecular Cancer Therapeutics, 11.4 (2012): 909-920.
Hardenbol, P., et al. Multiplexed genotyping with sequence-tagged molecular inversion probes, Nature Biotechnology, vol. 21, No. 6, pp. 673-678, Jun. 2003.
Hatzivassilious, G., et al., RAF inhibitors prime wild-type RAF to activate the MAPK pathway and enhance growh.' Nature 464.7287 (2010), pp. 431-435.
King, A.J., et al., Dafrafenib; Preclinical Characterization, Increased Efficacy when Combined with Trametinib, while BRAF/MEK Tool Combination Reduced Skin Lesions, Plos one 8.7 (2013): e67583.
Little A.S., et al., Amplification of the Driving Ongogene, KRAS or BRAF, Underpinds Acquired Resistance to MEK ½Inhibitors in Colorectal Cancer Cells., Sci. Signal 4, ra17 (2011).
Manandahar, S.P., et al., Small-Molecule Inhibitors of the Rce1p CaaX Protease, J. Biomol. Screen, 2007; 12(7): 983-993.
Maurer, T., Small-molecule ligands bind to a distinct pocket in Ras and inhibit SOS-mediated nucleotide excange activity, PNAS 109(14): 5299-304 (2012).
Metzker, M. L., et al., Emerging technologies in DNA sequencing, Human Genome Sequencing Center and Dept. of Molecular and Human Genetics, Cold Spring Harbor Lab. Press,15: 1767-1776 (2005).
Mittal, R. et al., The Acetyltransferase Activity of the Backterial Toxin YopJ of Yersinia is Activated by Eukaryotic Host Cell Inositol Hexakisphosphate, Journal of Biological Chemistry 285.26 (2010): 19927-19934.
Nilsson, M., et al., Padlock Probes: Circularizing Oligonucleotides for Localized DNA Detection, Science, vol. 265, Sep. 30, 1994.
Ota, M., et al., Single nucleotide polymorphism detection by polymerase chain reaction-restriction fragment length plymorphism, Nature Protocols, vol. 2 No. 11: 2857-2864 (2007).
Patgiri, A., et al., An Orthosteric inhibitor of the Ras-Sos interaction, Na. Chem. Biol. 7:585-587 (2011).
Porter S.B., et al. Inhibition of the CaaX proteases Rce1p and Ste24p by peptidyl (acyloxy)methol ketones, Biochim. Biophys. Acta. 2007; 1773(b); 853-862.
Shima, F., et al., In silico discovery of small-molecule Ras inhibitors that display antitumor activity by blocking the Ras-effector interaction, Proc Natl Acad Sci U S A, 110(20):8182-7 (2013).
Flaherty. "BRAF Inhibitors and Melanoma." Cancer J. Nov.-Dec. 2011;17(6):505-11.
Kwong et al. "Oncogenic NRAS signaling differentially regulates survival and proliferation in melanoma." Nat Med. Oct. 2012;18(10):1503-10.
Hoeflich et al. "In vivo Antitumor Activity of MEK and Phosphatidylinositol 3-Kinase Inhibitors in Basal-Like Breast Cancer Models." Clin Cancer Res. Jul. 15, 2009;15(14):4649-64.
Serra et al. "PI3K inhibition results in enhanced HER signaling and acquired ERK dependency in HER2-overexpressing breast cancer." Oncogene. Jun. 2, 2011;30(22):2547-57.
Sherr and McCormick. "The RB and p53 pathways in cancer." Cancer Cell. Aug. 2002;2(2):103-12.
Tang et al. "Attenuation of the Retinoblastoma Pathway in Pancreatic Neuroendocrine Tumors Due to Increased Cdk4/Cdk6." Clin Cancer Res. Sep. 1, 2012;18(17):4612-20.

* cited by examiner

FIG. 1, Con't
C
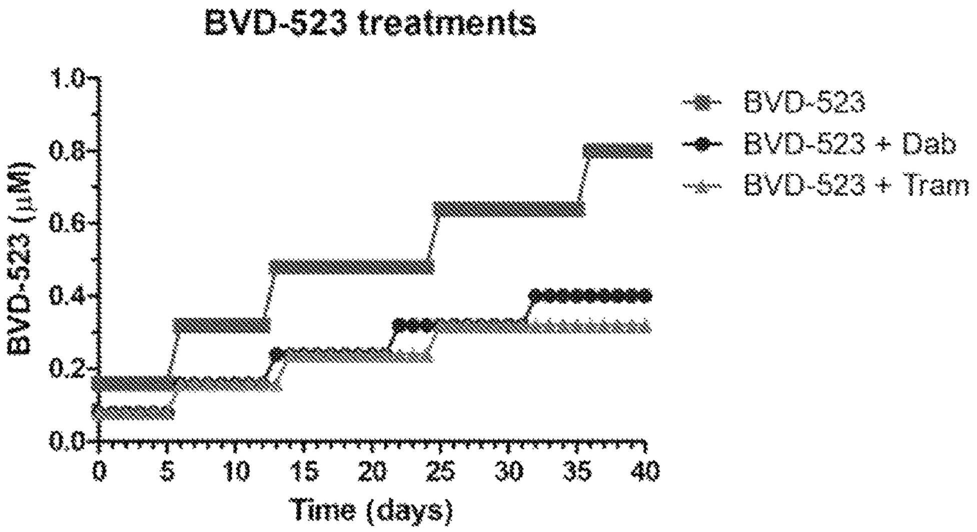

A

FIG. 2, Con't
B
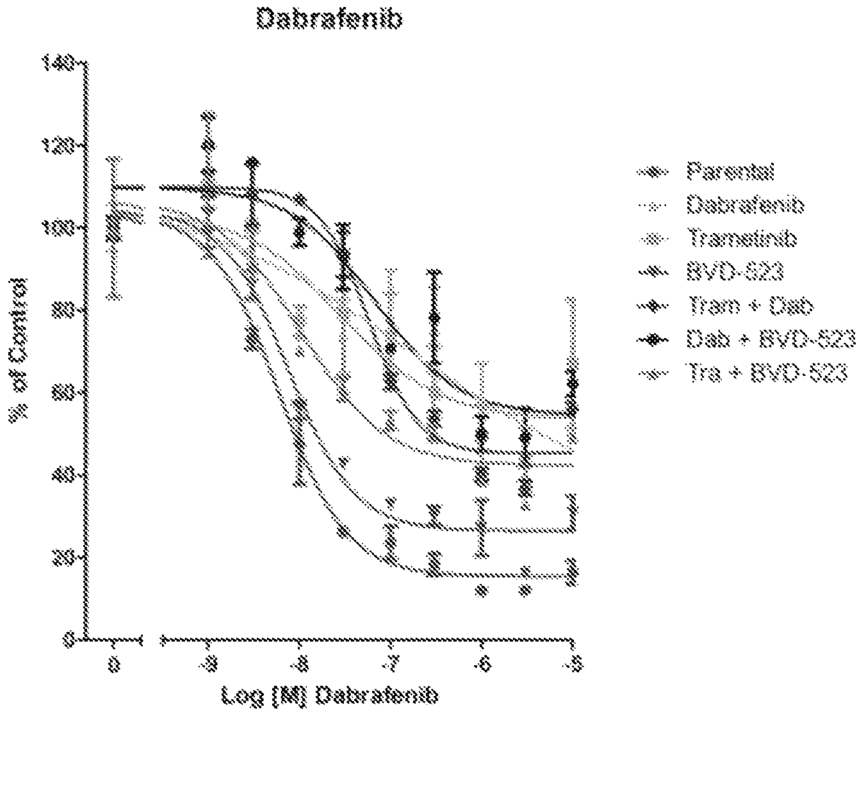

FIG. 2, Con't
C
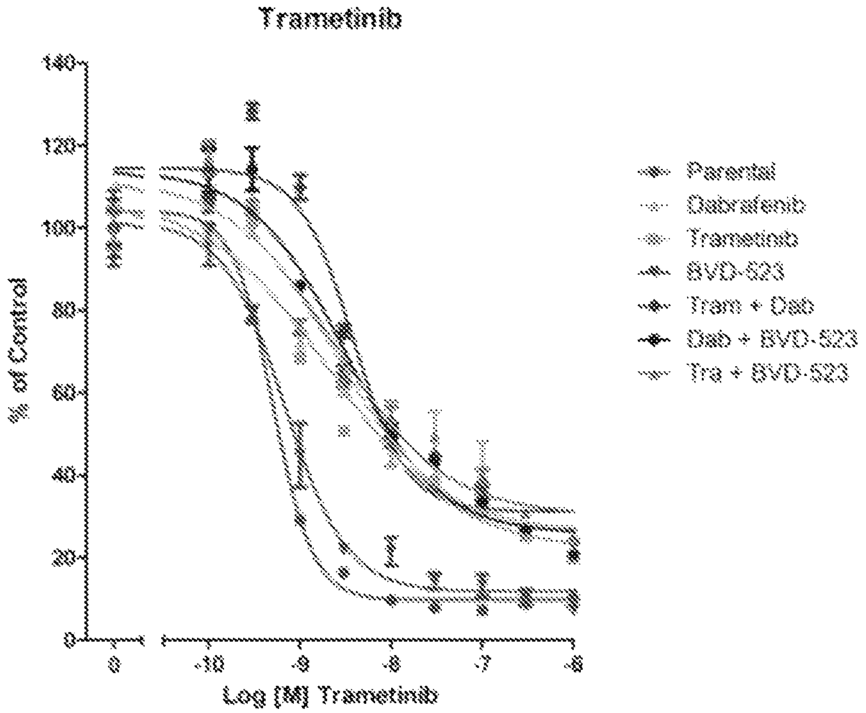

FIG. 2, Con't
D
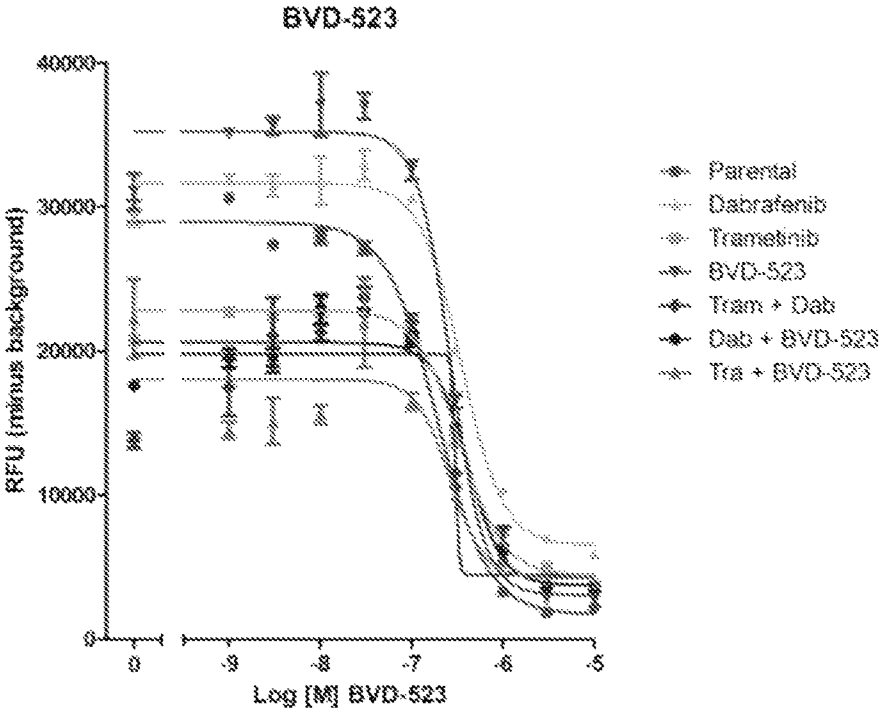

FIG. 2, Con't
E
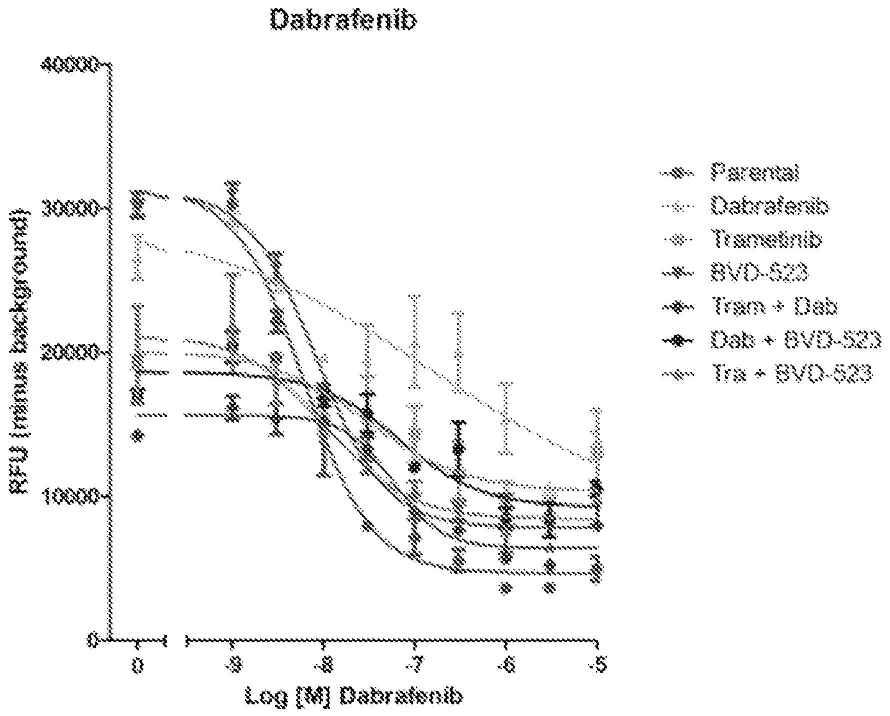

FIG. 2, Con't
F
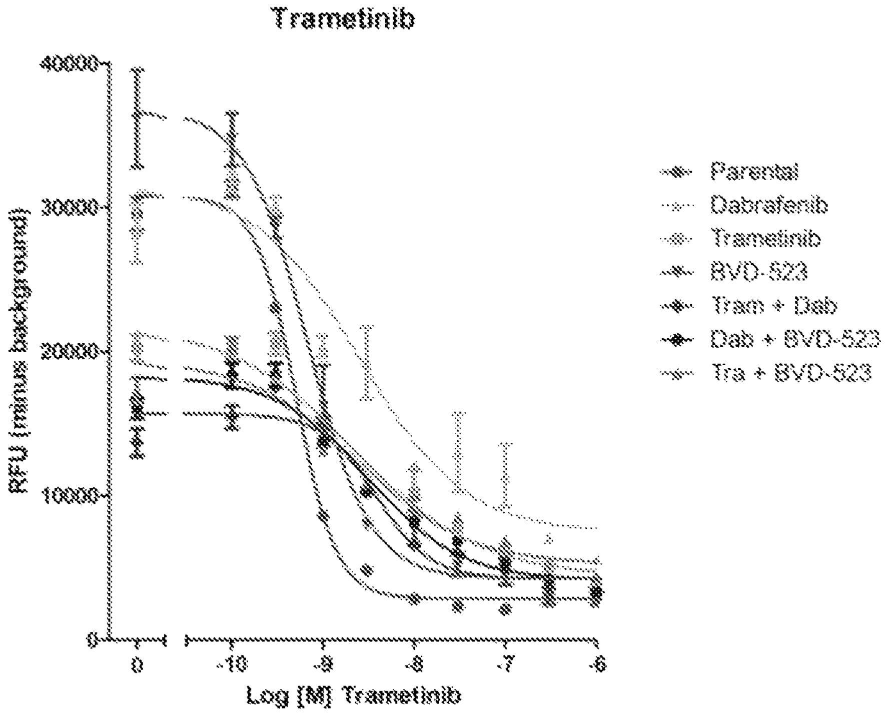

FIG. 2, Con't
G
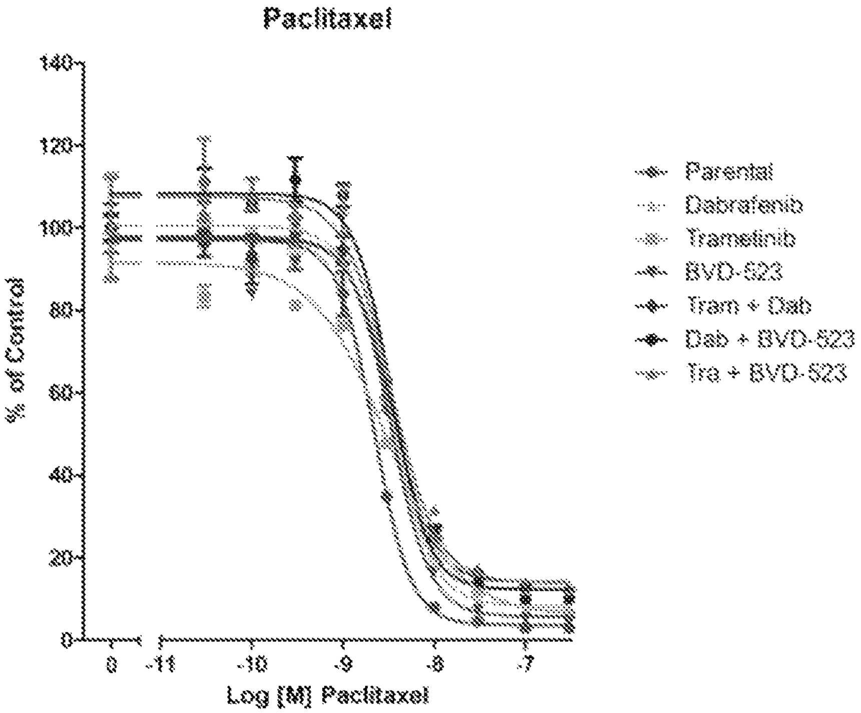

FIG. 2, Con't
H
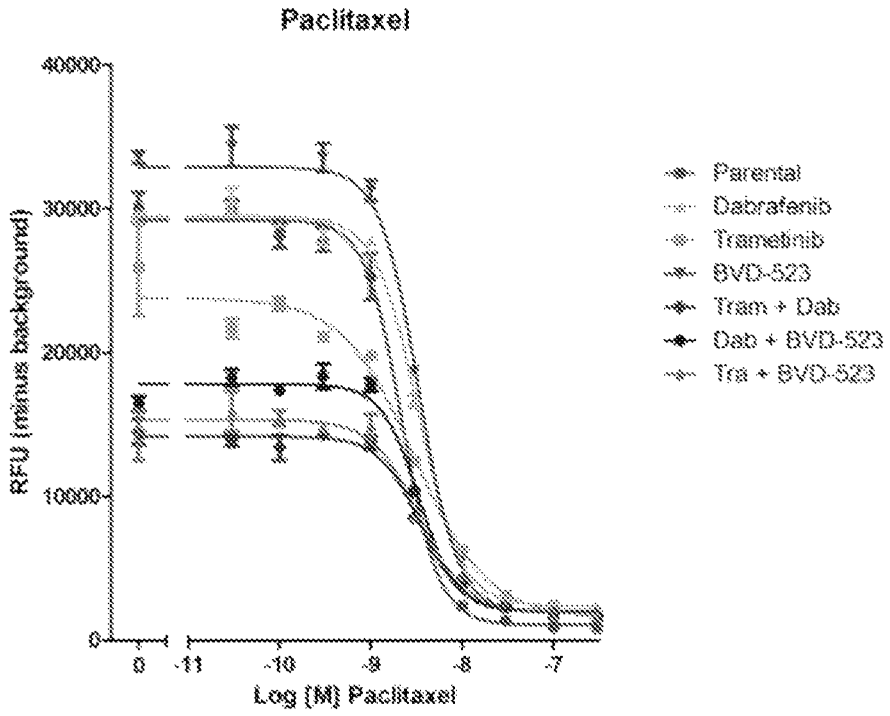

A

B

FIG. 3, Con't
C
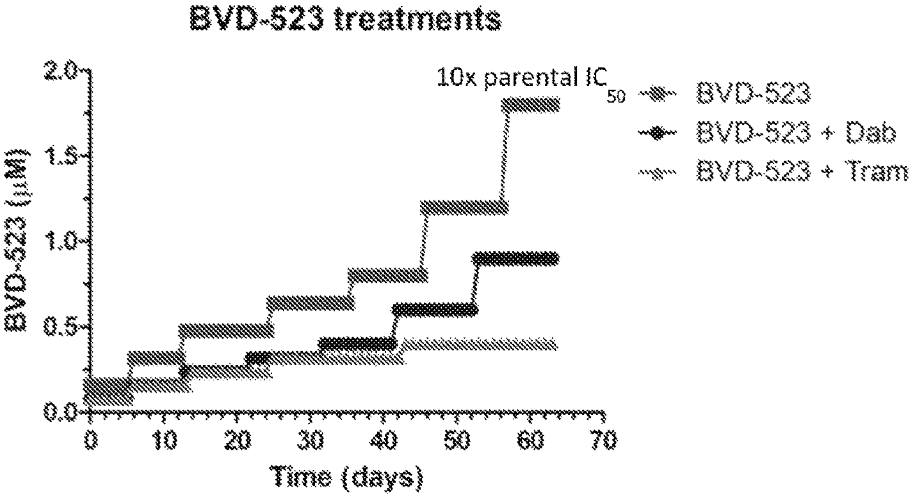
D
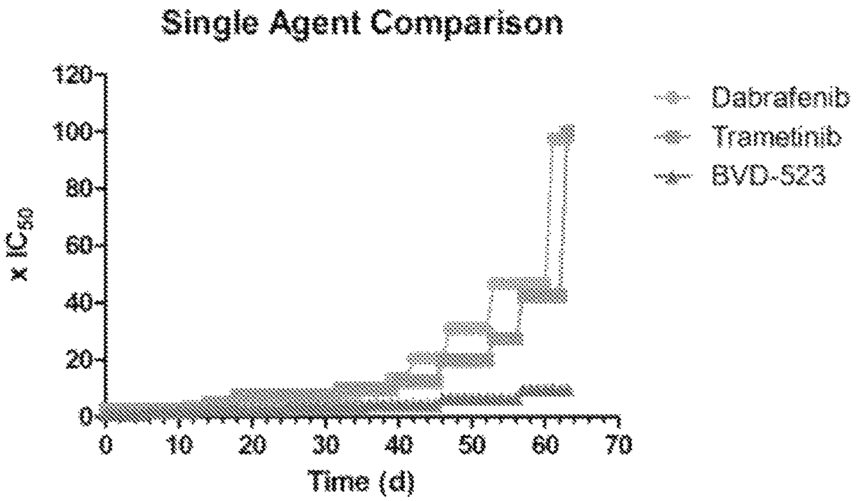

A

FIG. 4, Con't
B
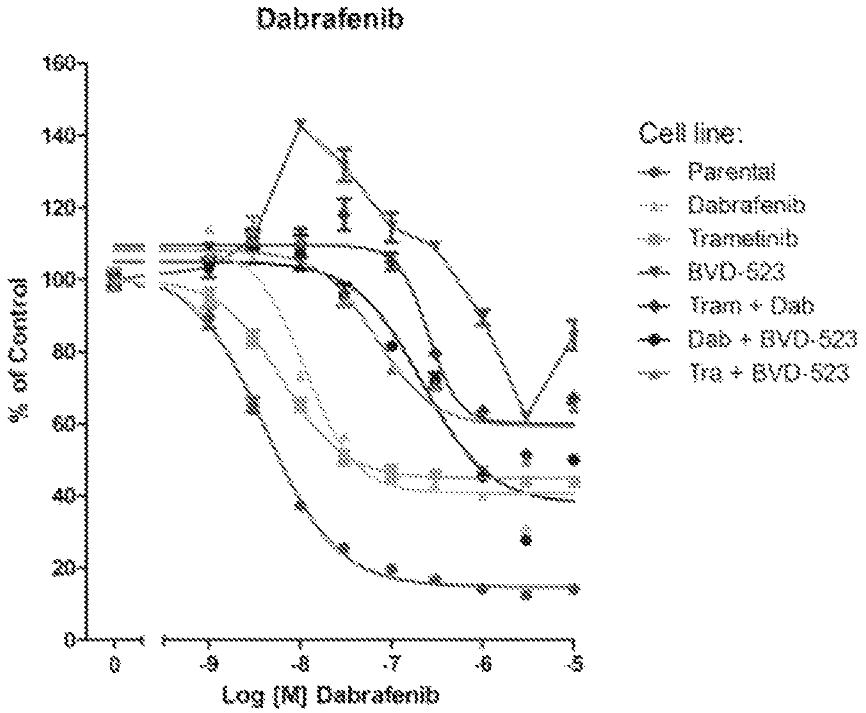

FIG. 4, Con't
C
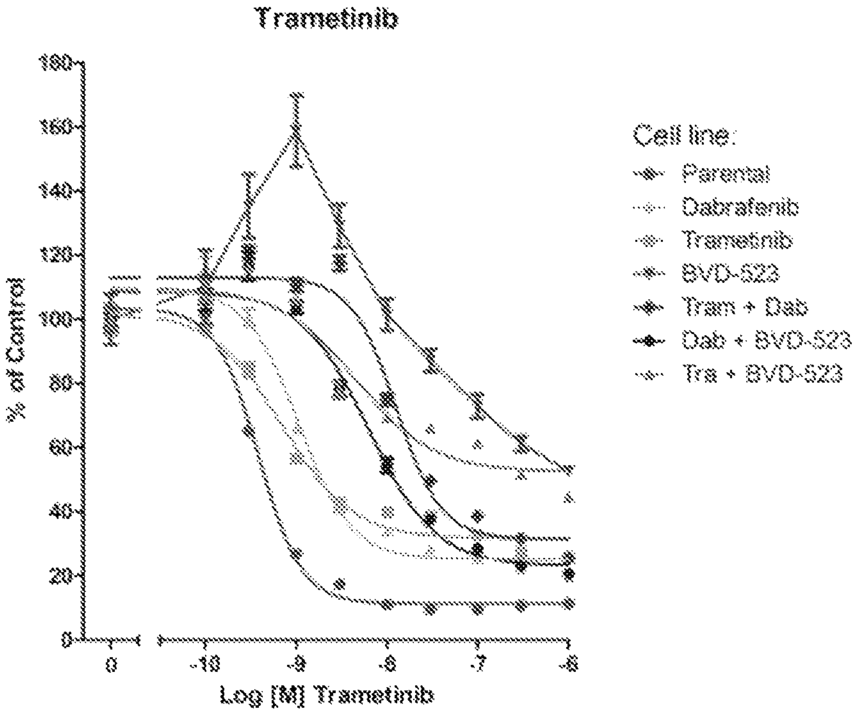

FIG. 4, Con't
D
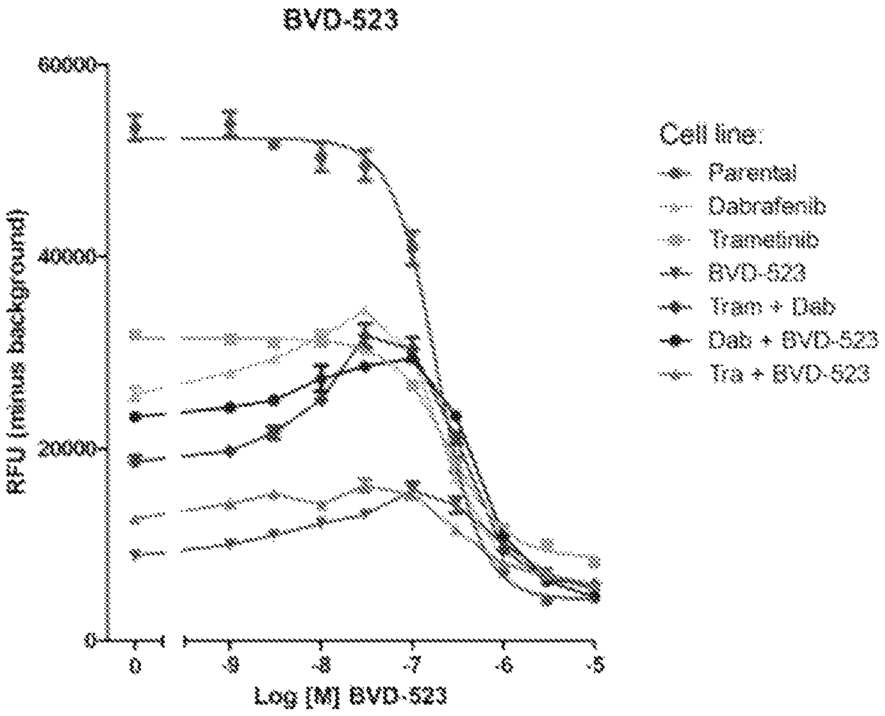

FIG. 4, Con't
E
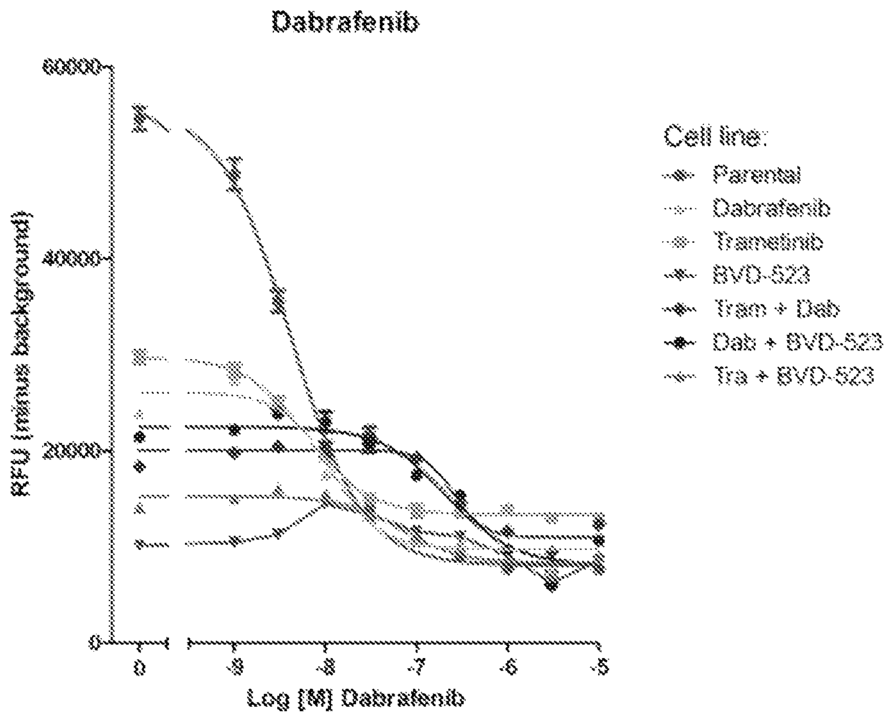

FIG. 4, Con't
F
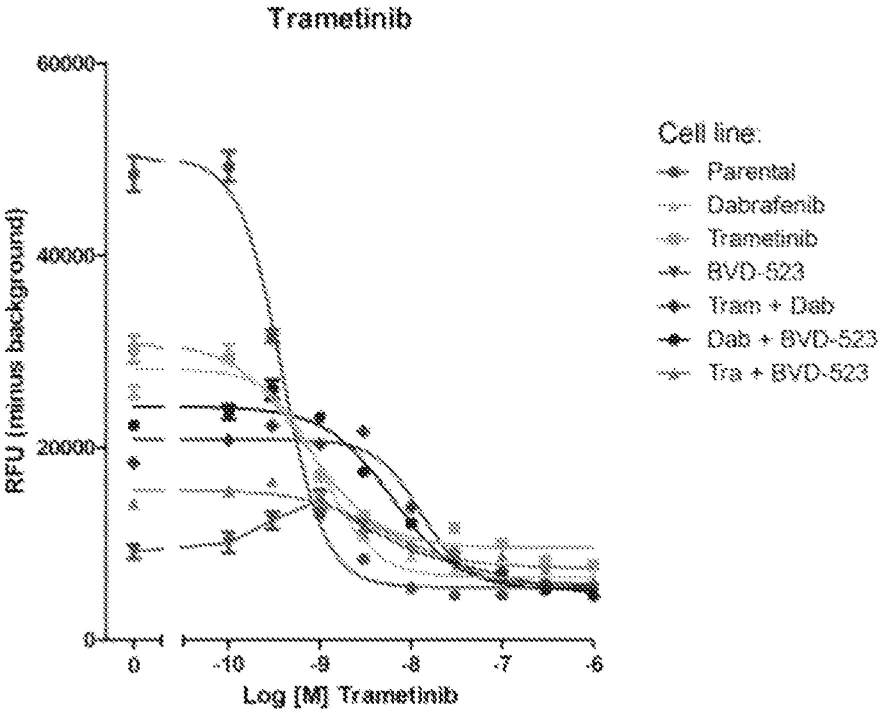

FIG. 4, Con't
G
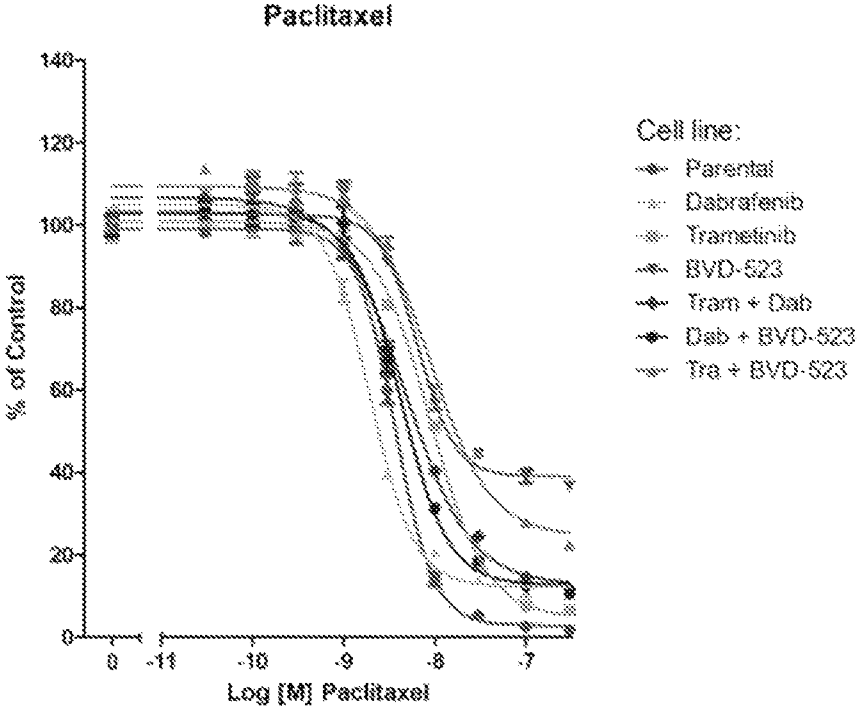

FIG. 4, Con't
H
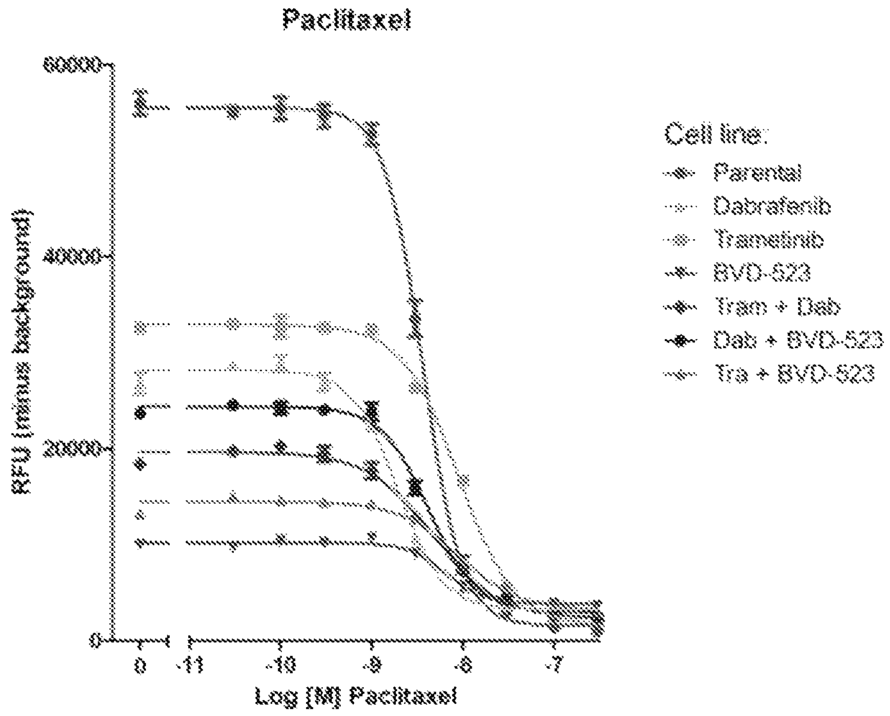

A

FIG. 5, Con't
B
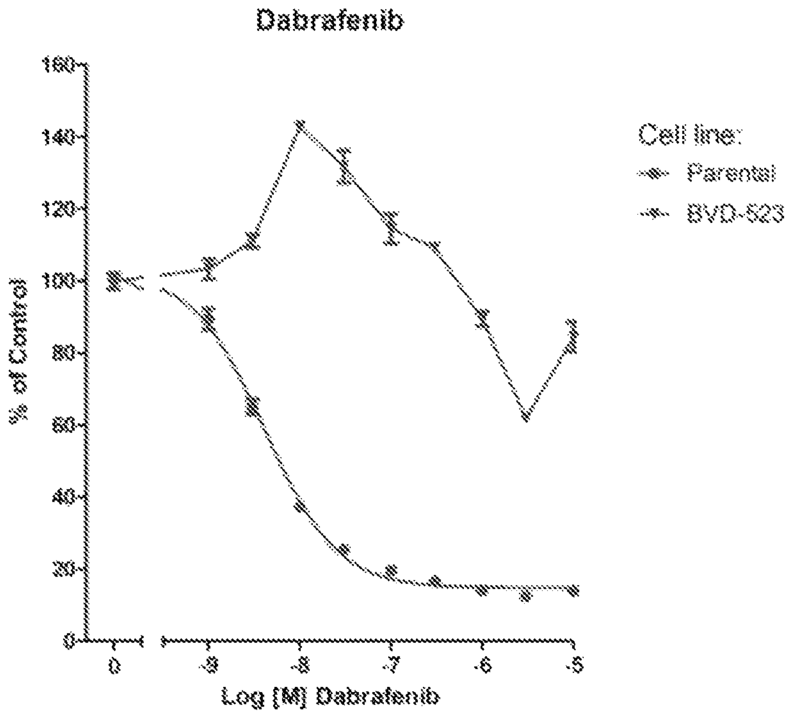

FIG. 5, Con't
C
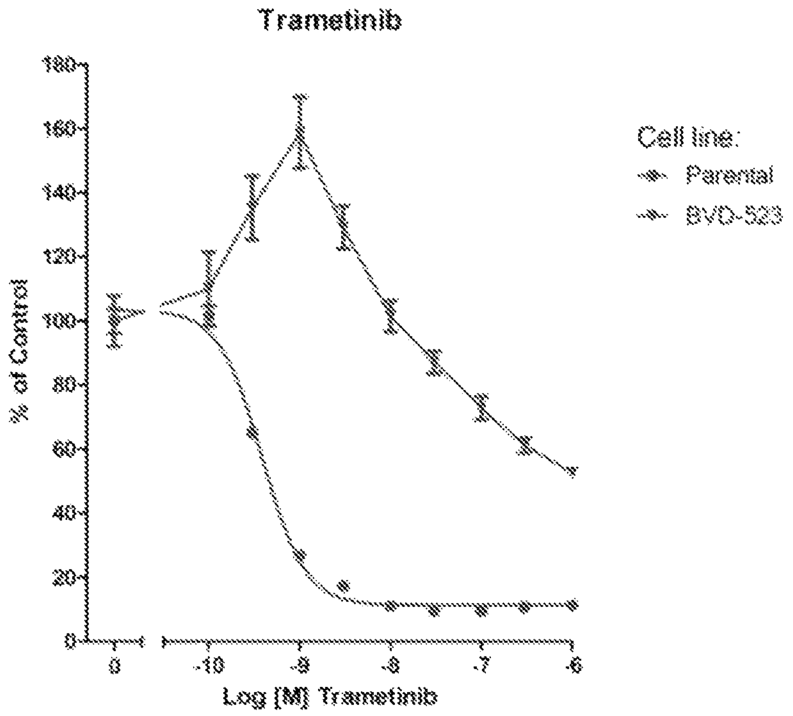

FIG. 5, Con't
D
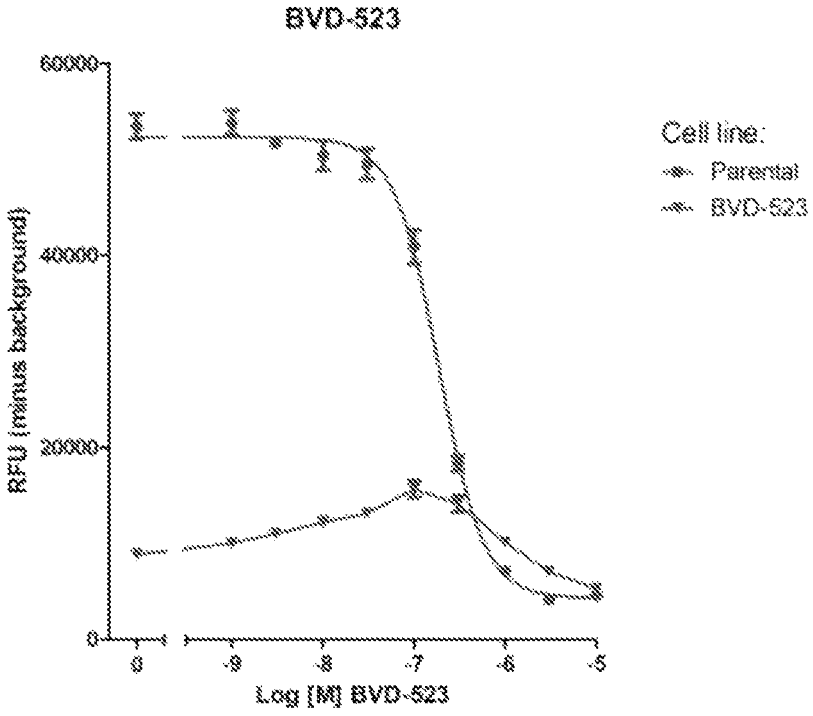

FIG. 5, Con't
E
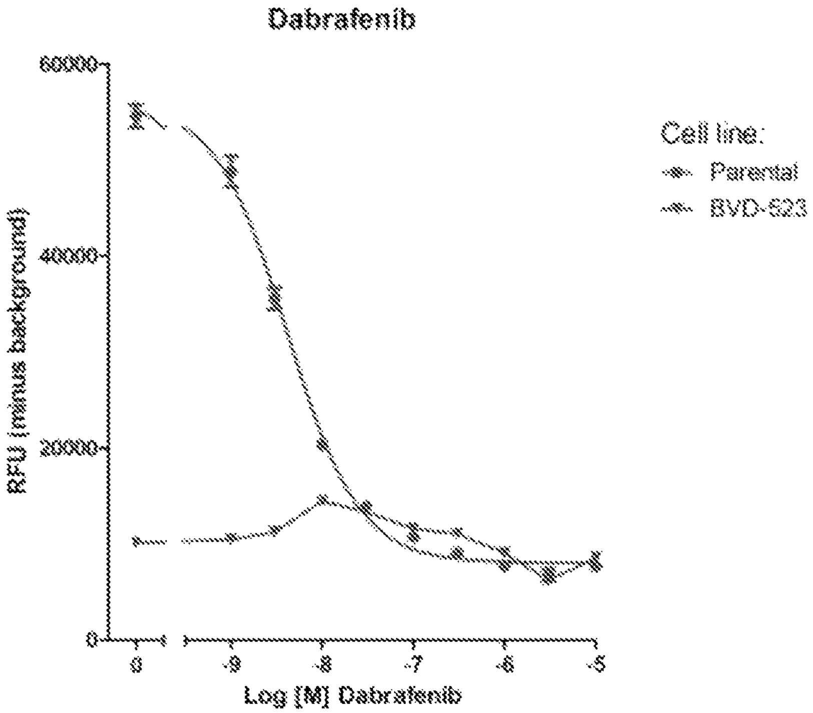

FIG. 5, Con't
F
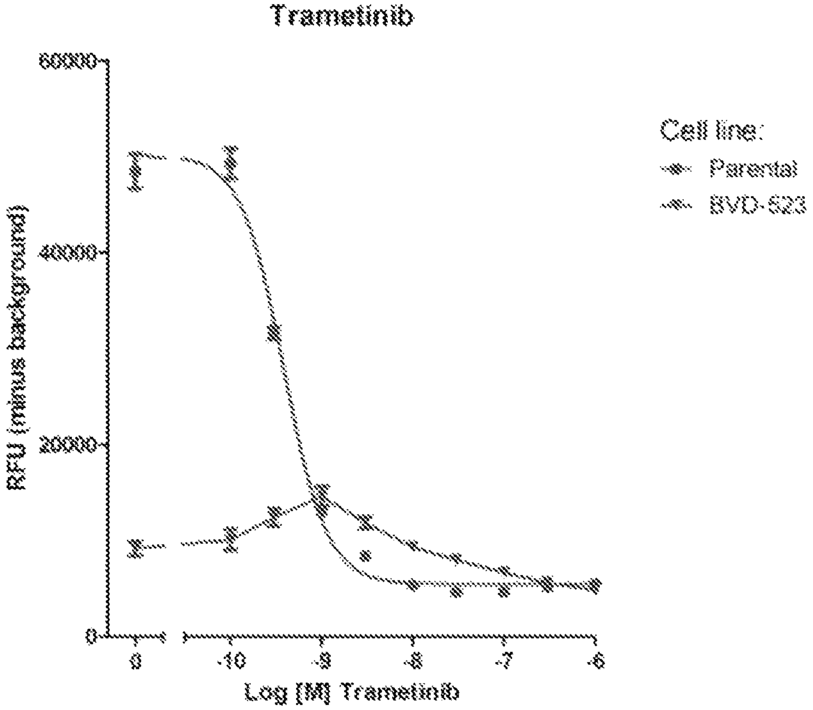

FIG. 5 Con't
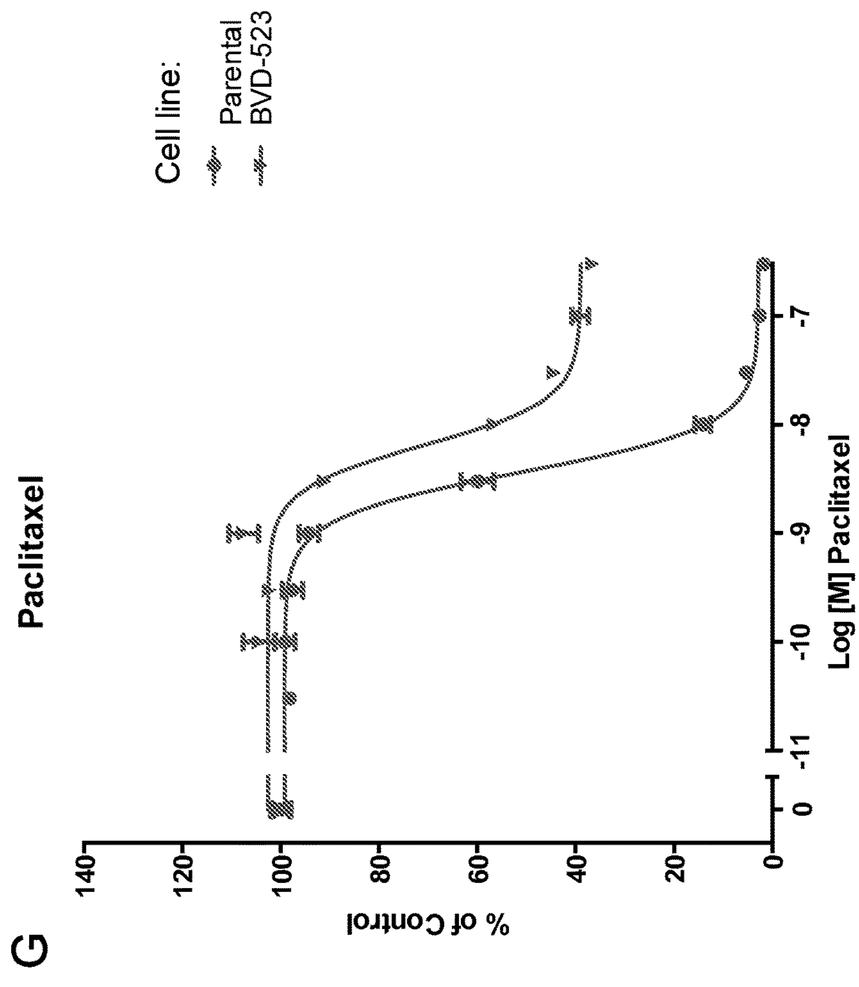

FIG. 5 Con't
H
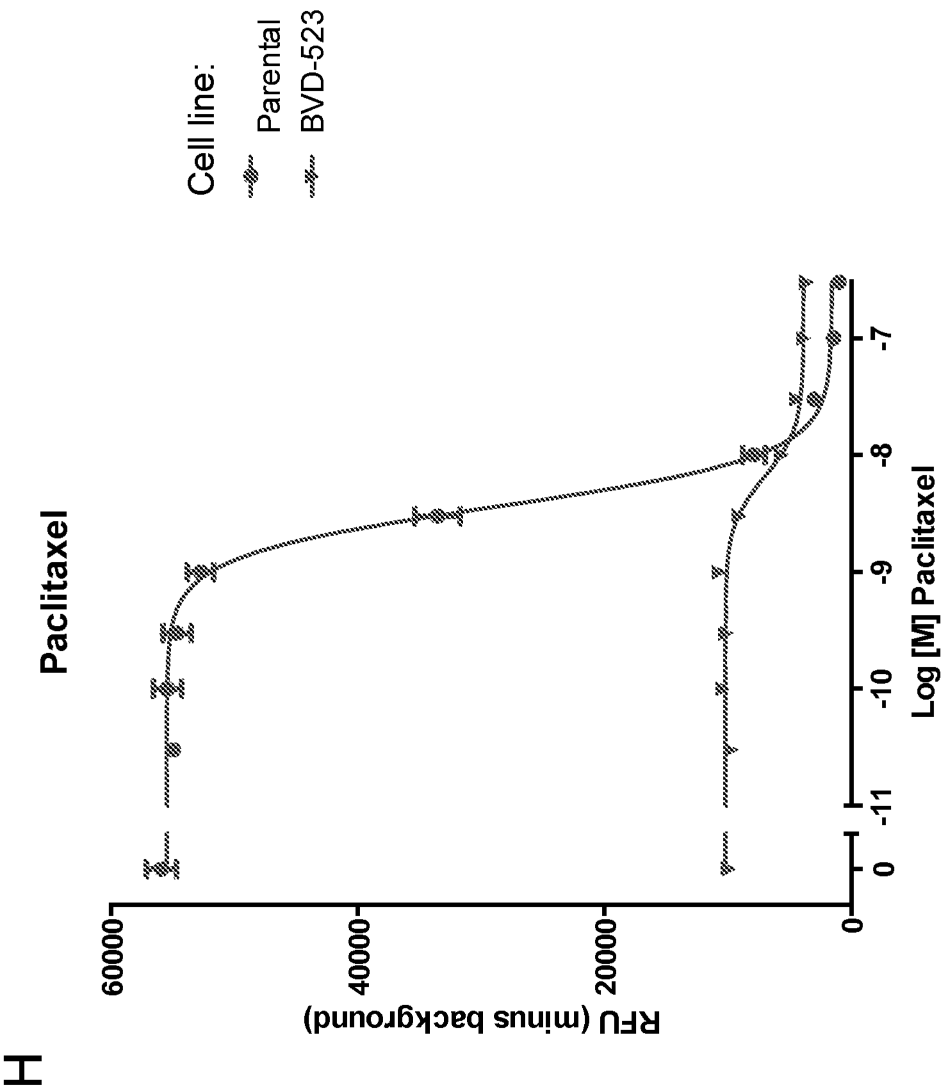

FIG. 6, Con't
C
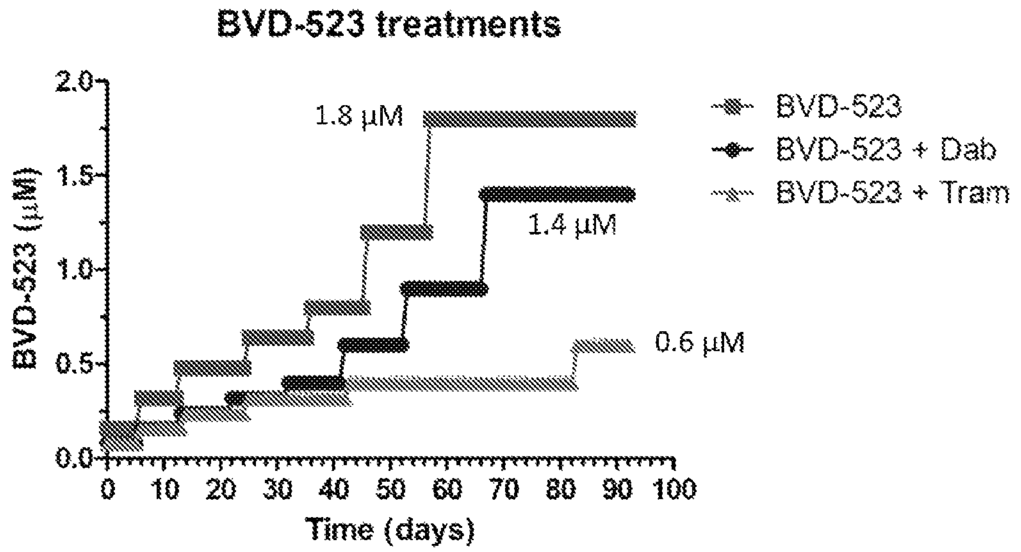
D
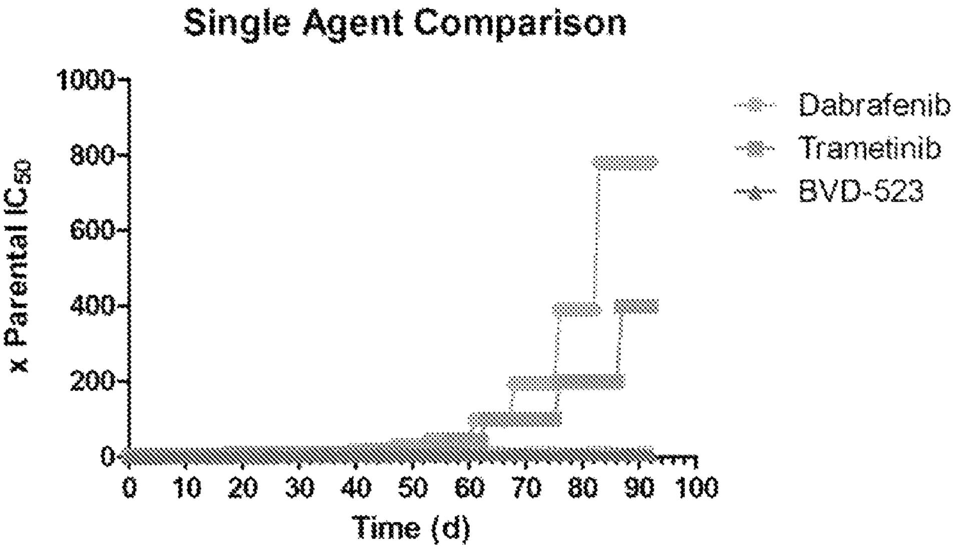

A

FIG. 8, Con't
B
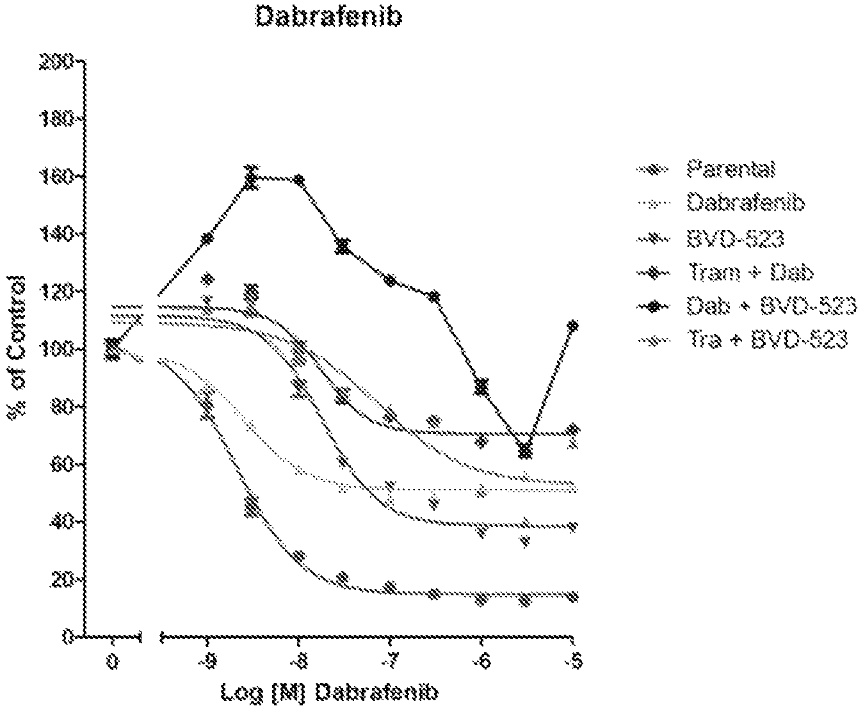

FIG. 8, Con't
C
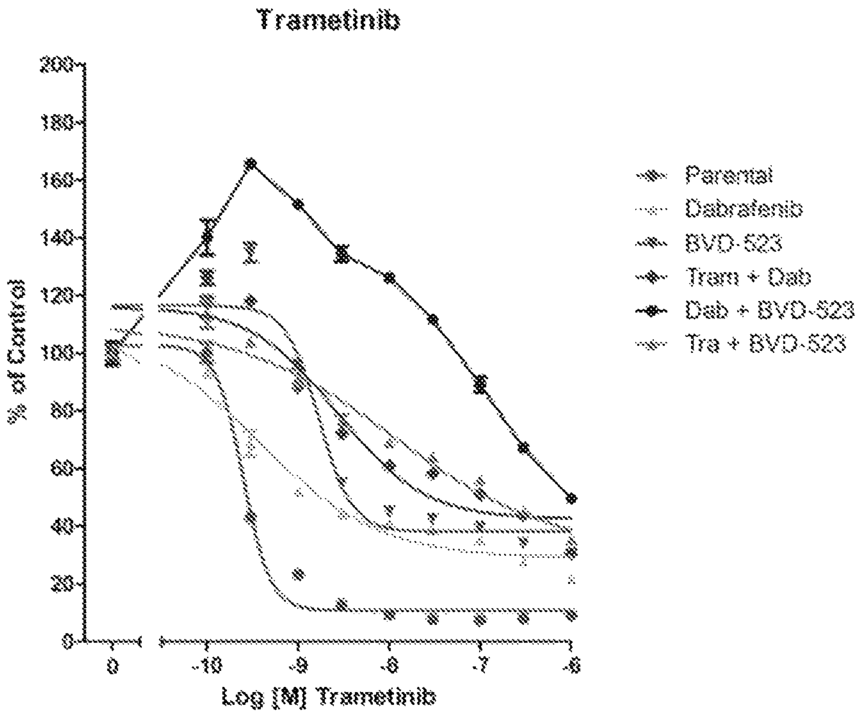

FIG. 8, Con't
D
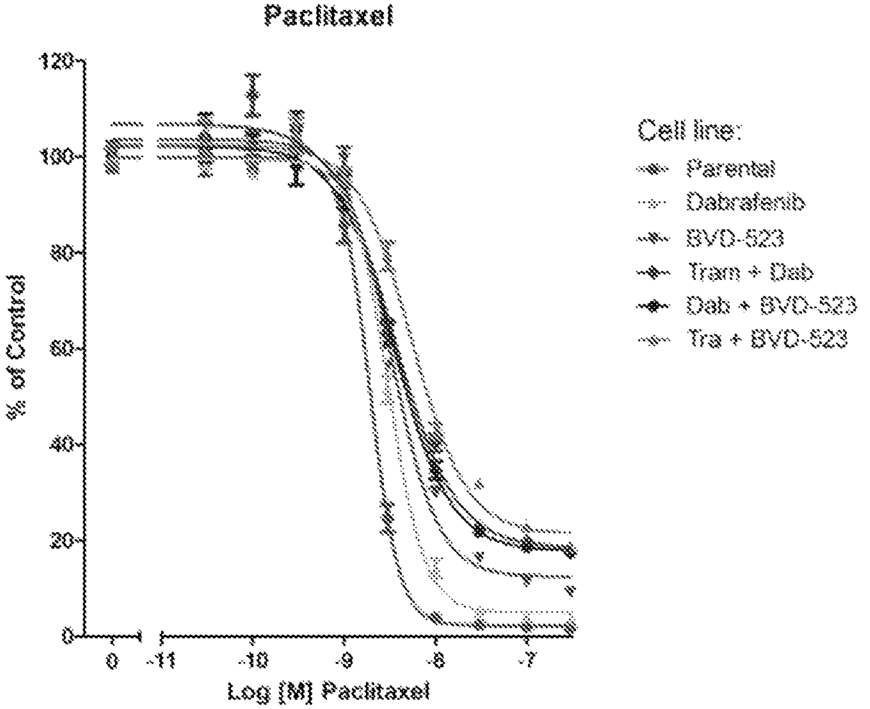

A

FIG. 9, Con't
B
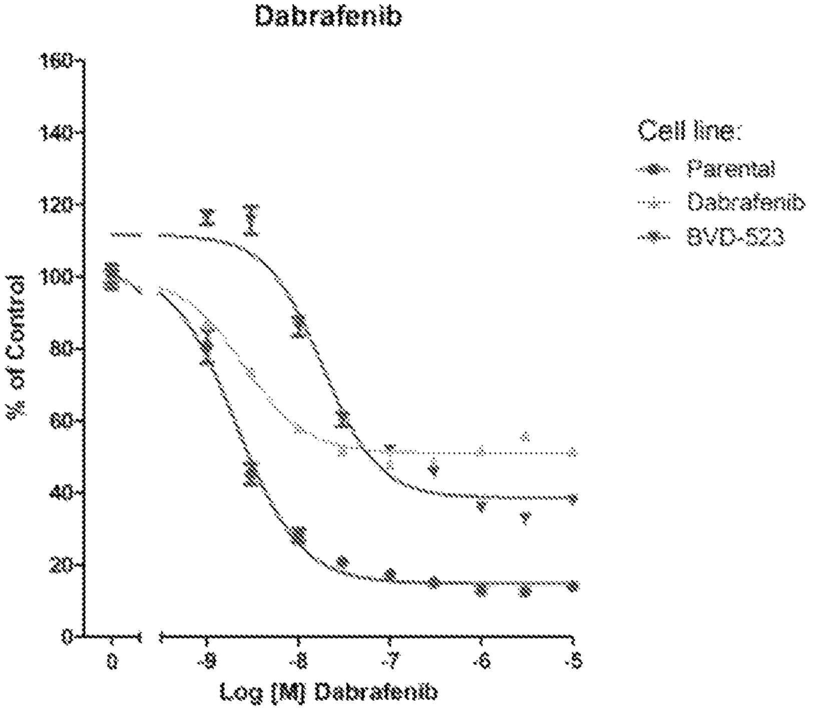

FIG. 9, Con't
C
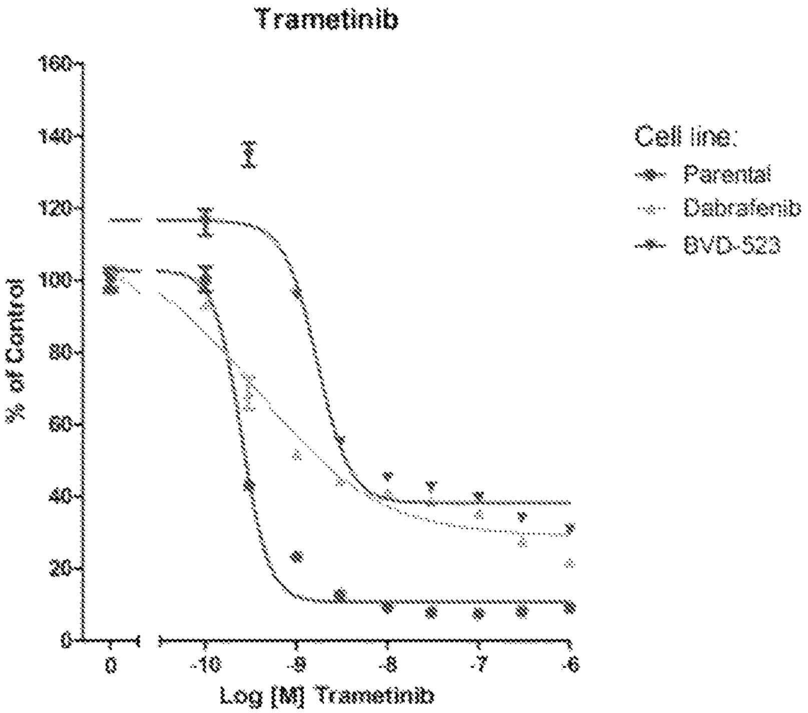

FIG. 9, Con't
D
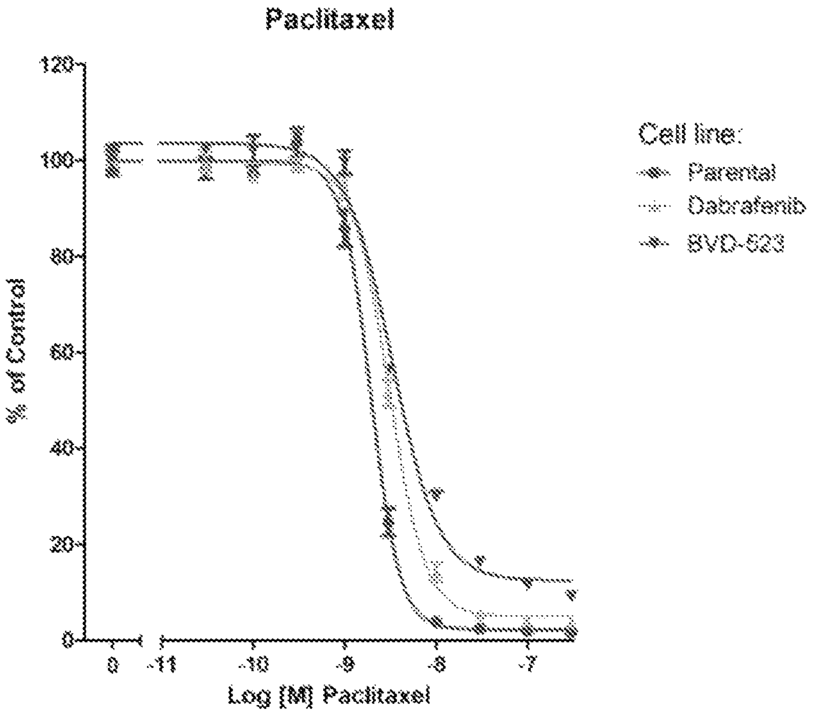

% Inhibition:

| Trametinib (nM) \ Dabrafenib (μM) | 0 | 0.001 | 0.003 | 0.01 | 0.03 | 0.1 | 0.3 | 1 | 3 | 10 |
|---|---|---|---|---|---|---|---|---|---|---|
| 10000 | 93 | 93 | 93 | 93 | 94 | 94 | 94 | 96 | 97 | 92 |
| 1000 | 87 | 87 | 88 | 88 | 89 | 89 | 90 | 92 | 93 | 86 |
| 100 | 87 | 86 | 88 | 88 | 89 | 89 | 90 | 91 | 92 | 87 |
| 10 | 82 | 83 | 83 | 84 | 85 | 86 | 86 | 88 | 89 | 86 |
| 1 | 67 | 70 | 73 | 78 | 81 | 83 | 84 | 86 | 88 | 86 |
| 0.1 | -17 | 3 | 27 | 58 | 72 | 79 | 82 | 85 | 86 | 83 |
| 0.01 | 3 | -4 | 15 | 45 | 68 | 76 | 80 | 83 | 85 | 81 |
| 0 | 0 | 4 | 10 | 43 | 67 | 76 | 79 | 83 | 85 | 82 |

Trametinib (nM)

Dabrafenib (μM)

FIG. 10, Con't
B
Excess over Bliss:
| Trametinib (nM) \ Dabrafenib (μM) | 0 | 0.001 | 0.003 | 0.01 | 0.03 | 0.1 | 0.3 | 1 | 3 | 10 |
|---|---|---|---|---|---|---|---|---|---|---|
| 10000 | 0.00 +/- 0.00 | 0.00 +/- 0.01 | 0.00 +/- 0.02 | -0.03 +/- 0.01 | -0.04 +/- 0.01 | -0.05 +/- 0.01 | -0.05 +/- 0.01 | -0.03 +/- 0.01 | -0.02 +/- 0.00 | -0.07 +/- 0.01 |
| 1000 | 0.00 +/- 0.00 | -0.01 +/- 0.02 | -0.01 +/- 0.02 | -0.05 +/- 0.01 | -0.07 +/- 0.01 | -0.08 +/- 0.00 | -0.08 +/- 0.01 | -0.06 +/- 0.01 | -0.05 +/- 0.01 | -0.10 +/- 0.02 |
| 100 | 0.00 +/- 0.00 | 0.00 +/- 0.01 | -0.01 +/- 0.02 | -0.04 +/- 0.00 | -0.07 +/- 0.00 | -0.08 +/- 0.00 | -0.08 +/- 0.01 | -0.06 +/- 0.01 | -0.06 +/- 0.01 | -0.10 +/- 0.01 |
| 10 | 0.00 +/- 0.00 | 0.00 +/- 0.01 | -0.01 +/- 0.03 | -0.06 +/- 0.01 | -0.09 +/- 0.00 | -0.10 +/- 0.00 | -0.10 +/- 0.01 | -0.09 +/- 0.01 | -0.08 +/- 0.01 | -0.11 +/- 0.01 |
| 1 | 0.00 +/- 0.00 | 0.02 +/- 0.03 | 0.02 +/- 0.04 | -0.03 +/- 0.02 | -0.08 +/- 0.00 | -0.09 +/- 0.01 | -0.09 +/- 0.01 | -0.08 +/- 0.01 | -0.07 +/- 0.01 | -0.08 +/- 0.01 |
| 0.1 | 0.00 +/- 0.00 | 0.14 +/- 0.09 | 0.32 +/- 0.17 | 0.25 +/- 0.10 | 0.10 +/- 0.06 | 0.07 +/- 0.03 | 0.06 +/- 0.03 | 0.05 +/- 0.02 | 0.03 +/- 0.02 | 0.04 +/- 0.02 |
| 0.01 | 0.00 +/- 0.00 | -0.11 +/- 0.09 | 0.02 +/- 0.13 | 0.00 +/- 0.07 | 0.00 +/- 0.04 | -0.01 +/- 0.03 | 0.00 +/- 0.03 | 0.00 +/- 0.01 | 0.00 +/- 0.02 | -0.01 +/- 0.02 |
| 0 | 0.00 +/- 0.00 | 0.00 +/- 0.00 | 0.00 +/- 0.00 | 0.00 +/- 0.00 | 0.00 +/- 0.00 | 0.00 +/- 0.00 | 0.00 +/- 0.00 | 0.00 +/- 0.00 | 0.00 +/- 0.00 | 0.00 +/- 0.00 |
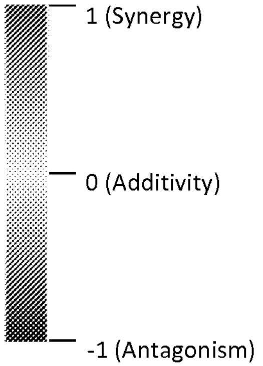

FIG. 10, Con't
C
D
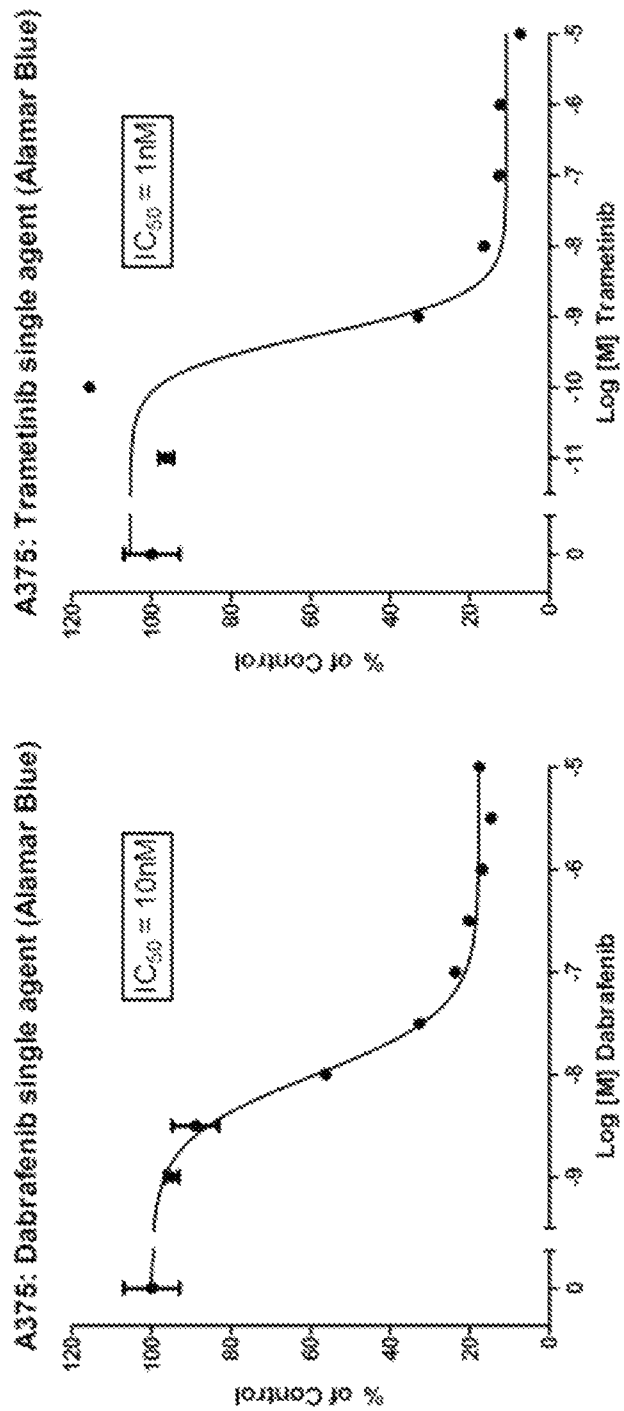

FIG. 10, Con't
E
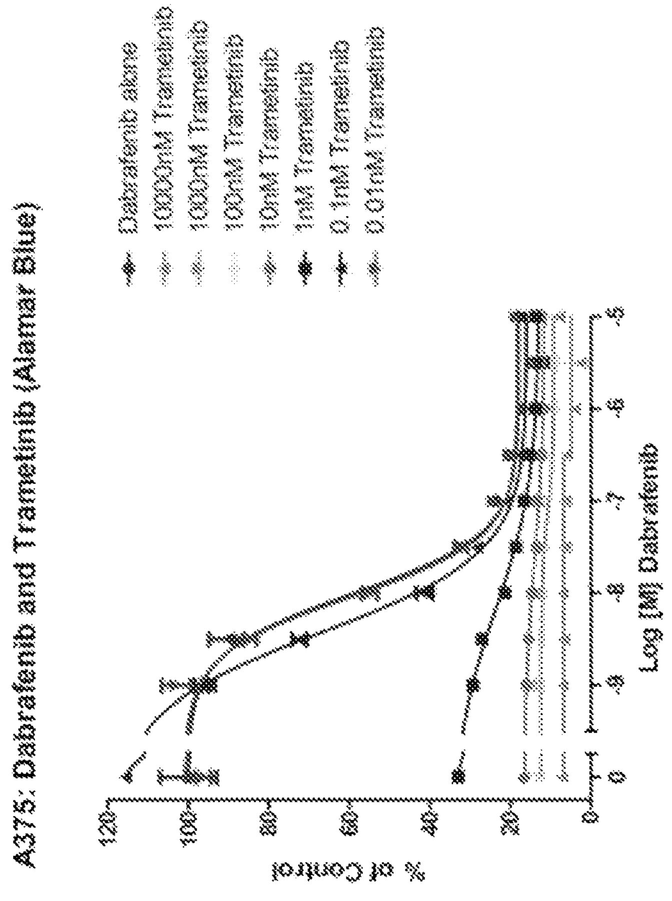

% Inhibition:

| Trametinib (nM) \ Dabrafenib (μM) | 0 | 0.001 | 0.003 | 0.01 | 0.03 | 0.1 | 0.3 | 1 | 3 | 10 |
|---|---|---|---|---|---|---|---|---|---|---|
| 10000 | 85 | 85 | 85 | 85 | 84 | 84 | 86 | 93 | 95 | 83 |
| 1000 | 72 | 74 | 73 | 73 | 72 | 74 | 76 | 84 | 89 | 76 |
| 100 | 74 | 74 | 73 | 73 | 74 | 75 | 77 | 84 | 88 | 75 |
| 10 | 67 | 66 | 67 | 68 | 68 | 70 | 72 | 80 | 86 | 77 |
| 1 | 46 | 49 | 50 | 57 | 61 | 64 | 69 | 77 | 83 | 76 |
| 0.1 | -6 | -6 | 12 | 31 | 48 | 58 | 66 | 75 | 80 | 72 |
| 0.01 | 5 | -4 | 1 | 18 | 42 | 54 | 63 | 72 | 79 | 68 |
| 0 | 0 | -3 | -2 | 16 | 40 | 53 | 61 | 70 | 78 | 69 |

FIG. 11, Con't
B
Excess over Bliss:
| Trametinib (nM) \ Dabrafenib (µM) | 0 | 0.001 | 0.003 | 0.01 | 0.03 | 0.1 | 0.3 | 1 | 3 | 10 |
|---|---|---|---|---|---|---|---|---|---|---|
| 10000 | 0.00 +/- 0.00 | 0.00 +/- 0.03 | 0.00 +/- 0.04 | -0.03 +/- 0.03 | -0.07 +/- 0.02 | -0.09 +/- 0.00 | -0.08 +/-0.00 | -0.03 +/-0.01 | -0.01 +/-0.01 | -0.12 +/-0.02 |
| 1000 | 0.00 +/- 0.00 | 0.03 +/- 0.01 | 0.01 +/- 0.07 | -0.04 +/- 0.01 | -0.11 +/- 0.02 | -0.13 +/- 0.03 | -0.13 +/-0.02 | -0.07 +/-0.02 | -0.05 +/-0.01 | -0.15 +/-0.02 |
| 100 | 0.00 +/- 0.00 | 0.01 +/- 0.01 | 0.00 +/- 0.03 | -0.05 +/- 0.02 | -0.11 +/- 0.01 | -0.12 +/- 0.01 | -0.13 +/-0.01 | -0.09 +/-0.01 | -0.07 +/-0.01 | -0.17 +/-0.01 |
| 10 | 0.00 +/- 0.00 | 0.00 +/- 0.02 | 0.00 +/- 0.06 | -0.04 +/- 0.03 | -0.11 +/- 0.01 | -0.15 +/- 0.01 | -0.15 +/-0.01 | -0.10 +/-0.00 | -0.07 +/-0.01 | -0.13 +/-0.04 |
| 1 | 0.00 +/- 0.00 | 0.05 +/- 0.03 | 0.05 +/- 0.07 | 0.03 +/- 0.07 | -0.06 +/- 0.05 | -0.10 +/- 0.03 | -0.10 +/-0.02 | -0.06 +/-0.01 | -0.05 +/-0.01 | -0.07 +/-0.02 |
| 0.1 | 0.00 +/- 0.00 | 0.03 +/- 0.04 | 0.20 +/- 0.08 | 0.20 +/- 0.08 | 0.12 +/- 0.06 | 0.08 +/- 0.05 | 0.07 +/-0.02 | 0.07 +/-0.03 | 0.03 +/-0.03 | 0.04 +/-0.01 |
| 0.01 | 0.00 +/- 0.00 | -0.06 +/- 0.12 | -0.03 +/- 0.13 | -0.02 +/- 0.10 | -0.01 +/- 0.09 | -0.02 +/- 0.08 | -0.01 +/-0.03 | 0.01 +/-0.02 | 0.00 +/-0.03 | -0.03 +/-0.02 |
| 0 | 0.00 +/- 0.00 | 0.00 +/- 0.00 | 0.00 +/- 0.00 | 0.00 +/- 0.00 | 0.00 +/- 0.00 | 0.00 +/-0.00 | 0.00 +/-0.00 | 0.00 +/-0.00 | 0.00 +/-0.00 | 0.00 +/-0.00 |
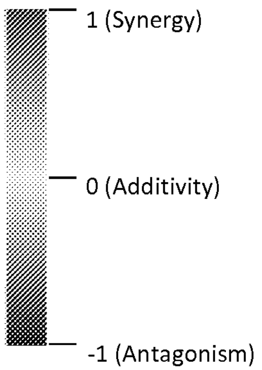

FIG. 11, Con't
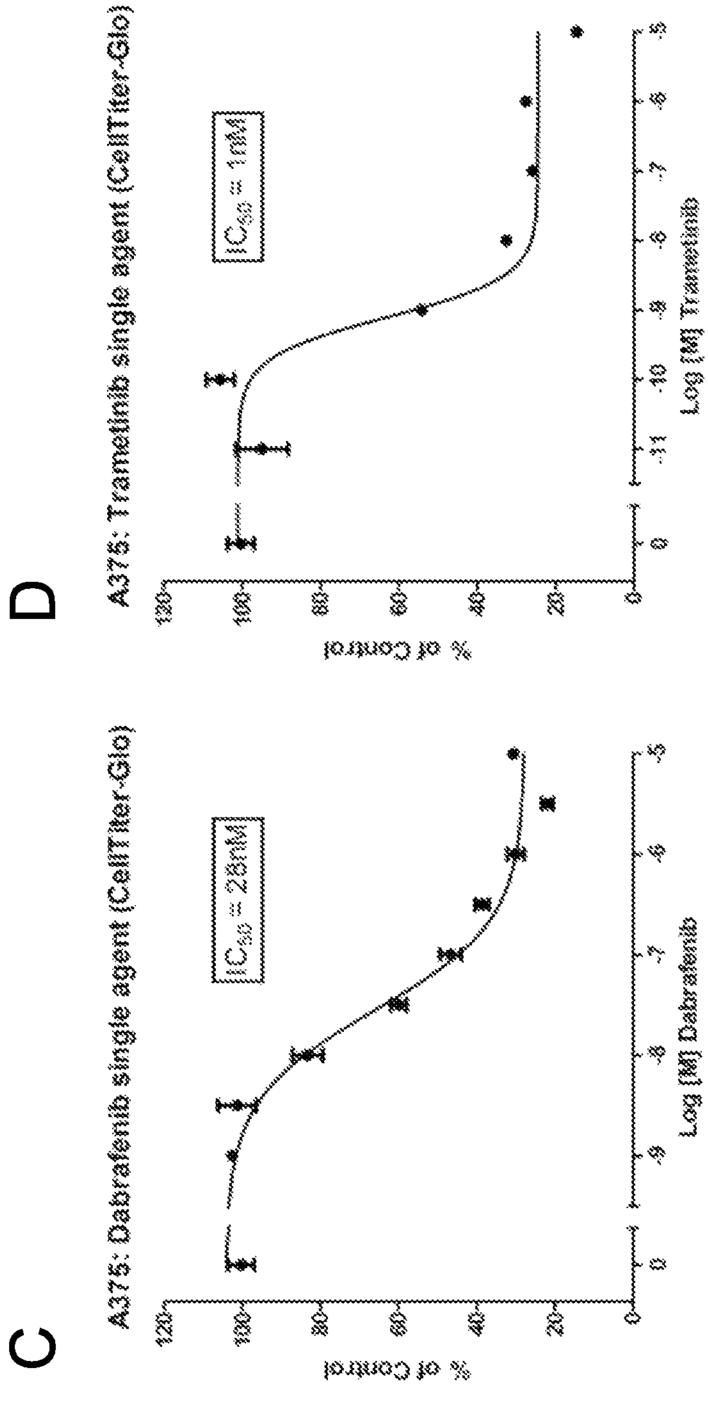

FIG. 11, Con't
E
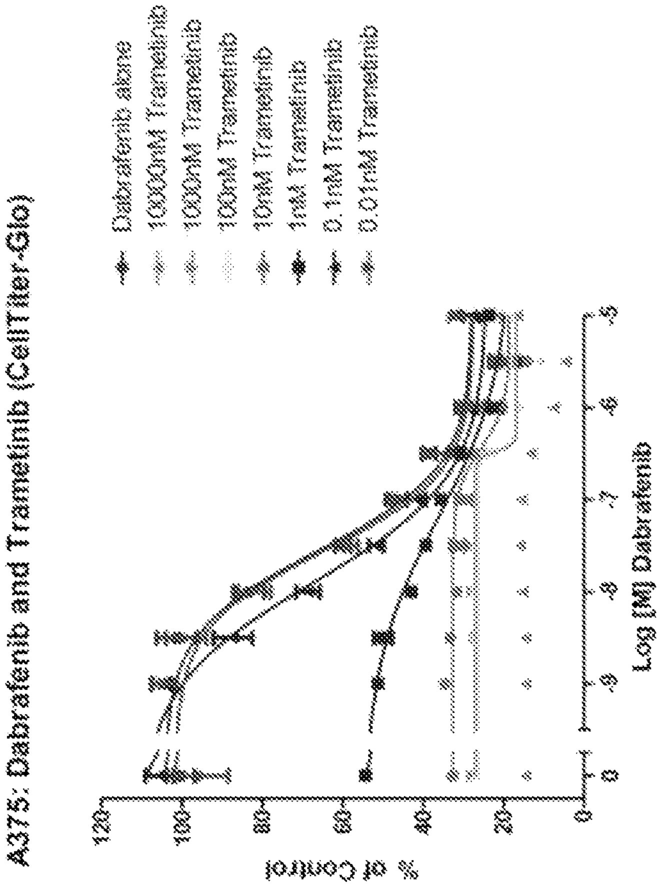

% Inhibition:

| BVD-0523 (μM) \ Dabrafenib (μM) | 0 | 0.001 | 0.003 | 0.01 | 0.03 | 0.1 | 0.3 | 1 | 3 | 10 |
|---|---|---|---|---|---|---|---|---|---|---|
| 10 | 91 | 91 | 91 | 93 | 93 | 93 | 94 | 94 | 95 | 92 |
| 3 | 91 | 91 | 92 | 92 | 93 | 93 | 94 | 94 | 95 | 92 |
| 1 | 84 | 85 | 87 | 89 | 90 | 90 | 91 | 92 | 93 | 90 |
| 0.3 | 49 | 60 | 69 | 77 | 82 | 85 | 87 | 88 | 89 | 87 |
| 0.1 | 11 | 25 | 47 | 67 | 77 | 82 | 84 | 87 | 88 | 86 |
| 0.03 | -6 | 5 | 27 | 58 | 74 | 81 | 83 | 86 | 87 | 85 |
| 0.01 | -2 | -1 | 15 | 49 | 70 | 78 | 82 | 85 | 86 | 84 |
| 0 | 0 | -2 | 9 | 50 | 68 | 77 | 81 | 84 | 86 | 85 |

FIG. 12, Con't
B
Excess over Bliss:
| BVD-0523 (μM) | 0 | 0.001 | 0.003 | 0.01 | 0.03 | 0.1 | 0.3 | 1 | 3 | 10 |
|---|---|---|---|---|---|---|---|---|---|---|
| 10 | 0.00 +/-0.00 | 0.00 +/-0.01 | -0.01 +/-0.01 | -0.03 +/-0.00 | -0.04 +/-0.01 | -0.05 +/-0.01 | -0.04 +/-0.01 | -0.04 +/-0.01 | -0.04 +/-0.01 | -0.07 +/-0.01 |
| 3 | 0.00 +/-0.00 | 0.00 +/-0.00 | 0.00 +/-0.00 | -0.03 +/-0.01 | -0.04 +/-0.01 | -0.05 +/-0.01 | -0.05 +/-0.00 | -0.05 +/-0.00 | -0.04 +/-0.01 | -0.06 +/-0.00 |
| 1 | 0.00 +/-0.00 | 0.02 +/-0.01 | 0.02 +/-0.01 | -0.03 +/-0.00 | -0.05 +/-0.01 | -0.07 +/-0.01 | -0.06 +/-0.01 | -0.05 +/-0.01 | -0.05 +/-0.00 | -0.07 +/-0.01 |
| 0.3 | 0.00 +/-0.00 | 0.13 +/-0.03 | 0.16 +/-0.02 | 0.03 +/-0.02 | -0.01 +/-0.01 | -0.03 +/-0.01 | -0.03 +/-0.01 | -0.04 +/-0.02 | -0.04 +/-0.01 | -0.05 +/-0.01 |
| 0.1 | 0.00 +/-0.00 | 0.16 +/-0.09 | 0.29 +/-0.08 | 0.11 +/-0.03 | 0.05 +/-0.02 | 0.03 +/-0.02 | 0.01 +/-0.01 | 0.02 +/-0.01 | 0.01 +/-0.00 | 0.00 +/-0.01 |
| 0.03 | 0.00 +/-0.00 | 0.13 +/-0.07 | 0.23 +/-0.04 | 0.11 +/-0.01 | 0.08 +/-0.02 | 0.05 +/-0.02 | 0.03 +/-0.02 | 0.03 +/-0.01 | 0.02 +/-0.01 | 0.01 +/-0.01 |
| 0.01 | 0.00 +/-0.00 | 0.03 +/-0.09 | 0.08 +/-0.10 | 0.00 +/-0.03 | 0.02 +/-0.02 | 0.02 +/-0.02 | 0.01 +/-0.02 | 0.01 +/-0.00 | 0.01 +/-0.00 | 0.00 +/-0.02 |
| 0 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 |
Dabrafenib (μM)
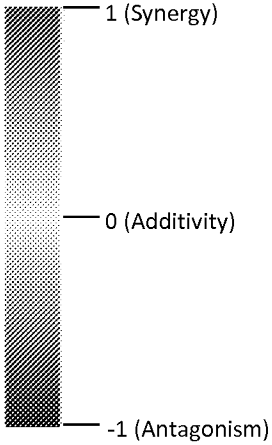

FIG. 12, Con't
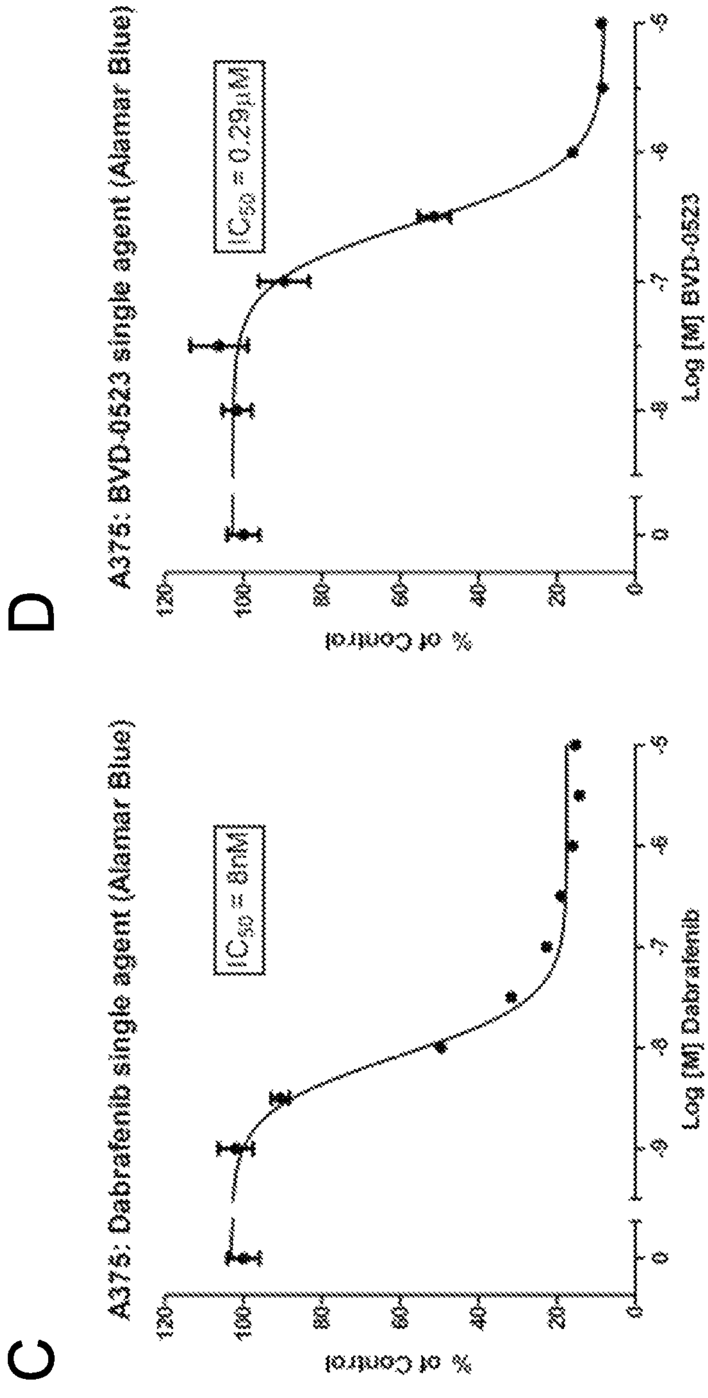

FIG. 12, Con't
E
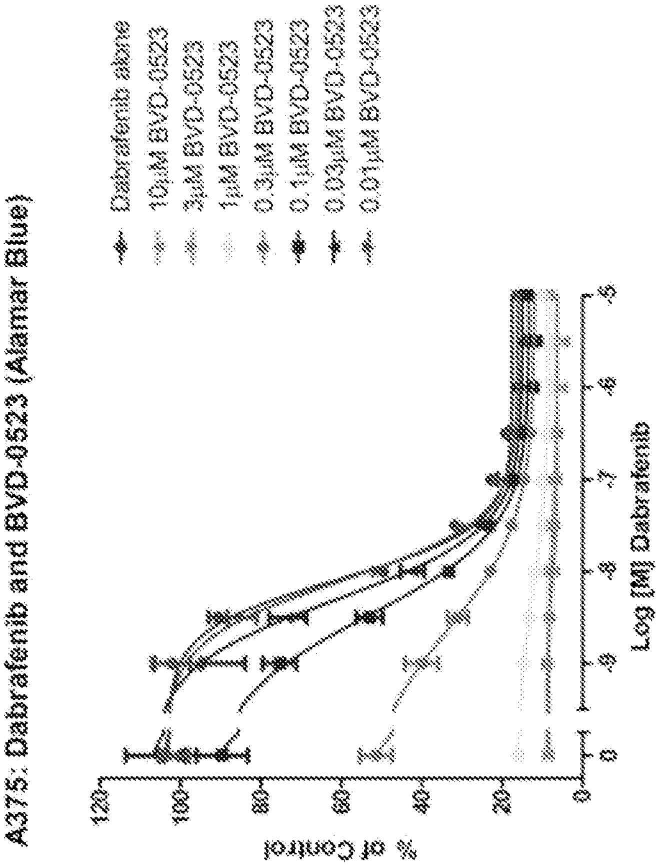

% Inhibition:

| BVD-0523 (μM) \ Dabrafenib (μM) | 0 | 0.001 | 0.003 | 0.01 | 0.03 | 0.1 | 0.3 | 1 | 3 | 10 |
|---|---|---|---|---|---|---|---|---|---|---|
| 10 | 78 | 79 | 79 | 81 | 81 | 81 | 83 | 86 | 89 | 79 |
| 3 | 80 | 80 | 81 | 82 | 81 | 82 | 85 | 87 | 91 | 81 |
| 1 | 68 | 69 | 71 | 74 | 75 | 75 | 79 | 84 | 89 | 80 |
| 0.3 | 28 | 35 | 41 | 53 | 61 | 66 | 70 | 76 | 82 | 75 |
| 0.1 | 4 | 11 | 21 | 39 | 51 | 60 | 66 | 75 | 80 | 74 |
| 0.03 | -4 | -3 | 12 | 32 | 50 | 58 | 64 | 73 | 79 | 71 |
| 0.01 | -2 | -4 | 4 | 26 | 47 | 57 | 63 | 72 | 78 | 71 |
| 0 | 0 | -3 | -2 | 24 | 44 | 54 | 62 | 70 | 78 | 70 |

FIG. 13, Con't
B
Excess over Bliss:
| BVD-0523 (μM) | 0 | 0.001 | 0.003 | 0.01 | 0.03 | 0.1 | 0.3 | 1 | 3 | 10 |
|---|---|---|---|---|---|---|---|---|---|---|
| 10 | 0.00 +/-0.00 | 0.01 +/-0.00 | 0.02 +/-0.01 | -0.02 +/-0.01 | -0.07 +/-0.01 | -0.09 +/-0.02 | -0.09 +/-0.01 | -0.07 +/-0.01 | -0.06 +/-0.01 | -0.14 +/-0.02 |
| 3 | 0.00 +/-0.00 | 0.01 +/-0.02 | 0.01 +/-0.01 | -0.03 +/-0.00 | -0.08 +/-0.02 | -0.09 +/-0.02 | -0.08 +/-0.01 | -0.07 +/-0.01 | -0.05 +/-0.01 | -0.13 +/-0.02 |
| 1 | 0.00 +/-0.00 | 0.02 +/-0.01 | 0.04 +/-0.01 | -0.02 +/-0.01 | -0.08 +/-0.02 | -0.11 +/-0.01 | -0.09 +/-0.01 | -0.07 +/-0.01 | -0.04 +/-0.01 | -0.11 +/-0.01 |
| 0.3 | 0.00 +/-0.00 | 0.10 +/-0.05 | 0.14 +/-0.04 | 0.07 +/-0.00 | 0.01 +/-0.02 | -0.01 +/-0.01 | -0.03 +/-0.01 | -0.02 +/-0.01 | -0.02 +/-0.01 | -0.03 +/-0.01 |
| 0.1 | 0.00 +/-0.00 | 0.10 +/-0.11 | 0.19 +/-0.13 | 0.12 +/-0.05 | 0.05 +/-0.06 | 0.04 +/-0.06 | 0.02 +/-0.03 | 0.03 +/-0.03 | 0.02 +/-0.01 | 0.03 +/-0.03 |
| 0.03 | 0.00 +/-0.00 | 0.04 +/-0.13 | 0.18 +/-0.14 | 0.11 +/-0.06 | 0.08 +/-0.06 | 0.06 +/-0.05 | 0.03 +/-0.02 | 0.04 +/-0.04 | 0.03 +/-0.01 | 0.02 +/-0.03 |
| 0.01 | 0.00 +/-0.00 | 0.01 +/-0.14 | 0.08 +/-0.13 | 0.04 +/-0.05 | 0.04 +/-0.05 | 0.03 +/-0.04 | 0.01 +/-0.03 | 0.02 +/-0.03 | 0.01 +/-0.01 | 0.01 +/-0.04 |
| 0 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 |
Dabrafenib (μM)
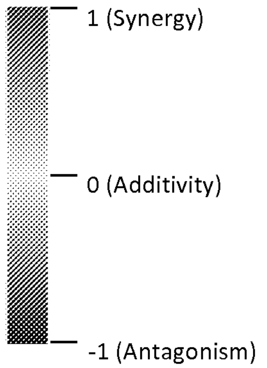

FIG. 13, Con't
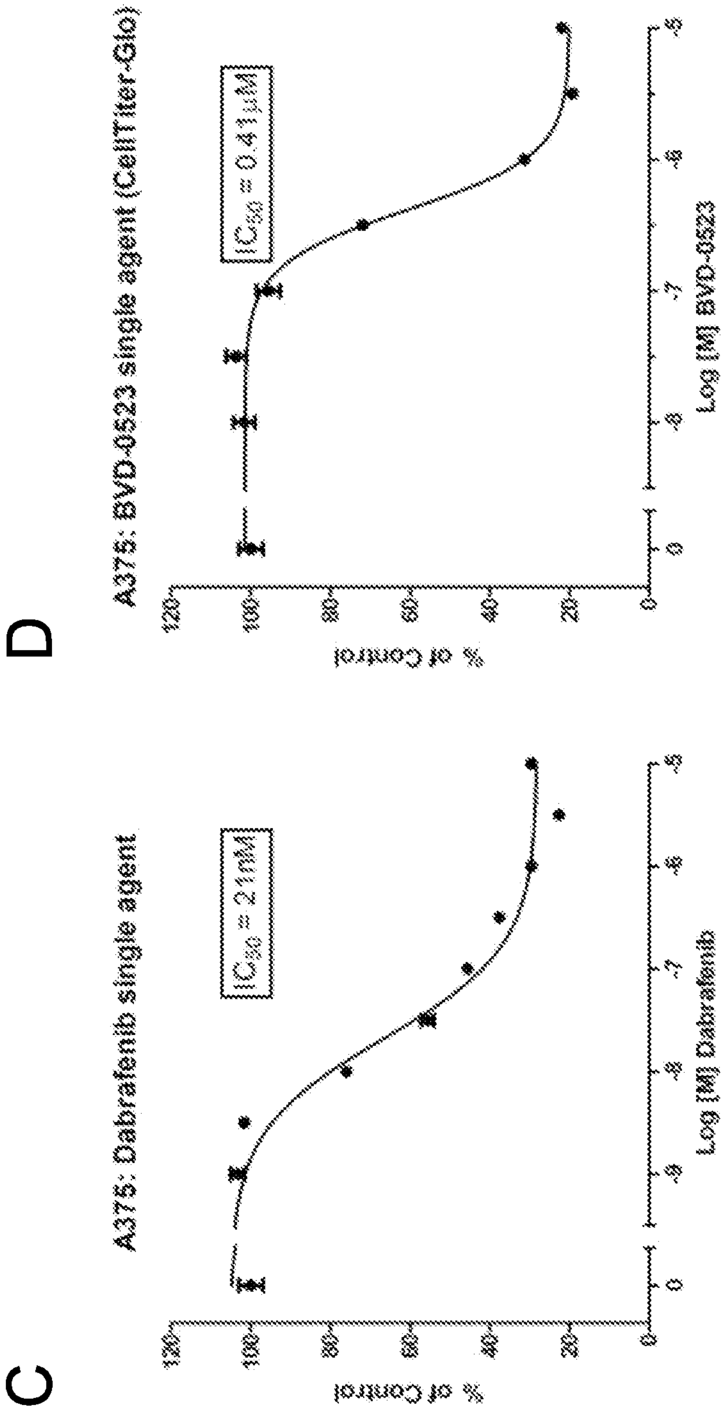

FIG. 13, Con't
E
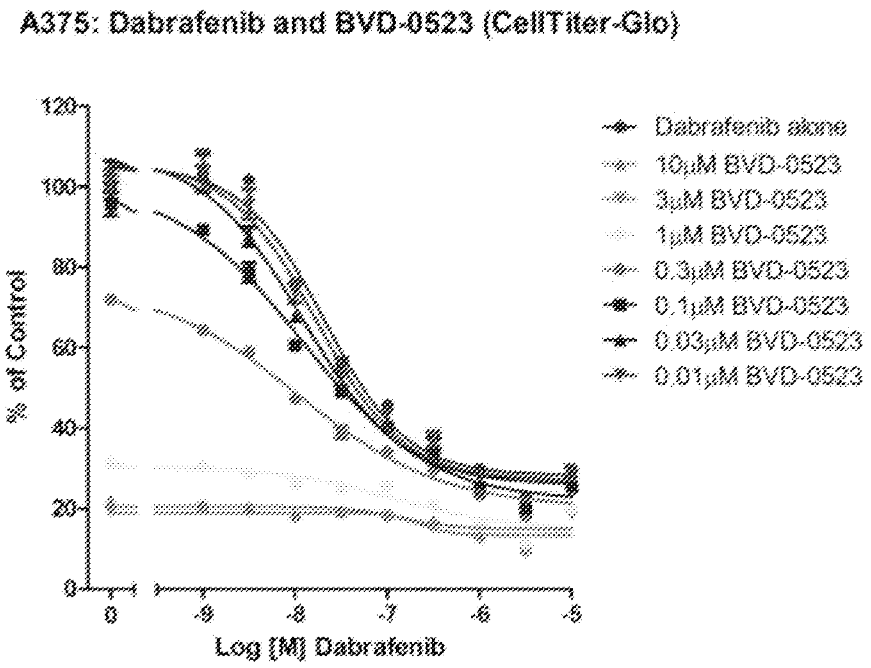

% Inhibition:

| BVD-0523 (µM) \ Trametinib (nM) | 0 | 0.0001 | 0.001 | 0.01 | 0.1 | 1 | 10 | 100 | 1000 | 10000 |
|---|---|---|---|---|---|---|---|---|---|---|
| 10 | 88 | 88 | 88 | 90 | 89 | 90 | 89 | 89 | 89 | 94 |
| 3 | 89 | 86 | 89 | 90 | 89 | 89 | 90 | 89 | 90 | 94 |
| 1 | 81 | 82 | 84 | 83 | 82 | 86 | 89 | 89 | 89 | 93 |
| 0.3 | 41 | 43 | 49 | 46 | 49 | 72 | 85 | 88 | 86 | 93 |
| 0.1 | -3 | -7 | 1 | -4 | 2 | 59 | 82 | 88 | 86 | 93 |
| 0.03 | -35 | -35 | -29 | -27 | -30 | 47 | 81 | 87 | 86 | 92 |
| 0.01 | -19 | -33 | -36 | -33 | -37 | 34 | 78 | 86 | 86 | 93 |
| 0 | 0 | -10 | -14 | -1 | -30 | 41 | 81 | 89 | 89 | 95 |

FIG. 14, Con't
B
Excess over Bliss:
| BVD-0523 (µM) \ Trametinib (nM) | 0 | 0.0001 | 0.001 | 0.01 | 0.1 | 1 | 10 | 100 | 1000 | 10000 |
|---|---|---|---|---|---|---|---|---|---|---|
| 10 | 0.00 +/-0.00 | 0.01 +/-0.02 | 0.02 +/-0.01 | 0.02 +/-0.02 | 0.04 +/-0.02 | -0.03 +/-0.01 | -0.08 +/-0.00 | -0.09 +/-0.00 | -0.09 +/-0.01 | -0.06 +/-0.01 |
| 3 | 0.00 +/-0.00 | -0.02 +/-0.06 | 0.02 +/-0.01 | 0.01 +/-0.01 | 0.03 +/-0.01 | -0.04 +/-0.00 | -0.08 +/-0.01 | -0.09 +/-0.01 | -0.09 +/-0.01 | -0.06 +/-0.01 |
| 1 | 0.00 +/-0.00 | 0.03 +/-0.04 | 0.06 +/-0.02 | 0.03 +/-0.02 | 0.07 +/-0.03 | -0.03 +/-0.01 | -0.08 +/-0.00 | -0.09 +/-0.00 | -0.09 +/-0.01 | -0.06 +/-0.01 |
| 0.3 | 0.00 +/-0.00 | 0.07 +/-0.12 | 0.17 +/-0.10 | 0.06 +/-0.06 | 0.25 +/-0.12 | 0.07 +/-0.04 | -0.04 +/-0.02 | -0.05 +/-0.01 | -0.07 +/-0.01 | -0.04 +/-0.01 |
| 0.1 | 0.00 +/-0.00 | 0.05 +/-0.19 | 0.18 +/-0.13 | 0.00 +/-0.10 | 0.36 +/-0.18 | 0.19 +/-0.07 | 0.02 +/-0.02 | -0.01 +/-0.02 | -0.02 +/-0.02 | -0.02 +/-0.01 |
| 0.03 | 0.00 +/-0.00 | 0.13 +/-0.19 | 0.25 +/-0.16 | 0.10 +/-0.16 | 0.46 +/-0.19 | 0.26 +/-0.06 | 0.06 +/-0.02 | 0.02 +/-0.02 | 0.02 +/-0.03 | -0.01 +/-0.01 |
| 0.01 | 0.00 +/-0.00 | -0.03 +/-0.12 | 0.00 +/-0.20 | -0.12 +/-0.09 | 0.17 +/-0.15 | 0.05 +/-0.09 | 0.01 +/-0.04 | 0.00 +/-0.02 | -0.01 +/-0.03 | -0.01 +/-0.01 |
| 0 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 |
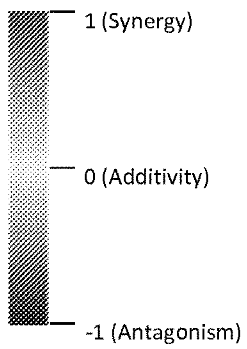

FIG. 14, Con't
C D
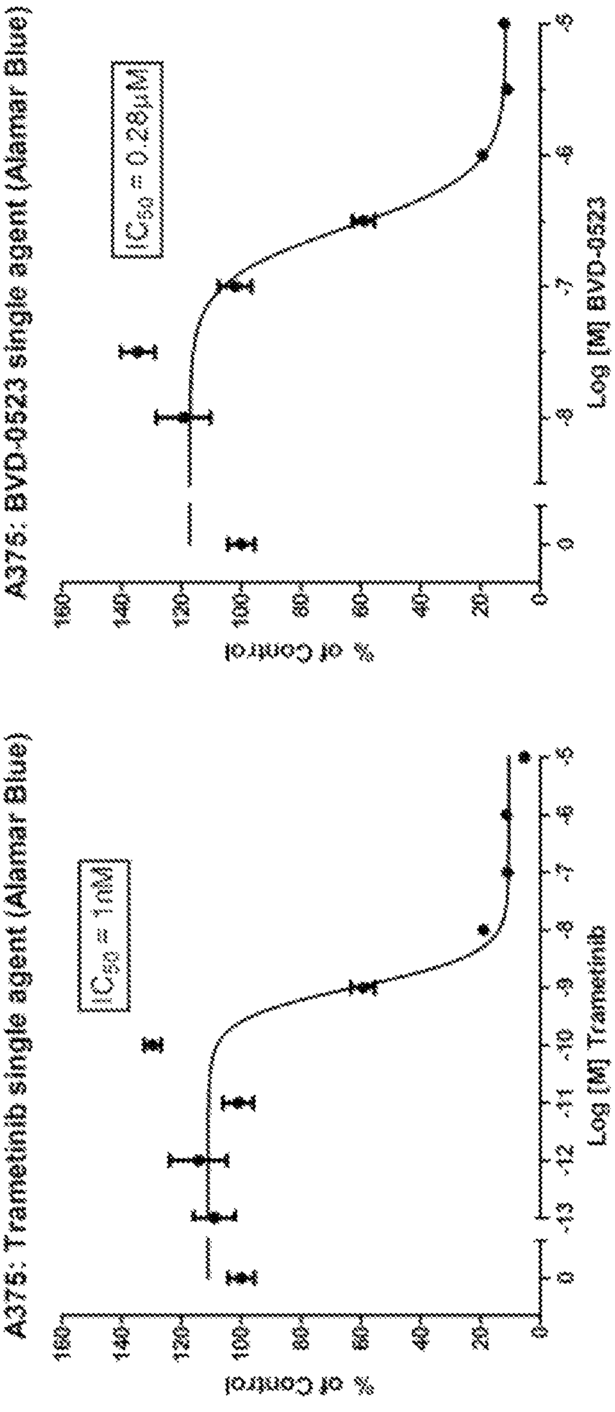

FIG. 14, Con't
E
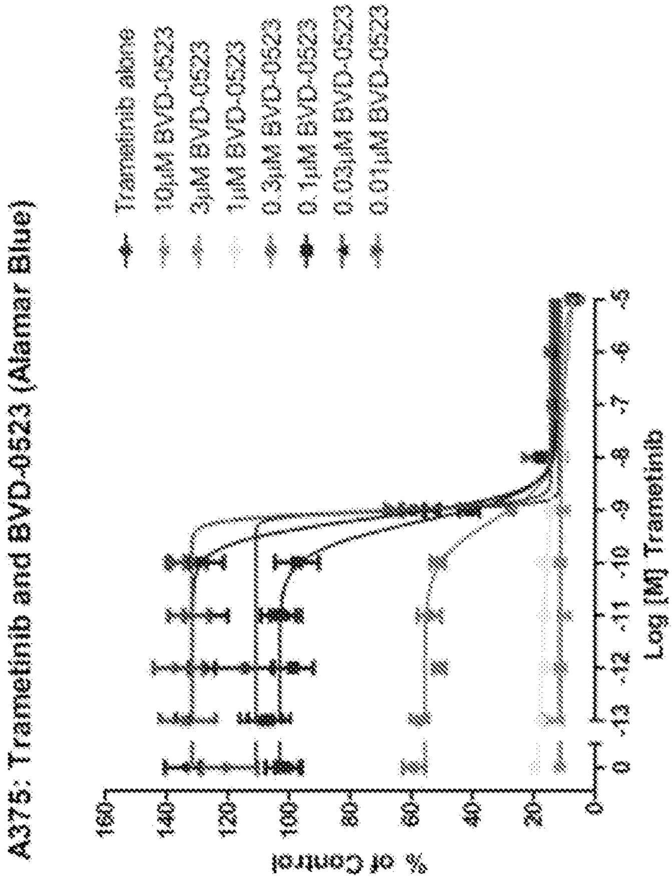

FIG. 15, Con't
B
Excess over Bliss:
| BVD-0523 (μM) \ Trametinib (nM) | 0 | 0.0001 | 0.001 | 0.01 | 0.1 | 1 | 10 | 100 | 1000 | 10000 |
|---|---|---|---|---|---|---|---|---|---|---|
| 10 | 0.00 +/-0.00 | 0.02 +/-0.05 | 0.04 +/-0.03 | 0.04 +/-0.04 | 0.07 +/-0.03 | 0.01 +/-0.03 | -0.14 +/-0.02 | -0.17 +/-0.01 | -0.18 +/-0.02 | -0.11 +/-0.02 |
| 3 | 0.00 +/-0.00 | -0.04 +/-0.11 | 0.04 +/-0.02 | 0.03 +/-0.04 | 0.06 +/-0.02 | 0.00 +/-0.00 | -0.11 +/-0.01 | -0.15 +/-0.01 | -0.14 +/-0.03 | -0.09 +/-0.02 |
| 1 | 0.00 +/-0.00 | 0.03 +/-0.06 | 0.06 +/-0.02 | 0.04 +/-0.02 | 0.07 +/-0.02 | 0.04 +/-0.03 | -0.09 +/-0.01 | -0.15 +/-0.01 | -0.12 +/-0.01 | -0.08 +/-0.00 |
| 0.3 | 0.00 +/-0.00 | 0.05 +/-0.10 | 0.15 +/-0.09 | 0.05 +/-0.12 | 0.23 +/-0.11 | 0.27 +/-0.09 | 0.04 +/-0.03 | -0.02 +/-0.04 | -0.05 +/-0.03 | -0.02 +/-0.02 |
| 0.1 | 0.00 +/-0.00 | 0.02 +/-0.16 | 0.11 +/-0.08 | 0.01 +/-0.15 | 0.25 +/-0.09 | 0.33 +/-0.12 | 0.09 +/-0.04 | 0.04 +/-0.04 | 0.04 +/-0.07 | 0.01 +/-0.01 |
| 0.03 | 0.00 +/-0.00 | 0.05 +/-0.15 | 0.16 +/-0.13 | 0.08 +/-0.23 | 0.27 +/-0.22 | 0.30 +/-0.12 | 0.11 +/-0.05 | 0.06 +/-0.05 | 0.06 +/-0.08 | 0.00 +/-0.04 |
| 0.01 | 0.00 +/-0.00 | -0.06 +/-0.12 | 0.05 +/-0.12 | -0.07 +/-0.11 | 0.08 +/-0.09 | 0.07 +/-0.11 | 0.02 +/-0.05 | 0.02 +/-0.03 | 0.00 +/-0.07 | -0.01 +/-0.03 |
| 0 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 | 0.00 +/-0.00 |
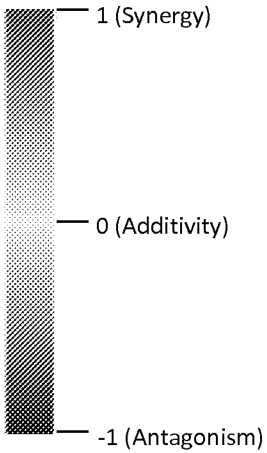

FIG. 15, Con't
C D
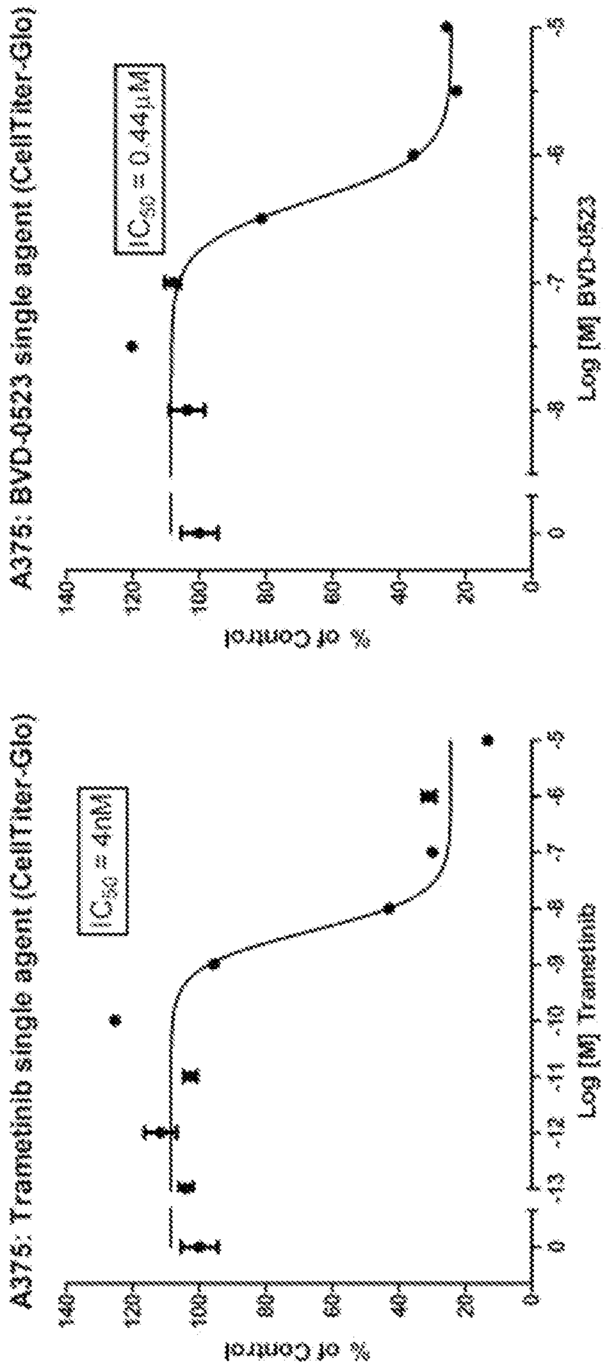

FIG. 15, Con't
E
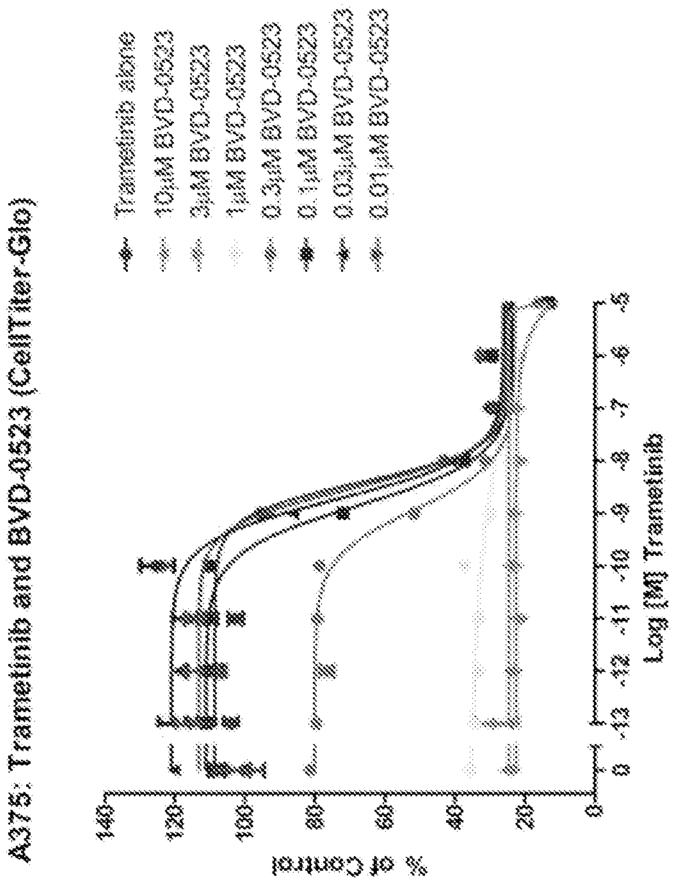

FIG. 16 Con't
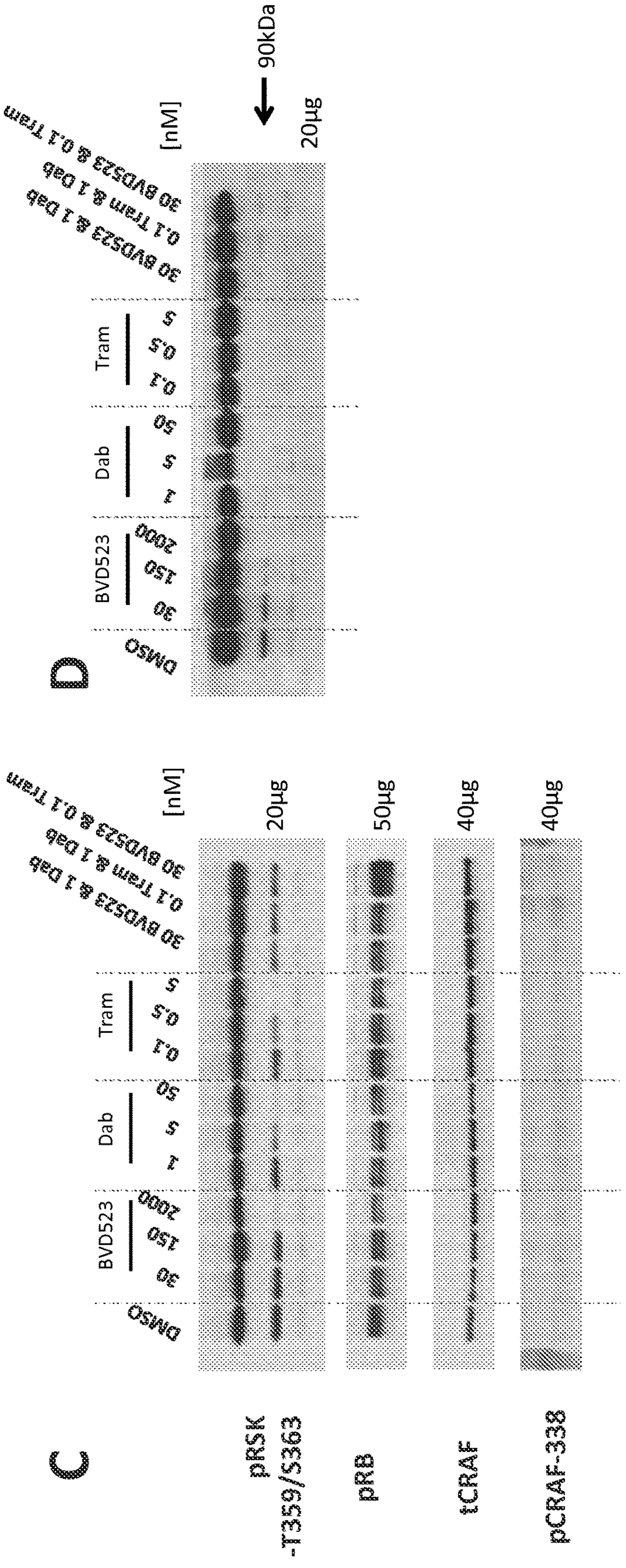

FIG. 17 Con't
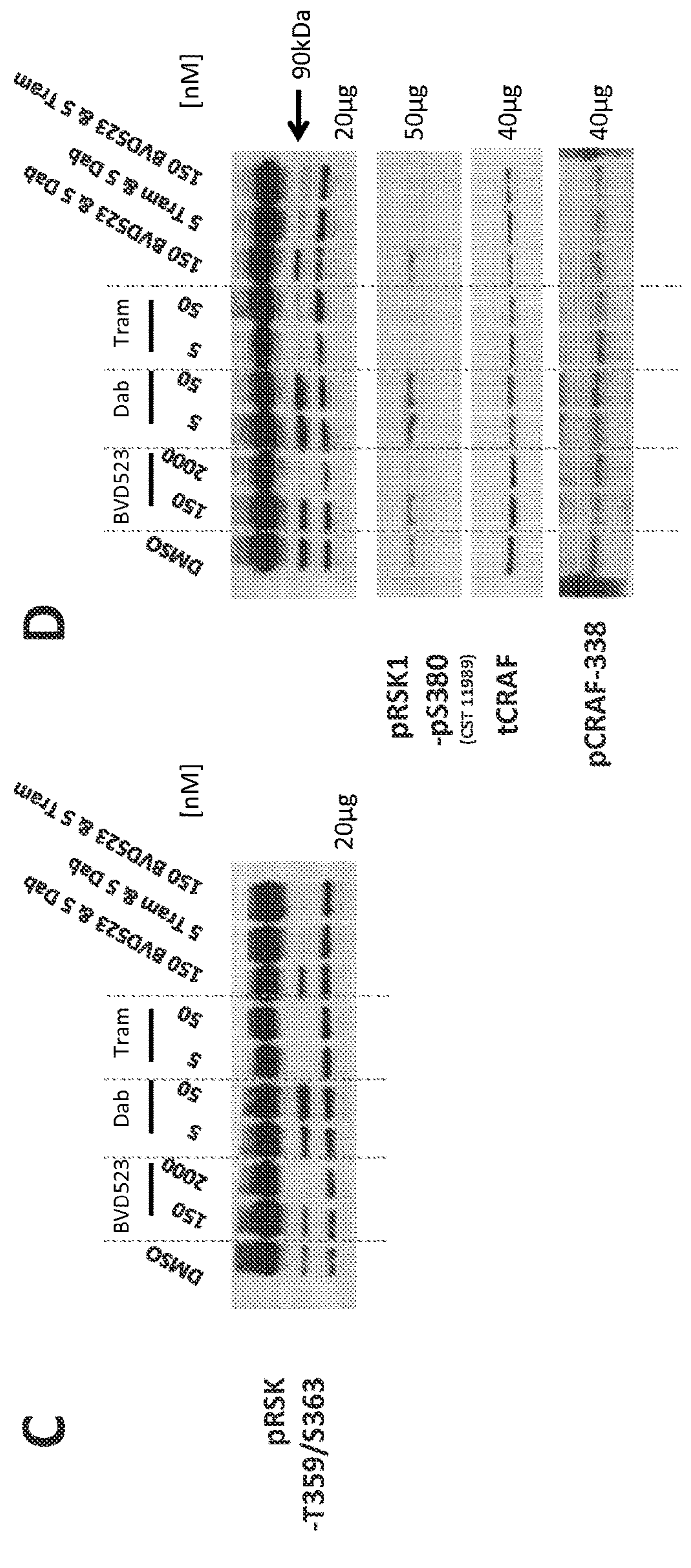

FIG. 18 Con't
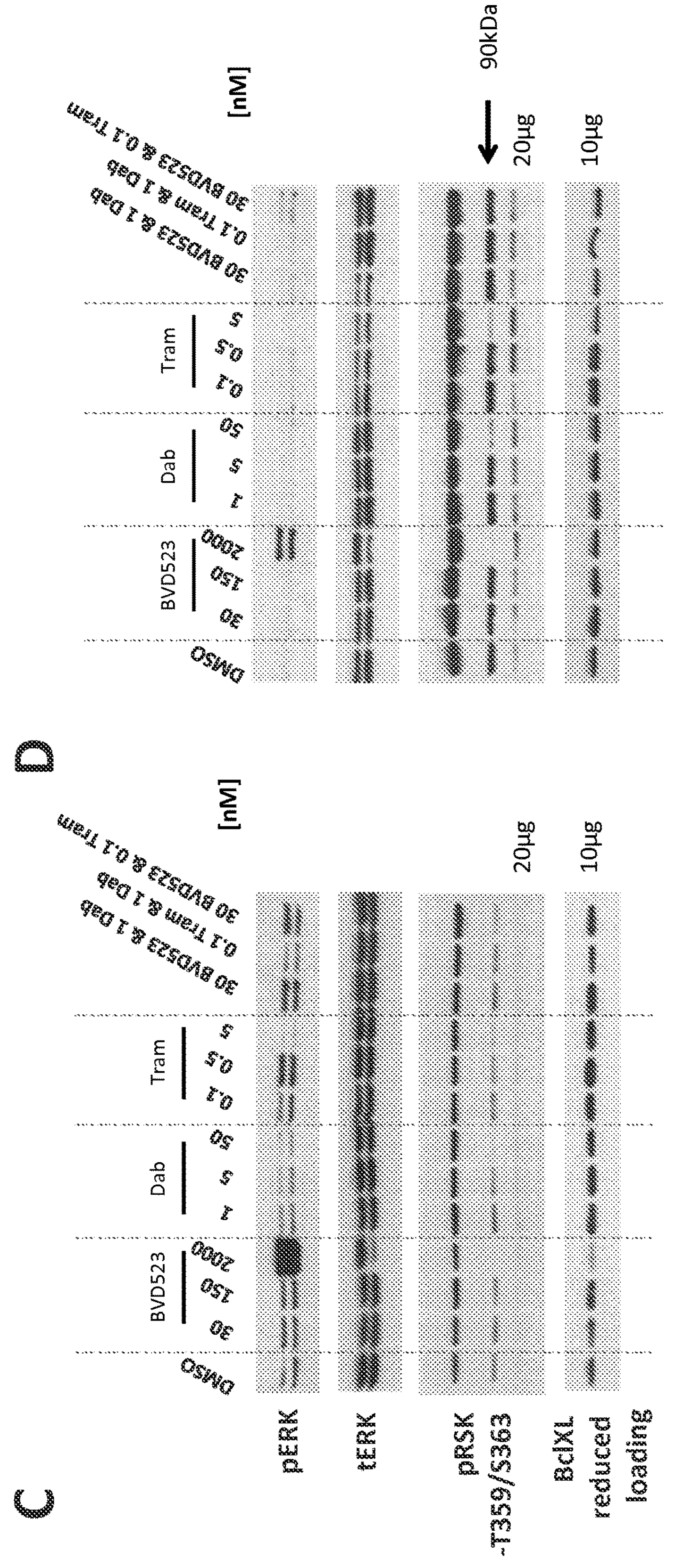

FIG. 20, Con't
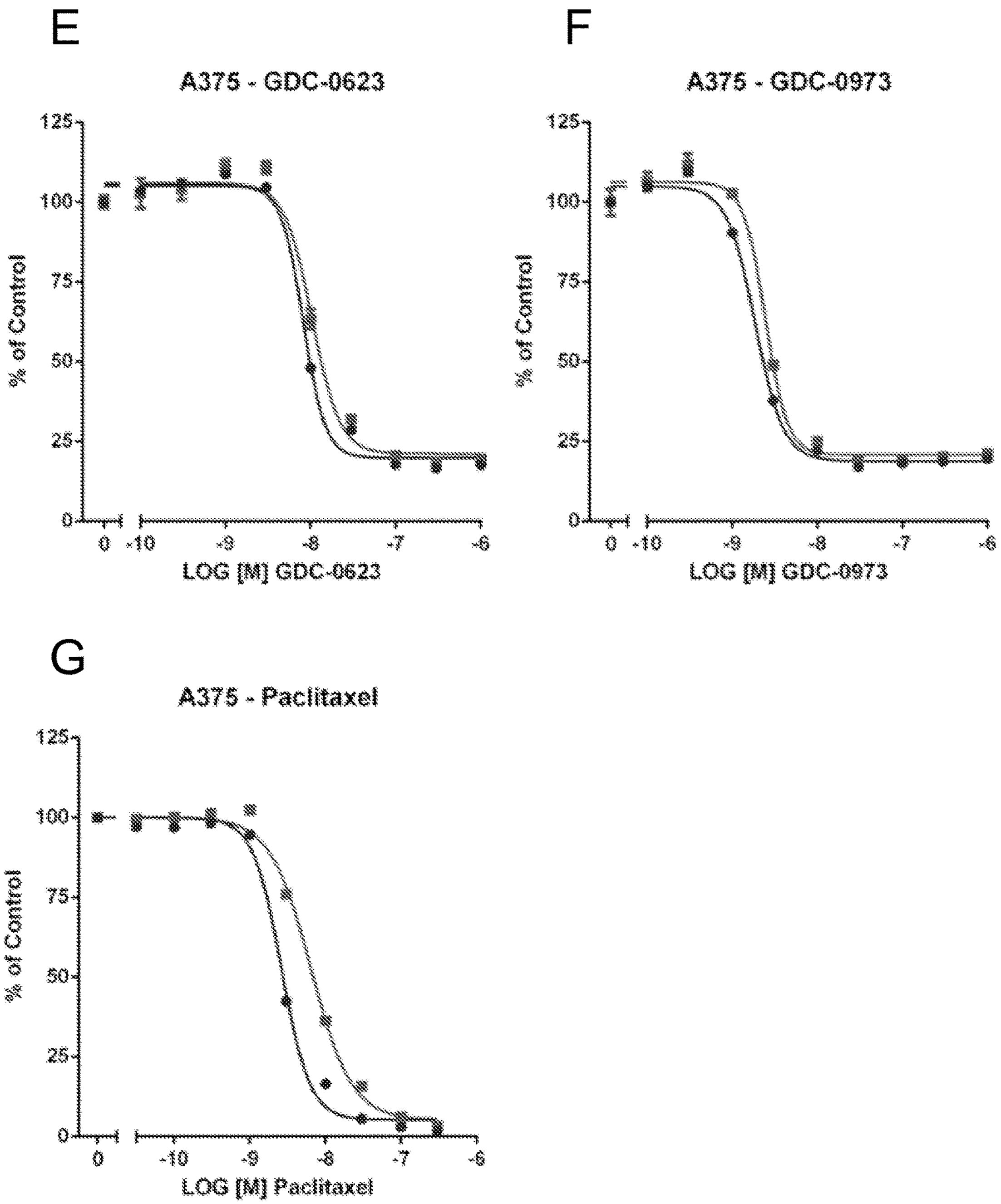

FIG. 21, Con't
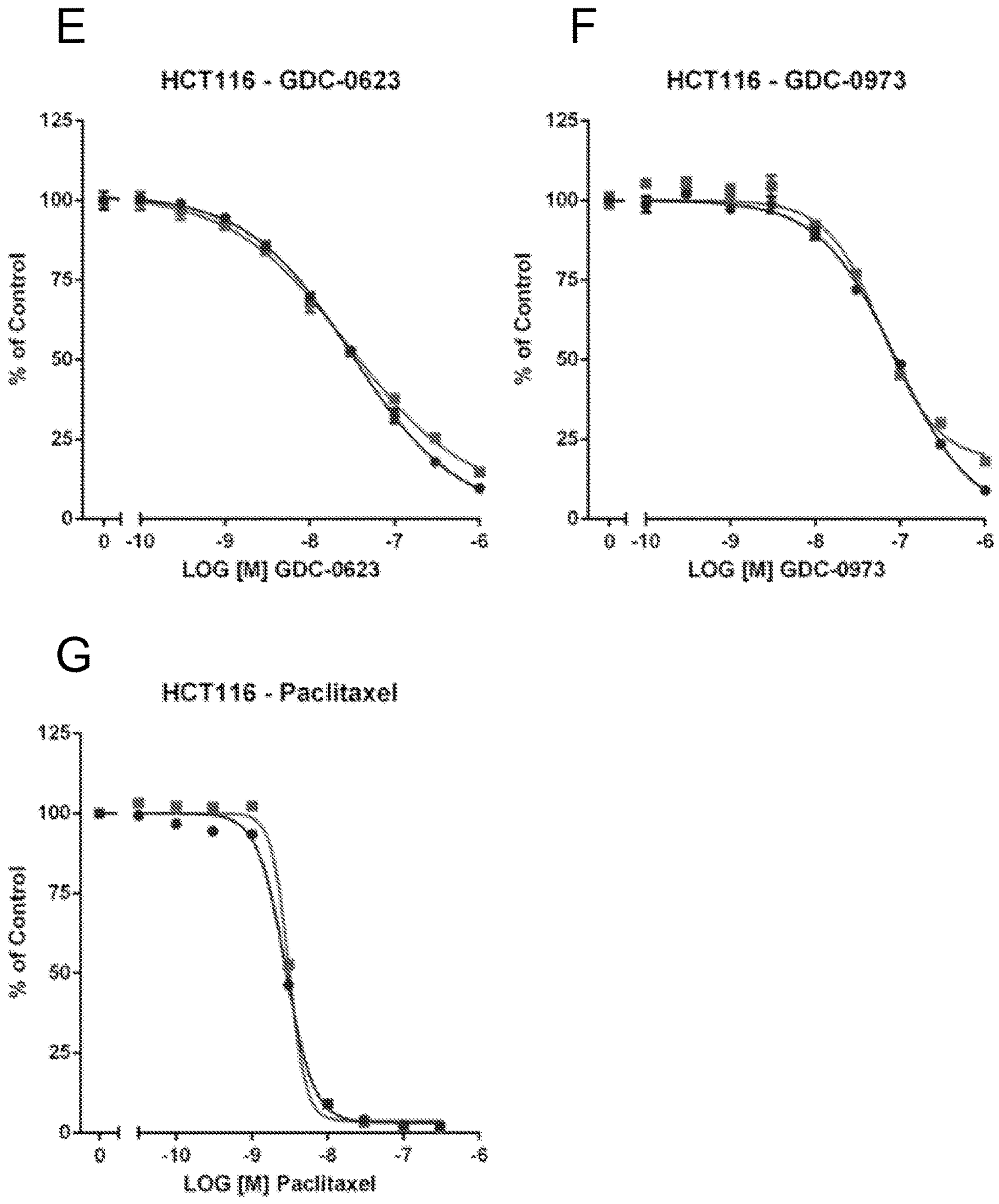

FIG. 22, Con't
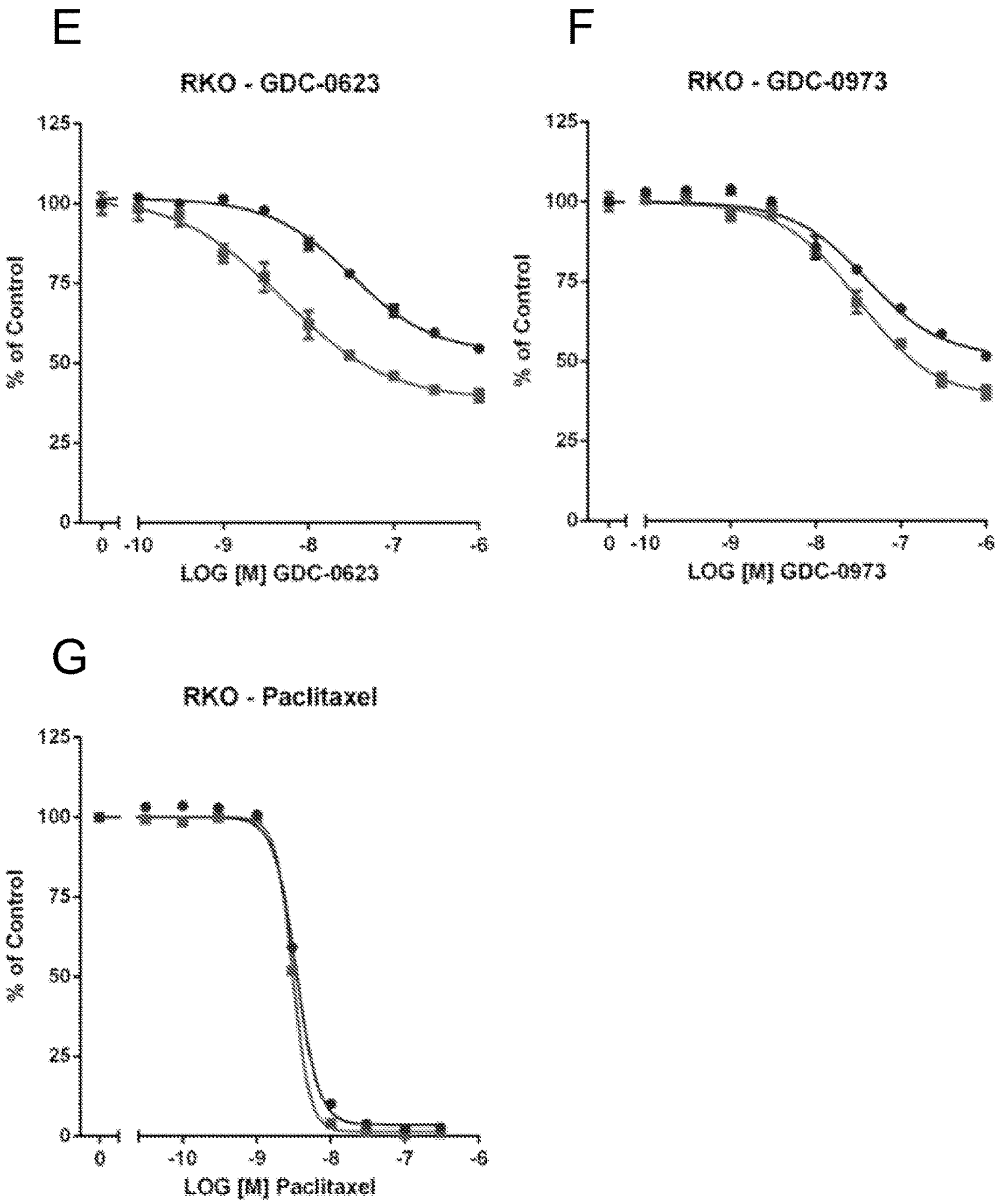

A

FIG. 23, Con't
C
B
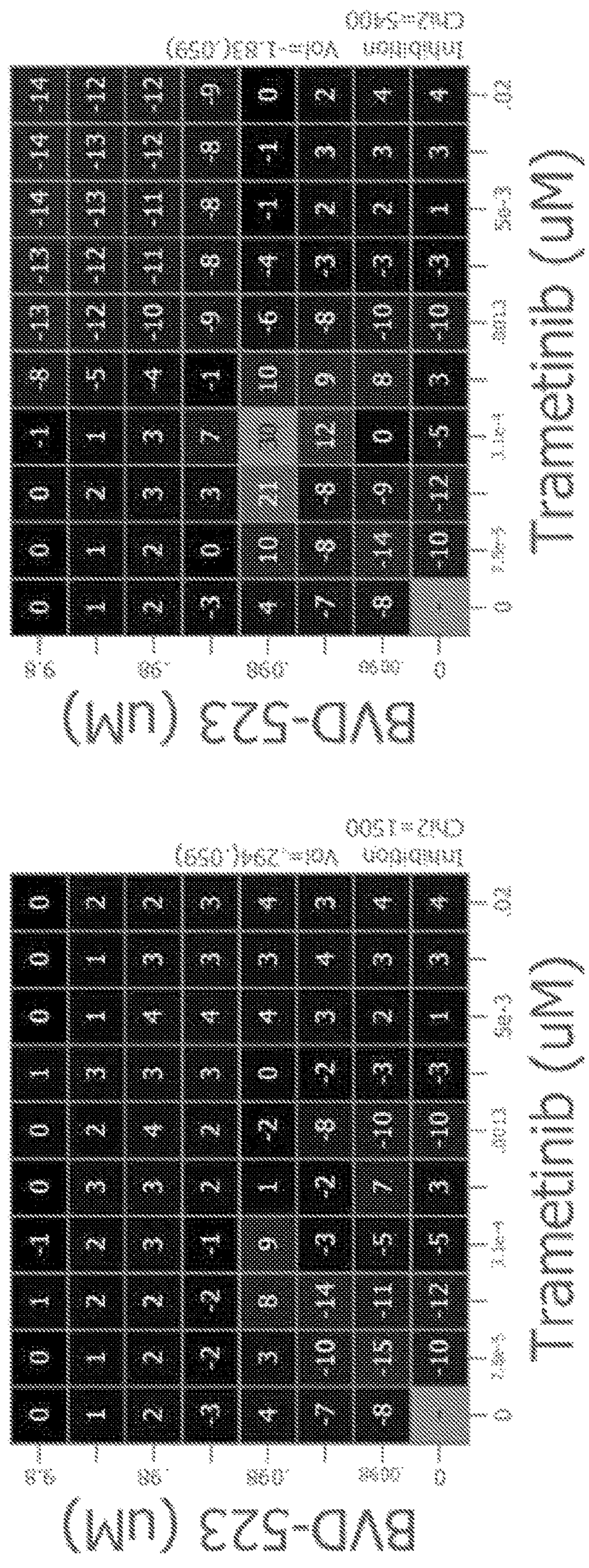

FIG. 23, Con't
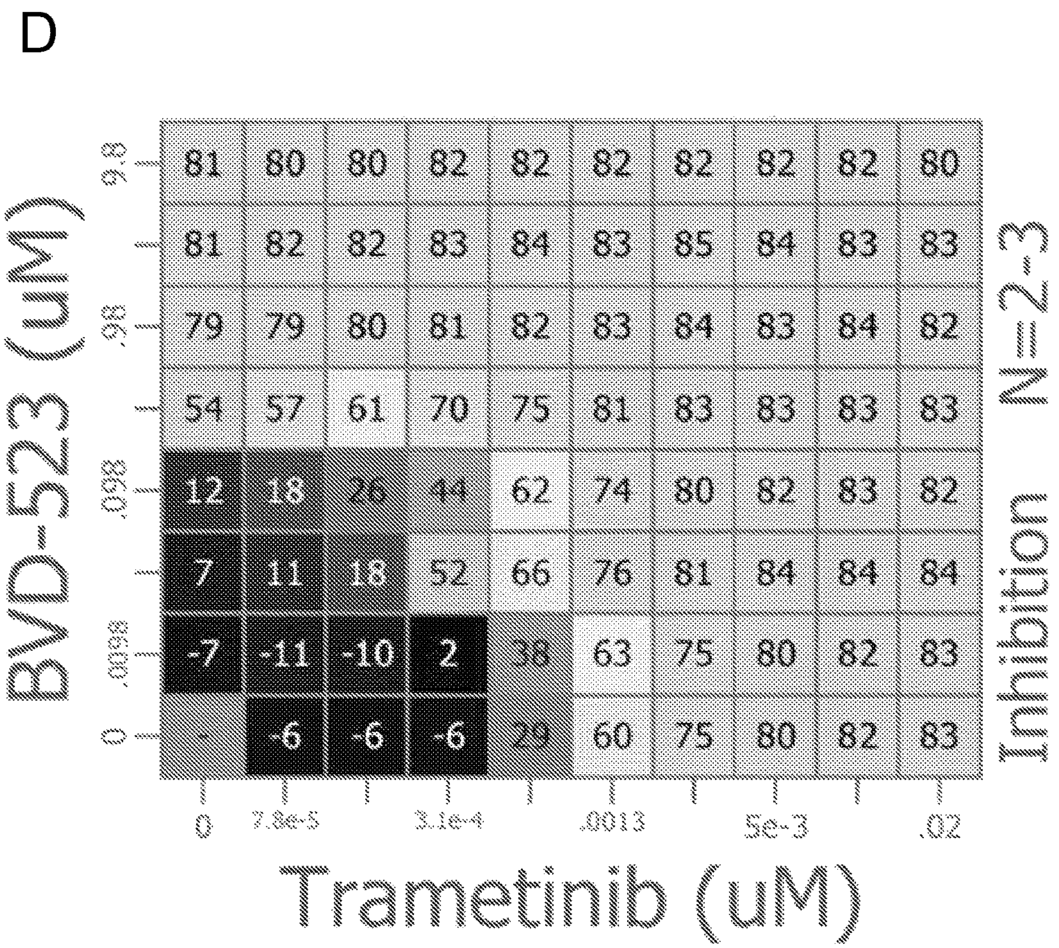

FIG. 23, Con't
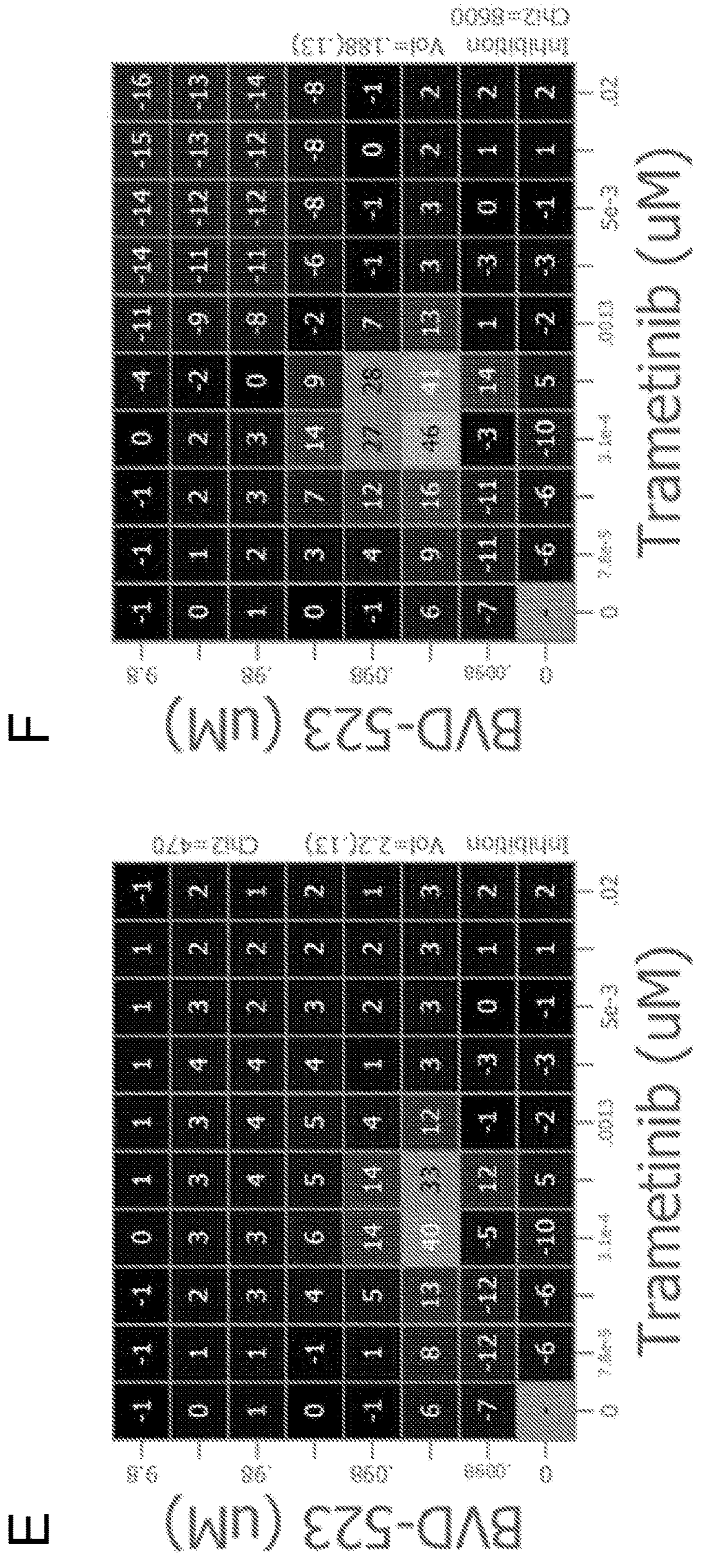

FIG. 23, Con't
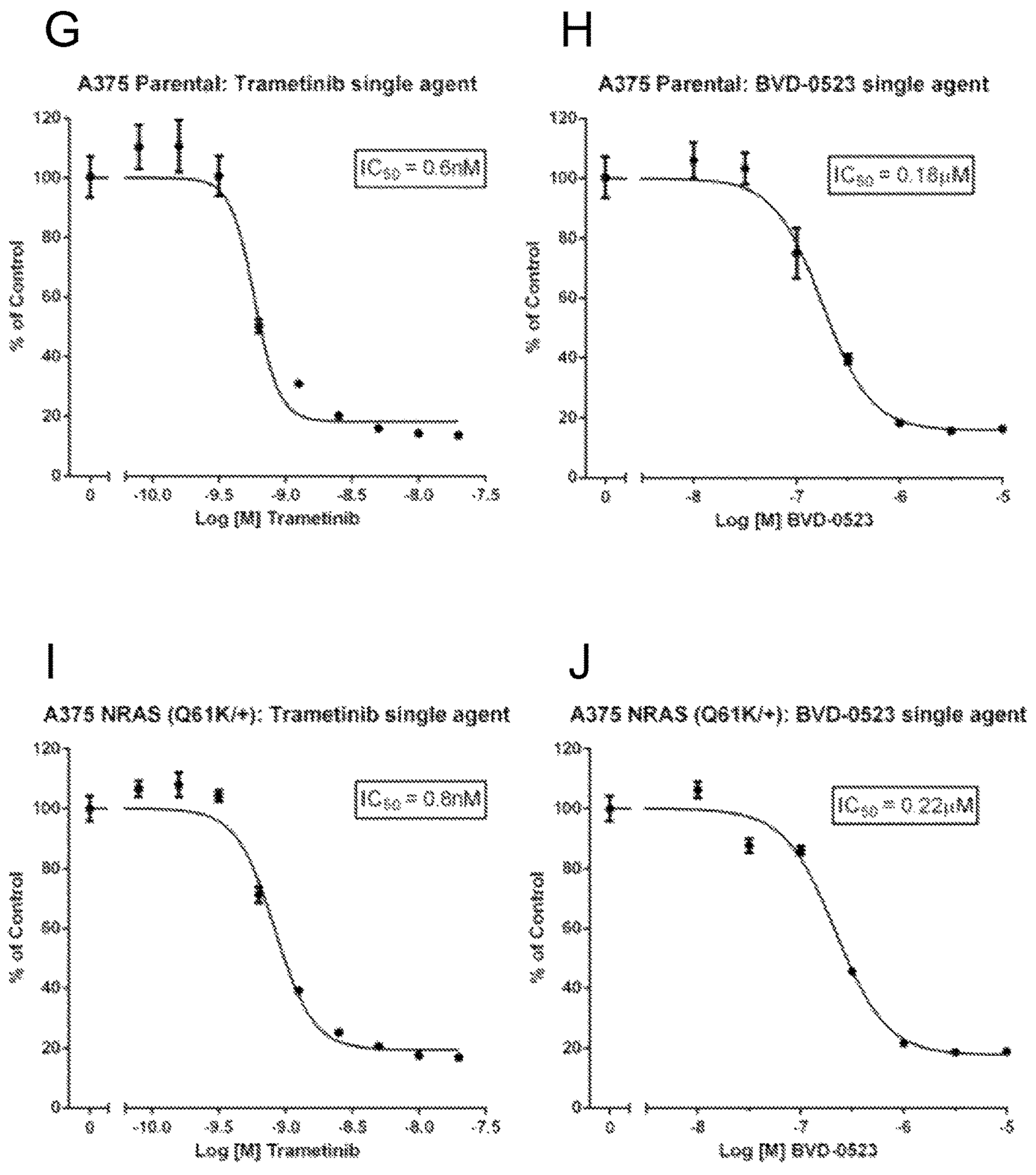

A

FIG. 24, Con't
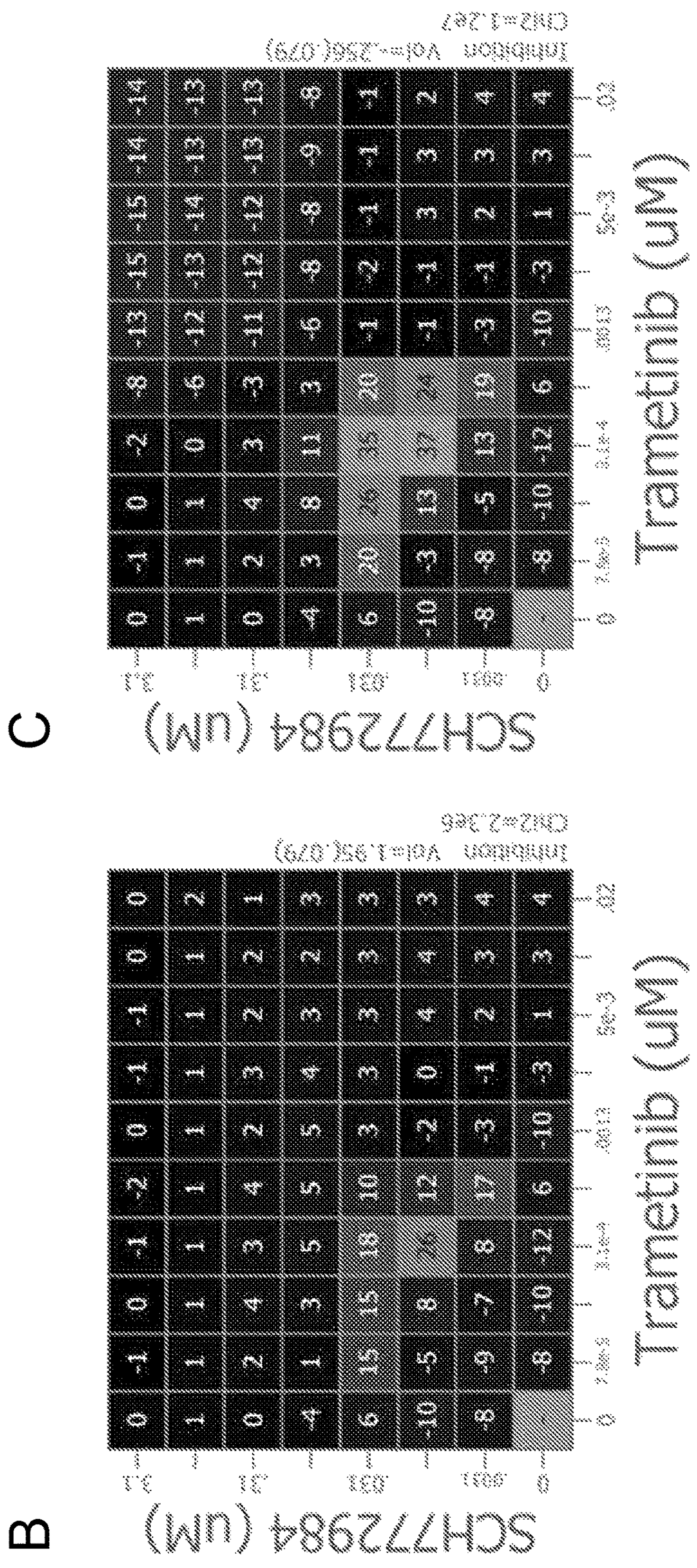

FIG. 24, Con't
D
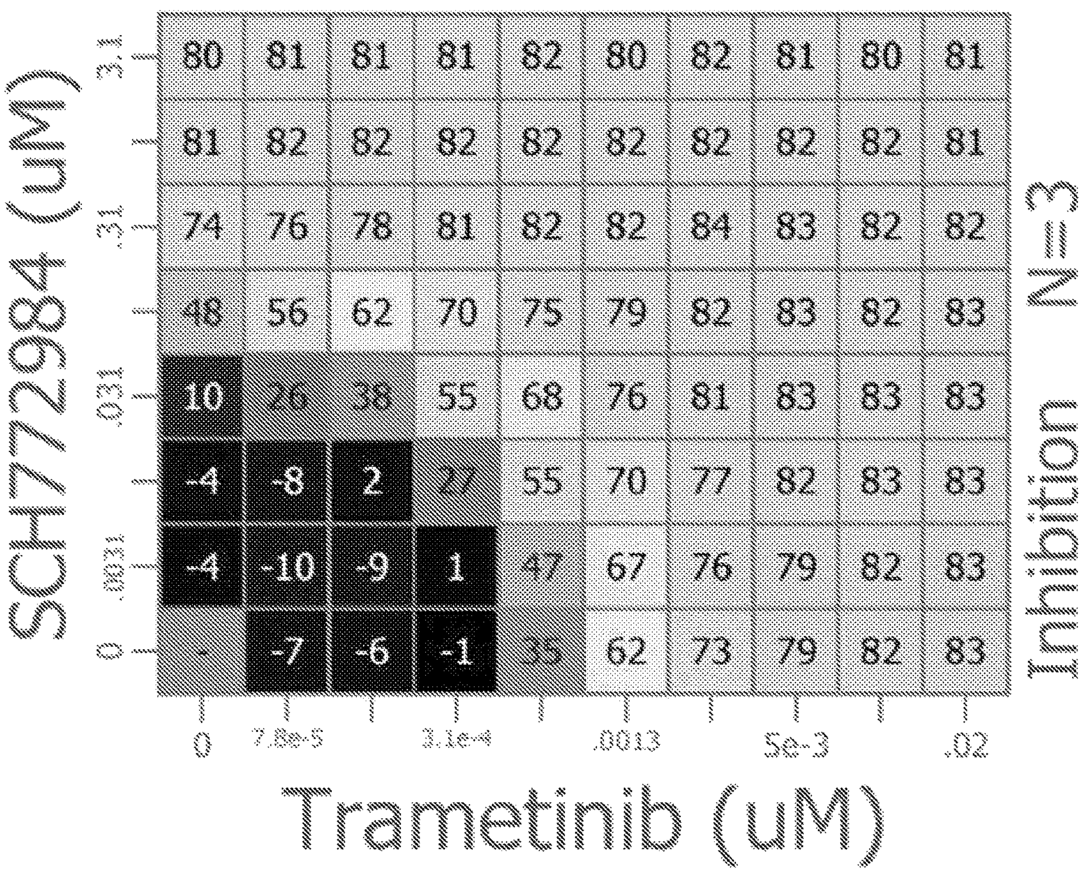

FIG. 24, Con't
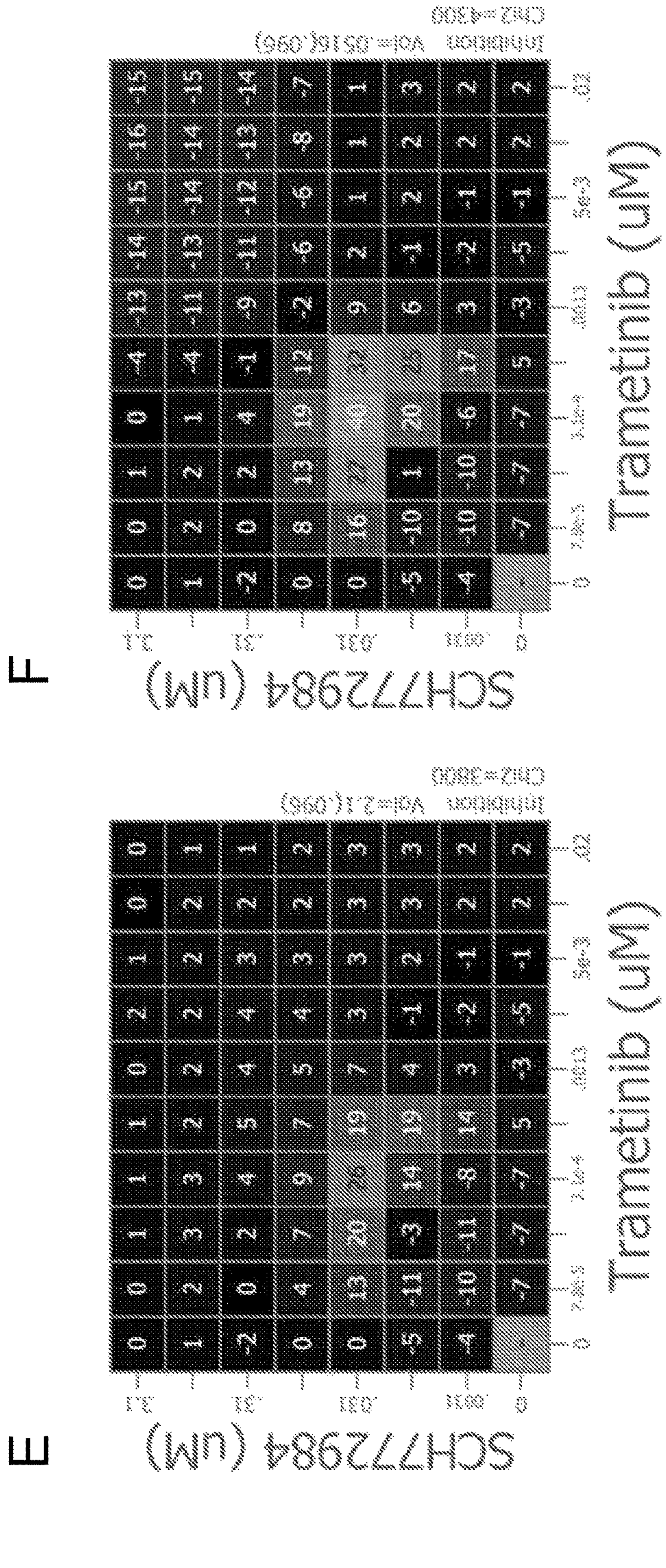

FIG. 24, Con't
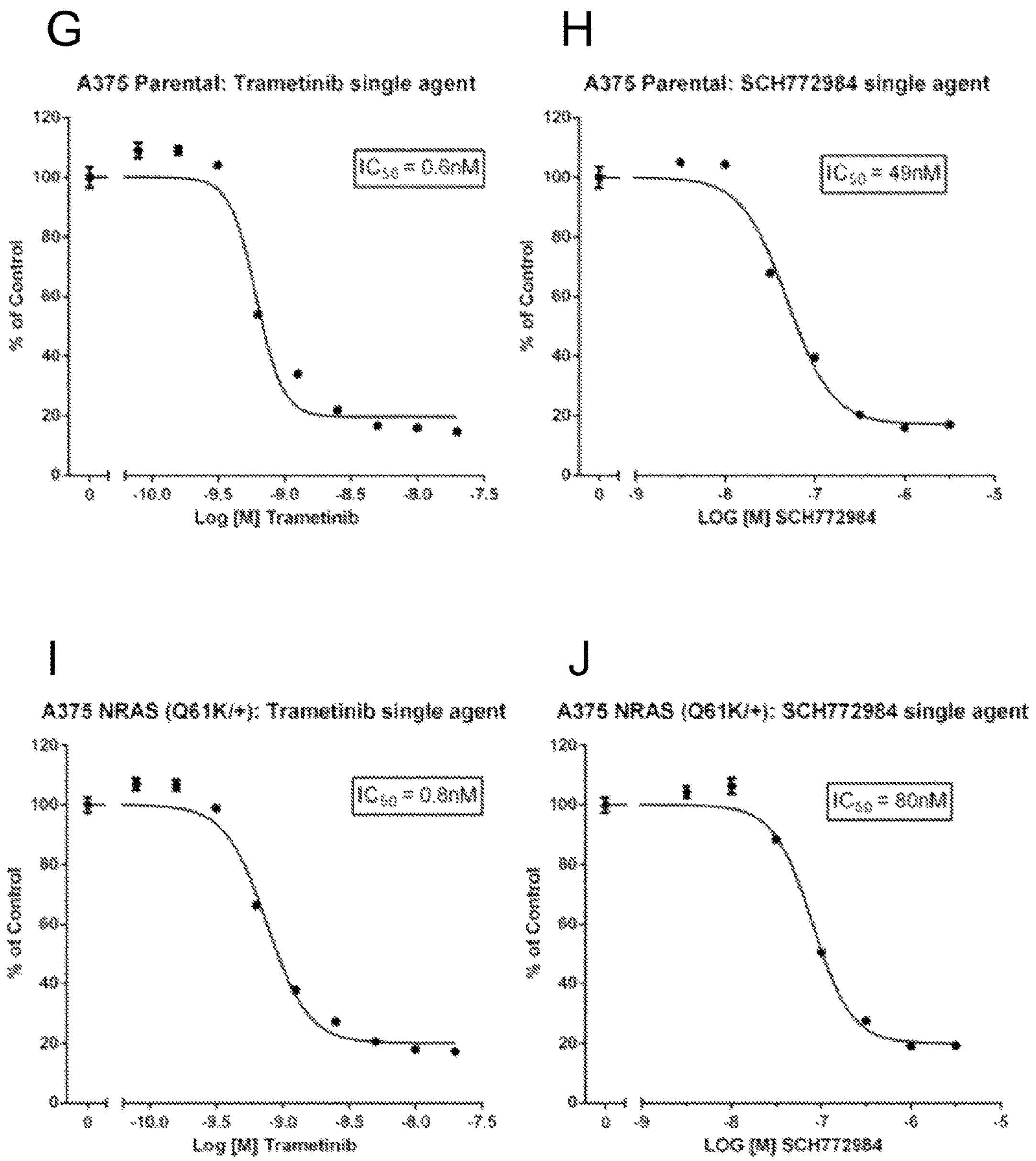

A

FIG. 25, Con't
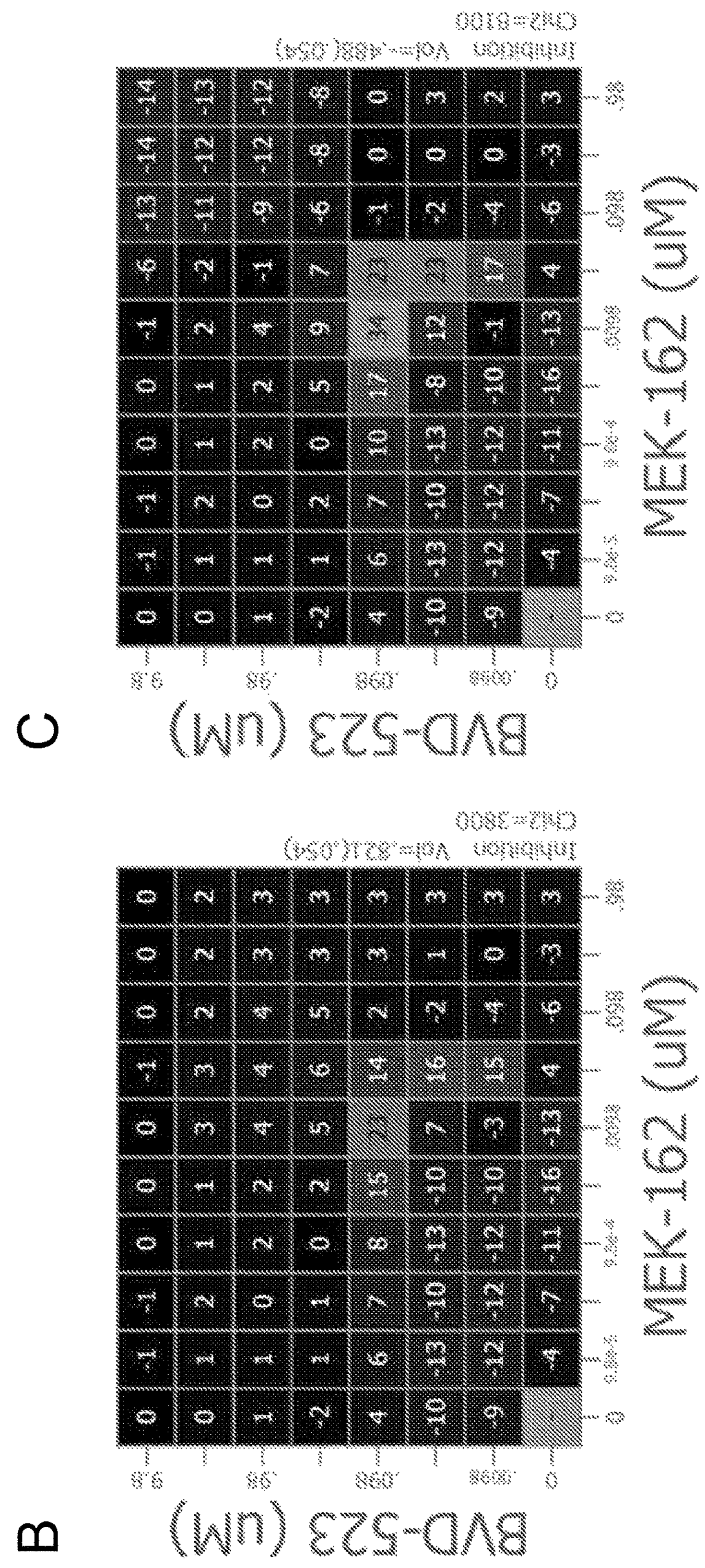

FIG. 25, Con't
D
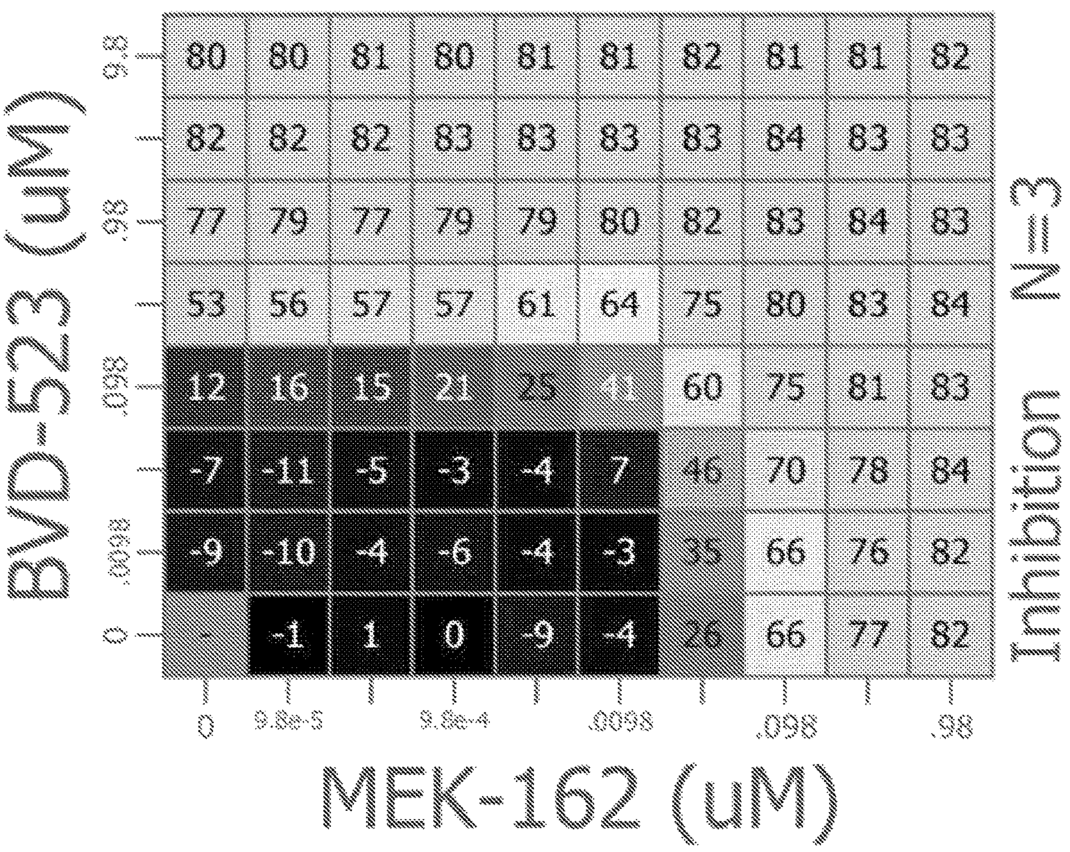

FIG. 25, Con't
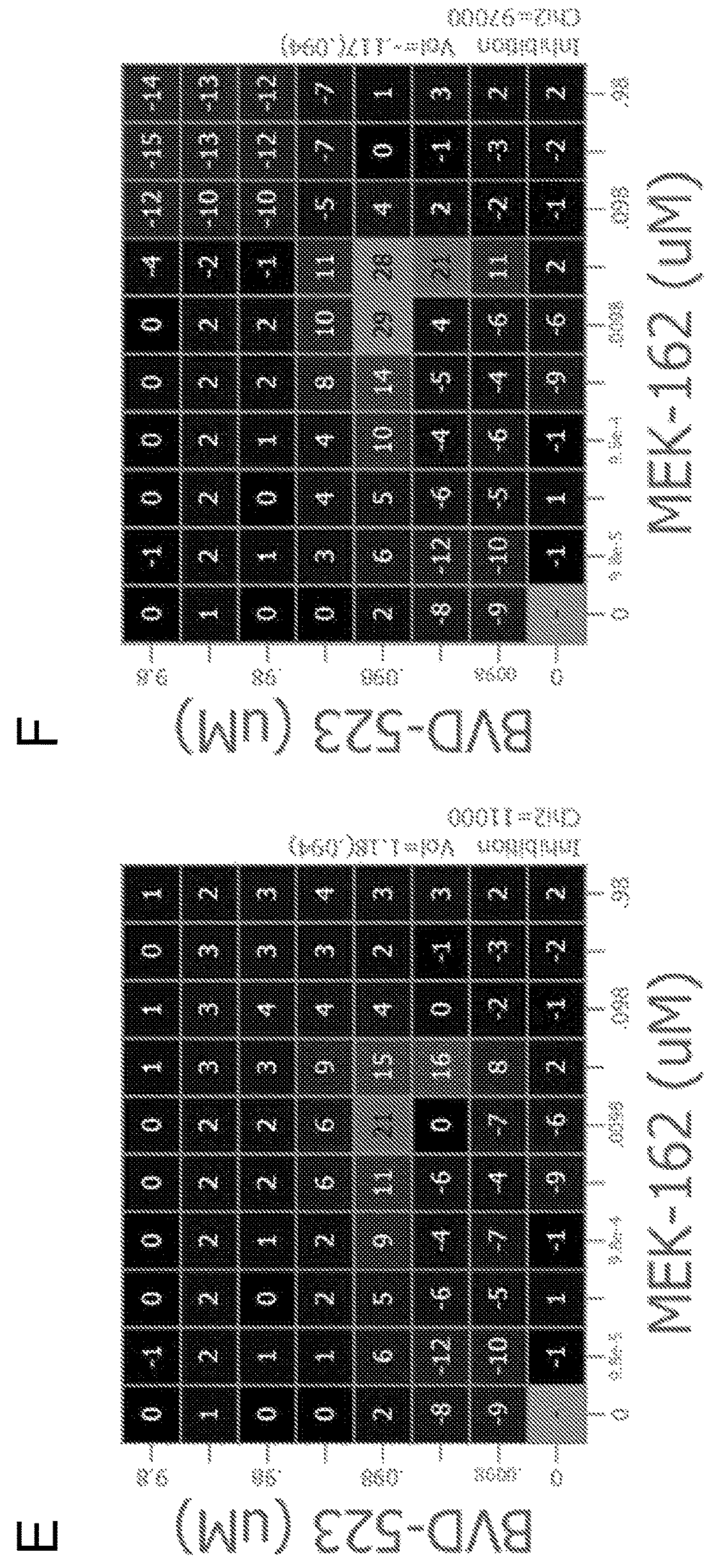

FIG. 25, Con't
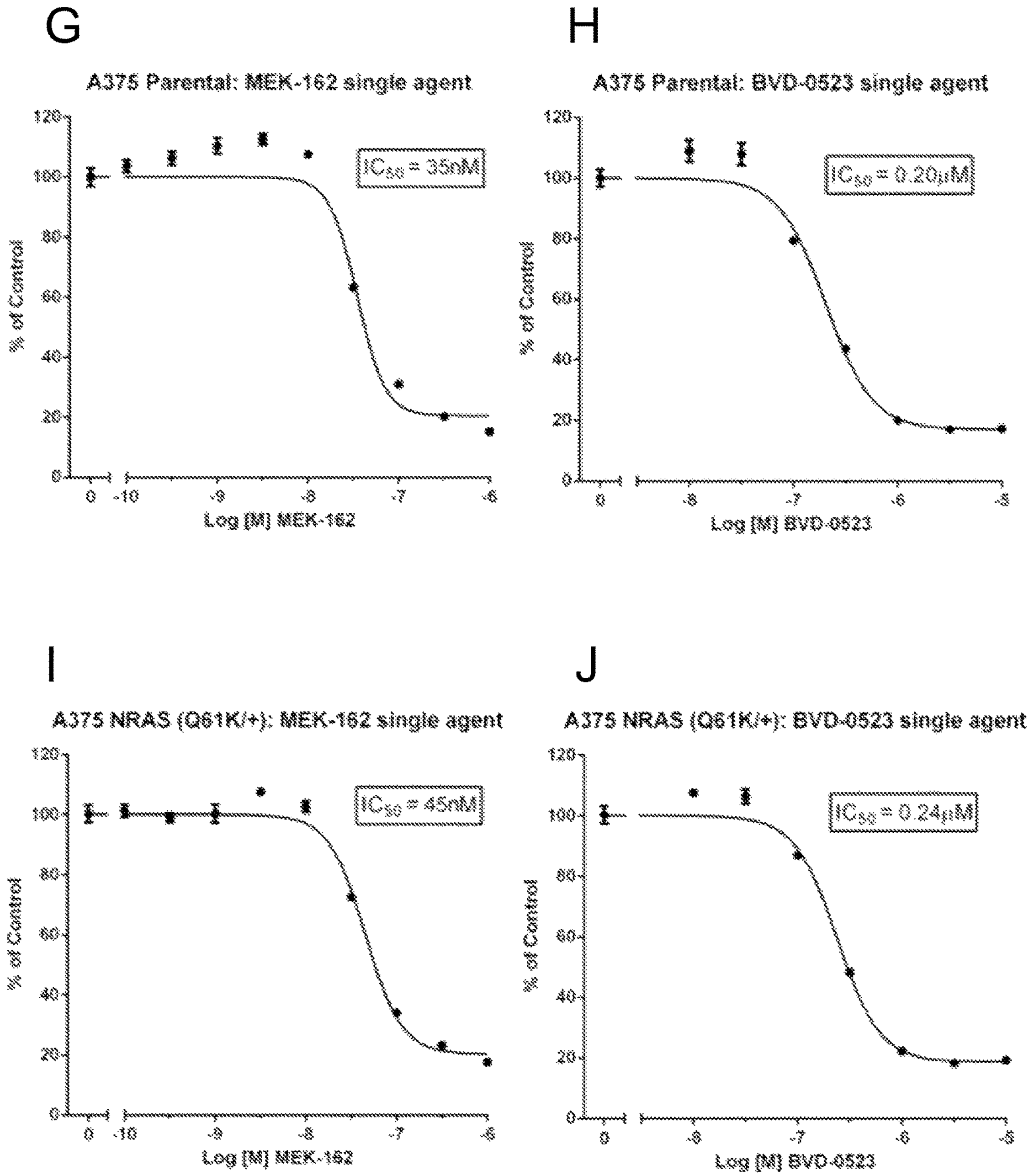

FIG. 26, Con't
C
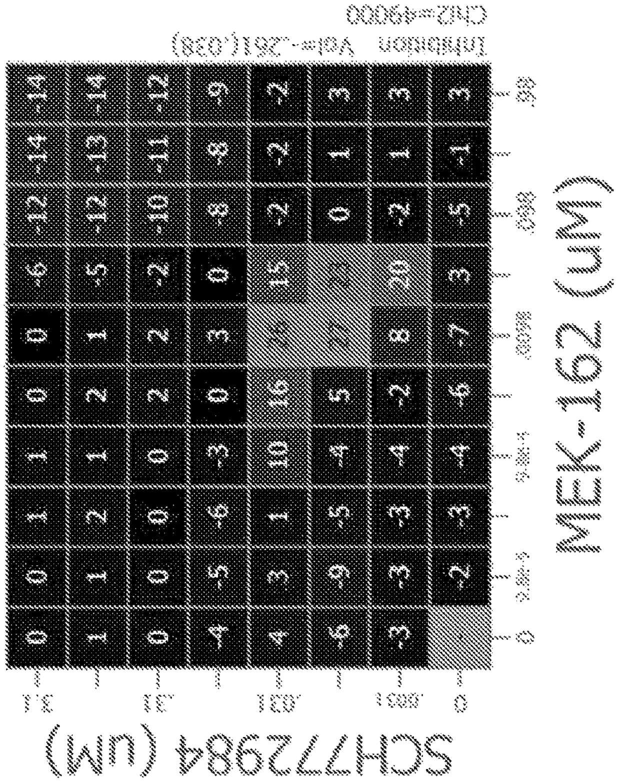
B
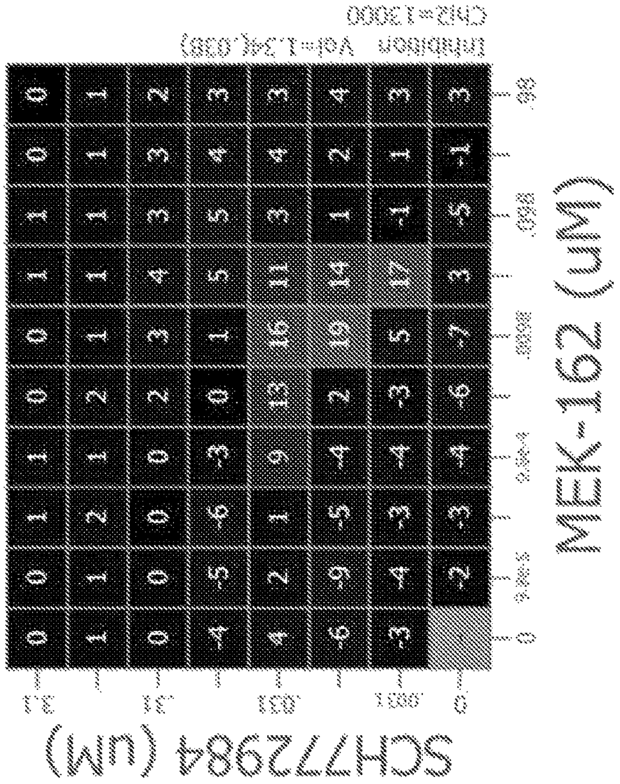

FIG. 26, Con't
D
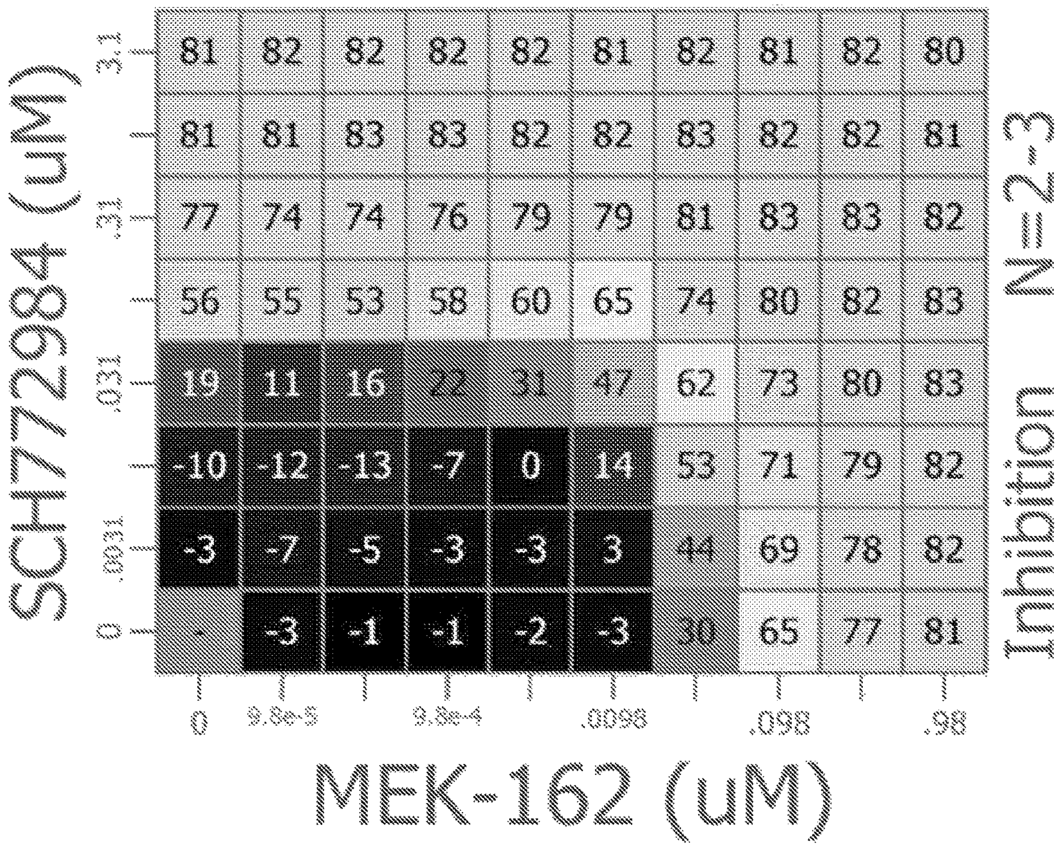

FIG. 26, Con't
F
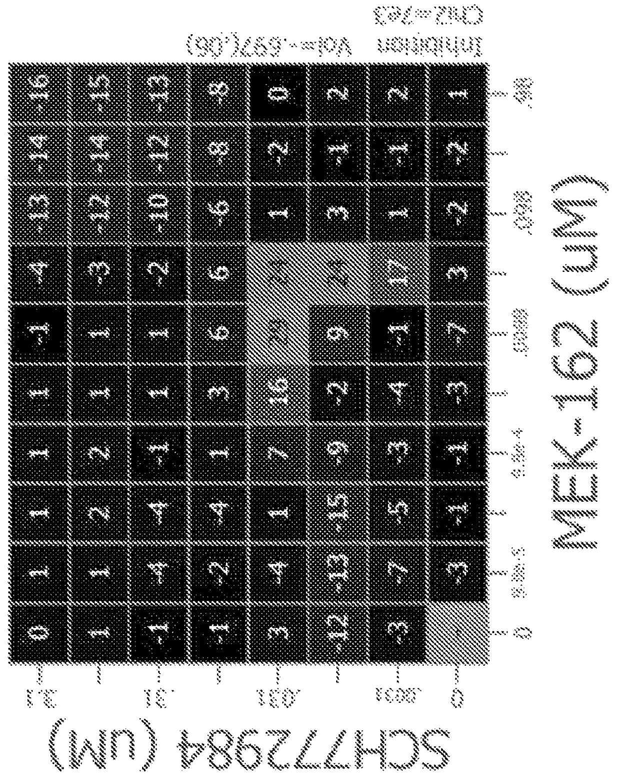
E
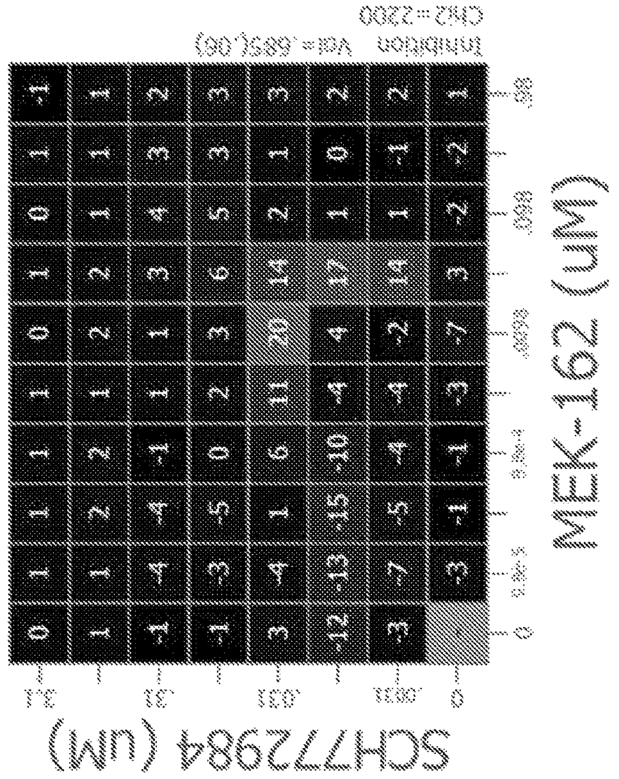

FIG. 26, Con't
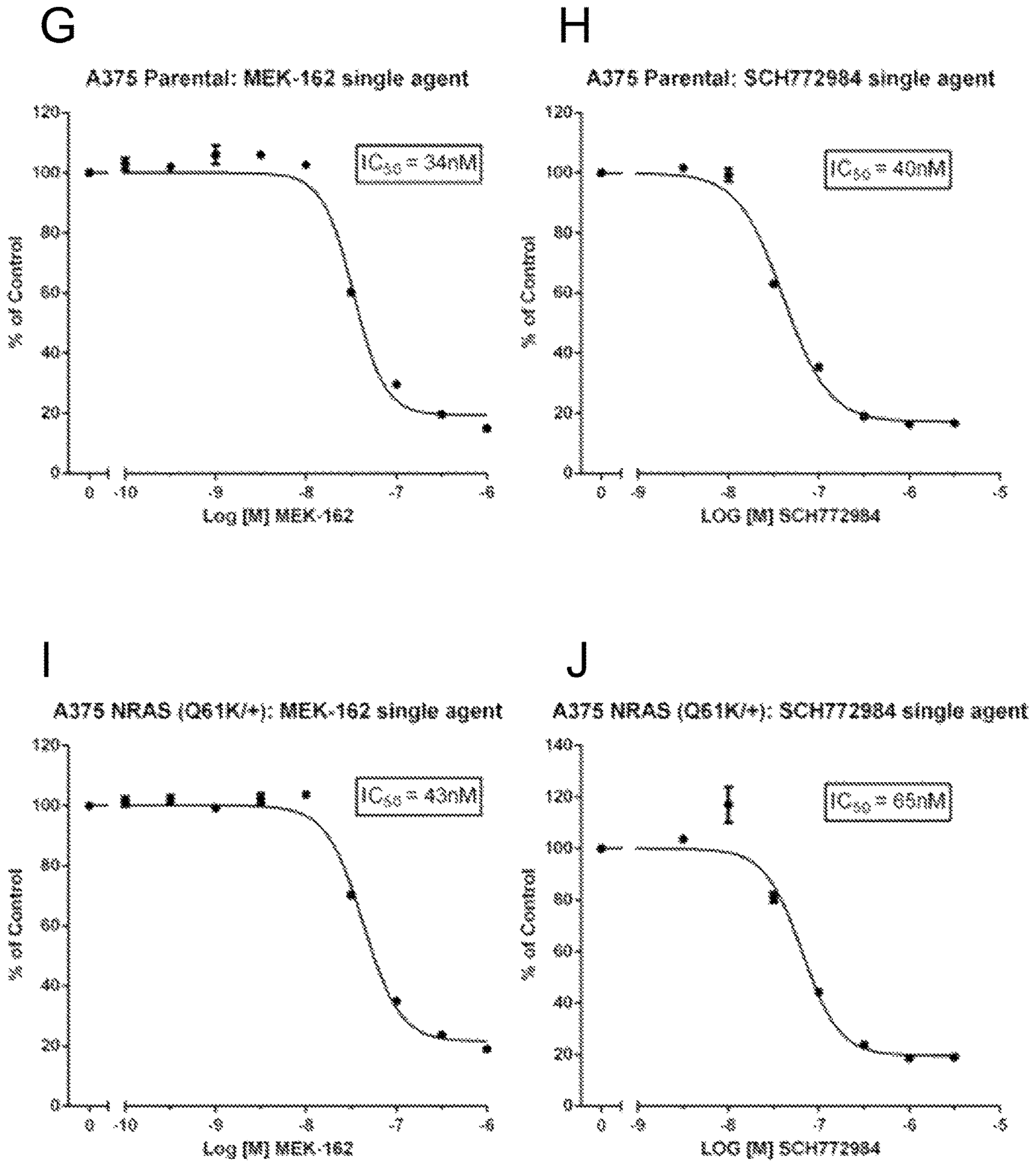

FIG. 27, Con't
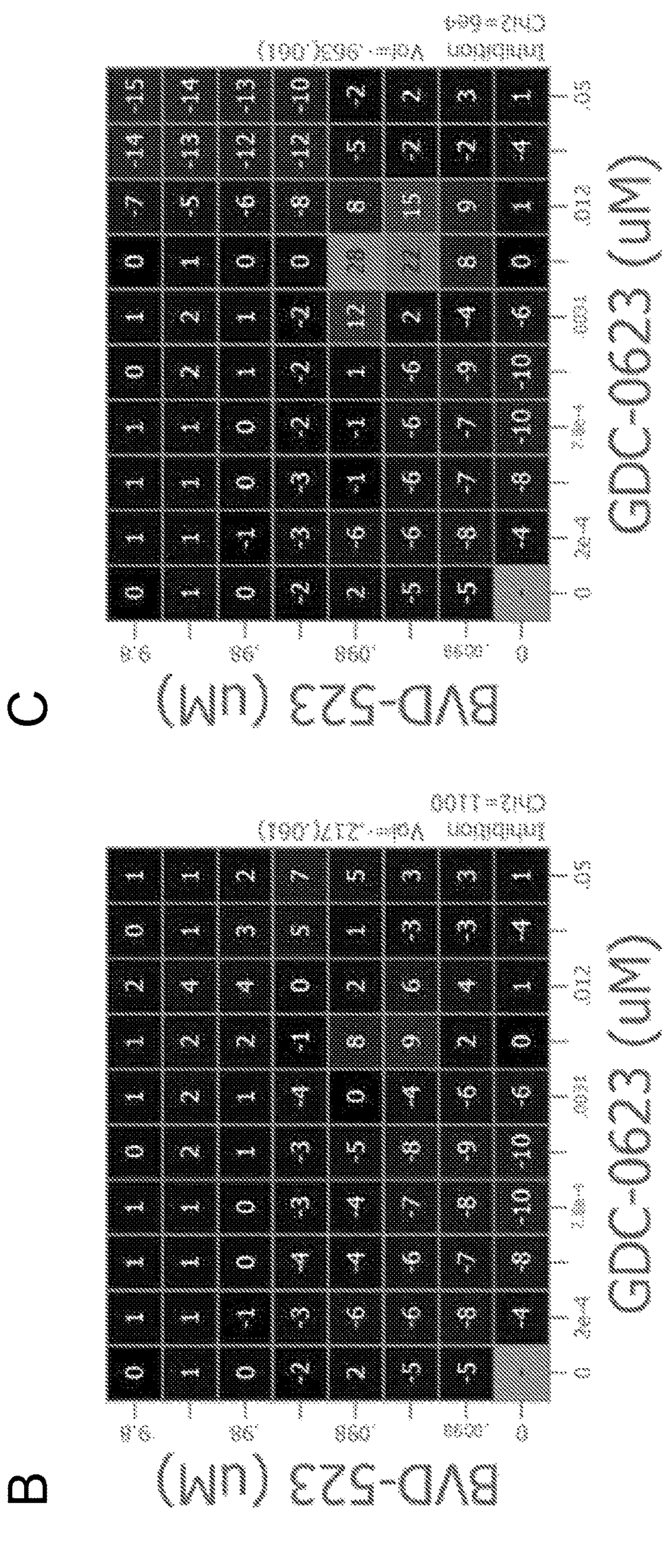

FIG. 27, Con't
D
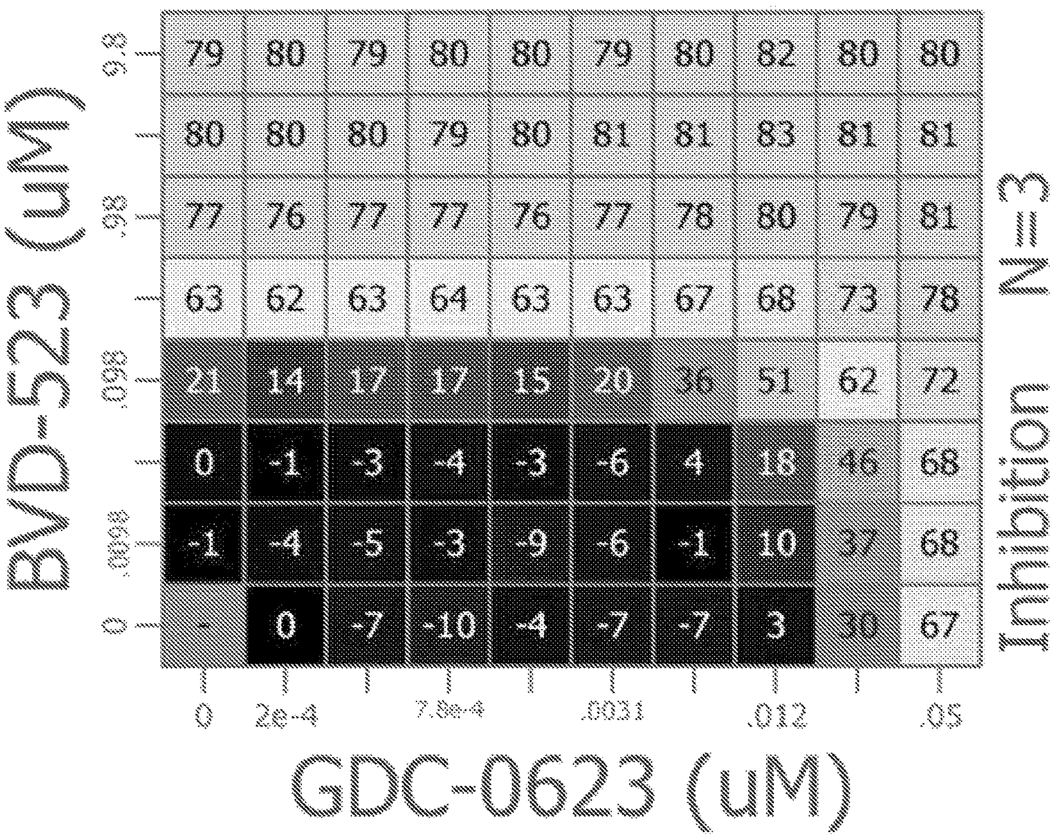

FIG. 27, Con't
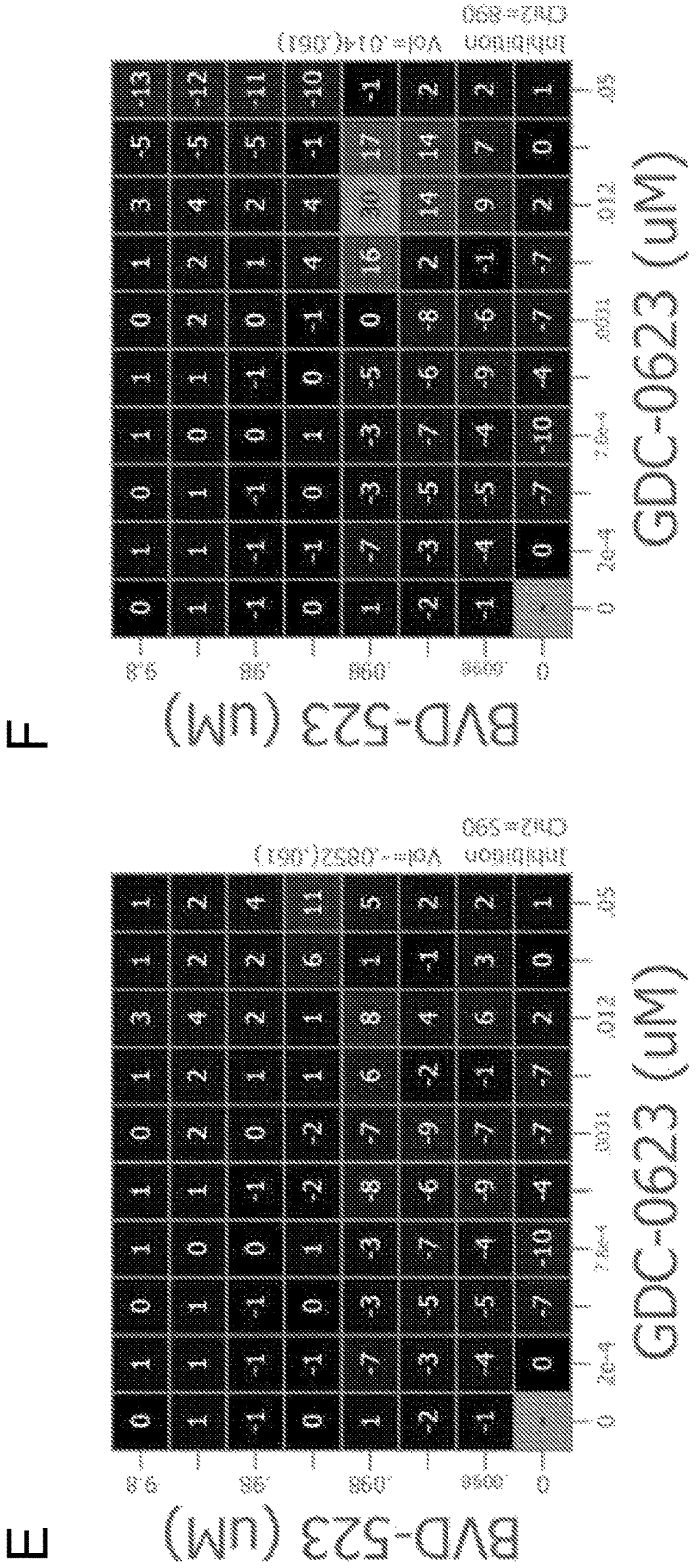

FIG. 27, Con't
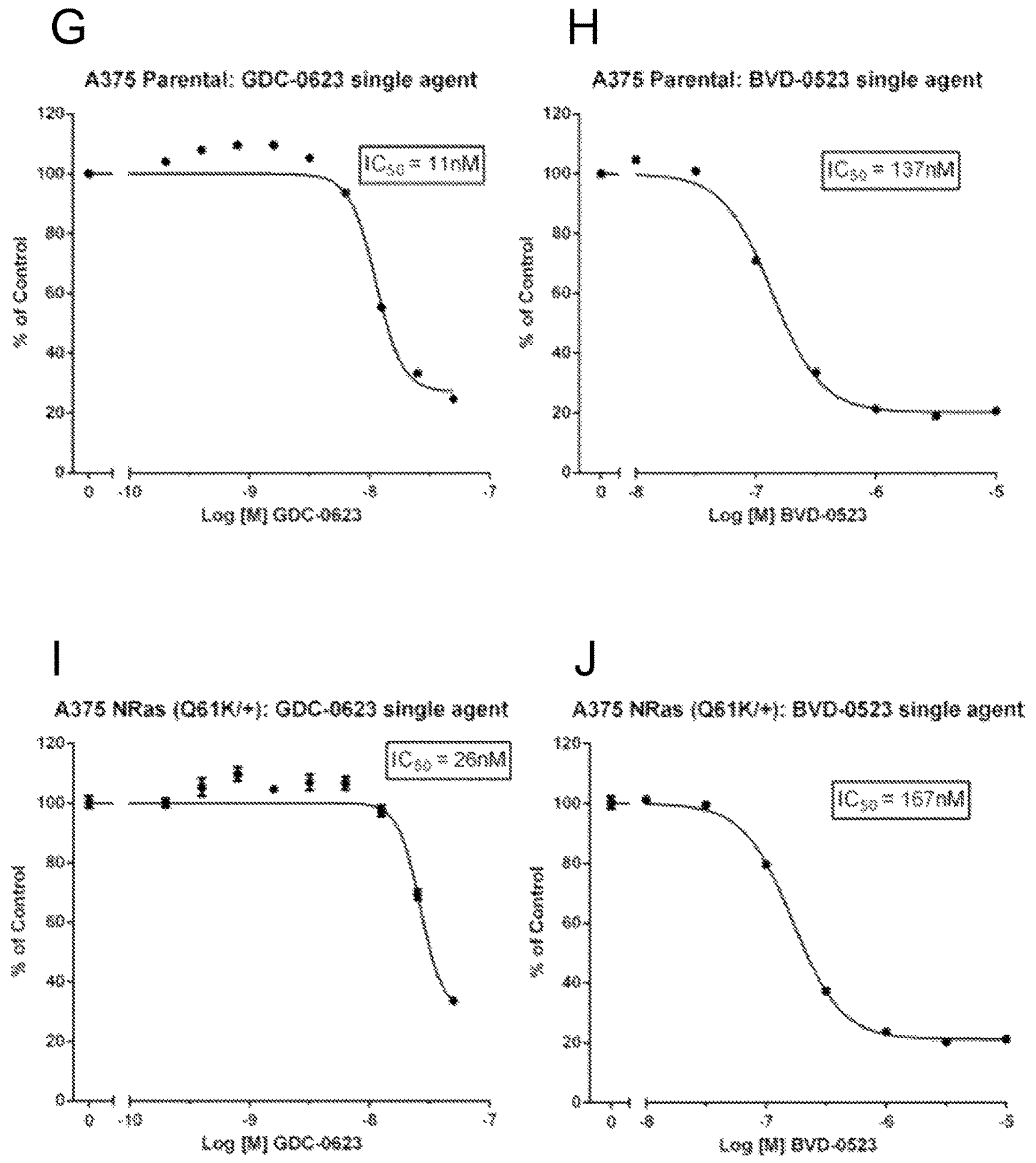

A

FIG. 28, Con't
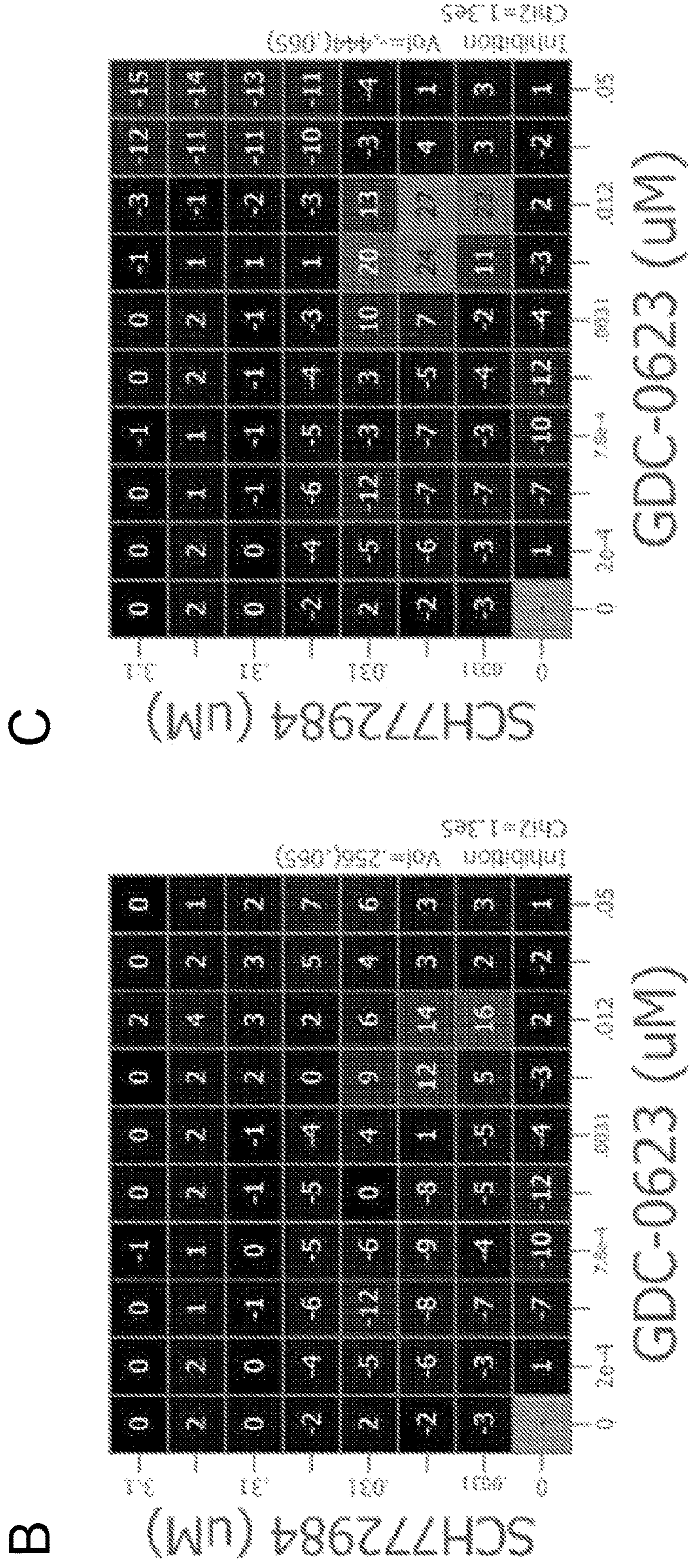

FIG. 28, Con't
D
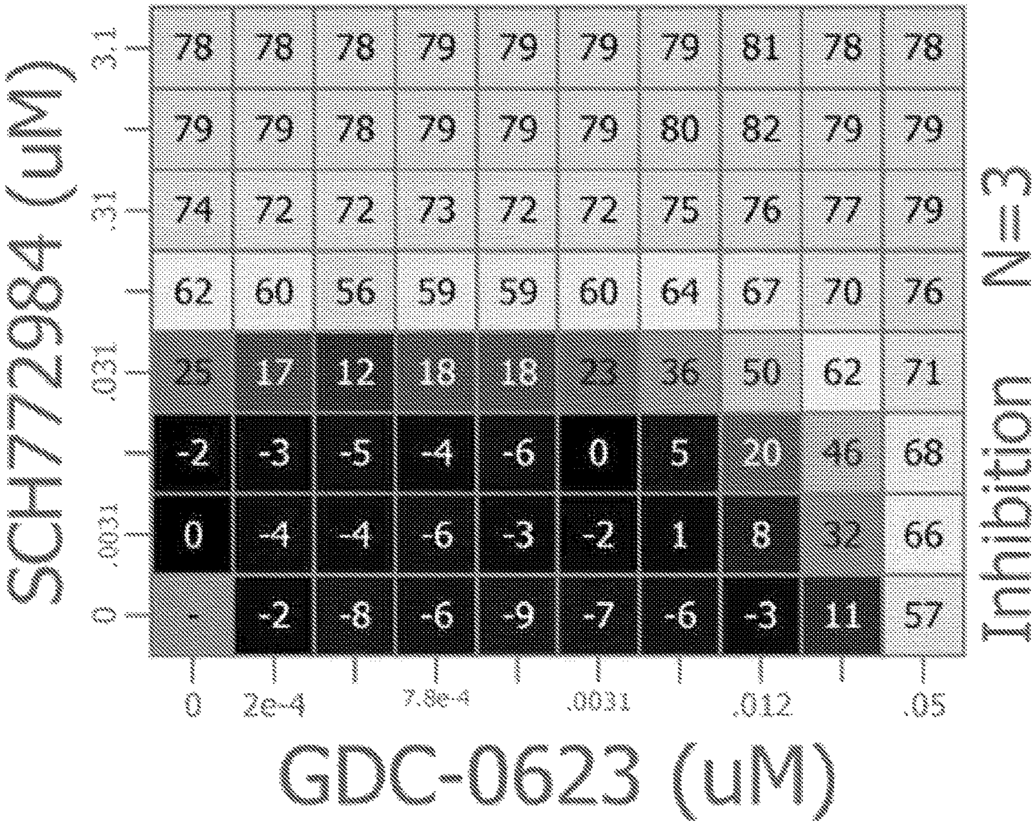

FIG. 28, Con't
E F
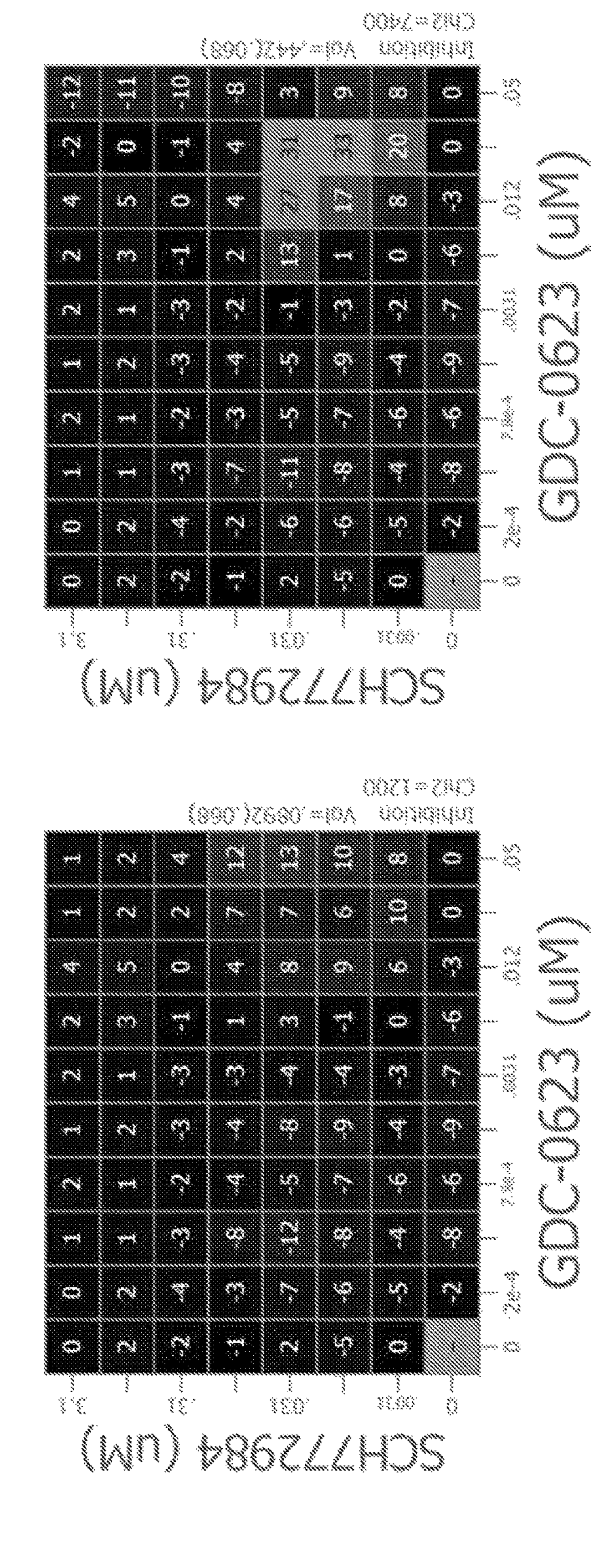

FIG. 28, Con't
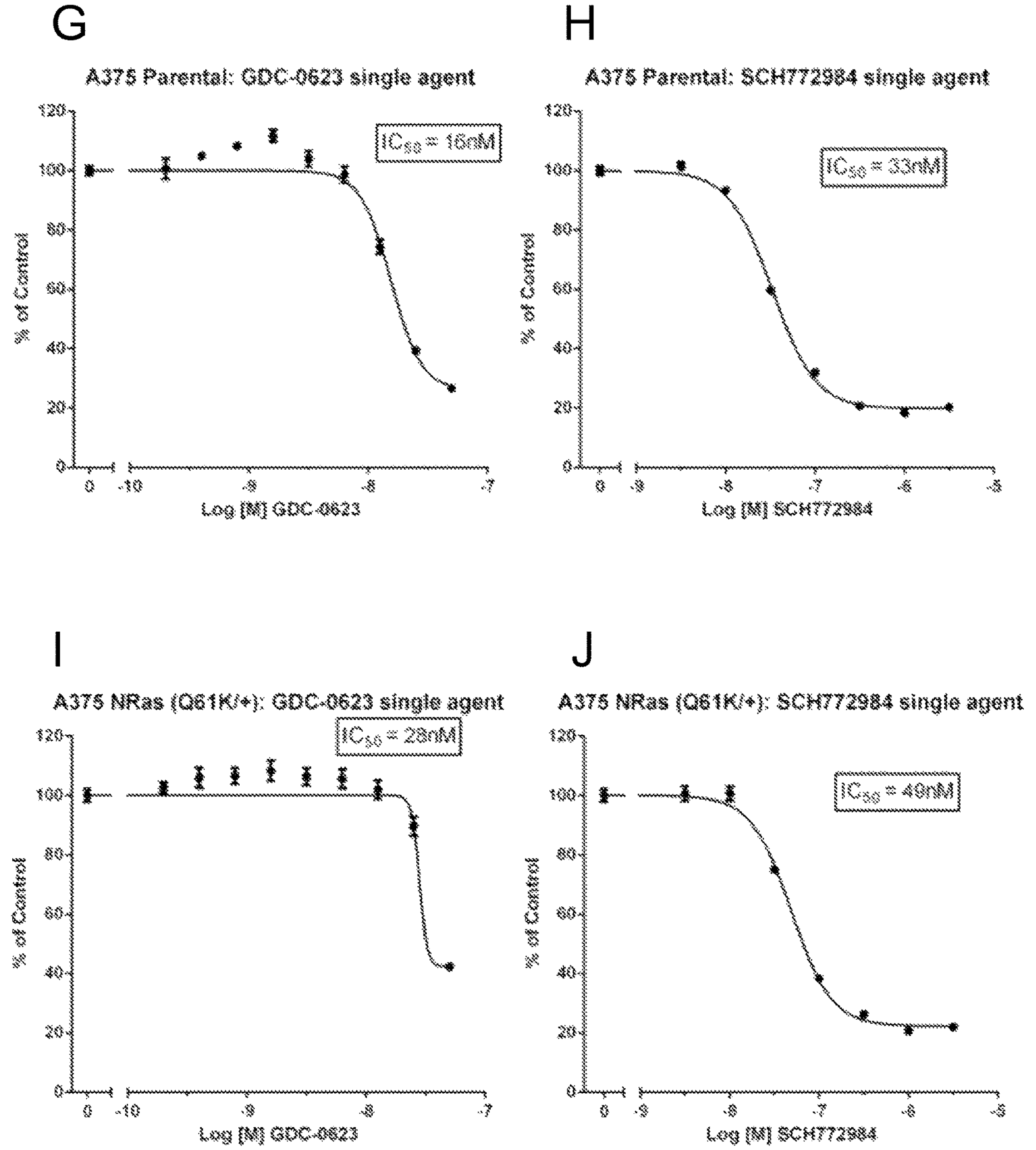

A

FIG. 29, Con't
C
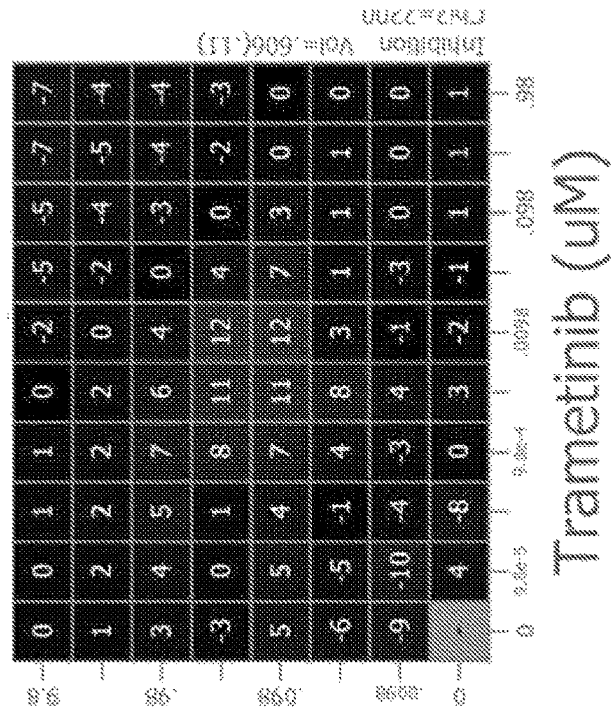
B
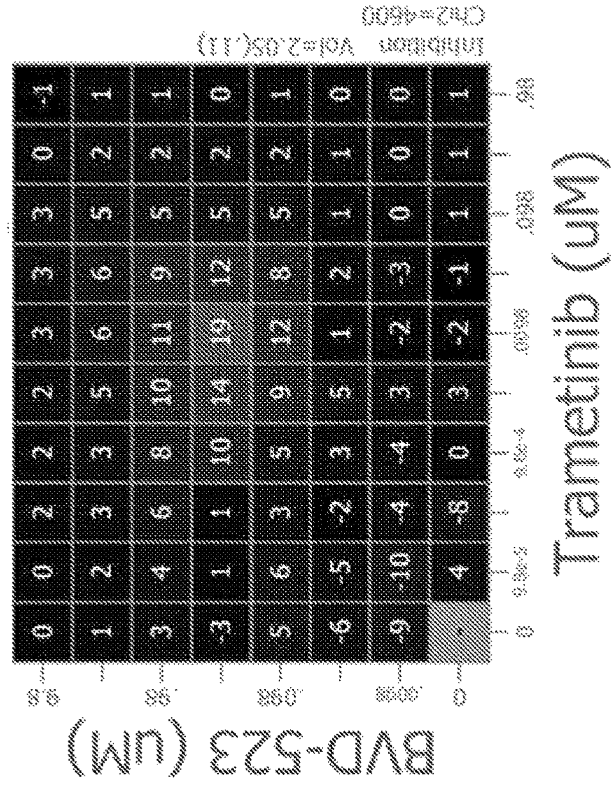

FIG. 29, Con't
D
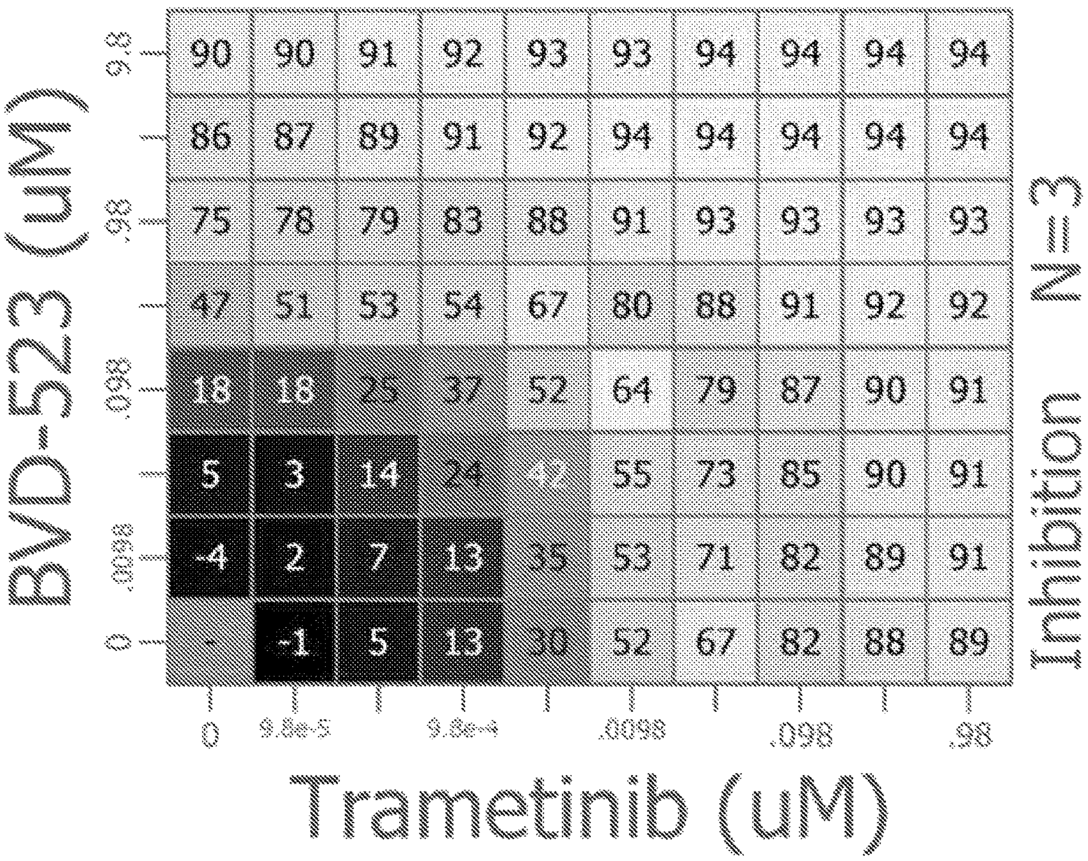

FIG. 29, Con't
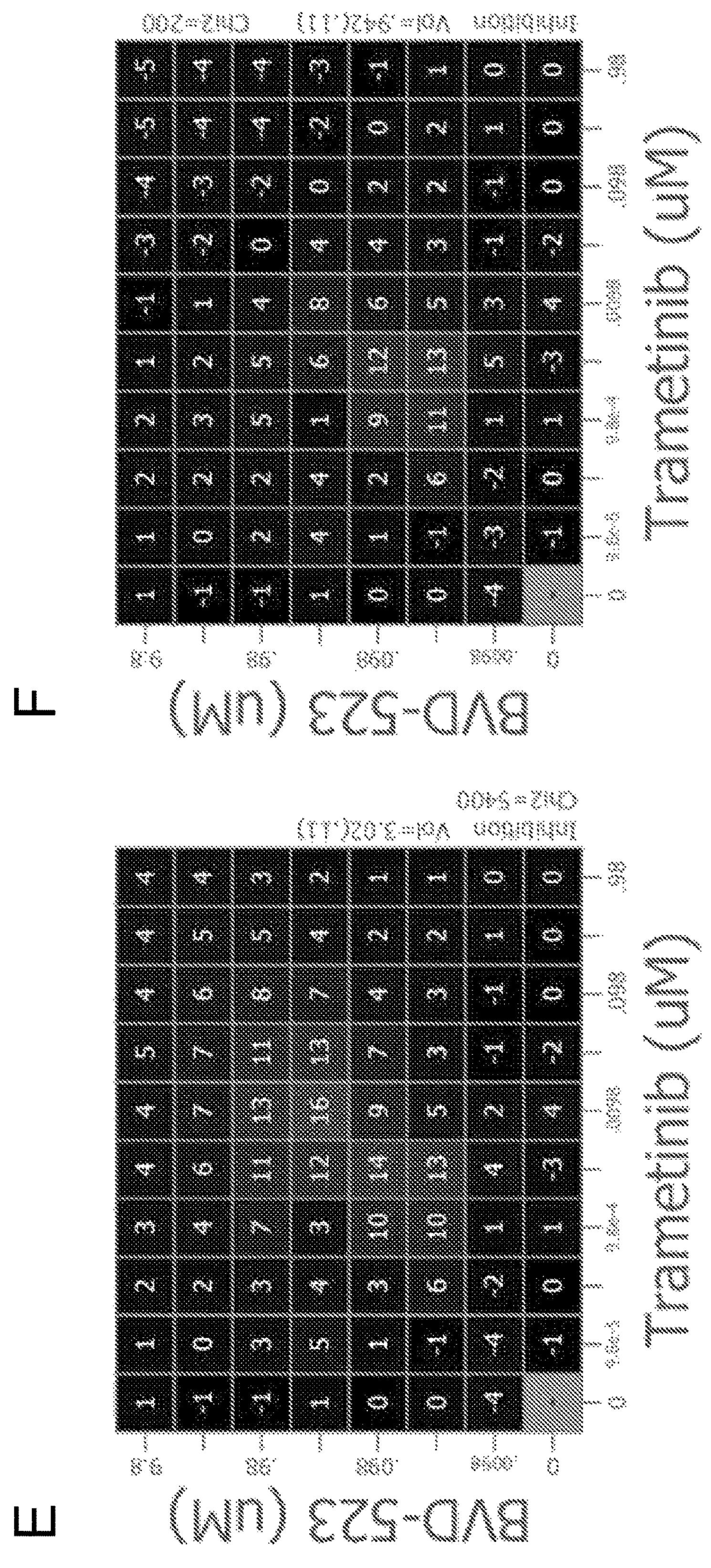

FIG. 29, Con't
G
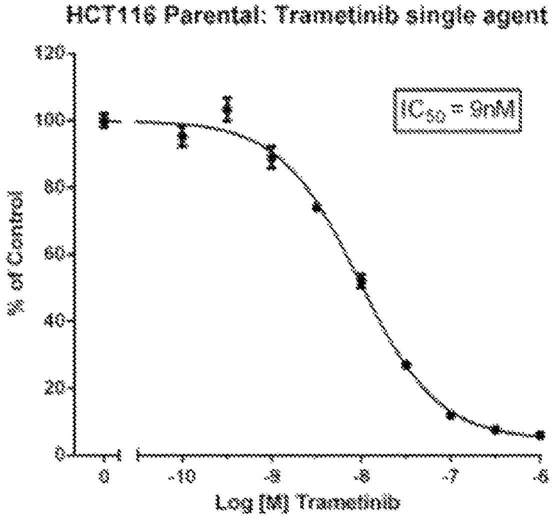
H
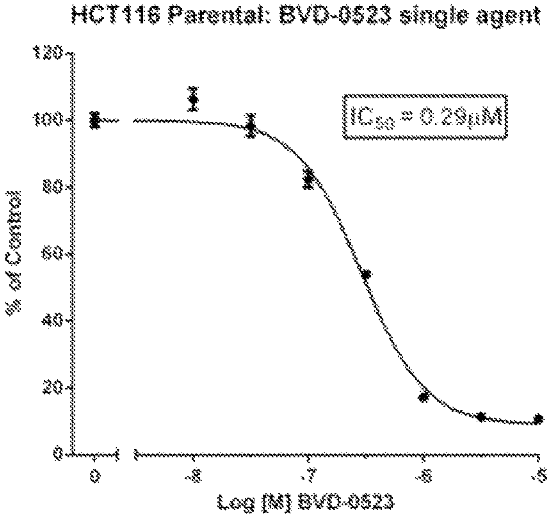
I
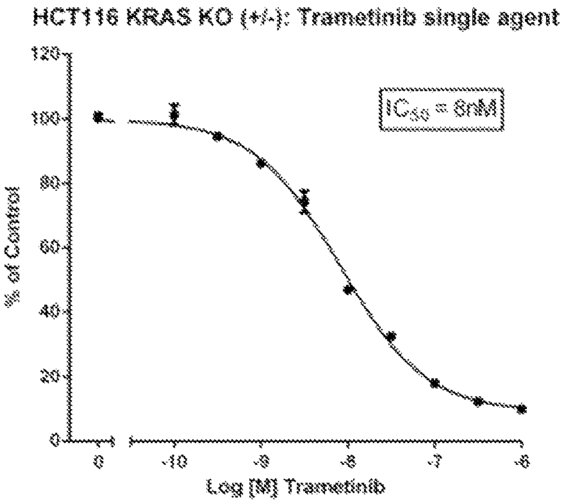
J
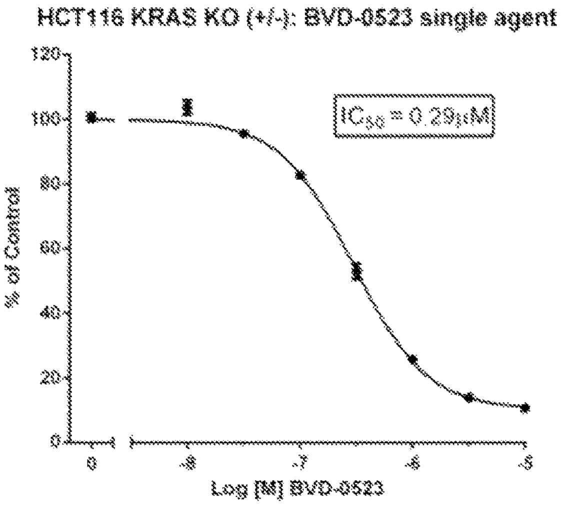

A

FIG. 30, Con't
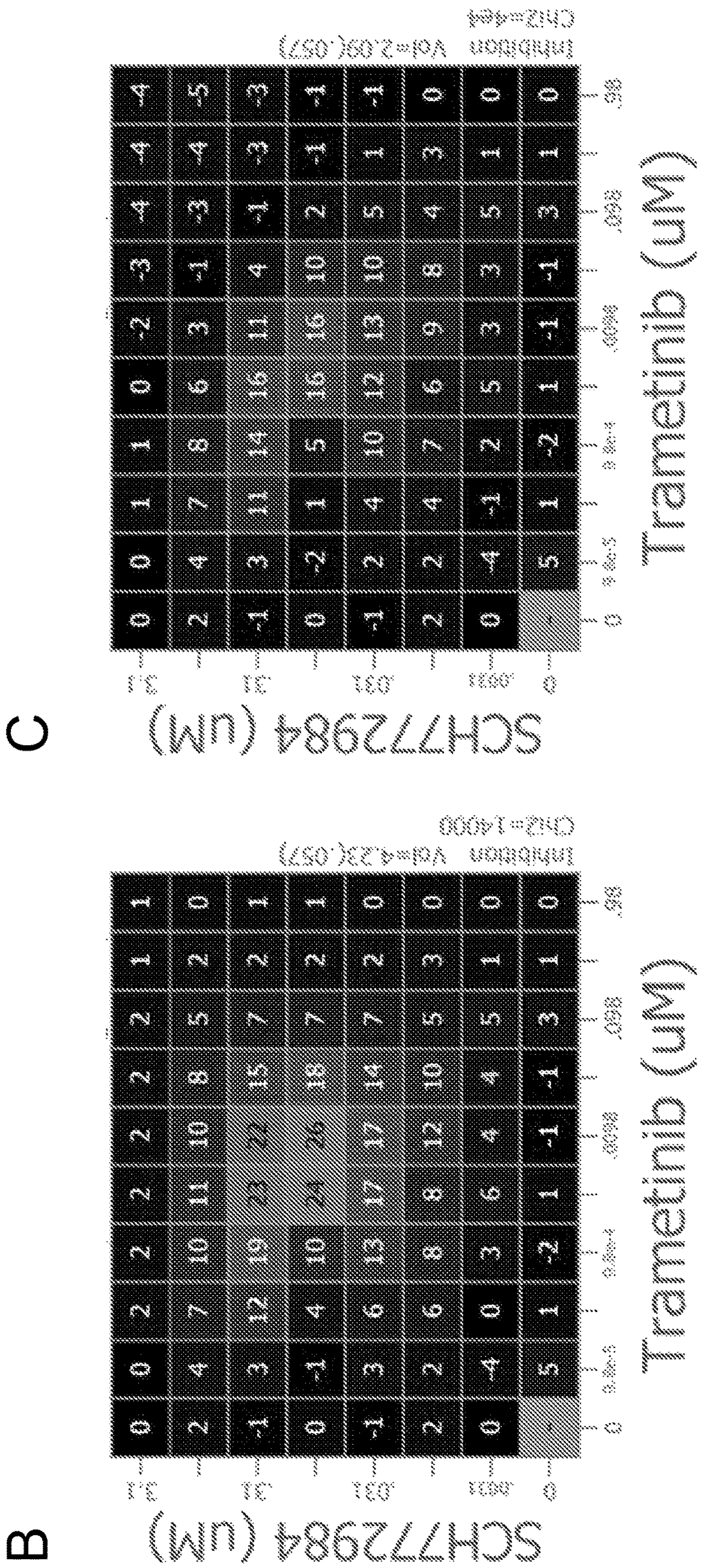

FIG. 30, Con't
D
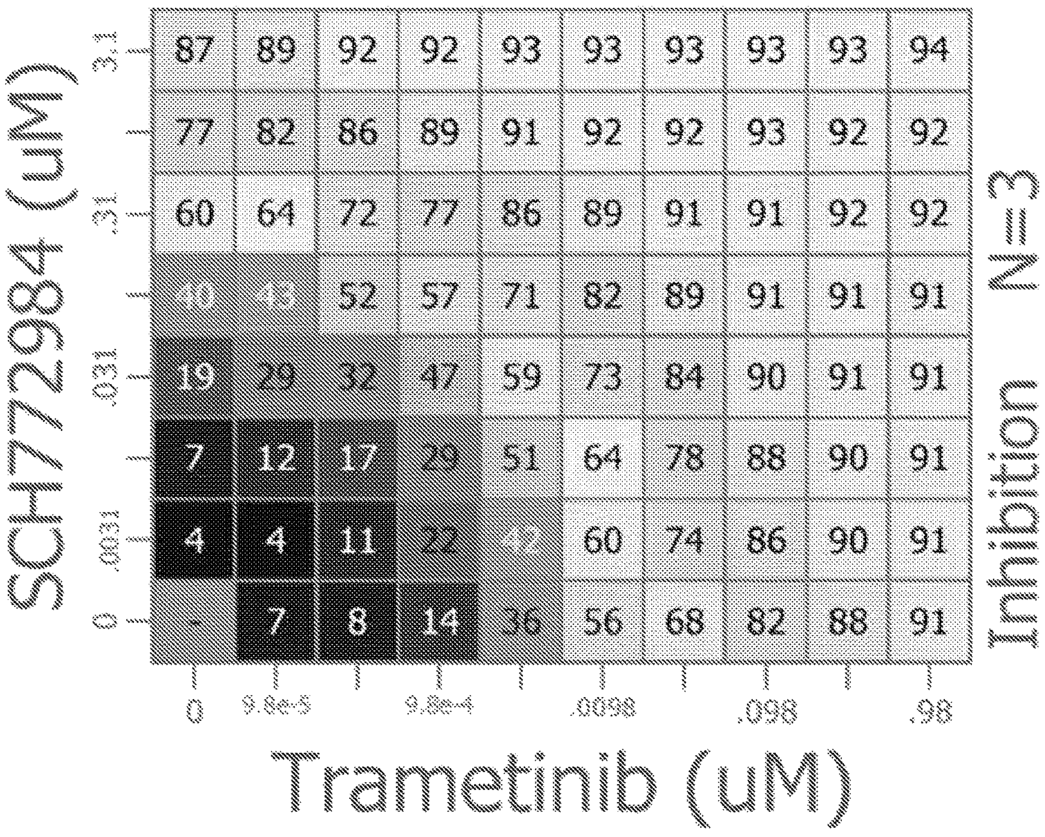

FIG. 30, Con't
F
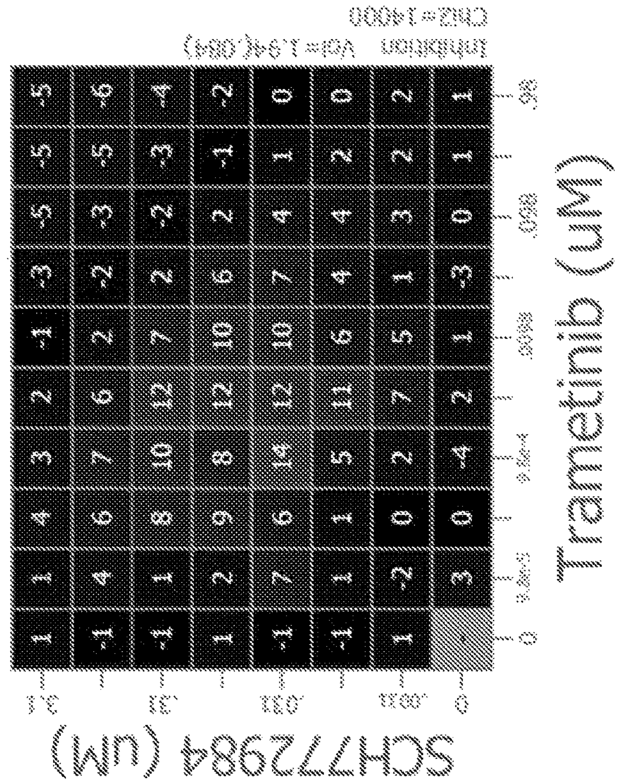
E
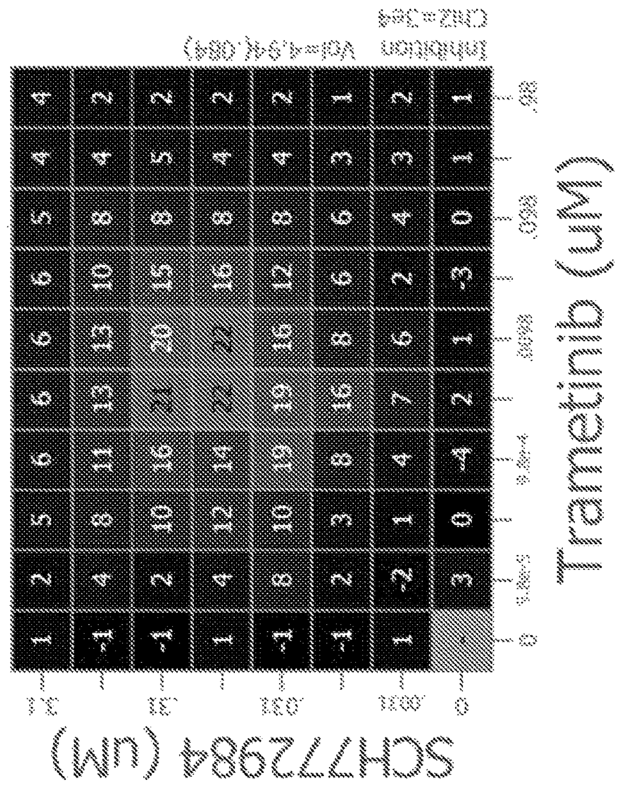

FIG. 30, Con't
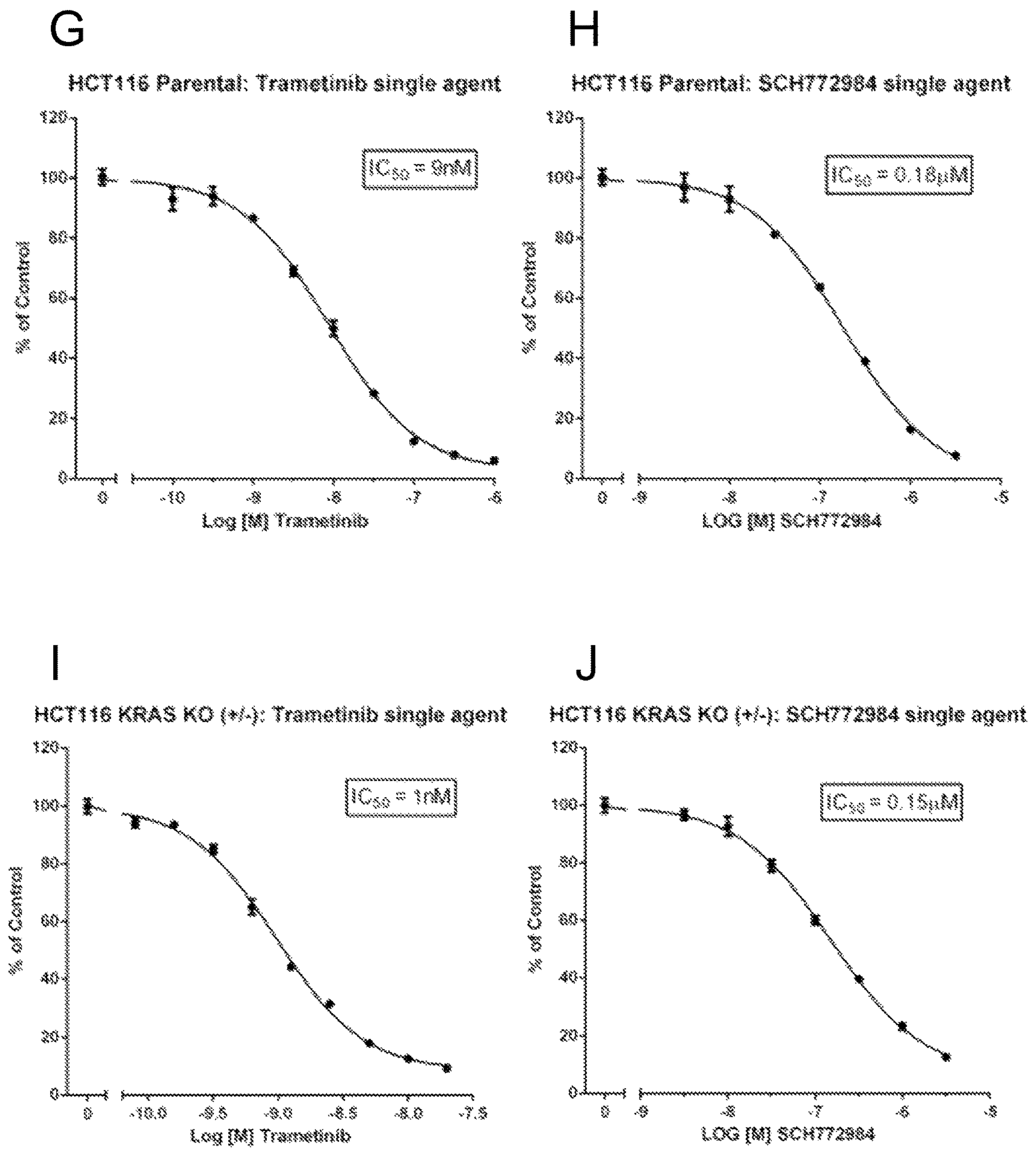

A

FIG. 31, Con't
C
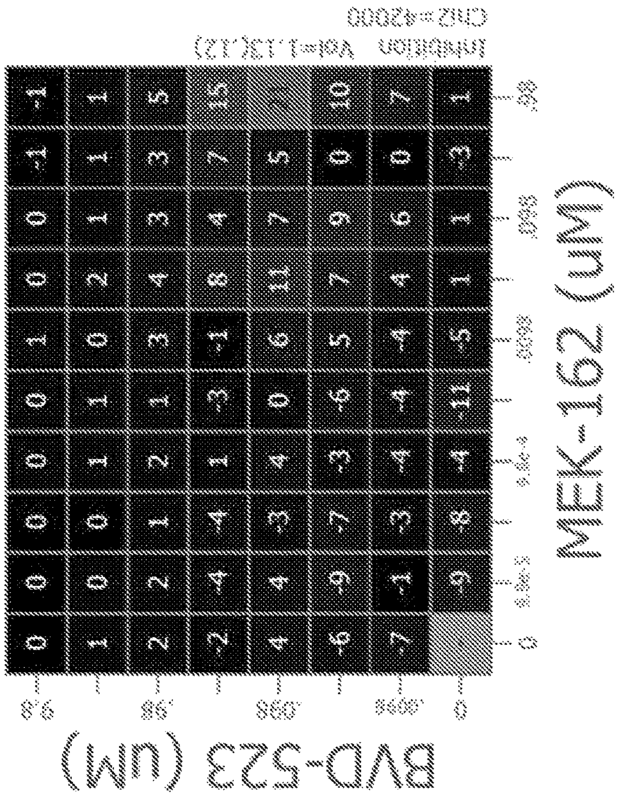
B
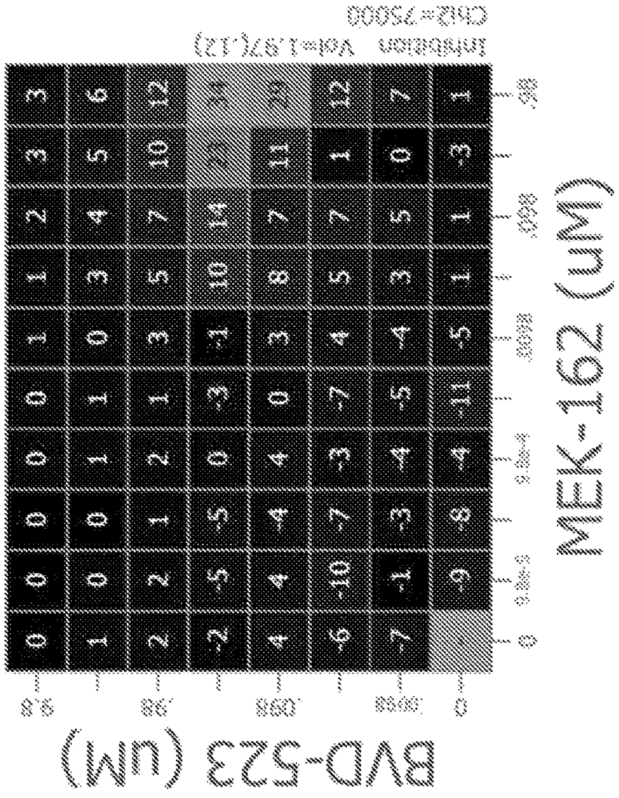

FIG. 31, Con't
D
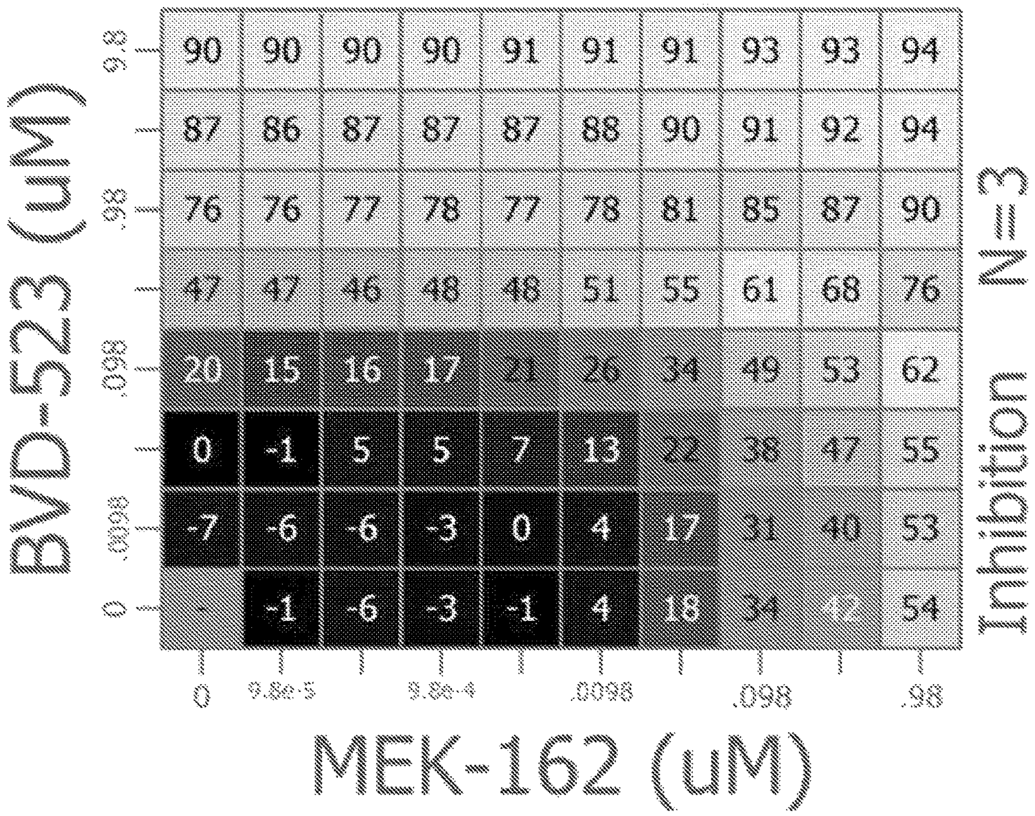

FIG. 31, Con't
E
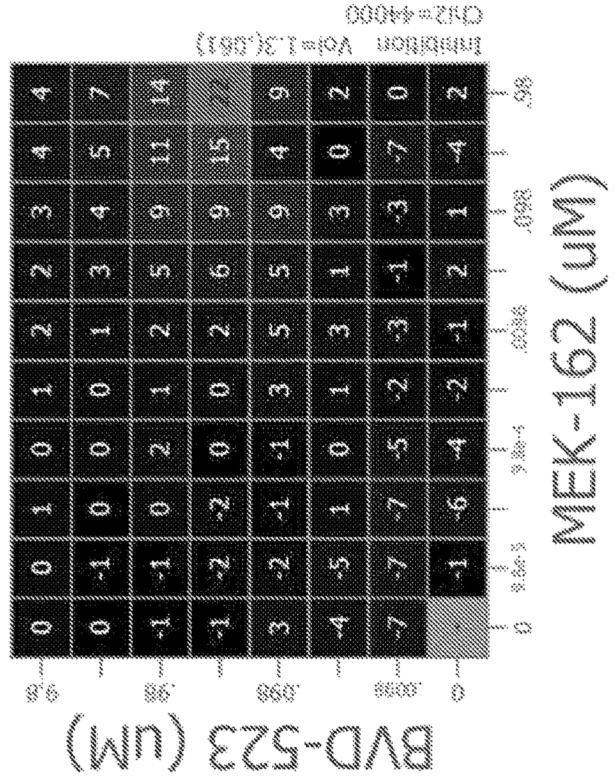
F
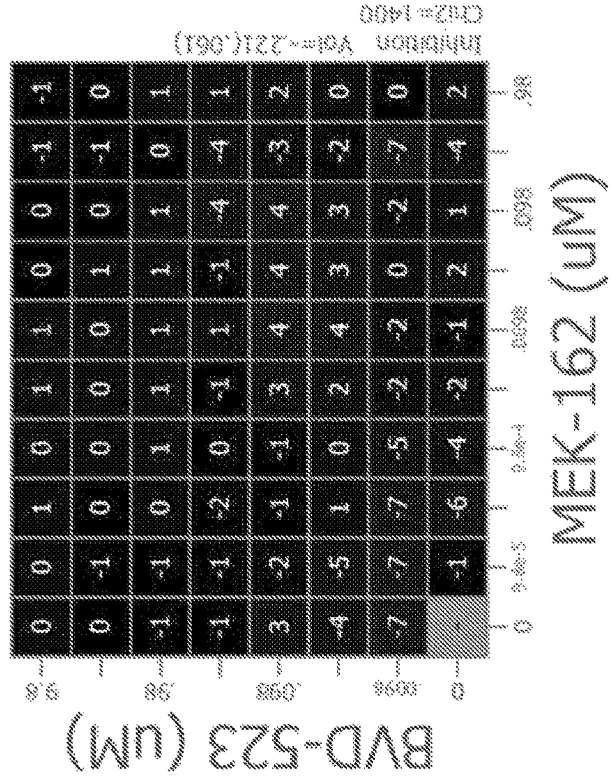

FIG. 31, Con't
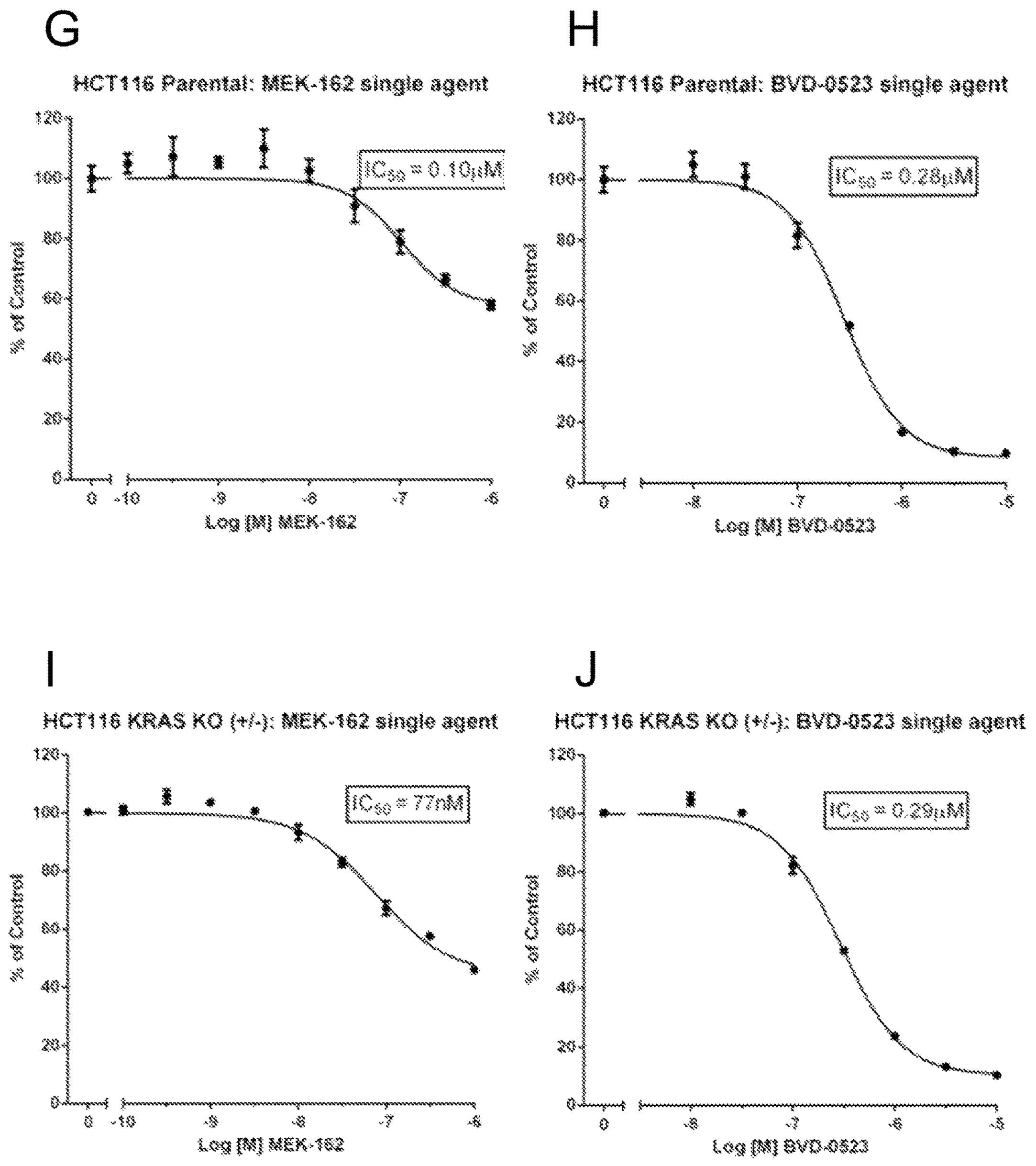

A

FIG. 32, Con't
B
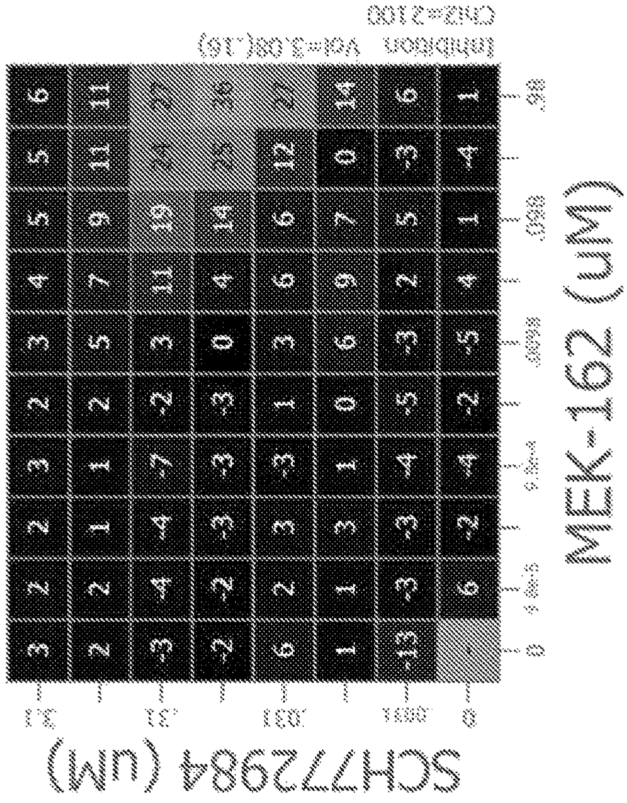
C
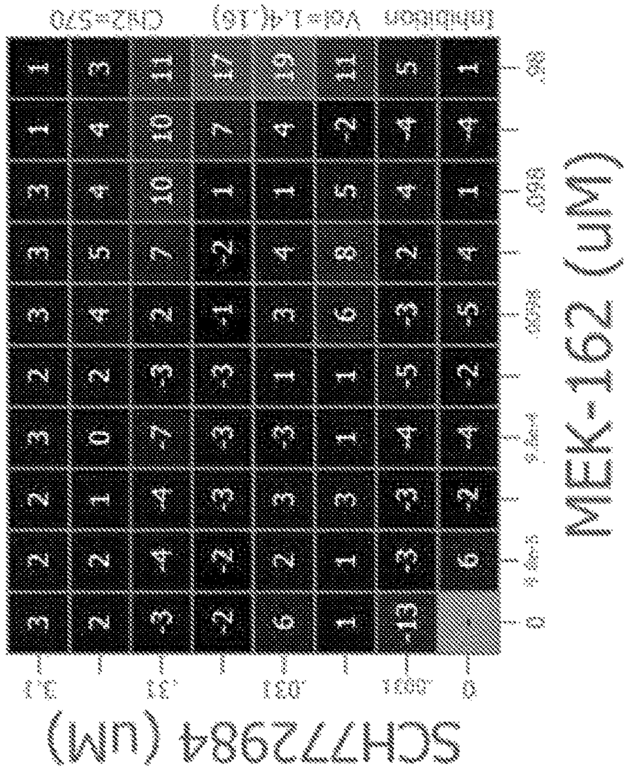

FIG. 32, Con't
D
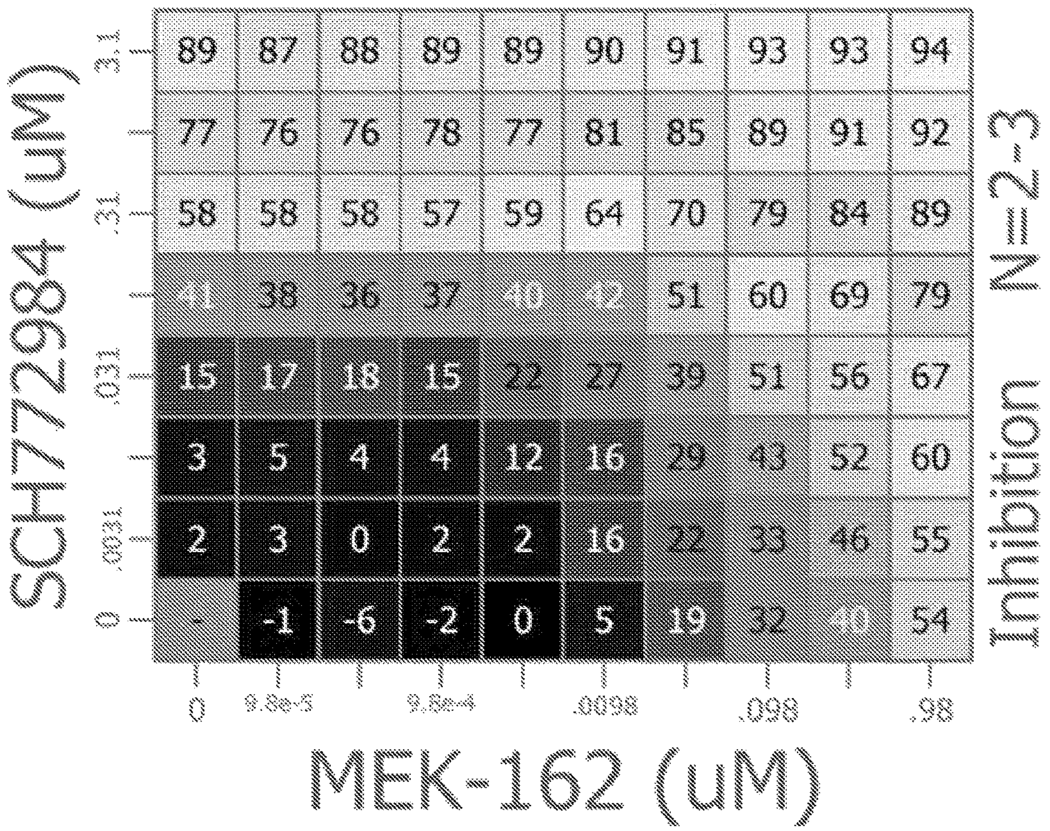

FIG. 32, Con't
F
E
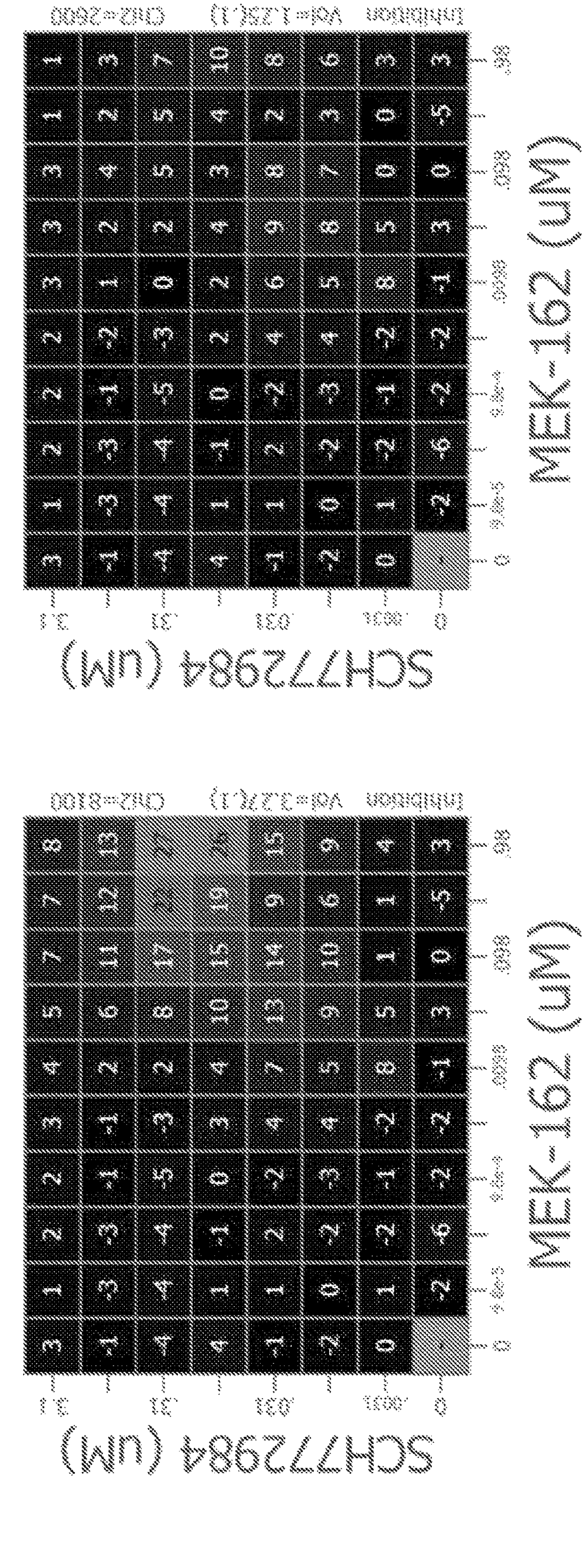

FIG. 32, Con't
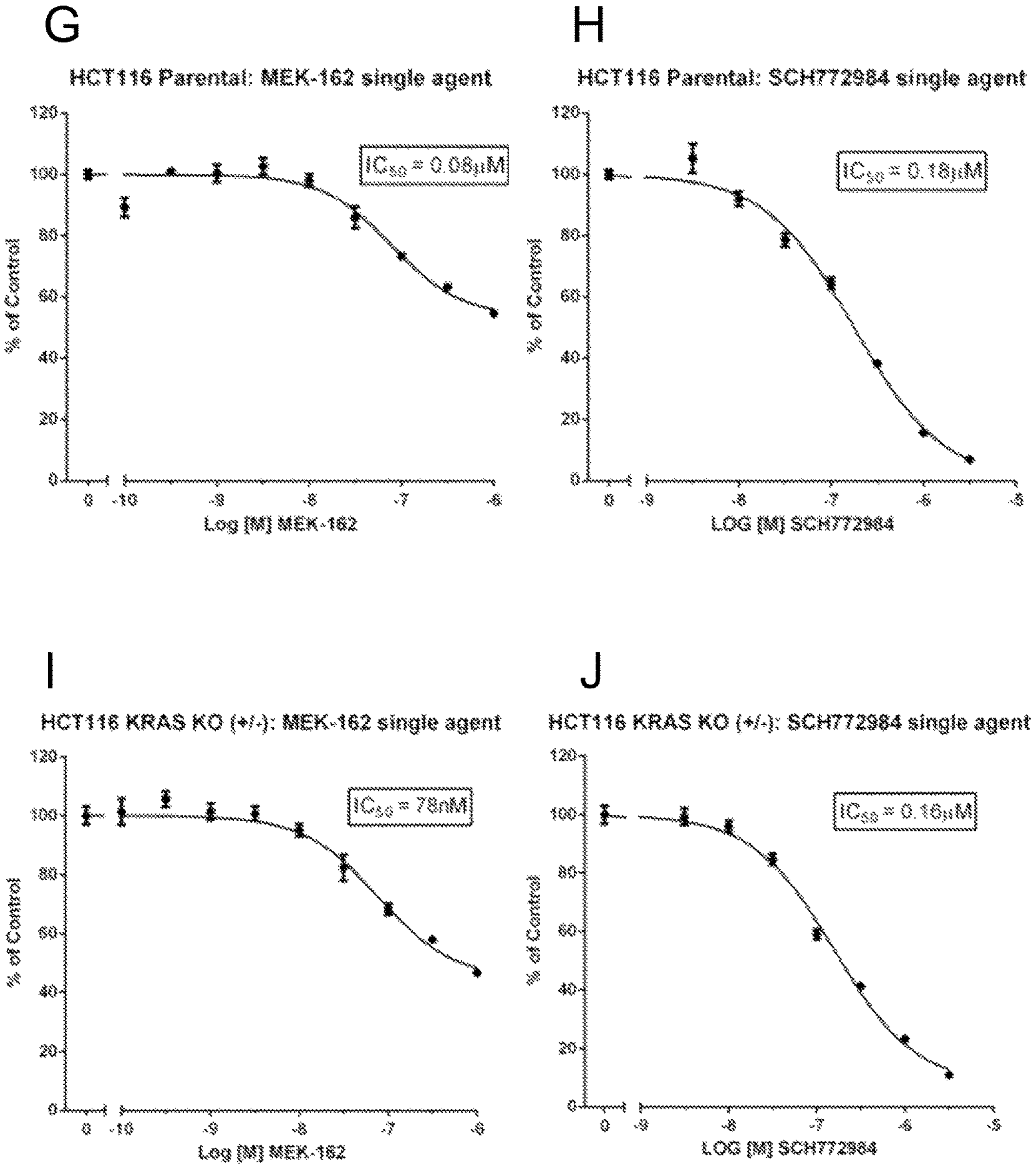

A

FIG. 33, Con't
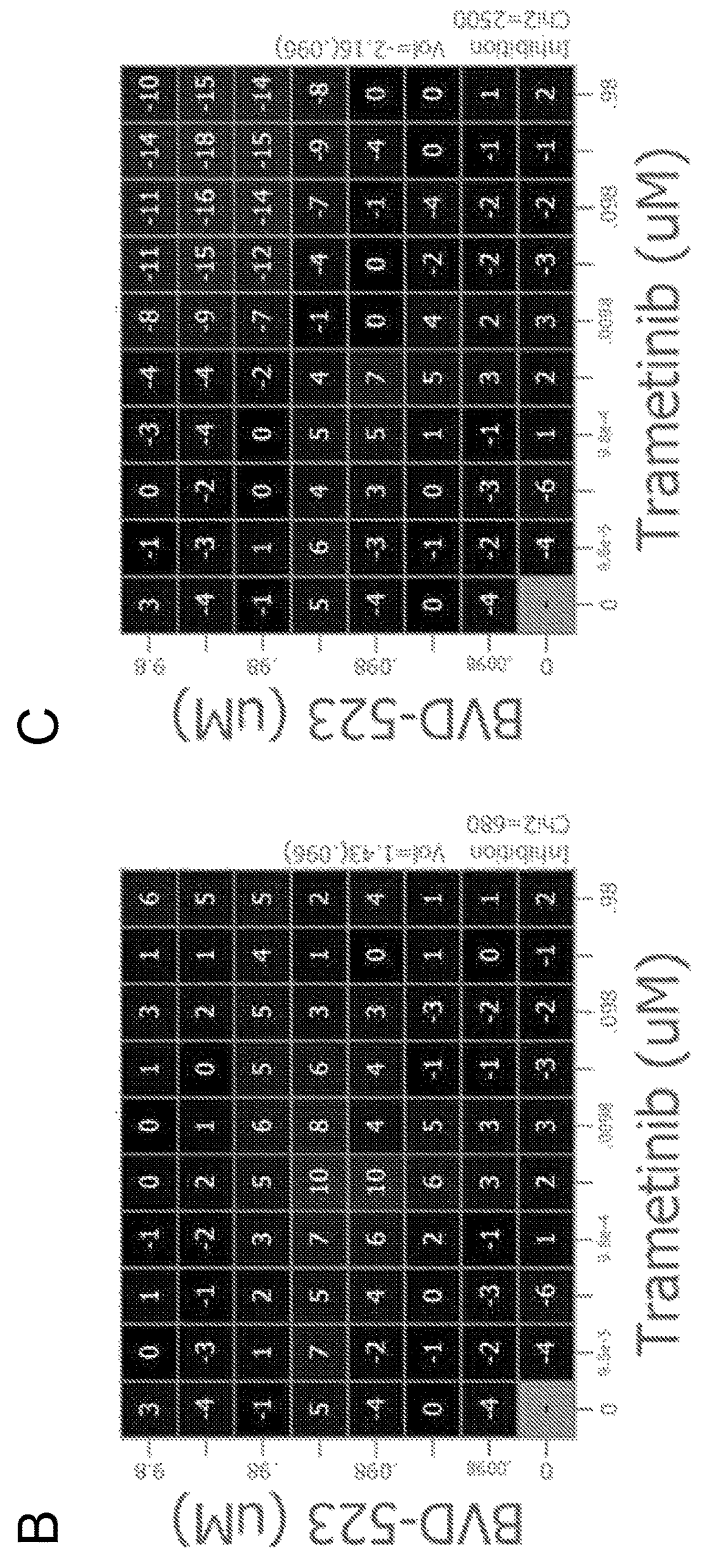

FIG. 33, Con't
D
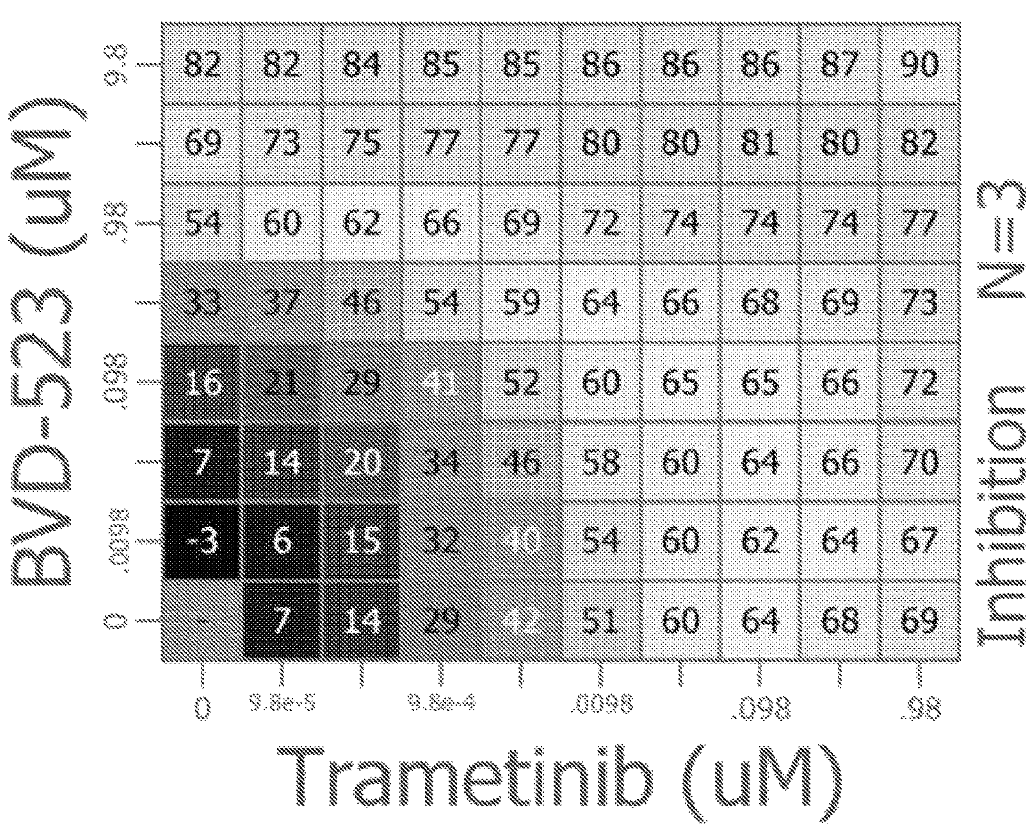

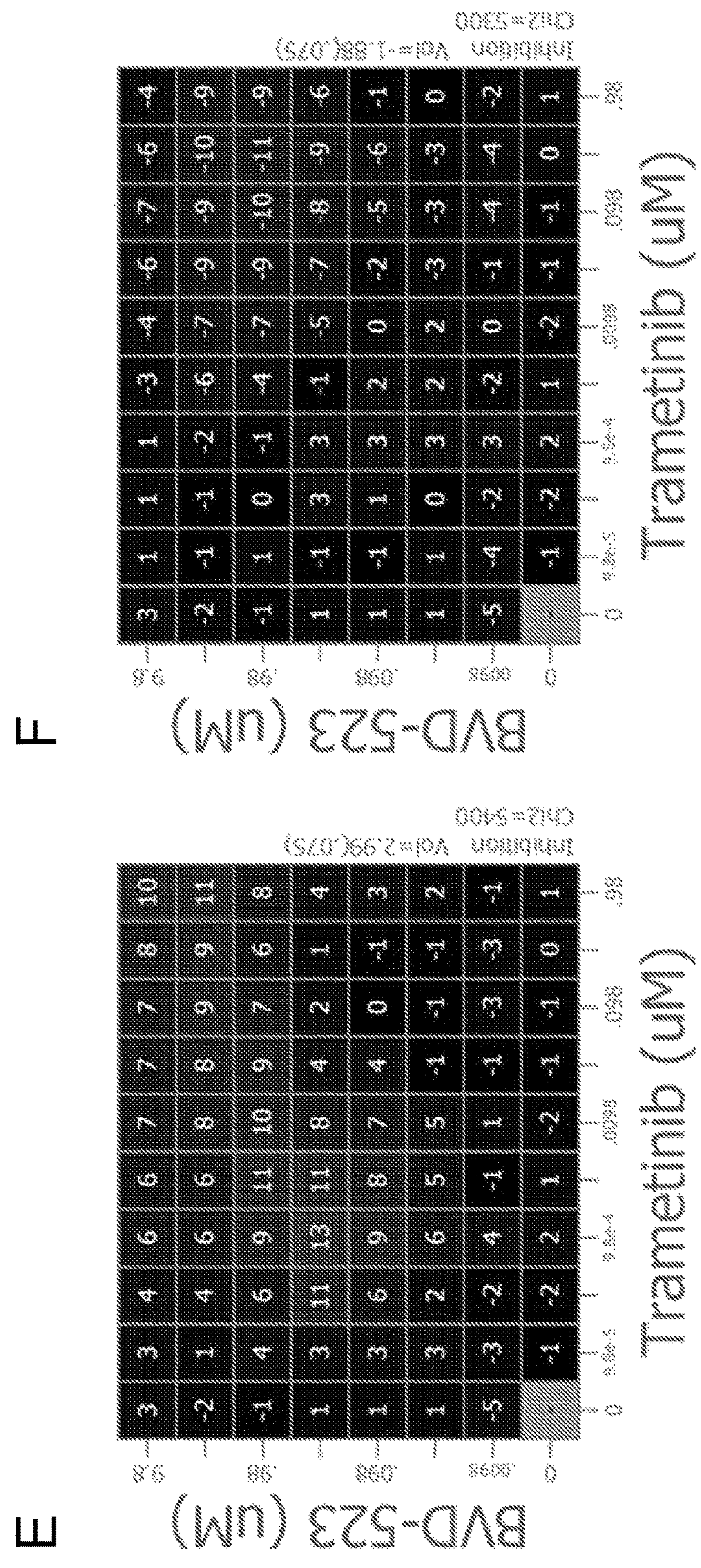
FIG. 33, Con't

FIG. 33, Con't
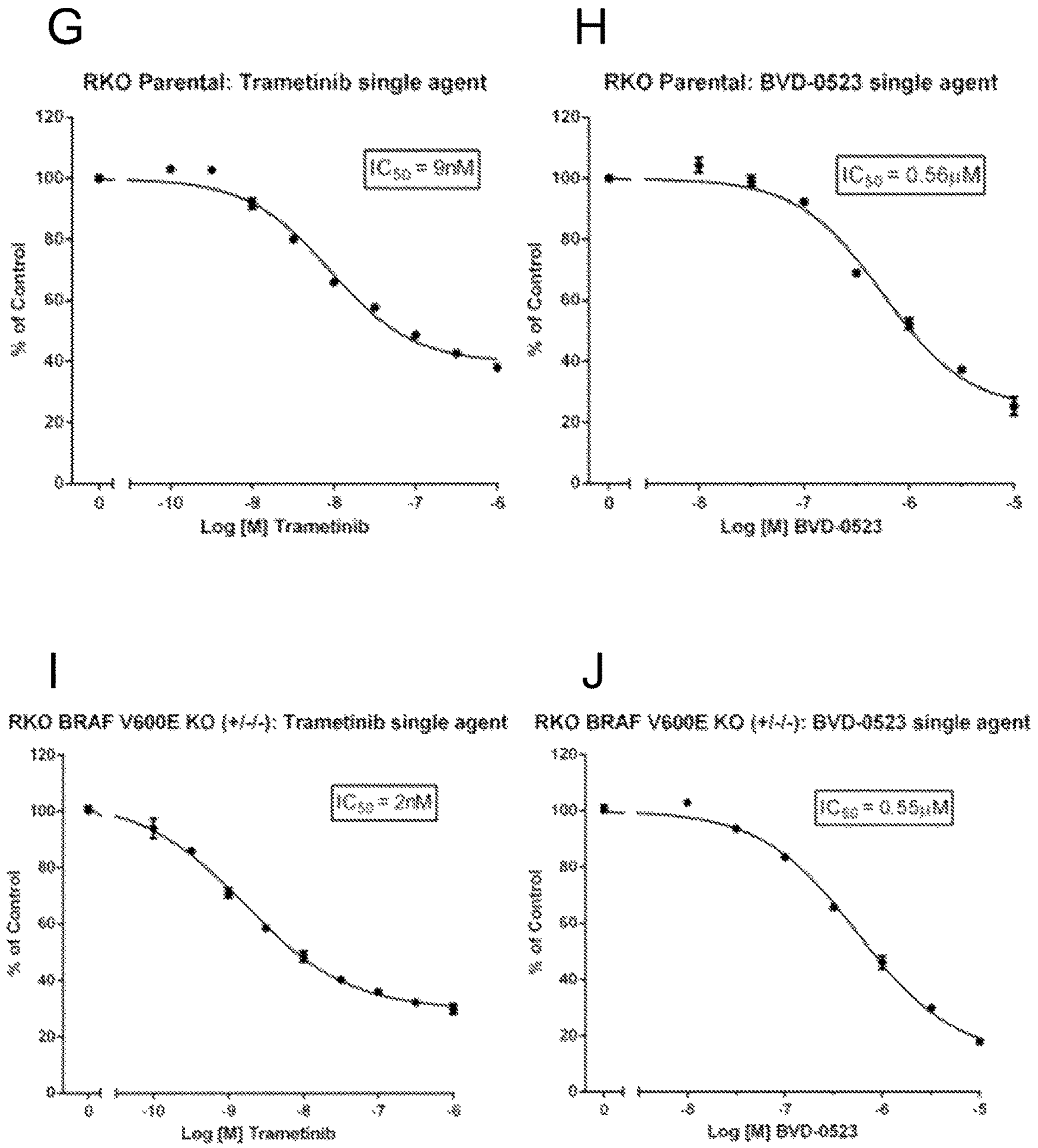

A

FIG. 34, Con't
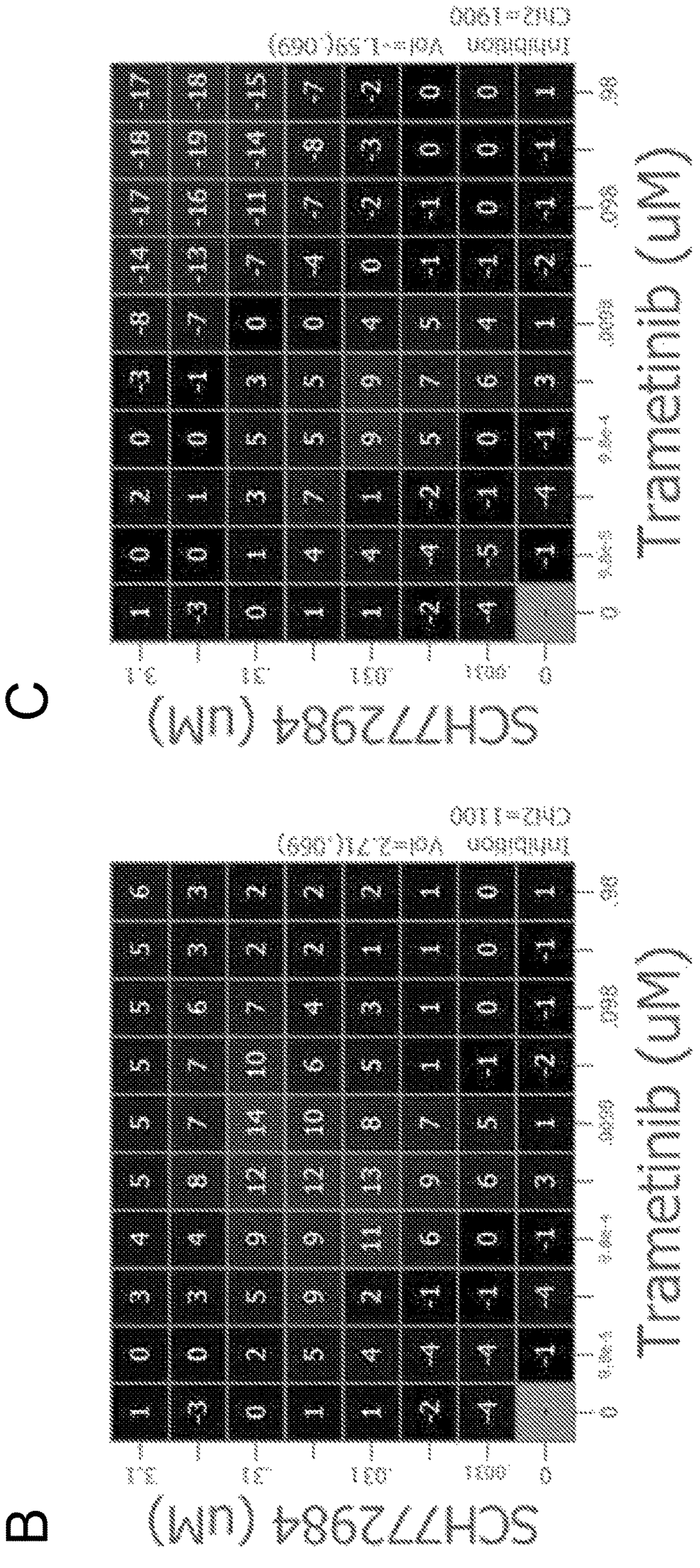

FIG. 34, Con't
D
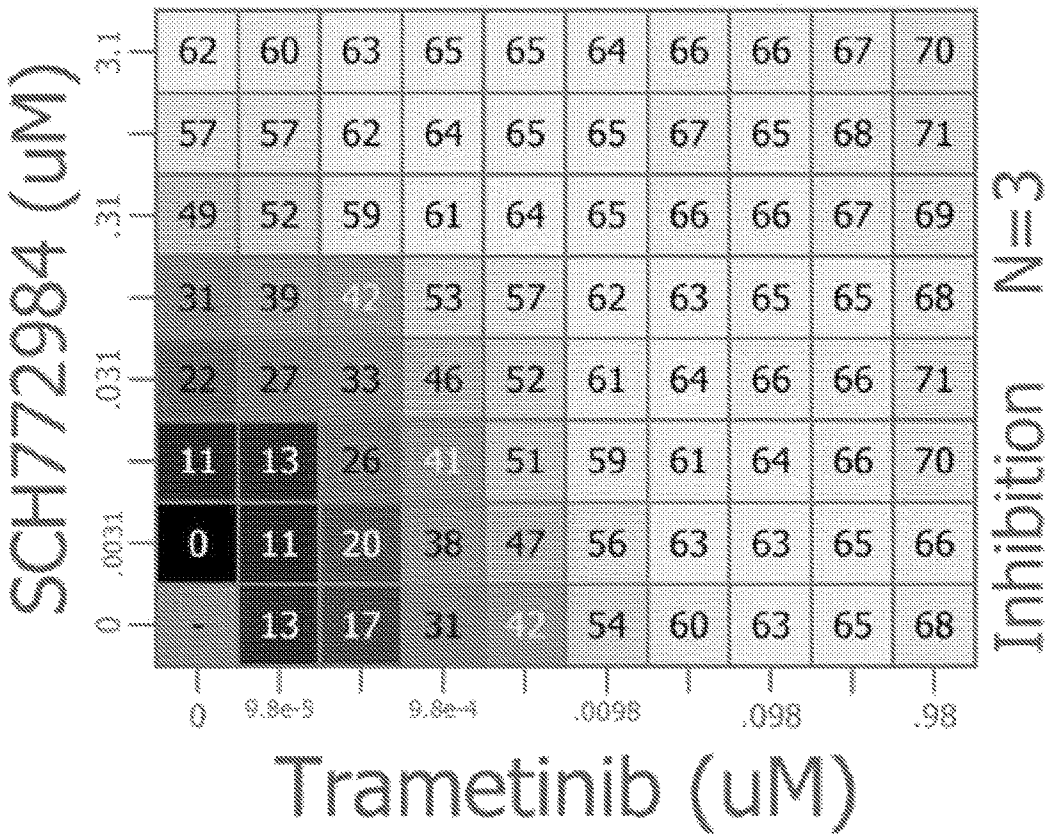

FIG. 34, Con't
F
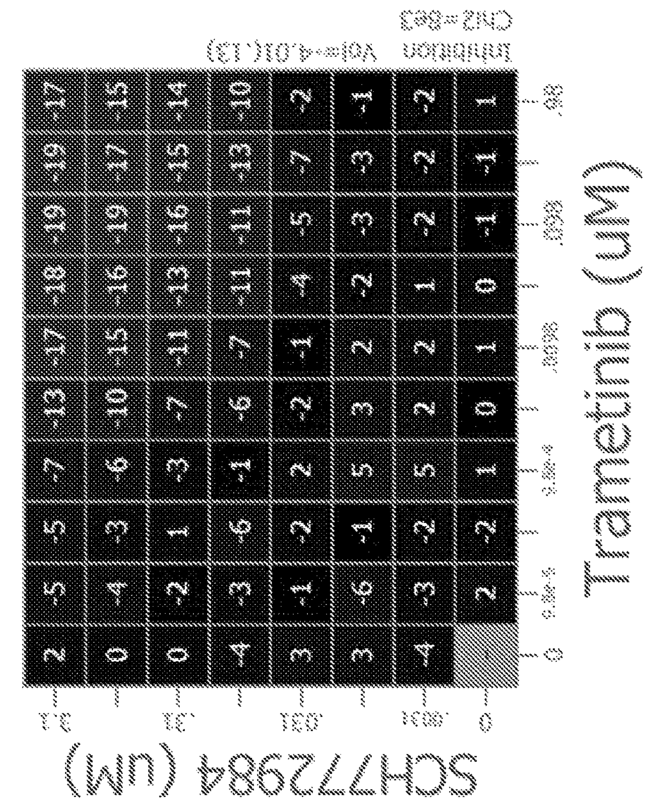
E
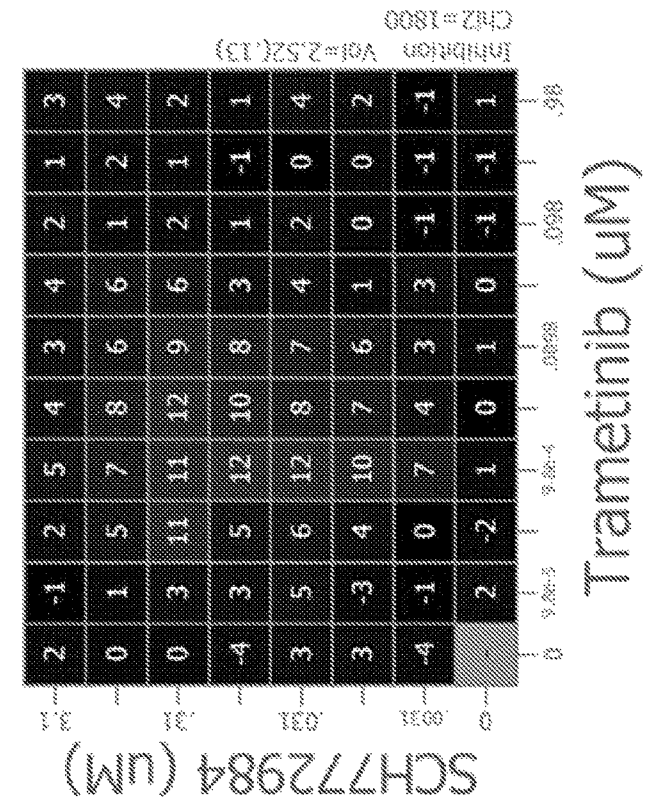

FIG. 34, Con't
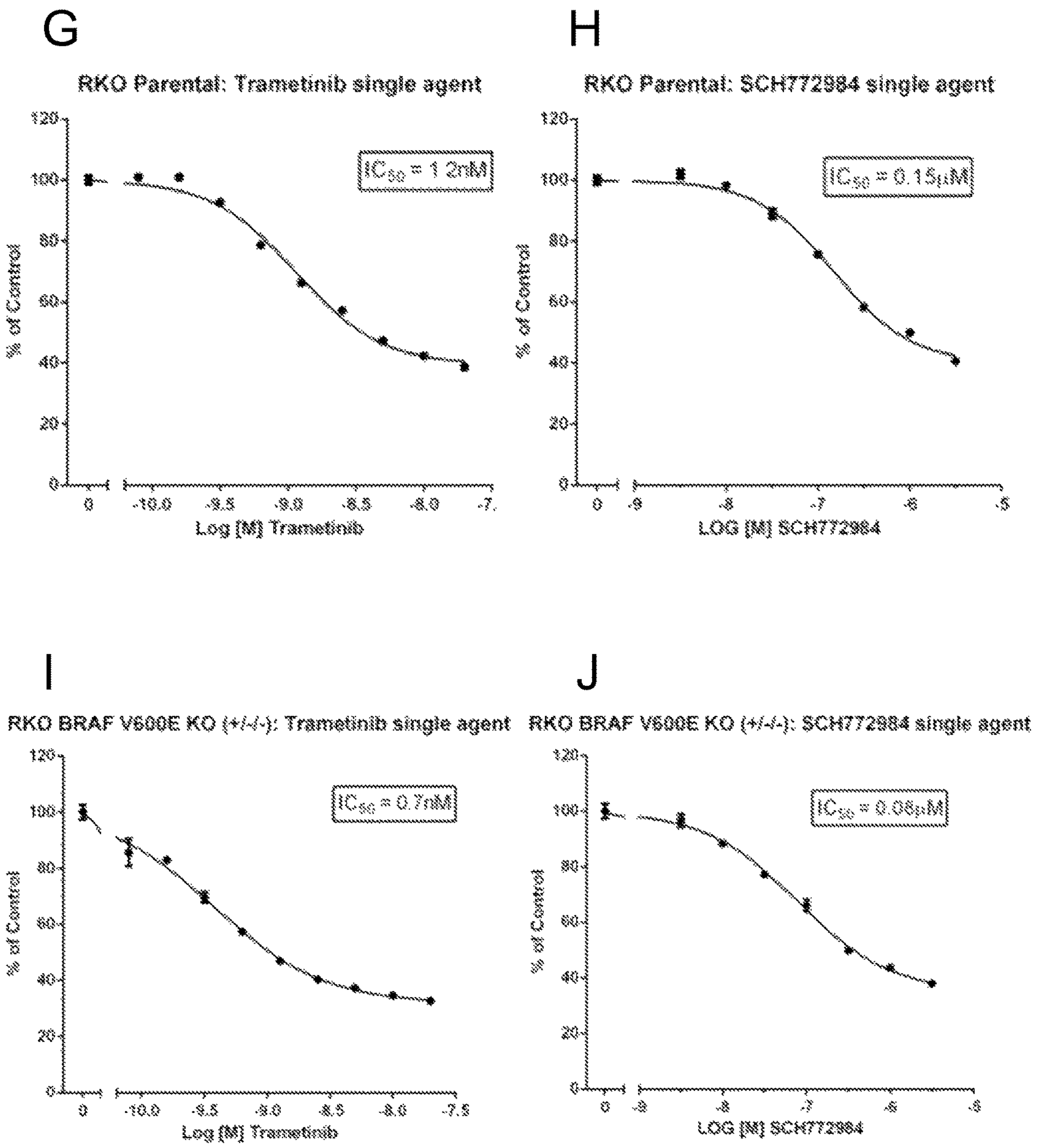

FIG. 35, Con't
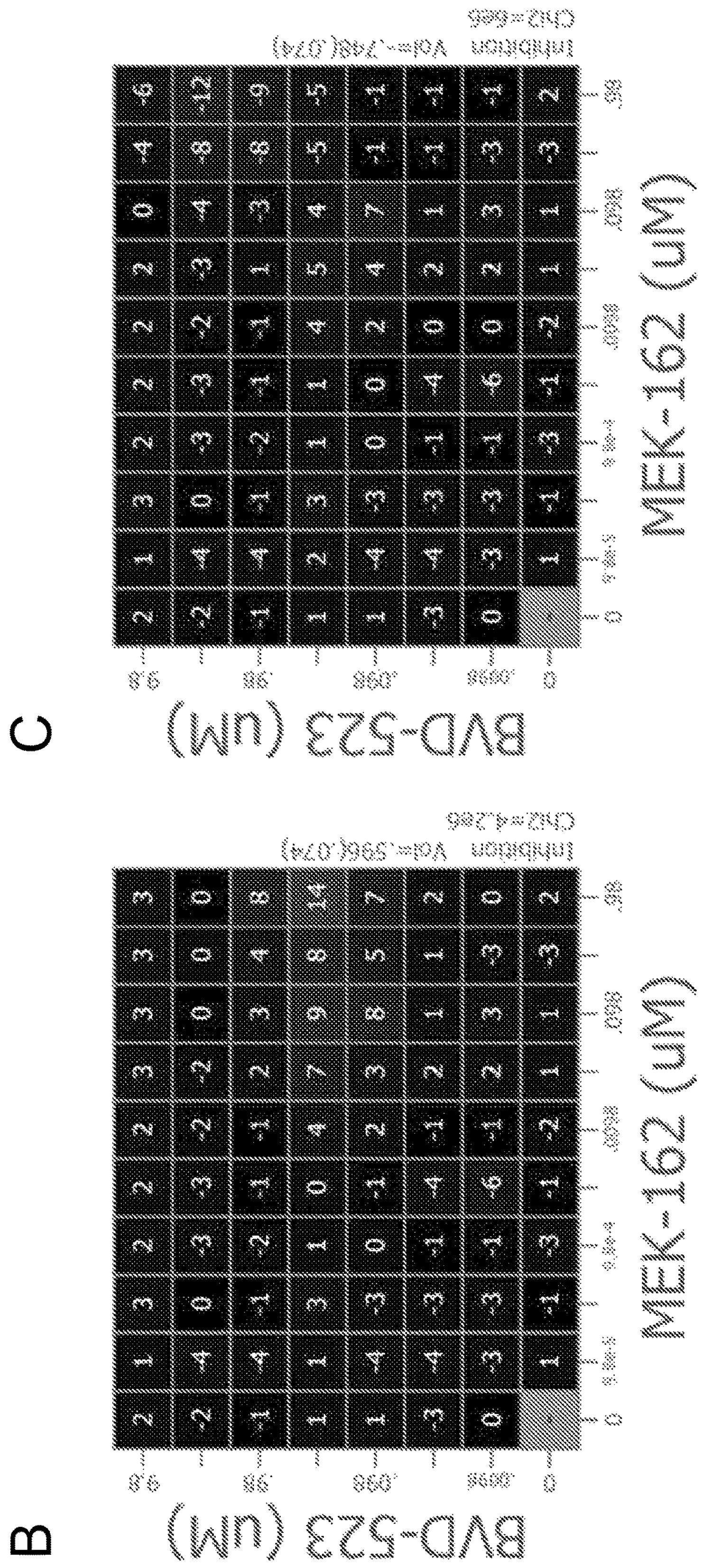

FIG. 35, Con't
D
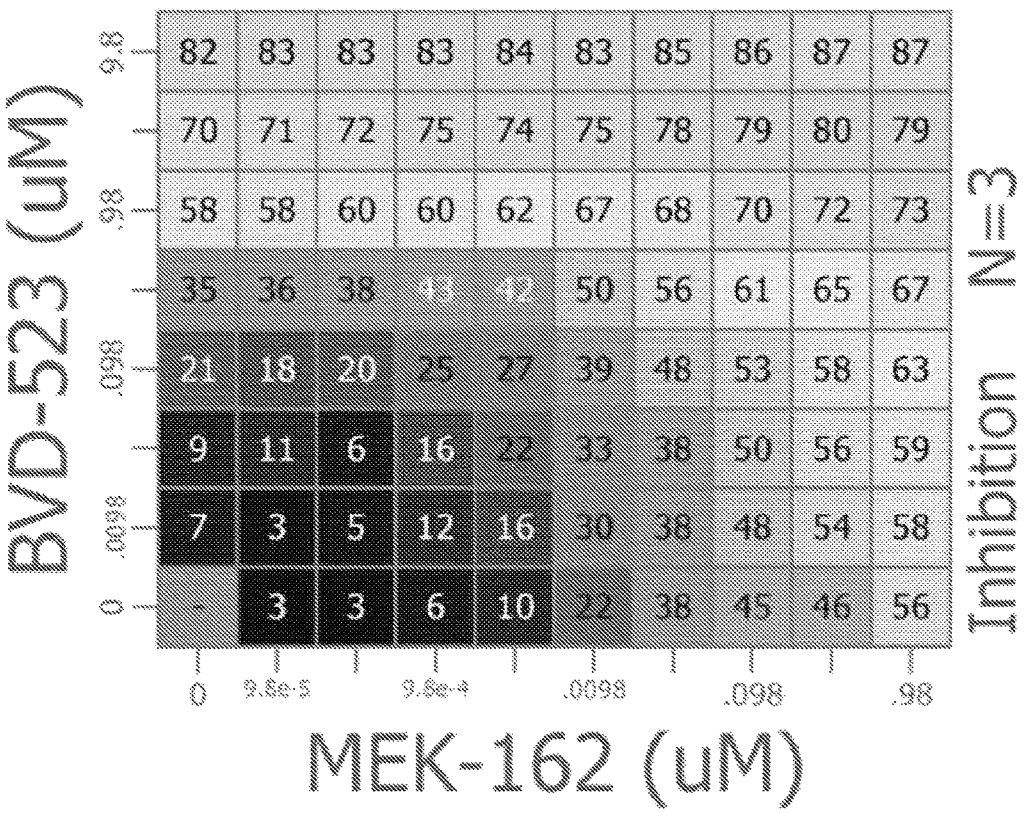

FIG. 35, Con't
F
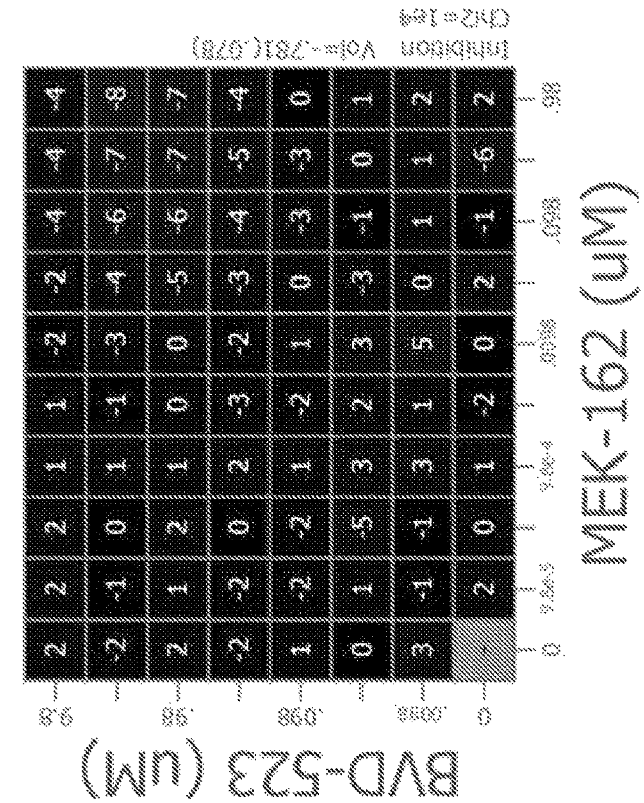
E
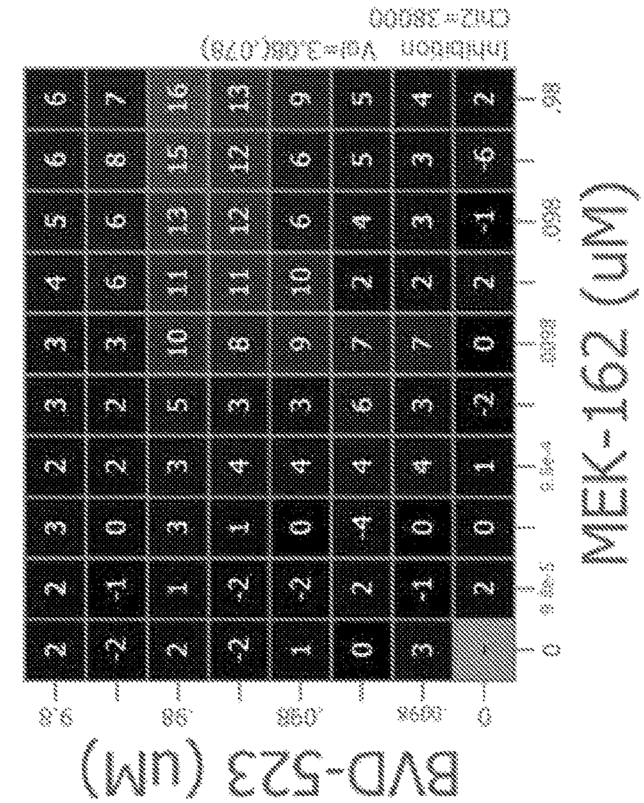

FIG. 35, Con't
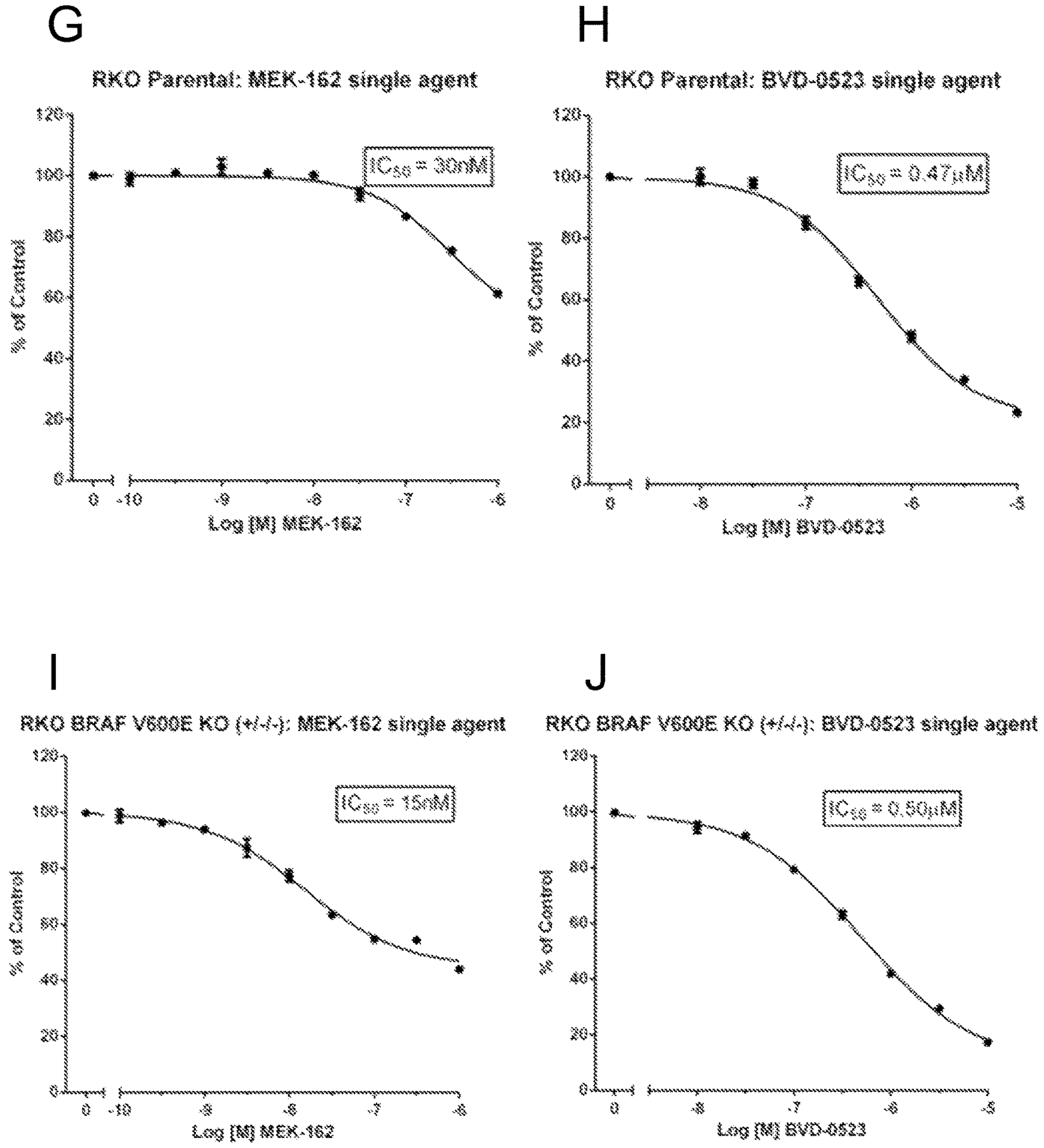

A

FIG. 36, Con't
C
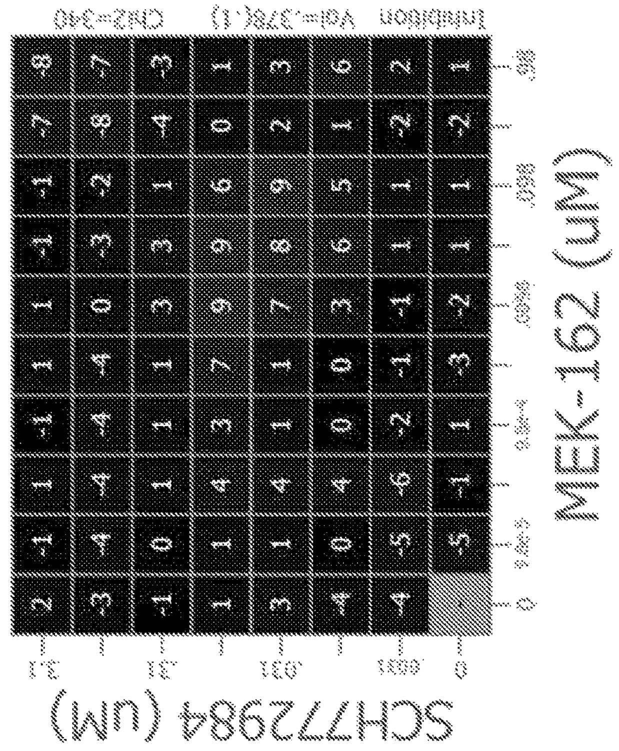
B
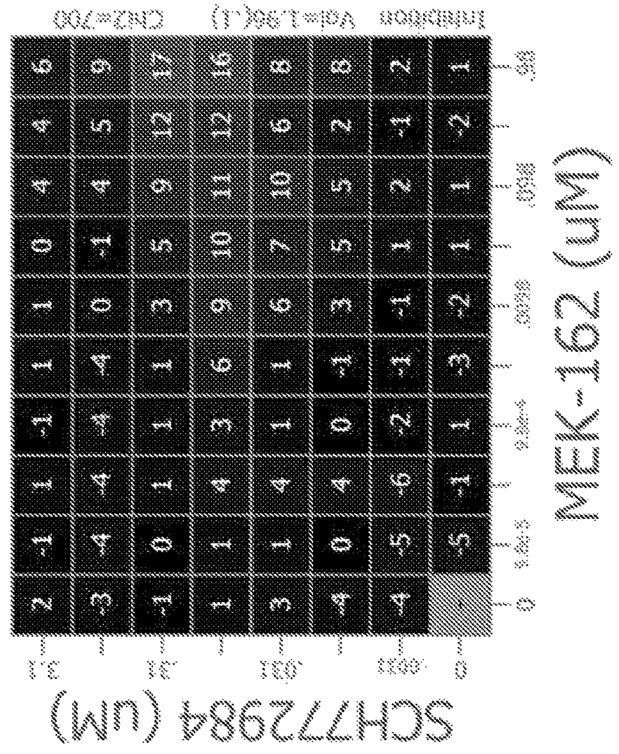

FIG. 36, Con't
D
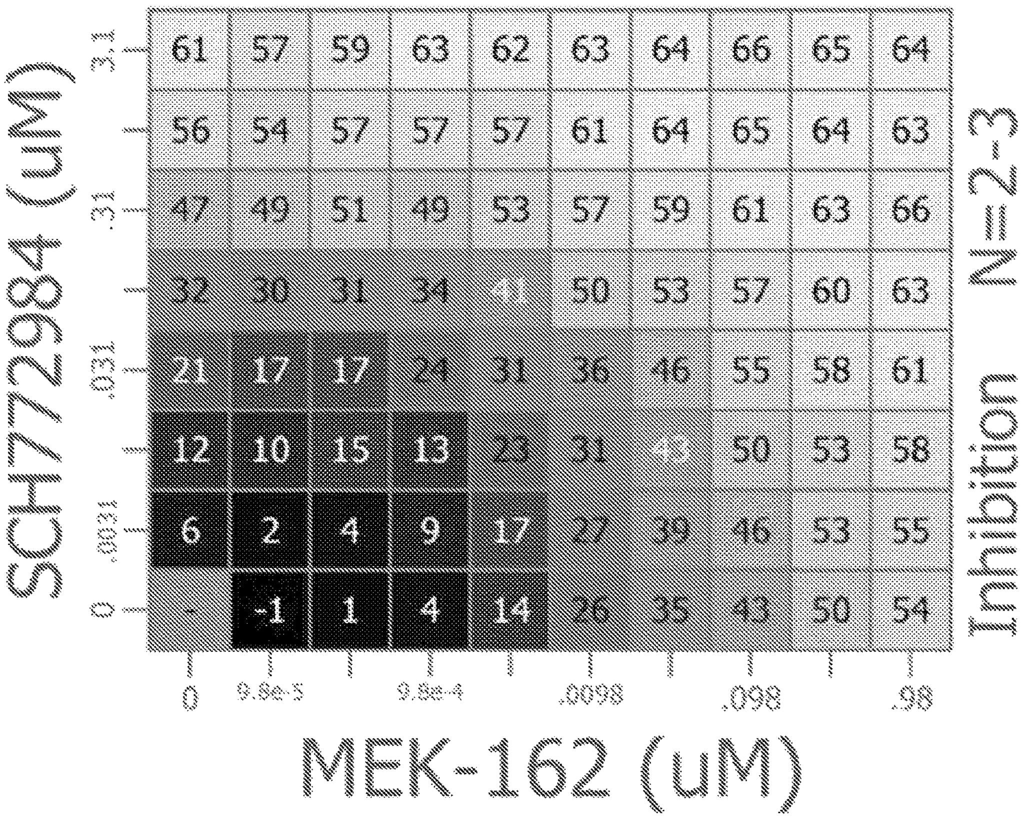

FIG. 36, Con't
E
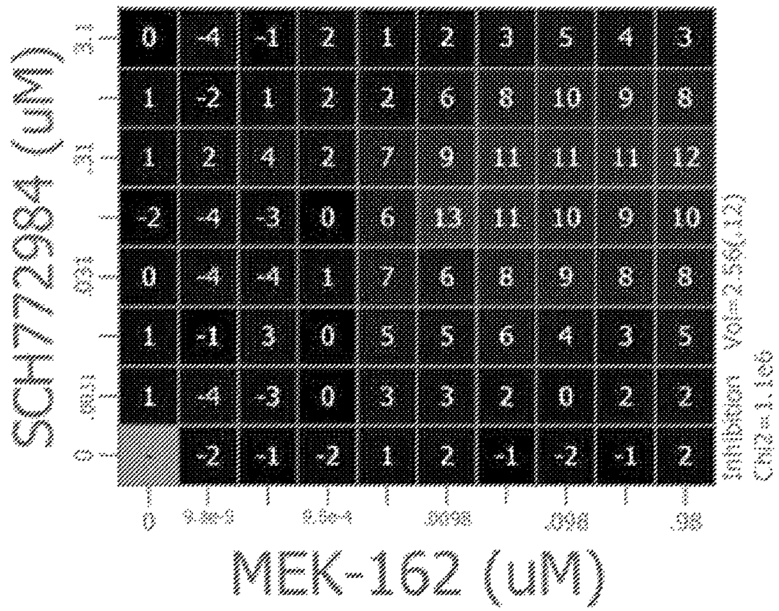
F
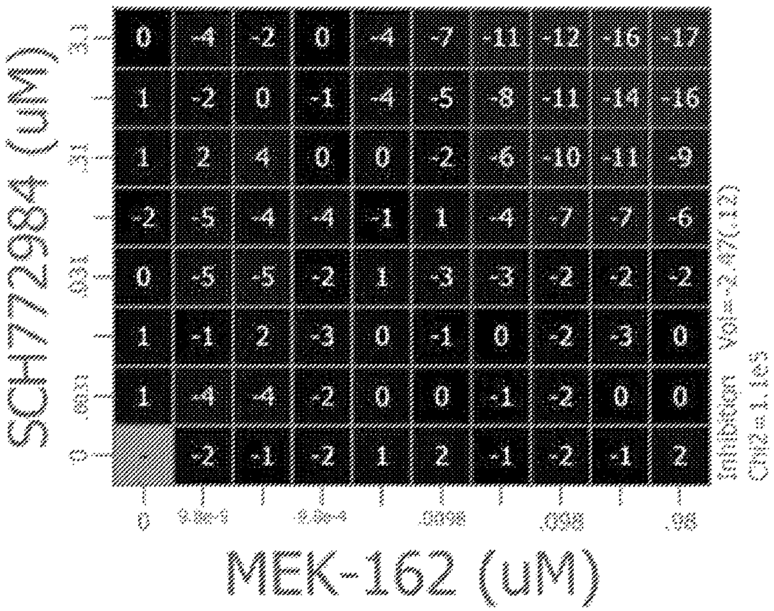

FIG. 36, Con't
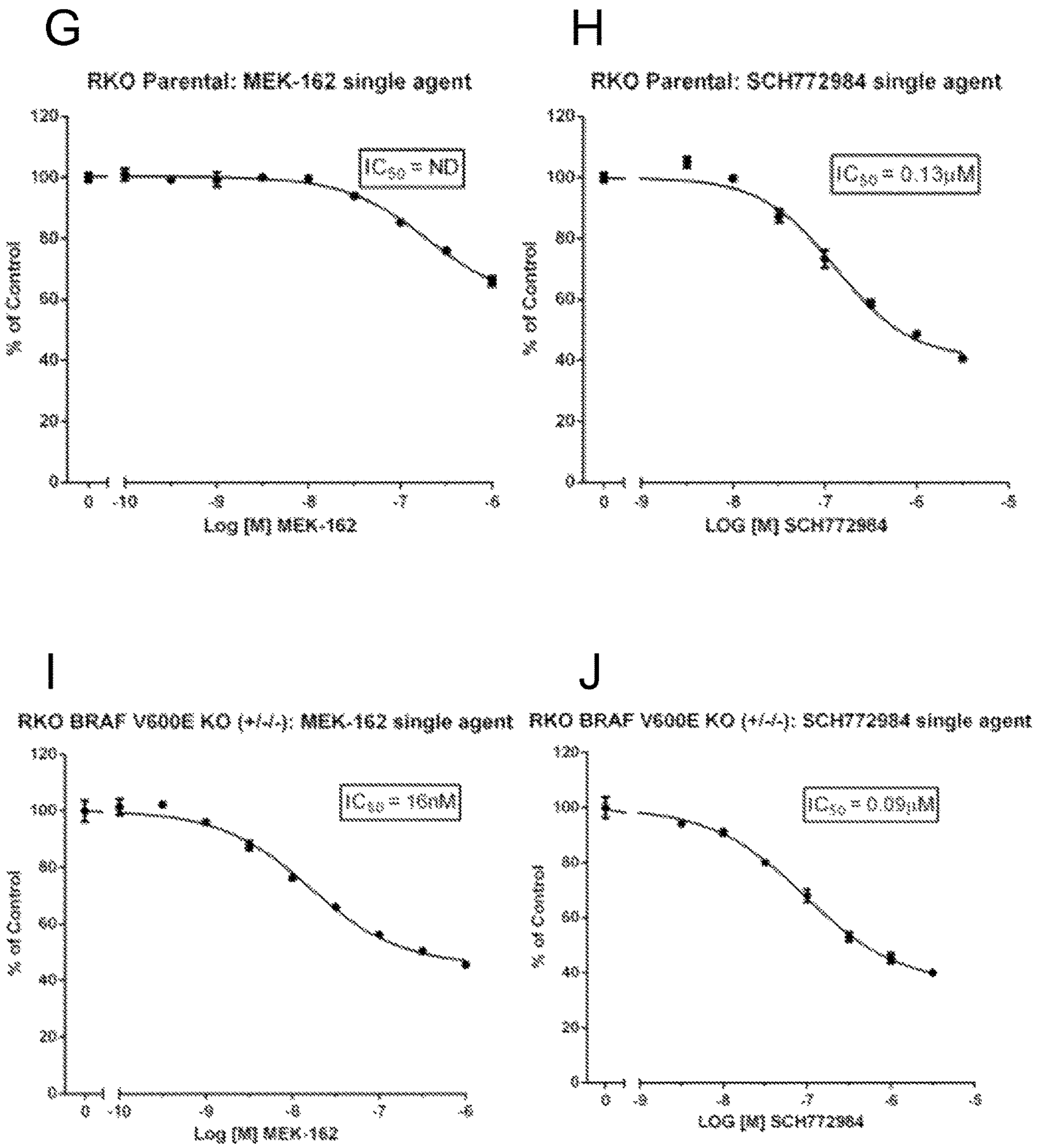

A

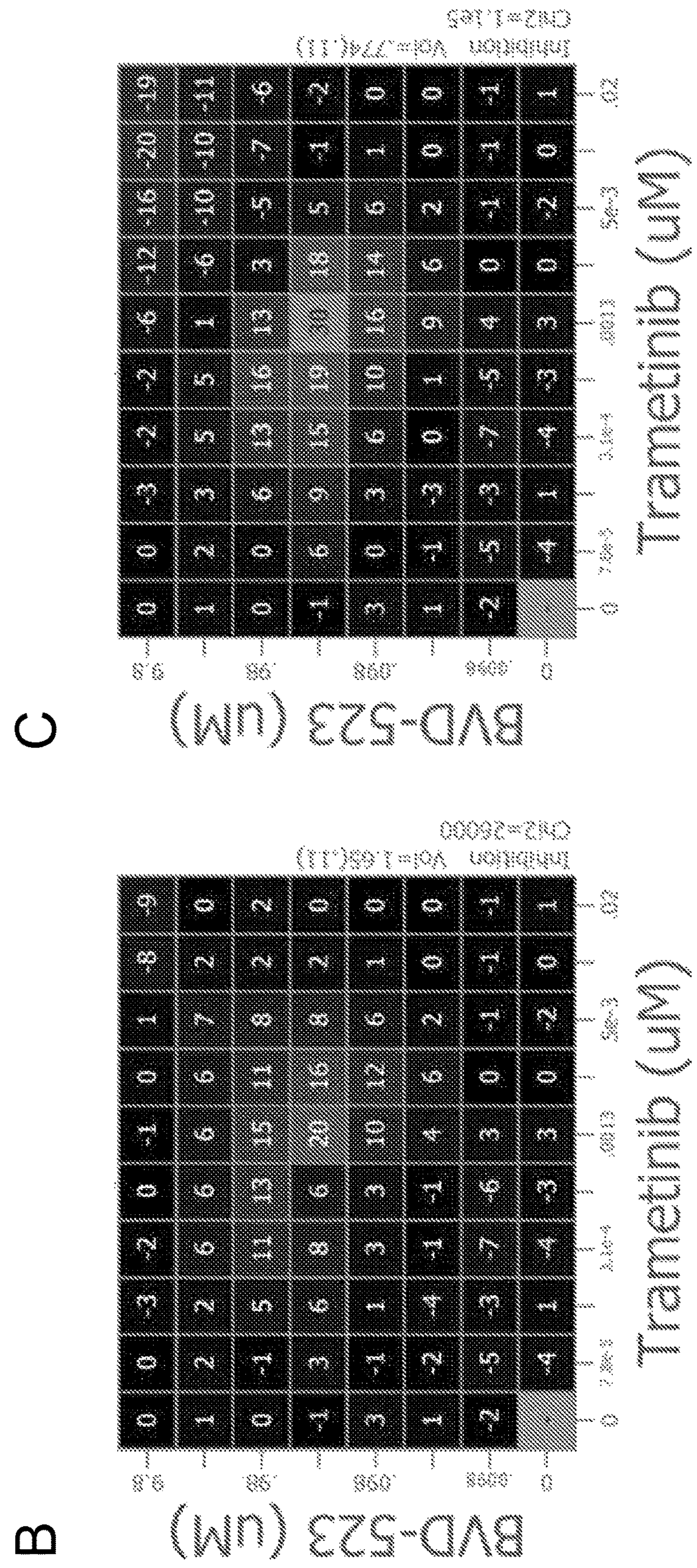
FIG. 37, Con't

FIG. 37, Con't
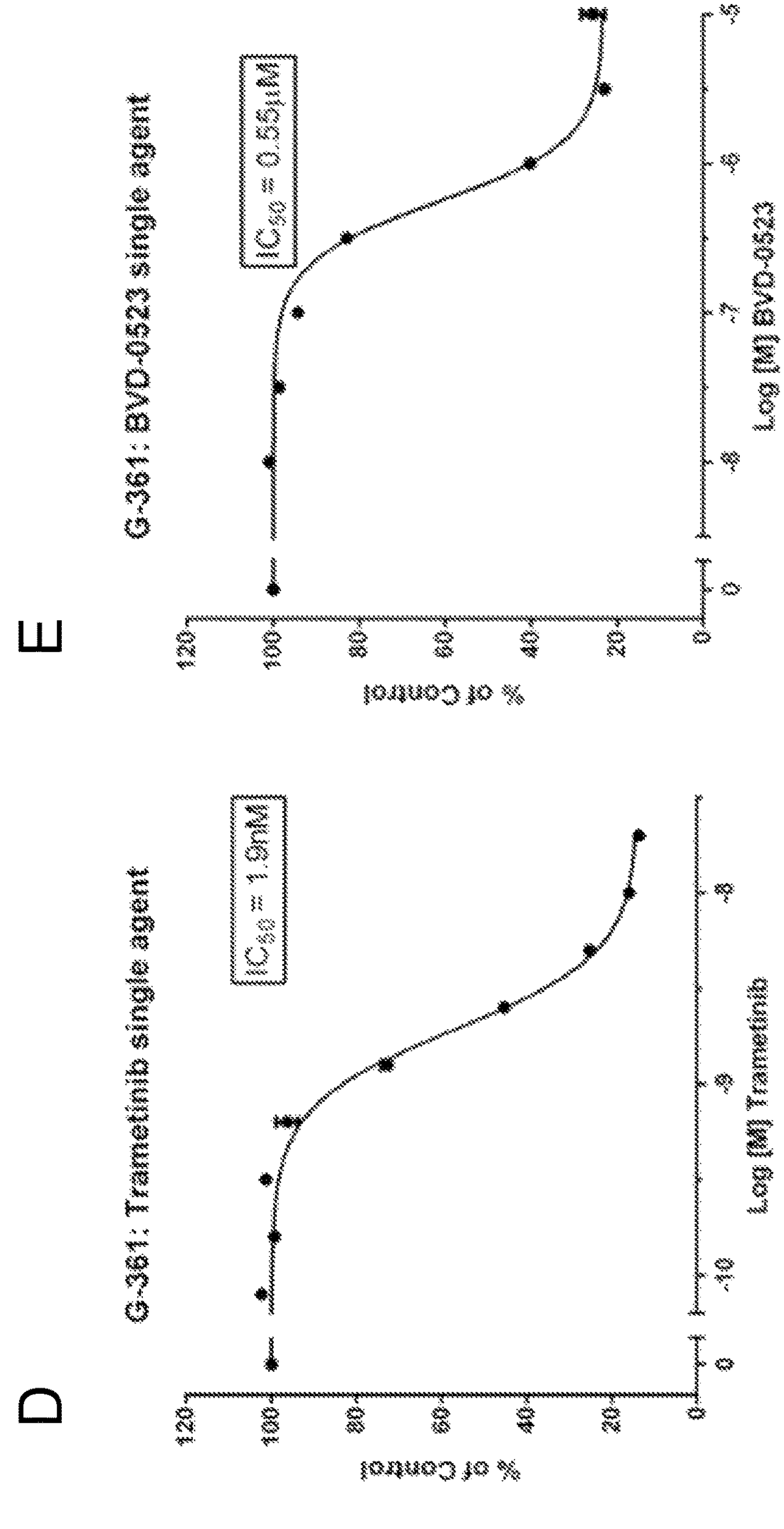

A

FIG. 38, Con't
C
B
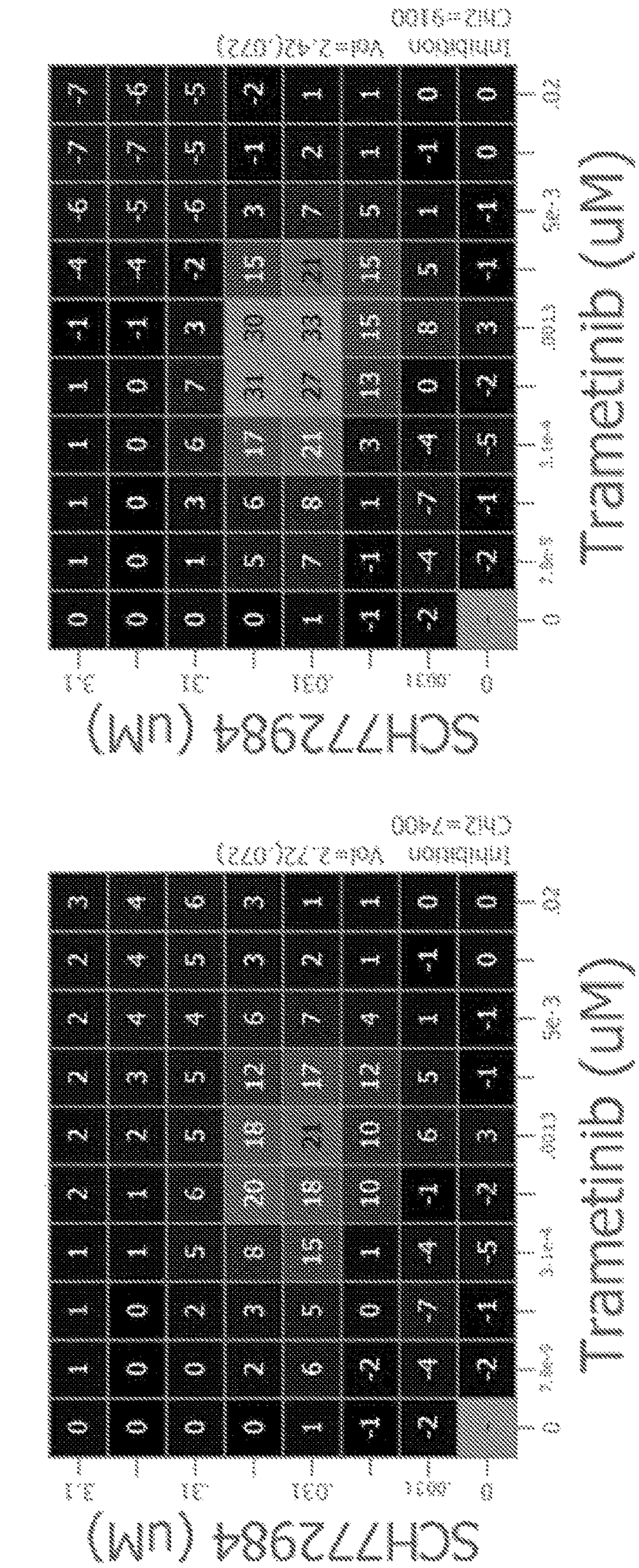

FIG. 38, Con't
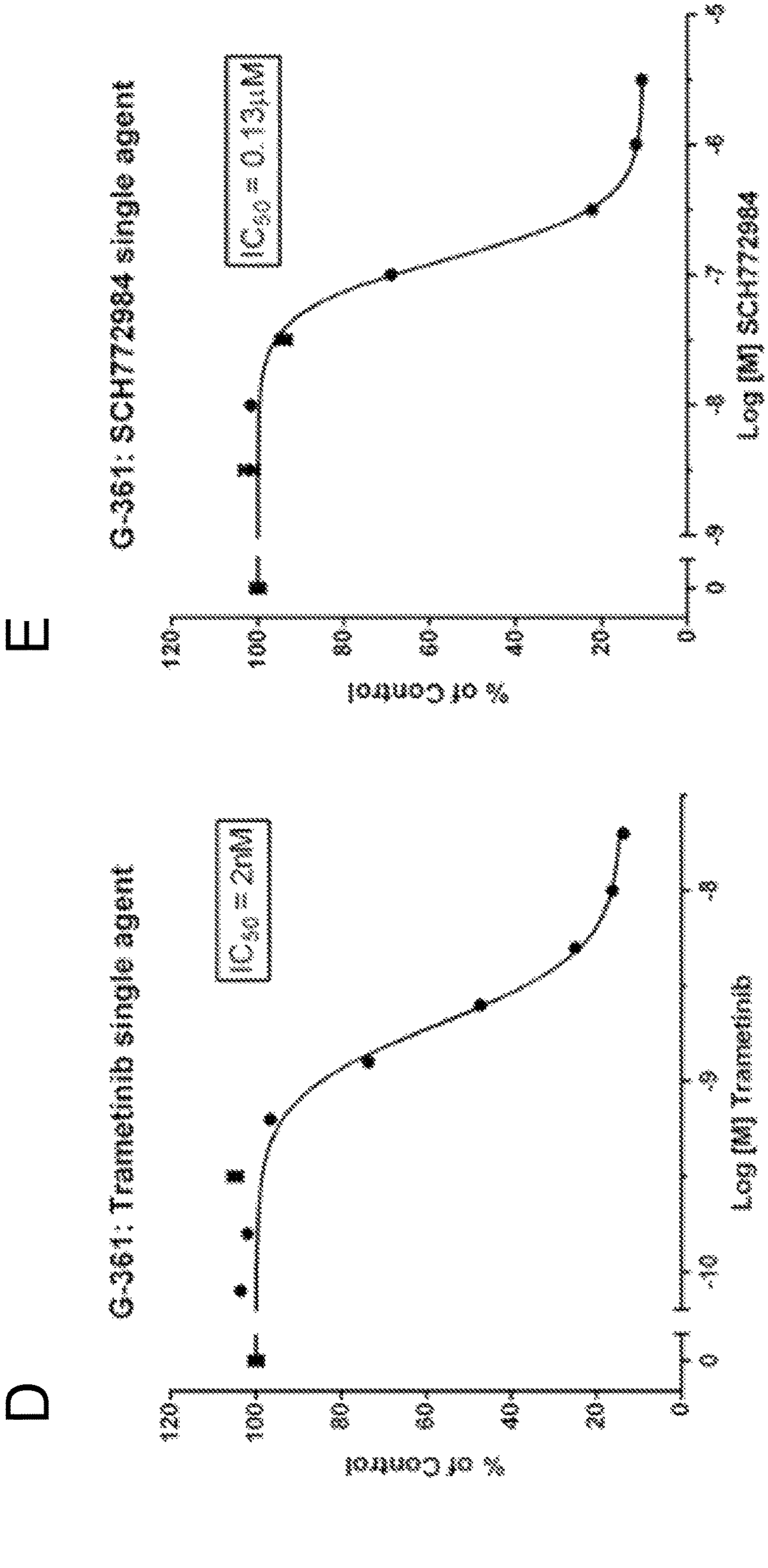

A

FIG. 39, Con't
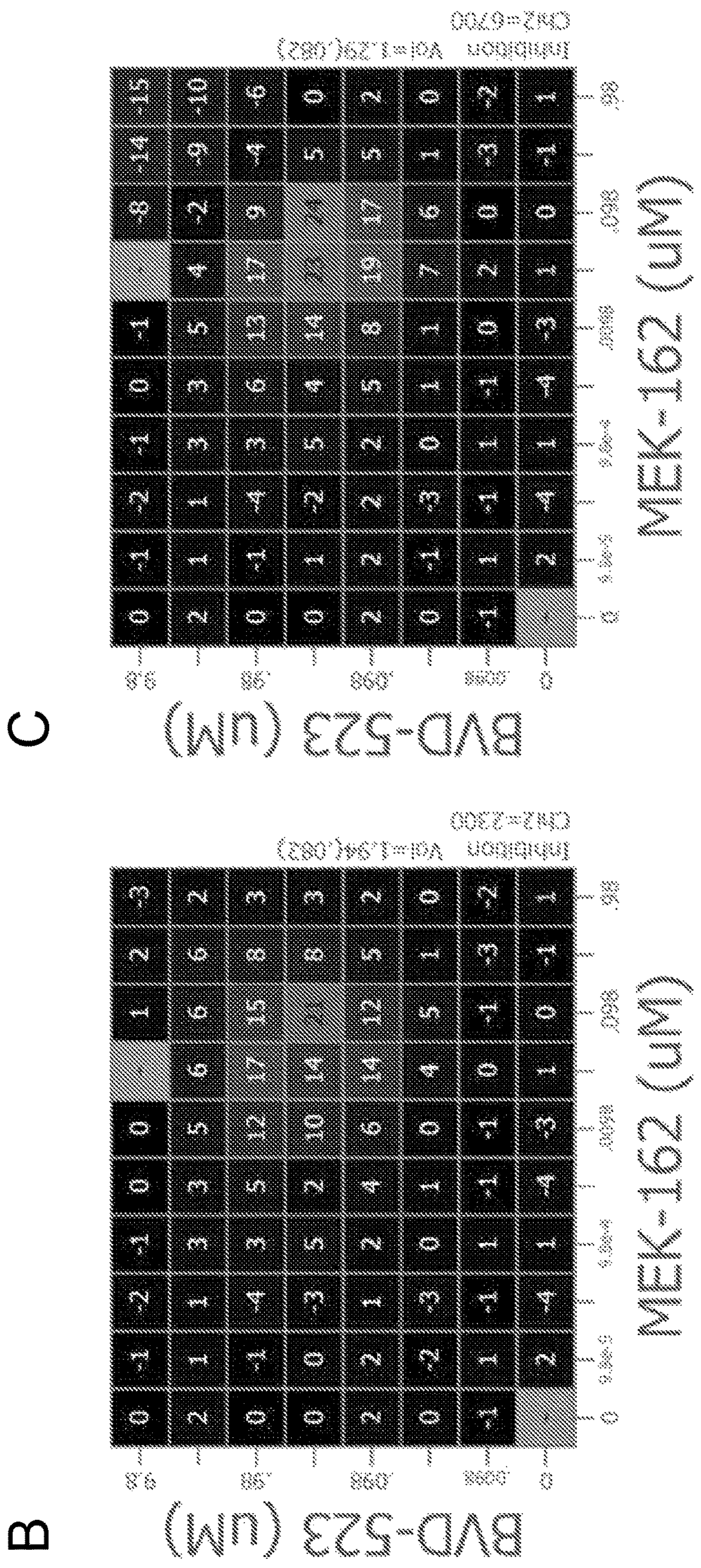

FIG. 39, Con't
D E
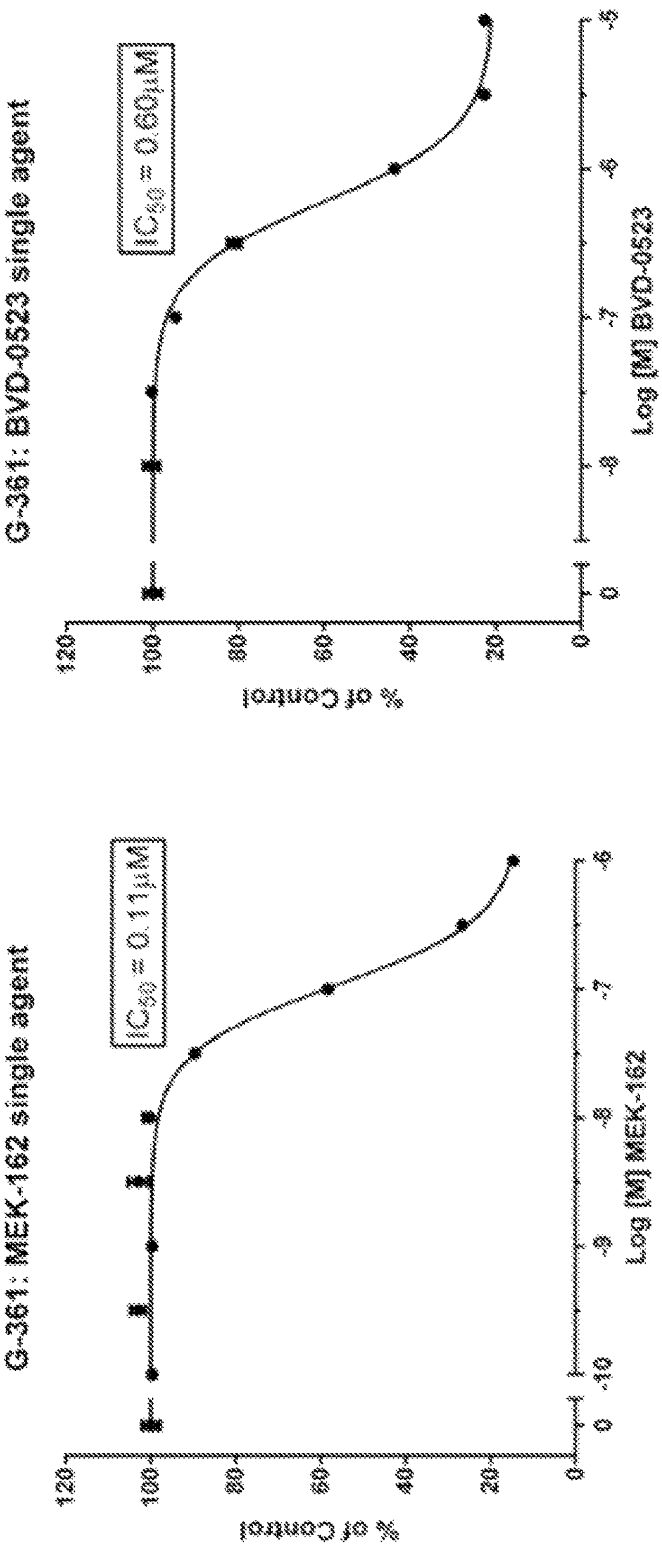

A

FIG. 40, Con't
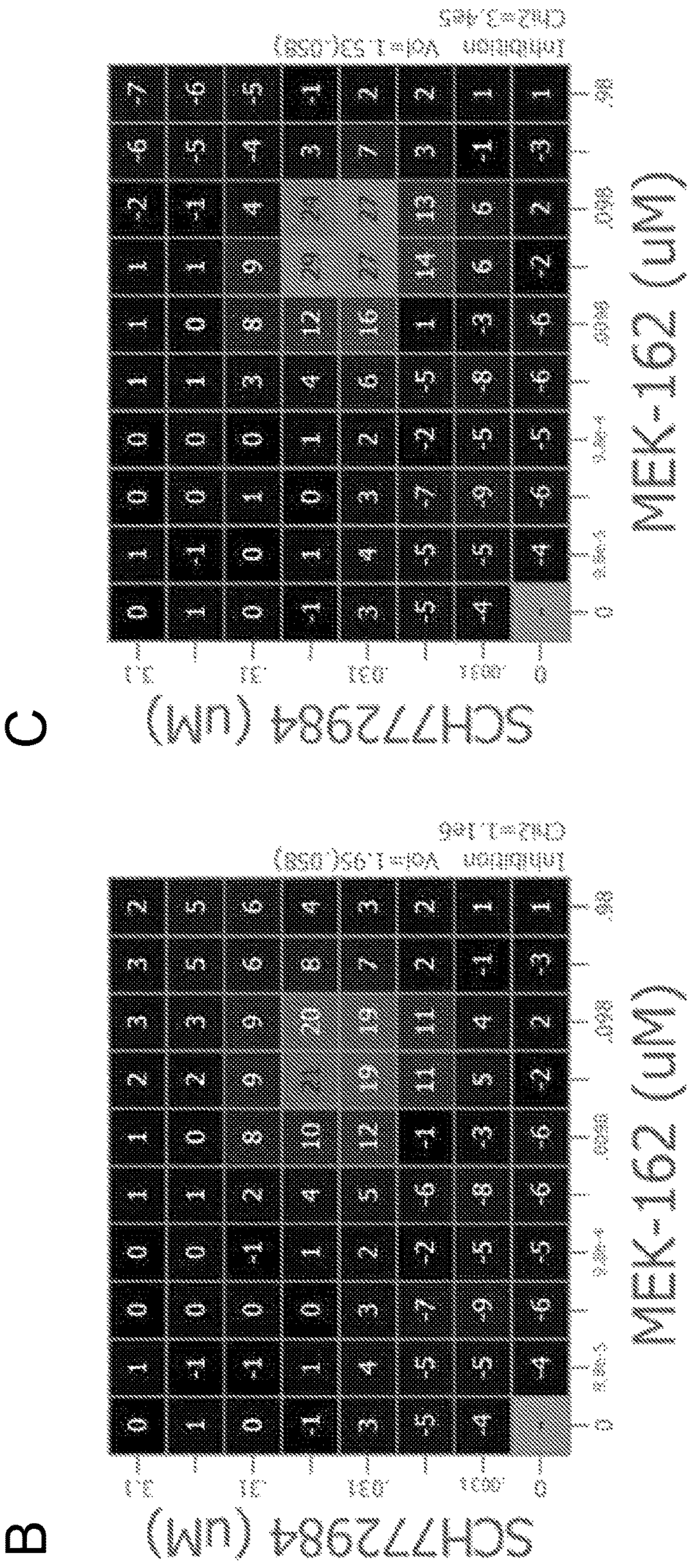

FIG. 40, Con't
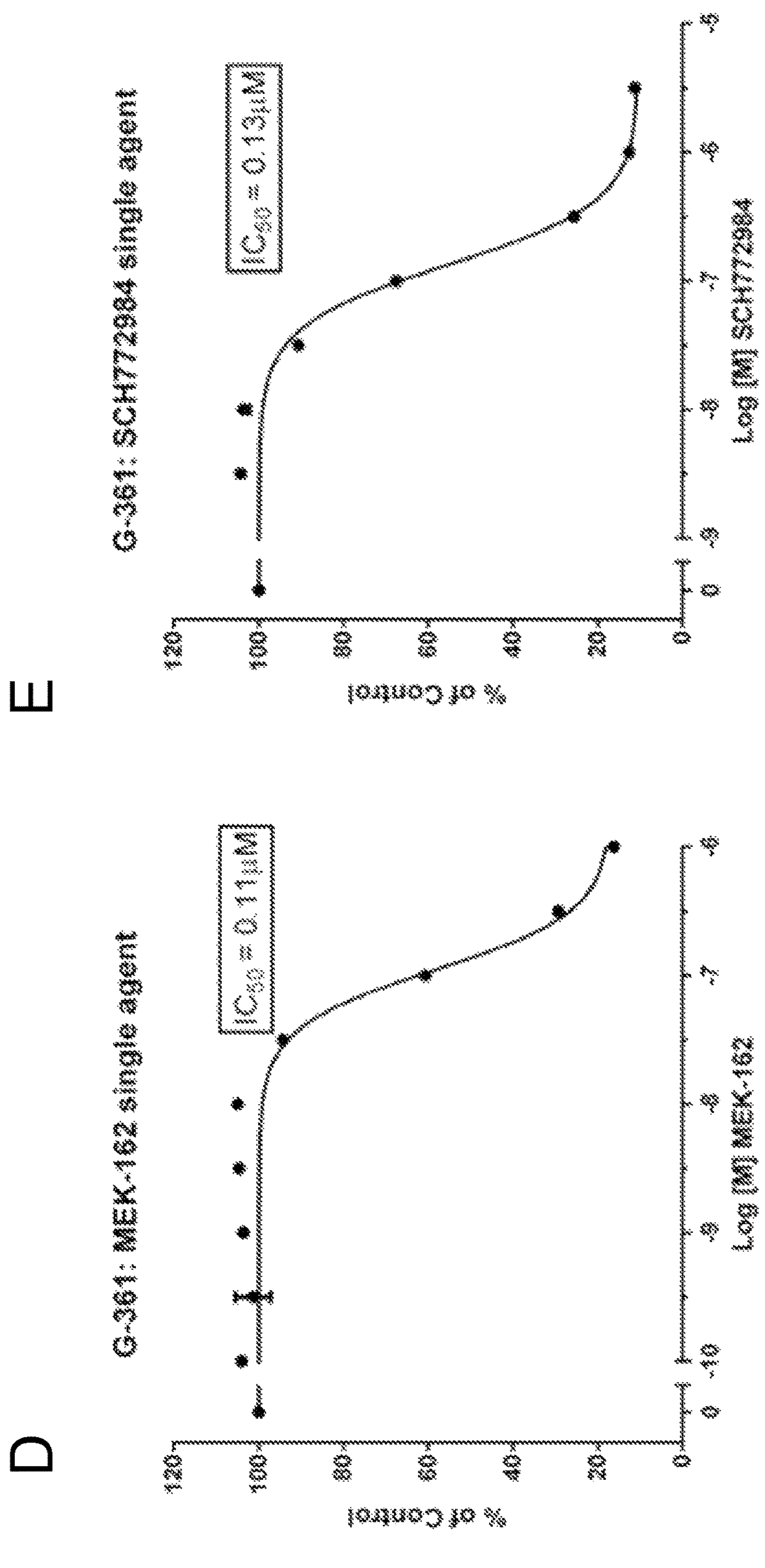

FIG. 41, Con't
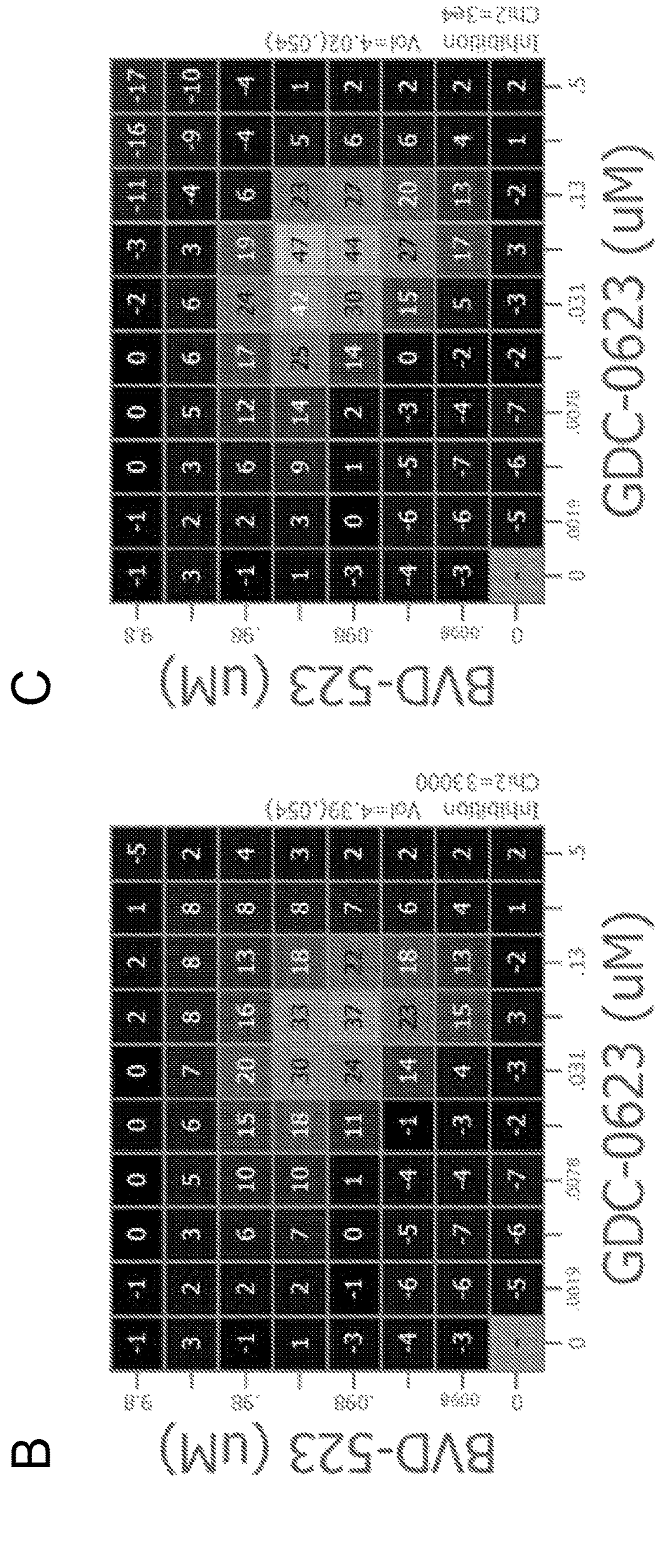

FIG. 41, Con't
E
D
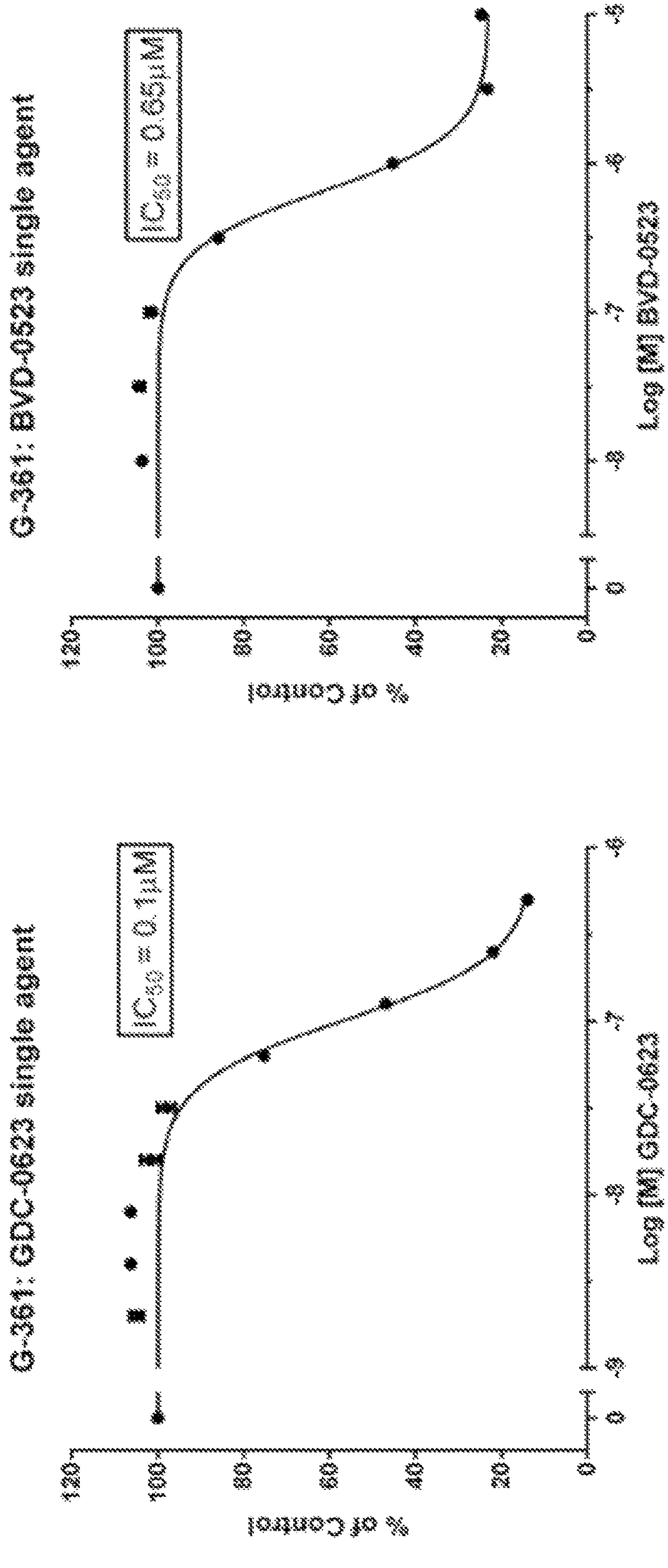

A

FIG. 42, Con't
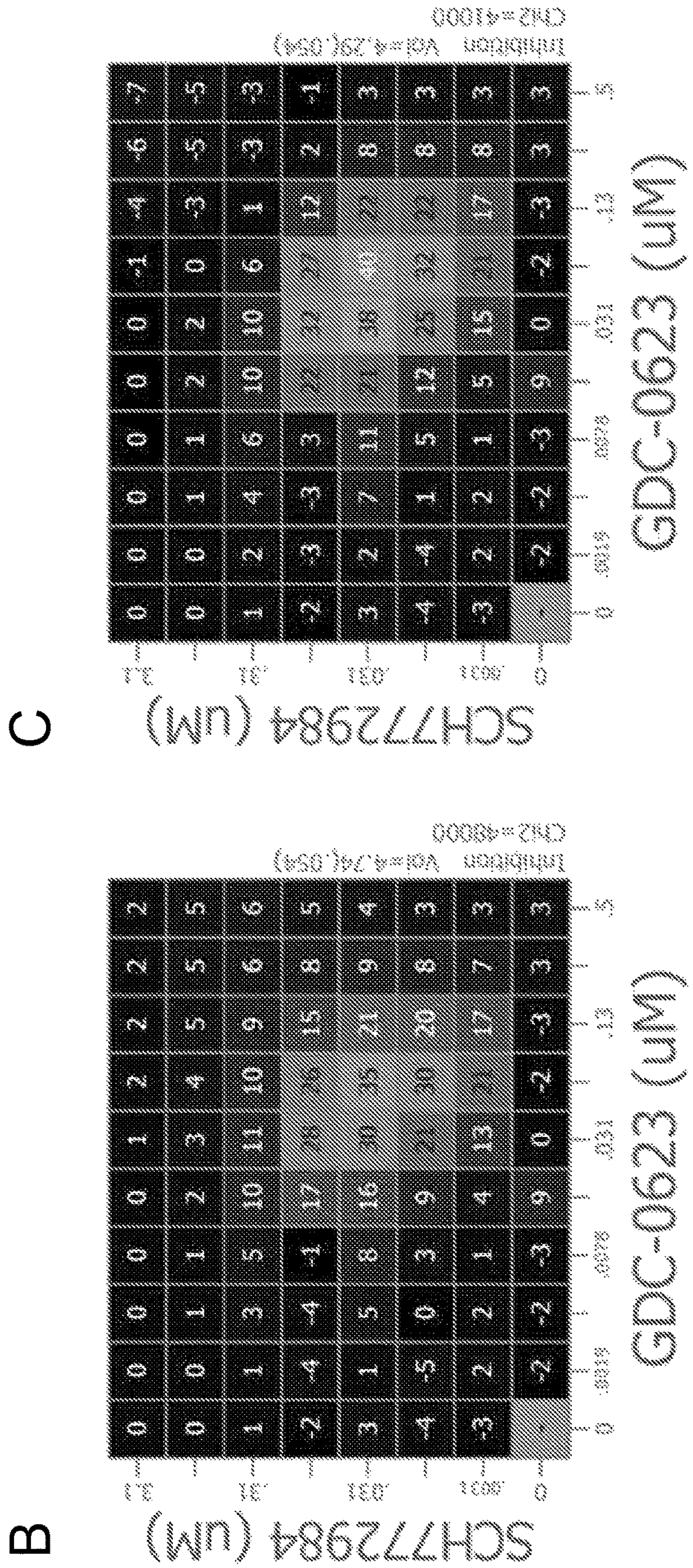

FIG. 42, Con't
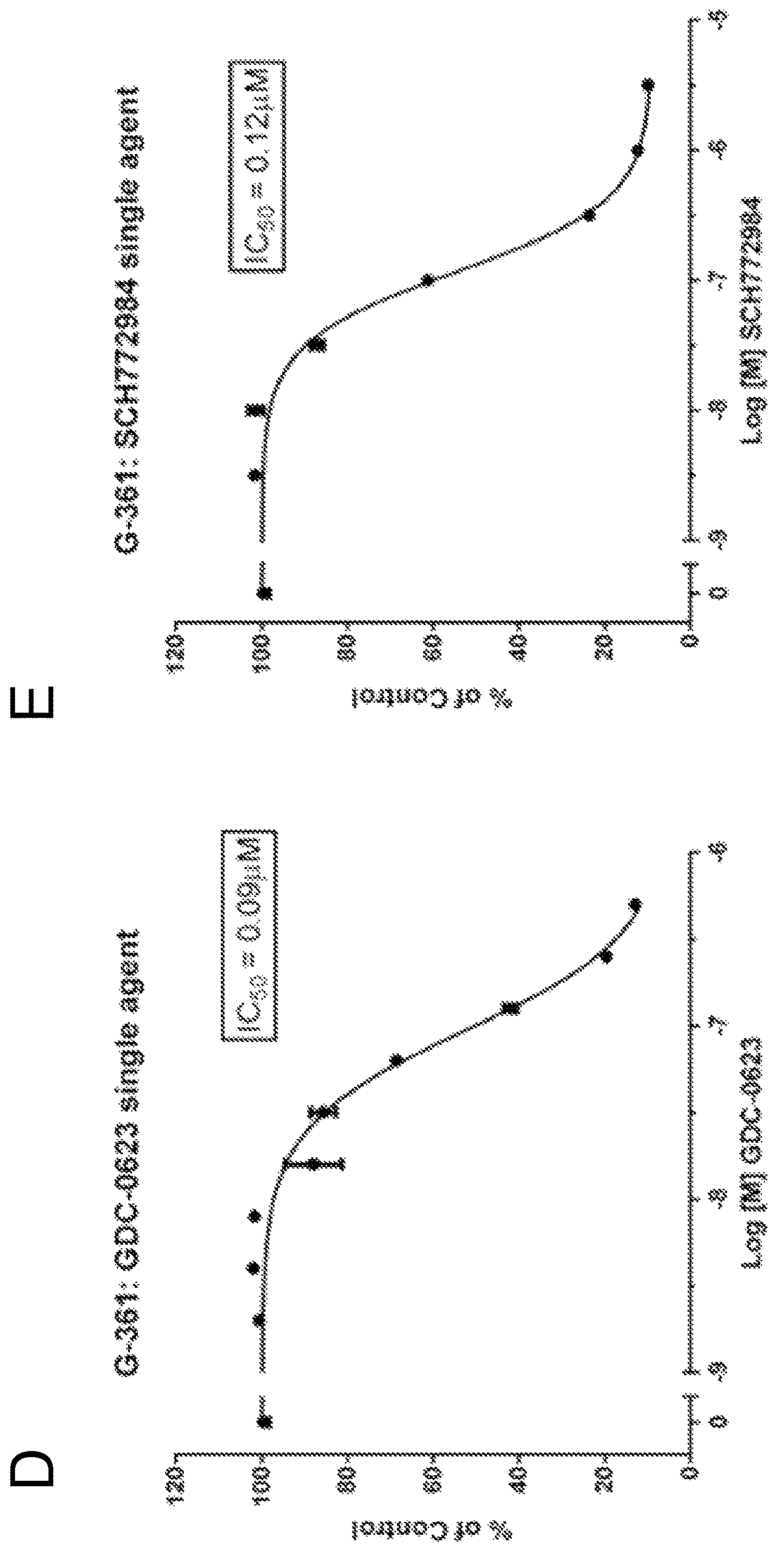

FIG. 43, Con't
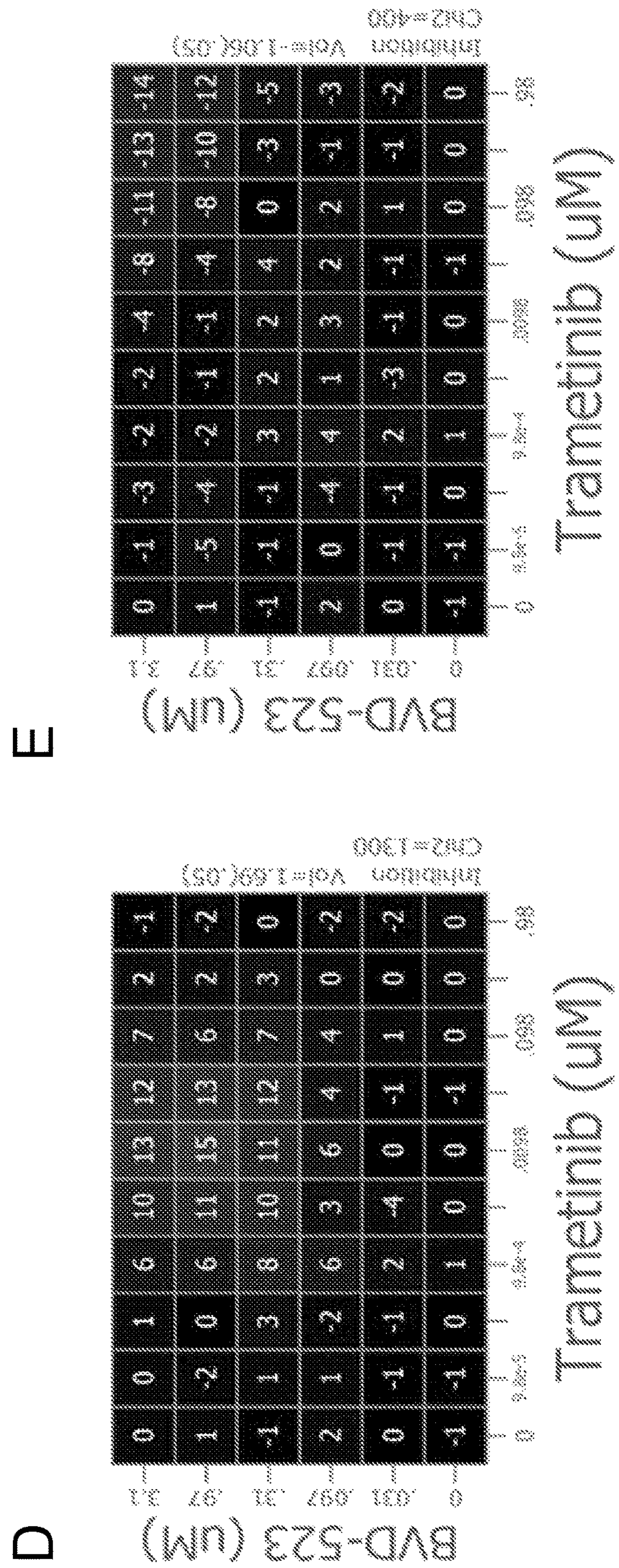

FIG. 44, Con't
E
D
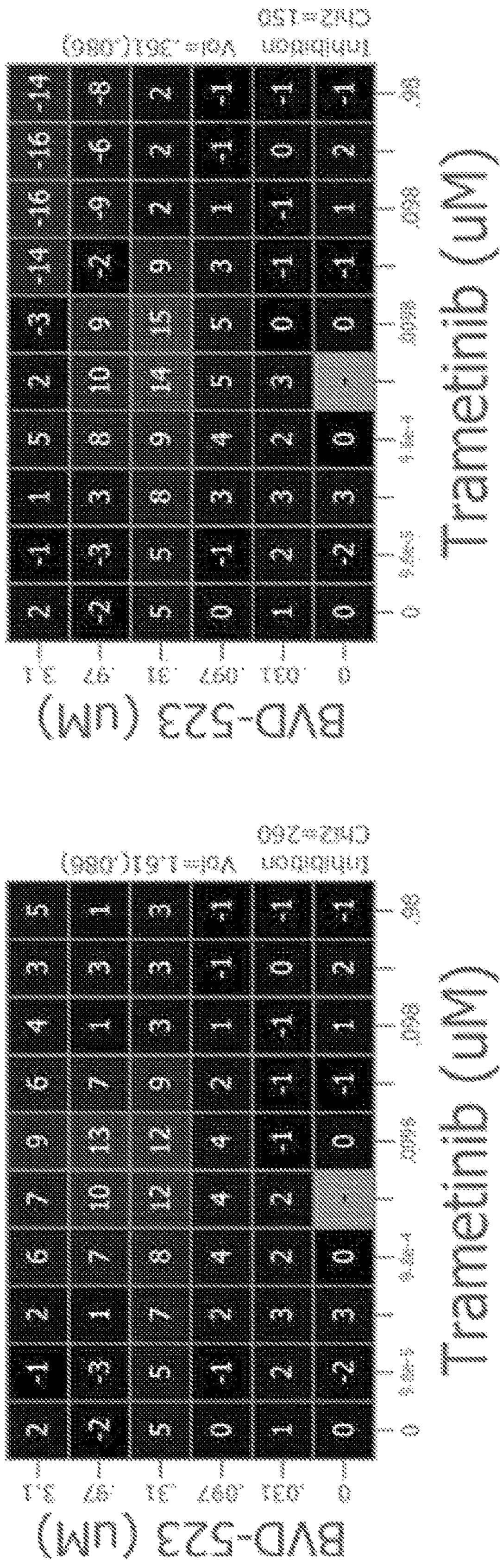

FIG. 45, Con't
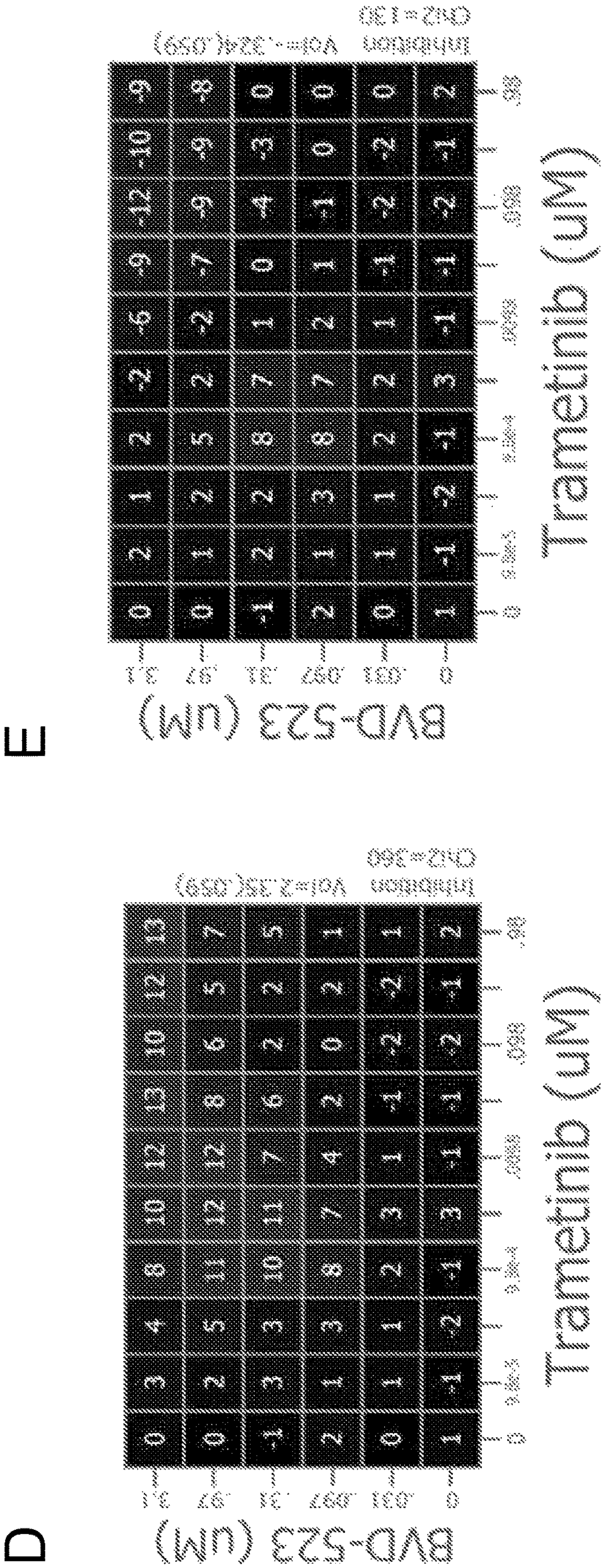

FIG. 46, Con't
E
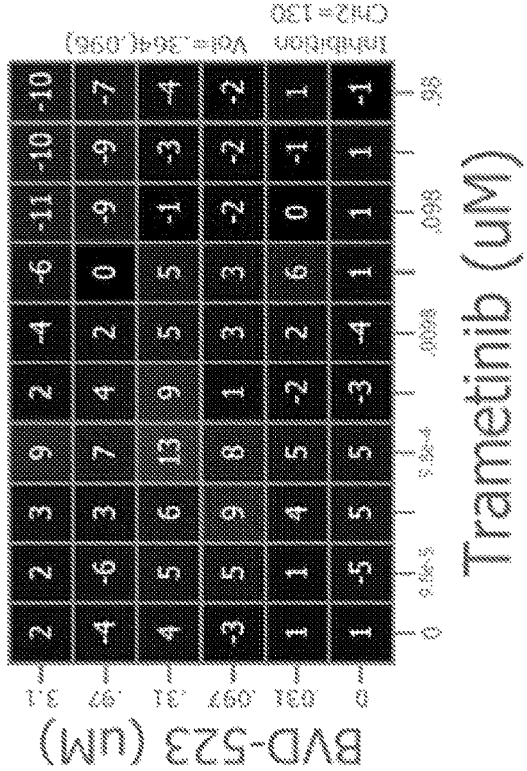
D
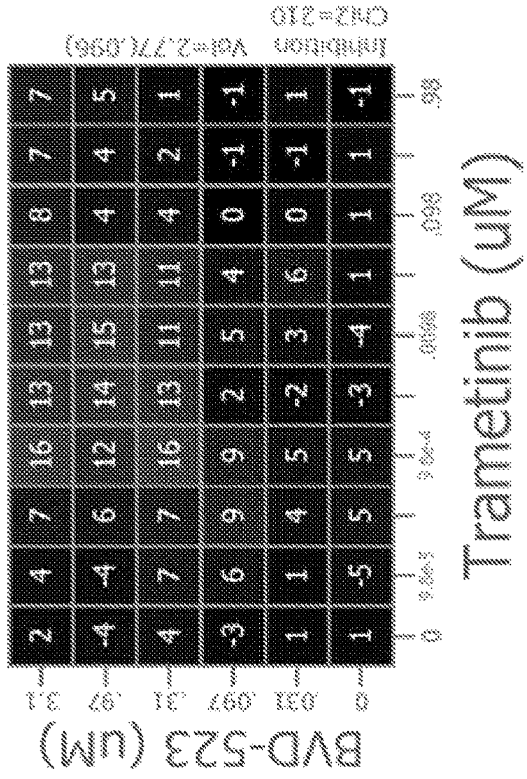

FIG. 47, Con't
E
D
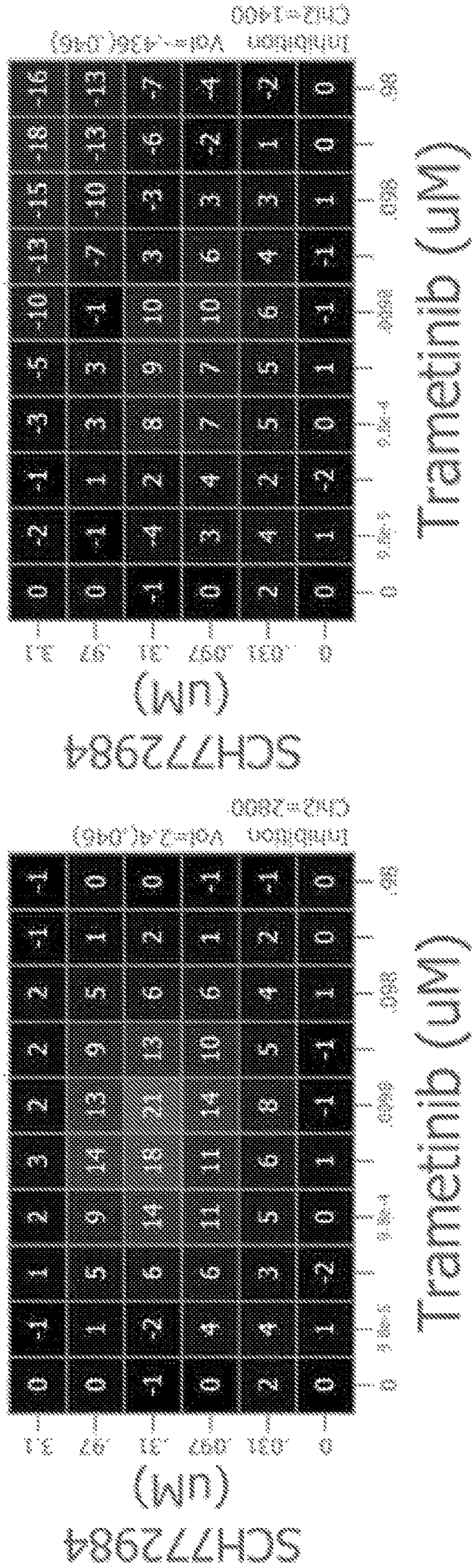

FIG. 48, Con't
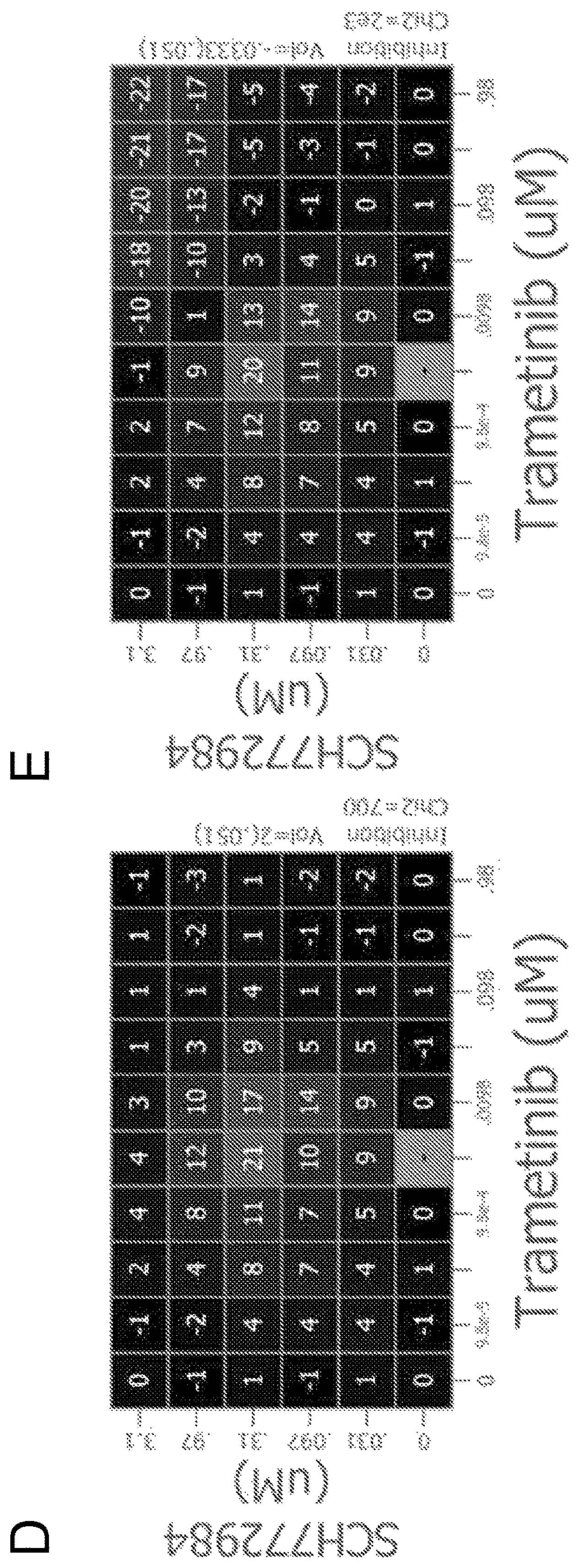

FIG. 49, Con't
E
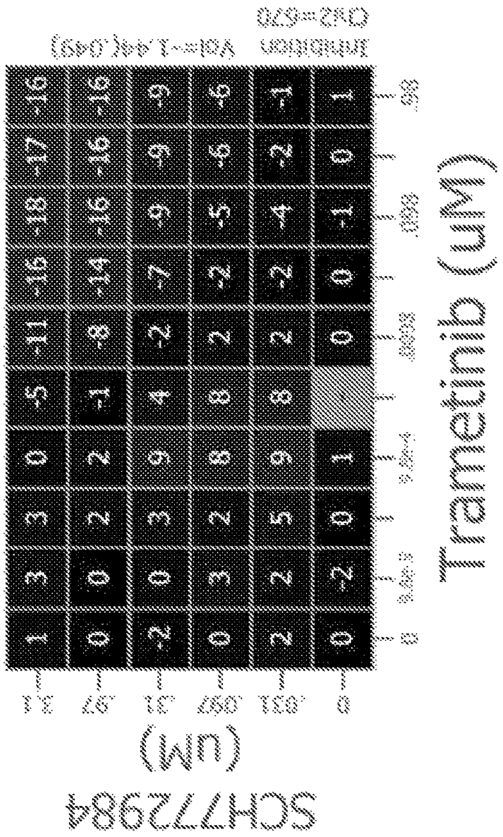
D
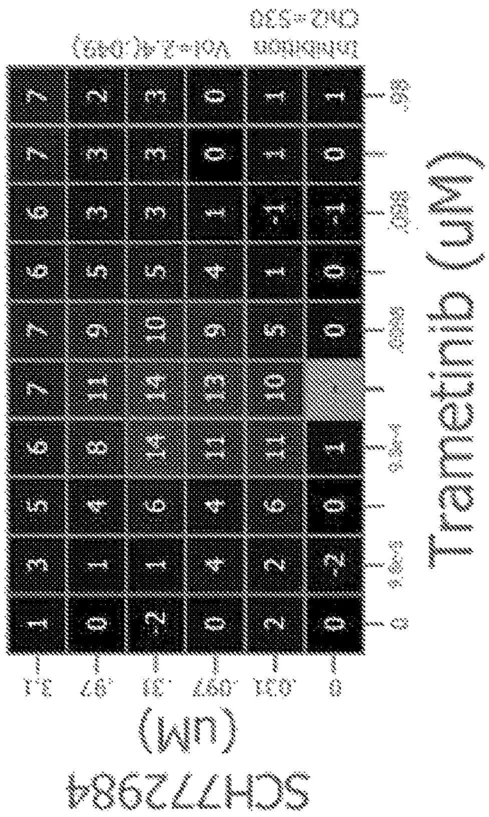

FIG. 50, Con't
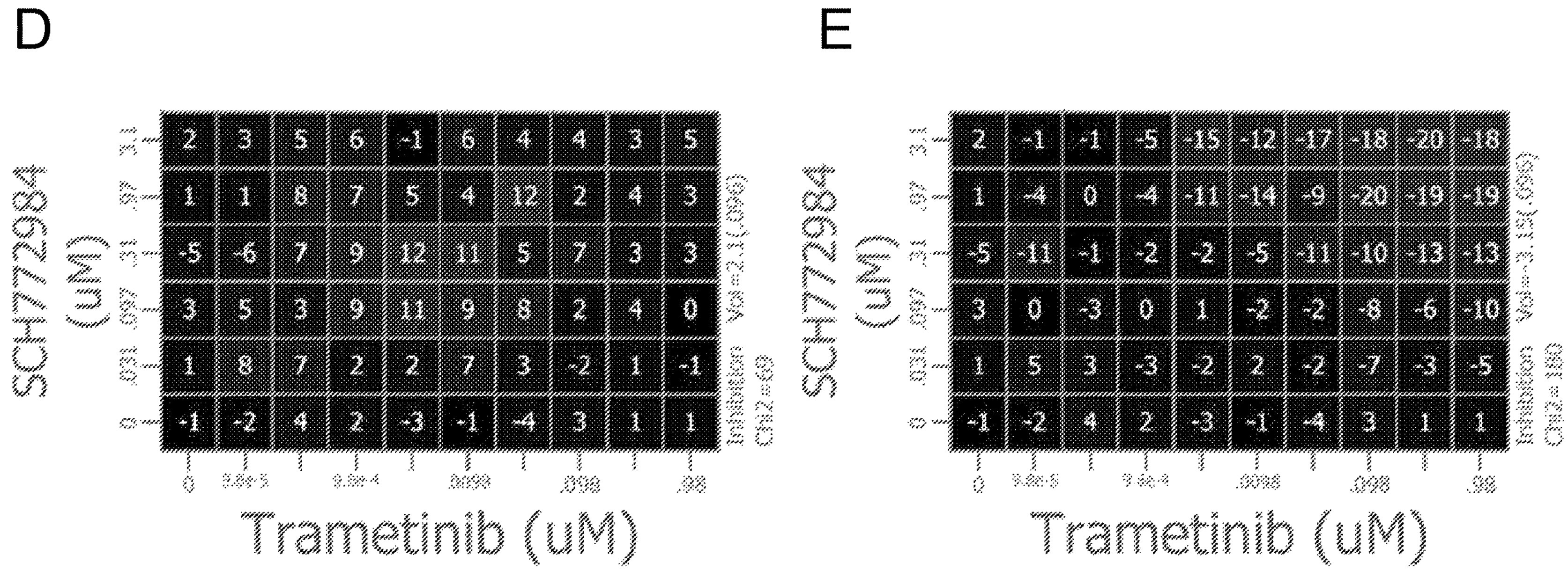

FIG. 51, Con't
E
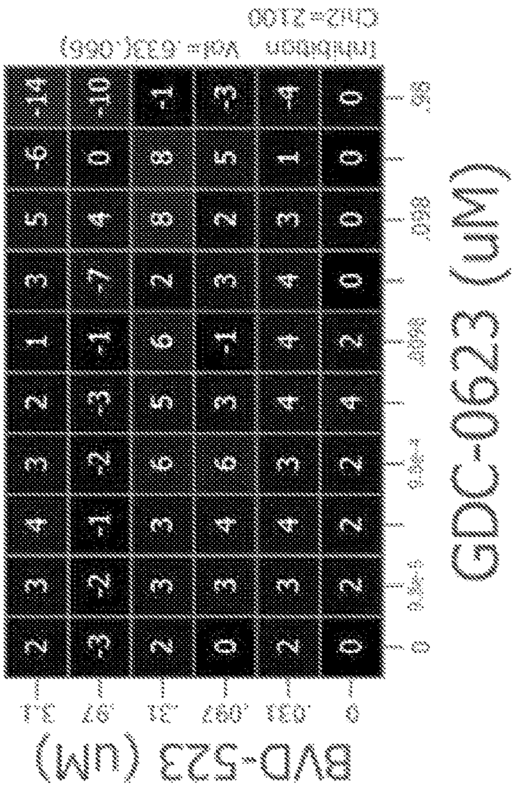
D
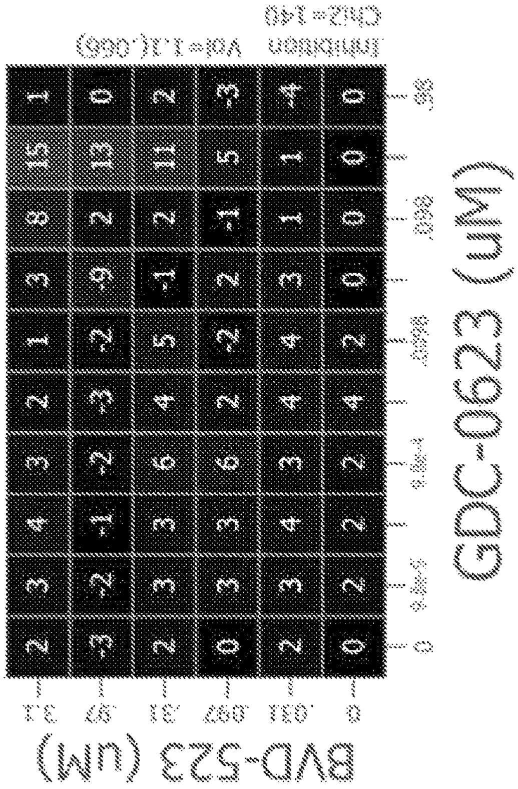

FIG. 52, Con't
E
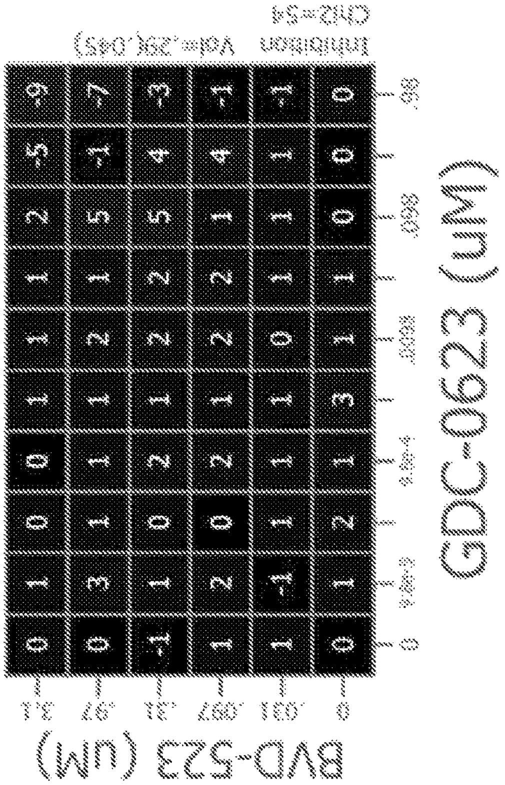
D
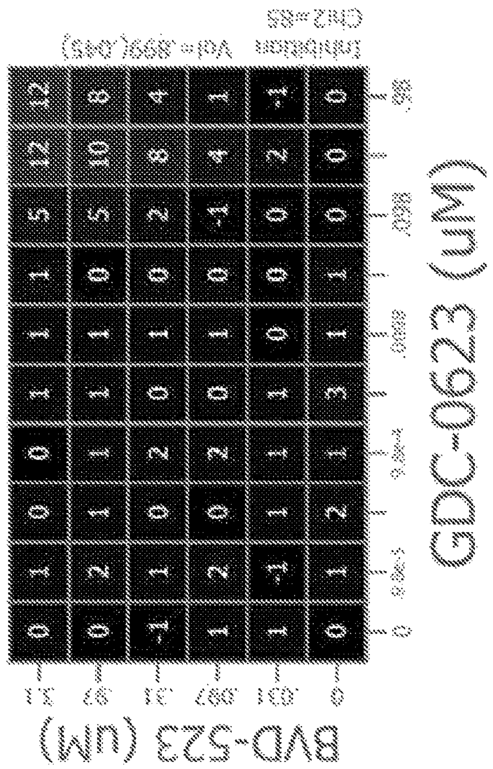

FIG. 53, Con't
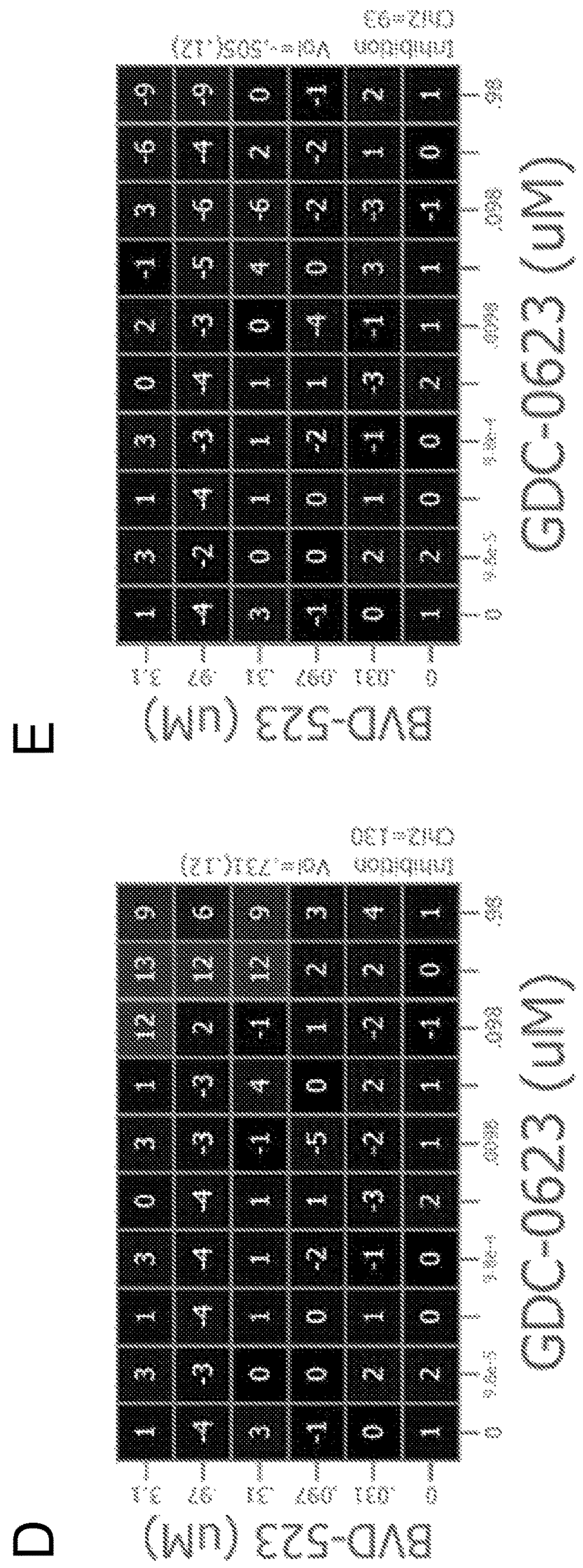

FIG. 54, Con't
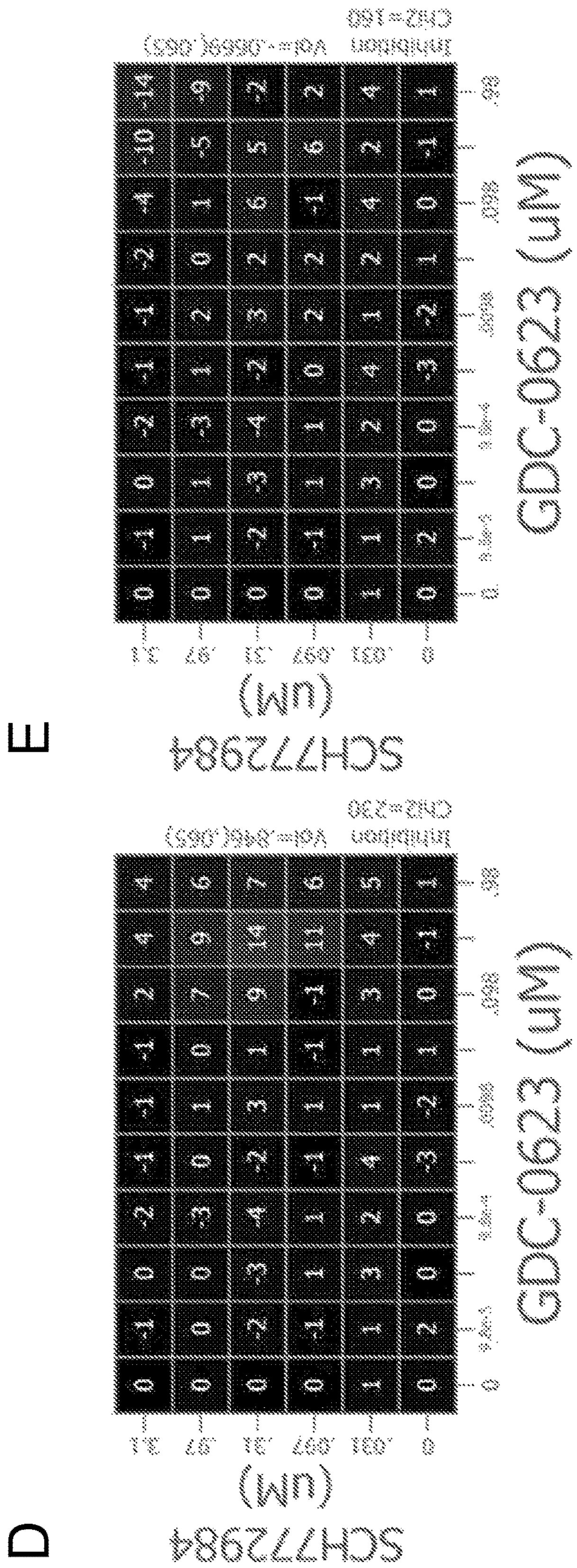

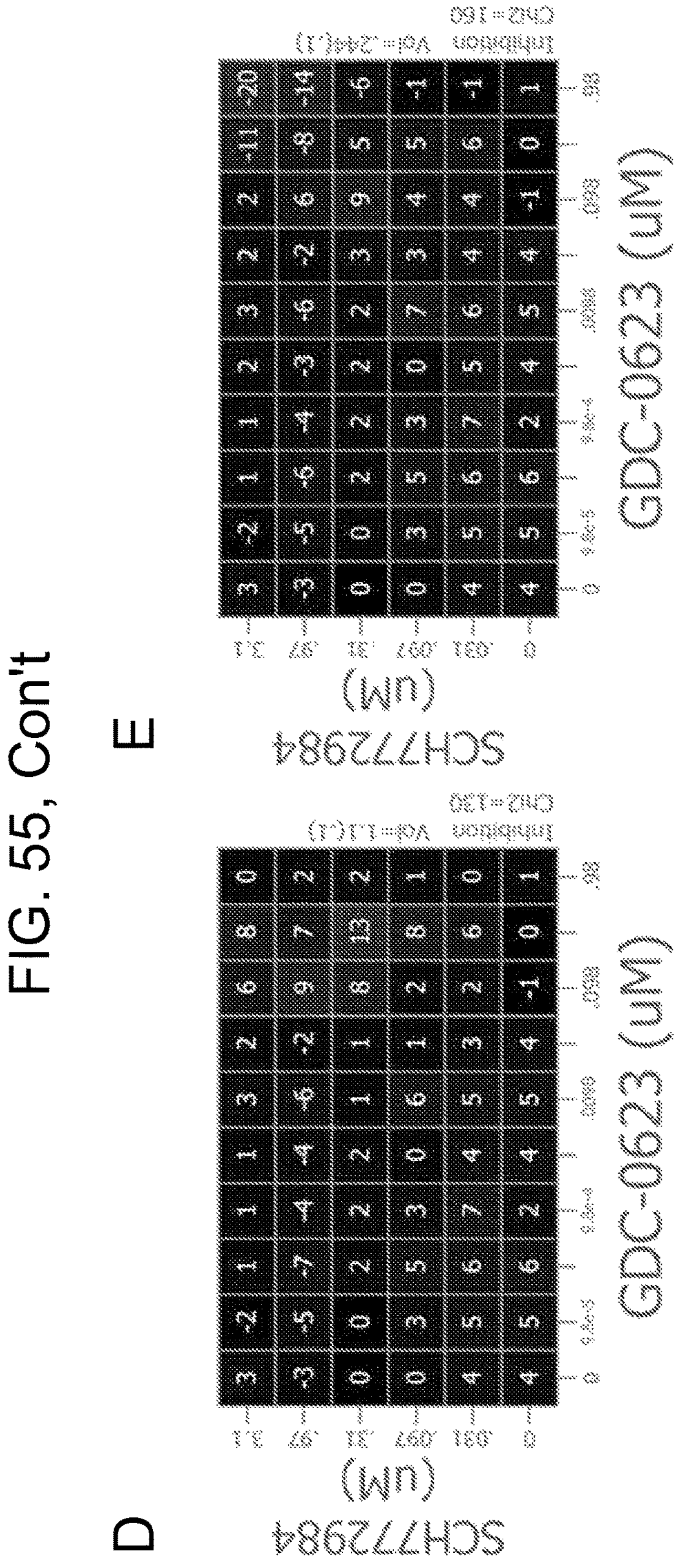
FIG. 55, Con't

FIG. 56, Con't
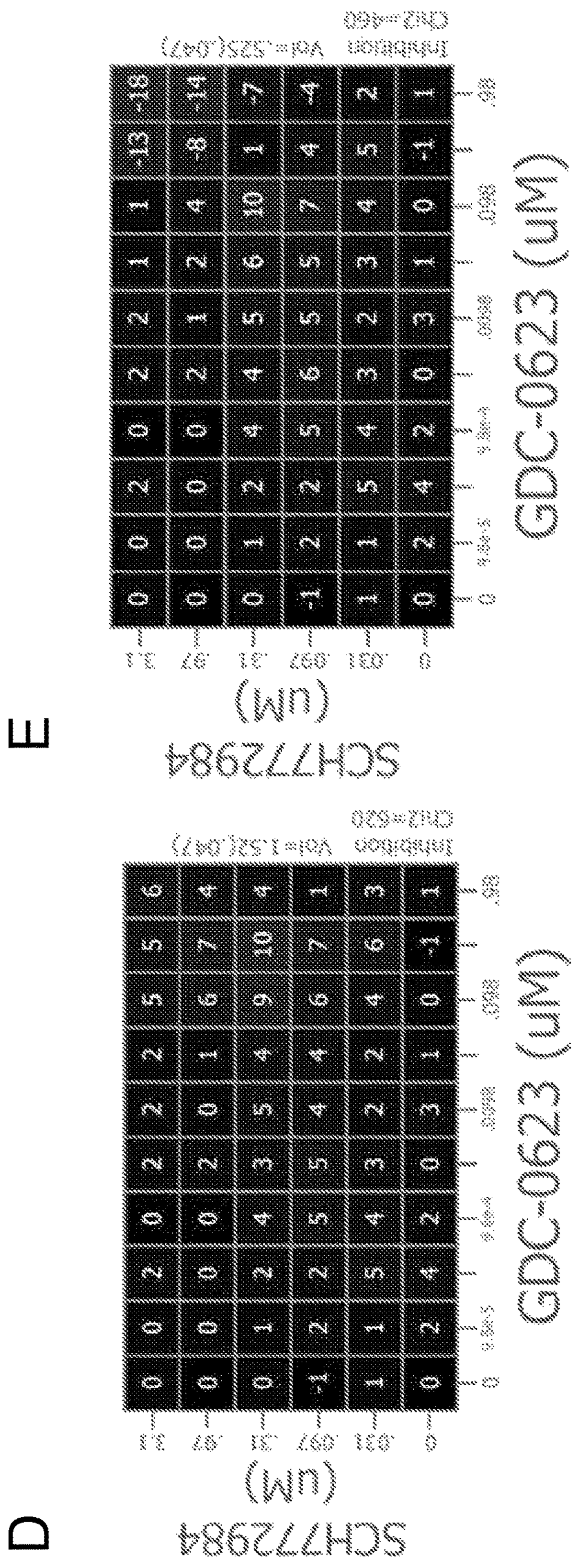

FIG. 57, Con't
E
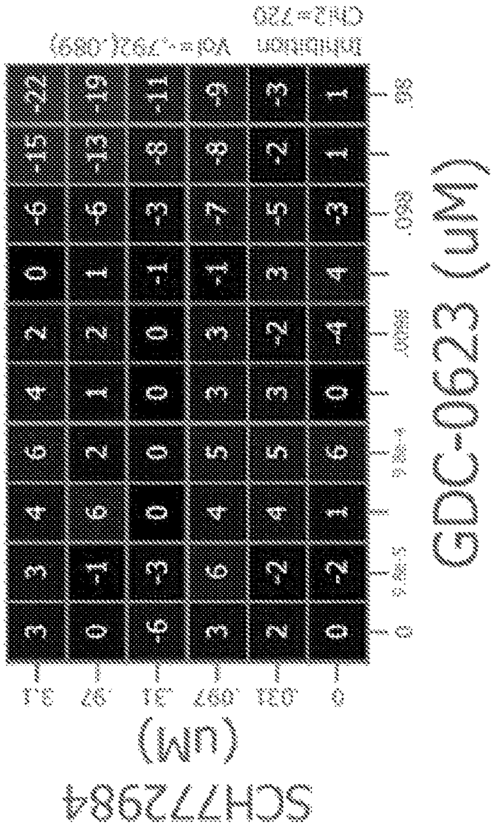
D
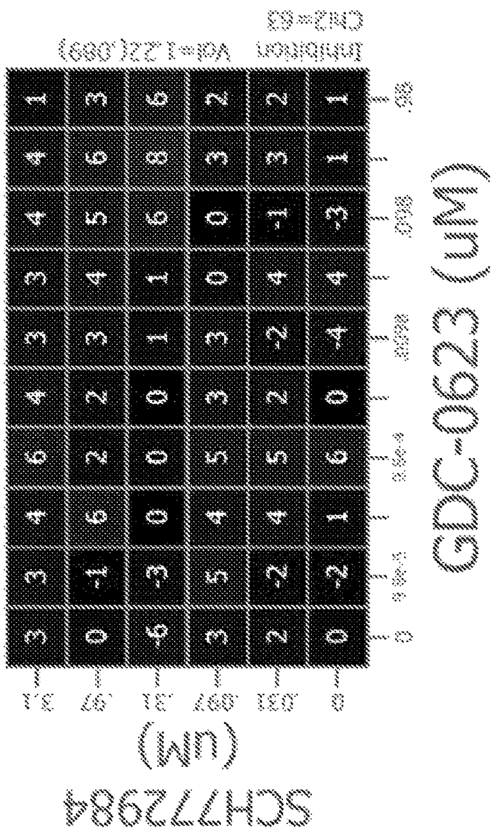

FIG. 58, Con't
D
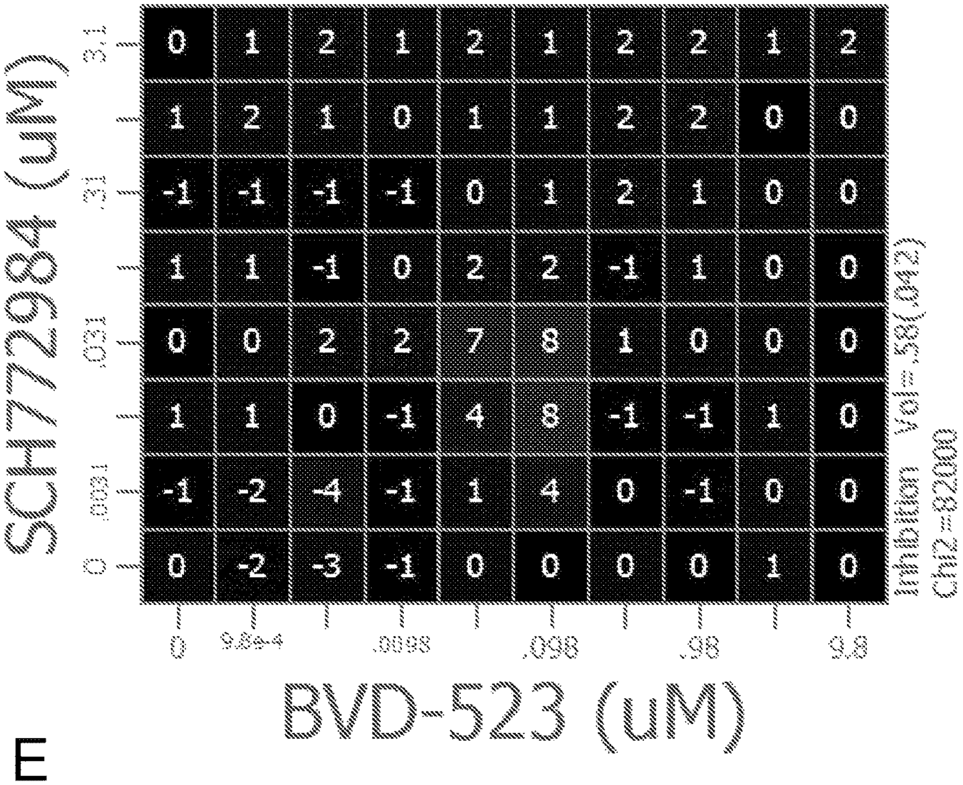
E
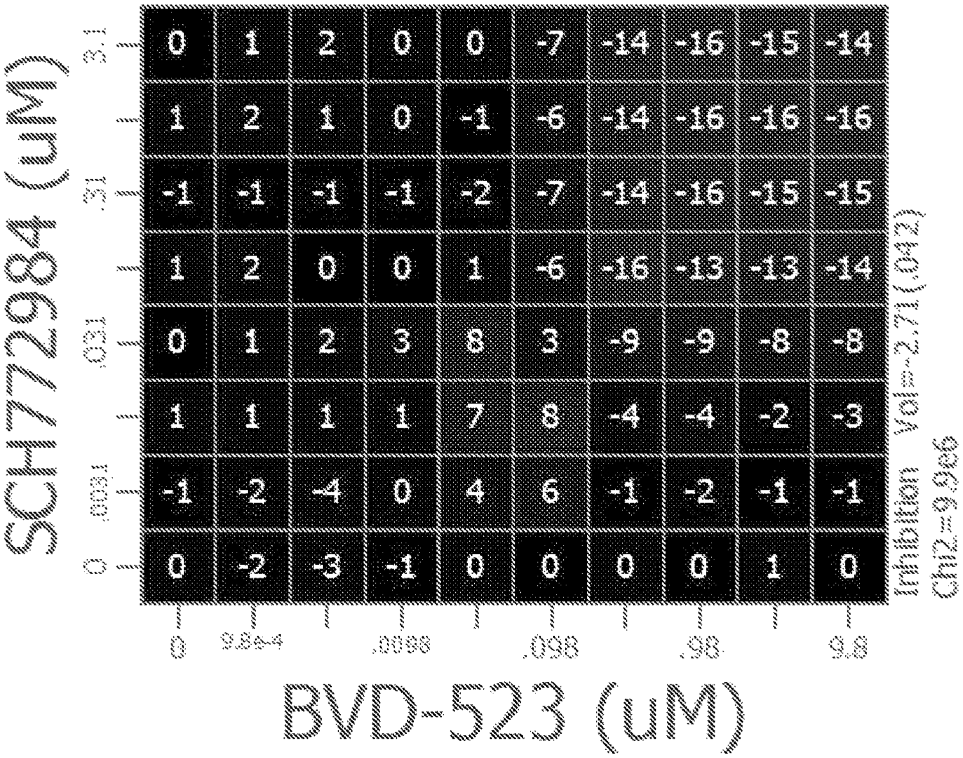

SEQUENCE LISTING

```
<160> NUMBER OF SEQ ID NOS: 128

<210> SEQ ID NO 1
<211> LENGTH: 1061
<212> TYPE: DNA
<213> ORGANISM: Homo sapiens

<400> SEQUENCE: 1

tgccctgcgc ccgcaacccg agccgcaccc gccgcggacg gagcccatgc gcggggcgaa      60

ccgcgcgccc ccgccccccgc cccgccccgg cctcggcccc ggccctggcc ccgggggcag    120

tcgcgcctgt gaacggtggg gcaggagacc ctgtaggagg accccgggcc gcaggcccct    180

gaggagcgat gacggaatat aagctggtgg tggtgggcgc cggcggtgtg ggcaagagtg    240

cgctgaccat ccagctgatc cagaaccatt ttgtggacga atacgacccc actatagagg    300

attcctaccg gaagcaggtg gtcattgatg gggagacgtg cctgttggac atcctggata    360

ccgccggcca ggaggagtac agcgccatgc gggaccagta catgcgcacc ggggagggct    420

tcctgtgtgt gtttgccatc aacaacacca agtcttttga ggacatccac cagtacaggg    480

agcagatcaa acgggtgaag gactcggatg acgtgcccat ggtgctggtg gggaacaagt    540

gtgacctggc tgcacgcact gtggaatctc ggcaggctca ggacctcgcc cgaagctacg    600

gcatccccta catcgagacc tcggccaaga cccggcaggg agtggaggat gccttctaca    660

cgttggtgcg tgagatccgg cagcacaagc tgcggaagct gaaccctcct gatgagagtg    720

gccccggctg catgagctgc aagtgtgtgc tctcctgacg cagcacaagc tcaggacatg    780

gaggtgccgg atgcaggaag gaggtgcaga cggaaggagg aggaaggaag gacggaagca    840

aggaaggaag gaagggctgc tggagcccag tcaccccggg accgtgggcc gaggtgactg    900

cagaccctcc cagggaggct gtgcacagac tgtcttgaac atcccaaatg ccaccggaac    960

cccagccctt agctcccctc ccaggcctct gtgggccctt gtcgggcaca gatgggatca   1020

cagtaaatta ttggatggtc ttgaaaaaaa aaaaaaaaaa a                       1061


<210> SEQ ID NO 2
<211> LENGTH: 189
<212> TYPE: PRT
<213> ORGANISM: Homo sapiens

<400> SEQUENCE: 2

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80
```

-continued

```
Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185


<210> SEQ ID NO 3
<211> LENGTH: 1251
<212> TYPE: DNA
<213> ORGANISM: Homo sapiens

<400> SEQUENCE: 3

tgccctgcgc ccgcaacccg agccgcaccc gccgcggacg gagcccatgc gcggggcgaa      60

ccgcgcgccc ccgccccgc cccgccccgg cctcggcccc ggccctggcc ccgggggcag    120

tcgcgcctgt gaacggtggg gcaggagacc ctgtaggagg accccgggcc gcaggcccct    180

gaggagcgat gacggaatat aagctggtgg tggtgggcgc cggcggtgtg ggcaagagtg    240

cgctgaccat ccagctgatc cagaaccatt ttgtggacga atacgacccc actatagagg    300

attcctaccg gaagcaggtg gtcattgatg gggagacgtg cctgttggac atcctggata    360

ccgccggcca ggaggagtac agcgccatgc gggaccagta catgcgcacc ggggagggct    420

tcctgtgtgt gtttgccatc aacaacacca agtcttttga ggacatccac cagtacaggg    480

agcagatcaa acgggtgaag gactcggatg acgtgcccat ggtgctggtg gggaacaagt    540

gtgacctggc tgcacgcact gtggaatctc ggcaggctca ggacctcgcc cgaagctacg    600

gcatccccta catcgagacc tcggccaaga cccggcaggg cagccgctct ggctctagct    660

ccagctccgg gaccctctgg gaccccccgg gacccatgtg acccagcggc ccctcgcgct    720

ggagtggagg atgccttcta cacgttggtg cgtgagatcc ggcagcacaa gctgcggaag    780

ctgaaccctc ctgatgagag tggccccggc tgcatgagct gcaagtgtgt gctctcctga    840

cgcaggtgag ggggactccc agggcggccg ccacgcccac cggatgaccc cggctccccg    900

cccctgccgg tctcctggcc tgcggtcagc agcctccctt gtgccccgcc cagcacaagc    960

tcaggacatg gaggtgccgg atgcaggaag gaggtgcaga cggaaggagg aggaaggaag   1020

gacggaagca aggaaggaag gaagggctgc tggagcccag tcaccccggg accgtgggcc   1080

gaggtgactg cagaccctcc cagggaggct gtgcacagac tgtcttgaac atcccaaatg   1140

ccaccggaac cccagccctt agctcccctc ccaggcctct gtgggccctt gtcgggcaca   1200

gatgggatca cagtaaatta ttggatggtc ttgaaaaaaa aaaaaaaaaa a            1251


<210> SEQ ID NO 4
<211> LENGTH: 170
<212> TYPE: PRT
<213> ORGANISM: Homo sapiens

<400> SEQUENCE: 4
```

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Ser Arg Ser Gly Ser Ser Ser Ser Ser
145                 150                 155                 160

Gly Thr Leu Trp Asp Pro Pro Gly Pro Met
                165                 170
```

<210> SEQ ID NO 5
<211> LENGTH: 1169
<212> TYPE: DNA
<213> ORGANISM: Homo sapiens

<400> SEQUENCE: 5

```
tgccctgcgc ccgcaacccg agccgcaccc gccgcggacg gagcccatgc gcggggcgaa     60

ccgcgcgccc ccgcccccgc cccgccccgg cctcggcccc ggccctggcc ccgggggcag    120

tcgcgcctgt gaacggtggg gcaggagacc ctgtaggagg accccgggcc gcaggcccct    180

gaggagcgat gacggaatat aagctggtgg tggtgggcgc cggcggtgtg ggcaagagtg    240

cgctgaccat ccagctgatc cagaaccatt ttgtggacga atacgacccc actatagagg    300

attcctaccg gaagcaggtg gtcattgatg gggagacgtg cctgttggac atcctggata    360

ccgccggcca ggaggagtac agcgccatgc gggaccagta catgcgcacc ggggagggct    420

tcctgtgtgt gtttgccatc aacaacacca agtcttttga ggacatccac cagtacaggg    480

agcagatcaa acgggtgaag gactcggatg acgtgcccat ggtgctggtg gggaacaagt    540

gtgacctggc tgcacgcact gtggaatctc ggcaggctca ggacctcgcc cgaagctacg    600

gcatccccta catcgagacc tcggccaaga cccggcaggg agtggaggat gccttctaca    660

cgttggtgcg tgagatccgg cagcacaagc tgcggaagct gaaccctcct gatgagagtg    720

gccccggctg catgagctgc aagtgtgtgc tctcctgacg caggtgaggg ggactcccag    780

ggcggccgcc acgcccaccg gatgaccccg gctccccgcc cctgccggtc tcctggcctg    840

cggtcagcag cctcccttgt gccccgccca gcacaagctc aggacatgga ggtgccggat    900

gcaggaagga ggtgcagacg gaaggaggag gaaggaagga cggaagcaag gaaggaagga    960

agggctgctg gagcccagtc accccgggac cgtgggccga ggtgactgca gaccctccca   1020

gggaggctgt gcacagactg tcttgaacat cccaaatgcc accggaaccc cagcccttag   1080

ctcccctccc aggcctctgt gggcccttgt cgggcacaga tgggatcaca gtaaattatt   1140
```

ggatggtctt gaaaaaaaaa aaaaaaaaa 1169

<210> SEQ ID NO 6
<211> LENGTH: 189
<212> TYPE: PRT
<213> ORGANISM: Homo sapiens

<400> SEQUENCE: 6

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly
35 40 45

Glu Thr Cys Leu Leu Asp Ile Leu Asp Thr Ala Gly Gln Glu Glu Tyr
50 55 60

Ser Ala Met Arg Asp Gln Tyr Met Arg Thr Gly Glu Gly Phe Leu Cys
65 70 75 80

Val Phe Ala Ile Asn Asn Thr Lys Ser Phe Glu Asp Ile His Gln Tyr
85 90 95

Arg Glu Gln Ile Lys Arg Val Lys Asp Ser Asp Asp Val Pro Met Val
100 105 110

Leu Val Gly Asn Lys Cys Asp Leu Ala Ala Arg Thr Val Glu Ser Arg
115 120 125

Gln Ala Gln Asp Leu Ala Arg Ser Tyr Gly Ile Pro Tyr Ile Glu Thr
130 135 140

Ser Ala Lys Thr Arg Gln Gly Val Glu Asp Ala Phe Tyr Thr Leu Val
145 150 155 160

Arg Glu Ile Arg Gln His Lys Leu Arg Lys Leu Asn Pro Pro Asp Glu
165 170 175

Ser Gly Pro Gly Cys Met Ser Cys Lys Cys Val Leu Ser
180 185

<210> SEQ ID NO 7
<211> LENGTH: 1246
<212> TYPE: DNA
<213> ORGANISM: Rattus norvegicus

<400> SEQUENCE: 7
gcccggcgcc cgcagcccga gccgcacccg ccgcggacgg agcccatgcg cgggcccagt 60
cggcgcccgt ccgcgccccc gccctgcccc ggccccggcc ccgggggcag tcgcgccagc 120
aagcggtggg gcaggagctc ctggtttggc agcccctgta gaagcgatga cagaatacaa 180
gcttgtggtg gtgggcgctg gaggcgtggg aaagagtgcc ctgaccatcc agctgatcca 240
gaaccatttt gtggacgagt atgatcccac tatagaggac tcctaccgga aacaggtagt 300
cattgatggg gagacgtgtt tactggacat cttagacaca gcaggtcaag aagagtatag 360
tgccatgcgg gaccagtaca tgcgcacagg ggagggcttc ctctgtgtat ttgccatcaa 420
caacaccaag tcctttgaag acatccatca gtacagggag cagatcaagc gggtgaaaga 480
ttcagatgat gtgccaatgg tgctggtggg caacaagtgt gacctggccg ctcgcactgt 540
tgagtctcgg caggcccagg accttgctcg cagctatggc atcccctaca ttgaaacatc 600
agccaagacc cggcagggtg tggaggatgc cttctacaca ctagtacgtg agattcggca 660
gcataaactg cggaaactga acccgcctga tgagagtggc cctggctgca tgagctgcaa 720

```
gtgtgtgctg tcctgacacc aggctcagga cgaggaggtg ccggatgcag ggaggaggtg    780

ctgtcggaag gaaggaaaga ggagggaagg aaggaaacga tgctggagcc agtccagtcc    840

agggatggtg gacagatgtg accaagacct tcgcatggac aatttgaaca gactgtcatg    900

aactatccct gttgccactg gcacccaagt cctccgcccc tctcagctcc cttgggcgcc    960

tatgagggca catgttgaat cacagtaaat tatttgatgg tcttgacttg tctctggctg   1020

gaagtaggag gtgtagtgcc tgtggcctca cagaagatac tggggacctg ggatctatca   1080

tctgccttgt tcctgtttct agaagaggct ggggaggctg gcctgggacc tgggactgtg   1140

cagcccttct cttctgcctg cctcaactgt cttgtgtttc ctgcagaaag ttataaataa   1200

cacaagaata gtcaggtgat atgaaaaaaa aaaaaaaaaa aaaaaa                  1246
```

<210> SEQ ID NO 8
<211> LENGTH: 189
<212> TYPE: PRT
<213> ORGANISM: Rattus norvegicus

<400> SEQUENCE: 8

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185
```

<210> SEQ ID NO 9
<211> LENGTH: 1392
<212> TYPE: DNA
<213> ORGANISM: Rattus norvegicus

<400> SEQUENCE: 9

```
gcccggcgcc cgcagcccga gccgcacccg ccgcggacgg agcccatgcg cgggcccagt     60

cggcgcccgt ccgcgccccc gccctgcccc ggccccggcc ccgggggcag tcgcgccagc    120

aagcggtggg gcaggagctc ctggtttggc agcccctgta gaagcgatga cagaatacaa    180

gcttgtggtg gtgggcgctg gaggcgtggg aaagagtgcc ctgaccatcc agctgatcca    240

gaaccatttt gtggacgagt atgatcccac tatagaggac tcctaccgga aacaggtagt    300
```

-continued

```
cattgatggg gagacgtgtt tactggacat cttagacaca gcaggtcaag aagagtatag    360

tgccatgcgg gaccagtaca tgcgcacagg ggagggcttc ctctgtgtat ttgccatcaa    420

caacaccaag tcctttgaag acatccatca gtacagggag cagatcaagc gggtgaaaga    480

ttcagatgat gtgccaatgg tgctggtggg caacaagtgt gacctggccg ctcgcactgt    540

tgagtctcgg caggcccagg accttgctcg cagctatggc atcccctaca ttgaaacatc    600

agccaagacc cggcagggtg tggaggatgc cttctacaca ctagtacgtg agattcggca    660

gcataaactg cggaaactga acccgcctga tgagagtggc cctggctgca tgagctgcaa    720

gtgtgtgctg tcctgacacc aggtgaggca gggaccagca agacatctgg ggcagtgacc    780

tcagctagcc agatgaactt catatccact ttgatgtccc tgctccccca attctgccaa    840

tccccctgcc tgcagtcagt catgtccttt gtgcccgtcc cggcacaggc tcaggacgag    900

gaggtgccgg atgcagggag gaggtgctgt cggaaggaag gaaagaggag ggaaggaagg    960

aaacgatgct ggagccagtc cagtccaggg atggtggaca gatgtgacca agaccttcgc   1020

atggacaatt tgaacagact gtcatgaact atccctgttg ccactggcac ccaagtcctc   1080

cgcccctctc agctcccttg ggcgcctatg agggcacatg ttgaatcaca gtaaattatt   1140

tgatggtctt gacttgtctc tggctggaag taggaggtgt agtgcctgtg gcctcacaga   1200

agatactggg gacctgggat ctatcatctg ccttgttcct gtttctagaa gaggctgggg   1260

aggctggcct gggacctggg actgtgcagc ccttctcttc tgcctgcctc aactgtcttg   1320

tgtttcctgc agaaagttat aaataacaca agaatagtca ggtgatatga aaaaaaaaaa   1380

aaaaaaaaaa aa                                                       1392
```

```
<210> SEQ ID NO 10
<211> LENGTH: 189
<212> TYPE: PRT
<213> ORGANISM: Rattus norvegicus

<400> SEQUENCE: 10

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175
```

```
Ser Gly Pro Gly Cys Met Ser Cys Lys Cys Val Leu Ser
            180                 185


<210> SEQ ID NO 11
<211> LENGTH: 504
<212> TYPE: DNA
<213> ORGANISM: Mus musculus

<400> SEQUENCE: 11

atggcggtaa atgattgctt cagtctgacc tatcctcaca acccacaccc aggagacttg      60

attgaagtgt tccgtccttg ctatcagcac tgggcactgt acttgggtga tggctacgtg     120

atcaacattg cacctataga tggcattcgc tcatcattta caagtgctaa gtccgtgttc     180

agcacaaagg ccttggtgaa aatgcagctt ttgaaggatg ttgtgggaaa tgacacatac     240

agaataaata acaagtacga cacaacatac cctcctcttc ctgtggagga ggtgatacaa     300

cggtcagagt tccctattgg gcaggaagta gcctatgact tgctggtcaa caactgtgag     360

cattttgtaa ccttgctgcg ctatggagaa ggagtgtcag agcaggccaa ccgagcaatc     420

ggcaccatcg gattggtggc agctggtatt gatatcttca cattcctcgg cttgtttccc     480

aaaagacaaa gaacgaaata ttag                                            504


<210> SEQ ID NO 12
<211> LENGTH: 167
<212> TYPE: PRT
<213> ORGANISM: Mus musculus

<400> SEQUENCE: 12

Met Ala Val Asn Asp Cys Phe Ser Leu Thr Tyr Pro His Asn Pro His
1               5                   10                  15

Pro Gly Asp Leu Ile Glu Val Phe Arg Pro Cys Tyr Gln His Trp Ala
            20                  25                  30

Leu Tyr Leu Gly Asp Gly Tyr Val Ile Asn Ile Ala Pro Ile Asp Gly
        35                  40                  45

Ile Arg Ser Ser Phe Thr Ser Ala Lys Ser Val Phe Ser Thr Lys Ala
    50                  55                  60

Leu Val Lys Met Gln Leu Leu Lys Asp Val Val Gly Asn Asp Thr Tyr
65                  70                  75                  80

Arg Ile Asn Asn Lys Tyr Asp Thr Thr Tyr Pro Pro Leu Pro Val Glu
                85                  90                  95

Glu Val Ile Gln Arg Ser Glu Phe Pro Ile Gly Gln Glu Val Ala Tyr
            100                 105                 110

Asp Leu Leu Val Asn Asn Cys Glu His Phe Val Thr Leu Leu Arg Tyr
        115                 120                 125

Gly Glu Gly Val Ser Glu Gln Ala Asn Arg Ala Ile Gly Thr Ile Gly
    130                 135                 140

Leu Val Ala Ala Gly Ile Asp Ile Phe Thr Phe Leu Gly Leu Phe Pro
145                 150                 155                 160

Lys Arg Gln Arg Thr Lys Tyr
                165


<210> SEQ ID NO 13
<211> LENGTH: 1455
<212> TYPE: DNA
<213> ORGANISM: Cavia porcellus

<400> SEQUENCE: 13
```

-continued

```
cgggctctgc ggcggggcag ctgcgccctg cgcgcgtgcc gcgcttcccg gggccccagc      60

tgtggccggg cgctcagcga ggcgccgccc gggctcgggg acgcgggccc gcggccatgt     120

cgctcggtgc gggacgccgc gcgtctctgt ccagctccgc ttccctgtcg cccgcgctcc     180

ccggccgccc gcgctccccc gctgtcccct gcgccctgga cccctagccg ctgctccgtg     240

gaccgcttgg gacgtgtcgg ccggggccgc gtctccccgc cgcccttccc ccgcgccgcg     300

tgcagccggc gcctgtggac gcacacgggc ctgcgccgct gtaggcgcgg ctgtcgggac     360

gctgcctgcc tcgacacgcc cgccggcggg caaggacctg ttcgggcggc cccgccagca     420

ggtggggcaa gagcccccga gtgccctgag cgtcagtccc tggaggagcc atgacggagt     480

acaagcttgt ggtggtgggt gcaggaggtg tggggaagag cgccctgact atccagctga     540

tccagaacca ttttgtggac gaatatgacc ccaccataga ggattcatac cggaagcagg     600

tggtcattga tggggagacc tgtctgctgg atatcttgga cacagctggc caagaggagt     660

atagtgccat gcgggaccaa tacatgcgca ctggggaggg cttcctttgt gtgttcgcca     720

tcaacaatac caaatctttc gaggacatcc atcagtacag ggagcagatc aagcgggtga     780

aggactcaga tgatgtgccc atggtgctgg tgggaaacaa atgtgacctg gctacacgca     840

ccgtggagtc tcggcaggcc caagaccttg cccgcagtta cggcattccc tacattgaga     900

catcagccaa gacccgccag ggagtagaag acgccttcta tacactagtt cgagagatcc     960

ggcagcacaa actgcggaag ctgaatccac cagatgagag tgggccaggg tgcatgagct    1020

gcaaatgtgt gctatcctga tccaggtgag cagggcccag ctggctcccc gagccacagc    1080

cctagccggc cagccagcta agctgcacat ctactctgat gttcctgggc ttcctgaacc    1140

tgctggtccc cttgtctacg atcagtggcg tccttcatgc tccatcctgg cccaggctca    1200

ggacacagag gtaccagatg tggggaagag gtacagaagg aaggaaggaa ggaaggaagg    1260

aagtgccact ggagtccagc cagcccaggg atggtggata gaggcgactg cagaccctcc    1320

tgtggatgct ttgcaagctg tcatgaactg tcccaaacac cactggcctc ccagccctaa    1380

ctcccctccc agtttttcca gcctctgaca ggtgcaggtt gatttgcagt aaattatttg    1440

atggtcttga ctcca                                                      1455
```

<210> SEQ ID NO 14
<211> LENGTH: 189
<212> TYPE: PRT
<213> ORGANISM: Cavia porcellus

<400> SEQUENCE: 14

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110
```

-continued

```
Leu Val Gly Asn Lys Cys Asp Leu Ala Thr Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185


<210> SEQ ID NO 15
<211> LENGTH: 1694
<212> TYPE: DNA
<213> ORGANISM: Cavia porcellus

<400> SEQUENCE: 15

cgggctctgc ggcggggcag ctgcgccctg cgcgcgtgcc gcgcttcccg gggccccagc     60

tgtggccggg cgctcagcga ggcgccgccc gggctcgggg acgcgggccc gcggccatgt    120

cgctcggtgc gggacgccgc gcgtctctgt ccagctccgc ttccctgtcg cccgcgctcc    180

ccggccgccc gcgctccccc gctgtcccct gcgccctgga cccctagccg ctgctccgtg    240

gaccgcttgg gacgtgtcgg ccggggccgc gtctccccgc cgcccttccc ccgcgccgcg    300

tgcagccggc gcctgtggac gcacacgggc ctgcgccgct gtaggcgcgg ctgtcgggac    360

gctgcctgcc tcgacacgcc cgccggcggg caaggacctg ttcgggcggc cccgccagca    420

ggtgcctatg acctaggctt tttgcctacc cagcaacttc taatttgggt gcctggttgg    480

gagcggctca gctgtcaccc tgcctcggcg ccggcccctg cttccttaca ggccacgagg    540

tgcagcgggg tgcggtgaga ccctcagccc gctggaggtg ccacaggtgc cgccatcctg    600

gctggcgccc ttccagccac tccgctgggt ggcgcttggc tgagctggtc ctcctcacag    660

gtggggcaag agcccccgag tgccctgagc gtcagtccct ggaggagcca tgacggagta    720

caagcttgtg gtggtgggtg caggaggtgt ggggaagagc gccctgacta tccagctgat    780

ccagaaccat tttgtggacg aatatgaccc caccatagag gattcatacc ggaagcaggt    840

ggtcattgat ggggagacct gtctgctgga tatcttggac acagctggcc aagaggagta    900

tagtgccatg cgggaccaat acatgcgcac tggggagggc ttcctttgtg tgttcgccat    960

caacaatacc aaatctttcg aggacatcca tcagtacagg gagcagatca agcgggtgaa   1020

ggactcagat gatgtgccca tggtgctggt gggaaacaaa tgtgacctgg ctacacgcac   1080

cgtggagtct cggcaggccc aagaccttgc ccgcagttac ggcattccct acattgagac   1140

atcagccaag acccgccagg gagtagaaga cgccttctat acactagttc gagagatccg   1200

gcagcacaaa ctgcggaagc tgaatccacc agatgagagt gggccagggt gcatgagctg   1260

caaatgtgtg ctatcctgat ccaggtgagc agggcccagc tggctccccg agccacagcc   1320

ctagccggcc agccagctaa gctgcacatc tactctgatg ttcctgggct tcctgaacct   1380

gctggtcccc ttgtctacga tcagtggcgt ccttcatgct ccatcctggc ccaggctcag   1440

gacacagagg taccagatgt ggggaagagg tacagaagga aggaaggaag gaaggaagga   1500

agtgccactg gagtccagcc agcccaggga tggtggatag aggcgactgc agaccctcct   1560

gtggatgctt tgcaagctgt catgaactgt cccaaacacc actggcctcc cagccctaac   1620

tcccctccca gtttttccag cctctgacag gtgcaggttg atttgcagta aattatttga   1680
```

-continued

```
tggtcttgac tcca                                                 1694


<210> SEQ ID NO 16
<211> LENGTH: 189
<212> TYPE: PRT
<213> ORGANISM: Cavia porcellus

<400> SEQUENCE: 16

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Thr Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185


<210> SEQ ID NO 17
<211> LENGTH: 1180
<212> TYPE: DNA
<213> ORGANISM: Cavia porcellus

<400> SEQUENCE: 17

actgggccta cagtccccac cgcccgcgcc gcgagcccgc agcccgagcc gcacccgctg      60

cggacggagc ccatgcgcgg gcccagccag cgcccgcccg cgccccegcc ccgccccggc     120

cccgggggca gttgcaccag cgagtggtgg ggcaagagcc cccgagtgcc ctgagcgtca     180

gtccctggag gagccatgac ggagtacaag cttgtggtgg tgggtgcagg aggtgtgggg     240

aagagcgccc tgactatcca gctgatccag aaccattttg tggacgaata tgaccccacc     300

atagaggatt cataccggaa gcaggtggtc attgatgggg agacctgtct gctggatatc     360

ttggacacag ctggccaaga ggagtatagt gccatgcggg accaatacat gcgcactggg     420

gagggcttcc tttgtgtgtt cgccatcaac aataccaaat ctttcgagga catccatcag     480

tacagggagc agatcaagcg ggtgaaggac tcagatgatg tgcccatggt gctggtggga     540

aacaaatgtg acctggctac acgcaccgtg gagtctcggc aggcccaaga ccttgcccgc     600

agttacggca ttccctacat tgagacatca gccaagaccc gccagggagt agaagacgcc     660

ttctatacac tagttcgaga gatccggcag cacaaactgc ggaagctgaa tccaccagat     720

gagagtgggc cagggtgcat gagctgcaaa tgtgtgctat cctgatccag gtgagcaggg     780
```

-continued

```
cccagctggc tccccgagcc acagccctag ccggccagcc agctaagctg cacatctact    840

ctgatgttcc tgggcttcct gaacctgctg gtccccttgt ctacgatcag tggcgtcctt    900

catgctccat cctggcccag gctcaggaca cagaggtacc agatgtgggg aagaggtaca    960

gaaggaagga aggaaggaag gaaggaagtg ccactggagt ccagccagcc cagggatggt   1020

ggatagaggc gactgcagac cctcctgtgg atgctttgca agctgtcatg aactgtccca   1080

aacaccactg gcctcccagc cctaactccc ctcccagttt ttccagcctc tgacaggtgc   1140

aggttgattt gcagtaaatt atttgatggt cttgactcca                         1180
```

<210> SEQ ID NO 18
<211> LENGTH: 189
<212> TYPE: PRT
<213> ORGANISM: Cavia porcellus

<400> SEQUENCE: 18

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Thr Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185
```

<210> SEQ ID NO 19
<211> LENGTH: 1270
<212> TYPE: DNA
<213> ORGANISM: Cavia porcellus

<400> SEQUENCE: 19

```
cgggctctgc ggcggggcag ctgcgccctg cgcgcgtgcc gcgcttcccg gggccccagc     60

tgtggccggg cgctcagcga ggcgccgccc gggctcgggg acgcgggccc gcggccatgt    120

cgctcggtgc gggacgccgc gcgtctctgt ccagctccgc ttccctgtcg cccgcgctcc    180

ccggccgccc gcgctccccc gctgtcccct gcgccctgga cccctagccg ctgctccgtg    240

gaccgcttgg gacgtgtcgg ccggggccgc gtctccccgc cgcccttccc ccgcgccgcg    300

tgcagccggc gcctgtggac gcacacgggc ctgcgccgct gtaggcgcgg ctgtcgggac    360
```

-continued gctgcctgcc tcgacacgcc cgccggcggg caaggacctg ttcgggcggc cccgccagca 420
ggtgcctatg acctaggctt tttgcctacc cagcaacttc taatttgggt gcctggttgg 480
gagcggctca gctgtcaccc tgcctcggcg ccggcccctg cttccttaca ggccacgagg 540
tgcagcgggg tgcggtgaga ccctcagccc gctggaggtg ccacaggtgc cgccatcctg 600
gctggcgccc ttccagccac tccgctgggt ggcgcttggc tgagctggtc ctcctcacag 660
gtggggcaag agcccccgag tgccctgagc gtcagtccct ggaggagcca tgacggagta 720
caagcttgtg gtggtgggtg caggaggtgt ggggaagagc gccctgacta tccagctgat 780
ccagaaccat tttgtggacg aatatgaccc caccatagag gattcatacc ggaagcaggt 840
ggtcattgat ggggagacct gtctgctgga tatcttggac acagctggcc aagaggagta 900
tagtgccatg cgggaccaat acatgcgcac tggggagggc ttcctttgtg tgttcgccat 960
caacaatacc aaatctttcg aggacatcca tcagtacagg gagcagatca agcgggtgaa 1020
ggactcagat gatgtgccca tggtgctggt gggaaacaaa tgtgacctgg ctacacgcac 1080
cgtggagtct cggcaggccc aagaccttgc ccgcagttac ggcattccct acattgagac 1140
atcagccaag acccgccagg gcagccgctc tggctctggc ttcagctccg ggacccactg 1200
ggaacccctg ggatccatgt gacccatcgg cccccatgct ggagtagaag acgccttcta 1260
tacactagtt 1270

<210> SEQ ID NO 20
<211> LENGTH: 170
<212> TYPE: PRT
<213> ORGANISM: Cavia porcellus

<400> SEQUENCE: 20

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Thr Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Ser Arg Ser Gly Ser Gly Phe Ser Ser
145                 150                 155                 160

Gly Thr His Trp Glu Pro Leu Gly Ser Met
                165                 170

<210> SEQ ID NO 21
<211> LENGTH: 696
<212> TYPE: DNA
<213> ORGANISM: Canis lupus

<400> SEQUENCE: 21

```
ggctgagagc agcttcctca gcaggtggga caggagacct cgttggcgtc ctgtgctgcg     60

tcccgtgagg agccatgacg gagtataagc tggtggtggt gggcgctgga ggcgtgggca    120

agagcgccct gaccatccag ctcatccaga accacttcgt ggatgagtac gaccccacca    180

tcgaggactc ctatcggaag caagtggtca tcgacgggga gacgtgcctg ctggacatcc    240

tggacacagc gggccaggag gagtacagcg ccatgcggga ccagtacatg cgcacggggg    300

agggctttct ctgtgtattt gccatcaaca acaccaagtc ctttgaggac atccaccagt    360

acagggagca gatcaagcga gtgaaggact ctgacgacgt gcccatggtg ctggtgggga    420

acaagtgtga cctggctgct cgcaccgtgg agtcccggca ggcgcaggac ctcgcccgca    480

gctacggcat cccctacatc gagacgtcag ccaagacgcg ccagggcagc cggtctggct    540

ctggctccag ctccgggacc ctctgggacc ctccgggacc cccgtgaccc agcggcccct    600

agcgctggcg tggaggatgc cttctacacg ctggtgcgag agattcgaca gcacaaggtg    660

cgcaagctga gcccgcccga cgagggaggc ccaggc                             696
```

<210> SEQ ID NO 22
<211> LENGTH: 170
<212> TYPE: PRT
<213> ORGANISM: Canis lupus

<400> SEQUENCE: 22

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Ser Arg Ser Gly Ser Gly Ser Ser Ser
145                 150                 155                 160

Gly Thr Leu Trp Asp Pro Pro Gly Pro Pro
                165                 170
```

<210> SEQ ID NO 23
<211> LENGTH: 956
<212> TYPE: DNA
<213> ORGANISM: Canis lupus

<400> SEQUENCE: 23

```
gctgagagca gcttcctcag caggtgggac aggagacctc gttggcgtcc tgtgctgcgt     60

cccgtgagga gccatgacgg agtataagct ggtggtggtg ggcgctggag gcgtgggcaa    120
```

-continued

```
gagcgccctg accatccagc tcatccagaa ccacttcgtg gatgagtacg accccaccat    180

cgaggactcc tatcggaagc aagtggtcat cgacggggag acgtgcctgc tggacatcct    240

ggacacagcg ggccaggagg agtacagcgc catgcgggac cagtacatgc gcacggggga    300

gggctttctc tgtgtatttg ccatcaacaa caccaagtcc tttgaggaca tccaccagta    360

cagggagcag atcaagcgag tgaaggactc tgacgacgtg cccatggtgc tggtggggaa    420

caagtgtgac ctggctgctc gcaccgtgga gtcccggcag gcgcaggacc tcgcccgcag    480

ctacggcatc ccctacatcg agacgtcagc caagacgcgc cagggcgtgg aggatgcctt    540

ctacacgctg gtgcgagaga ttcgacagca caaggtgcgc aagctgagcc cgcccgacga    600

gggaggccca ggctgcatga gctgcaagtg cctgctgtcc tgacgtcccc tccagggcca    660

cgttggcagc cccgctggtc ctctgtgccc caggcgcaca ggctcggggc gaggaggtgc    720

cggaagctgg gaggaggcgc ggaaggagga aggaggaggg cgaggaagga aggaagcgcc    780

cccggggccc ggccagccca ggccccctgg acagggggag cacggacctc ccagggcgct    840

ttgcacagac tgtcgtgaac tgaggccacg ggcccccccg gctgtcactc tcccccagtc    900

ccgtccttgc ccgcggggca aaggctgagt cgcagtaaat tatttgatgg tcttga        956
```

<210> SEQ ID NO 24
<211> LENGTH: 189
<212> TYPE: PRT
<213> ORGANISM: Canis lupus

<400> SEQUENCE: 24

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Val Arg Lys Leu Ser Pro Pro Asp Glu
                165                 170                 175

Gly Gly Pro Gly Cys Met Ser Cys Lys Cys Leu Leu Ser
            180                 185
```

<210> SEQ ID NO 25
<211> LENGTH: 593
<212> TYPE: DNA
<213> ORGANISM: Felis catus

<400> SEQUENCE: 25

```
gccgcgatcc cctgaggaac gatgacggaa tataagctcg tggtggtggg cgctggaggt     60

gtggggaaga gtgccctgac catccagctc atccagaacc acttcgtgga tgagtatgac    120

cccaccatcg aggactccta tcggaagcaa gtggttattg atggcgagac gtgcctactg    180

gacattttgg acacggcggg ccaggaggag tatagcgcca tgcgggacca gtacatgcgc    240

actggagaag gcttcctctg tgtgtttgcc atcaacaata ccaagtcctt tgaggacatc    300

caccagtaca gggagcaaat caagcgagtg aaggactccg atgacgtgcc catggtgttg    360

gtggggaaca agtgcgacct ggccgcgcgc accgtggagt cccggcaggc gcaggacctc    420

gcccgcagct acggcatccc gtacatcgag acgtcggcca agactcgcca gggtgtggag    480

gacgctttct acacgctggt ccgagagatc cggcaacaca aggtgcggaa gctgagcccg    540

cccgacgagg gtggccccgg ctgcatgagc tgcaagtgcc tgctctcctg acg           593


<210> SEQ ID NO 26
<211> LENGTH: 189
<212> TYPE: PRT
<213> ORGANISM: Felis catus

<400> SEQUENCE: 26

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Val Arg Lys Leu Ser Pro Pro Asp Glu
                165                 170                 175

Gly Gly Pro Gly Cys Met Ser Cys Lys Cys Leu Leu Ser
            180                 185


<210> SEQ ID NO 27
<211> LENGTH: 675
<212> TYPE: DNA
<213> ORGANISM: Felis catus

<400> SEQUENCE: 27

gccgcgatcc cctgaggaac gatgacggaa tataagctcg tggtggtggg cgctggaggt     60

gtggggaaga gtgccctgac catccagctc atccagaacc acttcgtgga tgagtatgac    120

cccaccatcg aggactccta tcggaagcaa gtggttattg atggcgagac gtgcctactg    180
```

-continued

```
gacattttgg acacggcggg ccaggaggag tatagcgcca tgcgggacca gtacatgcgc    240

actggagaag gcttcctctg tgtgtttgcc atcaacaata ccaagtcctt tgaggacatc    300

caccagtaca gggagcaaat caagcgagtg aaggactccg atgacgtgcc catggtgttg    360

gtggggaaca agtgcgacct ggccgcgcgc accgtggagt cccggcaggc gcaggacctc    420

gcccgcagct acggcatccc gtacatcgag acgtcggcca agactcgcca gggcagccgc    480

tctggctctg gctccagctc cgggaccctc tgggaccctc cgggaccccc gtgacccagc    540

ggcccctagc gctggtgtgg aggacgcttt ctacacgctg gtccgagaga tccggcaaca    600

caaggtgcgg aagctgagcc cgcccgacga gggtggcccc ggctgcatga gctgcaagtg    660

cctgctctcc tgacg                                                     675
```

<210> SEQ ID NO 28
<211> LENGTH: 170
<212> TYPE: PRT
<213> ORGANISM: Felis catus

<400> SEQUENCE: 28

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Ser Arg Ser Gly Ser Gly Ser Ser Ser
145                 150                 155                 160

Gly Thr Leu Trp Asp Pro Pro Gly Pro Pro
                165                 170
```

<210> SEQ ID NO 29
<211> LENGTH: 978
<212> TYPE: DNA
<213> ORGANISM: Bos taurus

<400> SEQUENCE: 29

```
ccgccgcgga cgggacccat gcgtcgggcg agccctgcgc cccggccccg gcccctgccg     60

ccgcccccgc tccggccccg gcccgggggg cagtcgagcc agtgagcggt gggaccggcg    120

accactgcag cgcctcgtgc tgcggtctct tgaggagcaa tgacggagta taagctcgtg    180

gtggtgggcg ccggtggcgt ggggaagagc gccctgacta tccagctcat tcagaatcac    240

ttcgtggacg agtacgaccc caccatcgag gactcctacc ggaagcaagt ggtcatcgat    300

ggggagacgt gcctgctgga catcctggac acagcgggcc aggaggaata cagcgccatg    360
```

-continued

```
cgagaccagt acatgcgcac cggggagggc tttctctgcg tgtttgctat caaccacgtc    420

aagtccttcg aggacatcca ccagtaccgg gagcagatca agcgggtgaa ggactcggat    480

gacgtgccca tggtgttggt tgggaacaag tgcgacctgg ccgcgcgcac cgtggagtct    540

cggcaggccc aggacctcgc ccgcagctac ggcatcccgt acatcgagac ctccgccaag    600

acccgccagg gcgtggagga tgctttctac accctggtgc gcgagatccg gcagcacaag    660

gtgcgcaagc tgagcccgcc ggacgagggc ggccccggct gcctgagctg caggtgcctg    720

ctctcctgac ggcagcgtgg gcgcggagcg ctgggtgcca tgcaggaggc ggcgcagcag    780

gggtggaggg aggtgccgcc agagcccagc cccccaggcc agtgggcagt gcccgcgggc    840

ctcccgggac gcttcgcaca gactctggtg aactgatgct gctggccccc agcctcgctc    900

tcctccagcc ctgtcctggc ccagcgggcg caggccgagt cgcagtaaat tatttcatgg    960

tcttgaaaaa aaaaaaaa                                                  978


<210> SEQ ID NO 30
<211> LENGTH: 189
<212> TYPE: PRT
<213> ORGANISM: Bos taurus

<400> SEQUENCE: 30

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn His Val Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Val Arg Lys Leu Ser Pro Pro Asp Glu
                165                 170                 175

Gly Gly Pro Gly Cys Leu Ser Cys Arg Cys Leu Leu Ser
            180                 185


<210> SEQ ID NO 31
<211> LENGTH: 1060
<212> TYPE: DNA
<213> ORGANISM: Bos taurus

<400> SEQUENCE: 31

ccgccgcgga cgggacccat gcgtcgggcg agccctgcgc cccggccccg gcccctgccg     60

ccgcccccgc tccggccccg gcccgggggg cagtcgagcc agtgagcggt gggaccggcg    120

accactgcag cgcctcgtgc tgcggtctct tgaggagcaa tgacggagta taagctcgtg    180
```

-continued

```
gtggtgggcg ccggtggcgt ggggaagagc gccctgacta tccagctcat tcagaatcac    240

ttcgtggacg agtacgaccc caccatcgag gactcctacc ggaagcaagt ggtcatcgat    300

ggggagacgt gcctgctgga catcctggac acagcgggcc aggaggaata cagcgccatg    360

cgagaccagt acatgcgcac cggggagggc tttctctgcg tgtttgctat caaccacgtc    420

aagtccttcg aggacatcca ccagtaccgg gagcagatca agcgggtgaa ggactcggat    480

gacgtgccca tggtgttggt tgggaacaag tgcgacctgg ccgcgcgcac cgtggagtct    540

cggcaggccc aggacctcgc ccgcagctac ggcatcccgt acatcgagac ctccgccaag    600

acccgccagg gcagccgctc tggctctggc tccagctccg ggaccctctg ggaccctccg    660

ggacccccgt gacccagccg cccctctcgc tggcgtggag gatgctttct acaccctggt    720

gcgcgagatc cggcagcaca aggtgcgcaa gctgagcccg ccggacgagg gcggccccgg    780

ctgcctgagc tgcaggtgcc tgctctcctg acggcagcgt gggcgcggag cgctgggtgc    840

catgcaggag gcggcgcagc aggggtggag ggaggtgccg ccagagccca gccccccagg    900

ccagtgggca gtgcccgcgg gcctcccggg acgcttcgca cagactctgg tgaactgatg    960

ctgctggccc ccagcctcgc tctcctccag ccctgtcctg gcccagcggg cgcaggccga   1020

gtcgcagtaa attatttcat ggtcttgaaa aaaaaaaaaa                        1060
```

<210> SEQ ID NO 32
<211> LENGTH: 170
<212> TYPE: PRT
<213> ORGANISM: Bos taurus

<400> SEQUENCE: 32

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn His Val Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Ser Arg Ser Gly Ser Gly Ser Ser Ser
145                 150                 155                 160

Gly Thr Leu Trp Asp Pro Pro Gly Pro Pro
                165                 170
```

<210> SEQ ID NO 33
<211> LENGTH: 1531
<212> TYPE: DNA
<213> ORGANISM: Bos taurus

<400> SEQUENCE: 33

```
cccatttaaa acatcgggag aactttctag atttgcagct ggcctcctgc tgcctcagga     60
cagctgtcta gctgcataaa acactccgtt tgctcaaaat cgcaaataaa ctctgatatt    120
acttcagcat cgtcctttcc agcccgacca atttccagtg gaaacctggc tggcagaaga    180
cacacagagt gaacttctgg tggtgggtag agaggtgccc agcaagatgt ggggagaatg    240
aaccggccac ggctcactgc gtttgatgag gccctgcagg aggcaaactt cagctggaat    300
ggggagagcc caggcgttct gagacctgtg gctcgaaaaa tacaacggct tctcaactca    360
aatcagtgac aagaaaaatg aagaaaggcg tggagttaga aagaccccat gagattcggc    420
ctcggggaga aaccggttgc caggcacttg ctgcccttgg gtggtgctag gaggaccaag    480
gcctgagacc cccggttcca gtgattgagt ctgcagagac agaaatgctg cagcagctgc    540
cagtggagtg gctttgcatg gttggcactg gatacaagtg tgctaggaag cacgcccgcc    600
gagggccacg gcctggaccg aggttgaccg tggtcatcag agaccaggag tccgggcttc    660
tctcacacag gcagtgggac cggcgaccac tgcagcgcct cgtgctgcgg tctcttgagg    720
agcaatgacg gagtataagc tcgtggtggt gggcgccggt ggcgtgggga agagcgccct    780
gactatccag ctcattcaga atcacttcgt ggacgagtac gaccccacca tcgaggactc    840
ctaccggaag caagtggtca tcgatgggga gacgtgcctg ctggacatcc tggacacagc    900
gggccaggag gaatacagcg ccatgcgaga ccagtacatg cgcaccgggg agggctttct    960
ctgcgtgttt gctatcaacc acgtcaagtc cttcgaggac atccaccagt accgggagca   1020
gatcaagcgg gtgaaggact cggatgacgt gcccatggtg ttggttggga acaagtgcga   1080
cctggccgcg cgcaccgtgg agtctcggca ggcccaggac ctcgcccgca gctacggcat   1140
cccgtacatc gagacctccg ccaagacccg ccagggcgtg gaggatgctt tctacaccct   1200
ggtgcgcgag atccggcagc acaaggtgcg caagctgagc ccgccggacg agggcggccc   1260
cggctgcctg agctgcaggt gcctgctctc ctgacggcag cgtgggcgcg gagcgctggg   1320
tgccatgcag gaggcggcgc agcaggggtg gagggaggtg ccgccagagc ccagcccccc   1380
aggccagtgg gcagtgcccg cgggcctccc gggacgcttc gcacagactc tggtgaactg   1440
atgctgctgg cccccagcct cgctctcctc cagccctgtc ctggcccagc gggcgcaggc   1500
cgagtcgcag taaattattt catggtcttg a                                  1531
```

```
<210> SEQ ID NO 34
<211> LENGTH: 189
<212> TYPE: PRT
<213> ORGANISM: Bos taurus

<400> SEQUENCE: 34

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn His Val Lys Ser Phe Glu Asp Ile His Gln Tyr
                85                  90                  95
```

-continued

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Val Arg Lys Leu Ser Pro Pro Asp Glu
                165                 170                 175

Gly Gly Pro Gly Cys Leu Ser Cys Arg Cys Leu Leu Ser
            180                 185

<210> SEQ ID NO 35
<211> LENGTH: 962
<212> TYPE: DNA
<213> ORGANISM: Gallus gallus

<400> SEQUENCE: 35
gggttgatgg ccggaccgtc gattccctga cgactacgag cacctacacc tgaggtggtg 60
gtgctcctgg aggccctgag ctggggtcag ctggaagatg accgagtaca agctggtggt 120
agtgggagct ggaggtgtcg ggaagagcgc tttgacgata cagctcattc agaaccattt 180
tgttgatgag tacgacccca caatagagga ttcctacaga aagcaagtcg tcatcgatgg 240
agagacctgt ttgctggaca tcctggatac ggcggggcag gaggagtaca gtgccatgcg 300
agaccagtac atgagaacgg gggaaggatt cctgtgcgtc tttgccatta acaacaccaa 360
gtcctttgag gacatccacc agtacaggga gcagatcaag agggtgaaag actcagatga 420
tgtccccatg gtgctggtgg gaaataaatg tgatctgcca gcacggacag tggagacccg 480
gcaagcgcag gacctggccc ggagttacgg gatcccctac atagaaacgt cggccaaaac 540
cagacagggc gtcgaagatg ccttctatac cttagtgcgg gagatccgtc agcataaact 600
gcgcaagctg aacccaccag atgagagtgg ccctggctgc atgaactgta aatgcgtgat 660
atcgtgactg tgctgactgg accctgactt ggagaggtgt ccgctgtgca gagcacaagg 720
aaagaggtga tgcgaaggaa gaaacaaatg gattcagggg aggagtggag ggggagggag 780
agaggaagaa gaggacggga ggagtgccag cccctccaag gactatctcg cacttcaccc 840
aggccggcag cagatgactt ttggttcttt ccccatcccc tcctcctttg gcctcctcca 900
ccccggcaac tgtacaaagc cacagattga atcacagtaa attattattt gatggtctcg 960
ac 962

<210> SEQ ID NO 36
<211> LENGTH: 189
<212> TYPE: PRT
<213> ORGANISM: Gallus gallus

<400> SEQUENCE: 36

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65 70 75 80

Val Phe Ala Ile Asn Asn Thr Lys Ser Phe Glu Asp Ile His Gln Tyr
85 90 95

Arg Glu Gln Ile Lys Arg Val Lys Asp Ser Asp Asp Val Pro Met Val
100 105 110

Leu Val Gly Asn Lys Cys Asp Leu Pro Ala Arg Thr Val Glu Thr Arg
115 120 125

Gln Ala Gln Asp Leu Ala Arg Ser Tyr Gly Ile Pro Tyr Ile Glu Thr
130 135 140

Ser Ala Lys Thr Arg Gln Gly Val Glu Asp Ala Phe Tyr Thr Leu Val
145 150 155 160

Arg Glu Ile Arg Gln His Lys Leu Arg Lys Leu Asn Pro Pro Asp Glu
165 170 175

Ser Gly Pro Gly Cys Met Asn Cys Lys Cys Val Ile Ser
180 185

<210> SEQ ID NO 37
<211> LENGTH: 5436
<212> TYPE: DNA
<213> ORGANISM: Homo sapiens

<400> SEQUENCE: 37
ggccgcggcg gcggaggcag cagcggcggc ggcagtggcg gcggcgaagg tggcggcggc 60
tcggccagta ctcccggccc ccgccatttc ggactgggag cgagcgcggc gcaggcactg 120
aaggcggcgg cggggccaga ggctcagcgg ctcccaggtg cgggagagag gcctgctgaa 180
aatgactgaa tataaacttg tggtagttgg agctggtggc gtaggcaaga gtgccttgac 240
gatacagcta attcagaatc attttgtgga cgaatatgat ccaacaatag aggattccta 300
caggaagcaa gtagtaattg atggagaaac ctgtctcttg gatattctcg acacagcagg 360
tcaagaggag tacagtgcaa tgagggacca gtacatgagg actggggagg gctttctttg 420
tgtatttgcc ataaataata ctaaatcatt tgaagatatt caccattata gagaacaaat 480
taaaagagtt aaggactctg aagatgtacc tatggtccta gtaggaaata aatgtgattt 540
gccttctaga acagtagaca caaaacaggc tcaggactta gcaagaagtt atggaattcc 600
ttttattgaa acatcagcaa agacaagaca gagagtggag gatgcttttt atacattggt 660
gagggagatc cgacaataca gattgaaaaa aatcagcaaa gaagaaaaga ctcctggctg 720
tgtgaaaatt aaaaaatgca ttataatgta atctgggtgt tgatgatgcc ttctatacat 780
tagttcgaga aattcgaaaa cataaagaaa agatgagcaa agatggtaaa aagaagaaaa 840
agaagtcaaa gacaaagtgt gtaattatgt aaatacaatt tgtacttttt tcttaaggca 900
tactagtaca agtggtaatt tttgtacatt acactaaatt attagcattt gttttagcat 960
tacctaattt ttttcctgct ccatgcagac tgttagcttt taccttaaat gcttatttta 1020
aaatgacagt ggaagttttt ttttcctcta agtgccagta ttcccagagt tttggttttt 1080
gaactagcaa tgcctgtgaa aaagaaactg aatacctaag atttctgtct tggggttttt 1140
ggtgcatgca gttgattact tcttattttt cttaccaatt gtgaatgttg gtgtgaaaca 1200
aattaatgaa gcttttgaat catccctatt ctgtgtttta tctagtcaca taaatggatt 1260
aattactaat ttcagttgag accttctaat tggtttttac tgaaacattg agggaacaca 1320
aatttatggg cttcctgatg atgattcttc taggcatcat gtcctatagt ttgtcatccc 1380

```
tgatgaatgt aaagttacac tgttcacaaa ggttttgtct cctttccact gctattagtc   1440
atggtcactc tccccaaaat attatatttt ttctataaaa agaaaaaaat ggaaaaaaat   1500
tacaaggcaa tggaaactat tataaggcca tttccttttc acattagata aattactata   1560
aagactccta atagcttttc ctgttaaggc agacccagta tgaaatgggg attattatag   1620
caaccatttt ggggctatat ttacatgcta ctaaattttt ataataattg aaaagatttt   1680
aacaagtata aaaaattctc ataggaatta aatgtagtct ccctgtgtca gactgctctt   1740
tcatagtata actttaaatc ttttcttcaa cttgagtctt tgaagatagt tttaattctg   1800
cttgtgacat taaaagatta tttgggccag ttatagctta ttaggtgttg aagagaccaa   1860
ggttgcaagg ccaggccctg tgtgaacctt tgagctttca tagagagttt cacagcatgg   1920
actgtgtccc cacggtcatc cagtgttgtc atgcattggt tagtcaaaat ggggagggac   1980
tagggcagtt tggatagctc aacaagatac aatctcactc tgtggtggtc ctgctgacaa   2040
atcaagagca ttgcttttgt ttcttaagaa aacaaactct tttttaaaaa ttacttttaa   2100
atattaactc aaaagttgag atttggggt ggtggtgtgc caagacatta attttttttt   2160
taaacaatga agtgaaaaag ttttacaatc tctaggtttg gctagttctc ttaacactgg   2220
ttaaattaac attgcataaa cacttttcaa gtctgatcca tatttaataa tgctttaaaa   2280
taaaaataaa aacaatcctt ttgataaatt taaaatgtta cttattttaa aataaatgaa   2340
gtgagatggc atggtgaggt gaaagtatca ctggactagg aagaaggtga cttaggttct   2400
agataggtgt cttttaggac tctgattttg aggacatcac ttactatcca tttcttcatg   2460
ttaaaagaag tcatctcaaa ctcttagttt ttttttttta caactatgta atttatattc   2520
catttacata aggatacact tatttgtcaa gctcagcaca atctgtaaat ttttaaccta   2580
tgttacacca tcttcagtgc cagtcttggg caaaattgtg caagaggtga agtttatatt   2640
tgaatatcca ttctcgtttt aggactcttc ttccatatta gtgtcatctt gcctccctac   2700
cttccacatg ccccatgact tgatgcagtt ttaatacttg taattcccct aaccataaga   2760
tttactgctg ctgtggatat ctccatgaag ttttcccact gagtcacatc agaaatgccc   2820
tacatcttat ttcctcaggg ctcaagagaa tctgacagat accataaagg gatttgacct   2880
aatcactaat tttcaggtgg tggctgatgc tttgaacatc tctttgctgc ccaatccatt   2940
agcgacagta ggatttttca aacctggtat gaatagacag aaccctatcc agtggaagga   3000
gaatttaata aagatagtgc tgaaagaatt ccttaggtaa tctataacta ggactactcc   3060
tggtaacagt aatacattcc attgttttag taaccagaaa tcttcatgca atgaaaaata   3120
ctttaattca tgaagcttac tttttttttt tggtgtcaga gtctcgctct tgtcacccag   3180
gctggaatgc agtggcgcca tctcagctca ctgcaacctc catctcccag gttcaagcga   3240
ttctcgtgcc tcggcctcct gagtagctgg gattacaggc gtgtgccact acactcaact   3300
aatttttgta tttttaggag agacggggtt tcaccctgtt ggccaggctg gtctcgaact   3360
cctgacctca agtgattcac ccaccttggc ctcataaacc tgttttgcag aactcattta   3420
ttcagcaaat atttattgag tgcctaccag atgccagtca ccgcacaagg cactgggtat   3480
atggtatccc caaacaagag acataatccc ggtccttagg tagtgctagt gtggtctgta   3540
atatcttact aaggcctttg gtatacgacc cagagataac acgatgcgta ttttagtttt   3600
gcaaagaagg ggtttggtct ctgtgccagc tctataattg ttttgctacg attccactga   3660
aactcttcga tcaagctact ttatgtaaat cacttcattg ttttaaagga ataaacttga   3720
ttatattgtt tttttatttg gcataactgt gattctttta ggacaattac tgtacacatt   3780
```

aaggtgtatg tcagatattc atattgaccc aaatgtgtaa tattccagtt ttctctgcat 3840
aagtaattaa aatatactta aaaattaata gttttatctg ggtacaaata aacaggtgcc 3900
tgaactagtt cacagacaag gaaacttcta tgtaaaaatc actatgattt ctgaattgct 3960
atgtgaaact acagatcttt ggaacactgt ttaggtaggg tgttaagact tacacagtac 4020
ctcgtttcta cacagagaaa gaaatggcca tacttcagga actgcagtgc ttatgagggg 4080
atatttaggc ctcttgaatt tttgatgtag atgggcattt ttttaaggta gtggttaatt 4140
acctttatgt gaactttgaa tggtttaaca aaagatttgt ttttgtagag attttaaagg 4200
gggagaattc tagaaataaa tgttacctaa ttattacagc cttaaagaca aaaatccttg 4260
ttgaagtttt tttaaaaaaa gctaaattac atagacttag gcattaacat gtttgtggaa 4320
gaatatagca gacgtatatt gtatcatttg agtgaatgtt cccaagtagg cattctaggc 4380
tctatttaac tgagtcacac tgcataggaa tttagaacct aacttttata ggttatcaaa 4440
actgttgtca ccattgcaca attttgtcct aatatataca tagaaacttt gtggggcatg 4500
ttaagttaca gtttgcacaa gttcatctca tttgtattcc attgattttt tttttcttct 4560
aaacattttt tcttcaaaca gtatataact ttttttaggg gatttttttt tagacagcaa 4620
aaactatctg aagatttcca tttgtcaaaa agtaatgatt tcttgataat tgtgtagtaa 4680
tgttttttag aacccagcag ttaccttaaa gctgaattta tatttagtaa cttctgtgtt 4740
aatactggat agcatgaatt ctgcattgag aaactgaata gctgtcataa aatgaaactt 4800
tctttctaaa gaaagatact cacatgagtt cttgaagaat agtcataact agattaagat 4860
ctgtgtttta gtttaatagt ttgaagtgcc tgtttgggat aatgataggt aatttagatg 4920
aatttagggg aaaaaaaagt tatctgcaga tatgttgagg gcccatctct ccccccacac 4980
ccccacagag ctaactgggt tacagtgttt tatccgaaag tttccaattc cactgtcttg 5040
tgttttcatg ttgaaaatac ttttgcattt ttcctttgag tgccaatttc ttactagtac 5100
tatttcttaa tgtaacatgt ttacctggaa tgtattttaa ctatttttgt atagtgtaaa 5160
ctgaaacatg cacattttgt acattgtgct ttcttttgtg ggacatatgc agtgtgatcc 5220
agttgttttc catcatttgg ttgcgctgac ctaggaatgt tggtcatatc aaacattaaa 5280
aatgaccact cttttaattg aaattaactt ttaaatgttt ataggagtat gtgctgtgaa 5340
gtgatctaaa atttgtaata tttttgtcat gaactgtact actcctaatt attgtaatgt 5400
aataaaaata gttacagtga caaaaaaaaa aaaaaa 5436

<210> SEQ ID NO 38
<211> LENGTH: 189
<212> TYPE: PRT
<213> ORGANISM: Homo sapiens

<400> SEQUENCE: 38

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly
35 40 45

Glu Thr Cys Leu Leu Asp Ile Leu Asp Thr Ala Gly Gln Glu Glu Tyr
50 55 60

Ser Ala Met Arg Asp Gln Tyr Met Arg Thr Gly Glu Gly Phe Leu Cys
65 70 75 80

```
Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185


<210> SEQ ID NO 39
<211> LENGTH: 5312
<212> TYPE: DNA
<213> ORGANISM: Homo sapiens

<400> SEQUENCE: 39

ggccgcggcg gcggaggcag cagcggcggc ggcagtggcg gcggcgaagg tggcggcggc      60

tcggccagta ctcccggccc ccgccatttc ggactgggag cgagcgcggc gcaggcactg     120

aaggcggcgg cggggccaga ggctcagcgg ctcccaggtg cgggagagag gcctgctgaa     180

aatgactgaa tataaacttg tggtagttgg agctggtggc gtaggcaaga gtgccttgac     240

gatacagcta attcagaatc attttgtgga cgaatatgat ccaacaatag aggattccta     300

caggaagcaa gtagtaattg atggagaaac ctgtctcttg gatattctcg acacagcagg     360

tcaagaggag tacagtgcaa tgagggacca gtacatgagg actggggagg gctttctttg     420

tgtatttgcc ataaataata ctaaatcatt tgaagatatt caccattata gagaacaaat     480

taaaagagtt aaggactctg aagatgtacc tatggtccta gtaggaaata aatgtgattt     540

gccttctaga acagtagaca caaaacaggc tcaggactta gcaagaagtt atggaattcc     600

ttttattgaa acatcagcaa agacaagaca gggtgttgat gatgccttct atacattagt     660

tcgagaaatt cgaaaacata aagaaaagat gagcaaagat ggtaaaaaga agaaaaagaa     720

gtcaaagaca aagtgtgtaa ttatgtaaat acaatttgta ctttttttctt aaggcatact     780

agtacaagtg gtaatttttg tacattacac taaattatta gcatttgttt tagcattacc     840

taattttttt cctgctccat gcagactgtt agcttttacc ttaaatgctt attttaaaat     900

gacagtggaa gttttttttt cctctaagtg ccagtattcc cagagttttg gtttttgaac     960

tagcaatgcc tgtgaaaaag aaactgaata cctaagattt ctgtcttggg gtttttggtg    1020

catgcagttg attacttctt atttttctta ccaattgtga atgttggtgt gaaacaaatt    1080

aatgaagctt ttgaatcatc cctattctgt gttttatcta gtcacataaa tggattaatt    1140

actaatttca gttgagacct tctaattggt ttttactgaa acattgaggg aacacaaatt    1200

tatgggcttc ctgatgatga ttcttctagg catcatgtcc tatagtttgt catccctgat    1260

gaatgtaaag ttacactgtt cacaaaggtt ttgtctcctt tccactgcta ttagtcatgg    1320

tcactctccc caaaatatta tatttttttct ataaaaagaa aaaaatggaa aaaaattaca    1380

aggcaatgga aactattata aggccatttc cttttcacat tagataaatt actataaaga    1440

ctcctaatag cttttcctgt taaggcagac ccagtatgaa atggggatta ttatagcaac    1500
```

-continued

```
cattttgggg ctatatttac atgctactaa atttttataa taattgaaaa gattttaaca   1560
agtataaaaa attctcatag gaattaaatg tagtctccct gtgtcagact gctctttcat   1620
agtataactt taaatctttt cttcaacttg agtctttgaa gatagtttta attctgcttg   1680
tgacattaaa agattatttg ggccagttat agcttattag gtgttgaaga gaccaaggtt   1740
gcaaggccag gccctgtgtg aacctttgag ctttcataga gagtttcaca gcatggactg   1800
tgtccccacg gtcatccagt gttgtcatgc attggttagt caaaatgggg agggactagg   1860
gcagtttgga tagctcaaca agatacaatc tcactctgtg gtggtcctgc tgacaaatca   1920
agagcattgc ttttgtttct taagaaaaca aactcttttt taaaaattac ttttaaatat   1980
taactcaaaa gttgagattt tggggtggtg gtgtgccaag acattaattt ttttttttaaa   2040
caatgaagtg aaaaagtttt acaatctcta ggtttggcta gttctcttaa cactggttaa   2100
attaacattg cataaacact tttcaagtct gatccatatt taataatgct ttaaaataaa   2160
aataaaaaca atccttttga taaatttaaa atgttactta ttttaaaata aatgaagtga   2220
gatggcatgg tgaggtgaaa gtatcactgg actaggaaga aggtgactta ggttctagat   2280
aggtgtcttt taggactctg attttgagga catcacttac tatccatttc ttcatgttaa   2340
aagaagtcat ctcaaactct tagttttttt tttttacaac tatgtaattt atattccatt   2400
tacataagga tacacttatt tgtcaagctc agcacaatct gtaaattttt aacctatgtt   2460
acaccatctt cagtgccagt cttgggcaaa attgtgcaag aggtgaagtt tatatttgaa   2520
tatccattct cgttttagga ctcttcttcc atattagtgt catcttgcct ccctaccttc   2580
cacatgcccc atgacttgat gcagttttaa tacttgtaat tcccctaacc ataagattta   2640
ctgctgctgt ggatatctcc atgaagtttt cccactgagt cacatcagaa atgccctaca   2700
tcttatttcc tcagggctca agagaatctg acagatacca taaagggatt tgacctaatc   2760
actaattttc aggtggtggc tgatgctttg aacatctctt tgctgcccaa tccattagcg   2820
acagtaggat ttttcaaacc tggtatgaat agacagaacc ctatccagtg gaaggagaat   2880
ttaataaaga tagtgctgaa agaattcctt aggtaatcta taactaggac tactcctggt   2940
aacagtaata cattccattg ttttagtaac cagaaatctt catgcaatga aaaatacttt   3000
aattcatgaa gcttactttt tttttttggt gtcagagtct cgctcttgtc acccaggctg   3060
gaatgcagtg gcgccatctc agctcactgc aacctccatc tcccaggttc aagcgattct   3120
cgtgcctcgg cctcctgagt agctgggatt acaggcgtgt gccactacac tcaactaatt   3180
tttgtatttt taggagagac ggggtttcac cctgttggcc aggctggtct cgaactcctg   3240
acctcaagtg attcacccac cttggcctca taaacctgtt ttgcagaact catttattca   3300
gcaaatattt attgagtgcc taccagatgc cagtcaccgc acaaggcact gggtatatgg   3360
tatccccaaa caagagacat aatcccggtc cttaggtagt gctagtgtgg tctgtaatat   3420
cttactaagg cctttggtat acgacccaga gataacacga tgcgtatttt agttttgcaa   3480
agaaggggtt tggtctctgt gccagctcta taattgtttt gctacgattc cactgaaact   3540
cttcgatcaa gctactttat gtaaatcact tcattgtttt aaaggaataa acttgattat   3600
attgtttttt tatttggcat aactgtgatt cttttaggac aattactgta cacattaagg   3660
tgtatgtcag atattcatat tgacccaaat gtgtaatatt ccagttttct ctgcataagt   3720
aattaaaata tacttaaaaa ttaatagttt tatctgggta caaataaaca ggtgcctgaa   3780
ctagttcaca gacaaggaaa cttctatgta aaaatcacta tgatttctga attgctatgt   3840
```

gaaactacag atctttggaa cactgtttag gtagggtgtt aagacttaca cagtacctcg 3900
tttctacaca gagaaagaaa tggccatact tcaggaactg cagtgcttat gaggggatat 3960
ttaggcctct tgaatttttg atgtagatgg gcattttttt aaggtagtgg ttaattacct 4020
ttatgtgaac tttgaatggt ttaacaaaag atttgttttt gtagagattt taaaggggga 4080
gaattctaga aataaatgtt acctaattat tacagcctta aagacaaaaa tccttgttga 4140
agttttttta aaaaaagcta aattacatag acttaggcat taacatgttt gtggaagaat 4200
atagcagacg tatattgtat catttgagtg aatgttccca agtaggcatt ctaggctcta 4260
tttaactgag tcacactgca taggaattta gaacctaact tttataggtt atcaaaactg 4320
ttgtcaccat tgcacaattt tgtcctaata tatacataga aactttgtgg ggcatgttaa 4380
gttacagttt gcacaagttc atctcatttg tattccattg attttttttt tcttctaaac 4440
atttttttctt caaacagtat ataacttttt ttaggggatt tttttttaga cagcaaaaac 4500
tatctgaaga tttccatttg tcaaaaagta atgatttctt gataattgtg tagtaatgtt 4560
ttttagaacc cagcagttac cttaaagctg aatttatatt tagtaacttc tgtgttaata 4620
ctggatagca tgaattctgc attgagaaac tgaatagctg tcataaaatg aaactttctt 4680
tctaaagaaa gatactcaca tgagttcttg aagaatagtc ataactagat taagatctgt 4740
gttttagttt aatagtttga agtgcctgtt tgggataatg ataggtaatt tagatgaatt 4800
taggggaaaa aaaagttatc tgcagatatg ttgagggccc atctctcccc ccacaccccc 4860
acagagctaa ctgggttaca gtgttttatc cgaaagtttc caattccact gtcttgtgtt 4920
ttcatgttga aaatactttt gcatttttcc tttgagtgcc aatttcttac tagtactatt 4980
tcttaatgta acatgtttac ctggaatgta ttttaactat ttttgtatag tgtaaactga 5040
aacatgcaca ttttgtacat tgtgctttct tttgtgggac atatgcagtg tgatccagtt 5100
gttttccatc atttggttgc gctgacctag gaatgttggt catatcaaac attaaaaatg 5160
accactcttt taattgaaat taacttttaa atgtttatag gagtatgtgc tgtgaagtga 5220
tctaaaattt gtaatatttt tgtcatgaac tgtactactc ctaattattg taatgtaata 5280
aaaatagtta cagtgacaaa aaaaaaaaaa aa 5312

<210> SEQ ID NO 40
<211> LENGTH: 188
<212> TYPE: PRT
<213> ORGANISM: Homo sapiens

<400> SEQUENCE: 40

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly
35 40 45

Glu Thr Cys Leu Leu Asp Ile Leu Asp Thr Ala Gly Gln Glu Glu Tyr
50 55 60

Ser Ala Met Arg Asp Gln Tyr Met Arg Thr Gly Glu Gly Phe Leu Cys
65 70 75 80

Val Phe Ala Ile Asn Asn Thr Lys Ser Phe Glu Asp Ile His His Tyr
85 90 95

Arg Glu Gln Ile Lys Arg Val Lys Asp Ser Glu Asp Val Pro Met Val
100 105 110

```
Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

<210> SEQ ID NO 41
<211> LENGTH: 661
<212> TYPE: DNA
<213> ORGANISM: Rattus norvegicus

<400> SEQUENCE: 41

```
atgactgagt ataaacttgt ggtagttgga gctggtggcg taggcaagag tgccttgacg     60

atacagctaa ttcagaatca ctttgtggat gaatatgatc ctacgataga ggactcctac    120

aggaaacaag tagtaattga tggagaaacc tgtctcttgg atattctcga cacagcaggt    180

caagaggagt acagtgcaat gagggaccag tacatgagaa ctggggaggg ctttctttgt    240

gtatttgcca taaataatac taaatcattt gaagatattc accattatag agaacaaatt    300

aaaagagtaa aggactctga agatgtgcct atggtcctag tagggaataa gtgtgacttg    360

ccttctagaa cagtagacac gaaacaggct caggagttag caaggagtta tgggattcca    420

ttcattgaga cctcagcgaa gacaagacag ggtgttgacg atgccttcta tacattagtc    480

cgagaaattc gaaaacataa agaaaagatg agcaaagatg ggaaaaagaa gaagaagaag    540

tcaaggacaa ggtgtatagt catgtgaata gtttgtactc tttcttaagg cacacttaag    600

taaagtgtga tttttgtaca ttacactaaa ttattagcat ttgttttagc attacctaat    660

c                                                                    661
```

<210> SEQ ID NO 42
<211> LENGTH: 188
<212> TYPE: PRT
<213> ORGANISM: Rattus norvegicus

<400> SEQUENCE: 42

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125
```

```
Gln Ala Gln Glu Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Arg Thr Arg Cys Ile Val Met
            180                 185


<210> SEQ ID NO 43
<211> LENGTH: 4670
<212> TYPE: DNA
<213> ORGANISM: Mus musculus

<400> SEQUENCE: 43

aggcggcggc cgcggcggct gaggcggcag cgctgtggcg gcggctgaga cggcagggga     60

aggcggcggc ggctcggccc ggagtcccgc tcccgcgcca tttcggaccc ggagcgagcg    120

cggcgcgggc ctgaaggcgg cggcgggagc ctgaggcgcg gcggctccgc ggcgcggaga    180

gaggcctgct gaaaatgact gagtataaac ttgtggtggt tggagctggt ggcgtaggca    240

agagcgcctt gacgatacag ctaattcaga atcactttgt ggatgagtat gaccctacga    300

tagaggactc ctacaggaaa caagtagtaa ttgatggaga aacctgtctc ttggatattc    360

tcgacacagc aggtcaagag gagtacagtg caatgaggga ccagtacatg agaactgggg    420

agggctttct ttgtgtattt gccataaata atactaaatc atttgaagat attcaccatt    480

atagagaaca aattaaaaga gtaaaggact ctgaagatgt gcctatggtc ctggtaggga    540

ataagtgtga tttgccttct agaacagtag acacgaaaca ggctcaggag ttagcaagga    600

gttacgggat tccgttcatt gagacctcag caaagacaag acagggtgtt gacgatgcct    660

tctatacatt agtccgagaa attcgaaaac ataaagaaaa gatgagcaaa gatgggaaga    720

agaagaagaa gaagtcaagg acaaggtgta cagttatgtg aatactttgt actctttctt    780

aaggcacact taagtaaaag tgtgattttt gtacattaca ctaaattatt agcatttgtt    840

ttagcattac ctaatctttt tttttcttct gttcgtgcaa actgtcagct tttatctcaa    900

atgcttattt taaaagaaca gtggaaacct tctttttttct aagtgccagt attccctggg    960

ttttggactt aaactagcaa tgcctgtgga agagactaaa gacctgagac tctgtcttgg   1020

gatttggtgc atgcagttga ttccttgcta gttctcttac caactgtgaa cactgatggg   1080

aagcaggata atgaagcttc cggaccatcc ctgctctgtg tccatctact catccaatgg   1140

agtcattagc agtcaatcgc cgcttcactg gacactgagg ggtcacagac ttaggctccc   1200

tttgagtcgc gtccagcgtg tcctagactt tatcatcttt cagaggcgta ggcagactgt   1260

tcacaaaggc tttctgtagc tttccactgc aattaatctt ggtcactccc tcaaatagta   1320

tattttttct agaaaagggg aaaaatggaa aaaaaaaggc aatggaaaat gttgaaatcc   1380

attcagtttc catgttagct aaattactgt aagattccta taatagcttt tcctggtaag   1440

gcagacccag tatgaaatag taataaccat ttgggctata tttacatgct actaaatttt   1500

tgtaataatt caaacaactt tagcatatat aaaaagttct cataagaatt aagtacaatt   1560

ccccttttgtc agattgttct tatcctaact ttcaagtctt ttttgaattt ctgttgttga   1620

aagtagtttt aatggttgtg aagctgaaga tgatctgaga cagttatagc ttggcaggtg   1680

ttgaggagac cagagttgca gggttgggcc ttacgtgaac ctgtgacgaa cgctactggg   1740

ttttgcagca ctgctgcatt caatgttggc gacgcattgt ttggtcaaca taggggataa   1800
```

ggagactttg atggcttagt ataatgcatt ctcaccatgt aacagtccta ctgacaaatc 1860
aagaaatttg tttataataa taaaaaattt ttaaaaattt cgatgttcgc ttcaaggttg 1920
agattttggg gtaggaggct acaacaagag taaatcttaa agcaaggttt taagaaggtt 1980
tgaaaatgca ggtttgacta gtctctcaac tctagctaaa caaacattcc caagtacttc 2040
ccaaatctga taggtattta aaattatcta atgctttaag aatagttaac aggaaaaaaa 2100
tctcctcagt gcacttaaag caacccttca catcatttga aatgagatgg aaatatcact 2160
ggactatgag gactggatgt ctgtctgatt ttaagcaaat cactgtctgc ttggttttga 2220
atcatctcaa agacattaac ctcccagccg tgtaacatag tttacatgtt gacacaccta 2280
gttatcaagc tcagcacaat ctgtaactgt tttacatgga ttaacatctt cactgccagt 2340
cttgggcaaa ttgtgcaaga ggtaaaattt atatttcagt atccattctc ccatttcagg 2400
actcccctcc aacattatgc tggctttcag cctgtctctc acctgcccat cacttagtgt 2460
agttttaata atttccccca cttcaaactt tgtttccact atggacaact tcatgaactt 2520
tgcccactaa ggtaggtaca tcaaagctgc cctatggctt tcttccccgg gactgaaaat 2580
aacagacacc atagtgggat ttaaactaat agatggtttt cagggccact acaacaattc 2640
aatctcaatc ctttggactt cattcctgct gcccaggcca ctggtgcctc agtaggaatt 2700
ttcaaaatta gtgtgaacag acagagcaca gtccagtgga aggtgagctt aatcttcatc 2760
tagccatcat catggtaagt gatagattct attgttttaa taaatacagt ctaacaatga 2820
aaaacacttc gaagtttcaa tcataaagct gtctttttaa aaattttatt tactcaacat 2880
ttattcagtg cttgtcatat tctgggaatt acactaggca ctcagggtgc ggtgtcctca 2940
atccttggcc agtggtatgt agcatgatct gtaataccac taaataaggc atatagcata 3000
tgacttagac ataatgaaat acatgatttg agttttgcag agaggagttt gggtttgtac 3060
attcccttcc cccccagttt agcaagaatt gtttgctgtg aatccaatgc aacttttaaa 3120
tcaaactact ttatataatt atttcatttt tctaaaggaa cagaagtacc ctaaactatt 3180
tttttgaaat gttctaaact gtacatattc atagaacatt ctttgggtga attttaagtc 3240
ttaaaatgca attagtaata cttctcattt ctattcagag gaacaggtgt acttcaaaag 3300
ctgcagtgta taatcagata tttttaatgg acaatgtgtt aaagaagtgg taattaccac 3360
tatgtaaatt tgaattgtgt tacactttgg ttaacaaaag gggaaagaat cctagaaaca 3420
aatatgttat ctagttactg cagccttaaa gtccttgttg aagttaaaaa gcaatgctaa 3480
gttacagtca taggcattaa catgtttatg ggaaggatat agtaggcaaa tacaatttga 3540
gtaaatattt tcagtaggga attttaggct ctactgactg agtcacactg cataggaatt 3600
tagatcttaa cttttatagg ttatcgacct ttgccaccat tgcacaattt tgtcctaaca 3660
taaatacaag ttctgtgagg catgtcaaaa gttacagttt gcataaattc atctcatttt 3720
gtattccact gattttacat tttcctcaaa catacataca tacatacata caacacacac 3780
acactcacac atgaagggtt tttttttgt aggcaataaa aatttaacta atttccattt 3840
gttaaaaagt agtgatttat tgagaattat gcagtcattt tttaaaccca aaagttattt 3900
aaaggtgaat ttatactcaa taacttctgt gtaatactgg gtagcatgaa ttctgcattg 3960
aaaaattgaa cagataatac caatagctgt aaattctgtc aaaacatgaa aattatttct 4020
aaagaagtac attagttttc aaagaacagt tattagaatc agatctgtgg tttagttcaa 4080
taatttgaag tgcctgtttg ggatggtggt aggcattta gatgaatttg ggaaaaataa 4140
agttctgcag aaatgccagt ttcagacccc gctaacccgc tgagtgggct gtgtgctgtg 4200
ttagctccag tgccccaatc ccgtttcatg tcttcatgtt gaaacacttc tgcattttta 4260
tttgagtgcc aatttcttac tagtgctatt tcttagtgta acatgtttac ctggatgta 4320 ttttaactat ttttgtatag tgtaaactga aacatgcaca ttttgtacat tgtgctttcc 4380
ttctttccat tccttttctt tctgttttgt ttgtttgttt gtttgtttgt ttgttatggg 4440
acatatgcag tgtgatccag ttgttttcca tcctttggtt gcgctgacct agggaatgtt 4500
ggtcatatca aacattaaat ttaaaagtga ccactcttaa ttaaaattaa cttttaaatg 4560
tttataggag tacgtgctgt gaagtgatct gaaatttgta atatttttgt catgaaccgt 4620
actgctccta atcattgtaa tgtaataaaa atagttatgg tgactatgaa 4670

<210> SEQ ID NO 44
<211> LENGTH: 188
<212> TYPE: PRT
<213> ORGANISM: Mus musculus

<400> SEQUENCE: 44

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly
35 40 45

Glu Thr Cys Leu Leu Asp Ile Leu Asp Thr Ala Gly Gln Glu Glu Tyr
50 55 60

Ser Ala Met Arg Asp Gln Tyr Met Arg Thr Gly Glu Gly Phe Leu Cys
65 70 75 80

Val Phe Ala Ile Asn Asn Thr Lys Ser Phe Glu Asp Ile His His Tyr
85 90 95

Arg Glu Gln Ile Lys Arg Val Lys Asp Ser Glu Asp Val Pro Met Val
100 105 110

Leu Val Gly Asn Lys Cys Asp Leu Pro Ser Arg Thr Val Asp Thr Lys
115 120 125

Gln Ala Gln Glu Leu Ala Arg Ser Tyr Gly Ile Pro Phe Ile Glu Thr
130 135 140

Ser Ala Lys Thr Arg Gln Gly Val Asp Asp Ala Phe Tyr Thr Leu Val
145 150 155 160

Arg Glu Ile Arg Lys His Lys Glu Lys Met Ser Lys Asp Gly Lys Lys
165 170 175

Lys Lys Lys Lys Ser Arg Thr Arg Cys Thr Val Met
180 185

<210> SEQ ID NO 45
<211> LENGTH: 2068
<212> TYPE: DNA
<213> ORGANISM: Oryctolagus cuniculus

<400> SEQUENCE: 45
acacacgcgc ccacccagcc acccggccac cagccgccat gggcaaggac aggcagcccc 60
gcgggcagca gaggcagggg gacgccgccg ggcccgacga cccggggccg aagaaaggcg 120
ccgggacccg cgagcagcgc ggggaggagg aggcccagac gtgctgcggc tgccgcttcc 180
cgctgctgct cgcgctgctg cagctggccc tgggcgtcgc cgtgaccgtg gtgggcttcc 240
tcatggcgag cgtcagctcc tccctgctag tcagagccac tccatattgg gctgggatca 300
ttgtctgcgt ggtggcctat cttggcttgt ttatgctttg tgtctcgtac caagttgatg 360
aacggacgtg tatccagttt tctatgaaac tgctgtactt cgtgctgagc gccctggggc 420
tggtggtgtg cgtgctggcc gtggccttcg ccgcccacca ctactcgctg ctcacgcacc 480
tgacctgtga gaacgccccc gactcctgcc agtgcaagct gccgtcctcg gagccgctga 540
gccggacctt cgtgtaccgg gatgtgactg actgtaccag catcacgggc accttccagg 600
tgttcctgct cgtccagatg gttctgaact tggtctgtgg ccttgtgtgc ttggtggcct 660
gctttgtgat gtggaaacac aggtatcagg tcttttatgt gggggtcagg atgtgccccc 720
tgtcggcttc cgaaggccag cagcagaagg tgtaggaatc ttgctcagaa ttgggagaga 780
aaatggcaca ctggctagct gaggttaaaa agaaaaatta tttttaagga gaaagagaga 840
aaacttttgc caatatttac tgctctaaat gaatattttt tatatttttc aagaaacaaa 900
agagcatttc ttcaggtttc tattgtattt ttaaacattc gtataggttc aacaagatac 960
acattgattt gcgggatatt caaagtcaaa agcacaccaa actgggaagc aatggcacag 1020
aactgtcctc acagtctggg gtttactctt catgctcact ttcgccacca ctgacgtacg 1080
gctttctggt taatacggtc taaggtttgt agtggctgcc ccaggtcctt cccgcctcct 1140
accacaatcc cccactgcgt cttagagaaa ggcaaggtgt ggagaagtca ctgggcaacc 1200
aggtggaatc tcttcatttc ccctactgcg gatgttgtca aggcccaaaa catgagcgaa 1260
cttcaaaaac ctcatgggaa gtggagttcg aagtttattt tgctgccaaa aaattaagat 1320
ccacacatat atagggatct tcagaaagtt cacagaaaat gcataatatg ggaaaaaaaa 1380
agattcacgg atttcagaat tttgtttgga ccaaactaaa gttatctttt aatgccattt 1440
ctgaagtgcc ctcatagctt ggaaagccaa gcagaaaaga ggctttgcaa aaatacaagt 1500
aattataaac acctgggcca gggcggctgt ctcagctgcc ttcgcttggc tctgtacgta 1560
gatcactcgc gcggggcttg gcagggctct ctgcttctca ataattgaaa tatggtggta 1620
gttgtattct taatgatgta gaaggtttaa aaataattac attacgcttc cattctatca 1680
tctacaacaa atcattcaac ctaatttcta gctaattgtt aattataatt atgctcagaa 1740
gtctatttaa tgagctctgg ctgtacttag gcagctctgc cagtgtaaag agaaattatt 1800
ctcgtaagag aagaggccta aagattcttt cttctgaaag tcaagcgtta taagggaaaa 1860 cttttttttta attaatagct caggataaaa acaccaattt aaacaaaaac aagagcattt 1920
ataataggaa gtacttgtac aaatagcacg tttgtggcac attgcagagt gtctctcttt 1980
gcagctaaat agctttgaag aaggctggcg agtgcagatg tattctgtgc acaaaactgt 2040
atttggctca taaccctatt attgattc 2068

<210> SEQ ID NO 46
<211> LENGTH: 238
<212> TYPE: PRT
<213> ORGANISM: Oryctolagus cuniculus

<400> SEQUENCE: 46

Met Gly Lys Asp Arg Gln Pro Arg Gly Gln Gln Arg Gln Gly Asp Ala
1 5 10 15

Ala Gly Pro Asp Asp Pro Gly Pro Lys Lys Gly Ala Gly Thr Arg Glu
20 25 30

Gln Arg Gly Glu Glu Glu Ala Gln Thr Cys Cys Gly Cys Arg Phe Pro
35 40 45

Leu Leu Leu Ala Leu Leu Gln Leu Ala Leu Gly Val Ala Val Thr Val

-continued

```
    50                  55                  60

Val Gly Phe Leu Met Ala Ser Val Ser Ser Ser Leu Leu Val Arg Ala
65                  70                  75                  80

Thr Pro Tyr Trp Ala Gly Ile Ile Val Cys Val Val Ala Tyr Leu Gly
                85                  90                  95

Leu Phe Met Leu Cys Val Ser Tyr Gln Val Asp Glu Arg Thr Cys Ile
            100                 105                 110

Gln Phe Ser Met Lys Leu Leu Tyr Phe Val Leu Ser Ala Leu Gly Leu
        115                 120                 125

Val Val Cys Val Leu Ala Val Ala Phe Ala Ala His His Tyr Ser Leu
    130                 135                 140

Leu Thr His Leu Thr Cys Glu Asn Ala Pro Asp Ser Cys Gln Cys Lys
145                 150                 155                 160

Leu Pro Ser Ser Glu Pro Leu Ser Arg Thr Phe Val Tyr Arg Asp Val
                165                 170                 175

Thr Asp Cys Thr Ser Ile Thr Gly Thr Phe Gln Val Phe Leu Leu Val
            180                 185                 190

Gln Met Val Leu Asn Leu Val Cys Gly Leu Val Cys Leu Val Ala Cys
        195                 200                 205

Phe Val Met Trp Lys His Arg Tyr Gln Val Phe Tyr Val Gly Val Arg
    210                 215                 220

Met Cys Pro Leu Ser Ala Ser Glu Gly Gln Gln Gln Lys Val
225                 230                 235
```

<210> SEQ ID NO 47
<211> LENGTH: 1039
<212> TYPE: DNA
<213> ORGANISM: Cavia porcellus

<400> SEQUENCE: 47

```
ggtggcttct cggccagacc tcccggcccc cgccatttcg gaccgggagc cagcgcgacg     60

cgggcactga gggcggcggc gggggccaca ggctcggcgg ctcccaggtg cgggagagag    120

gcctgctgaa aatgactgaa tataaacttg tggtagttgg agctggtggc gtaggcaaga    180

gtgccttgac gatacagcta attcagaatc actttgtgga tgaatatgat cctacaatag    240

aggattccta caggaaacaa gtagtaattg atggagaaac ctgtctcttg gatattctcg    300

acacagcagg tcaagaggag tacagtgcaa tgagggacca gtacatgagg actggggagg    360

gctttctttg tgtatttgcc ataaataata ctaaatcttt tgaagatatt caccattata    420

gagaacaaat taaaagagtt aaagactctg aagatgtacc tatggtccta gtaggaaata    480

aatgtgattt gccttctaga acagtagaca caaaacaagc tcaggactta gcaagaagtt    540

atggaattcc ttttattgaa acatcagcaa agacaagaca gagagtggag gatgcttttt    600

atacattggt gagagagatt cgacaataca gattgaaaaa aatcagcaaa gaagaaaaga    660

ctcctggctg tgtgaaaatt aaaaaatgca ttataatggg tgttgatgat gccttctata    720

cgttagttcg agaaattcga aaacataaag aaaagatgag caaagatggt aaaaagaaga    780

aaaagaagtc gaagacaaag tgtataatta tgtaaataca atttgtactt ttttcttaag    840

gcatacttaa gtaaaagtgg taatttttgt acattacact aaattattag cttttgtttt    900

agcattactt aattcttttc ctatttcatg caaactgtta gcttttatct taaatgctca    960

ttttaaaatg acagtggaaa ccttttattt cctcttaagt gccagtattc cctgcatttt   1020

ggtttttgaa ctagcaatg                                                1039
```

<210> SEQ ID NO 48
<211> LENGTH: 227
<212> TYPE: PRT
<213> ORGANISM: Cavia porcellus

<400> SEQUENCE: 48

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met Gly Val Asp
            180                 185                 190

Asp Ala Phe Tyr Thr Leu Val Arg Glu Ile Arg Lys His Lys Glu Lys
        195                 200                 205

Met Ser Lys Asp Gly Lys Lys Lys Lys Lys Lys Ser Lys Thr Lys Cys
    210                 215                 220

Ile Ile Met
225
```

<210> SEQ ID NO 49
<211> LENGTH: 835
<212> TYPE: DNA
<213> ORGANISM: Cavia porcellus

<400> SEQUENCE: 49

```
acaggctcgg cggctcccag gtgcgggaga gaggcctgct gaaaatgact gaatataaac      60

ttgtggtagt tggagctggt ggcgtaggca agagtgcctt gacgatacag ctaattcaga     120

atcactttgt ggatgaatat gatcctacaa tagaggattc ctacaggaaa caagtagtaa     180

ttgatggaga aacctgtctc ttggatattc tcgacacagc aggtcaagag gagtacagtg     240

caatgaggga ccagtacatg aggactgggg agggctttct ttgtgtattt gccataaata     300

atactaaatc ttttgaagat attcaccatt atagagaaca aattaaaaga gttaaagact     360

ctgaagatgt acctatggtc ctagtaggaa ataaatgtga tttgccttct agaacagtag     420

acacaaaaca agctcaggac ttagcaagaa gttatggaat tcctttttatt gaaacatcag     480

caaagacaag acagggtgtt gatgatgcct tctatacgtt agttcgagaa attcgaaaac     540
```

-continued

```
ataaagaaaa gatgagcaaa gatggtaaaa agaagaaaaa gaagtcgaag acaaagtgta    600

taattatgta aatacaattt gtactttttt cttaaggcat acttaagtaa aagtggtaat    660

ttttgtacat tacactaaat tattagcttt tgttttagca ttacttaatt cttttcctat    720

ttcatgcaaa ctgttagctt ttatcttaaa tgctcatttt aaaatgacag tggaaacctt    780

ttatttcctc ttaagtgcca gtattccctg cattttggtt tttgaactag caatg         835
```

<210> SEQ ID NO 50
<211> LENGTH: 188
<212> TYPE: PRT
<213> ORGANISM: Cavia porcellus

<400> SEQUENCE: 50

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Ile Ile Met
            180                 185
```

<210> SEQ ID NO 51
<211> LENGTH: 4993
<212> TYPE: DNA
<213> ORGANISM: Canis lupus

<400> SEQUENCE: 51

```
gctgaaaatg actgaatata aacttgtggt agttggagct ggtggcgtag gcaagagtgc     60

cttgacgata cagctaattc agaatcactt tgtggatgaa tatgatccta caatagagga    120

ttcctacagg aaacaagtag taattgatgg agaaacctgt ctcttggata ttctcgacac    180

agcaggtcaa gaggagtaca gtgcaatgag ggaccagtac atgaggactg gggagggctt    240

tctttgtgta tttgccataa ataatactaa atcatttgaa gatattcacc attatagaga    300

acaaattaaa agagttaaag actctgaaga tgtacctatg gtcctagtag gaaataaatg    360

tgatttgcct tctagaacag tagacacaaa acaggctcag gacttagcaa gaagttatgg    420

aattcctttt attgaaacat cagcaaagac aagacagaga gtggaggatg ctttttatac    480

attggtgaga gagatccgac aatacagatt gaaaaaaatc aacaaagaag aaaagactcc    540
```

```
tggctgtgtg aaaattaaaa aatgcattgt aatgggtgtt gacgatgcct tctatacatt    600
agttcgagaa attcgaaaac ataaagaaaa gatgagcaaa gatggtaaaa agaagaaaaa    660
gaagtcaaag acaaagtgta taattatgta aatacaattt gtactttttt cttaaggcat    720
acttaagtaa aagtggtaat ttttgtacat tacactaaat tattagcatt tgttttagca    780
ttacctaatt ttctgctcca tccaaactgt tagcttttat cttgaatgct tattttaaaa    840
tgacagtgga aactttttcc tctaagtgcc agtattccct gagttttggt tttgaactag    900
caatgcctgt gaaaaagaaa ctgaatacct gagatttctg tcttggggtt tttggtgcat    960
gcagttgatt acttcctatt tttcttacca attgtgaact ttggtgtgaa acaaattaat   1020
gaagctttcg aatcatccct attctgtgtt ttacctagtc acatacatgg attaattact   1080
aattataact tcagttgata tttcatgatt ggttttactg aaacattgag ggaacatgaa   1140
tttatgggct gcttcttata ggtataatgt cctatagttt cagtcaccct taatgaatgt   1200
aaagctacac tgttcacaaa ggttttctcc atcttttcac tgctatttgt catagccacg   1260
ctcccaaaaa tattatattt tttctataaa aaagggaaaa aatagaaaaa aatacaaggc   1320
aatggaaaat attaaaaggc atttactttc catattagat aaattcctat aatactctga   1380
atagcttttc ctgttaaggc agacccagta tgtaatgagg attatagcaa ccattttggg   1440
gctatattta catgctacta aatttttgta ttaattgaaa aagttttaac atgtataaaa   1500
aattcccata ggaattaaat atagtctccc tgtgtcagat tgctctttct tagcataact   1560
ttaaatcttt tcttgatctt caatcttaga aaatagtttt aattcttgta gtgatgttaa   1620
agattatttg ggccagttag tttttaatag atgttaaaga gaccacagtt ccaaggccag   1680
gccttgtgtg aacctttaag cttcattaag agtttcatag tacagactgc atccctgtgg   1740
tctcccaggg tcatcatgca ttgattgggt ggtcaaaagt ggggacaaag agtgtttaga   1800
taagatgcat cctcactgta tggtggtcct gctgacagat caggaccatc acttttgttt   1860
tttaaaaaac caacagagct ttttaaaaac attatttaaa atgagatttt tgggggcagg   1920
gggtggcaag acttgaattt tttttaaaca atgaagtaaa aaggtttcaa aatctctagt   1980
gttggctagt tctcaacatt ggctaaagta acatttcata aacactttac aagtattggt   2040
ccatatttaa gaatatctaa tgcttaaata atagattaat aacaattctt tcagtgcatt   2100
taaaatgtat ttttaaatat ctgaagtgag atggtgtgtt gaggtgaaaa tatcactgga   2160
ctaggaggaa ggtgacttag attctagtta cgtgtctttt acaacttcag ttttgggcaa   2220
atcactcact atccatttct tcatgttaag tcatctcaaa ggctatatct agcatcaact   2280
atgtgattta cattcagttt acataaggat atacctattt gtcaatctca gcacaatctg   2340
taacttttta cctatgttct cttcagcgcc agtcttaggc aaagttgtgc aagaggtgag   2400
gtttattttt gagaatctga tctccggtag caggtactcc tctcccatgt tagtgtcatc   2460
ttgcctgcct accttctaca tgccccatga cttgatgctt tctaattccc cgaacctcaa   2520
gatgtagtgc tgctttggat atctccatga ggtaataagt cacattagtc aggctcaaca   2580
taatctgaca gatactgtag tgggatttga tctaatagct aattttcagg tggtaactgt   2640
atcaatttaa ttttgatctt ttgaacatca tctctgctac ctggtccatt agtgactaag   2700
taggaaaagt aggaattttc atatctgtga tgtgtagaca gaccctatcc agtagaagaa   2760
tttaataaat ttaattaata aatactgaaa gatttcctta gataatccaa aactaggact   2820
agccctggta acggtgatac attccattat tttaataagt aaaatcttct tacaatgaaa   2880
```

-continued

```
aatactttaa aatttaattc ataaagctta ctttttagca gaattcattt attcaacaaa   2940
tacttgagtg cctgctagat gccaggttct acacaaggca ccggggatat tatggtattc   3000
ccaacaaggg acataatccc tatccttaag tagtactgtt attttagagt ggtctgtagt   3060
atattagtga ggcatttggc acatgaccca gagataatat aatgcatatt ttagttttgc   3120
acagaaggga tatggtctct aaggtttttt ccagctctaa aataattgtt cgctctgatt   3180
ccaataaact gtttaatcaa gctactttat ataaatcact ttacttcatt attttaaaga   3240
agtaaacttg actatattgt tttttatttg ggataattat gtgattctgt tgggatactt   3300
atatagtaca cattaaattg tatgtcagat gataacatta aaattcccaa gtgtaatatt   3360
ctacttggtc tctgtgtatc ataattaaaa tagatttaaa tattgagttc aaaaatagtt   3420
ttatttatct gggtgtgaat aaacagatgc ctgaactaat tcacagaaaa ggaaacttct   3480
gtgtaaaaag tcagtccaat ttctgaaatg ctatgctaaa ctacaggttt atggaacatt   3540
agatagggtg ttaagacttt atatagtact tcctcttgtt tctatacaag agaaagaaat   3600
ggccatactt caggaattgc agtgcataac tgagggattt ttaggactct tgaatttttg   3660
atgtagccgg gcaacttttt ttaggcagtg gtaattatcc tttattatgt gaattttgaa   3720
tggtttgaca aaacgtttgt ttttgtagag attttaaaag gggagcgcta atcctagaaa   3780
taaatattat gtaattatta cggccttaaa gataaaaatc cttgttgaaa gttgaaaaaa   3840
attgctaaat tacatagtct tagacattaa catgtttgtg gaagaatgta gcagaggtat   3900
gtagtataat ttgagtgaat attcccaatt aggaattcta ggctctagtt taactgagtc   3960
acactgcata ggaatttaga acctaacttc taggttatca aaatctttgc caccattgca   4020
caattttgtc ctaatatata gagaaacttt gtgaggcatg ttcagttgcg gtttgcacaa   4080
gttcatctca tttgtattcc agtgattttt tttcttctaa ccattttttt aaacaacatg   4140
tacacattgt tttttttggt aggcaatgaa aactgtcatt tccattgtca aacagtaatt   4200
cctcgataac tgtattaatg gtttttaaaa aaccatcagt tactttaaaa ctgaatttat   4260
atttaataac ttctgtatta gtattgggta gcatgaaatc tctattgaga aattgaacag   4320
catacaacta gtagctgtaa attccttcag aaagtgaaaa ttatttcttc ctaaagatat   4380
cttgacatca gtgcttgaag aatagtcata actagattaa taattgtttt agttaaacag   4440
ttttaagtgc ctgtttcaga tgatgatagg caatttagat gaatttagga aaaatcaaag   4500
tttttacttg cagaaatgtc cattataggg ggcccccctc ctcatagagc tgaatgggtt   4560
atgtaatgtt ttatccaaaa gtttccaatt ccactgtctt gtgttttcat gttgaaaata   4620
cttttgcatt tttcctttga gtgccaattt cttactagta ctatttctta atgtaacatg   4680
tttacctgga atgtatttta actatttttg tatagtgtaa actgaaacat gcacattttg   4740
tacattgtgc ttttttttgt gggacatatg cagtgtgatc cagttgtttt ccatcatttg   4800
gttgcgctga cctaggaatg ttggtcatat caaacattaa atttaaaaat gaccactctt   4860
ttaattaaaa ttaactttta aatgtttata ggagtatgtg ctgtgaagtg atctgaaatt   4920
tgtaatattt ttgtcatgaa ctgtactgct cctaattatt gtaatgtaat aaaaatagtt   4980
atggtgacta tga                                                      4993
```

<210> SEQ ID NO 52
<211> LENGTH: 4993
<212> TYPE: PRT
<213> ORGANISM: Canis lupus

<400> SEQUENCE: 52

```
Gly Cys Thr Gly Ala Ala Ala Ala Thr Gly Ala Cys Thr Gly Ala Ala
1               5                   10                  15

Thr Ala Thr Ala Ala Ala Cys Thr Thr Gly Thr Gly Gly Thr Ala Gly
            20                  25                  30

Thr Thr Gly Gly Ala Gly Cys Thr Gly Gly Thr Gly Gly Cys Gly Thr
        35                  40                  45

Ala Gly Gly Cys Ala Ala Gly Ala Gly Thr Gly Cys Cys Thr Thr Gly
    50                  55                  60

Ala Cys Gly Ala Thr Ala Cys Ala Gly Cys Thr Ala Ala Thr Thr Cys
65                  70                  75                  80

Ala Gly Ala Ala Thr Cys Ala Cys Thr Thr Thr Gly Thr Gly Gly Ala
                85                  90                  95

Thr Gly Ala Ala Thr Ala Thr Gly Ala Thr Cys Cys Thr Ala Cys Ala
            100                 105                 110

Ala Thr Ala Gly Ala Gly Gly Ala Thr Thr Cys Cys Thr Ala Cys Ala
        115                 120                 125

Gly Gly Ala Ala Ala Cys Ala Ala Gly Thr Ala Gly Thr Ala Ala Thr
    130                 135                 140

Thr Gly Ala Thr Gly Gly Ala Gly Ala Ala Ala Cys Cys Thr Gly Thr
145                 150                 155                 160

Cys Thr Cys Thr Thr Gly Gly Ala Thr Ala Thr Thr Cys Thr Cys Gly
                165                 170                 175

Ala Cys Ala Cys Ala Gly Cys Ala Gly Gly Thr Cys Ala Ala Gly Ala
            180                 185                 190

Gly Gly Ala Gly Thr Ala Cys Ala Gly Thr Gly Cys Ala Ala Thr Gly
        195                 200                 205

Ala Gly Gly Gly Ala Cys Cys Ala Gly Thr Ala Cys Ala Thr Gly Ala
    210                 215                 220

Gly Gly Ala Cys Thr Gly Gly Gly Gly Ala Gly Gly Gly Cys Thr Thr
225                 230                 235                 240

Thr Cys Thr Thr Thr Gly Thr Gly Thr Ala Thr Thr Thr Gly Cys Cys
                245                 250                 255

Ala Thr Ala Ala Ala Thr Ala Ala Thr Ala Cys Thr Ala Ala Ala Thr
            260                 265                 270

Cys Ala Thr Thr Thr Gly Ala Ala Gly Ala Thr Ala Thr Thr Cys Ala
        275                 280                 285

Cys Cys Ala Thr Thr Ala Thr Ala Gly Ala Gly Ala Ala Cys Ala Ala
    290                 295                 300

Ala Thr Thr Ala Ala Ala Ala Gly Ala Gly Thr Thr Ala Ala Ala Gly
305                 310                 315                 320

Ala Cys Thr Cys Thr Gly Ala Ala Gly Ala Thr Gly Thr Ala Cys Cys
                325                 330                 335

Thr Ala Thr Gly Gly Thr Cys Cys Thr Ala Gly Thr Ala Gly Gly Ala
            340                 345                 350

Ala Ala Thr Ala Ala Ala Thr Gly Thr Gly Ala Thr Thr Thr Gly Cys
        355                 360                 365

Cys Thr Thr Cys Thr Ala Gly Ala Ala Cys Ala Gly Thr Ala Gly Ala
    370                 375                 380

Cys Ala Cys Ala Ala Ala Ala Cys Ala Gly Gly Cys Thr Cys Ala Gly
385                 390                 395                 400

Gly Ala Cys Thr Thr Ala Gly Cys Ala Ala Gly Ala Ala Gly Thr Thr
                405                 410                 415
```

-continued

Ala Thr Gly Gly Ala Ala Thr Thr Cys Cys Thr Thr Thr Thr Ala Thr
420 425 430

Thr Gly Ala Ala Ala Cys Ala Thr Cys Ala Gly Cys Ala Ala Ala Gly
435 440 445

Ala Cys Ala Ala Gly Ala Cys Ala Gly Ala Gly Ala Gly Thr Gly Gly
450 455 460

Ala Gly Gly Ala Thr Gly Cys Thr Thr Thr Thr Thr Ala Thr Ala Cys
465 470 475 480

Ala Thr Thr Gly Gly Thr Gly Ala Gly Ala Gly Ala Gly Ala Thr Cys
485 490 495

Cys Gly Ala Cys Ala Ala Thr Ala Cys Ala Gly Ala Thr Thr Gly Ala
500 505 510

Ala Ala Ala Ala Ala Ala Thr Cys Ala Ala Cys Ala Ala Ala Gly Ala
515 520 525

Ala Gly Ala Ala Ala Ala Gly Ala Cys Thr Cys Cys Thr Gly Gly Cys
530 535 540

Thr Gly Thr Gly Thr Gly Ala Ala Ala Ala Thr Thr Ala Ala Ala Ala
545 550 555 560

Ala Ala Thr Gly Cys Ala Thr Thr Gly Thr Ala Ala Thr Gly Gly Gly
565 570 575

Thr Gly Thr Thr Gly Ala Cys Gly Ala Thr Gly Cys Cys Thr Thr Cys
580 585 590

Thr Ala Thr Ala Cys Ala Thr Thr Ala Gly Thr Thr Cys Gly Ala Gly
595 600 605

Ala Ala Ala Thr Thr Cys Gly Ala Ala Ala Ala Cys Ala Thr Ala Ala
610 615 620

Ala Gly Ala Ala Ala Ala Gly Ala Thr Gly Ala Gly Cys Ala Ala Ala
625 630 635 640

Gly Ala Thr Gly Gly Thr Ala Ala Ala Ala Ala Gly Ala Ala Gly Ala
645 650 655

Ala Ala Ala Ala Gly Ala Ala Gly Thr Cys Ala Ala Ala Gly Ala Cys
660 665 670

Ala Ala Ala Gly Thr Gly Thr Ala Thr Ala Ala Thr Thr Ala Thr Gly
675 680 685

Thr Ala Ala Ala Thr Ala Cys Ala Ala Thr Thr Thr Gly Thr Ala Cys
690 695 700

Thr Thr Thr Thr Thr Thr Cys Thr Thr Ala Ala Gly Gly Cys Ala Thr
705 710 715 720

Ala Cys Thr Thr Ala Ala Gly Thr Ala Ala Ala Ala Gly Thr Gly Gly
725 730 735

Thr Ala Ala Thr Thr Thr Thr Thr Gly Thr Ala Cys Ala Thr Thr Ala
740 745 750

Cys Ala Cys Thr Ala Ala Ala Thr Thr Ala Thr Thr Ala Gly Cys Ala
755 760 765

Thr Thr Thr Gly Thr Thr Thr Thr Ala Gly Cys Ala Thr Thr Ala Cys
770 775 780

Cys Thr Ala Ala Thr Thr Thr Thr Cys Thr Gly Cys Thr Cys Cys Ala
785 790 795 800

Thr Cys Cys Ala Ala Ala Cys Thr Gly Thr Thr Ala Gly Cys Thr Thr
805 810 815

Thr Thr Ala Thr Cys Thr Thr Gly Ala Ala Thr Gly Cys Thr Thr Ala
820 825 830

Thr Thr Thr Thr Ala Ala Ala Ala Thr Gly Ala Cys Ala Gly Thr Gly 835 840 845

Gly Ala Ala Ala Cys Thr Thr Thr Thr Thr Cys Cys Thr Cys Thr Ala
850 855 860

Ala Gly Thr Gly Cys Cys Ala Gly Thr Ala Thr Thr Cys Cys Cys Thr
865 870 875 880

Gly Ala Gly Thr Thr Thr Thr Gly Gly Thr Thr Thr Thr Gly Ala Ala
885 890 895

Cys Thr Ala Gly Cys Ala Ala Thr Gly Cys Cys Thr Gly Thr Gly Ala
900 905 910

Ala Ala Ala Ala Gly Ala Ala Ala Cys Thr Gly Ala Ala Thr Ala Cys
915 920 925

Cys Thr Gly Ala Gly Ala Thr Thr Thr Cys Thr Gly Thr Cys Thr Thr
930 935 940

Gly Gly Gly Gly Thr Thr Thr Thr Thr Gly Gly Thr Gly Cys Ala Thr
945 950 955 960

Gly Cys Ala Gly Thr Thr Gly Ala Thr Thr Ala Cys Thr Thr Cys Cys
965 970 975

Thr Ala Thr Thr Thr Thr Thr Cys Thr Thr Ala Cys Cys Ala Ala Thr
980 985 990

Thr Gly Thr Gly Ala Ala Cys Thr Thr Thr Gly Gly Thr Gly Thr Gly
995 1000 1005

Ala Ala Ala Cys Ala Ala Ala Thr Thr Ala Ala Thr Gly Ala Ala
1010 1015 1020

Gly Cys Thr Thr Thr Cys Gly Ala Ala Thr Cys Ala Thr Cys Cys
1025 1030 1035

Cys Thr Ala Thr Thr Cys Thr Gly Thr Gly Thr Thr Thr Thr Ala
1040 1045 1050

Cys Cys Thr Ala Gly Thr Cys Ala Cys Ala Thr Ala Cys Ala Thr
1055 1060 1065

Gly Gly Ala Thr Thr Ala Ala Thr Thr Ala Cys Thr Ala Ala Thr
1070 1075 1080

Thr Ala Thr Ala Ala Cys Thr Thr Cys Ala Gly Thr Thr Gly Ala
1085 1090 1095

Thr Ala Thr Thr Thr Cys Ala Thr Gly Ala Thr Thr Gly Gly Thr
1100 1105 1110

Thr Thr Thr Ala Cys Thr Gly Ala Ala Ala Cys Ala Thr Thr Gly
1115 1120 1125

Ala Gly Gly Gly Ala Ala Cys Ala Thr Gly Ala Ala Thr Thr Thr
1130 1135 1140

Ala Thr Gly Gly Gly Cys Thr Gly Cys Thr Thr Cys Thr Thr Ala
1145 1150 1155

Thr Ala Gly Gly Thr Ala Thr Ala Ala Thr Gly Thr Cys Cys Thr
1160 1165 1170

Ala Thr Ala Gly Thr Thr Thr Cys Ala Gly Thr Cys Ala Cys Cys
1175 1180 1185

Cys Thr Thr Ala Ala Thr Gly Ala Ala Thr Gly Thr Ala Ala Ala
1190 1195 1200

Gly Cys Thr Ala Cys Ala Cys Thr Gly Thr Thr Cys Ala Cys Ala
1205 1210 1215

Ala Ala Gly Gly Thr Thr Thr Thr Cys Thr Cys Cys Ala Thr Cys
1220 1225 1230

Thr Thr Thr Thr Cys Ala Cys Thr Gly Cys Thr Ala Thr Thr Thr
1235 1240 1245

```
Gly Thr Cys Ala Thr Ala Gly Cys Cys Ala Cys Gly Cys Thr Cys
    1250                1255                1260

Cys Cys Ala Ala Ala Ala Ala Thr Ala Thr Thr Ala Thr Ala Thr
    1265                1270                1275

Thr Thr Thr Thr Thr Cys Thr Ala Thr Ala Ala Ala Ala Ala Ala
    1280                1285                1290

Gly Gly Gly Ala Ala Ala Ala Ala Ala Thr Ala Gly Ala Ala Ala
    1295                1300                1305

Ala Ala Ala Ala Thr Ala Cys Ala Ala Gly Gly Cys Ala Ala Thr
    1310                1315                1320

Gly Gly Ala Ala Ala Ala Thr Ala Thr Thr Ala Ala Ala Ala Gly
    1325                1330                1335

Gly Cys Ala Thr Thr Thr Ala Cys Thr Thr Thr Cys Cys Ala Thr
    1340                1345                1350

Ala Thr Thr Ala Gly Ala Thr Ala Ala Ala Thr Thr Cys Cys Thr
    1355                1360                1365

Ala Thr Ala Ala Thr Ala Cys Thr Cys Thr Gly Ala Ala Thr Ala
    1370                1375                1380

Gly Cys Thr Thr Thr Thr Cys Cys Thr Gly Thr Thr Ala Ala Gly
    1385                1390                1395

Gly Cys Ala Gly Ala Cys Cys Cys Ala Gly Thr Ala Thr Gly Thr
    1400                1405                1410

Ala Ala Thr Gly Ala Gly Gly Ala Thr Thr Ala Thr Ala Gly Cys
    1415                1420                1425

Ala Ala Cys Cys Ala Thr Thr Thr Thr Gly Gly Gly Gly Cys Thr
    1430                1435                1440

Ala Thr Ala Thr Thr Thr Ala Cys Ala Thr Gly Cys Thr Ala Cys
    1445                1450                1455

Thr Ala Ala Ala Thr Thr Thr Thr Thr Gly Thr Ala Thr Thr Ala
    1460                1465                1470

Ala Thr Thr Gly Ala Ala Ala Ala Ala Gly Thr Thr Thr Thr Ala
    1475                1480                1485

Ala Cys Ala Thr Gly Thr Ala Thr Ala Ala Ala Ala Ala Ala Thr
    1490                1495                1500

Thr Cys Cys Cys Ala Thr Ala Gly Gly Ala Ala Thr Thr Ala Ala
    1505                1510                1515

Ala Thr Ala Thr Ala Gly Thr Cys Thr Cys Cys Cys Thr Gly Thr
    1520                1525                1530

Gly Thr Cys Ala Gly Ala Thr Thr Gly Cys Thr Cys Thr Thr Thr
    1535                1540                1545

Cys Thr Thr Ala Gly Cys Ala Thr Ala Ala Cys Thr Thr Thr Ala
    1550                1555                1560

Ala Ala Thr Cys Thr Thr Thr Thr Cys Thr Thr Gly Ala Thr Cys
    1565                1570                1575

Thr Thr Cys Ala Ala Thr Cys Thr Thr Ala Gly Ala Ala Ala Ala
    1580                1585                1590

Thr Ala Gly Thr Thr Thr Thr Ala Ala Thr Thr Cys Thr Thr Gly
    1595                1600                1605

Thr Ala Gly Thr Gly Ala Thr Gly Thr Thr Ala Ala Ala Gly Ala
    1610                1615                1620

Thr Thr Ala Thr Thr Thr Gly Gly Gly Cys Cys Ala Gly Thr Thr
    1625                1630                1635
```

-continued

```
Ala Gly  Thr Thr Thr Thr Thr  Ala Ala Thr Ala Gly  Ala Thr Gly
    1640                 1645                 1650

Thr Thr  Ala Ala Ala Gly Ala  Gly Ala Cys Cys Ala  Cys Ala Gly
    1655                 1660                 1665

Thr Thr  Cys Cys Ala Ala Gly  Gly Cys Cys Ala Gly  Gly Cys Cys
    1670                 1675                 1680

Thr Thr  Gly Thr Gly Thr Gly  Ala Ala Cys Cys Thr  Thr Thr Ala
    1685                 1690                 1695

Ala Gly  Cys Thr Thr Cys Ala  Thr Thr Ala Ala Gly  Ala Gly Thr
    1700                 1705                 1710

Thr Thr  Cys Ala Thr Ala Gly  Thr Ala Cys Ala Gly  Ala Cys Thr
    1715                 1720                 1725

Gly Cys  Ala Thr Cys Cys Cys  Thr Gly Thr Gly Gly  Thr Cys Thr
    1730                 1735                 1740

Cys Cys  Cys Ala Gly Gly Gly  Thr Cys Ala Thr Cys  Ala Thr Gly
    1745                 1750                 1755

Cys Ala  Thr Thr Gly Ala Thr  Thr Gly Gly Gly Thr  Gly Gly Thr
    1760                 1765                 1770

Cys Ala  Ala Ala Ala Gly Thr  Gly Gly Gly Gly Ala  Cys Ala Ala
    1775                 1780                 1785

Ala Gly  Ala Gly Thr Gly Thr  Thr Thr Ala Gly Ala  Thr Ala Ala
    1790                 1795                 1800

Gly Ala  Thr Gly Cys Ala Thr  Cys Cys Thr Cys Ala  Cys Thr Gly
    1805                 1810                 1815

Thr Ala  Thr Gly Gly Thr Gly  Gly Thr Cys Cys Thr  Gly Cys Thr
    1820                 1825                 1830

Gly Ala  Cys Ala Gly Ala Thr  Cys Ala Gly Gly Ala  Cys Cys Ala
    1835                 1840                 1845

Thr Cys  Ala Cys Thr Thr Thr  Thr Gly Thr Thr Thr  Thr Thr Thr
    1850                 1855                 1860

Ala Ala  Ala Ala Ala Ala Cys  Cys Ala Ala Cys Ala  Gly Ala Gly
    1865                 1870                 1875

Cys Thr  Thr Thr Thr Thr Ala  Ala Ala Ala Ala Cys  Ala Thr Thr
    1880                 1885                 1890

Ala Thr  Thr Thr Ala Ala Ala  Ala Thr Gly Ala Gly  Ala Thr Thr
    1895                 1900                 1905

Thr Thr  Thr Gly Gly Gly Gly  Gly Cys Ala Gly Gly  Gly Gly Gly
    1910                 1915                 1920

Thr Gly  Gly Cys Ala Ala Gly  Ala Cys Thr Thr Gly  Ala Ala Thr
    1925                 1930                 1935

Thr Thr  Thr Thr Thr Thr Thr  Ala Ala Ala Cys Ala  Ala Thr Gly
    1940                 1945                 1950

Ala Ala  Gly Thr Ala Ala Ala  Ala Ala Gly Gly Thr  Thr Thr Cys
    1955                 1960                 1965

Ala Ala  Ala Ala Thr Cys Thr  Cys Thr Ala Gly Thr  Gly Thr Thr
    1970                 1975                 1980

Gly Gly  Cys Thr Ala Gly Thr  Thr Cys Thr Cys Ala  Ala Cys Ala
    1985                 1990                 1995

Thr Thr  Gly Gly Cys Thr Ala  Ala Ala Gly Thr Ala  Ala Cys Ala
    2000                 2005                 2010

Thr Thr  Thr Cys Ala Thr Ala  Ala Ala Cys Ala Cys  Thr Thr Thr
    2015                 2020                 2025

Ala Cys  Ala Ala Gly Thr Ala  Thr Thr Gly Gly Thr  Cys Cys Ala
```

```
    2030                2035                2040

Thr Ala  Thr Thr Thr Ala Ala  Gly Ala Ala Thr Ala  Thr Cys Thr
    2045                2050                2055

Ala Ala  Thr Gly Cys Thr Thr  Ala Ala Ala Thr Ala  Ala Thr Ala
    2060                2065                2070

Gly Ala  Thr Thr Ala Ala Thr  Ala Ala Cys Ala Ala  Thr Thr Cys
    2075                2080                2085

Thr Thr  Thr Cys Ala Gly Thr  Gly Cys Ala Thr Thr  Thr Ala Ala
    2090                2095                2100

Ala Ala  Thr Gly Thr Ala Thr  Thr Thr Thr Thr Ala  Ala Ala Thr
    2105                2110                2115

Ala Thr  Cys Thr Gly Ala Ala  Gly Thr Gly Ala Gly  Ala Thr Gly
    2120                2125                2130

Gly Thr  Gly Thr Gly Thr Thr  Gly Ala Gly Gly Thr  Gly Ala Ala
    2135                2140                2145

Ala Ala  Thr Ala Thr Cys Ala  Cys Thr Gly Gly Ala  Cys Thr Ala
    2150                2155                2160

Gly Gly  Ala Gly Gly Ala Ala  Gly Gly Thr Gly Ala  Cys Thr Thr
    2165                2170                2175

Ala Gly  Ala Thr Thr Cys Thr  Ala Gly Thr Thr Ala  Cys Gly Thr
    2180                2185                2190

Gly Thr  Cys Thr Thr Thr Thr  Ala Cys Ala Ala Cys  Thr Thr Cys
    2195                2200                2205

Ala Gly  Thr Thr Thr Thr Gly  Gly Gly Cys Ala Ala  Ala Thr Cys
    2210                2215                2220

Ala Cys  Thr Cys Ala Cys Thr  Ala Thr Cys Cys Ala  Thr Thr Thr
    2225                2230                2235

Cys Thr  Thr Cys Ala Thr Gly  Thr Thr Ala Ala Gly  Thr Cys Ala
    2240                2245                2250

Thr Cys  Thr Cys Ala Ala Ala  Gly Gly Cys Thr Ala  Thr Ala Thr
    2255                2260                2265

Cys Thr  Ala Gly Cys Ala Thr  Cys Ala Ala Cys Thr  Ala Thr Gly
    2270                2275                2280

Thr Gly  Ala Thr Thr Thr Ala  Cys Ala Thr Thr Cys  Ala Gly Thr
    2285                2290                2295

Thr Thr  Ala Cys Ala Thr Ala  Ala Gly Gly Ala Thr  Ala Thr Ala
    2300                2305                2310

Cys Cys  Thr Ala Thr Thr Thr  Gly Thr Cys Ala Ala  Thr Cys Thr
    2315                2320                2325

Cys Ala  Gly Cys Ala Cys Ala  Ala Thr Cys Thr Gly  Thr Ala Ala
    2330                2335                2340

Cys Thr  Thr Thr Thr Thr Ala  Cys Cys Thr Ala Thr  Gly Thr Thr
    2345                2350                2355

Cys Thr  Cys Thr Thr Cys Ala  Gly Cys Gly Cys Cys  Ala Gly Thr
    2360                2365                2370

Cys Thr  Thr Ala Gly Gly Cys  Ala Ala Ala Gly Thr  Thr Gly Thr
    2375                2380                2385

Gly Cys  Ala Ala Gly Ala Gly  Gly Thr Gly Ala Gly  Gly Thr Thr
    2390                2395                2400

Thr Ala  Thr Thr Thr Thr Thr  Gly Ala Gly Ala Ala  Thr Cys Thr
    2405                2410                2415

Gly Ala  Thr Cys Thr Cys Cys  Gly Gly Thr Ala Gly  Cys Ala Gly
    2420                2425                2430
```

-continued

```
Gly Thr  Ala Cys Thr Cys Cys  Thr Cys Thr Cys Cys  Cys Ala Thr
    2435                 2440                 2445

Gly Thr  Thr Ala Gly Thr Gly  Thr Cys Ala Thr Cys  Thr Thr Gly
    2450                 2455                 2460

Cys Cys  Thr Gly Cys Cys Thr  Ala Cys Cys Thr Thr  Cys Thr Ala
    2465                 2470                 2475

Cys Ala  Thr Gly Cys Cys Cys  Cys Ala Thr Gly Ala  Cys Thr Thr
    2480                 2485                 2490

Gly Ala  Thr Gly Cys Thr Thr  Thr Cys Thr Ala Ala  Thr Thr Cys
    2495                 2500                 2505

Cys Cys  Cys Gly Ala Ala Cys  Cys Thr Cys Ala Ala  Gly Ala Thr
    2510                 2515                 2520

Gly Thr  Ala Gly Thr Gly Cys  Thr Gly Cys Thr Thr  Thr Gly Gly
    2525                 2530                 2535

Ala Thr  Ala Thr Cys Thr Cys  Cys Ala Thr Gly Ala  Gly Gly Thr
    2540                 2545                 2550

Ala Ala  Thr Ala Ala Gly Thr  Cys Ala Cys Ala Thr  Thr Ala Gly
    2555                 2560                 2565

Thr Cys  Ala Gly Gly Cys Thr  Cys Ala Ala Cys Ala  Thr Ala Ala
    2570                 2575                 2580

Thr Cys  Thr Gly Ala Cys Ala  Gly Ala Thr Ala Cys  Thr Gly Thr
    2585                 2590                 2595

Ala Gly  Thr Gly Gly Gly Ala  Thr Thr Thr Gly Ala  Thr Cys Thr
    2600                 2605                 2610

Ala Ala  Thr Ala Gly Cys Thr  Ala Ala Thr Thr Thr  Thr Cys Ala
    2615                 2620                 2625

Gly Gly  Thr Gly Gly Thr Ala  Ala Cys Thr Gly Thr  Ala Thr Cys
    2630                 2635                 2640

Ala Ala  Thr Thr Thr Ala Ala  Thr Thr Thr Thr Gly  Ala Thr Cys
    2645                 2650                 2655

Thr Thr  Thr Thr Gly Ala Ala  Cys Ala Thr Cys Ala  Thr Cys Thr
    2660                 2665                 2670

Cys Thr  Gly Cys Thr Ala Cys  Cys Thr Gly Gly Thr  Cys Cys Ala
    2675                 2680                 2685

Thr Thr  Ala Gly Thr Gly Ala  Cys Thr Ala Ala Gly  Thr Ala Gly
    2690                 2695                 2700

Gly Ala  Ala Ala Ala Gly Thr  Ala Gly Gly Ala Ala  Thr Thr Thr
    2705                 2710                 2715

Thr Cys  Ala Thr Ala Thr Cys  Thr Gly Thr Gly Ala  Thr Gly Thr
    2720                 2725                 2730

Gly Thr  Ala Gly Ala Cys Ala  Gly Ala Cys Cys Cys  Thr Ala Thr
    2735                 2740                 2745

Cys Cys  Ala Gly Thr Ala Gly  Ala Ala Gly Ala Ala  Thr Thr Thr
    2750                 2755                 2760

Ala Ala  Thr Ala Ala Ala Thr  Thr Thr Ala Ala Thr  Thr Ala Ala
    2765                 2770                 2775

Thr Ala  Ala Ala Thr Ala Cys  Thr Gly Ala Ala Ala  Gly Ala Thr
    2780                 2785                 2790

Thr Thr  Cys Cys Thr Thr Ala  Gly Ala Thr Ala Ala  Thr Cys Cys
    2795                 2800                 2805

Ala Ala  Ala Ala Cys Thr Ala  Gly Gly Ala Cys Thr  Ala Gly Cys
    2810                 2815                 2820
```

Cys Cys Thr Gly Gly Thr Ala Ala Cys Gly Gly Thr Gly Ala Thr
2825 2830 2835

Ala Cys Ala Thr Thr Cys Cys Ala Thr Thr Ala Thr Thr Thr Thr
2840 2845 2850

Ala Ala Thr Ala Ala Gly Thr Ala Ala Ala Ala Thr Cys Thr Thr
2855 2860 2865

Cys Thr Thr Ala Cys Ala Ala Thr Gly Ala Ala Ala Ala Ala Thr
2870 2875 2880

Ala Cys Thr Thr Thr Ala Ala Ala Ala Thr Thr Thr Ala Ala Thr
2885 2890 2895

Thr Cys Ala Thr Ala Ala Ala Gly Cys Thr Thr Ala Cys Thr Thr
2900 2905 2910

Thr Thr Thr Ala Gly Cys Ala Gly Ala Ala Thr Thr Cys Ala Thr
2915 2920 2925

Thr Thr Ala Thr Thr Cys Ala Ala Cys Ala Ala Ala Thr Ala Cys
2930 2935 2940

Thr Thr Gly Ala Gly Thr Gly Cys Cys Thr Gly Cys Thr Ala Gly
2945 2950 2955

Ala Thr Gly Cys Cys Ala Gly Gly Thr Thr Cys Thr Ala Cys Ala
2960 2965 2970

Cys Ala Ala Gly Gly Cys Ala Cys Cys Gly Gly Gly Gly Ala Thr
2975 2980 2985

Ala Thr Thr Ala Thr Gly Gly Thr Ala Thr Thr Cys Cys Cys Ala
2990 2995 3000

Ala Cys Ala Ala Gly Gly Gly Ala Cys Ala Thr Ala Ala Thr Cys
3005 3010 3015

Cys Cys Thr Ala Thr Cys Cys Thr Thr Ala Ala Gly Thr Ala Gly
3020 3025 3030

Thr Ala Cys Thr Gly Thr Thr Ala Thr Thr Thr Thr Ala Gly Ala
3035 3040 3045

Gly Thr Gly Gly Thr Cys Thr Gly Thr Ala Gly Thr Ala Thr Ala
3050 3055 3060

Thr Thr Ala Gly Thr Gly Ala Gly Gly Cys Ala Thr Thr Thr Gly
3065 3070 3075

Gly Cys Ala Cys Ala Thr Gly Ala Cys Cys Cys Ala Gly Ala Gly
3080 3085 3090

Ala Thr Ala Ala Thr Ala Thr Ala Ala Thr Gly Cys Ala Thr Ala
3095 3100 3105

Thr Thr Thr Thr Ala Gly Thr Thr Thr Thr Gly Cys Ala Cys Ala
3110 3115 3120

Gly Ala Ala Gly Gly Gly Ala Thr Ala Thr Gly Gly Thr Cys Thr
3125 3130 3135

Cys Thr Ala Ala Gly Gly Thr Thr Thr Thr Thr Thr Cys Cys Ala
3140 3145 3150

Gly Cys Thr Cys Thr Ala Ala Ala Ala Thr Ala Ala Thr Thr Gly
3155 3160 3165

Thr Thr Cys Gly Cys Thr Cys Thr Gly Ala Thr Thr Cys Cys Ala
3170 3175 3180

Ala Thr Ala Ala Ala Cys Thr Gly Thr Thr Thr Ala Ala Thr Cys
3185 3190 3195

Ala Ala Gly Cys Thr Ala Cys Thr Thr Thr Ala Thr Ala Thr Ala
3200 3205 3210

Ala Ala Thr Cys Ala Cys Thr Thr Thr Ala Cys Thr Thr Cys Ala

```
    3215                3220                3225

Thr Thr  Ala Thr Thr Thr Thr  Ala Ala Ala Gly Ala  Ala Gly Thr
    3230                3235                3240

Ala Ala  Ala Cys Thr Thr Gly  Ala Cys Thr Ala Thr  Ala Thr Thr
    3245                3250                3255

Gly Thr  Thr Thr Thr Thr Thr  Ala Thr Thr Thr Gly  Gly Gly Ala
    3260                3265                3270

Thr Ala  Ala Thr Thr Ala Thr  Gly Thr Gly Ala Thr  Thr Cys Thr
    3275                3280                3285

Gly Thr  Thr Gly Gly Gly Ala  Thr Ala Cys Thr Thr  Ala Thr Ala
    3290                3295                3300

Thr Ala  Gly Thr Ala Cys Ala  Cys Ala Thr Thr Ala  Ala Ala Thr
    3305                3310                3315

Thr Gly  Thr Ala Thr Gly Thr  Cys Ala Gly Ala Thr  Gly Ala Thr
    3320                3325                3330

Ala Ala  Cys Ala Thr Thr Ala  Ala Ala Ala Thr Thr  Cys Cys Cys
    3335                3340                3345

Ala Ala  Gly Thr Gly Thr Ala  Ala Thr Ala Thr Thr  Cys Thr Ala
    3350                3355                3360

Cys Thr  Thr Gly Gly Thr Cys  Thr Cys Thr Gly Thr  Gly Thr Ala
    3365                3370                3375

Thr Cys  Ala Thr Ala Ala Thr  Thr Ala Ala Ala Ala  Thr Ala Gly
    3380                3385                3390

Ala Thr  Thr Thr Ala Ala Ala  Thr Ala Thr Thr Gly  Ala Gly Thr
    3395                3400                3405

Thr Cys  Ala Ala Ala Ala Ala  Thr Ala Gly Thr Thr  Thr Thr Ala
    3410                3415                3420

Thr Thr  Thr Ala Thr Cys Thr  Gly Gly Gly Thr Gly  Thr Gly Ala
    3425                3430                3435

Ala Thr  Ala Ala Ala Cys Ala  Gly Ala Thr Gly Cys  Cys Thr Gly
    3440                3445                3450

Ala Ala  Cys Thr Ala Ala Thr  Thr Cys Ala Cys Ala  Gly Ala Ala
    3455                3460                3465

Ala Ala  Gly Gly Ala Ala Ala  Cys Thr Thr Cys Thr  Gly Thr Gly
    3470                3475                3480

Thr Ala  Ala Ala Ala Ala Gly  Thr Cys Ala Gly Thr  Cys Cys Ala
    3485                3490                3495

Ala Thr  Thr Thr Cys Thr Gly  Ala Ala Ala Thr Gly  Cys Thr Ala
    3500                3505                3510

Thr Gly  Cys Thr Ala Ala Ala  Cys Thr Ala Cys Ala  Gly Gly Thr
    3515                3520                3525

Thr Thr  Ala Thr Gly Gly Ala  Ala Cys Ala Thr Thr  Ala Gly Ala
    3530                3535                3540

Thr Ala  Gly Gly Gly Thr Gly  Thr Thr Ala Ala Gly  Ala Cys Thr
    3545                3550                3555

Thr Thr  Ala Thr Ala Thr Ala  Gly Thr Ala Cys Thr  Thr Cys Cys
    3560                3565                3570

Thr Cys  Thr Thr Gly Thr Thr  Thr Cys Thr Ala Thr  Ala Cys Ala
    3575                3580                3585

Ala Gly  Ala Gly Ala Ala Ala  Gly Ala Ala Ala Thr  Gly Gly Cys
    3590                3595                3600

Cys Ala  Thr Ala Cys Thr Thr  Cys Ala Gly Gly Ala  Ala Thr Thr
    3605                3610                3615
```

-continued

```
Gly Cys  Ala Gly Thr Gly Cys  Ala Thr Ala Ala Cys  Thr Gly Ala
    3620                 3625                 3630

Gly Gly  Gly Ala Thr Thr Thr  Thr Thr Ala Gly Gly  Ala Cys Thr
    3635                 3640                 3645

Cys Thr  Thr Gly Ala Ala Thr  Thr Thr Thr Thr Gly  Ala Thr Gly
    3650                 3655                 3660

Thr Ala  Gly Cys Cys Gly Gly  Gly Cys Ala Ala Cys  Thr Thr Thr
    3665                 3670                 3675

Thr Thr  Thr Thr Ala Gly Gly  Cys Ala Gly Thr Gly  Gly Thr Ala
    3680                 3685                 3690

Ala Thr  Thr Ala Thr Cys Cys  Thr Thr Thr Ala Thr  Thr Ala Thr
    3695                 3700                 3705

Gly Thr  Gly Ala Ala Thr Thr  Thr Thr Gly Ala Ala  Thr Gly Gly
    3710                 3715                 3720

Thr Thr  Thr Gly Ala Cys Ala  Ala Ala Ala Cys Gly  Thr Thr Thr
    3725                 3730                 3735

Gly Thr  Thr Thr Thr Thr Gly  Thr Ala Gly Ala Gly  Ala Thr Thr
    3740                 3745                 3750

Thr Thr  Ala Ala Ala Ala Gly  Gly Gly Gly Ala Gly  Cys Gly Cys
    3755                 3760                 3765

Thr Ala  Ala Thr Cys Cys Thr  Ala Gly Ala Ala Ala  Thr Ala Ala
    3770                 3775                 3780

Ala Thr  Ala Thr Thr Ala Thr  Gly Thr Ala Ala Thr  Thr Ala Thr
    3785                 3790                 3795

Thr Ala  Cys Gly Gly Cys Cys  Thr Thr Ala Ala Ala  Gly Ala Thr
    3800                 3805                 3810

Ala Ala  Ala Ala Ala Thr Cys  Cys Thr Thr Gly Thr  Thr Gly Ala
    3815                 3820                 3825

Ala Ala  Gly Thr Thr Gly Ala  Ala Ala Ala Ala Ala  Ala Thr Thr
    3830                 3835                 3840

Gly Cys  Thr Ala Ala Ala Thr  Thr Ala Cys Ala Thr  Ala Gly Thr
    3845                 3850                 3855

Cys Thr  Thr Ala Gly Ala Cys  Ala Thr Thr Ala Ala  Cys Ala Thr
    3860                 3865                 3870

Gly Thr  Thr Thr Gly Thr Gly  Gly Ala Ala Gly Ala  Ala Thr Gly
    3875                 3880                 3885

Thr Ala  Gly Cys Ala Gly Ala  Gly Gly Thr Ala Thr  Gly Thr Ala
    3890                 3895                 3900

Gly Thr  Ala Thr Ala Ala Thr  Thr Thr Gly Ala Gly  Thr Gly Ala
    3905                 3910                 3915

Ala Thr  Ala Thr Thr Cys Cys  Cys Ala Ala Thr Thr  Ala Gly Gly
    3920                 3925                 3930

Ala Ala  Thr Thr Cys Thr Ala  Gly Gly Cys Thr Cys  Thr Ala Gly
    3935                 3940                 3945

Thr Thr  Thr Ala Ala Cys Thr  Gly Ala Gly Thr Cys  Ala Cys Ala
    3950                 3955                 3960

Cys Thr  Gly Cys Ala Thr Ala  Gly Gly Ala Ala Thr  Thr Thr Ala
    3965                 3970                 3975

Gly Ala  Ala Cys Cys Thr Ala  Ala Cys Thr Thr Cys  Thr Ala Gly
    3980                 3985                 3990

Gly Thr  Thr Ala Thr Cys Ala  Ala Ala Ala Thr Cys  Thr Thr Thr
    3995                 4000                 4005
```

-continued

```
Gly Cys  Cys Ala Cys Cys Ala  Thr Thr Gly Cys Ala  Cys Ala Ala
    4010                 4015                 4020

Thr Thr  Thr Thr Gly Thr Cys  Cys Thr Ala Ala Thr  Ala Thr Ala
    4025                 4030                 4035

Thr Ala  Gly Ala Gly Ala Ala  Ala Cys Thr Thr Thr  Gly Thr Gly
    4040                 4045                 4050

Ala Gly  Gly Cys Ala Thr Gly  Thr Thr Cys Ala Gly  Thr Thr Gly
    4055                 4060                 4065

Cys Gly  Gly Thr Thr Thr Gly  Cys Ala Cys Ala Ala  Gly Thr Thr
    4070                 4075                 4080

Cys Ala  Thr Cys Thr Cys Ala  Thr Thr Thr Gly Thr  Ala Thr Thr
    4085                 4090                 4095

Cys Cys  Ala Gly Thr Gly Ala  Thr Thr Thr Thr Thr  Thr Thr Thr
    4100                 4105                 4110

Cys Thr  Thr Cys Thr Ala Ala  Cys Cys Ala Thr Thr  Thr Thr Thr
    4115                 4120                 4125

Thr Thr  Ala Ala Ala Cys Ala  Ala Cys Ala Thr Gly  Thr Ala Cys
    4130                 4135                 4140

Ala Cys  Ala Thr Thr Gly Thr  Thr Thr Thr Thr Thr  Thr Thr Gly
    4145                 4150                 4155

Gly Thr  Ala Gly Gly Cys Ala  Ala Thr Gly Ala Ala  Ala Ala Cys
    4160                 4165                 4170

Thr Gly  Thr Cys Ala Thr Thr  Thr Cys Cys Ala Thr  Thr Gly Thr
    4175                 4180                 4185

Cys Ala  Ala Ala Cys Ala Gly  Thr Ala Ala Thr Thr  Cys Cys Thr
    4190                 4195                 4200

Cys Gly  Ala Thr Ala Ala Cys  Thr Gly Thr Ala Thr  Thr Ala Ala
    4205                 4210                 4215

Thr Gly  Gly Thr Thr Thr Thr  Thr Ala Ala Ala Ala  Ala Ala Cys
    4220                 4225                 4230

Cys Ala  Thr Cys Ala Gly Thr  Thr Ala Cys Thr Thr  Thr Ala Ala
    4235                 4240                 4245

Ala Ala  Cys Thr Gly Ala Ala  Thr Thr Thr Ala Thr  Ala Thr Thr
    4250                 4255                 4260

Thr Ala  Ala Thr Ala Ala Cys  Thr Thr Cys Thr Gly  Thr Ala Thr
    4265                 4270                 4275

Thr Ala  Gly Thr Ala Thr Thr  Gly Gly Gly Thr Ala  Gly Cys Ala
    4280                 4285                 4290

Thr Gly  Ala Ala Ala Thr Cys  Thr Cys Thr Ala Thr  Thr Gly Ala
    4295                 4300                 4305

Gly Ala  Ala Ala Thr Thr Gly  Ala Ala Cys Ala Gly  Cys Ala Thr
    4310                 4315                 4320

Ala Cys  Ala Ala Cys Thr Ala  Gly Thr Ala Gly Cys  Thr Gly Thr
    4325                 4330                 4335

Ala Ala  Ala Thr Thr Cys Cys  Thr Thr Cys Ala Gly  Ala Ala Ala
    4340                 4345                 4350

Gly Thr  Gly Ala Ala Ala Ala  Thr Thr Ala Thr Thr  Thr Cys Thr
    4355                 4360                 4365

Thr Cys  Cys Thr Ala Ala Ala  Gly Ala Thr Ala Thr  Cys Thr Thr
    4370                 4375                 4380

Gly Ala  Cys Ala Thr Cys Ala  Gly Thr Gly Cys Thr  Thr Gly Ala
    4385                 4390                 4395

Ala Gly  Ala Ala Thr Ala Gly  Thr Cys Ala Thr Ala  Ala Cys Thr
```

4400 4405 4410

Ala Gly Ala Thr Thr Ala Ala Thr Ala Ala Thr Thr Gly Thr Thr
4415 4420 4425

Thr Thr Ala Gly Thr Thr Ala Ala Ala Cys Ala Gly Thr Thr Thr
4430 4435 4440

Thr Ala Ala Gly Thr Gly Cys Cys Thr Gly Thr Thr Thr Cys Ala
4445 4450 4455

Gly Ala Thr Gly Ala Thr Gly Ala Thr Ala Gly Gly Cys Ala Ala
4460 4465 4470

Thr Thr Thr Ala Gly Ala Thr Gly Ala Ala Thr Thr Thr Ala Gly
4475 4480 4485

Gly Ala Ala Ala Ala Ala Thr Cys Ala Ala Ala Gly Thr Thr Thr
4490 4495 4500

Thr Thr Ala Cys Thr Thr Gly Cys Ala Gly Ala Ala Ala Thr Gly
4505 4510 4515

Thr Cys Cys Ala Thr Thr Ala Thr Ala Gly Gly Gly Gly Gly Cys
4520 4525 4530

Cys Cys Cys Cys Cys Thr Cys Cys Thr Cys Ala Thr Ala Gly Ala
4535 4540 4545

Gly Cys Thr Gly Ala Ala Thr Gly Gly Gly Thr Thr Ala Thr Gly
4550 4555 4560

Thr Ala Ala Thr Gly Thr Thr Thr Thr Ala Thr Cys Cys Ala Ala
4565 4570 4575

Ala Ala Gly Thr Thr Thr Cys Cys Ala Ala Thr Thr Cys Cys Ala
4580 4585 4590

Cys Thr Gly Thr Cys Thr Thr Gly Thr Gly Thr Thr Thr Thr Cys
4595 4600 4605

Ala Thr Gly Thr Thr Gly Ala Ala Ala Ala Thr Ala Cys Thr Thr
4610 4615 4620

Thr Thr Gly Cys Ala Thr Thr Thr Thr Thr Cys Cys Thr Thr Thr
4625 4630 4635

Gly Ala Gly Thr Gly Cys Cys Ala Ala Thr Thr Thr Cys Thr Thr
4640 4645 4650

Ala Cys Thr Ala Gly Thr Ala Cys Thr Ala Thr Thr Thr Cys Thr
4655 4660 4665

Thr Ala Ala Thr Gly Thr Ala Ala Cys Ala Thr Gly Thr Thr Thr
4670 4675 4680

Ala Cys Cys Thr Gly Gly Ala Ala Thr Gly Thr Ala Thr Thr Thr
4685 4690 4695

Thr Ala Ala Cys Thr Ala Thr Thr Thr Thr Thr Gly Thr Ala Thr
4700 4705 4710

Ala Gly Thr Gly Thr Ala Ala Ala Cys Thr Gly Ala Ala Ala Cys
4715 4720 4725

Ala Thr Gly Cys Ala Cys Ala Thr Thr Thr Thr Gly Thr Ala Cys
4730 4735 4740

Ala Thr Thr Gly Thr Gly Cys Thr Thr Thr Thr Thr Thr Thr Thr
4745 4750 4755

Gly Thr Gly Gly Gly Ala Cys Ala Thr Ala Thr Gly Cys Ala Gly
4760 4765 4770

Thr Gly Thr Gly Ala Thr Cys Cys Ala Gly Thr Thr Gly Thr Thr
4775 4780 4785

Thr Thr Cys Cys Ala Thr Cys Ala Thr Thr Thr Gly Gly Thr Thr
4790 4795 4800

```
Gly Cys  Gly Cys Thr Gly Ala  Cys Cys Thr Ala Gly  Gly Ala Ala
    4805                4810                4815

Thr Gly  Thr Thr Gly Gly Thr  Cys Ala Thr Ala Thr  Cys Ala Ala
    4820                4825                4830

Ala Cys  Ala Thr Thr Ala Ala  Ala Thr Thr Thr Ala  Ala Ala Ala
    4835                4840                4845

Ala Thr  Gly Ala Cys Cys Ala  Cys Thr Cys Thr Thr  Thr Thr Ala
    4850                4855                4860

Ala Thr  Thr Ala Ala Ala Ala  Thr Thr Ala Ala Cys  Thr Thr Thr
    4865                4870                4875

Thr Ala  Ala Ala Thr Gly Thr  Thr Thr Ala Thr Ala  Gly Gly Ala
    4880                4885                4890

Gly Thr  Ala Thr Gly Thr Gly  Cys Thr Gly Thr Gly  Ala Ala Gly
    4895                4900                4905

Thr Gly  Ala Thr Cys Thr Gly  Ala Ala Ala Thr Thr  Thr Gly Thr
    4910                4915                4920

Ala Ala  Thr Ala Thr Thr Thr  Thr Thr Gly Thr Cys  Ala Thr Gly
    4925                4930                4935

Ala Ala  Cys Thr Gly Thr Ala  Cys Thr Gly Cys Thr  Cys Cys Thr
    4940                4945                4950

Ala Ala  Thr Thr Ala Thr Thr  Gly Thr Ala Ala Thr  Gly Thr Ala
    4955                4960                4965

Ala Thr  Ala Ala Ala Ala Ala  Thr Ala Gly Thr Thr  Ala Thr Gly
    4970                4975                4980

Gly Thr  Gly Ala Cys Thr Ala  Thr Gly Ala
    4985                4990
```

<210> SEQ ID NO 53
<211> LENGTH: 4876
<212> TYPE: DNA
<213> ORGANISM: Canis lupus

<400> SEQUENCE: 53

```
gctgaaaatg actgaatata aacttgtggt agttggagct ggtggcgtag gcaagagtgc     60

cttgacgata cagctaattc agaatcactt tgtggatgaa tatgatccta caatagagga    120

ttcctacagg aaacaagtag taattgatgg agaaacctgt ctcttggata ttctcgacac    180

agcaggtcaa gaggagtaca gtgcaatgag ggaccagtac atgaggactg gggagggctt    240

tctttgtgta tttgccataa ataatactaa atcatttgaa gatattcacc attatagaga    300

acaaattaaa agagttaaag actctgaaga tgtacctatg gtcctagtag gaaataaatg    360

tgatttgcct tctagaacag tagacacaaa acaggctcag gacttagcaa gaagttatgg    420

aattcctttt attgaaacat cagcaaagac aagacagggt gttgacgatg ccttctatac    480

attagttcga gaaattcgaa aacataaaga aaagatgagc aaagatggta aaaagaagaa    540

aaagaagtca aagacaaagt gtataattat gtaaatacaa tttgtacttt tttcttaagg    600

catacttaag taaaagtggt aatttttgta cattacacta aattattagc atttgtttta    660

gcattaccta attttctgct ccatccaaac tgttagcttt tatcttgaat gcttatttta    720

aaatgacagt ggaaactttt tcctctaagt gccagtattc cctgagtttt ggttttgaac    780

tagcaatgcc tgtgaaaaag aaactgaata cctgagattt ctgtcttggg gtttttggtg    840

catgcagttg attacttcct atttttctta ccaattgtga actttggtgt gaaacaaatt    900

aatgaagctt tcgaatcatc cctattctgt gttttaccta gtcacataca tggattaatt    960
```

actaattata acttcagttg atatttcatg attggtttta ctgaaacatt gagggaacat 1020
gaatttatgg gctgcttctt ataggtataa tgtcctatag tttcagtcac ccttaatgaa 1080
tgtaaagcta cactgttcac aaaggttttc tccatctttt cactgctatt tgtcatagcc 1140
acgctcccaa aaatattata ttttttctat aaaaaaggga aaaaatagaa aaaaatacaa 1200
ggcaatggaa aatattaaaa ggcatttact ttccatatta gataaattcc tataatactc 1260
tgaatagctt ttcctgttaa ggcagaccca gtatgtaatg aggattatag caaccatttt 1320
ggggctatat ttacatgcta ctaaattttt gtattaattg aaaaagtttt aacatgtata 1380
aaaaattccc ataggaatta aatatagtct ccctgtgtca gattgctctt tcttagcata 1440
actttaaatc ttttcttgat cttcaatctt agaaaatagt tttaattctt gtagtgatgt 1500
taaagattat ttgggccagt tagtttttaa tagatgttaa agagaccaca gttccaaggc 1560
caggccttgt gtgaaccttt aagcttcatt aagagtttca tagtacagac tgcatccctg 1620
tggtctccca gggtcatcat gcattgattg ggtggtcaaa agtggggaca aagagtgttt 1680
agataagatg catcctcact gtatggtggt cctgctgaca gatcaggacc atcacttttg 1740
tttttaaaa aaccaacaga gctttttaaa aacattattt aaaatgagat ttttgggggc 1800
agggggtggc aagacttgaa tttttttaa acaatgaagt aaaaaggttt caaaatctct 1860
agtgttggct agttctcaac attggctaaa gtaacatttc ataaacactt tacaagtatt 1920
ggtccatatt taagaatatc taatgcttaa ataatagatt aataacaatt ctttcagtgc 1980
atttaaaatg tatttttaaa tatctgaagt gagatggtgt gttgaggtga aaatatcact 2040
ggactaggag gaaggtgact tagattctag ttacgtgtct tttacaactt cagttttggg 2100
caaatcactc actatccatt tcttcatgtt aagtcatctc aaaggctata tctagcatca 2160
actatgtgat ttacattcag tttacataag gatataccta tttgtcaatc tcagcacaat 2220
ctgtaacttt ttacctatgt tctcttcagc gccagtctta ggcaaagttg tgcaagaggt 2280
gaggtttatt tttgagaatc tgatctccgg tagcaggtac tcctctccca tgttagtgtc 2340
atcttgcctg cctaccttct acatgcccca tgacttgatg ctttctaatt ccccgaacct 2400
caagatgtag tgctgctttg gatatctcca tgaggtaata agtcacatta gtcaggctca 2460
acataatctg acagatactg tagtgggatt tgatctaata gctaattttc aggtggtaac 2520
tgtatcaatt taattttgat cttttgaaca tcatctctgc tacctggtcc attagtgact 2580
aagtaggaaa agtaggaatt ttcatatctg tgatgtgtag acagacccta tccagtagaa 2640
gaatttaata aatttaatta ataaatactg aaagatttcc ttagataatc caaaactagg 2700
actagccctg gtaacggtga tacattccat tattttaata agtaaaatct tcttacaatg 2760
aaaaatactt taaaatttaa ttcataaagc ttacttttta gcagaattca tttattcaac 2820
aaatacttga gtgcctgcta gatgccaggt tctacacaag gcaccgggga tattatggta 2880
ttcccaacaa gggacataat ccctatcctt aagtagtact gttattttag agtggtctgt 2940
agtatattag tgaggcattt ggcacatgac ccagagataa tataatgcat attttagttt 3000
tgcacagaag ggatatggtc tctaaggttt tttccagctc taaaataatt gttcgctctg 3060
attccaataa actgtttaat caagctactt tatataaatc actttacttc attattttaa 3120
agaagtaaac ttgactatat tgttttttat ttgggataat tatgtgattc tgttgggata 3180
cttatatagt acacattaaa ttgtatgtca gatgataaca ttaaaattcc caagtgtaat 3240
attctacttg gtctctgtgt atcataatta aaatagattt aaatattgag ttcaaaaata 3300

-continued

```
gttttattta tctgggtgtg aataaacaga tgcctgaact aattcacaga aaaggaaact   3360

tctgtgtaaa aagtcagtcc aatttctgaa atgctatgct aaactacagg tttatggaac   3420

attagatagg gtgttaagac tttatatagt acttcctctt gtttctatac aagagaaaga   3480

aatggccata cttcaggaat tgcagtgcat aactgaggga tttttaggac tcttgaattt   3540

ttgatgtagc cgggcaactt tttttaggca gtggtaatta tcctttatta tgtgaatttt   3600

gaatggtttg acaaaacgtt tgtttttgta gagattttaa aaggggagcg ctaatcctag   3660

aaataaatat tatgtaatta ttacggcctt aaagataaaa atccttgttg aaagttgaaa   3720

aaaattgcta aattacatag tcttagacat taacatgttt gtggaagaat gtagcagagg   3780

tatgtagtat aatttgagtg aatattccca attaggaatt ctaggctcta gtttaactga   3840

gtcacactgc ataggaattt agaacctaac ttctaggtta tcaaaatctt tgccaccatt   3900

gcacaatttt gtcctaatat atagagaaac tttgtgaggc atgttcagtt gcggtttgca   3960

caagttcatc tcatttgtat tccagtgatt tttttttcttc taaccatttt tttaaacaac   4020

atgtacacat tgtttttttt ggtaggcaat gaaaactgtc atttccattg tcaaacagta   4080

attcctcgat aactgtatta atggttttta aaaaaccatc agttacttta aaactgaatt   4140

tatatttaat aacttctgta ttagtattgg gtagcatgaa atctctattg agaaattgaa   4200

cagcatacaa ctagtagctg taaattcctt cagaaagtga aaattatttc ttcctaaaga   4260

tatcttgaca tcagtgcttg aagaatagtc ataactagat taataattgt tttagttaaa   4320

cagttttaag tgcctgtttc agatgatgat aggcaattta gatgaattta ggaaaaatca   4380

aagtttttac ttgcagaaat gtccattata gggggccccc ctcctcatag agctgaatgg   4440

gttatgtaat gttttatcca aaagtttcca attccactgt cttgtgtttt catgttgaaa   4500

atacttttgc atttttcctt tgagtgccaa tttcttacta gtactatttc ttaatgtaac   4560

atgtttacct ggaatgtatt ttaactattt ttgtatagtg taaactgaaa catgcacatt   4620

ttgtacattg tgcttttttt tgtgggacat atgcagtgtg atccagttgt tttccatcat   4680

ttggttgcgc tgacctagga atgttggtca tatcaaacat taaatttaaa aatgaccact   4740

cttttaatta aaattaactt ttaaatgttt ataggagtat gtgctgtgaa gtgatctgaa   4800

atttgtaata tttttgtcat gaactgtact gctcctaatt attgtaatgt aataaaaata   4860

gttatggtga ctatga                                                   4876
```

<210> SEQ ID NO 54
<211> LENGTH: 188
<212> TYPE: PRT
<213> ORGANISM: Canis lupus

<400> SEQUENCE: 54

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95
```

```
Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Ile Ile Met
            180                 185
```

<210> SEQ ID NO 55
<211> LENGTH: 1394
<212> TYPE: DNA
<213> ORGANISM: Felis catus

<400> SEQUENCE: 55

```
gctgaaaatg actgaatata aacttgtggt agttggagct ggtggcgtag gcaagagtgc     60

cttgacgata cagctaattc agaatcactt tgtggatgaa tatgatccta caatagagga    120

ttcctacagg aaacaagtag taattgatgg agaaacctgt ctcttggata ttctcgacac    180

agcaggtcaa gaggagtaca gtgcaatgag ggaccagtac atgaggactg ggagggcctt    240

tctttgcgta tttgccataa ataatactaa atcatttgaa gatattcacc actatagaga    300

acaaataaaa agagttaaag actctgaaga tgtacctatg gtcctagtag gaaataaatg    360

tgatttgcct tctagaacag tagatacaaa acaggctcag gacttagcaa gaagttatgg    420

aattcctttt attgaaacat cagcaaagac aagacagggt gttgacgatg ccttctatac    480

attagttcga gaaattcgaa aacataaaga aaagatgagc aaagatggta aaaagaagaa    540

aaagaagtca aagacaaagt gtataattat gtaaatacaa tttgtacttt tttcttaagg    600

catacttaag taaaagtggt aatttttgta cattacacta aattattagc atttgtttta    660

gcattaccta attttctgct ccatccaaac tgttagcttt tatcttgaat gcttatttta    720

aatgacagtg gaaacttttt ttcctctaag tgccagtatt ccctgagttt tggtttttga    780

actagcaatg cctgtgaaaa agaaactgaa tacctgagat ttctgtcttg ggtttttgg     840

tgcatgcagt tgattacttc ctatttttct taccaattgt gaactttggt gtgaaacaaa    900

ttaatgaaac tttcgaatca tccctattct gtgtttcatg tagtcacata catggattaa    960

ttactaatta taacttcagt tgagatttca tgattcgttt tactgaaaca ttgagggaac   1020

atgaatttat gggcttcttg tagattcatc ttgtaggtat taatgtccta tagtttcagt   1080

cacccttaat gaatgtaaag ttacactgtt cataaaagtt tctccatctt ttcactgctg   1140

tttgtcatcg tcacgctccc ccaaaatatt atattttttc tataaaaagg gaaaaaagga   1200

aaaaaataca aggcaatgga aaatattaaa aggcatttac tttctgtatt agataaattc   1260

ctataatact ctgaatagct tttcctgtta aggcagaccc agtatgtgat gaggattata   1320

gcaaccattt tggggctata tttacatgct actaaatttt tgtaataatt gaaaaaattt   1380

taacatgtat aaaa                                                     1394
```

<210> SEQ ID NO 56
<211> LENGTH: 188
<212> TYPE: PRT

<213> ORGANISM: Felis catus

<400> SEQUENCE: 56

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Ile Ile Met
            180                 185
```

<210> SEQ ID NO 57
<211> LENGTH: 1512
<212> TYPE: DNA
<213> ORGANISM: Felis catus

<400> SEQUENCE: 57

```
tgctgaaaat gactgaatat aaacttgtgg tagttggagc tggtggcgta ggcaagagtg      60

ccttgacgat acagctaatt cagaatcact ttgtggatga atatgatcct acaatagagg     120

attcctacag gaaacaagta gtaattgatg gagaaacctg tctcttggat attctcgaca     180

cagcaggtca agaggagtac agtgcaatga gggaccagta catgaggact ggggagggct     240

ttctttgcgt atttgccata aataatacta aatcatttga agatattcac cactatagag     300

aacaaataaa aagagttaaa gactctgaag atgtacctat ggtcctagta ggaaataaat     360

gtgatttgcc ttctagaaca gtagatacaa aacaggctca ggacttagca agaagttatg     420

gaattccttt tattgaaaca tcagcaaaga caagacagag agtggaggat gctttttata     480

cattggtgag agagatccga cagtacagat tgaaaaaaat caacaaagaa gaaaagactc     540

ctggctgtgt gaaaattaaa aaatgcattg taatgggtgt tgacgatgcc ttctatacat     600

tagttcgaga aattcgaaaa cataaagaaa agatgagcaa agatggtaaa aagaagaaaa     660

agaagtcaaa gacaaagtgt ataattatgt aaatacaatt tgtacttttt tcttaaggca     720

tacttaagta aaagtggtaa tttttgtaca ttacactaaa ttattagcat ttgttttagc     780

attacctaat tttctgctcc atccaaactg ttagctttta tcttgaatgc ttattttaaa     840

tgacagtgga aacttttttt cctctaagtg ccagtattcc ctgagttttg gtttttgaac     900

tagcaatgcc tgtgaaaaag aaactgaata cctgagattt ctgtcttggg gtttttggtg     960
```

```
catgcagttg attacttcct atttttctta ccaattgtga actttggtgt gaaacaaatt   1020

aatgaaactt tcgaatcatc cctattctgt gtttcatgta gtcacataca tggattaatt   1080

actaattata acttcagttg agatttcatg attcgtttta ctgaaacatt gagggaacat   1140

gaatttatgg gcttcttgta gattcatctt gtaggtatta atgtcctata gtttcagtca   1200

cccttaatga atgtaaagtt acactgttca taaaagtttc tccatctttt cactgctgtt   1260

tgtcatcgtc acgctccccc aaaatattat attttttcta taaaaaggga aaaaaggaaa   1320

aaaatacaag gcaatggaaa atattaaaag gcatttactt tctgtattag ataaattcct   1380

ataatactct gaatagcttt tcctgttaag gcagacccag tatgtgatga ggattatagc   1440

aaccattttg ggctatattt tacatgctac taaatttttg taataattga aaaaatttta   1500

acatgtataa aa                                                         1512
```

```
<210> SEQ ID NO 58
<211> LENGTH: 227
<212> TYPE: PRT
<213> ORGANISM: Felis catus

<400> SEQUENCE: 58

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Asn Lys Glu Glu Lys
                165                 170                 175

Thr Pro Gly Cys Val Lys Ile Lys Lys Cys Ile Val Met Gly Val Asp
            180                 185                 190

Asp Ala Phe Tyr Thr Leu Val Arg Glu Ile Arg Lys His Lys Glu Lys
        195                 200                 205

Met Ser Lys Asp Gly Lys Lys Lys Lys Lys Lys Ser Lys Thr Lys Cys
    210                 215                 220

Ile Ile Met
225


<210> SEQ ID NO 59
<211> LENGTH: 2144
<212> TYPE: DNA
<213> ORGANISM: Bos taurus
```

<400> SEQUENCE: 59
ggcggtggcg gcggcggcgg cggtggcggt ggcggttcgg ccagtactcc cggcccccgc 60
catttctgac tgggagcgag cgcggcgcag gcactgaagg cagcggcggg ggccagaggc 120
tcggcggctc ccaggtgagg gagagaggcc tgctgaaaat gactgaatat aaacttgtgg 180
tagttggagc tggtggcgta ggcaagagtg ccttgacgat acagctaatt cagaatcact 240
ttgtggatga atatgatcct acgatagagg attcctacag gaaacaagta gtaattgatg 300
gagaaacctg tctcttggat attctcgaca cagcaggtca agaggagtac agtgcaatga 360
gggaccagta catgaggact ggggagggct ttctttgtgt atttgccata aataatacta 420
aatcatttga agatattcac cattatagag aacaaataaa aagagttaaa gactctgaag 480
atgtacctat ggttctagta ggaaataaat gtgatttgcc ttctagaaca gtagacacaa 540
aacaggctca ggacttagca agaagttatg gaattccttt tattgaaaca tcagcaaaga 600
caagacaggg tgttgacgat gccttctata cattagttcg agaaattcga aaacataaag 660
aaaagatgag caaagatggt aaaaagaaga aaaagaagtc aaagacaaag tgtataatta 720
tgtaaataca atttgtactt ttttcttaag gcatacttaa gtaaaagtgg taatttttgt 780
atattacact aaattattag catttgtttt agcattatct aattttcttt ctgctccatc 840
catactgtta gcttttatct tgaatgctta ttttaaaatg acagtggaaa ctttttttcct 900
ctaagtgcca gtattccctg cgttttggtt tttgaactag caatgcctgt gaaaaagaaa 960
ctgaacaccc aagatttttg tcttggggtt tttggtgcat gcagttgatt acttcctatt 1020
tttcttatca attgtgaact ttagtgtgaa acaaattaat gaggctttca aatcatccct 1080
attgtattgt tttatctagt cacacacatg gattaattac taattataac ttcagttgag 1140
atttcatgat tggttttact gaaacatcga gggaacatga atttatgggc ttcctatagt 1200
ttcatcttgt aggtatcatt gtcctatagt ttcagttacc cttaatgaat gtcaggttac 1260
actgttcaca aaggttttct tctttccact gctatttgtc aaatggtcac gttccctaaa 1320
atactatatt ttttctataa aaaaaagaaa aaaatggaaa aaaatacaag gcaatggaaa 1380
atattaaaag gccacttact ttccacatta ggtaaattcc tataatgctc tgaatagctt 1440
tttatgttaa ggcagaccca gtaggtaatg aggattagaa caagcatttt gggactatat 1500
ttacatgctt taaatttttg taataacaaa aaaattttaa catgtataaa gaattctcat 1560
aggaattaaa tacagtctcc ctgtgtcaga ttgctctttc ttagcataaa tctttttctt 1620
gaacttcaat ctttaaaagt agttttaatt ctactgatag tgatgtaaaa gattatttgg 1680
gccagttagc ttggtaggtg ttacagagac cagggtggca tagccgggcc ttgtgtgaac 1740
ctttaagcta catggagagt ttcacagtgt ggactgcatc cctgtggtct tccattgttg 1800
ccatgccttg gttggtcaaa aacaaggact tgcagagaga ttgaatagct cagcaaggta 1860
cattctcatt atgtcgtagt cctactcagg aacatcactt ttttaaaata aaaaaacccca 1920
aaaaacagaa cttaaaaaaa aaaacaacat tattttaaat gagattttcg gtggggtgga 1980
aagattttaa tttttttaa acgatgaaat gaaaaaatgt caaaatcttg agtattggct 2040
agttctcttt aacactggct aaagtaacat ttttgtaaac acttcagtac agtctggtcc 2100
attattaaga atatctaatg cttatacaat aaagtaatgc taac 2144

<210> SEQ ID NO 60
<211> LENGTH: 188
<212> TYPE: PRT

<213> ORGANISM: Bos taurus

<400> SEQUENCE: 60

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly
35 40 45

Glu Thr Cys Leu Leu Asp Ile Leu Asp Thr Ala Gly Gln Glu Glu Tyr
50 55 60

Ser Ala Met Arg Asp Gln Tyr Met Arg Thr Gly Glu Gly Phe Leu Cys
65 70 75 80

Val Phe Ala Ile Asn Asn Thr Lys Ser Phe Glu Asp Ile His His Tyr
85 90 95

Arg Glu Gln Ile Lys Arg Val Lys Asp Ser Glu Asp Val Pro Met Val
100 105 110

Leu Val Gly Asn Lys Cys Asp Leu Pro Ser Arg Thr Val Asp Thr Lys
115 120 125

Gln Ala Gln Asp Leu Ala Arg Ser Tyr Gly Ile Pro Phe Ile Glu Thr
130 135 140

Ser Ala Lys Thr Arg Gln Gly Val Asp Asp Ala Phe Tyr Thr Leu Val
145 150 155 160

Arg Glu Ile Arg Lys His Lys Glu Lys Met Ser Lys Asp Gly Lys Lys
165 170 175

Lys Lys Lys Lys Ser Lys Thr Lys Cys Ile Ile Met
180 185

<210> SEQ ID NO 61
<211> LENGTH: 1010
<212> TYPE: DNA
<213> ORGANISM: Bos taurus

<400> SEQUENCE: 61
ggcggtggcg gcggcggcgg cggtggcggt ggcggttcgg ccagtactcc cggccccccgc 60 catttctgac tgggagcgag cgcggcgcag gcactgaagg cagcggcggg ggccagaggc 120
tcggcggctc ccaggtgagg gagagaggcc tgctgaaaat gactgaatat aaacttgtgg 180
tagttggagc tggtggcgta ggcaagagtg ccttgacgat acagctaatt cagaatcact 240
ttgtggatga atatgatcct acgatagagg attcctacag gaaacaagta gtaattgatg 300
gagaaacctg tctcttggat attctcgaca cagcaggtca agaggagtac agtgcaatga 360
gggaccagta catgaggact ggggagggct ttctttgtgt atttgccata aataatacta 420
aatcatttga agatattcac cattatagag aacaaataaa aagagttaaa gactctgaag 480
atgtacctat ggttctagta ggaaataaat gtgatttgcc ttctagaaca gtagacacaa 540
aacaggctca ggacttagca agaagttatg gaattccttt tattgaaaca tcagcaaaga 600
caagacagag agtggaggat gctttttata cattggtgag agagatccga caatacagat 660
tgaaaaaaat cagcaaagaa gaaaagactc ctggctgtgt gaaaattaaa aaatgcattg 720
taatgggtgt tgacgatgcc ttctatacat tagttcgaga aattcgaaaa cataaagaaa 780
agatgagcaa agatggtaaa aagaagaaaa agaagtcaaa gacaaagtgt ataattatgt 840
aaatacaatt tgtacttttt tcttaaggca tacttaagta aaagtggtaa tttttgtata 900
ttacactaaa ttattagcat ttgttttagc attatctaat tttctttctg ctccatccat 960
actgttagct tttatcttga atgcttattt taaaatgaca gtggaaactt 1010

<210> SEQ ID NO 62
<211> LENGTH: 227
<212> TYPE: PRT
<213> ORGANISM: Bos taurus

<400> SEQUENCE: 62

Met Thr Glu Tyr Lys Leu Val Val Val Gly Ala Gly Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly
35 40 45

Glu Thr Cys Leu Leu Asp Ile Leu Asp Thr Ala Gly Gln Glu Glu Tyr
50 55 60

Ser Ala Met Arg Asp Gln Tyr Met Arg Thr Gly Glu Gly Phe Leu Cys
65 70 75 80

Val Phe Ala Ile Asn Asn Thr Lys Ser Phe Glu Asp Ile His His Tyr
85 90 95

Arg Glu Gln Ile Lys Arg Val Lys Asp Ser Glu Asp Val Pro Met Val
100 105 110

Leu Val Gly Asn Lys Cys Asp Leu Pro Ser Arg Thr Val Asp Thr Lys
115 120 125

Gln Ala Gln Asp Leu Ala Arg Ser Tyr Gly Ile Pro Phe Ile Glu Thr
130 135 140

Ser Ala Lys Thr Arg Gln Arg Val Glu Asp Ala Phe Tyr Thr Leu Val
145 150 155 160

Arg Glu Ile Arg Gln Tyr Arg Leu Lys Lys Ile Ser Lys Glu Glu Lys
165 170 175

Thr Pro Gly Cys Val Lys Ile Lys Lys Cys Ile Val Met Gly Val Asp
180 185 190

Asp Ala Phe Tyr Thr Leu Val Arg Glu Ile Arg Lys His Lys Glu Lys
195 200 205

Met Ser Lys Asp Gly Lys Lys Lys Lys Lys Lys Ser Lys Thr Lys Cys
210 215 220

Ile Ile Met
225

<210> SEQ ID NO 63
<211> LENGTH: 797
<212> TYPE: DNA
<213> ORGANISM: Bos taurus

<400> SEQUENCE: 63
gcggtggcgg cggcggcggc ggtggcggtg gcggttcggc cagtactccc ggcccccgcc 60
atttctgact gggagcgagc gcggcgcagg cactgaaggc agcggcgggg gccagaggct 120
cggcggctcc caggtgaggg agagaggcct gctgaaaatg actgaatata aacttgtggt 180
agttggagct ggtggcgtag gcaagagtgc cttgacgata cagctaattc agaatcactt 240
tgtggatgaa tatgatccta cgatagagga ttcctacagg aaacaagtag taattgatgg 300
agaaacctgt ctcttggata ttctcgacac agcaggtcaa gaggagtaca gtgcaatgag 360
ggaccagtac atgaggactg gggagggctt tctttgtgta tttgccataa ataatactaa 420
atcatttgaa gatattcacc attatagaga acaaataaaa agagttaaag actctgaaga 480

```
tgtacctatg gttctagtag gaaataaatg tgatttgcct tctagaacag tagacacaaa    540

acaggctcag gacttagcaa gaagttatgg aattcctttt attgaaacat cagcaaagac    600

aagacagaga gtggaggatg ctttttatac attggtgaga gagatccgac aatacagatt    660

gaaaaaaatc agcaaagaag aaaagactcc tggctgtgtg aaaattaaaa aatgcattgt    720

aatgtaatct gggtgttgac gatgccttct atacattagt tcgagaaatt cgaaaacata    780

aagaaaagat gagcaaa                                                   797
```

<210> SEQ ID NO 64
<211> LENGTH: 189
<212> TYPE: PRT
<213> ORGANISM: Bos taurus

<400> SEQUENCE: 64

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Val Met
            180                 185
```

<210> SEQ ID NO 65
<211> LENGTH: 1112
<212> TYPE: DNA
<213> ORGANISM: Gallus gallus

<400> SEQUENCE: 65

```
caggtctgct aaaaaatgac agagtataag cttgttgtcg ttggagctgg tggtgtgggc     60

aagagcgcct tgacaataca gctcattcag aaccactttg tggatgagta tgaccctacc    120

atagaggatt cctacagaaa gcaagtagta attgatgggg aaacctgtct cttggatatt    180

cttgatacag caggtcaaga agaatatagt gcaatgaggg accaatatat gagaacagga    240

gaaggctttc tgtgtgtttt tgctataaac aatacaaaat cttttgaaga tattcaccat    300

tatagggaac aaataaagag agttaaagac tctgaagatg tcccaatggt gctagtagga    360

aacaaatgtg atttgccttc cagaacagta gatacaaaac aagctcagga tttagcaaga    420
```

```
agttatggaa ttccttttat tgaaacatca gcaaagacaa gacagggtgt tgatgatgcc    480

ttctatacat tagttcgaga aatcagaaaa cacaaagaga agatgagcaa agatggtaaa    540

aagaagaaaa agaagacaaa gacaaagtgt ataattatgt aaatacaatg tatccttatt    600

cttaagacgt actgaagtaa tttttgtaca ttacactaaa ttattagcat ttgtttttag    660

cattacttta ctttctgctt catgatcctg ttagctttac ctgaatgctt gttttaaatg    720

acagtggaaa cttcattcct cttaaagtgc cagtattctt tgagtgttgg ttcttgaact    780

agcaatgcct gtgaagaaaa ataaaaacaa atgaaaaaaa aaaaaacaca caaaaacctg    840

agaactgtct taggactctt tggtgcatgc acagttgcta acttcctatt tttcttactg    900

attgtgaact tctgttccgt gcgtaaacaa aacaatgaaa cgatctacac gttctaacat    960

ccccccttcat ttgtactctc ttattttta catctggttg ggaaaacgga ccagttagtg   1020

acaaagactt tattttcaga cttccttcta atttcgactg actgcaatat agagagacca   1080

gaagccttta tagtcttcct gtagattttg ct                                 1112
```

<210> SEQ ID NO 66
<211> LENGTH: 188
<212> TYPE: PRT
<213> ORGANISM: Gallus gallus

<400> SEQUENCE: 66

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Thr Lys Thr Lys Cys Ile Ile Met
            180                 185
```

<210> SEQ ID NO 67
<211> LENGTH: 4454
<212> TYPE: DNA
<213> ORGANISM: Homo sapiens

<400> SEQUENCE: 67

```
gaaacgtccc gtgtgggagg ggcgggtctg ggtgcggcct gccgcatgac tcgtggttcg     60

gaggcccacg tggccggggc ggggactcag gcgcctgggg cgccgactga ttacgtagcg    120
```

```
ggcggggccg gaagtgccgc tccttggtgg gggctgttca tggcggttcc ggggtctcca    180
acatttttcc cggctgtggt cctaaatctg tccaaagcag aggcagtgga gcttgaggtt    240
cttgctggtg tgaaatgact gagtacaaac tggtggtggt tggagcaggt ggtgttggga    300
aaagcgcact gacaatccag ctaatccaga accactttgt agatgaatat gatcccacca    360
tagaggattc ttacagaaaa caagtggtta tagatggtga aacctgtttg ttggacatac    420
tggatacagc tggacaagaa gagtacagtg ccatgagaga ccaatacatg aggacaggcg    480
aaggcttcct ctgtgtattt gccatcaata atagcaagtc atttgcggat attaacctct    540
acagggagca gattaagcga gtaaaagact cggatgatgt acctatggtg ctagtgggaa    600
acaagtgtga tttgccaaca aggacagttg atacaaaaca agcccacgaa ctggccaaga    660
gttacgggat tccattcatt gaaacctcag ccaagaccag acagggtgtt gaagatgctt    720
tttacacact ggtaagagaa atacgccagt accgaatgaa aaaactcaac agcagtgatg    780
atgggactca gggttgtatg ggattgccat gtgtggtgat gtaacaagat acttttaaag    840
ttttgtcaga aaagagccac tttcaagctg cactgacacc ctggtcctga cttccctgga    900
ggagaagtat tcctgttgct gtcttcagtc tcacagagaa gctcctgcta cttccccagc    960
tctcagtagt ttagtacaat aatctctatt tgagaagttc tcagaataac tacctcctca   1020
cttggctgtc tgaccagaga atgcacctct tgttactccc tgttattttt ctgccctggg   1080
ttcttccaca gcacaaacac acctctgcca ccccaggttt ttcatctgaa aagcagttca   1140
tgtctgaaac agagaaccaa accgcaaacg tgaaattcta ttgaaaacag tgtcttgagc   1200
tctaaagtag caactgctgg tgattttttt tttcttttta ctgttgaact tagaactatg   1260
ctaatttttg gagaaatgtc ataaattact gttttgccaa gaatatagtt attattgctg   1320
tttggtttgt ttataatgtt atcggctcta ttctctaaac tggcatctgc tctagattca   1380
taaatacaaa aatgaatact gaattttgag tctatcctag tcttcacaac tttgacgtaa   1440
ttaaatccaa ctttcacagt gaagtgcctt tttcctagaa gtggtttgta gacttccttt   1500
ataatatttc agtggaatag atgtctcaaa aatccttatg catgaaatga atgtctgaga   1560
tacgtctgtg acttatctac cattgaagga aagctatatc tatttgagag cagatgccat   1620
tttgtacatg tatgaaattg gttttccaga ggcctgtttt ggggctttcc caggagaaag   1680
atgaaactga aagcacatga ataatttcac ttaataattt ttacctaatc tccacttttt   1740
tcataggtta ctacctatac aatgtatgta atttgtttcc cctagcttac tgataaacct   1800
aatattcaat gaacttccat ttgtattcaa atttgtgtca taccagaaag ctctacattt   1860
gcagatgttc aaatattgta aaactttggt gcattgttat ttaatagctg tgatcagtga   1920
ttttcaaacc tcaaatatag tatattaaca aattacattt tcactgtata tcatggtatc   1980
ttaatgatgt atataattgc cttcaatccc cttctcaccc caccctctac agcttccccc   2040
acagcaatag gggcttgatt atttcagttg agtaaagcat ggtgctaatg gaccagggtc   2100
acagtttcaa aacttgaaca atccagttag catcacagag aaagaaattc ttctgcattt   2160
gctcattgca ccagtaactc cagctagtaa ttttgctagg tagctgcagt tagccctgca   2220
aggaaagaag aggtcagtta gcacaaaccc tttaccatga ctggaaaact cagtatcacg   2280
tatttaaaca tttttttttc ttttagccat gtagaaactc taaattaagc caatattctc   2340
atttgagaat gaggatgtct cagctgagaa acgttttaaa ttctctttat tcataatgtt   2400
ctttgaaggg tttaaaacaa gatgttgata aatctaagct gatgagtttg ctcaaaacag   2460
```

-continued

```
gaagttgaaa ttgttgagac aggaatggaa aatataatta attgatacct atgaggattt   2520

ggaggcttgg cattttaatt tgcagataat accctggtaa ttctcatgaa aaatagactt   2580

ggataacttt tgataaaaga ctaattccaa aatggccact ttgttcctgt ctttaatatc   2640

taaatactta ctgaggtcct ccatcttcta tattatgaat tttcatttat taagcaaatg   2700

tcatattacc ttgaaattca gaagagaaga aacatatact gtgtccagag tataatgaac   2760

ctgcagagtt gtgcttctta ctgctaattc tgggagcttt cacagtactg tcatcatttg   2820

taaatggaaa ttctgctttt ctgtttctgc tccttctgga gcagtgctac tctgtaattt   2880

tcctgaggct tatcacctca gtcatttctt ttttaaatgt ctgtgactgg cagtgattct   2940

ttttcttaaa aatctattaa atttgatgtc aaattaggga gaaagatagt tactcatctt   3000

gggctcttgt gccaatagcc cttgtatgta tgtacttaga gttttccaag tatgttctaa   3060

gcacagaagt ttctaaatgg ggccaaaatt cagacttgag tatgttcttt gaatacctta   3120

agaagttaca attagccggg catggtggcc cgtgcctgta gtcccagcta cttgagaggc   3180

tgaggcagga gaatcacttc aacccaggag gtggaggtta cagtgagcag agatcgtgcc   3240

actgcactcc agcctgggtg acaagagaga cttgtctcca aaaaaaaagt tacacctagg   3300

tgtgaatttt ggcacaaagg agtgacaaac ttatagttaa aagctgaata acttcagtgt   3360

ggtataaaac gtggttttta ggctatgttt gtgattgctg aaaagaattc tagtttacct   3420

caaaatcctt ctctttcccc aaattaagtg cctggccagc tgtcataaat tacatattcc   3480

ttttggtttt tttaaaggtt acatgttcaa gagtgaaaat aagatgttct gtctgaaggc   3540

taccatgccg gatctgtaaa tgaacctgtt aaatgctgta tttgctccaa cggcttacta   3600

tagaatgtta cttaatacaa tatcatactt attacaattt ttactatagg agtgtaatag   3660

gtaaaattaa tctctatttt agtgggccca tgtttagtct ttcaccatcc tttaaactgc   3720

tgtgaatttt tttgtcatga cttgaaagca aggatagaga aacactttag agatatgtgg   3780

ggttttttta ccattccaga gcttgtgagc ataatcatat ttgctttata tttatagtca   3840

tgaactccta agttggcagc tacaaccaag aaccaaaaaa tggtgcgttc tgcttcttgt   3900

aattcatctc tgctaataaa ttataagaag caaggaaaat tagggaaaat attttatttg   3960

gatggtttct ataaacaagg gactataatt cttgtacatt atttttcatc tttgctgttt   4020

ctttgagcag tctaatgtgc cacacaatta tctaaggtat ttgttttcta taagaattgt   4080

tttaaaagta ttcttgttac cagagtagtt gtattatatt tcaaaacgta agatgatttt   4140

taaaagcctg agtactgacc taagatggaa ttgtatgaac tctgctctgg agggaggga    4200

ggatgtccgt ggaagttgta agacttttat tttttgtgc catcaaatat aggtaaaaat    4260

aattgtgcaa ttctgctgtt taaacaggaa ctattggcct ccttggccct aaatggaagg   4320

gccgatattt taagttgatt attttattgt aaattaatcc aacctagttc tttttaattt   4380

ggttgaatgt tttttcttgt taaatgatgt ttaaaaaata aaaactggaa gttcttggct   4440

tagtcataat tctt                                                      4454
```

<210> SEQ ID NO 68
<211> LENGTH: 189
<212> TYPE: PRT
<213> ORGANISM: Homo sapiens

<400> SEQUENCE: 68

```
Met Thr Glu Tyr Lys Leu Val Val Val Gly Ala Gly Gly Val Gly Lys
1               5                   10                  15
```

```
Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185
```

<210> SEQ ID NO 69
<211> LENGTH: 1326
<212> TYPE: DNA
<213> ORGANISM: Rattus norvegicus

<400> SEQUENCE: 69

```
gccgttcatg gcggtttcgg ggtctccaac agcttctcag gttgaaatcc aaaagcctcc     60

cgaggcgggg tctgcggagt ttgagatttt tgcaggtgtg aaatgactga gtacaaactg    120

gtggtggttg gagcaggtgg cgttgggaaa agtgctttga caatccagct aatccagaac    180

cactttgtgg atgaatatga tcccaccata gaggattctt accgaaaaca agtggtgatt    240

gacggtgaga cctgtctact ggacatactg gacacagctg gacaagagga gtacagtgcc    300

atgagagacc aatacatgag gacaggcgaa gggttcctct gtgtgtttgc catcaataat    360

agcaaatcct ttgcagatat taacctctac agggagcaaa ttaagcgcgt gaaagactct    420

gatgatgtac ccatggtgct ggtagggaac aagtgtgact tgccaacaag gacagttgac    480

acaaagcaag cccacgagct ggccaagagt tatggaattc cattcattga aacctcagcc    540

aagacccgac agggtgtgga ggatgccttt tacacgcttg taagggagat acgccagtac    600

cggatgaaga agctcaacag cagtgaggat ggcactcaag gctgtatggg gctgccctgt    660

gtggtgatgt agtaagaccc tttaaaagtt ctgtcatcag aaacgagcca ctttcaagcc    720

tcactgatgc cctggttctg acatccctgg aggagacgtg tttctgctgc tctctgcatc    780

tcagagaagc tcctgcttcc tgcttcccca acttagttac tgagcacagc catctaacct    840

gagacctctt cagaataact acctcctcac tcggctgtcc gaccagagaa atgaacctgt    900

ttctccccag tagttctctg ccctgggttt cccctagaaa caaacacacc tgccagctgg    960

ctttgtcctc cgaaaagcag tttacattga tgcagagaac caaactatag acaagcaatt   1020

ctgttgtcaa cagtttctta agctctaagg taacaattgc tggtgatttc cccctttgcc   1080

cccaactgtt gaacttggcc ttgttagttt tgggggaaat gtcaaaaatt aatctcttcc   1140
```

```
cgagaataga attagtgttg ctgattgcct gatttgcaat gtgatcagct atattctata   1200

agctggcgtc tgctctgtat tcataaatgc aaacatgagt actgacgtaa gtgcatccct   1260

agtcttctca gctgcatgca attaaatcca acgttcacaa caaaaaaaaa aaaaaaaaaa   1320

aaaaaa                                                              1326


<210> SEQ ID NO 70
<211> LENGTH: 189
<212> TYPE: PRT
<213> ORGANISM: Rattus norvegicus

<400> SEQUENCE: 70

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Glu Asp
                165                 170                 175

Gly Thr Gln Gly Cys Met Gly Leu Pro Cys Val Val Met
            180                 185


<210> SEQ ID NO 71
<211> LENGTH: 4470
<212> TYPE: DNA
<213> ORGANISM: Mus musculus

<400> SEQUENCE: 71

gggactgggg cgccttgggc gcctagtgat tacgtagcgg gtggggccgg aagtgccgct     60

ccctggcggg ggctgttcat ggcggtttcg gggtctccaa cagcttctca ggttgaagtc    120

caaaagcctc ccgaggcggg gtctgcggag tttgaggttt ttgctggtgt gaaatgactg    180

agtacaaact ggtggtggtt ggagcaggtg gtgttgggaa aagcgccttg acgatccagc    240

taatccagaa ccactttgtg gatgaatatg atcccaccat agaggattct taccgaaagc    300

aagtggtgat tgatggtgag acctgcctgc tggacatact ggacacagct ggacaagagg    360

agtacagtgc catgagagac cagtacatga ggacaggcga agggttcctc tgtgtatttg    420

ccatcaataa tagcaaatca tttgcagata ttaacctcta cagggagcaa attaagcgtg    480

tgaaagattc tgatgatgtc cccatggtgc tggtaggcaa caagtgtgac ttgccaacaa    540

ggacagttga cacaaagcaa gcccacgaac tggccaagag ttacggaatt ccattcattg    600
```

-continued

```
agacctcagc caagacccga cagggtgtgg aggatgcctt ttacacactg gtaagggaga    660
tacgccagta ccgaatgaaa aagctcaaca gcagtgacga tggcactcaa ggttgtatgg    720
ggctgccctg tgtgctgatg tagtaagaca ctttgaaagt tctgtcatca gaaaagagcc    780
actttgaagc tgcactgatg ccctggttct gacatccctg gaggagacct gttcctgctg    840
ctctctgcat ctcagagaag ctcctgcttc ctgcttcccc gactcagtta ctgagcacag    900
ccatctaacc tgagacctct tcagaataac tacctcctca ctcggctgtc tgaccagaga    960
aatagacctg tctctcccgg tcgttctctg ccctgggttc ccctagaaac agacacagcc   1020
tccagctggc tttgtcctct gaaaagcagt ttacattgat gcagagaacc aaactagaca   1080
tgccattctg ttgacaacag tttcttatac tctaaggtaa caactgctgg tgattttccc   1140
ctgcccccaa ctgttgaact tggccttgtt ggtttggggg gaaaatgtca taaattactt   1200
tcttcccaaa atataattag tgttgctgat tgatttgtaa tgtgatcagc tatattccat   1260
aaactggcat ctgctctgta ttcataaatg caaacacgaa tactctcaac tgcatgcaat   1320
taaatccaac attcacaaca aagtgccttt ttcctaaaag tgctctgtag gctccattac   1380
agtttgtaat tggaatagat gtgtcaagaa ccattgtata ggaaagtgac tctgagccat   1440
ctacctttga gggaaaggtg tatgtacctg atggcagatg ctttgtgtat gcacatgaag   1500
atagtttccc tgtctgggat tctcccagga gaaagatgga actgaaacaa ttacaagtaa   1560
tttcatttaa ttctagctaa tcttttttttt ttttttttt ttttttggta gactatcacc   1620
tataaatatt tggaatatct tctagcttac tgataatcta ataattaatg agcttccatt   1680
ataatgaatt ggttcatacc aggaagccct ccatttatag tatagatact gtaaaaattg   1740
gcatgttgtt actttatagc tgtgattaat gattcctcag accttgctga gatatagtta   1800
ttagcagaca ggttatatct ttgctgcata gtttcttcat ggaatatata tctatctgta   1860
tgtggagaga acgtggccct cagttccctt ctcagcatcc ctcatctctc agcctagaga   1920
agttcgagca tcctagaggg gcttgaacag ttatctcggt taaaccatgg tgctaatgga   1980
ccgggtcatg gtttcaaaac ttgaacaagc cagttagcat cacagagaaa cagtccatcc   2040
atatttgctc cctgcctatt attcctgctt acagactttt gcctgatgcc tgctgttagt   2100
gctacaagga taaagcttgt gtggttctca ccaggactgg aagtacctgg tgagctctgg   2160
ggtaagccta gatatcttta cattttcaga cccttattct tagccacgtg gaaactgaag   2220
ccagagtcca tacctccatc tccttccccc cccaaaaaaa ttagattaat gttctttata   2280
tagctttttt aaagtattta aaacatgtct ataagttagg ctgccaacta acaaaagctg   2340
atgtgtttgt tcaaataaag aggtatcctt cgctactcga gagaagaatg taaaatgcca   2400
ttgattgttg tcacttggag gcttgatgtt tgccctgata attcattagt gggttttgtt   2460
tgtcacatga tacctaagat gtaactcagc tcagtaattc taatgaaaac ataaattgga   2520
taccttaatt gaaaaaagca aacctaattc caaaatggcc attttctctt ctgatcttgt   2580
aatacctaaa attctgaggt ccttgggatt cttttgttta taacaggatc ttgctgtgta   2640
gtcctagctg gcctcaaact cacaatactc ttcctggatc aatctcccaa gtgctgggat   2700
tacaggcaca ttccaccaca cacacctgac tgagctcgtt cctaatgagt tttcattaag   2760
caaattcccc atcaccttga aactaatcag aagggggaag aaacatttgc tatgctcctg   2820
agtgctaaca ctgggatcat tcacatgggg tttgcattcc taggcaaact aaactgctgc   2880
cttttacaac aaggctcagt catcttcctg aagctgctga gaccagcact tggtcttgtt   2940
```

-continued

```
ttgttttaat atgtctatat gactggtggt ggatccctaa atagtttatt aattaaactc   3000

cagttaagga gaaagttact caccttgacc cgtttgacca tatcccgtgt gtgtgtgtgt   3060

gtgtgtgtgt gtgtgtgtgt gtgtgtgtgt gtgcacgcgt atgtacgtac gtatgtatgt   3120

aggtatgtag gtggtttcca gtataaacac agaaacaaat ggagccaatt caggtttcag   3180

atgcccttac taacatatat tcccacgggg tgtgggtttt ggcacaacag tgacaaactt   3240

aaaagccaag taagagccgg gcgtggtggc gcacgccttt aatcccagca cttgggaggc   3300

agaggcaggc ggatttctga gttctaggcc atcctggtct acagtgagtt ccaggacagc   3360

cagtgctaca cagagaaacc ctgtctcgaa aagccaaaaa aaaaaaaaaa aaaaaaaaaa   3420

aaaagccaag taggtccagt tggtatagta tcaaagtgtt tttagagtaa ttagtgaagg   3480

tctgctttac ctcaaagttg cagagcctct cttcctgagt ttaagtgcct ggccggcagt   3540

cacaaattaa catgttgctg taaggcagtt agttgaagct ttgttcacac attggagagt   3600

atgaaaataa agtgttctaa gagcgctgat actggatctg tgtaaacctg gtaaatgccg   3660

tttgtccagg acttagcgtg tgtgagttgg tagctcagta cgagtttact agttccgcag   3720

tgtgtacaat ggaggcgggt ttgttttagc tggccacctg tagaatcagc ctttaaactg   3780

ctgtgaactt tgtcatgact tgaatatgaa gatagacaaa aactctgtaa agacaaatgt   3840

ttgttttccc ccttacagaa cgtgtgagct tggttttatc ttcctttgta tttagtcata   3900

acctctcaag ctggcagctc cgaccaagga tcagaagctg tgtgcgttcc acctggtgga   3960

attagctcag ctctatatga gaagtggagt taatggaaaa cgtgttgact gggtggtttc   4020

tatttaaaag agtgatgata attcttgaac agtagttttt attttgctat ttctttaagc   4080

tgactgatgt gccacaaaat tattttaagg tatttgtgtt ttaagagtgt tctcatgaga   4140

ttagttgtag atatttttta aaatacaact ggtttttaaa atctgagtat tgctctaagc   4200

aagtgtttag actcttacgg gaaggtgggt ggaagttgtt tggcttccgt atttccatgc   4260

gtgccgtcag acataggtca gaacgccaac tgtgcatcct gctgtttaaa gacctcttgg   4320

cctctgtgac cctcatgaag ggctgatat tttaagttga ctgtttgatt gtaaattaat   4380

cctttctaat ttttaaagac ttgcttgact gttttccttg ttaaataatt ttaaaaaaat   4440

aaaaaactgg aagttctttg cttaactgta                                    4470
```

```
<210> SEQ ID NO 72
<211> LENGTH: 189
<212> TYPE: PRT
<213> ORGANISM: Mus musculus

<400> SEQUENCE: 72

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
```

```
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Leu Met
            180                 185


<210> SEQ ID NO 73
<211> LENGTH: 570
<212> TYPE: DNA
<213> ORGANISM: Cavia porcellus

<400> SEQUENCE: 73

atgactgagt ataaactggt ggtggttgga gcaggtggtg tcgggaaaag tgcactgacc      60

atccagctaa ttcagaacca ctttgtcgat gaatatgatc ccaccataga ggattcttac     120

cgaaaacagg tggttataga tggtgaaact tgtctgttgg atattctgga tacagctgga     180

caagaggagt acagtgccat gagagaccaa tacatgagga caggcgaagg cttcctctgt     240

gtgtttgcca tcaataatag caaatcattt gcagatatta acctctacag ggagcagatt     300

aaacgagtaa aagactcaga tgatgtacct atggtgctgg tagggaacaa gtgtgatttg     360

ccaacaagga ctgttgacac aaaacaagcc catgaactgg ccaagagtta cgggattcca     420

ttcattgaaa cctcagccaa gaccagacag ggtgttgaag atgcatttta cacactcgta     480

agagaaatac gccagtacag aatgaaaaaa ctcaacagca atgatgatgg gactcaaggt     540

tgtatggggt tgccatgtgt ggtgatgtaa                                      570


<210> SEQ ID NO 74
<211> LENGTH: 189
<212> TYPE: PRT
<213> ORGANISM: Cavia porcellus

<400> SEQUENCE: 74

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140
```

```
Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Asn Asp Asp
                165                 170                 175

Gly Thr Gln Gly Cys Met Gly Leu Pro Cys Val Val Met
            180                 185


<210> SEQ ID NO 75
<211> LENGTH: 1220
<212> TYPE: DNA
<213> ORGANISM: Cavia porcellus

<400> SEQUENCE: 75

gttccggggt cctcaacgtt tctcagggtt gagattctat atccttttga agctggggcg      60

gcagagcttg aggttcttgc tggtgtgaaa tgactgagta taaactggtg gtggttggag     120

caggtggtgt cgggaaaagt gcactgacca tccagctaat tcagaaccac tttgtcgatg     180

aatatgatcc caccatagag gattcttacc gaaaacaggt ggttatagat ggtgaaactt     240

gtctgttgga tattctggat acagctggac aagaggagta cagtgccatg agagaccaat     300

acatgaggac aggcgaaggc ttcctctgtg tgtttgccat caataatagc aaatcatttg     360

cagatattaa cctctacagg gagcagatta aacgagtaaa agactcagat gatgtaccta     420

tggtgctggt agggaacaag tgtgatttgc caacaaggac tgttgacaca aaacaagccc     480

atgaactggc caagagttac gggattccat tcattgaaac ctcagccaag accagacagg     540

gtgttgaaga tgcattttac acactcgtaa gagaaatacg ccagtacaga atgaaaaaac     600

tcaacagcaa tgatgatggg actcaaggtt gtatggggtt gccatgtgtg gtgatgtaac     660

aagatattta acaaagttct atcagaaaag agccactttc aagctgcact gataccctgg     720

tcctgacttc cctggaggag aagtatccct gttgctctct tcatctcaga gaagctcctg     780

ctgtttgtcc acctctcagt gtatgagcac agtctctgct tgagaacttc tcagaataac     840

tacctcctca cttggttgtc tgaccagaga aatgcacctc ttgttaattc cccaataatt     900

ttctgccctg ggctctcccc aacaaaaaac aaacacttct gccatccaaa aagcaacttg     960

gtctgaaaca gaaccaaact gtagattgaa attctcttaa aaagtcttga gctctaaagt    1020

tagcaaccgc tggtgatttt tattttcctt tttattttg aacttggaac tgacctatgt    1080

tagattttgg agaaatgtca taaagtactg ttgtgccaag aagataatta tgttgctgaa    1140

tggttgattt atagtgttat cagctatatt ttacaaactg gcatctgctc tgtattcata    1200

aatacaaaaa tgaagccagg                                                1220


<210> SEQ ID NO 76
<211> LENGTH: 189
<212> TYPE: PRT
<213> ORGANISM: Cavia porcellus

<400> SEQUENCE: 76

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60
```

Ser Ala Met Arg Asp Gln Tyr Met Arg Thr Gly Glu Gly Phe Leu Cys
65 70 75 80

Val Phe Ala Ile Asn Asn Ser Lys Ser Phe Ala Asp Ile Asn Leu Tyr
85 90 95

Arg Glu Gln Ile Lys Arg Val Lys Asp Ser Asp Asp Val Pro Met Val
100 105 110

Leu Val Gly Asn Lys Cys Asp Leu Pro Thr Arg Thr Val Asp Thr Lys
115 120 125

Gln Ala His Glu Leu Ala Lys Ser Tyr Gly Ile Pro Phe Ile Glu Thr
130 135 140

Ser Ala Lys Thr Arg Gln Gly Val Glu Asp Ala Phe Tyr Thr Leu Val
145 150 155 160

Arg Glu Ile Arg Gln Tyr Arg Met Lys Lys Leu Asn Ser Asn Asp Asp
165 170 175

Gly Thr Gln Gly Cys Met Gly Leu Pro Cys Val Val Met
180 185

<210> SEQ ID NO 77
<211> LENGTH: 1307
<212> TYPE: DNA
<213> ORGANISM: Canis lupus

<400> SEQUENCE: 77
tgattacgta gcgggcgggg ccggaagtgc cgctccctag tgggggctgt tcatggcggt 60
tccggggtct ccaacctttc tcctagttgt ggtcctaaat acgtcggaag cggaggcggc 120
gaagcttgag gttcttgctg gtgtgaaatg actgagtaca aactggtggt ggttggagca 180
ggtggtgttg ggaaaagcgc actgacaatc cagctaatcc agaaccactt tgtagatgaa 240
tatgatccca ccatagagga ttcttaccga aaacaggtgg ttatagacgg tgaaacctgt 300
ctgttggata tactggatac agctggtcaa gaagagtaca gtgccatgag agaccaatac 360
atgaggacag gcgaaggctt cctctgtgta tttgccatca ataatagcaa atcatttgca 420
gacattaacc tctacaggga acagattaag cgagtaaaag attcagatga tgtacctatg 480
gtgctagtag gaaacaagtg tgatttgcca acaaggacag ttgacacaaa acaagcccat 540
gaactggcca agagttatgg gattccattc attgaaacct cagccaagac cagacagggt 600
gtcgaggatg ccttttacac actggtaaga gaaatacgtc agtaccgaat gaagaaactc 660
aacagcagtg atgatgggac tcaaggttgt atggggttac catgtgtggt gatgtaacaa 720
gacactttta aagttctagc atcagaaaag agccactgtc aagctgcact gacaccctgg 780
tcctgacttc cctggaggag aagtattcct gttgctatct tcagtctcac aaagaagctc 840
ctgctacttc cccaactctc agtagatcag tacaatgttc tctatttgag aagttctccg 900
aacaactacc tcctcacttg gttgtctgac cagagaaatg aacctcttgt tccttcccgc 960
tgtttttcca ccctgaattc tcccccaaca cacataaaca aacctctgcc atcccaggtt 1020
tttcatctga aaaataattc atgctctgaa acagagaaca aaactgtaga catgaaattc 1080
tgtaggaaac aaggtcttga gctcaaaagt agcaactgct ggtgaccttt ttttcccccc 1140
tttttactgt tgaacttgga actatgttgg tttttggaga aatgtcataa gttactgttt 1200
tgctgagaat atagttaagt tgacatttgg tttgtttgta atatcattag ctattttcta 1260
taaattggca tctgctctgc attcataaat acacgagtga attctga 1307

<210> SEQ ID NO 78

<211> LENGTH: 189
<212> TYPE: PRT
<213> ORGANISM: Canis lupus

<400> SEQUENCE: 78

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185
```

<210> SEQ ID NO 79
<211> LENGTH: 3104
<212> TYPE: DNA
<213> ORGANISM: Felis catus

<400> SEQUENCE: 79

```
aaaaaataaa taaatttaag aaaccatttt aaaattatgc acagttgcag cctggaaaac     60
ttaaggtggc gccttatagt atcaatctta ggagctttat ttggtgcatt taacgcaact    120
ggtaattgca aaatccactt cgcctgtgta agtgaaaaat atagactgtt atcttgttgg    180
ccctatgaaa ttctgcactt ggtatttagc atatactcta ccttcattac tatctggcaa    240
gatgttctgc cttagcactc agttgcattc ttttcctttt ctttcctgtt cattatgctt    300
taattctgag gaccatatga gggtagaata tattaaaaat tacaaaaatt ataaaaattt    360
gtataggcaa accatttcct taagttgatg gccaaatgtt aaaatgttat ttttcatatc    420
atttataatc ttgtcacagt ccacttaacg aagtttggtt agatttcagt gaaaattatc    480
ttccagagta gttttttttt ttttttcctg ggattaggga ggggggtaac tttactgcaa    540
ttagtatgta tggtgcagaa tttcatgcaa atgaggtgtg ccagcagtgt ggtaatttaa    600
tcgtatttaa acaaaaacaa acaaaaaaaa aacgaatgca caaacttgct gctgcttaga    660
tcactgcagc ttctaggacc cagtttcttt tactgatttc aaaacaaaac aaaacaaaaa    720
aataaaaaaa gttgtgcctg aaatgaatct tgtttttttt ataagtagcc gcctggttcc    780
tgtgtcctgt gaaatacagg cacttgaccc ttggtgtagc ttctgttcga ctttatatca    840
cgggaatgga ttggtctgat ttcttggccc tcatcttgaa ttggccacat ccagggtccc    900
```

```
tggccagtgg actgaaggct ttgtctaaga ggacaagggc agctcagggg atgtggggga    960
gggcgctttt atcttccccg ttgtcgtttg aggttttgat cttctctggg taaagaggcc   1020
gtttatcttt gtaaacacaa aacatttttg ctttctccag ttttctgtta atggcgaaag   1080
aatggaagcg aataaagttt tactgatttt tgagactcta gcacctagcg ctttcatttt   1140
tgaaacgtcc tgtgtgggag gggcgggtct gggtgcggcc cgccgcgtga ctcctgagtc   1200
gggggcccac gtggctgggg cggggactcg gacgccccgg gcgccgactg attacgtagc   1260
gggcggggcc ggaagtgccg ctccctagtg ggggctgttc atggcggttc cggggtctcc   1320
atcctttttc ccagttgttc taaatcagtc ggaagcggag gcagcgaagt ttgaggttct   1380
cgctggtgtg aaatgactga gtacaaactg gtggtggttg gagcaggtgg tgttgggaaa   1440
agcgcactga caatccagct aatccagaac cactttgtag atgaatatga tcccaccata   1500
gaggattctt accgaaaaca ggtggttata gacggtgaaa cctgtctgtt ggacatactg   1560
gatacagctg gtcaagaaga gtacagtgcc atgagagacc aatacatgag gacaggcgaa   1620
ggcttcctct gtgtatttgc catcaacaat agcaaatcat ttgcagatat taacctttac   1680
agggaacaga ttaagcgagt aaaagactcc gatgatgtac ctatggtgct agtaggaaac   1740
aagtgtgatt tgccaacaag gaccgtcgac acaaaacaag cccacgaact ggccaagagt   1800
tatgggattc cattcattga aacctcagcc aagaccagac agggtgttga agatgccttt   1860
tacacactgg taagagaaat acgtcagtac cgaatgaaga aactcaacag cagtgatgac   1920
gggactcaag gttgtatggg gttaccgtgt gtggtgatgt aacaagatac ttttaaagtt   1980
ctagcatcag aaaagagcca ctgtcaagct gcactgacac cctggtcctg acttccctgg   2040
aggagaagcg ttcctgttgc tattttcagt ttcacaaaga agctcctgct atttccccaa   2100
ctctccgtag atcagtacat tattctctgt ttgagaagtt ctccgaataa ctacctcctc   2160
acttggttgt ctgaccagag aaatgaacct cttgttactc cccactgttt ttccaccctg   2220
gttctccccc agcacatata aacaaacctc ccaggttttt catctgaaaa gtaattcatg   2280
ctctgaaaca gagaaccaaa ctgtagacat gaaattctgt aggaaacaat gtcttgagct   2340
ctaaagtagc aactgctggt gacttttttt tttttttttt ccttttttact gttgaacttg   2400
gaactatgtt ggtttttgga gaaatgtcgt aagttactgt tttgctgagt atatagttaa   2460
gtttaccatt cggtttgttt gtaatgtcat tggctatact ctgtacctgg catctgctct   2520
gcattcataa atacaaaagt gaattctgac ttttgagtct atcctagtgt tctcaacttc   2580
cacataatta aatctaactt ttgcagcaaa gtgccttttt cctagaagtg gtttgtagat   2640
ttgctttata atactttggt ggaatagatg tctcaaaaac cattatacat gaaaatgaat   2700
gtctgagata cgtctatgat ctgtctacct ttgagggaaa aatataccga cataatagca   2760
gatgccatgt cttacgtgta tgaagttgga tttccagaga cctgatttgg gtctcttcca   2820
agagaaagat gaaactggaa acaattatga ataacttcac ttaattttta cctaatctct   2880
acttcggggt gggagggcag ggagtaggtt accacttaca aaatatatgc aatttgtttc   2940
ttctagctta ctgataatga acttccattc ttatttaaat ttaggtcata tcctaaagct   3000
ttacatttgc aggtgttcga aattgtaagt ttaatgcagt tttatttaat agctatgatc   3060
aatgattttc aagcctcaga tgtattaacg gacacatttt cact                    3104
```

<210> SEQ ID NO 80
<211> LENGTH: 189
<212> TYPE: PRT

<213> ORGANISM: Felis catus

<400> SEQUENCE: 80

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185
```

<210> SEQ ID NO 81
<211> LENGTH: 4283
<212> TYPE: DNA
<213> ORGANISM: Bos taurus

<400> SEQUENCE: 81

```
ggccgctccc tagtgggggc tgttcatggc ggttccgggg tctcccaaca attttcccgg     60

ttgtggtcgt aatctatccg aagtggaggc agtggagcta gaggttcttg ctggtgtgaa    120

atgactgagt acaaactggt ggtggttgga gcaggtggtg ttgggaaaag tgcactgaca    180

atccagctaa tccagaacca ctttgtagat gaatatgatc ccaccataga ggattcctac    240

cgaaaacagg tggttataga tggtgaaacc tgtctgttgg acatactgga tacagctgga    300

caagaggagt acagtgccat gagagaccaa tacatgagga caggcgaagg cttcctttgt    360

gtgtttgcca tcaataatag caaatcattt gcagatatta acctctacag ggaacagata    420

aagcgtgtaa aggactcgga tgatgtacct atggtgctag taggaaacaa gtgtgatttg    480

ccaacaagga cagttgacac aaaacaagcc catgaactgg ccaaaagtta tgggattcca    540

ttcattgaaa cctcagccaa gaccagacag ggtgttgaag atgcctttta cacactggta    600

agagaaatac gtcagtaccg aatgaaaaag ctcaacagca gtgatgatgg cactcaaggc    660

tgtatggggt tgccgtgtgt ggtgatgtaa caagatactt ttaaagttct cacatcagaa    720

aagagccact gtcaagctgc actgacaccc tggtcctgac ttccctggag gagaagtatt    780

cctgttgcta tcttcagttt caaaaagaag ctcctgctat ttccccaact ctcagtagat    840

caatataata ttctctattt gagaagttct caagaataac tacctcctca cttggttgtc    900

tgaccagaga attgaacctc ttgttactcc cagtattttt ccaccctggg ttctccccca    960
```

-continued

```
gcacacacaa acgcacctct gccacccagg tttttcatct gaaaagcaat taatactctg   1020
aaacagagaa ccaaactgta gaaacatgaa attctgtaga aaacaatgtc ttgagctcta   1080
aagtagcaac tgctggtgat tttttttttt ttttttttcct ttttattgtt gaacttggaa   1140
ctatgttggt ttgtggagaa atgtcataaa ttactgtttt gctgagaata tagttaatgt   1200
tgctctctgg tttgtttgta atgttatcag ctatattcta taaactggca tctactctgt   1260
atttagaaat acaaaaatga atactgacct tttgagtcta ccctcatctt ctcgactttc   1320
ttgtaattaa atgtaacttt cacgatgaag tgccttttgc ctgggagtga ctcgtagact   1380
tcctttaaaa tacttcagtg gaatagatgt ctcagaaact gttatacata agaataaatg   1440
tctgagatat gtctatgacc catctagctt tgagggaaag atataccaat atgatagcag   1500
atgccatttc ttacatctat aacgttgatt ttctggagac ctattttggg gctctccgag   1560
agaaagatga gactataaat gattaggaat aatttcactt aatttttaca taacctccac   1620
tttttgtttt gtagtttact acctgcaaaa catataattt gattcctttt agcttacaga   1680
taatctaatg ttaaatgaac ttccattcat attttaattt ggatcatatc aggaagtcta   1740
catttgcagg tgttcaaaaa ttgtaaaagt gtgatgcagt tttatttaat agctgtgatc   1800
aatgattttc aagcctcaaa tatgttaata gacacatttt cactgtatat catggtatta   1860
ataattattg atgtatataa ttgtccttgg tccccttctc tgttcatcac ctcatggcaa   1920
tggcttgatt aattatttca gctgagtaaa gcatggtgct aatagaccag ggtcacagtg   1980
tcaaaacttc agtgagccag taagcatcac agagaaagaa attctttcac atttgctcac   2040
cattaactcc agctaatagt tttgccagat gtgtgtggtt agtcctgcaa ggaaaggaga   2100
agtcagttaa tacaaattct taaccaggac tggaaaaact tgttttcctg agaagggtca   2160
gcttagaagt ctttatctgg actctatttt tagccacatg gaaatcaaat taagctgatc   2220
tttttctca agtttttgag agtgaggatg cctcagatca acatttttaa aatattcttt   2280
attcttacgt tcttttaagg gtttaaaaca acgttgagta attagtctgg gcataccagg   2340
taacaagctg ataagtttgt gctgaacaag aagtagcctt tggattgaaa ttgctgtttt   2400
gagaagggat agaaaatata attaataatt atgagacttg acttttctat ttgcagataa   2460
tatcctgata attctgatga aaatagactt ggataatttt tgataaaaga atcgttccaa   2520
aatggccact tgctgttctt gtcttctaat gtgtaaatac ttactgaggt cctcttctaa   2580
tatgagttgt catttattaa gcaaattcca cattgccttg aaatgaattc ggaagagaag   2640
aaaaagtcat agtataccca gagaatgaaa aatccagaga attgtgctcc ttagtgttaa   2700
ttctgaagcc ttcgtagtcc acacccatag acagaaactc tctgccactt tgcttctgct   2760
cctcttggag cattgcgctg tcatttcctt gaggatagat tgaggcttgt caactcagtt   2820
gtattgtctt cctcctcttc ctcttgtctg tgtgactgac agtgtgactc ttactaatgt   2880
cagatgcggg gatgcgggga ggtggggggg agtagctcat tttaggctct tgcacccttt   2940
accgttgtat gtgtgtgtct tttagttttc tcaagaatgt tctaagcaca gaagtatcta   3000
aatggggcca aaattcagac ttgaaaatgt tcttttaata gcttcttaaa aagttacact   3060
ttggtgtgaa ttttggcagg atagagtgac aaactcttaa acgctgaata acttcagtta   3120
gtgtgttata gtttttagaa tatgtttgtg attgctgaaa acaattatag tttacctcaa   3180
aatctgaaag tctctttccc caagttaagt gcctggccag ctgtcaaaga ttacatatta   3240
ctttatgttt gtttgttttt taaaggttgc acattcaaga ttgtgaaaat aaggtgttct   3300
```

```
gtctgaaagc taccatgcct gtctgtaaat gaatccactg agtgctgtac ttgttccaac   3360

agcttactac agaatgctac ttggtaatat catactcgtt acagttttca cttcaggagt   3420

gtactaggta gaatgatcct gtgtgtattg tagtgggctc catgtttagt cttttcagca   3480

tcctttaaac tgctgtgaat ttttgtcttg acttgaaagc aaggatagag aaacacttta   3540

aagagatact ttgggttttt ttccattcca gaattggtga gcatagttag attttgcttt   3600

acatttacag tcatgaactc ttaagctggc agctacaacc aagaaccaaa agagggtgca   3660

ttctgcttct tgtaattcat ctttgctaat aaattatgag aagcaaagat aattaattag   3720

agaaactatt ttatttgggt ggtttctata aacaagggac tataattctt aaacattatt   3780

tttcattttt gctgtttctt taagaaacct aatgtgccac aacattattt taaggtgttt   3840

cttaaaagaa ttgtttttaa aagtgttctc attttcagag taattgtaga tatatttcaa   3900

aatataactg ataattttta aaggcctgag tactgaccta agaagcagtt gtatgaattc   3960

tctgggggga agggaggagc tcagtgaaag ttgtatgact tttatatttc tgtgccatca   4020

aataaaggta aaaatgtctt ttgtgcagtt ttgctgttca aacagaaact attggcctcc   4080

ttggccctaa atgaaagggc tggtatttta agttgactat tttattgtaa attaatccat   4140

cttaattttt ttaaatttgg ttgaatgttc tcttgttaaa tgtttaaaaa ataaaaactg   4200

gaagttcttt gcttagtcat aaaaaaaaaa aaaaaaaaaa aaaaaaaaaa aaaaaaaaaa   4260

aaaaaaataa aaaaaaaaaa aaa                                           4283
```

```
<210> SEQ ID NO 82
<211> LENGTH: 189
<212> TYPE: PRT
<213> ORGANISM: Bos taurus

<400> SEQUENCE: 82

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185
```

<210> SEQ ID NO 83
<211> LENGTH: 4825
<212> TYPE: DNA
<213> ORGANISM: Gallus gallus

<400> SEQUENCE: 83
gcgccgggac cggaagccgg aagctttgca gaagggtgtt ccgcgttcgc ggtgcgggag 60
cggtcagccg gggtggcggg gctggggccg gccggggcag gcggctccgc gctccgcact 120
gggccgctgg gagggcgatg actgaataca agctggtggt ggtgggagct ggcggcgtcg 180
ggaagagcgc gttgaccatc cagctcatcc agaaccactt cgtggacgag tacgacccca 240
ccatcgagga ttcgtacaga aagcaggttg tcatcgatgg agagacgtgc ttgttggaca 300
ttctggacac tgcaggacag gaagaataca gtgctatgcg tgatcagtac atgagaactg 360
gggaaggatt cctttgtgtg tttgccatta acaacagtaa atcattcgct gatattaacc 420
tttacagaga gcaaatcaag agagtgaaag attcagacga tgtgccaatg gtgctggtgg 480
ggaataagtg cgatttgcca acaaggacag tagacaccaa acaggctcaa gagttagcaa 540
aaagctacgg cattcccttc atagagacat cagccaaaac gagacagggt gtggaagatg 600
cgttttacac actggtgagg gagattcggc agtaccggat gaaaaagctc aacagcaacg 660
aagatgggaa tcagggctgt atggggttgt cctgcattgt gatgtgataa gatgccaggt 720
tcagatgtag ctgctggaca agtctcgatg ctactgtatt gtgtctcatg ctgatgccct 780
gcagtatttt ggtgccagcg accagactct tggtaccagt taattagctc aggatccttt 840
cctgtgctcc atctgaagaa aacatctctg gtatctacct ccttgctcag ctcacagagc 900
agtcatatct cttggtgtac tggattctt ttctagctgt gttgtctggg tttgttcaag 960
aagaaaacca gtcacaagaa aagtgaatta cagagactaa atgctgtgaa aaagatcaca 1020
ctttacctcc agagtaaaag ctagaagtgg cgtttgaccc ctttgcattg gattcagatt 1080
tgcggtgttg tcagaggagt ggcagaagta attttgccat tacaaaggtt tctgtcacca 1140
gtcggattgg tatctgctgt ctgtgcaccc acacagtgta tctgcaacat ctgcattgtg 1200
ccagaagtat cacttaactg atgaactgat cctttatttt tctgtaataa aaaggagata 1260
tctttgctaa cttaagtgcc tgtttgctca gaaggttgga ggttgtatgc tgttcccttg 1320
ggctgaggag aaccccaagg atgaatttct tgggtgctca ttgtcttgag caggcaagtt 1380
ttgtgtgggt gatctctttt catggcagga tattaaaatg ggaatttgta gtctggaaga 1440
tggagcagct gtttgtgaga ctcttgagtt agggagagaa atgtatacca cgtctgttct 1500
cgatccatca gaatggatcc atccacctct ttgtgtgtgg aactgtgtat agtctgtatt 1560
ggttttctac agcacttgga tctctttgga ccaaattagc gagctgttca ttttaacata 1620
actgccagta tttatagaca atttcttacg gacagataat gaatttagaa actggaggtt 1680
actttgggca gctgttcctc agctctgtct gtaacttgca aattattctg agttattttc 1740
tgcagaacct ccttccttat cacgggagga gcctgggagt tgaggttgac tgtaattggg 1800
tcaatggttg tcacagactt aaggtgtcca ggctgattgg aggaggcact gagccctaac 1860
agagcactga gctgacttct aattgcagca tccttgcaaa atgaggaagg gagttcagtg 1920
atgtctgcac tgaagatgta tgatacactg atagcagttc tgggtatgtt gtaacagctt 1980
caaagtagaa ccgcagtact gcgtgagctg tgtgacttct tcctagaaca cagcactgtc 2040
accccatatg gttgggacgt gcaggtgaga ccaacaccta ccaggttccc tggcgtaccg 2100
tggccttctc agttcttgtg ccagtgatac tgggttctgt tctgtggtgt cagacagcgt 2160

-continued

```
cctgtagcaa agctgaattc ccacttagtc tggtgagaga ataaagagcc atcagccaac   2220
agagggagcg ttcattctgc tggagcagtg cgagctgtaa gcattacgag aggcgtagtt   2280
tcagtttgtt gcagtcaggt tcctatattt tcaaagctga aatcagaaat aagtaaatac   2340
ggagaaaata agctgttgct tttaatgctc tttcctccac taattgtact cttaattttc   2400
ttcttgggag gccgaggatc catctgcata actttagctg tgatgctcca gataagtgtt   2460
tagaattcat tttatctttg actgatggga ctgataagaa gttaacgcac aatattttta   2520
catacaacat cgttttccag tgacctcctg agcggtggga agcattatgg gatagcaccg   2580
gctgtgactc gagttcattt gaaggcgatc tcttgcctgc aggttaaatg ggacggagtc   2640
agaatcactg tgagccgtct gtaatcagca aacagtctgt gggcttttct tactgtgttc   2700
tctctgtttg ccttagtttg gtgcaggaag agttccttgt gacagcgtcc tttgaggtgt   2760
gttgcaggag ctgaccattt gctccttgag ctgtgtgatg aactgttgtc cacttaatgg   2820
agttacagaa gcagcttctg ggagtcgcat ctggtcgcat acattcagtg ttttgggaag   2880
ctgtcagtgt ggtgtttgca ctgtgtttga atggtgttca tggtgggtct gttatgctcc   2940
tggatgattt ggggagatgt ggggctgctt ccgtggcaga caggatcagc tcagggcgct   3000
gctgcctatg gctgtgggaa acctcacagt tggtgtttga atagtggcca agtatgtcaa   3060
ttaaaaatac attttgaagg gaggtttgtc atagctctgt actttggcat gctctgctta   3120
ctgaaaacat actagctgta gctcaaaaaa agttgtgaat cctcagaata atacaggagc   3180
tggcaattgt ggctgctttc tctttgtgtt ccttttctct tgggttggat gaagctttaa   3240
aaaggaagga gccctggtga gggttggtca gtgtgcattt cattcttgga accagagagg   3300
aagttgcatc aactttcagg acgctgcaga gctcacttgc acaggtggtg ctccagtcta   3360
tgtgattttt ggggtcaaat cttgagatga tcttacaaaa tcagattttg tacccatcat   3420
gagcatgagg tgagtggttg tgctcggttt ctagctgcat gtatgtatac agacacgtgt   3480
atgcagacat gtctatgtgt gagtagttcg agtcagtcaa ggttactggc agcacctaaa   3540
gcgtatgcac cacataatgc atgcaggcaa aagtcctatc ttaggagcca tctcttcatg   3600
ggtttgggtt tatataggca gtatttttaa acagaatatc cgaagcactt tctggagttc   3660
tgtggtaatg cagtgacacc tatttggatg aaggaagatg tgtctgagga gcacgtaagc   3720
agatttgctg ccctaacaga gaggttttgg taaccgtgga aaaggttttc tcctggatct   3780
gtgtgtgctc ttggtgagct gcaatccatg acagggcaca accagatgag aaggaaaccc   3840
ggccatccca tgcttgagca cagctctgac tcagtagttc caccagatgt gccctttcag   3900
tcaaagtgtt ctgatctctt agagctttct gtagttcaag ttaccactca ctctccagct   3960
tgctcggtta atgtctgttg gcggcgttga gttggacttg ggaaaggtgt gtgtggtagg   4020
aacaagcaga gtgtgatgtg cttctgttat caggacttaa gctagagtgg ttggcagata   4080
ggaaatgcag ctattccttg aaagcaagca gatcatggat ggtcagccaa actgccctgg   4140
ctttggtggg agctgcactg cagaaggacc aaaccccaac aagatttggc acatttgttt   4200
agaagataag cacagatggt tttgcacaag gcagctcctc ataatggtgg ctttgtagat   4260
ttagtccaaa tgttcttatt tagatctagc agcacatcac tgtgtccgtg cccatctaac   4320
ctcgctatcc taagtagagc agaccccaaa caaccttgtt caaaaactac cagtgcaaat   4380
aactgaacta aatatttgtt actgctgact gagaacagct gttcgagtgt agcattgtgg   4440
cttgttaatg tgagtgcccc aactctatgg tcttattaaa gaaacccaaa cattgctcag   4500
attttgttct tattgtcatc ataagacttg aatagtgatg gtaatgctta cgtagacgtg   4560
```

```
tcttgtgagt gcacttcagt gatttagaaa gaactggatt tcaagcaact ttggacctgt   4620

gggggggaggg agattaatga aggtttgaat cacattctaa ttctatgtac agtccttcat   4680

tactccacaa gcctaaatcc tatacagcct ccaggatagc tggaaactgt tgagatctgg   4740

actttttttt tttaatccaa gggctaactt gttgtaactt ggtataatta tctgctttcg   4800

gaaatgcatc tctgttggtt tgaaa                                         4825


<210> SEQ ID NO 84
<211> LENGTH: 189
<212> TYPE: PRT
<213> ORGANISM: Gallus gallus

<400> SEQUENCE: 84

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala Gln Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Asn Glu Asp
                165                 170                 175

Gly Asn Gln Gly Cys Met Gly Leu Ser Cys Ile Val Met
            180                 185


<210> SEQ ID NO 85
<211> LENGTH: 2949
<212> TYPE: DNA
<213> ORGANISM: Homo sapiens

<400> SEQUENCE: 85

cgcctccctt ccccctcccc gcccgacagc ggccgctcgg gccccggctc tcggttataa     60

gatggcggcg ctgagcggtg gcggtggtgg cggcgcggag ccgggccagg ctctgttcaa    120

cggggacatg gagcccgagg ccggcgccgg cgccggcgcc gcggcctctt cggctgcgga    180

ccctgccatt ccggaggagg tgtggaatat caaacaaatg attaagttga cacaggaaca    240

tatagaggcc ctattggaca aatttggtgg ggagcataat ccaccatcaa tatatctgga    300

ggcctatgaa gaatacacca gcaagctaga tgcactccaa caaagagaac aacagttatt    360

ggaatctctg gggaacggaa ctgatttttc tgtttctagc tctgcatcaa tggataccgt    420

tacatcttct tcctcttcta gcctttcagt gctaccttca tctctttcag tttttcaaaa    480
```

-continued

```
tcccacagat gtggcacgga gcaaccccaa gtcaccacaa aaacctatcg ttagagtctt    540
cctgcccaac aaacagagga cagtggtacc tgcaaggtgt ggagttacag tccgagacag    600
tctaaagaaa gcactgatga tgagaggtct aatcccagag tgctgtgctg tttacagaat    660
tcaggatgga gagaagaaac caattggttg ggacactgat atttcctggc ttactggaga    720
agaattgcat gtggaagtgt tggagaatgt tccacttaca acacacaact ttgtacgaaa    780
aacgtttttc accttagcat tttgtgactt ttgtcgaaag ctgcttttcc agggtttccg    840
ctgtcaaaca tgtggttata aatttcacca gcgttgtagt acagaagttc cactgatgtg    900
tgttaattat gaccaacttg atttgctgtt tgtctccaag ttctttgaac accacccaat    960
accacaggaa gaggcgtcct tagcagagac tgccctaaca tctggatcat cccettccgc   1020
acccgcctcg gactctattg ggccccaaat tctcaccagt ccgtctcctt caaaatccat   1080
tccaattcca cagcccttcc gaccagcaga tgaagatcat cgaaatcaat ttgggcaacg   1140
agaccgatcc tcatcagctc ccaatgtgca tataaacaca atagaacctg tcaatattga   1200
tgacttgatt agagaccaag gatttcgtgg tgatggagga tcaaccacag gtttgtctgc   1260
tacccccect gcctcattac ctggctcact aactaacgtg aaagccttac agaaatctcc   1320
aggacctcag cgagaaagga agtcatcttc atcctcagaa gacaggaatc gaatgaaaac   1380
acttggtaga cgggactcga gtgatgattg ggagattcct gatgggcaga ttacagtggg   1440
acaaagaatt ggatctggat catttggaac agtctacaag ggaaagtggc atggtgatgt   1500
ggcagtgaaa atgttgaatg tgacagcacc tacacctcag cagttacaag ccttcaaaaa   1560
tgaagtagga gtactcagga aaacacgaca tgtgaatatc ctactcttca tgggctattc   1620
cacaaagcca caactggcta ttgttaccca gtggtgtgag ggctccagct tgtatcacca   1680
tctccatatc attgagacca aatttgagat gatcaaactt atagatattg cacgacagac   1740
tgcacagggc atggattact tacacgccaa gtcaatcatc cacagagacc tcaagagtaa   1800
taatatattt cttcatgaag acctcacagt aaaaataggt gattttggtc tagctacagt   1860
gaaatctcga tggagtgggt cccatcagtt tgaacagttg tctggatcca ttttgtggat   1920
ggcaccagaa gtcatcagaa tgcaagataa aaatccatac agctttcagt cagatgtata   1980
tgcatttgga attgttctgt atgaattgat gactggacag ttaccttatt caaacatcaa   2040
caacagggac cagataattt ttatggtggg acgaggatac ctgtctccag atctcagtaa   2100
ggtacggagt aactgtccaa aagccatgaa gagattaatg gcagagtgcc tcaaaaagaa   2160
aagagatgag agaccactct ttccccaaat tctcgcctct attgagctgc tggcccgctc   2220
attgccaaaa attcaccgca gtgcatcaga accctccttg aatcgggctg gtttccaaac   2280
agaggatttt agtctatatg cttgtgcttc tccaaaaaca cccatccagg caggggggata   2340
tggtgcgttt cctgtccact gaaacaaatg agtgagagag ttcaggagag tagcaacaaa   2400
aggaaaataa atgaacatat gtttgcttat atgttaaatt gaataaaata ctctcttttt   2460
ttttaaggtg aaccaaagaa cacttgtgtg gttaaagact agatataatt tttccccaaa   2520
ctaaaattta tacttaacat tggattttta acatccaagg gttaaaatac atagacattg   2580
ctaaaaattg gcagagcctc ttctagaggc tttactttct gttccgggtt tgtatcattc   2640
acttggttat tttaagtagt aaacttcagt ttctcatgca acttttgttg ccagctatca   2700
catgtccact agggactcca gaagaagacc ctacctatgc ctgtgtttgc aggtgagaag   2760
ttggcagtcg gttagcctgg gttagataag gcaaactgaa cagatctaat ttaggaagtc   2820
agtagaattt aataattcta ttattattct taataatttt tctataacta tttcttttta   2880
```

taacaatttg gaaaatgtgg atgtctttta tttccttgaa gcaataaact aagtttcttt 2940
ttataaaaa 2949

<210> SEQ ID NO 86
<211> LENGTH: 765
<212> TYPE: PRT
<213> ORGANISM: Homo sapiens

<400> SEQUENCE: 86

Ala Ala Leu Ser Gly Gly Gly Gly Gly Gly Ala Glu Pro Gly Gln Ala
1 5 10 15

Leu Phe Asn Gly Asp Met Glu Pro Glu Ala Gly Ala Gly Ala Gly Ala
20 25 30

Ala Ala Ser Ser Ala Ala Asp Pro Ala Ile Pro Glu Glu Val Trp Asn
35 40 45

Ile Lys Gln Met Ile Lys Leu Thr Gln Glu His Ile Glu Ala Leu Leu
50 55 60

Asp Lys Phe Gly Gly Glu His Asn Pro Pro Ser Ile Tyr Leu Glu Ala
65 70 75 80

Tyr Glu Glu Tyr Thr Ser Lys Leu Asp Ala Leu Gln Gln Arg Glu Gln
85 90 95

Gln Leu Leu Glu Ser Leu Gly Asn Gly Thr Asp Phe Ser Val Ser Ser
100 105 110

Ser Ala Ser Met Asp Thr Val Thr Ser Ser Ser Ser Ser Ser Leu Ser
115 120 125

Val Leu Pro Ser Ser Leu Ser Val Phe Gln Asn Pro Thr Asp Val Ala
130 135 140

Arg Ser Asn Pro Lys Ser Pro Gln Lys Pro Ile Val Arg Val Phe Leu
145 150 155 160

Pro Asn Lys Gln Arg Thr Val Val Pro Ala Arg Cys Gly Val Thr Val
165 170 175

Arg Asp Ser Leu Lys Lys Ala Leu Met Met Arg Gly Leu Ile Pro Glu
180 185 190

Cys Cys Ala Val Tyr Arg Ile Gln Asp Gly Glu Lys Lys Pro Ile Gly
195 200 205

Trp Asp Thr Asp Ile Ser Trp Leu Thr Gly Glu Glu Leu His Val Glu
210 215 220

Val Leu Glu Asn Val Pro Leu Thr Thr His Asn Phe Val Arg Lys Thr
225 230 235 240

Phe Phe Thr Leu Ala Phe Cys Asp Phe Cys Arg Lys Leu Leu Phe Gln
245 250 255

Gly Phe Arg Cys Gln Thr Cys Gly Tyr Lys Phe His Gln Arg Cys Ser
260 265 270

Thr Glu Val Pro Leu Met Cys Val Asn Tyr Asp Gln Leu Asp Leu Leu
275 280 285

Phe Val Ser Lys Phe Phe Glu His His Pro Ile Pro Gln Glu Glu Ala
290 295 300

Ser Leu Ala Glu Thr Ala Leu Thr Ser Gly Ser Ser Pro Ser Ala Pro
305 310 315 320

Ala Ser Asp Ser Ile Gly Pro Gln Ile Leu Thr Ser Pro Ser Pro Ser
325 330 335

Lys Ser Ile Pro Ile Pro Gln Pro Phe Arg Pro Ala Asp Glu Asp His
340 345 350

```
Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Gly Asp Gly Gly Ser Thr Thr Gly Leu Ser Ala Thr
385                 390                 395                 400

Pro Pro Ala Ser Leu Pro Gly Ser Leu Thr Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Ile Leu Ala Ser Ile Glu Leu Leu Ala Arg Ser Leu
705                 710                 715                 720

Pro Lys Ile His Arg Ser Ala Ser Glu Pro Ser Leu Asn Arg Ala Gly
                725                 730                 735

Phe Gln Thr Glu Asp Phe Ser Leu Tyr Ala Cys Ala Ser Pro Lys Thr
            740                 745                 750

Pro Ile Gln Ala Gly Gly Tyr Gly Ala Phe Pro Val His
        755                 760                 765
```

<210> SEQ ID NO 87
<211> LENGTH: 3906
<212> TYPE: DNA
<213> ORGANISM: Rattus norvegicus

<400> SEQUENCE: 87
atggcggcgc tgagtggcgg cggtggcagc agcagcggtg gcggtggcgg cggcggcggc 60
ggcggtggtg gcggcggcgg cggcggcgcc gaacagggac aggctctgtt caatggcgac 120
atggagccgg aggccggcgc tggcgccgcg gcctcttcgg ccgcggaccc ggccattcct 180
gaagaggtgt ggaatatcaa gcaaatgatt aagttgacac aggaacatat agaggcccta 240
ttggacaagt ttggtgggga gcataaccca ccgtcaatat acctggaggc ctatgaagag 300
tacaccagca agctagatgc ccttcagcag agagagcagc agctgttgga atccctggtt 360
tttcaaactc ccacagatgt atcacggaac aaccccaagt caccacagaa acctatcgtt 420
cgtgtcttcc tgcccaacaa acagaggaca gtggtgcccg caagatgtgg tgtaacggtc 480
cgagacagtc taaagaaagc actaatgatg aggggtctca tcccagagtg ctgtgctgtt 540
tacagaattc aggacggaga gaagaaacca attggctggg acactgacat ttcctggctt 600
actggagagg agctacatgt tgaagtacta gagaatgttc ctctgacaac ccacaacttc 660
gtacggaaaa ctttttcac cttagcattt tgtgactttt gccgaaagct gcttttccag 720
ggtttccgct gtcaaacatg tggttataag tttcaccagc gttgtagtac agaggttcca 780
ctgatgtgtg ttaattatga ccaacttgat ttgctgtttg tctccaagtt ctttgagcat 840
cacccagtac cacaggagga ggccttctca gcagagacta cccttccatc tggatgctct 900
tccgcacccc cctcagactc tattgggccc caaatcctca ccagtccatc tccttcaaaa 960
tccattccaa ttccacagcc cttccggcca gcagatgaag atcatcgcaa tcagtttggg 1020
caacgagacc gctcctcctc cgctcccaat gttcatataa acacaatcga acctgtcaat 1080
attgatgaaa aattcccaga agtggaatta caggatcaaa gggatttgat tagagaccag 1140
gggtttcgtg gggatggagc ccctttgaac cagctgatgc gctgtcttcg gaaataccaa 1200
tcccggactc ccagcccccct cctccattct gtccccagtg aaatagtgtt tgattttgag 1260
cctggcccag tgttcagagg gtcaaccaca ggcttgtcgg ccaccccacc tgcctcatta 1320
cctggctcac tcactaacgt gaaagcctta cagaaatctc caggacctca gcgggaaagg 1380
aagtcctcct cctcctcctc ctccacggaa gacagaagtc ggatgaaaac acttggtaga 1440
agagattcaa gtgatgattg ggagattcct gatggacaga ttacagtggg acagagaatt 1500
ggatctgggt cctttggaac tgtctacaag ggaaagtggc atggcgacgt ggcagtgaaa 1560
atgctgaatg tgacagcacc cacacctcag cagttacagg ccttcaaaaa cgaagtcgga 1620
gtactcagga aaactcgaca tgtgaacatc ctcctttca tgggctattc tacaaagcca 1680
cagctggcta ttgttacaca gtggtgtgaa ggctccagct tatatcacca tctccacatc 1740
attgagacca aatttgagat gatcaaactt atagatattg cacggcagac tgcacagggc 1800
atggattact tacacgccaa gtcaatcatc cacagagacc tcaagagtaa taatatattt 1860
cttcatgaag acctcacggt aaaaataggt gactttggtt tagccacagt gaagtcccga 1920
tggagtgggt cccatcagtt tgaacagttg tctggatcta ttttgtggat ggcacccgaa 1980
gtaatcagaa tgcaagataa aaacccatat agctttcagt cagacgtgta tgcatttggg 2040
attgttctgt atgaactgat gactggtcag ctaccttatt caaacatcaa caacagggat 2100
cagataattt ttatggtggg acgaggatac ctatctccag atctcagtaa ggtacggagt 2160

```
aactgtccaa aagccatgaa gagattaatg gcagagtgcc tcaaaaagaa aagagacgag   2220
agaccactct ttccccaaat tctcgcctct attgagctgc tggcccgctc attgccaaaa   2280
attcaccgca gtgcatcaga accctccttg aatcgggctg gtttccaaac agaagatttt   2340
agtctgtatg cttgtgcttc tccaaaaaca cccatccaag caggggggata tggagaattt   2400
gcagccttca agtagccact ccatcatggc agcatctact ctttatttct taagtcttgt   2460
gttcatacaa tttgttaaca tcaaaacaca gttctgttcc tcaaattttt tttaaagata   2520
caaaattttc aatgcataag ctcgtgtgga acagaatgga atttcctatt caacaaaaga   2580
gggaagaatg ttttaggaac cagaattctc tgctgcccgt gtttcttctt caacacaaat   2640
atcatgtgca tacaactctg cccattccca agaagaaaga ggagagaccc cgaattctgc   2700
ccttttggtg gtcaggcatg atggaaagaa tttgctgctg cagcttggga aaaattgcta   2760
tggaaagtct gccagtcaac tttgcccttc taaccaccag atccatttgt ggctggtcat   2820
ctgatggggc gatttcaatc accaagcatc gttcttgcct gttgtgggat tatgtcgtgg   2880
agcactttcc ctatccacca ccgttaattt ccgagggatg gagtaaatgc agcataccct   2940
ttgtgtagca cctgtccagt cctcaaccaa tgctatcaca gtgaagctct ttaaatttaa   3000
gtggtgggtg agtgttgagg agagactgcc ttgggggcag agaaaagggg atgctgcatc   3060
ttcttcctca cctccagctc tctcacctcg ggttgccttg cacactgggc tccgcctaac   3120
cactcgggct gggcagtgct ggcacacatt gccgcctttt ctcattgggt ccagcaattg   3180
agcagagggt tgggggattg tttcctccac aatgtagcaa attctcagga aaatacagtc   3240
catatcttcc tctcagctct tccagtcacc aaatacttac gtggctcctt tgtccaggac   3300
ataaaacacc gtggacaaca cctaattaaa agcctacaaa actgcttact gacagttttg   3360
aatgtgagac atttgtgtaa tttaaatgta aggtacaggt cttaatttct tctattaagt   3420
ttcttctatt tttatttaaa cgaagaaaat aattttcagg tttaattgga ataaacgaat   3480
acttcccaaa agactatata ccctgaaaat tatatttttg ttaattgtaa acaactttta   3540
aaaaatggtt attatccttt tctctaccta aaattatggg aaatcttagc ataatgacaa   3600
ttatttatac tttttaaata aatggtactt gctggatcca cactaacatc tttgctaaca   3660
ttcccattgt ttcttccaac ttcactccta cactacatcc tccatcctct ttctagtctt   3720
ttatctataa tatgcaacct aaaataaaag tggtggtgtc tccattcatt cttcttcttc   3780
ctttttttccc caagcctggt cttcaaaagg ttgggtaatt tagtagctga gttccctagg   3840
tagaaataga actattaggg acattggggt tgtaggaaag cgtgaggcct gtcaccagtt   3900
gttctt                                                              3906
```

<210> SEQ ID NO 88
<211> LENGTH: 804
<212> TYPE: PRT
<213> ORGANISM: Rattus norvegicus

<400> SEQUENCE: 88

```
Met Ala Ala Leu Ser Gly Gly Gly Gly Ser Ser Ser Gly Gly Gly Gly
1               5                   10                  15

Gly Gly Gly Gly Gly Gly Gly Gly Gly Gly Gly Gly Gly Ala Glu Gln
            20                  25                  30

Gly Gln Ala Leu Phe Asn Gly Asp Met Glu Pro Glu Ala Gly Ala Gly
        35                  40                  45

Ala Ala Ala Ser Ser Ala Ala Asp Pro Ala Ile Pro Glu Glu Val Trp
    50                  55                  60
```

```
Asn Ile Lys Gln Met Ile Lys Leu Thr Gln Glu His Ile Glu Ala Leu
65                  70                  75                  80

Leu Asp Lys Phe Gly Gly Glu His Asn Pro Pro Ser Ile Tyr Leu Glu
                85                  90                  95

Ala Tyr Glu Glu Tyr Thr Ser Lys Leu Asp Ala Leu Gln Gln Arg Glu
            100                 105                 110

Gln Gln Leu Leu Glu Ser Leu Val Phe Gln Thr Pro Thr Asp Val Ser
        115                 120                 125

Arg Asn Asn Pro Lys Ser Pro Gln Lys Pro Ile Val Arg Val Phe Leu
    130                 135                 140

Pro Asn Lys Gln Arg Thr Val Val Pro Ala Arg Cys Gly Val Thr Val
145                 150                 155                 160

Arg Asp Ser Leu Lys Lys Ala Leu Met Met Arg Gly Leu Ile Pro Glu
                165                 170                 175

Cys Cys Ala Val Tyr Arg Ile Gln Asp Gly Glu Lys Lys Pro Ile Gly
            180                 185                 190

Trp Asp Thr Asp Ile Ser Trp Leu Thr Gly Glu Glu Leu His Val Glu
        195                 200                 205

Val Leu Glu Asn Val Pro Leu Thr Thr His Asn Phe Val Arg Lys Thr
    210                 215                 220

Phe Phe Thr Leu Ala Phe Cys Asp Phe Cys Arg Lys Leu Leu Phe Gln
225                 230                 235                 240

Gly Phe Arg Cys Gln Thr Cys Gly Tyr Lys Phe His Gln Arg Cys Ser
                245                 250                 255

Thr Glu Val Pro Leu Met Cys Val Asn Tyr Asp Gln Leu Asp Leu Leu
            260                 265                 270

Phe Val Ser Lys Phe Phe Glu His His Pro Val Pro Gln Glu Glu Ala
        275                 280                 285

Phe Ser Ala Glu Thr Thr Leu Pro Ser Gly Cys Ser Ser Ala Pro Pro
    290                 295                 300

Ser Asp Ser Ile Gly Pro Gln Ile Leu Thr Ser Pro Ser Pro Ser Lys
305                 310                 315                 320

Ser Ile Pro Ile Pro Gln Pro Phe Arg Pro Ala Asp Glu Asp His Arg
                325                 330                 335

Asn Gln Phe Gly Gln Arg Asp Arg Ser Ser Ser Ala Pro Asn Val His
            340                 345                 350

Ile Asn Thr Ile Glu Pro Val Asn Ile Asp Glu Lys Phe Pro Glu Val
        355                 360                 365

Glu Leu Gln Asp Gln Arg Asp Leu Ile Arg Asp Gln Gly Phe Arg Gly
    370                 375                 380

Asp Gly Ala Pro Leu Asn Gln Leu Met Arg Cys Leu Arg Lys Tyr Gln
385                 390                 395                 400

Ser Arg Thr Pro Ser Pro Leu Leu His Ser Val Pro Ser Glu Ile Val
                405                 410                 415

Phe Asp Phe Glu Pro Gly Pro Val Phe Arg Gly Ser Thr Thr Gly Leu
            420                 425                 430

Ser Ala Thr Pro Pro Ala Ser Leu Pro Gly Ser Leu Thr Asn Val Lys
        435                 440                 445

Ala Leu Gln Lys Ser Pro Gly Pro Gln Arg Glu Arg Lys Ser Ser Ser
    450                 455                 460

Ser Ser Ser Ser Thr Glu Asp Arg Ser Arg Met Lys Thr Leu Gly Arg
465                 470                 475                 480
```

```
Arg Asp Ser Ser Asp Asp Trp Glu Ile Pro Asp Gly Gln Ile Thr Val
                485                 490                 495

Gly Gln Arg Ile Gly Ser Gly Ser Phe Gly Thr Val Tyr Lys Gly Lys
            500                 505                 510

Trp His Gly Asp Val Ala Val Lys Met Leu Asn Val Thr Ala Pro Thr
        515                 520                 525

Pro Gln Gln Leu Gln Ala Phe Lys Asn Glu Val Gly Val Leu Arg Lys
    530                 535                 540

Thr Arg His Val Asn Ile Leu Leu Phe Met Gly Tyr Ser Thr Lys Pro
545                 550                 555                 560

Gln Leu Ala Ile Val Thr Gln Trp Cys Glu Gly Ser Ser Leu Tyr His
                565                 570                 575

His Leu His Ile Ile Glu Thr Lys Phe Glu Met Ile Lys Leu Ile Asp
            580                 585                 590

Ile Ala Arg Gln Thr Ala Gln Gly Met Asp Tyr Leu His Ala Lys Ser
        595                 600                 605

Ile Ile His Arg Asp Leu Lys Ser Asn Asn Ile Phe Leu His Glu Asp
    610                 615                 620

Leu Thr Val Lys Ile Gly Asp Phe Gly Leu Ala Thr Val Lys Ser Arg
625                 630                 635                 640

Trp Ser Gly Ser His Gln Phe Glu Gln Leu Ser Gly Ser Ile Leu Trp
                645                 650                 655

Met Ala Pro Glu Val Ile Arg Met Gln Asp Lys Asn Pro Tyr Ser Phe
            660                 665                 670

Gln Ser Asp Val Tyr Ala Phe Gly Ile Val Leu Tyr Glu Leu Met Thr
        675                 680                 685

Gly Gln Leu Pro Tyr Ser Asn Ile Asn Asn Arg Asp Gln Ile Ile Phe
    690                 695                 700

Met Val Gly Arg Gly Tyr Leu Ser Pro Asp Leu Ser Lys Val Arg Ser
705                 710                 715                 720

Asn Cys Pro Lys Ala Met Lys Arg Leu Met Ala Glu Cys Leu Lys Lys
                725                 730                 735

Lys Arg Asp Glu Arg Pro Leu Phe Pro Gln Ile Leu Ala Ser Ile Glu
            740                 745                 750

Leu Leu Ala Arg Ser Leu Pro Lys Ile His Arg Ser Ala Ser Glu Pro
        755                 760                 765

Ser Leu Asn Arg Ala Gly Phe Gln Thr Glu Asp Phe Ser Leu Tyr Ala
    770                 775                 780

Cys Ala Ser Pro Lys Thr Pro Ile Gln Ala Gly Gly Tyr Gly Glu Phe
785                 790                 795                 800

Ala Ala Phe Lys


<210> SEQ ID NO 89
<211> LENGTH: 9728
<212> TYPE: DNA
<213> ORGANISM: Mus musculus

<400> SEQUENCE: 89

ccctcaggct cggctgcgcc ggggccgccg gcgggttcca gaggtggcct ccgccccggc     60

cgctccgccc acgccccccg cgcctccgcg cccgcctccg cccgccctgc gcctcccttc    120

cccctccccg ccccgcggcg gccgctcggc ccggctcgcg cttcgaagat ggcggcgctg    180

agtggcggcg gtggcagcag cagcggtggc ggcggcggcg gtggcggcgg cggtggcggt    240

ggcgacggcg gcggcggcgc cgagcagggc caggctctgt tcaatggcga catggagccg    300
```

```
gaggccggcg ctggcgccgc ggcctcttcg gctgcggacc cggccattcc tgaagaggta    360
tggaatatca agcaaatgat taagttgaca caggaacata tagaggccct attggacaaa    420
tttggtggag agcataaccc accatcaata tacctggagg cctatgaaga gtacaccagc    480
aagctagatg cccttcagca aagagaacag cagcttttgg aatccctggt ttttcaaact    540
cccacagatg catcacggaa caaccccaag tcaccacaga aacctatcgt tagagtcttc    600
ctgcccaaca aacagaggac agtggtaccc gcaagatgtg gtgttacagt tcgagacagt    660
ctaaagaaag cactgatgat gagaggtctc atcccagaat gctgtgctgt ttacagaatt    720
caggatggag agaagaaacc aattggctgg gacacggaca tttcctggct tactggagag    780
gagttacatg ttgaagtact ggagaatgtc ccacttacaa cacacaactt tgtacggaaa    840
actttttca ccttagcatt ttgtgacttt tgccgaaagc tgcttttcca gggtttccgt    900
tgtcaaacat gtggttataa atttcaccag cgttgtagta cagaggttcc actgatgtgt    960
gtaaattatg accaacttga tttgctgttt gtctccaagt tctttgagca tcacccagta   1020
ccacaggagg aggcctcctt cccagagact gcccttccat ctggatcctc ttccgcaccc   1080
ccctcagact ctactgggcc ccaaatcctc accagtccat ctccttcaaa atccattcca   1140
attccacagc ccttccgacc agcagatgaa gatcatcgca atcagtttgg gcaacgagac   1200
cggtcctcct cagctcccaa tgttcatata aacacaattg agcctgtgaa tatcgatgaa   1260
aaattcccag aagtggaatt acaggatcaa agggatttga ttagagacca ggggtttcgt   1320
ggtgatggag ccccccttgaa ccaactgatg cgctgtcttc ggaaatacca atcccggact   1380
cccagccccc tcctccattc tgtccccagt gaaatagtgt ttgattttga gcctggccca   1440
gtgttcagag ggtcaaccac aggcttgtcc gccaccccgc ctgcctcatt acctggctca   1500
ctcactaacg tgaaagcctt acagaaatct ccaggtcctc agcgggaaag gaagtcatct   1560
tcttcctcat cctcggagga cagaagtcgg atgaaaacac ttggtagaag agattcaagt   1620
gatgactggg agattcctga tggacagatt acagtgggac agagaattgg atctgggtca   1680
tttggaactg tctacaaggg aaagtggcat ggtgatgtgg cagtgaaaat gttgaatgtg   1740
acagcaccca cacctcaaca gctacaggcc ttcaaaaatg aagtaggagt gctcaggaaa   1800
actcgacatg tgaatatcct ccttttcatg ggctattcta caaagccaca actggcaatt   1860
gttacacagt ggtgtgaggg ctccagctta tatcaccatc tccacatcat tgagaccaaa   1920
tttgagatga tcaaacttat agatattgct cggcagactg cacagggcat ggattactta   1980
cacgccaagt caatcatcca cagagacctc aagagtaata atatatttct tcatgaagac   2040
ctcacggtaa aaataggtga ctttggtcta gccacagtga aatctcggtg gagtgggtcc   2100
catcagtttg aacagttgtc tggatctatt ttgtggatgg caccagaagt aatcagaatg   2160
caagataaaa acccgtatag ctttcagtca gacgtgtatg cgtttgggat tgttctgtac   2220
gaactgatga ccggccagct accttattca aacatcaaca acagggatca gataattttt   2280
atggtgggac gaggatacct atctccagat ctcagtaagg tacggagtaa ctgtccaaaa   2340
gccatgaaga gattaatggc agagtgcctc aaaaagaaaa gagacgagag accactcttt   2400
ccccaaattc tcgcctccat tgagctgctg gcccgctcat tgccaaaaat tcaccgcagt   2460
gcatcagaac cttccttgaa tcgggctggt ttccaaacag aagattttag tctgtatgct   2520
tgtgcttctc cgaaaacacc catccaagca gggggatatg gagaatttgc agccttcaag   2580
tagccagtcc atcatggcag catctactct ttatttctta agtcttgtgt tcatacagtt   2640
```

-continued

```
tgttaacatc aaaacacagt tctgttcctc aaaaaatttt ttaaagatac aaaattttca   2700
atgcataagt tcatgtggaa cagaatggaa tttcctattc aacaaaagag ggaagaatgt   2760
tttaggaacc agaattctct gctgcccgtg tttcttcttc aacataacta tcacgtgcat   2820
acaagtctgc ccattcccaa gaagaaagag gagagaccct gaattctgcc cttttggtgg   2880
tcaggcatga tggaaagaat ttgctgctgc agcttgggaa aattgctatg gaaagtctgc   2940
cagtcgactt tgcccttcta accaccagat cagcctgtgg ctggtcatct gatggggcga   3000
tttccatcac caagcatcgt tcttgcctat tctgggatta tgttgtggag cactttccct   3060
gtccagcacc gttcatttct gagggatgga gtaaatgcag cattcccttg tgtagcgcct   3120
gttcagtcct cagcagctgc tgtcacagcg aagcttttta cagttaagtg gtgggggaga   3180
gttgaggaga gcctgcctcg ggcagagaa aagggggtgc tgcatcttct tcctcacctc   3240
cagctctctc acctcgggtt gccttgctca ctgggctccg cctaaccact caggctgctc   3300
agtgctggca cacattgcct tcttttctca ttgggtccag caattgagga gagggttggg   3360
ggattgtttc ctcctcaatg tagcaaattc tcaggaaaat acagtccata tcttcctctc   3420
agctcttcca gtcaccaaat acttacgtgg ctcctttgtc caggacataa aacaccgtgg   3480
acaacaccta attaaaagcc tacaaaactg cttactgaca gttttgaatg tgagacactt   3540
gtgtaattta aatgtaaggt acaggtttta atttctgagt ttcttctatt tttatttaaa   3600
agaagaaaat aattttcagt tttaattgga ataaatgagt acttcccaca agactatata   3660
ccctgaaaat tatatttttg ttaattgtaa acaactttta aagaataatt attatccttt   3720
tctctaccta aaaattatgg ggaatcttag cataatgaca attatttata ctttttaaat   3780
aaatggtact tgctggatcc acactaacat ctttgctaac aatcccattg tttcttccaa   3840
cttaactcct acactacatc ctacatcctc tttctagtct tttatctata atatgcaacc   3900
taaaataaac gtggtggcgt ctccattcat tctccctctt cctgttttcc ccaagcctgg   3960
tcttcaaaag gttgggtaat cggtccctga gctccctagc tggcaatgca actattaggg   4020
acattggagt tgcaggagag caggaagcct gtccccagct gttcttctag aaccctaaat   4080
cttatctttg cacagatcaa aagtatcacc tcgtcacagt tctccttagc ctttacttac   4140
aggtaatata aataaaaatc accatagtag taaagaaaac aactggatgg attgatgacc   4200
agtacctctc agagccagga atcttgaatc tccaggattt atacgtgcaa atttaaggag   4260
atgtacttag caacttcaag ccaagaactt ccaaaatact agcgaatcta aaataaaatg   4320
gaattttgag ttatttttaa agttcaaatt ataattgata ccactatgta tttaagccta   4380
ctcacagcaa gttagatgga ttttgctaaa ctcattgcca gactgtggtg gtggtggtgg   4440
tagtgtgcac ctttaatcca agcaactcag caatcagaat gaggtaaatc tctgtgaata   4500
caaggcctgc ctagtctgca gcgctagttc caggatagcc agggctacac acacaaaaac   4560
cctctctcaa aaaaaacaaa attaattagt tgataataaa aaataactaa agtatcatca   4620
aaggaaggcc tactggaagt tttatatatt cccagtaaat tgaaaaatat tctgaagtta   4680
ttaaccagtt agcaacaatg tgtttttaag tcttacataa acagagcaaa gtcttcaaat   4740
gtttcagagc tgagaagata attgtgcttg atatgaaaaa tagcctctcc atatgatgtg   4800
ccacattgaa aggcgtcatt accctttttaa atacttctta atgtggcttt gttcccttta   4860
cccaggatta gctagaaaga gctaggtagg cttcggccac agttgcacat ttcgggcctg   4920
ctgaagaatg ggagctttga aggctggcct tggtggagga gcccctcagt gctggagggt   4980
ggggcgtgta cgcagcatgg aagtggtcta gacagagtgc aaagggacag acttctttct   5040
```

```
cattttagta tagggtgatg tctcacttga aatgagaaag tagagttgat attaaacgaa   5100
gctgtgccca gaaaccaggc tcagggtatt gtgagatttt ctttttaaat agagaatata   5160
aaagatagaa ataaatattt aaaccttcct tcttattttc tatcaaatag atttttttta   5220
tcatttgcaa acaacataaa aaaaggtttc ttttgtgggg ttttctttcc ttcttttttt   5280
tttttttttt tttttaagac tgcagataat cttgttgagc tcctcggaaa atacaaggaa   5340
gtccgtgttt gtgcagagcg ctttatgagt aactgtatag acagtgtggc tgcttcactc   5400
atcccagagg gctgcagctg tcggcccatg aagtggctgc agtgcctcgt gagatctgct   5460
ttgttttgtt tggagtgaag tctttgaaag gtttgagtgc aactatatag gactgttttt   5520
aaataagtag tattcctcat gaactttctc attgttaagc tacaggaccc aaactctacc   5580
actaagatat tattaacctc aaaatgtagt ttatagaagg aatttgcaaa tagaatatcc   5640
agttcgtact tatatgcatc ttcaacaaag attctctgtg acttgttgga tttggttcct   5700
gaacagccca tttctgtatt tgaggttagg agggcataat gaggcatcct aaaagacaat   5760
ctgatataaa ctgtatgcta gatgtatgct ggtaggggag aaagcattct gtaaagacat   5820
gatttaagac ttcagctctg tcaaccagaa accttgtaaa tacttcctgt cttggtgcag   5880
ccccgcccct ttgatcacac gatgttgtct tgtgcttgtc agacactgtc agagctgctg   5940
ttcgtccctc tgcagatctc acctgtcccc actgcacacc cacctcctgc ctcttgcaga   6000
cctcagcatc tagctttagt tggaaacagt tcagggttca ggtgacttct taaaaaaaaa   6060
aaaaaaccct acctcctcag aatgaggtaa tgaatagtta tttatttaaa gtatgaagag   6120
tcaggagcgc tcgaacatga aggtgattta agatggttcc tttcgtgtgt attgtagctg   6180
agcacttgtt tttgtcctaa agggcattat acatttaagc agtgattctg tttaaagatg   6240
tttttcttta aaggtgtagc tcagagtatc tgttgttgga attggtgcca gagtctgctt   6300
aatagatttc agaatcctaa gcttaagtca gtcgcatgaa gttaagtagt tatggtaaca   6360
ctttgctagc catgatataa ttctactttt taggagtagg tttggcaaaa ctgtatgcct   6420
tcaaagtgag ttggccacag ctttgtcaca tgcacagata ctcatctgaa gagactgccc   6480
agctaagagg gcggaaggat accctttttt cctacgattc gcttctttgt ccacgttggc   6540
attgttagta ctagtttatc agcaccttga ccagcagatg tcaaccaata agctattttt   6600
aaaaccatag ccagagatgg agaggtcact gtgagtagaa acagcaggac gcttacagga   6660
gtgaaatggt gtagggaggc tctagaaaaa tatcttgaca atttgccaaa tgatcttact   6720
gtgccttcat gatgcaataa aaaagctaac attttagcag aaatcagtga tttacgaaga   6780
gagtggccag tctggtttaa ctcagctggg ataatatttt tagagtgcaa tttagactgc   6840
gaagataaat gcactaaaga gtttatagcc aattcacatt tgaaaaaataa gaaaatggta   6900
aattttcagt gaaatatttt tttaaagcac ataatcccta gtgtagccag aaatatttac   6960
cacatagagc agctaggctg agatacagtc cagtgacatt tctagagaaa ccttttctac   7020
tcccacgggc tcctcaaagc atggaaattt tatacaaaat gtttgacatt ttaagatact   7080
gctgtagttt agttttgaaa tagtatgtgc tgagcagcaa tcatgtacta actcagagag   7140
agaaaacaac aacaaattgt gcatctgatt tgttttcaga gaaatgctgc caacttagat   7200
actgagttct cagagcttca agtgtaaact tgcctcccaa gtcctgtttg caaatgaagt   7260
tggctagtgc tactgactgc tccagcacat gatggaaggc agggggctgt ctctgaagtg   7320
tcttctataa agggacaata gaatagtgag agacctggtc agtgtgtgtc agctggacac   7380
```

-continued

```
tccatgctat gggacttgca tcttctgtcc tcaccatccc caagacattg tgctttcctc   7440
agttgtcctc tagctgtttc actcagacac caagatgaat tactgatgcc agaaggggcc   7500
aaaatggcca gtgtgttttg ggggttgtat cagttgactg gacaataact ttaatagttt   7560
cagatcattt atttttactt ccattttgac agacatttaa atggaaattt agtcctaact   7620
tttgtcattt gaaaggaaaa attaacagtt cctataagat acttttgagg tggaatctga   7680
catcctaatt ttttttcttt tcagtgggtt tgcagcgagg gtcttgtatg cactaggcaa   7740
gggttctacc actaagccac atttcccagg aaataaaatg ttaacagtta aaacatacac   7800
acaaatacac aaacacctta ttaccacttt agtaaagtga gagatgtgcg tcctttgtct   7860
cagtctccac gatttcagct gccccttgta tgaataactc agtctcgcta aactgtttac   7920
ttttatttac ctggtttgac tagttgcagc tatataacca gttgtgcatg aggacaacag   7980
ccagtgtgtt tgttttgttt ttggtttttt gtggtacatt ttttgtaaag aattctgtag   8040
attgaagtgc tctttgaaaa cagaactgag atatatttat tcttgttagc atcaaaaaac   8100
attttgtgca aatgatttgc ttttcctggc aggctgagta ccatatccag cgcccacaat   8160
tgcgggttcc catctaccat gtccacaggg gagacagacg ggaagcacat gaggggtgtg   8220
tttacagagt tgtaggagtt atgtagttct cttgttgcct tggaaatcac tgttgtttta   8280
agactgttga acccgtgtgt ttggctgggc tgtgagttac atgaagaaac tgcaaactag   8340
catatgcaga caaagctcac agactaggcg taaatggagg aaaatggacc aaaataaggc   8400
agggtgacac ataaaccttg ggcttcggag aaaactaagg gtggagatga actataatca   8460
cctgaataca atgtaagagt gcaataagtg tgcttattct aagctgtgaa cttcttttaa   8520
atcattcctt tctaatacat ttatgtatgt tccattgctg actaaaacca gctatgagaa   8580
catatgcctt tttattcatg ttaactacca gtttaagtgg ctaaccttaa tgtcttattt   8640
atcttcattt tgtattagtt tacataccag gtatgtgtgt gtgctgtact cttcttccct   8700
ttatttgaaa acacttttca ctgggtcatc tccttggcca ttccacaaca caactttggt   8760
ttggctttca atgtcacctt atttgatggc ctgtgtccca gtagcagaat ttatggtatt   8820
cccattgctg gctgctcttc cgaccctttg cttctacagc acttgtctct cctaagatag   8880
tcagaaacta actgatcagg ggatggactt caccattcat cgtgtctctt caattctatt   8940
aaatagacca ctcttgggct ttagaccagg aaaaaggaga cagctctagc catctaccaa   9000
gcctcaccct aaaaggtcac ccgtacttct tggtctgagg acaagtctcc actccagtaa   9060
gggagagggg aggaaatgct tcctgtttga aatgcagtga attcctatgg ctcctgtttc   9120
accacccgca cctatggcaa cccatataca ttcctcttgt ctgtaactgc caaaggttgg   9180
gtttatgtca cttcagttcc actcaagcat tgaaaaggtt ctcatggagt ctggggtgtg   9240
cccagtgaaa agatggggac tttttcatta tccacagacc tctctatacc tgctttgcaa   9300
aaattataat ggagtaacta tttttaaagc ttatttttca attcataaga aaaagacatt   9360
tattttcaat caaatggatg atgtctctta tcccttatcc ctcaatgttt gcttgaattt   9420
tgtttgttcc ctatacctac tccctaattc tttagttcct tcctgctcag gtcccttcat   9480
ttgtactttg gagtttttct catgtaaatt tgtataatgg aaaatattgt tcagtttgga   9540
tagaaagcat ggagaaataa ataaaaaaag atagctgaaa atcaaattga agaaatttat   9600
ttctgtgtaa agttatttaa aaactctgta ttatatttaa agaaaaaagc ccaaccccccc  9660
aaaaagtgct atgtaattga tgtgaatatg cgaatactgc tataataaag attgactgca   9720
tggagaaa                                                             9728
```

<210> SEQ ID NO 90
<211> LENGTH: 804
<212> TYPE: PRT
<213> ORGANISM: Mus musculus

<400> SEQUENCE: 90

```
Met Ala Ala Leu Ser Gly Gly Gly Gly Ser Ser Ser Gly Gly Gly Gly
1               5                   10                  15

Gly Gly Gly Gly Gly Gly Gly Gly Gly Asp Gly Gly Gly Gly Ala Glu
            20                  25                  30

Gln Gly Gln Ala Leu Phe Asn Gly Asp Met Glu Pro Glu Ala Gly Ala
        35                  40                  45

Gly Ala Ala Ala Ser Ser Ala Ala Asp Pro Ala Ile Pro Glu Glu Val
    50                  55                  60

Trp Asn Ile Lys Gln Met Ile Lys Leu Thr Gln Glu His Ile Glu Ala
65                  70                  75                  80

Leu Leu Asp Lys Phe Gly Gly Glu His Asn Pro Pro Ser Ile Tyr Leu
                85                  90                  95

Glu Ala Tyr Glu Glu Tyr Thr Ser Lys Leu Asp Ala Leu Gln Gln Arg
            100                 105                 110

Glu Gln Gln Leu Leu Glu Ser Leu Val Phe Gln Thr Pro Thr Asp Ala
        115                 120                 125

Ser Arg Asn Asn Pro Lys Ser Pro Gln Lys Pro Ile Val Arg Val Phe
    130                 135                 140

Leu Pro Asn Lys Gln Arg Thr Val Val Pro Ala Arg Cys Gly Val Thr
145                 150                 155                 160

Val Arg Asp Ser Leu Lys Lys Ala Leu Met Met Arg Gly Leu Ile Pro
                165                 170                 175

Glu Cys Cys Ala Val Tyr Arg Ile Gln Asp Gly Glu Lys Lys Pro Ile
            180                 185                 190

Gly Trp Asp Thr Asp Ile Ser Trp Leu Thr Gly Glu Glu Leu His Val
        195                 200                 205

Glu Val Leu Glu Asn Val Pro Leu Thr Thr His Asn Phe Val Arg Lys
    210                 215                 220

Thr Phe Phe Thr Leu Ala Phe Cys Asp Phe Cys Arg Lys Leu Leu Phe
225                 230                 235                 240

Gln Gly Phe Arg Cys Gln Thr Cys Gly Tyr Lys Phe His Gln Arg Cys
                245                 250                 255

Ser Thr Glu Val Pro Leu Met Cys Val Asn Tyr Asp Gln Leu Asp Leu
            260                 265                 270

Leu Phe Val Ser Lys Phe Phe Glu His His Pro Val Pro Gln Glu Glu
        275                 280                 285

Ala Ser Phe Pro Glu Thr Ala Leu Pro Ser Gly Ser Ser Ser Ala Pro
    290                 295                 300

Pro Ser Asp Ser Thr Gly Pro Gln Ile Leu Thr Ser Pro Ser Pro Ser
305                 310                 315                 320

Lys Ser Ile Pro Ile Pro Gln Pro Phe Arg Pro Ala Asp Glu Asp His
                325                 330                 335

Arg Asn Gln Phe Gly Gln Arg Asp Arg Ser Ser Ser Ala Pro Asn Val
            340                 345                 350

His Ile Asn Thr Ile Glu Pro Val Asn Ile Asp Glu Lys Phe Pro Glu
        355                 360                 365

Val Glu Leu Gln Asp Gln Arg Asp Leu Ile Arg Asp Gln Gly Phe Arg
```

-continued

```
    370                 375                 380

Gly Asp Gly Ala Pro Leu Asn Gln Leu Met Arg Cys Leu Arg Lys Tyr
385                 390                 395                 400

Gln Ser Arg Thr Pro Ser Pro Leu Leu His Ser Val Pro Ser Glu Ile
                405                 410                 415

Val Phe Asp Phe Glu Pro Gly Pro Val Phe Arg Gly Ser Thr Thr Gly
            420                 425                 430

Leu Ser Ala Thr Pro Pro Ala Ser Leu Pro Gly Ser Leu Thr Asn Val
        435                 440                 445

Lys Ala Leu Gln Lys Ser Pro Gly Pro Gln Arg Glu Arg Lys Ser Ser
    450                 455                 460

Ser Ser Ser Ser Ser Glu Asp Arg Ser Arg Met Lys Thr Leu Gly Arg
465                 470                 475                 480

Arg Asp Ser Ser Asp Asp Trp Glu Ile Pro Asp Gly Gln Ile Thr Val
                485                 490                 495

Gly Gln Arg Ile Gly Ser Gly Ser Phe Gly Thr Val Tyr Lys Gly Lys
            500                 505                 510

Trp His Gly Asp Val Ala Val Lys Met Leu Asn Val Thr Ala Pro Thr
        515                 520                 525

Pro Gln Gln Leu Gln Ala Phe Lys Asn Glu Val Gly Val Leu Arg Lys
    530                 535                 540

Thr Arg His Val Asn Ile Leu Leu Phe Met Gly Tyr Ser Thr Lys Pro
545                 550                 555                 560

Gln Leu Ala Ile Val Thr Gln Trp Cys Glu Gly Ser Ser Leu Tyr His
                565                 570                 575

His Leu His Ile Ile Glu Thr Lys Phe Glu Met Ile Lys Leu Ile Asp
            580                 585                 590

Ile Ala Arg Gln Thr Ala Gln Gly Met Asp Tyr Leu His Ala Lys Ser
        595                 600                 605

Ile Ile His Arg Asp Leu Lys Ser Asn Asn Ile Phe Leu His Glu Asp
    610                 615                 620

Leu Thr Val Lys Ile Gly Asp Phe Gly Leu Ala Thr Val Lys Ser Arg
625                 630                 635                 640

Trp Ser Gly Ser His Gln Phe Glu Gln Leu Ser Gly Ser Ile Leu Trp
                645                 650                 655

Met Ala Pro Glu Val Ile Arg Met Gln Asp Lys Asn Pro Tyr Ser Phe
            660                 665                 670

Gln Ser Asp Val Tyr Ala Phe Gly Ile Val Leu Tyr Glu Leu Met Thr
        675                 680                 685

Gly Gln Leu Pro Tyr Ser Asn Ile Asn Asn Arg Asp Gln Ile Ile Phe
    690                 695                 700

Met Val Gly Arg Gly Tyr Leu Ser Pro Asp Leu Ser Lys Val Arg Ser
705                 710                 715                 720

Asn Cys Pro Lys Ala Met Lys Arg Leu Met Ala Glu Cys Leu Lys Lys
                725                 730                 735

Lys Arg Asp Glu Arg Pro Leu Phe Pro Gln Ile Leu Ala Ser Ile Glu
            740                 745                 750

Leu Leu Ala Arg Ser Leu Pro Lys Ile His Arg Ser Ala Ser Glu Pro
        755                 760                 765

Ser Leu Asn Arg Ala Gly Phe Gln Thr Glu Asp Phe Ser Leu Tyr Ala
    770                 775                 780

Cys Ala Ser Pro Lys Thr Pro Ile Gln Ala Gly Gly Tyr Gly Glu Phe
785                 790                 795                 800
```

Ala Ala Phe Lys

<210> SEQ ID NO 91
<211> LENGTH: 2232
<212> TYPE: DNA
<213> ORGANISM: Oryctolagus cuniculus

<400> SEQUENCE: 91
atggggaatg tgtggaatat caaacaaatg attaagttga cacaggagca tatagaggcc 60
ctattggaca aatttggtgg ggagcataat ccaccatcaa tatatctgga ggcctacgaa 120
gaatacacca gcaagctaga tgccctccaa caaagagaac agcagttatt ggaatcccta 180
gtttttcaaa atcccacaga tgtgtcacgg agcaacccca agtcaccaca aaaacctatt 240
gttagagtct tcctgcccaa caaacagagg acagtggtac ctgcaagatg tggagttacg 300
gttcgagaca gtctaaagaa agcgctgatg atgagaggtc tgatcccaga atgctgtgct 360
gtttacagaa ttcaggatgg agagaagaag ccaattggct gggacactga tatttcctgg 420
ctcactggag aagagctgca tgtggaagtg ttagagaatg tcccactcac cacacataac 480
tttgtacgga aaactttttt caccttagca ttttgtgact tctgtagaaa gctgcttttc 540
cagggtttcc gctgtcaaac atgtggctac aaatttcacc agcgttgtag tacggaagtt 600
ccactgatgt gtgttaatta tgaccaactt gatttgctgt ttgtctccaa gttctttgaa 660
caccacccag taccacagga ggaggcctcc ttagcagaga ctgccctcac atctgggtca 720
tcgccttccg cacctccctc agactctatt gggcaccaaa ttctcaccag tccgtcccct 780
tcaaaatcca ttccgattcc acagtccttc cgaccagcag atgaagatca tcgaaatcag 840
tttgggcaac gagaccggtc ttcatcagcg cctaatgttc acattaacac aatagaacct 900
gtcaatattg atgaaaaatt cccagaagtg gaattacagg atcaaaggga cttgattaga 960
gaccaagggt ttcgtggtga tggagcccct ttgaaccagc tgatgcgctg tcttcggaaa 1020
taccaatccc ggactcccag tcccctccta ccttctgtcc ccagtgacat agtgtttgat 1080
tttgagcctg gcccagtgtt cagaggatcg accacgggtt tgtctgccac tccccctgcc 1140
tcattacctg gctcactcac tagtgtgaaa gctgtacaga gatccccagg acctcagcga 1200
gagaggaagt cgtcttcctc ctcagaagac aggaatcgaa tgaaaactct tggtagacgg 1260
gattcaagtg atgattggga gattcctgat gggcagatca ccgtgggaca gagaattgga 1320
tctggatcat ttggaaccgt ctacaaggga aaatggcacg gtgatgtggc agtaaaaatg 1380
ttgaatgtga cagcacctac acctcagcag ttacaggcct tcaaaaatga agtaggagta 1440
ctcaggaaaa cacgacatgt gaatatccta cttttcatgg gctattccac aaagccacag 1500
ctggctattg ttacccagtg gtgtgagggc tccagtttat atcaccatct ccacatcatt 1560
gagaccaaat tcgagatgat caaacttata gatattgcac ggcagactgc acagggcatg 1620
gattacttac acgccaagtc aatcatccac agagacctca agagtaataa tatatttctt 1680
catgaagacc tcacagtaaa aataggtgat tttggtctag ccacagtgaa atctcgatgg 1740
agtgggtccc atcagtttga acaattgtct ggatccattt tgtggatggc accagaagta 1800
atcagaatgc aagacaaaaa cccatatagc tttcagtcag atgtatatgc atttgggatt 1860
gttctgtatg aattgatgac tggccagtta ccttactcaa acatcaacaa cagggaccag 1920
atcattttta tggtgggacg tggctacctg tctccagacc tcagtaaggt acggagtaac 1980
tgtccgaaag ccatgaagag attaatggca gagtgcctca aaaagaaaag agatgagaga 2040
ccactctttc cccaaattct cgcctccatt gagctgctgg cccgctcatt gccaaaaatc 2100
caccgcagtg catcagaacc ctccttgaat cgggctggtt tccagacaga ggattttagt 2160
ctatatgctt gtgcttctcc aaaaacaccc atccaggcag ggggatatgg agaatttgca 2220
gccttcaagt ag 2232

<210> SEQ ID NO 92
<211> LENGTH: 743
<212> TYPE: PRT
<213> ORGANISM: Oryctolagus cuniculus

<400> SEQUENCE: 92

Met Gly Asn Val Trp Asn Ile Lys Gln Met Ile Lys Leu Thr Gln Glu
1 5 10 15

His Ile Glu Ala Leu Leu Asp Lys Phe Gly Gly Glu His Asn Pro Pro
20 25 30

Ser Ile Tyr Leu Glu Ala Tyr Glu Glu Tyr Thr Ser Lys Leu Asp Ala
35 40 45

Leu Gln Gln Arg Glu Gln Gln Leu Leu Glu Ser Leu Val Phe Gln Asn
50 55 60

Pro Thr Asp Val Ser Arg Ser Asn Pro Lys Ser Pro Gln Lys Pro Ile
65 70 75 80

Val Arg Val Phe Leu Pro Asn Lys Gln Arg Thr Val Val Pro Ala Arg
85 90 95

Cys Gly Val Thr Val Arg Asp Ser Leu Lys Lys Ala Leu Met Met Arg
100 105 110

Gly Leu Ile Pro Glu Cys Cys Ala Val Tyr Arg Ile Gln Asp Gly Glu
115 120 125

Lys Lys Pro Ile Gly Trp Asp Thr Asp Ile Ser Trp Leu Thr Gly Glu
130 135 140

Glu Leu His Val Glu Val Leu Glu Asn Val Pro Leu Thr Thr His Asn
145 150 155 160

Phe Val Arg Lys Thr Phe Phe Thr Leu Ala Phe Cys Asp Phe Cys Arg
165 170 175

Lys Leu Leu Phe Gln Gly Phe Arg Cys Gln Thr Cys Gly Tyr Lys Phe
180 185 190

His Gln Arg Cys Ser Thr Glu Val Pro Leu Met Cys Val Asn Tyr Asp
195 200 205

Gln Leu Asp Leu Leu Phe Val Ser Lys Phe Phe Glu His His Pro Val
210 215 220

Pro Gln Glu Glu Ala Ser Leu Ala Glu Thr Ala Leu Thr Ser Gly Ser
225 230 235 240

Ser Pro Ser Ala Pro Pro Ser Asp Ser Ile Gly His Gln Ile Leu Thr
245 250 255

Ser Pro Ser Pro Ser Lys Ser Ile Pro Ile Pro Gln Ser Phe Arg Pro
260 265 270

Ala Asp Glu Asp His Arg Asn Gln Phe Gly Gln Arg Asp Arg Ser Ser
275 280 285

Ser Ala Pro Asn Val His Ile Asn Thr Ile Glu Pro Val Asn Ile Asp
290 295 300

Glu Lys Phe Pro Glu Val Glu Leu Gln Asp Gln Arg Asp Leu Ile Arg
305 310 315 320

Asp Gln Gly Phe Arg Gly Asp Gly Ala Pro Leu Asn Gln Leu Met Arg
325 330 335

```
Cys Leu Arg Lys Tyr Gln Ser Arg Thr Pro Ser Pro Leu Leu Pro Ser
            340                 345                 350

Val Pro Ser Asp Ile Val Phe Asp Phe Glu Pro Gly Pro Val Phe Arg
        355                 360                 365

Gly Ser Thr Thr Gly Leu Ser Ala Thr Pro Pro Ala Ser Leu Pro Gly
    370                 375                 380

Ser Leu Thr Ser Val Lys Ala Val Gln Arg Ser Pro Gly Pro Gln Arg
385                 390                 395                 400

Glu Arg Lys Ser Ser Ser Ser Ser Glu Asp Arg Asn Arg Met Lys Thr
                405                 410                 415

Leu Gly Arg Arg Asp Ser Ser Asp Asp Trp Glu Ile Pro Asp Gly Gln
            420                 425                 430

Ile Thr Val Gly Gln Arg Ile Gly Ser Gly Ser Phe Gly Thr Val Tyr
        435                 440                 445

Lys Gly Lys Trp His Gly Asp Val Ala Val Lys Met Leu Asn Val Thr
    450                 455                 460

Ala Pro Thr Pro Gln Gln Leu Gln Ala Phe Lys Asn Glu Val Gly Val
465                 470                 475                 480

Leu Arg Lys Thr Arg His Val Asn Ile Leu Leu Phe Met Gly Tyr Ser
                485                 490                 495

Thr Lys Pro Gln Leu Ala Ile Val Thr Gln Trp Cys Glu Gly Ser Ser
            500                 505                 510

Leu Tyr His His Leu His Ile Ile Glu Thr Lys Phe Glu Met Ile Lys
        515                 520                 525

Leu Ile Asp Ile Ala Arg Gln Thr Ala Gln Gly Met Asp Tyr Leu His
    530                 535                 540

Ala Lys Ser Ile Ile His Arg Asp Leu Lys Ser Asn Asn Ile Phe Leu
545                 550                 555                 560

His Glu Asp Leu Thr Val Lys Ile Gly Asp Phe Gly Leu Ala Thr Val
                565                 570                 575

Lys Ser Arg Trp Ser Gly Ser His Gln Phe Glu Gln Leu Ser Gly Ser
            580                 585                 590

Ile Leu Trp Met Ala Pro Glu Val Ile Arg Met Gln Asp Lys Asn Pro
        595                 600                 605

Tyr Ser Phe Gln Ser Asp Val Tyr Ala Phe Gly Ile Val Leu Tyr Glu
    610                 615                 620

Leu Met Thr Gly Gln Leu Pro Tyr Ser Asn Ile Asn Asn Arg Asp Gln
625                 630                 635                 640

Ile Ile Phe Met Val Gly Arg Gly Tyr Leu Ser Pro Asp Leu Ser Lys
                645                 650                 655

Val Arg Ser Asn Cys Pro Lys Ala Met Lys Arg Leu Met Ala Glu Cys
            660                 665                 670

Leu Lys Lys Lys Arg Asp Glu Arg Pro Leu Phe Pro Gln Ile Leu Ala
        675                 680                 685

Ser Ile Glu Leu Leu Ala Arg Ser Leu Pro Lys Ile His Arg Ser Ala
    690                 695                 700

Ser Glu Pro Ser Leu Asn Arg Ala Gly Phe Gln Thr Glu Asp Phe Ser
705                 710                 715                 720

Leu Tyr Ala Cys Ala Ser Pro Lys Thr Pro Ile Gln Ala Gly Gly Tyr
                725                 730                 735

Gly Glu Phe Ala Ala Phe Lys
            740
```

<210> SEQ ID NO 93
<211> LENGTH: 2186
<212> TYPE: DNA
<213> ORGANISM: Cavia porcellus

<400> SEQUENCE: 93
atggcggcgc tcagcggcgg cggtggcgcg gagcagggcc aggctctgtt caacggggac 60
atggagctcg aggccggcgc cggcgccgca gcctcttcgg ctgcagaccc tgccattccc 120
gaggaggtat ggaatatcaa acaaatgatt aagttgacgc aggaacacat agaggcccta 180
ttggacaaat ttggtggaga gcataatcca ccatcaatat acctggaggc ctatgaagaa 240
tacaccagca aactagatgc cctccaacaa agagaacagc agttactgga atccctcggg 300
aatggaactg atttttctgt ttctagctct gcatcactgg acaccgttac atcttcttct 360
tcttctagcc tttcagtact accttcatct ctttcagttt ttcaaaatcc tacagatgtg 420
tcacggagca accccaaatc accacaaaaa cctattgtta gagtcttcct gcccaacaaa 480
cagaggacag tggtacctgc aaggtgtgga gttacagtcc gagacagtct gaagaaagca 540
ctcatgatga gaggtcttat cccagagtgc tgtgctgtgt acagaattca ggatggagaa 600
aagaaaccaa ttggctggga cactgacatt tcctggctta ctggggaaga attacatgta 660
gaagtattgg agaatgttcc acttacaaca cacaattttg tatgtatctt tatatttttt 720
ttgctgtttg tctccaagtt ctttgaacac cacccaatac cacaggagga ggcttcctta 780
gcagagacca cccttacatc tggatcatcc ccttctgcac ccccctcaga gtccattggg 840
cccccaattc tcaccagccc atctccttca aaatccattc caattccaca gcctttccgg 900
ccaggagagg aagatcatcg aaatcaattt gggcagcgag accggtcctc atctgctccc 960
aatgtgcata taaacacaat agaacctgtc aatattgatg atttgattag agaccaaggg 1020
tttcgtagtg atggaggatc aactacaggt ttgtctgcca ccccacctgc ctcattacct 1080
ggctcactca ctaatgtgaa agccttacag aaatctccag gacctcagcg agaaaggaag 1140
tcatcttcat cctcagaaga cagaaatcga atgaaaacgc ttggtagacg ggactcaagt 1200
gatgattggg agattcctga tgggcagatt acagtgggac aaagaattgg atctgggtca 1260
tttggaacag tctacaaggg gaagtggcat ggtgacgtgg cagtgaaaat gttgaatgtg 1320
acagcaccca cacctcaaca gttacaggcc ttcaaaaatg aagtaggagt actcaggaaa 1380
acacgacatg tgaatatcct actcttcatg ggctattcca caaagccaca gctagctatt 1440
gttacccagt ggtgtgaggg ctccagctta taccaccatc tccacatcat cgagaccaaa 1500
tttgagatga tcaaacttat agatattgca cgacagactg cccagggcat ggattactta 1560
cacgccaagt caatcatcca cagagacctc aagagtaata atatatttct tcacgaagac 1620
ctcacggtta aaataggtga ttttggtcta gccacagtga aatctcgatg gagtgggtcc 1680
catcagtttg aacagttgtc tggatccatt ttgtggatgg caccagaagt aatcagaatg 1740
cgagataaaa acccatacag ttttcagtcc gatgtatatg catttgggat tgttctatat 1800
gaattgatga ctgggcagtt accctattca aatatcaaca acagggacca gataattttt 1860
atggtgggac gaggatatct atctccagat ctcagcaagg tacggagtaa ctgtccaaaa 1920
gccatgaaga ggttaatggc ggagtgcctc aaaaagaaaa gagatgagag accactcttt 1980
ccccaaattc tcgcctctat tgagctgctg gcccgctcat tgccaaaaat tcaccgcagt 2040
gcatcagaac cctccttgaa tcgggctggt ttccaaacag aggattttag tctctatgct 2100
tgtgcttctc caaaaacacc catccaggca gggggatatg gtgcgtttcc tgtccactga 2160

-continued tgcaaattaa atgagtgaga aataaa 2186

<210> SEQ ID NO 94
<211> LENGTH: 719
<212> TYPE: PRT
<213> ORGANISM: Cavia porcellus

<400> SEQUENCE: 94

Met Ala Ala Leu Ser Gly Gly Gly Gly Ala Glu Gln Gly Gln Ala Leu
1 5 10 15

Phe Asn Gly Asp Met Glu Leu Glu Ala Gly Ala Gly Ala Ala Ala Ser
20 25 30

Ser Ala Ala Asp Pro Ala Ile Pro Glu Glu Val Trp Asn Ile Lys Gln
35 40 45

Met Ile Lys Leu Thr Gln Glu His Ile Glu Ala Leu Leu Asp Lys Phe
50 55 60

Gly Gly Glu His Asn Pro Pro Ser Ile Tyr Leu Glu Ala Tyr Glu Glu
65 70 75 80

Tyr Thr Ser Lys Leu Asp Ala Leu Gln Gln Arg Glu Gln Gln Leu Leu
85 90 95

Glu Ser Leu Gly Asn Gly Thr Asp Phe Ser Val Ser Ser Ser Ala Ser
100 105 110

Leu Asp Thr Val Thr Ser Ser Ser Ser Ser Ser Leu Ser Val Leu Pro
115 120 125

Ser Ser Leu Ser Val Phe Gln Asn Pro Thr Asp Val Ser Arg Ser Asn
130 135 140

Pro Lys Ser Pro Gln Lys Pro Ile Val Arg Val Phe Leu Pro Asn Lys
145 150 155 160

Gln Arg Thr Val Val Pro Ala Arg Cys Gly Val Thr Val Arg Asp Ser
165 170 175

Leu Lys Lys Ala Leu Met Met Arg Gly Leu Ile Pro Glu Cys Cys Ala
180 185 190

Val Tyr Arg Ile Gln Asp Gly Glu Lys Lys Pro Ile Gly Trp Asp Thr
195 200 205

Asp Ile Ser Trp Leu Thr Gly Glu Glu Leu His Val Glu Val Leu Glu
210 215 220

Asn Val Pro Leu Thr Thr His Asn Phe Val Cys Ile Phe Ile Phe Phe
225 230 235 240

Leu Leu Phe Val Ser Lys Phe Phe Glu His His Pro Ile Pro Gln Glu
245 250 255

Glu Ala Ser Leu Ala Glu Thr Thr Leu Thr Ser Gly Ser Ser Pro Ser
260 265 270

Ala Pro Pro Ser Glu Ser Ile Gly Pro Pro Ile Leu Thr Ser Pro Ser
275 280 285

Pro Ser Lys Ser Ile Pro Ile Pro Gln Pro Phe Arg Pro Gly Glu Glu
290 295 300

Asp His Arg Asn Gln Phe Gly Gln Arg Asp Arg Ser Ser Ser Ala Pro
305 310 315 320

Asn Val His Ile Asn Thr Ile Glu Pro Val Asn Ile Asp Asp Leu Ile
325 330 335

Arg Asp Gln Gly Phe Arg Ser Asp Gly Gly Ser Thr Thr Gly Leu Ser
340 345 350

Ala Thr Pro Pro Ala Ser Leu Pro Gly Ser Leu Thr Asn Val Lys Ala
355 360 365

-continued

```
Leu Gln Lys Ser Pro Gly Pro Gln Arg Glu Arg Lys Ser Ser Ser Ser
    370                 375                 380

Ser Glu Asp Arg Asn Arg Met Lys Thr Leu Gly Arg Arg Asp Ser Ser
385                 390                 395                 400

Asp Asp Trp Glu Ile Pro Asp Gly Gln Ile Thr Val Gly Gln Arg Ile
                405                 410                 415

Gly Ser Gly Ser Phe Gly Thr Val Tyr Lys Gly Lys Trp His Gly Asp
            420                 425                 430

Val Ala Val Lys Met Leu Asn Val Thr Ala Pro Thr Pro Gln Gln Leu
        435                 440                 445

Gln Ala Phe Lys Asn Glu Val Gly Val Leu Arg Lys Thr Arg His Val
    450                 455                 460

Asn Ile Leu Leu Phe Met Gly Tyr Ser Thr Lys Pro Gln Leu Ala Ile
465                 470                 475                 480

Val Thr Gln Trp Cys Glu Gly Ser Ser Leu Tyr His His Leu His Ile
                485                 490                 495

Ile Glu Thr Lys Phe Glu Met Ile Lys Leu Ile Asp Ile Ala Arg Gln
            500                 505                 510

Thr Ala Gln Gly Met Asp Tyr Leu His Ala Lys Ser Ile Ile His Arg
        515                 520                 525

Asp Leu Lys Ser Asn Asn Ile Phe Leu His Glu Asp Leu Thr Val Lys
    530                 535                 540

Ile Gly Asp Phe Gly Leu Ala Thr Val Lys Ser Arg Trp Ser Gly Ser
545                 550                 555                 560

His Gln Phe Glu Gln Leu Ser Gly Ser Ile Leu Trp Met Ala Pro Glu
                565                 570                 575

Val Ile Arg Met Arg Asp Lys Asn Pro Tyr Ser Phe Gln Ser Asp Val
            580                 585                 590

Tyr Ala Phe Gly Ile Val Leu Tyr Glu Leu Met Thr Gly Gln Leu Pro
        595                 600                 605

Tyr Ser Asn Ile Asn Asn Arg Asp Gln Ile Ile Phe Met Val Gly Arg
    610                 615                 620

Gly Tyr Leu Ser Pro Asp Leu Ser Lys Val Arg Ser Asn Cys Pro Lys
625                 630                 635                 640

Ala Met Lys Arg Leu Met Ala Glu Cys Leu Lys Lys Lys Arg Asp Glu
                645                 650                 655

Arg Pro Leu Phe Pro Gln Ile Leu Ala Ser Ile Glu Leu Leu Ala Arg
            660                 665                 670

Ser Leu Pro Lys Ile His Arg Ser Ala Ser Glu Pro Ser Leu Asn Arg
        675                 680                 685

Ala Gly Phe Gln Thr Glu Asp Phe Ser Leu Tyr Ala Cys Ala Ser Pro
    690                 695                 700

Lys Thr Pro Ile Gln Ala Gly Gly Tyr Gly Ala Phe Pro Val His
705                 710                 715
```

<210> SEQ ID NO 95
<211> LENGTH: 3229
<212> TYPE: DNA
<213> ORGANISM: Canis lupus

<400> SEQUENCE: 95

```
gtaatgctgg attttcatgg aataagtttg acctgtgctg cagtggcctc cagcaaggta     60

cccgcaagat gtggagttac agtccgggac agtctaaaga aagctctgat gatgagaggt    120

ctaatcccag agtgctgtgc tgtttacaga attcaggatg gagagaagaa accgattggc    180
```

```
tgggacactg atatttcctg gctcactgga gaggaattgc atgtagaagt gttggaaaat    240
gttccgctta ccacacacaa ctttgtacgg aaaacttttt tcaccttagc attttgtgac    300
ttttgtcgaa agctgctttt ccagggtttt cgctgtcaaa catgtggtta taaatttcac    360
cagcgttgta gtacagaggt tccactgatg tgtgttaatt atgaccaact tgatttgctg    420
tttgtctcca agttctttga acaccaccca ataccacagg aggaggcctc catagcagag    480
actgccctta cgtctggatc atccccttct gctccccccct ccgattctcc tgggccccca    540
attctgacca gtccgtctcc ttcaaaatcc attccaattc cacagccttt ccgaccagca    600
gatgaagatc atcgaaatca gtttggacaa cgagaccggt cctcatcagc tccaaatgtg    660
catataaaca caatagaacc cgtcaacatt gatgacttga ttagagacca agggtttcgt    720
agtgatggag gatcaaccac aggtttgtct gccaccccccc ctgcctcatt gcctggctca    780
ctcactaatg taaaagcatt acagaaatct ccaggacctc agcgggaaag aaaatcatct    840
tcatcctcag aagataggaa tcgaatgaaa acacttggta gacgggattc aagtgatgat    900
tgggagatac ctgatgggca gatcacagtg ggacagagaa ttggatccgg gtcatttggg    960
acagtctaca agggaaagtg gcatggtgac gtggcagtga aaatgttgaa tgtgacagca   1020
cccacacctc agcagttaca ggccttcaaa aatgaagtag gagtactcag gaaaactcga   1080
catgtgaata tcctactctt tatgggctat tcaacaaagc cccaactggc tattgttacc   1140
cagtggtgtg agggctccag cttatatcac catctccaca tcattgagac caaatttgag   1200
atgataaagc ttatagatat tgcacggcag actgcacagg gcatggatta cttacacgcc   1260
aagtcaatca tccacagaga cctcaagagt aataatattt ttcttcatga agacctcaca   1320
gtaaaaatag gtgattttgg tctagccaca gtgaaatctc gatggagtgg gtcccatcag   1380
tttgaacagt tgtctggatc cattttgtgg atggcaccag aagtgatccg aatgcaagac   1440
aaaaacccat atagcttcca gtcagatgta tacgcatttg ggattgttct atatgaattg   1500
atgacagggc agttacctta ttcaaacatc aacaacaggg accagataat tttatggtg   1560
ggacgaggat atctttctcc agatctcagt aaggtacgga gtaactgtcc aaaagccatg   1620
aagagattga tggcagagtg cctaaaaaag aaaagagatg agaggccact ctttccccaa   1680
attctcgcct ctattgagct gctggcccgc tcattgccaa aaattcaccg cagtgcatca   1740
gaaccctcct tgaatcgggc tggcttccaa acagaggatt ttagtctcta tgcttgcgct   1800
tctccaaaaa cacccatcca ggcagggggga tacggagaat ttgcagcctt caagtagcca   1860
caccatcatg gcaacaacta ctcttatttc ttaagtcttg tgttcgtaca atttgttaac   1920
atcaaaacac agttctgttc ctcaaatctt tttttaaaga tacagaattt tcaatgcata   1980
agctggtgtg gaacagaatg gaatttccca tccaacaaaa gagggaagaa tgttttagga   2040
accagaattc tctgctgcca gtgtttcttc ttcaacacaa ataccacgtg catacaagtc   2100
tgcccactcc caggaaggaa gaggagagcc tgagttctga ccttttgatg gtcaggcatg   2160
atggaaagaa actgctgcta cagcttggga gattggctgt ggagagcctg cccgtcagct   2220
ctgcccttct aaccgccaga tgagtgtgtg gctggtcacc tgacagggca gctgcaatcg   2280
ccaagcatcg ttctctttcc tgtcctggga ttttgtcgtg gagctctttc cccctagtca   2340
ccaccggttc atttctgagg gatggaacaa aaatgcagca tggcctttct gtgtggtgca   2400
tgtccggtct ttgacaaatt tttatcaagt gaagctcttg tatttaaatg gagaatgaga   2460
ggcgaggggg ggggatcacg ttttggtgta ggggcaaagg gaatgctgca tctttttcct   2520
```

```
gacccactgg gtttctggcc tttgtttcct tgctcactga gggtgtctgc ctataaccac   2580

gcaggctgga aagtgctggc acacattgcc ttctcttctc actgggtcca gcaatgaaga   2640

caagtgttgg ggattttttt ttttgccctc cacaatgtag caagttctca ggaaaataca   2700

gttaatatct tcctcctaag ctcttccagt catcaagtac ttatgtggct actttgtcca   2760

gggcacaaaa tgccatggcg gtatccaatt aaaagcctac aaaactgctt gataacagtt   2820

ttgaatgtgt gagacattta tgtaatttaa atgtaaggta caagttttaa tttctgagtt   2880

tctctattat atttttatta aaaagaaaat aattttcaga tttaattgaa ttggaataaa   2940

ataatacttc ccaccagaat tatatatcct ggaaaattgt atttttgtta tataaacaac   3000

ttttaaagaa agatcattat ccttttctct acctaaatat ggggagtctt agcataatga   3060

cagatattta taatttttaa attaatggta cttgctggat ccacactaac atctttgcta   3120

atatctcatg ttttcctcca acttactcct acactacatc ctccatcctc tttccagtct   3180

tttatctaga atatgcaacc taaaataaaa atggtggtgt ctccattca              3229
```

```
<210> SEQ ID NO 96
<211> LENGTH: 617
<212> TYPE: PRT
<213> ORGANISM: Canis lupus

<400> SEQUENCE: 96

Met Leu Asp Phe His Gly Ile Ser Leu Thr Cys Ala Ala Val Ala Ser
1               5                   10                  15

Ser Lys Val Pro Ala Arg Cys Gly Val Thr Val Arg Asp Ser Leu Lys
            20                  25                  30

Lys Ala Leu Met Met Arg Gly Leu Ile Pro Glu Cys Cys Ala Val Tyr
        35                  40                  45

Arg Ile Gln Asp Gly Glu Lys Lys Pro Ile Gly Trp Asp Thr Asp Ile
    50                  55                  60

Ser Trp Leu Thr Gly Glu Glu Leu His Val Glu Val Leu Glu Asn Val
65                  70                  75                  80

Pro Leu Thr Thr His Asn Phe Val Arg Lys Thr Phe Phe Thr Leu Ala
                85                  90                  95

Phe Cys Asp Phe Cys Arg Lys Leu Leu Phe Gln Gly Phe Arg Cys Gln
            100                 105                 110

Thr Cys Gly Tyr Lys Phe His Gln Arg Cys Ser Thr Glu Val Pro Leu
        115                 120                 125

Met Cys Val Asn Tyr Asp Gln Leu Asp Leu Leu Phe Val Ser Lys Phe
    130                 135                 140

Phe Glu His His Pro Ile Pro Gln Glu Glu Ala Ser Ile Ala Glu Thr
145                 150                 155                 160

Ala Leu Thr Ser Gly Ser Ser Pro Ser Ala Pro Pro Ser Asp Ser Pro
                165                 170                 175

Gly Pro Pro Ile Leu Thr Ser Pro Ser Pro Ser Lys Ser Ile Pro Ile
            180                 185                 190

Pro Gln Pro Phe Arg Pro Ala Asp Glu Asp His Arg Asn Gln Phe Gly
        195                 200                 205

Gln Arg Asp Arg Ser Ser Ser Ala Pro Asn Val His Ile Asn Thr Ile
    210                 215                 220

Glu Pro Val Asn Ile Asp Asp Leu Ile Arg Asp Gln Gly Phe Arg Ser
225                 230                 235                 240

Asp Gly Gly Ser Thr Thr Gly Leu Ser Ala Thr Pro Pro Ala Ser Leu
                245                 250                 255
```

```
Pro Gly Ser Leu Thr Asn Val Lys Ala Leu Gln Lys Ser Pro Gly Pro
            260                 265                 270

Gln Arg Glu Arg Lys Ser Ser Ser Ser Ser Glu Asp Arg Asn Arg Met
        275                 280                 285

Lys Thr Leu Gly Arg Arg Asp Ser Ser Asp Asp Trp Glu Ile Pro Asp
    290                 295                 300

Gly Gln Ile Thr Val Gly Gln Arg Ile Gly Ser Gly Ser Phe Gly Thr
305                 310                 315                 320

Val Tyr Lys Gly Lys Trp His Gly Asp Val Ala Val Lys Met Leu Asn
                325                 330                 335

Val Thr Ala Pro Thr Pro Gln Gln Leu Gln Ala Phe Lys Asn Glu Val
            340                 345                 350

Gly Val Leu Arg Lys Thr Arg His Val Asn Ile Leu Leu Phe Met Gly
        355                 360                 365

Tyr Ser Thr Lys Pro Gln Leu Ala Ile Val Thr Gln Trp Cys Glu Gly
    370                 375                 380

Ser Ser Leu Tyr His His Leu His Ile Ile Glu Thr Lys Phe Glu Met
385                 390                 395                 400

Ile Lys Leu Ile Asp Ile Ala Arg Gln Thr Ala Gln Gly Met Asp Tyr
                405                 410                 415

Leu His Ala Lys Ser Ile Ile His Arg Asp Leu Lys Ser Asn Asn Ile
            420                 425                 430

Phe Leu His Glu Asp Leu Thr Val Lys Ile Gly Asp Phe Gly Leu Ala
        435                 440                 445

Thr Val Lys Ser Arg Trp Ser Gly Ser His Gln Phe Glu Gln Leu Ser
    450                 455                 460

Gly Ser Ile Leu Trp Met Ala Pro Glu Val Ile Arg Met Gln Asp Lys
465                 470                 475                 480

Asn Pro Tyr Ser Phe Gln Ser Asp Val Tyr Ala Phe Gly Ile Val Leu
                485                 490                 495

Tyr Glu Leu Met Thr Gly Gln Leu Pro Tyr Ser Asn Ile Asn Asn Arg
            500                 505                 510

Asp Gln Ile Ile Phe Met Val Gly Arg Gly Tyr Leu Ser Pro Asp Leu
        515                 520                 525

Ser Lys Val Arg Ser Asn Cys Pro Lys Ala Met Lys Arg Leu Met Ala
    530                 535                 540

Glu Cys Leu Lys Lys Lys Arg Asp Glu Arg Pro Leu Phe Pro Gln Ile
545                 550                 555                 560

Leu Ala Ser Ile Glu Leu Leu Ala Arg Ser Leu Pro Lys Ile His Arg
                565                 570                 575

Ser Ala Ser Glu Pro Ser Leu Asn Arg Ala Gly Phe Gln Thr Glu Asp
            580                 585                 590

Phe Ser Leu Tyr Ala Cys Ala Ser Pro Lys Thr Pro Ile Gln Ala Gly
        595                 600                 605

Gly Tyr Gly Glu Phe Ala Ala Phe Lys
    610                 615
```

<210> SEQ ID NO 97
<211> LENGTH: 1889
<212> TYPE: DNA
<213> ORGANISM: Canis lupus

<400> SEQUENCE: 97

```
ggaatatcaa acaaatgatt aagttgacac aggaacatat agaagcccta ttggacaagt     60
```

-continued

```
ttggtgggga gcataatcca ccatcaatat atctggaggc ctatgaagaa tacaccagca    120
aactagatgc cctccaacag cgagaacaac agttattgga atccctgggg aatggaactg    180
atttttctgt ttctagctct gcatcaacgg acaccgttac atcttcttcc tcttctagcc    240
tttcagtgct accttcatct ctttcagttt ttcaaaatcc cacagatata tcacggagca    300
atcccaagtc accacaaaaa cctatcgtta gagtcttcct gcccaataaa cagaggacgg    360
tggtacccgc aagatgtgga gttacagtcc gggacagtct aaagaaagct ctgatgatga    420
gaggtctaat cccagagtgc tgtgctgttt acagaattca ggatggagag aagaaaccga    480
ttggctggga cactgatatt tcctggctca ctggagagga attgcatgta gaagtgttgg    540
aaaatgttcc gcttaccaca cacaactttg tacggaaaac ttttttcacc ttagcatttt    600
gtgacttttg tcgaaagctg cttttccagg gttttcgctg tcaaacatgt ggttataaat    660
ttcaccagcg ttgtagtaca gaggttccac tgatgtgtgt taattatgac caacttgatt    720
tgctgtttgt ctccaagttc tttgaacacc acccaatacc acaggaggag gcctccatag    780
cagagactgc ccttacgtct ggatcatccc cttctgctcc cccctccgat tctcctgggc    840
cccaattct gaccagtccg tctccttcaa aatccattcc aattccacag cctttccgac     900
cagcagatga agatcatcga aatcagtttg gacaacgaga ccggtcctca tcagctccaa    960
atgtgcatat aaacacaata gaacccgtca acattgatga cttgattaga gaccaagggt   1020
ttcgtagtga tggaggatca accacaggtt tgtctgccac ccccccctgcc tcattgcctg   1080
gctcactcac taatgtaaaa gcattacaga aatctccagg acctcagcgg gaaagaaaat   1140
catcttcatc ctcagaagat aggaatcgaa tgaaaacact tggtagacgg gattcaagtg   1200
atgattggga gatacctgat gggcagatca cagtgggaca gagaattgga tccgggtcat   1260
ttgggacagt ctacaaggga aagtggcatg gtgacgtggc agtgaaaatg ttgaatgtga   1320
cagcacccac acctcagcag ttacaggcct tcaaaaatga agtaggagta ctcaggaaaa   1380
ctcgacatgt gaatatccta ctctttatgg gctattcaac aaagccccaa ctggctattg   1440
ttacccagtg gtgtgagggc tccagcttat atcaccatct ccacatcatt gagaccaaat   1500
ttgagatgat aaagcttata gatattgcac ggcagactgc acagggcatg gattacttac   1560
acgccaagtc aatcatccac agagacctca agagtaataa tatttttctt catgaagacc   1620
tcacagtaaa aataggtgat tttggtctag ccacagtgaa atctcgatgg agtgggtccc   1680
atcagtttga acagttgtct ggatccattt tgtggatggc accagaagtg atccgaatgc   1740
aagacaaaaa cccatatagc ttccagtcag atgtatacgc atttgggatt gttctatatg   1800
aattgatgac agggcagtta ccttattcaa acatcaacaa cagggaccag ctcagatcat   1860
gatcacggtg tcatgagatc aagccccac                                     1889
```

<210> SEQ ID NO 98
<211> LENGTH: 615
<212> TYPE: PRT
<213> ORGANISM: Canis lupus

<400> SEQUENCE: 98

```
Met Ile Lys Leu Thr Gln Glu His Ile Glu Ala Leu Leu Asp Lys Phe
1               5                   10                  15

Gly Gly Glu His Asn Pro Pro Ser Ile Tyr Leu Glu Ala Tyr Glu Glu
            20                  25                  30

Tyr Thr Ser Lys Leu Asp Ala Leu Gln Gln Arg Glu Gln Gln Leu Leu
        35                  40                  45
```

```
Glu Ser Leu Gly Asn Gly Thr Asp Phe Ser Val Ser Ser Ser Ala Ser
    50                  55                  60

Thr Asp Thr Val Thr Ser Ser Ser Ser Ser Ser Leu Ser Val Leu Pro
65                  70                  75                  80

Ser Ser Leu Ser Val Phe Gln Asn Pro Thr Asp Ile Ser Arg Ser Asn
                85                  90                  95

Pro Lys Ser Pro Gln Lys Pro Ile Val Arg Val Phe Leu Pro Asn Lys
            100                 105                 110

Gln Arg Thr Val Val Pro Ala Arg Cys Gly Val Thr Val Arg Asp Ser
        115                 120                 125

Leu Lys Lys Ala Leu Met Met Arg Gly Leu Ile Pro Glu Cys Cys Ala
    130                 135                 140

Val Tyr Arg Ile Gln Asp Gly Glu Lys Lys Pro Ile Gly Trp Asp Thr
145                 150                 155                 160

Asp Ile Ser Trp Leu Thr Gly Glu Glu Leu His Val Glu Val Leu Glu
                165                 170                 175

Asn Val Pro Leu Thr Thr His Asn Phe Val Arg Lys Thr Phe Phe Thr
            180                 185                 190

Leu Ala Phe Cys Asp Phe Cys Arg Lys Leu Leu Phe Gln Gly Phe Arg
        195                 200                 205

Cys Gln Thr Cys Gly Tyr Lys Phe His Gln Arg Cys Ser Thr Glu Val
    210                 215                 220

Pro Leu Met Cys Val Asn Tyr Asp Gln Leu Asp Leu Leu Phe Val Ser
225                 230                 235                 240

Lys Phe Phe Glu His His Pro Ile Pro Gln Glu Glu Ala Ser Ile Ala
                245                 250                 255

Glu Thr Ala Leu Thr Ser Gly Ser Ser Pro Ser Ala Pro Pro Ser Asp
            260                 265                 270

Ser Pro Gly Pro Pro Ile Leu Thr Ser Pro Ser Pro Ser Lys Ser Ile
        275                 280                 285

Pro Ile Pro Gln Pro Phe Arg Pro Ala Asp Glu Asp His Arg Asn Gln
    290                 295                 300

Phe Gly Gln Arg Asp Arg Ser Ser Ser Ala Pro Asn Val His Ile Asn
305                 310                 315                 320

Thr Ile Glu Pro Val Asn Ile Asp Asp Leu Ile Arg Asp Gln Gly Phe
                325                 330                 335

Arg Ser Asp Gly Gly Ser Thr Thr Gly Leu Ser Ala Thr Pro Pro Ala
            340                 345                 350

Ser Leu Pro Gly Ser Leu Thr Asn Val Lys Ala Leu Gln Lys Ser Pro
        355                 360                 365

Gly Pro Gln Arg Glu Arg Lys Ser Ser Ser Ser Ser Glu Asp Arg Asn
    370                 375                 380

Arg Met Lys Thr Leu Gly Arg Arg Asp Ser Ser Asp Asp Trp Glu Ile
385                 390                 395                 400

Pro Asp Gly Gln Ile Thr Val Gly Gln Arg Ile Gly Ser Gly Ser Phe
                405                 410                 415

Gly Thr Val Tyr Lys Gly Lys Trp His Gly Asp Val Ala Val Lys Met
            420                 425                 430

Leu Asn Val Thr Ala Pro Thr Pro Gln Gln Leu Gln Ala Phe Lys Asn
        435                 440                 445

Glu Val Gly Val Leu Arg Lys Thr Arg His Val Asn Ile Leu Leu Phe
    450                 455                 460
```

-continued

```
Met Gly Tyr Ser Thr Lys Pro Gln Leu Ala Ile Val Thr Gln Trp Cys
465                 470                 475                 480

Glu Gly Ser Ser Leu Tyr His His Leu His Ile Ile Glu Thr Lys Phe
                485                 490                 495

Glu Met Ile Lys Leu Ile Asp Ile Ala Arg Gln Thr Ala Gln Gly Met
            500                 505                 510

Asp Tyr Leu His Ala Lys Ser Ile Ile His Arg Asp Leu Lys Ser Asn
        515                 520                 525

Asn Ile Phe Leu His Glu Asp Leu Thr Val Lys Ile Gly Asp Phe Gly
    530                 535                 540

Leu Ala Thr Val Lys Ser Arg Trp Ser Gly Ser His Gln Phe Glu Gln
545                 550                 555                 560

Leu Ser Gly Ser Ile Leu Trp Met Ala Pro Glu Val Ile Arg Met Gln
                565                 570                 575

Asp Lys Asn Pro Tyr Ser Phe Gln Ser Asp Val Tyr Ala Phe Gly Ile
            580                 585                 590

Val Leu Tyr Glu Leu Met Thr Gly Gln Leu Pro Tyr Ser Asn Ile Asn
        595                 600                 605

Asn Arg Asp Gln Leu Arg Ser
    610                 615
```

<210> SEQ ID NO 99
<211> LENGTH: 3521
<212> TYPE: DNA
<213> ORGANISM: Felis catus
<220> FEATURE:
<221> NAME/KEY: misc_feature
<222> LOCATION: (630)..(649)
<223> OTHER INFORMATION: n is a, c, g, or t

<400> SEQUENCE: 99

```
atgcctaacc tcagtctctg ccaccacggc caatttgctc atgtgcccac tgtgtcggca     60
ctgggatatt ttgtgatttg ccttggccat tgtccactgt ccttgacatt gcctgaagga    120
gaaccactga tgctaatgtt gaaggtgacc tttgcaggct ctccactact cataccaaag    180
atgcggcccc ctgataatcc cagagccact gtctgcacat gggcaaaaca ggctacattc    240
tgtgcagact ggggagaaag gttccaagaa cacagtgcca tagttttggg cagagagttt    300
caacacagca tagtgtctat ggcagtatct ggatttggcc gggggaagtg cccaagagga    360
gacagtcagg ctgtgtccta cggccaagga cctgcactta tttttgcatg cagtggttta    420
gcacagggaa gagaacgaag taggaaatcg gagccatgga aacggcagag cggaggaaac    480
gtgcacgcgc gagggtgggc acgaaaggaa agaaccctcc ccagaagact gcgcgagggc    540
gctcctagga ttacgtcacg caccccgcga aaactgaaat gtactgtgtg tggtctttta    600
attgaactat cttccttatg tgcacttaan nnnnnnnnnn nnnnnnnnng cggcggcggc    660
ggtggcgcgg agcagggcca ggctctgttc aacggggaca tggagcccga agccggcgcc    720
gcggcctctt cggctgcgga ccctgccatt cccgaggagg tgtggaatat caaacaaatg    780
attaagttga cacaggaaca tatagaggcc ctattggaca aatttggtgg ggagcataat    840
ccaccatcaa tatatctaga ggcctatgaa gaatacacca gcaagctaga tgccctccaa    900
cagagagaac aacagttatt ggaatccctg gggaatggaa ctgatttttc tgtttctagc    960
tctgcatcaa cagacaccgt tacatcttcc tcctcttcta gcctttcagt gctaccttca   1020
tctctttcag tttttcaaaa ccccacagat gtgtcacgga gcaatcccaa gtcaccacag   1080
aaacctatcg ttagagtctt cctgcctaat aaacagagga cagtggtacc tgcaagatgt   1140
```

```
ggagttacag tccgggacag tctaaagaaa gctctgatga tgagaggtct aatccctgag   1200
tgctgtgctg tttacagaat tcaggatgga gagaagaaac caattggctg ggacactgat   1260
atctcctggc tcaccggaga ggaattgcat gtagaagtgt tggaaaatgt tccacttaca   1320
actcacaact ttgtatgtac ggaaaacgtt ttcaccttag cattttgtga cttttgtcga   1380
aagctgcttt tccaaggttt tcgctgtcaa acgtgtggtt ataaatttca ccagcgttgt   1440
agtacagagg ttccactgat gtgtgttaat tatgaccaac ttgatttgct gtttgtctcc   1500
aagttctttg aacaccaccc aataccacag gaggaggcct ccatagcaga gactgcccta   1560
acgtctggat cgtccccttc tgcccccccc tccgattcta ctgggcccca aattctcacc   1620
agtccgtctc cttcaaaatc cattccaatt ccacagcctt tccgaccagc agatgaagat   1680
catcgaaatc aatttggaca gcgagaccgg tcctcatcag ctccaaatgt gcatataaat   1740
acaatagaac ctgtcaatat tgatgacttg attagagacc aggggtttcg tagtgatgga   1800
ggatcaacca caggcttgtc tgccaccccc cctgcctcat tgccgggctc tctcactaat   1860
gtaaaagcat tacagaaatc tccagggcct cagcgggaaa ggaaatcttc ttcatcctca   1920
gaagatagga atcgaatgaa aacacttggt agaagggatt caagtgatga ttgggagatt   1980
cctgatgggc agatcacagt gggacagaga attggatccg ggtcatttgg gacagtctac   2040
aagggaaagt ggcatggtga tgtggcagtg aaaatgttga atgtgacagc acccacacct   2100
cagcagttac aggccttcaa aaatgaagta ggagtactca ggaaaactcg gcatgtgaac   2160
atcctgctct tcatgggcta ttcaacaaag ccccagctgg ctattgtcac ccagtggtgt   2220
gagggctcca gcttatacca ccatctccac atcatcgaga ccaaattcga gatgatcaag   2280
ctgatagata ttgctcggca gactgcgcag ggcatggatt acttacacgc caagtcaatc   2340
atccacagag acctcaagag taataatatt tttcttcacg aagacctcac agtaaaaata   2400
ggtgattttg gtctagccac agtgaaatct cgatggagtg ggtcccatca gtttgaacag   2460
ttgtctggat ccattttgtg gatggcacca gaagtaattc gaatgcaaga taaaaaccca   2520
tatagctttc agtcagatgt atatgcattt gggattgttc tatatgaatt gatgactgga   2580
cagttacctt attcaaacat caacaacagg gaccagataa tttttatggt gggacgagga   2640
tatctttctc cagatctcag taaggtacga agtaactgtc caaaagccat gaagagattg   2700
atggcagagt gcctaaaaaa gaaaagagat gagaggccac tgtttcccca aattcttgcc   2760
tctattgagc tgctggcccg ctcattgcca aaaattcacc gcagtgcatc agaaccctcc   2820
ttgaatcggg ctggcttcca gacagaggat tttagtctct atgcttgtgc ttctccaaaa   2880
acacccatcc aggcaggggg atatggtgcg tttcccgtcc actgagataa gttagatgag   2940
tgcgcgagtg caggggggccg gggccaagga ggtggaaatg tgcgtgcttc tgtactaagt   3000
tggatagcat cttctttttt aaaaaaagat gaaccaaaga atgtgtatgt ttttaaagac   3060
tagatataat tatttcctga tctaaaatgt atacttagct ttggatttcc aatatccaag   3120
ggttttcaaa atgcacagac attgctgaac atttgcagta cctcttctgg aggctttact   3180
tcctgttaca aattggtttt gtttactggc ttatcctaat tattaaactt caattaaact   3240
tttctcctgc accttttgtt atgagctatc acatgtccct tagggactcg caagagcagt   3300
actgcccccg tgtacgggct tgcaggtaga aaggggatga cgggttttaa cacctgtgtg   3360
aggcaaggca gtccgaacag atctcattta ggaagccacg agagttgaat aagttatttt   3420
tattcttagt atttttctg taactacttt ttattataac ttggaaaata tggatgtcct   3480
```

ttatacacct tagcaataga ctgaatttct ttttataaat t 3521

<210> SEQ ID NO 100
<211> LENGTH: 974
<212> TYPE: PRT
<213> ORGANISM: Felis catus
<220> FEATURE:
<221> NAME/KEY: misc_feature
<222> LOCATION: (210)..(217)
<223> OTHER INFORMATION: Xaa can be any naturally occurring amino acid

<400> SEQUENCE: 100

Met Pro Asn Leu Ser Leu Cys His His Gly Gln Phe Ala His Val Pro
1 5 10 15

Thr Val Ser Ala Leu Gly Tyr Phe Val Ile Cys Leu Gly His Cys Pro
20 25 30

Leu Ser Leu Thr Leu Pro Glu Gly Glu Pro Leu Met Leu Met Leu Lys
35 40 45

Val Thr Phe Ala Gly Ser Pro Leu Leu Ile Pro Lys Met Arg Pro Pro
50 55 60

Asp Asn Pro Arg Ala Thr Val Cys Thr Trp Ala Lys Gln Ala Thr Phe
65 70 75 80

Cys Ala Asp Trp Gly Glu Arg Phe Gln Glu His Ser Ala Ile Val Leu
85 90 95

Gly Arg Glu Phe Gln His Ser Ile Val Ser Met Ala Val Ser Gly Phe
100 105 110

Gly Arg Gly Lys Cys Pro Arg Gly Asp Ser Gln Ala Val Ser Tyr Gly
115 120 125

Gln Gly Pro Ala Leu Ile Phe Ala Cys Ser Gly Leu Ala Gln Gly Arg
130 135 140

Glu Arg Ser Arg Lys Ser Glu Pro Trp Lys Arg Gln Ser Gly Gly Asn
145 150 155 160

Val His Ala Arg Gly Trp Ala Arg Lys Glu Arg Thr Leu Pro Arg Arg
165 170 175

Leu Arg Glu Gly Ala Pro Arg Ile Thr Ser Arg Thr Pro Arg Lys Leu
180 185 190

Lys Cys Thr Val Cys Gly Leu Leu Ile Glu Leu Ser Ser Leu Cys Ala
195 200 205

Leu Xaa Xaa Xaa Xaa Xaa Xaa Xaa Xaa Gly Gly Gly Gly Gly Ala Glu
210 215 220

Gln Gly Gln Ala Leu Phe Asn Gly Asp Met Glu Pro Glu Ala Gly Ala
225 230 235 240

Ala Ala Ser Ser Ala Ala Asp Pro Ala Ile Pro Glu Glu Val Trp Asn
245 250 255

Ile Lys Gln Met Ile Lys Leu Thr Gln Glu His Ile Glu Ala Leu Leu
260 265 270

Asp Lys Phe Gly Gly Glu His Asn Pro Pro Ser Ile Tyr Leu Glu Ala
275 280 285

Tyr Glu Glu Tyr Thr Ser Lys Leu Asp Ala Leu Gln Gln Arg Glu Gln
290 295 300

Gln Leu Leu Glu Ser Leu Gly Asn Gly Thr Asp Phe Ser Val Ser Ser
305 310 315 320

Ser Ala Ser Thr Asp Thr Val Thr Ser Ser Ser Ser Ser Ser Leu Ser
325 330 335

Val Leu Pro Ser Ser Leu Ser Val Phe Gln Asn Pro Thr Asp Val Ser
340 345 350

```
Arg Ser Asn Pro Lys Ser Pro Gln Lys Pro Ile Val Arg Val Phe Leu
        355                 360                 365

Pro Asn Lys Gln Arg Thr Val Val Pro Ala Arg Cys Gly Val Thr Val
    370                 375                 380

Arg Asp Ser Leu Lys Lys Ala Leu Met Met Arg Gly Leu Ile Pro Glu
385                 390                 395                 400

Cys Cys Ala Val Tyr Arg Ile Gln Asp Gly Glu Lys Lys Pro Ile Gly
                405                 410                 415

Trp Asp Thr Asp Ile Ser Trp Leu Thr Gly Glu Glu Leu His Val Glu
            420                 425                 430

Val Leu Glu Asn Val Pro Leu Thr Thr His Asn Phe Val Cys Thr Glu
        435                 440                 445

Asn Val Phe Thr Leu Ala Phe Cys Asp Phe Cys Arg Lys Leu Leu Phe
    450                 455                 460

Gln Gly Phe Arg Cys Gln Thr Cys Gly Tyr Lys Phe His Gln Arg Cys
465                 470                 475                 480

Ser Thr Glu Val Pro Leu Met Cys Val Asn Tyr Asp Gln Leu Asp Leu
                485                 490                 495

Leu Phe Val Ser Lys Phe Phe Glu His His Pro Ile Pro Gln Glu Glu
            500                 505                 510

Ala Ser Ile Ala Glu Thr Ala Leu Thr Ser Gly Ser Ser Pro Ser Ala
        515                 520                 525

Pro Pro Ser Asp Ser Thr Gly Pro Gln Ile Leu Thr Ser Pro Ser Pro
    530                 535                 540

Ser Lys Ser Ile Pro Ile Pro Gln Pro Phe Arg Pro Ala Asp Glu Asp
545                 550                 555                 560

His Arg Asn Gln Phe Gly Gln Arg Asp Arg Ser Ser Ser Ala Pro Asn
                565                 570                 575

Val His Ile Asn Thr Ile Glu Pro Val Asn Ile Asp Asp Leu Ile Arg
            580                 585                 590

Asp Gln Gly Phe Arg Ser Asp Gly Gly Ser Thr Thr Gly Leu Ser Ala
        595                 600                 605

Thr Pro Pro Ala Ser Leu Pro Gly Ser Leu Thr Asn Val Lys Ala Leu
    610                 615                 620

Gln Lys Ser Pro Gly Pro Gln Arg Glu Arg Lys Ser Ser Ser Ser Ser
625                 630                 635                 640

Glu Asp Arg Asn Arg Met Lys Thr Leu Gly Arg Arg Asp Ser Ser Asp
                645                 650                 655

Asp Trp Glu Ile Pro Asp Gly Gln Ile Thr Val Gly Gln Arg Ile Gly
            660                 665                 670

Ser Gly Ser Phe Gly Thr Val Tyr Lys Gly Lys Trp His Gly Asp Val
        675                 680                 685

Ala Val Lys Met Leu Asn Val Thr Ala Pro Thr Pro Gln Gln Leu Gln
    690                 695                 700

Ala Phe Lys Asn Glu Val Gly Val Leu Arg Lys Thr Arg His Val Asn
705                 710                 715                 720

Ile Leu Leu Phe Met Gly Tyr Ser Thr Lys Pro Gln Leu Ala Ile Val
                725                 730                 735

Thr Gln Trp Cys Glu Gly Ser Ser Leu Tyr His His Leu His Ile Ile
            740                 745                 750

Glu Thr Lys Phe Glu Met Ile Lys Leu Ile Asp Ile Ala Arg Gln Thr
        755                 760                 765
```

```
Ala Gln Gly Met Asp Tyr Leu His Ala Lys Ser Ile Ile His Arg Asp
    770                 775                 780

Leu Lys Ser Asn Asn Ile Phe Leu His Glu Asp Leu Thr Val Lys Ile
785                 790                 795                 800

Gly Asp Phe Gly Leu Ala Thr Val Lys Ser Arg Trp Ser Gly Ser His
                805                 810                 815

Gln Phe Glu Gln Leu Ser Gly Ser Ile Leu Trp Met Ala Pro Glu Val
            820                 825                 830

Ile Arg Met Gln Asp Lys Asn Pro Tyr Ser Phe Gln Ser Asp Val Tyr
        835                 840                 845

Ala Phe Gly Ile Val Leu Tyr Glu Leu Met Thr Gly Gln Leu Pro Tyr
    850                 855                 860

Ser Asn Ile Asn Asn Arg Asp Gln Ile Ile Phe Met Val Gly Arg Gly
865                 870                 875                 880

Tyr Leu Ser Pro Asp Leu Ser Lys Val Arg Ser Asn Cys Pro Lys Ala
                885                 890                 895

Met Lys Arg Leu Met Ala Glu Cys Leu Lys Lys Lys Arg Asp Glu Arg
            900                 905                 910

Pro Leu Phe Pro Gln Ile Leu Ala Ser Ile Glu Leu Leu Ala Arg Ser
        915                 920                 925

Leu Pro Lys Ile His Arg Ser Ala Ser Glu Pro Ser Leu Asn Arg Ala
    930                 935                 940

Gly Phe Gln Thr Glu Asp Phe Ser Leu Tyr Ala Cys Ala Ser Pro Lys
945                 950                 955                 960

Thr Pro Ile Gln Ala Gly Gly Tyr Gly Ala Phe Pro Val His
                965                 970


<210> SEQ ID NO 101
<211> LENGTH: 3853
<212> TYPE: DNA
<213> ORGANISM: Bos taurus

<400> SEQUENCE: 101

ctcagctgcg ccgggtctca caagacggtt cccgaggtgg cccaggcgcc gtcccaccgc      60

cgacgccgcc cgggccgccc gggccgtccc tccccgctgc cccccgtcct ccgcctccgc     120

ctccccccgc cctcagcctc ccttccccct ccccgcccag cagcggtcgc tcgggcccgg     180

ctctcggtta taagatggcg gcgctgagtg gcggcggcgg cggcggcggc ggtggcgcgg     240

agcagggcca ggctctgttc aacggggaca tggagcccga ggccggcgcc gcggcctctt     300

cggctgcgga ccccgccatt cccgaggagg tgtggaatat caaacaaatg attaagttga     360

cacaggagca tatagaggcc ctattggaca aatttggtgg ggagcataat ccaccatcaa     420

tatatctgga ggcctatgaa gaatacacca gcaagctaga tgccctccaa caaagagaac     480

aacagttatt ggaatccctg gggaatggaa ctgatttttc tgtttctagc tctgcatcaa     540

cggacaccgt tacatcttct tcctcttcta gcctttcagt gctgccttca tctctttcag     600

tttttcaaaa tcccacagat gtgtcacgga gcaaccccaa gtcaccacaa aaacctatcg     660

ttagagtctt cctgcccaat aaacagagga cagtggtacc tgcacggtgt ggagtcacag     720

tccgggacag cctgaagaag gcactgatga tgagaggtct aatcccagag tgctgtgctg     780

tttacagaat tcaggatggg gagaagaaac caattggctg ggacactgat atttcctggc     840

ttactggaga ggagttgcat gtagaagtgt tggagaatgt tccacttaca acacacaact     900

ttgtacggaa aactttttc accttagcat tttgtgactt ctgtagaaag ctgcttttcc     960
```

-continued

```
agggattccg ctgtcaaaca tgtggttata aatttcacca gcgttgtagt acagaggttc   1020
cactgatgtg tgttaattat gaccaactag atttgctgtt tgtctccaag ttctttgaac   1080
accacccaat accacaggag gaggcctcct tagcagagac tacccttcca tgtggctcat   1140
ccccttctgc acccccctcc gattctattg ggcccccaat tctcaccagt ccatctcctt   1200
caaaatccat tccaattcca cagcctttcc gaccagcaga tgaagatcat cgaaatcagt   1260
ttggacaacg agaccggtcc tcatcagctc caaatgtgca tataaacaca atagaacccg   1320
tcaatattga tgacttgatt agagaccaag ggtttcgtag tgatggagga tcaaccacag   1380
gtttatccgc cacacccct gcctcattac ctggctcact ctctaatgtg aaagcattgc   1440
agaaatctcc aggacctcag cgagaaagaa agtcctcttc atcctcagaa gacaggaatc   1500
gaatgaaaac gcttggtaga cgggattcaa gtgacgattg ggagattcct gatggacaga   1560
tcacagtggg acaaagaatt ggatcagggt catttgggac agtctacaag ggaaagtggc   1620
atggtgatgt ggcagtgaaa atgttgaatg tgacagcacc cacacctcag cagttacagg   1680
ccttcaaaaa tgaagtagga gtactcagga aaacgcgaca tgtgaatatc ctcctcttca   1740
tgggttattc aacaaagcca caactggcta ttgttaccca gtggtgtgag ggctccagtt   1800
tatatcatca tctccacatc attgagacca aattcgagat gatcaaactt atagatattg   1860
cacggcagac tgcacagggc atggattact tacacgccaa gtcaatcatc cacagagacc   1920
tcaagagtaa taatattttt cttcatgaag acctcacagt aaaaataggt gattttggtc   1980
tagccacagt gaaatctcga tggagtgggt cccatcagtt tgaacagttg tctggatcca   2040
ttttgtggat ggcaccagaa gtaatcagaa tgcaagataa aaacccatat agctttcagt   2100
cagatgtata tgcatttggg attgttctgt atgaattgat gaccggacag ttaccttatt   2160
caaatatcaa caacagggac cagataattt ttatggtggg acgaggatat ctgtctccag   2220
atctcagtaa ggtacggagt aactgtccaa aagccatgaa gagattaatg gcagagtgcc   2280
taaaaaagaa aagagatgaa agaccactct ttccccaaat tctcgcctct attgagctgc   2340
tggcccgctc attgccaaaa attcaccgca gtgcatcaga accctccttg aatcgggctg   2400
gcttccaaac agaggatttt agtctatatg cttgtgcttc tccaaaaaca cccattcagg   2460
caggggggata tggtacgttt cctgttcact gaaacaaacc gagtgagtga cagcatgtag   2520
gagggtaggg acaaaagaaa gtgaacaaat gtttgcttat atatttgtta aattgaatag   2580
gattttcttt ttctttaaag gtgaacaaga gaacatgtgt gtttttaaag tttggatata   2640
gttttcttcc cagtctaaaa cccatagtta gcattacatt ttcaacatcg aattttttt   2700
taattcatag acattgctga aaatttataa taccttttcc agaggcttta cttcccattc   2760
caagtttgtt ttgtttactt ggttagtcta atcattaaac tttaaacttt ccccacctac   2820
cttttgctgt tagctatccc gcatccatta ggggctccaa gaacagcact gtctgcgtgt   2880
gtgtgttggc aggtgggaag ctgatggtaa gttaggctgt gttagtgaag gtaaactgac   2940
caggtctaat taggagtcac tagaattgaa taagcttatt tttattaata ttttttctta   3000
taactatttc tttttgtaat aatttagaaa atataattgt tctttattcc cttacagcag   3060
tataaattat tggtgcaggt aaccaaagat attactgagg agtggcatgt ttgacatgag   3120
tgacatggtt taactttgga tttttagtta atatttcttt atatattaag gatgtcttac   3180
acattataga agtcaaattt actgacaaag gtattgcctc ctcttcctcc ccaaaaacac   3240
agcaaaattc tctgggaact cgtagcattg ttggttttct tttggatgac tatggttgcc   3300
aaacaaccaa gtaattgatt ttttttaaat tattattgct ttagattata ctcacctctc   3360
```

```
atgatgcctg ttagcaatca cctttatcca tgtgtcttgt aaaatatctt tcctccttat   3420

attctttgcc caacaagagt ctacttgtta tgaatgagta ctattttctt tttttgattc   3480

cccagtataa ttagtatgtt tagtgctttc taggacttcc actttcttat gttaaaaaaa   3540

aaaacaaact aatgtggcag tcagtatatt cttactgtga atcagagtct ttactgggaa   3600

tcaaagtgaa agaagcagct gttctgactt cagagtcagc ctagggacca aaaccagcct   3660

cttaaataca ccttcattta ttcagtttgg atttgtgatg attttcatta tagctgacag   3720

ttcaaggtta ttcagtggca cacagatagc atctgcataa atgcctttct tcttgaaaat   3780

aaaggagaaa attgggaaga ctttacacca atagtttagt ctttaagtac cacagataac   3840

acacaccata aat                                                      3853
```

```
<210> SEQ ID NO 102
<211> LENGTH: 764
<212> TYPE: PRT
<213> ORGANISM: Bos taurus

<400> SEQUENCE: 102

Ala Ala Leu Ser Gly Gly Gly Gly Gly Gly Gly Gly Gly Ala Glu Gln
1               5                   10                  15

Gly Gln Ala Leu Phe Asn Gly Asp Met Glu Pro Glu Ala Gly Ala Ala
            20                  25                  30

Ala Ser Ser Ala Ala Asp Pro Ala Ile Pro Glu Glu Val Trp Asn Ile
        35                  40                  45

Lys Gln Met Ile Lys Leu Thr Gln Glu His Ile Glu Ala Leu Leu Asp
    50                  55                  60

Lys Phe Gly Gly Glu His Asn Pro Pro Ser Ile Tyr Leu Glu Ala Tyr
65                  70                  75                  80

Glu Glu Tyr Thr Ser Lys Leu Asp Ala Leu Gln Gln Arg Glu Gln Gln
                85                  90                  95

Leu Leu Glu Ser Leu Gly Asn Gly Thr Asp Phe Ser Val Ser Ser Ser
            100                 105                 110

Ala Ser Thr Asp Thr Val Thr Ser Ser Ser Ser Ser Ser Leu Ser Val
        115                 120                 125

Leu Pro Ser Ser Leu Ser Val Phe Gln Asn Pro Thr Asp Val Ser Arg
    130                 135                 140

Ser Asn Pro Lys Ser Pro Gln Lys Pro Ile Val Arg Val Phe Leu Pro
145                 150                 155                 160

Asn Lys Gln Arg Thr Val Val Pro Ala Arg Cys Gly Val Thr Val Arg
                165                 170                 175

Asp Ser Leu Lys Lys Ala Leu Met Met Arg Gly Leu Ile Pro Glu Cys
            180                 185                 190

Cys Ala Val Tyr Arg Ile Gln Asp Gly Glu Lys Lys Pro Ile Gly Trp
        195                 200                 205

Asp Thr Asp Ile Ser Trp Leu Thr Gly Glu Glu Leu His Val Glu Val
    210                 215                 220

Leu Glu Asn Val Pro Leu Thr Thr His Asn Phe Val Arg Lys Thr Phe
225                 230                 235                 240

Phe Thr Leu Ala Phe Cys Asp Phe Cys Arg Lys Leu Leu Phe Gln Gly
                245                 250                 255

Phe Arg Cys Gln Thr Cys Gly Tyr Lys Phe His Gln Arg Cys Ser Thr
            260                 265                 270

Glu Val Pro Leu Met Cys Val Asn Tyr Asp Gln Leu Asp Leu Leu Phe
```

```
        275                 280                 285

Val Ser Lys Phe Phe Glu His His Pro Ile Pro Gln Glu Glu Ala Ser
    290                 295                 300

Leu Ala Glu Thr Thr Leu Pro Cys Gly Ser Ser Pro Ser Ala Pro Pro
305                 310                 315                 320

Ser Asp Ser Ile Gly Pro Pro Ile Leu Thr Ser Pro Ser Pro Ser Lys
                325                 330                 335

Ser Ile Pro Ile Pro Gln Pro Phe Arg Pro Ala Asp Glu Asp His Arg
            340                 345                 350

Asn Gln Phe Gly Gln Arg Asp Arg Ser Ser Ser Ala Pro Asn Val His
        355                 360                 365

Ile Asn Thr Ile Glu Pro Val Asn Ile Asp Asp Leu Ile Arg Asp Gln
    370                 375                 380

Gly Phe Arg Ser Asp Gly Gly Ser Thr Thr Gly Leu Ser Ala Thr Pro
385                 390                 395                 400

Pro Ala Ser Leu Pro Gly Ser Leu Ser Asn Val Lys Ala Leu Gln Lys
                405                 410                 415

Ser Pro Gly Pro Gln Arg Glu Arg Lys Ser Ser Ser Ser Ser Glu Asp
            420                 425                 430

Arg Asn Arg Met Lys Thr Leu Gly Arg Arg Asp Ser Ser Asp Asp Trp
        435                 440                 445

Glu Ile Pro Asp Gly Gln Ile Thr Val Gly Gln Arg Ile Gly Ser Gly
    450                 455                 460

Ser Phe Gly Thr Val Tyr Lys Gly Lys Trp His Gly Asp Val Ala Val
465                 470                 475                 480

Lys Met Leu Asn Val Thr Ala Pro Thr Pro Gln Gln Leu Gln Ala Phe
                485                 490                 495

Lys Asn Glu Val Gly Val Leu Arg Lys Thr Arg His Val Asn Ile Leu
            500                 505                 510

Leu Phe Met Gly Tyr Ser Thr Lys Pro Gln Leu Ala Ile Val Thr Gln
        515                 520                 525

Trp Cys Glu Gly Ser Ser Leu Tyr His His Leu His Ile Ile Glu Thr
    530                 535                 540

Lys Phe Glu Met Ile Lys Leu Ile Asp Ile Ala Arg Gln Thr Ala Gln
545                 550                 555                 560

Gly Met Asp Tyr Leu His Ala Lys Ser Ile Ile His Arg Asp Leu Lys
                565                 570                 575

Ser Asn Asn Ile Phe Leu His Glu Asp Leu Thr Val Lys Ile Gly Asp
            580                 585                 590

Phe Gly Leu Ala Thr Val Lys Ser Arg Trp Ser Gly Ser His Gln Phe
        595                 600                 605

Glu Gln Leu Ser Gly Ser Ile Leu Trp Met Ala Pro Glu Val Ile Arg
    610                 615                 620

Met Gln Asp Lys Asn Pro Tyr Ser Phe Gln Ser Asp Val Tyr Ala Phe
625                 630                 635                 640

Gly Ile Val Leu Tyr Glu Leu Met Thr Gly Gln Leu Pro Tyr Ser Asn
                645                 650                 655

Ile Asn Asn Arg Asp Gln Ile Ile Phe Met Val Gly Arg Gly Tyr Leu
            660                 665                 670

Ser Pro Asp Leu Ser Lys Val Arg Ser Asn Cys Pro Lys Ala Met Lys
        675                 680                 685

Arg Leu Met Ala Glu Cys Leu Lys Lys Lys Arg Asp Glu Arg Pro Leu
    690                 695                 700
```

```
Phe Pro Gln Ile Leu Ala Ser Ile Glu Leu Leu Ala Arg Ser Leu Pro
705                 710                 715                 720

Lys Ile His Arg Ser Ala Ser Glu Pro Ser Leu Asn Arg Ala Gly Phe
                725                 730                 735

Gln Thr Glu Asp Phe Ser Leu Tyr Ala Cys Ala Ser Pro Lys Thr Pro
            740                 745                 750

Ile Gln Ala Gly Gly Tyr Gly Thr Phe Pro Val His
        755                 760


<210> SEQ ID NO 103
<211> LENGTH: 4936
<212> TYPE: DNA
<213> ORGANISM: Bos taurus

<400> SEQUENCE: 103

ctcagctgcg ccgggtctca caagacggtt cccgaggtgg cccaggcgcc gtcccaccgc     60

cgacgccgcc cgggccgccc gggccgtccc tccccgctgc cccccgtcct ccgcctccgc    120

ctccccccgc cctcagcctc ccttccccct ccccgcccag cagcggtcgc tcgggcccgg    180

ctctcggtta taagatggcg gcgctgagtg gcggcggcgg cggcggcggc ggtggcgcgg    240

agcagggcca ggctctgttc aacggggaca tggagcccga ggccggcgcc gcggcctctt    300

cggctgcgga ccccgccatt cccgaggagg tgtggaatat caaacaaatg attaagttga    360

cacaggagca tatagaggcc ctattggaca aatttggtgg ggagcataat ccaccatcaa    420

tatatctgga ggcctatgaa gaatacacca gcaagctaga tgccctccaa caaagagaac    480

aacagttatt ggaatccctg gggaatggaa ctgatttttc tgtttctagc tctgcatcaa    540

cggacaccgt tacatcttct tcctcttcta gcctttcagt gctgccttca tctctttcag    600

tttttcaaaa tcccacagat gtgtcacgga gcaaccccaa gtcaccacaa aaacctatcg    660

ttagagtctt cctgcccaat aaacagagga cagtggtacc tgcacggtgt ggagtcacag    720

tccgggacag cctgaagaag gcactgatga tgagaggtct aatcccagag tgctgtgctg    780

tttacagaat tcaggatggg gagaagaaac caattggctg ggacactgat atttcctggc    840

ttactggaga ggagttgcat gtagaagtgt tggagaatgt tccacttaca acacacaact    900

ttgtacggaa aactttttc accttagcat tttgtgactt ctgtagaaag ctgcttttcc     960

agggattccg ctgtcaaaca tgtggttata aatttcacca gcgttgtagt acagaggttc   1020

cactgatgtg tgttaattat gaccaactag atttgctgtt tgtctccaag ttctttgaac   1080

accacccaat accacaggag gaggcctcct tagcagagac taccettcca tgtggctcat   1140

ccccttctgc acccccctcc gattctattg ggcccccaat tctcaccagt ccatctcctt   1200

caaaatccat tccaattcca cagcctttcc gaccagcaga tgaagatcat cgaaatcagt   1260

ttggacaacg agaccggtcc tcatcagctc caaatgtgca tataaacaca atagaacccg   1320

tcaatattga tgacttgatt agagaccaag ggtttcgtag tgatggagga tcaaccacag   1380

gtttatccgc cacacccccct gcctcattac ctggctcact ctctaatgtg aaagcattgc   1440

agaaatctcc aggacctcag cgagaaagaa agtcctcttc atcctcagaa gacaggaatc   1500

gaatgaaaac gcttggtaga cgggattcaa gtgacgattg ggagattcct gatggacaga   1560

tcacagtggg acaaagaatt ggatcagggt catttgggac agtctacaag ggaaagtggc   1620

atggtgatgt ggcagtgaaa atgttgaatg tgacagcacc cacacctcag cagttacagg   1680

ccttcaaaaa tgaagtagga gtactcagga aaacgcgaca tgtgaatatc ctcctcttca   1740
```

tgggttattc aacaaagcca caactggcta ttgttaccca gtggtgtgag ggctccagtt 1800
tatatcatca tctccacatc attgagacca aattcgagat gatcaaactt atagatattg 1860
cacggcagac tgcacagggc atggattact tacacgccaa gtcaatcatc cacagagacc 1920
tcaagagtaa taatattttt cttcatgaag acctcacagt aaaaataggt gattttggtc 1980
tagccacagt gaaatctcga tggagtgggt cccatcagtt tgaacagttg tctggatcca 2040
ttttgtggat ggcaccagaa gtaatcagaa tgcaagataa aaacccatat agctttcagt 2100
cagatgtata tgcatttggg attgttctgt atgaattgat gaccggacag ttaccttatt 2160
caaatatcaa caacagggac cagataattt ttatggtggg acgaggatat ctgtctccag 2220
atctcagtaa ggtacggagt aactgtccaa aagccatgaa gagattaatg gcagagtgcc 2280
taaaaaagaa aagagatgaa agaccactct ttccccaagt aggaaagact ctcctaagca 2340
agagacaaaa ttcagaagtt atcagggaaa aagataagca gattctcgcc tctattgagc 2400
tgctggcccg ctcattgcca aaaattcacc gcagtgcatc agaaccctcc ttgaatcggg 2460
ctggcttcca aacagaggat tttagtctat atgcttgtgc ttctccaaaa acacccattc 2520
aggcaggggg atatgaagca gatttggctc ttacatcaaa taaaaataga gtagaagttg 2580
ggatttagag atttcctgac atgcaagaag gaataagcaa gaaaaaaagg tttgttttcc 2640
ccaaatcata tctattgtct tttacttcta ttttttctta aatttttttgt gatttcagag 2700 acatgtagag ttttattgat acctaaacta tgagttcttt tttttttttt tttttcatta 2760
ttttgatttt tttggccaag aggcatatgg gatcttagct tgagaaagca acaattttct 2820
tgatgtcatt ttgggtgagg gcacatattg ctgtgaacag tgtggtgata gccaccaggg 2880
accaaactca cacccgctgc attgaaaggt gaagtcttaa acactggacc agcagagaaa 2940
ttcctactct atgagttctt tttgtcatcc cctccccgca ccctccaccc ccaacctaaa 3000
gtctgatgat gaaatcaaca actattccat tagaagcagt agattctggt agcatgatct 3060
ttagtttgtt agtaagattt tgtgctttgt ggggttgtgt cgttttaagg ctaatattta 3120
agtttgtcaa atagaatgct gttcagattg taaaaatgag taataaacat ctgaagtttt 3180
ttttaagtta tttttaacat ggtatataca gttgagctta gagtttatca ttttctgata 3240
ttctcttact tagtagatga attctagcca ttttttataa agatttctgt taagcaaatc 3300
ctgttttcac atgggcttcc tttaagggat tttagattct gctggatatg gtgactgctc 3360
ataagactgt tgaaaattac ttttaagatg tattagaata cttctgaaaa aaaatagcaa 3420
ccttaaaacc ataagcaaaa gtagtaaggg tgtttataca tttctagagt ccctgtttag 3480
gtaatagcct cctatgattg tactttaaat gttttgctct ccaaggtttt agtaacttgg 3540 cttttttttct aatcagtgcc aaactccccc agttttttta actttaaata tgaggtaata 3600
aatcttttac ccttccttga tcttttgact tataatacct tggtcagttg tttcttaaaa 3660
ggaatcctta aatggaaaga gacaatatca ctgtctgcag ttctgattag tagttttatt 3720
cagaatggaa aaacagatta ttcatttttg aaaattgttc aggggtatgt tcattgttag 3780
gaccttggac tttggagtca gtgcctagct atgcattcca ggtctgccat tttctggctg 3840
tgaaattttg gacaagttac ttaaccactt taaaccccag ctttaagaag taaattaacc 3900
ccagtaaatt aagaagtaat agcagccact tcgtagagtt gttatgaggc tcagatgcag 3960
tgcaaatgtg tataaagtat tcagggagtc acctggtata ctataataga cactagaata 4020
gttgccaata ttatcagcat acaatctgag gattctgtca gccaatcatt agcaatctgt 4080
tgtttgttgg gacatgccag tgttctccag ttgaaatcag tagcaatcta aaaatggata 4140

```
gattattcct catttaaata gtgtgttcat ataagtgatt gcttggatcc ttatcagaag   4200

ttgctgttac tgaaaaatga taaggctgac taaattgtga tagttgtcag ttactaacca   4260

actcccagaa atgaataaga ggaacctatc tctagttcct agtagaaggt atggacaaaa   4320

tagtaggtga aaaataatgt cttgaacccc caaattaagt aagctttaaa gagtacaata   4380

cctcaaaggg tctttgcggt ttaaaatttg tatgctgaga atgatgttca ttgacatgtg   4440

cctatatgta attttttgat agtttaaaag gtgaaatgaa ctacagatgg gagaggtctg   4500

aattttcttg ccttcagtca aatgtgtaat gtggacatat tatttgacct gtgaatttta   4560

tcttttaaaa aagattaatt cctgcttctt ccttcctaat agttgcatta taataatgaa   4620

aatgagttga taatttgggg ggaaagtatt ctacaaatca accttattat tttaccattg   4680

gtttctgaga aattttgttc atttgaaccg tttatagctt gattagaatc atagcatgta   4740

aaacccaact gagggattat ctgcagactt aatgtagtat tatgtaagtt gtcttctttc   4800

atttcgacct tttttgcttt tgttgttgct agatctgtag tatgtagcta gtcacctttc   4860

agcgaggttt cagcgaggct tttctgtgtc tctaggttat ttgagataac ttttttaaaa   4920

ttagctcttg tcctcc                                                   4936


<210> SEQ ID NO 104
<211> LENGTH: 797
<212> TYPE: PRT
<213> ORGANISM: Bos taurus

<400> SEQUENCE: 104

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220
```

-continued

```
Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
```

645 650 655

Asn Ile Asn Asn Arg Asp Gln Ile Ile Phe Met Val Gly Arg Gly Tyr
660 665 670

Leu Ser Pro Asp Leu Ser Lys Val Arg Ser Asn Cys Pro Lys Ala Met
675 680 685

Lys Arg Leu Met Ala Glu Cys Leu Lys Lys Lys Arg Asp Glu Arg Pro
690 695 700

Leu Phe Pro Gln Val Gly Lys Thr Leu Leu Ser Lys Arg Gln Asn Ser
705 710 715 720

Glu Val Ile Arg Glu Lys Asp Lys Gln Ile Leu Ala Ser Ile Glu Leu
725 730 735

Leu Ala Arg Ser Leu Pro Lys Ile His Arg Ser Ala Ser Glu Pro Ser
740 745 750

Leu Asn Arg Ala Gly Phe Gln Thr Glu Asp Phe Ser Leu Tyr Ala Cys
755 760 765

Ala Ser Pro Lys Thr Pro Ile Gln Ala Gly Gly Tyr Glu Ala Asp Leu
770 775 780

Ala Leu Thr Ser Asn Lys Asn Arg Val Glu Val Gly Ile
785 790 795

<210> SEQ ID NO 105
<211> LENGTH: 4154
<212> TYPE: DNA
<213> ORGANISM: Bos taurus

<400> SEQUENCE: 105
ctcagctgcg ccgggtctca caagacggtt cccgaggtgg cccaggcgcc gtcccaccgc 60
cgacgccgcc cgggccgccc gggccgtccc tccccgctgc cccccgtcct ccgcctccgc 120
ctccccccgc cctcagcctc ccttccccct ccccgcccag cagcggtcgc tcgggcccgg 180
ctctcggtta taagatggcg gcgctgagtg gcggcggcgg cggcggcggc ggtggcgcgg 240
agcagggcca ggctctgttc aacggggaca tggagcccga ggccggcgcc gcggcctctt 300
cggctgcgga ccccgccatt cccgaggagg tgtggaatat caaacaaatg attaagttga 360
cacaggagca tatagaggcc ctattggaca aatttggtgg ggagcataat ccaccatcaa 420
tatatctgga ggcctatgaa gaatacacca gcaagctaga tgccctccaa caaagagaac 480
aacagttatt ggaatccctg gggaatggaa ctgatttttc tgtttctagc tctgcatcaa 540
cggacaccgt tacatcttct tcctcttcta gcctttcagt gctgccttca tctctttcag 600
tttttcaaaa tcccacagat gtgtcacgga gcaaccccaa gtcaccacaa aaacctatcg 660
ttagagtctt cctgcccaat aaacagagga cagtggtacc tgcacggtgt ggagtcacag 720
tccgggacag cctgaagaag gcactgatga tgagaggtct aatcccagag tgctgtgctg 780
tttacagaat tcaggatggg gagaagaaac caattggctg ggacactgat atttcctggc 840
ttactggaga ggagttgcat gtagaagtgt tggagaatgt tccacttaca acacacaact 900
ttgtacggaa aactttttc accttagcat tttgtgactt ctgtagaaag ctgcttttcc 960
agggattccg ctgtcaaaca tgtggttata aatttcacca gcgttgtagt acagaggttc 1020
cactgatgtg tgttaattat gaccaactag atttgctgtt tgtctccaag ttctttgaac 1080
accacccaat accacaggag gaggcctcct tagcagagac taccctcca tgtggctcat 1140 ccccttctgc accccctcc gattctattg ggcccccaat tctcaccagt ccatctcctt 1200
caaaatccat tccaattcca cagcctttcc gaccagcaga tgaagatcat cgaaatcagt 1260

```
ttggacaacg agaccggtcc tcatcagctc caaatgtgca tataaacaca atagaacccg   1320
tcaatattga tgacttgatt agagaccaag ggtttcgtag tgatggagga tcaaccacag   1380
gtttatccgc cacacccccct gcctcattac ctggctcact ctctaatgtg aaagcattgc   1440
agaaatctcc aggacctcag cgagaaagaa agtcctcttc atcctcagaa gacaggaatc   1500
gaatgaaaac gcttggtaga cgggattcaa gtgacgattg ggagattcct gatggacaga   1560
tcacagtggg acaaagaatt ggatcagggt catttgggac agtctacaag ggaaagtggc   1620
atggtgatgt ggcagtgaaa atgttgaatg tgacagcacc cacacctcag cagttacagg   1680
ccttcaaaaa tgaagtagga gtactcagga aaacgcgaca tgtgaatatc ctcctcttca   1740
tgggttattc aacaaagcca caactggcta ttgttaccca gtggtgtgag ggctccagtt   1800
tatatcatca tctccacatc attgagacca aattcgagat gatcaaactt atagatattg   1860
cacggcagac tgcacagggc atggattact tacacgccaa gtcaatcatc cacagagacc   1920
tcaagagtaa taatattttt cttcatgaag acctcacagt aaaaataggt gattttggtc   1980
tagccacagt gaaatctcga tggagtgggt cccatcagtt tgaacagttg tctggatcca   2040
ttttgtggat ggcaccagaa gtaatcagaa tgcaagataa aaacccatat agctttcagt   2100
cagatgtata tgcatttggg attgttctgt atgaattgat gaccggacag ttaccttatt   2160
caaatatcaa caacagggac cagataattt ttatggtggg acgaggatat ctgtctccag   2220
atctcagtaa ggtacggagt aactgtccaa aagccatgaa gagattaatg gcagagtgcc   2280
taaaaaagaa aagagatgaa agaccactct ttccccaagt aggaaagact ctcctaagca   2340
agagacaaaa ttcagaagtt atcagggaaa aagataagca gattctcgcc tctattgagc   2400
tgctggcccg ctcattgcca aaaattcacc gcagtgcatc agaaccctcc ttgaatcggg   2460
ctggcttcca aacagaggat tttagtctat atgcttgtgc ttctccaaaa acacccattc   2520
aggcaggggg atatggctga gcacattgtc catcacccac aagtggctgg ttctcatcgc   2580
agaatctacg tagggaatcg ggcgtgaaat tcacttaaga gatagagcag aggaagtgtt   2640
ctgtttacag gaatggagat gagagttatg agtaagttgc ttagtcagtt ggctttgttt   2700
tgaaaattat tgtgttatat ttgtgttaac ctacttgtgt tttgacagta tatgtcacat   2760
aggaagaaac ctcagactag cataataaca aagctcagac taggcacaga tgtacacaga   2820
atggaccaaa atgggatggg ggaaggtatg ggaataagtc taggggtagg gaaaaaattga   2880
tgtgagggtg ggaaataaac tgtaattacc tgaaataaaa tgtaagagtg caataagtgt   2940
gctttttatt ctaagctgtg aatgggtttt ttaaaaaaag cattccttcc caatgcattt   3000
gcctatgttc catagctgat taaaaccagc tatataaaca tatgcctttt tattcatgtt   3060
aattaccaat ataaatggct aacctttacg tcttatttat cttcatgtta tgttagttta   3120
catacaggga tgtgtgtgtg tgtgtatgct ataaatttc cctccttcgt ttaaaaacgc   3180
gtttgttgga tcctctctgt ttccttaggc catgccacag ctcatagtct cagcttggcc   3240
ttcctgtcac ctgatctgaa ggactatcac agtgacgtag ctcgttcatt ggttgtacac   3300
actctaaccc ttttccttgc tcagcaatta ctgtgtcttc taaaacagga gtgtacaacc   3360
atgagattgc aattaattgt ttgacatatg tccctttgaa ttctatttat tagttatgat   3420
tgattgctct ttggtttgga ccaagaaaaa cgaaatccca cctccccacc ttttcactta   3480
tttcttactt tgaggacaat tctgtaagag agaggaaagg gaactccttc atgttttaac   3540
tgcagcaagt taatggccct ggtttacacc aaacattatg gtgattcaca ttcacattcc   3600
tctcctctct tgctgccaga ggtttgggtt ttgttcagtt ctgctcaagc actgaaaaag   3660
```

ttttcatgga gtctggagag tgcccagtga aaagatggtt tttaattgtc cacagacctt 3720
tctgttcctg ctttgcaaaa attacaaagg agtaactatt tttaaagctt atttttcaat 3780
tcataaaaaa gacatttatt ttcagtcaga tgatgtctcc ttgtccctta atcctcaatg 3840
tttgcttgaa tctttttttt ttttctgatt ttctcccatc cccacttctt gatacttctt 3900
gagttctctt tcctgctcag gtcctttcat ttgtactttg gagtttttc tcatgtaaat 3960 ttgtacaatg gaaaatattg ttcagtttgg atagaacgca tggagaatta aataaaaaag 4020
atagctgaaa ttcagattga aatttatttg tgtaaagtta tttaaaaact ctgtactata 4080
taaaaggcaa aaaaagttct atgtacttga tgtgaatatg cgaatactgc tataataaag 4140
attgactgca tgga 4154

<210> SEQ ID NO 106
<211> LENGTH: 781
<212> TYPE: PRT
<213> ORGANISM: Bos taurus

<400> SEQUENCE: 106

Met Ala Ala Leu Ser Gly Gly Gly Gly Gly Gly Gly Gly Gly Ala Glu
1 5 10 15

Gln Gly Gln Ala Leu Phe Asn Gly Asp Met Glu Pro Glu Ala Gly Ala
20 25 30

Ala Ala Ser Ser Ala Ala Asp Pro Ala Ile Pro Glu Glu Val Trp Asn
35 40 45

Ile Lys Gln Met Ile Lys Leu Thr Gln Glu His Ile Glu Ala Leu Leu
50 55 60

Asp Lys Phe Gly Gly Glu His Asn Pro Pro Ser Ile Tyr Leu Glu Ala
65 70 75 80

Tyr Glu Glu Tyr Thr Ser Lys Leu Asp Ala Leu Gln Gln Arg Glu Gln
85 90 95

Gln Leu Leu Glu Ser Leu Gly Asn Gly Thr Asp Phe Ser Val Ser Ser
100 105 110

Ser Ala Ser Thr Asp Thr Val Thr Ser Ser Ser Ser Ser Ser Leu Ser
115 120 125

Val Leu Pro Ser Ser Leu Ser Val Phe Gln Asn Pro Thr Asp Val Ser
130 135 140

Arg Ser Asn Pro Lys Ser Pro Gln Lys Pro Ile Val Arg Val Phe Leu
145 150 155 160

Pro Asn Lys Gln Arg Thr Val Val Pro Ala Arg Cys Gly Val Thr Val
165 170 175

Arg Asp Ser Leu Lys Lys Ala Leu Met Met Arg Gly Leu Ile Pro Glu
180 185 190

Cys Cys Ala Val Tyr Arg Ile Gln Asp Gly Glu Lys Lys Pro Ile Gly
195 200 205

Trp Asp Thr Asp Ile Ser Trp Leu Thr Gly Glu Glu Leu His Val Glu
210 215 220

Val Leu Glu Asn Val Pro Leu Thr Thr His Asn Phe Val Arg Lys Thr
225 230 235 240

Phe Phe Thr Leu Ala Phe Cys Asp Phe Cys Arg Lys Leu Leu Phe Gln
245 250 255

Gly Phe Arg Cys Gln Thr Cys Gly Tyr Lys Phe His Gln Arg Cys Ser
260 265 270

Thr Glu Val Pro Leu Met Cys Val Asn Tyr Asp Gln Leu Asp Leu Leu

```
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700
```

```
Leu Phe Pro Gln Val Gly Lys Thr Leu Leu Ser Lys Arg Gln Asn Ser
705                 710                 715                 720

Glu Val Ile Arg Glu Lys Asp Lys Gln Ile Leu Ala Ser Ile Glu Leu
                725                 730                 735

Leu Ala Arg Ser Leu Pro Lys Ile His Arg Ser Ala Ser Glu Pro Ser
            740                 745                 750

Leu Asn Arg Ala Gly Phe Gln Thr Glu Asp Phe Ser Leu Tyr Ala Cys
        755                 760                 765

Ala Ser Pro Lys Thr Pro Ile Gln Ala Gly Gly Tyr Gly
    770                 775                 780


<210> SEQ ID NO 107
<211> LENGTH: 7914
<212> TYPE: DNA
<213> ORGANISM: Bos taurus

<400> SEQUENCE: 107

ctcagctgcg ccgggtctca caagacggtt cccgaggtgg cccaggcgcc gtcccaccgc     60

cgacgccgcc cgggccgccc gggccgtccc tccccgctgc cccccgtcct ccgcctccgc    120

ctccccccgc cctcagcctc ccttccccct ccccgcccag cagcggtcgc tcgggcccgg    180

ctctcggtta taagatggcg gcgctgagtg gcggcggcgg cggcggcggc ggtggcgcgg    240

agcagggcca ggctctgttc aacggggaca tggagcccga ggccggcgcc gcggcctctt    300

cggctgcgga ccccgccatt cccgaggagg tgtggaatat caaacaaatg attaagttga    360

cacaggagca tatagaggcc ctattggaca aatttggtgg ggagcataat ccaccatcaa    420

tatatctgga ggcctatgaa gaatacacca gcaagctaga tgccctccaa caaagagaac    480

aacagttatt ggaatccctg gggaatggaa ctgatttttc tgtttctagc tctgcatcaa    540

cggacaccgt tacatcttct tcctcttcta gcctttcagt gctgccttca tctctttcag    600

tttttcaaaa tcccacagat gtgtcacgga gcaaccccaa gtcaccacaa aaacctatcg    660

ttagagtctt cctgcccaat aaacagagga cagtggtacc tgcacggtgt ggagtcacag    720

tccgggacag cctgaagaag gcactgatga tgagaggtct aatcccagag tgctgtgctg    780

tttacagaat tcaggatggg gagaagaaac caattggctg ggacactgat atttcctggc    840

ttactggaga ggagttgcat gtagaagtgt tggagaatgt tccacttaca acacacaact    900

ttgtacggaa aactttttc accttagcat tttgtgactt ctgtagaaag ctgcttttcc     960

agggattccg ctgtcaaaca tgtggttata aatttcacca gcgttgtagt acagaggttc   1020

cactgatgtg tgttaattat gaccaactag atttgctgtt tgtctccaag ttctttgaac   1080

accacccaat accacaggag gaggcctcct tagcagagac tacccttcca tgtggctcat   1140

ccccttctgc acccccctcc gattctattg ggcccccaat tctcaccagt ccatctcctt   1200

caaaatccat tccaattcca cagcctttcc gaccagcaga tgaagatcat cgaaatcagt   1260

ttggacaacg agaccggtcc tcatcagctc caaatgtgca tataaacaca atagaacccg   1320

tcaatattga tgacttgatt agagaccaag ggtttcgtag tgatggagga tcaaccacag   1380

gtttatccgc cacacccccct gcctcattac ctggctcact ctctaatgtg aaagcattgc   1440

agaaatctcc aggacctcag cgagaaagaa agtcctcttc atcctcagaa gacaggaatc   1500

gaatgaaaac gcttggtaga cgggattcaa gtgacgattg ggagattcct gatggacaga   1560

tcacagtggg acaaagaatt ggatcagggt catttgggac agtctacaag ggaaagtggc   1620

atggtgatgt ggcagtgaaa atgttgaatg tgacagcacc cacacctcag cagttacagg   1680
```

```
ccttcaaaaa tgaagtagga gtactcagga aaacgcgaca tgtgaatatc ctcctcttca   1740
tgggttattc aacaaagcca caactggcta ttgttaccca gtggtgtgag ggctccagtt   1800
tatatcatca tctccacatc attgagacca aattcgagat gatcaaactt atagatattg   1860
cacggcagac tgcacagggc atggattact tacacgccaa gtcaatcatc cacagagacc   1920
tcaagagtaa taatattttt cttcatgaag acctcacagt aaaaataggt gattttggtc   1980
tagccacagt gaaatctcga tggagtgggt cccatcagtt tgaacagttg tctggatcca   2040
ttttgtggat ggcaccagaa gtaatcagaa tgcaagataa aaacccatat agctttcagt   2100
cagatgtata tgcatttggg attgttctgt atgaattgat gaccggacag ttaccttatt   2160
caaatatcaa caacagggac cagataattt ttatggtggg acgaggatat ctgtctccag   2220
atctcagtaa ggtacggagt aactgtccaa aagccatgaa gagattaatg gcagagtgcc   2280
taaaaaagaa aagagatgaa agaccactct ttccccaaat tctcgcctct attgagctgc   2340
tggcccgctc attgccaaaa attcaccgca gtgcatcaga accctccttg aatcgggctg   2400
gcttccaaac agaggatttt agtctatatg cttgtgcttc tccaaaaaca cccattcagg   2460
caggggggata tggagaattt gcagccttca agtagccaca ccatcatgac agcatctact   2520
cttatttctt aagtcttgtg ttcgtacaat ttgttaacat caaaacacag ttctgttcct   2580
caactctttt taaagttaaa atttttcagt gcataagctg gtgtggaaca gaaggaaatt   2640
tcccatccaa caaaagaggg aagaatgttt taggaaccag aattctctgc tgccagtgtt   2700
tcttcttcaa cacaaatatc acaagtctgc ccactcccag gaagaaagag gagagaccct   2760
gagttctgac cttttgatgg tcaggcatga tggaaagaaa ctgctgctac agcttgggag   2820
atttgctctg ggaagtctgc cagtcaactt tgcccttcta accaccagat caatatgtgg   2880
ctgatcatct gatggggcag ttgcaatcac caagccttgt tctctttcct gttctgggat   2940
tgtgttgtgg aacccttttc cctagccacc accagttcat ttctgaggga tggaacaaaa   3000
atgcagcatg cccttcctgt gtggtgcatg ttcagtcctt gacaaatttt taccaaaatg   3060
aagctacttt atttaaaagg agggtgagag gtgaggaggt cactttgggt gtggcggaaa   3120
gggaatgctg catctttttc ctgggctgct ggggctctgg ccttggcttg ccagccggaa   3180
gcgctggcac gcatcgcctt cttttcccat tgggtccagc aatgaagacg agtgtttggg   3240
gttttttttt tctccaccat gtagcaagtt ctcaggaaaa tacaattgat atcttcctcc   3300
taagctcttc caatcagtca ccaagtactt atgtggttac tttgtccagg gcacaaaatg   3360
cctgtatcta attaaaagcc tacaaaactg cttgataaca gttttgaatg tgagacattt   3420
atgtaattta aatgtaaggt acaagtttta atttctgagt ttcttctatt atatttttat   3480
taaaaaaaga aaataatttt cagattgaat tggagtaaaa taatattact tcccactaga   3540
attatatatc ctggaaaatt gtatttttgt tacataagca gcttttaaag aaagatcatt   3600
acccttttct ctacataaat atatggggag tcttagccta atgacaaata tttataattt   3660
ttaaattaat ggtacttgct ggatccatac taacatcttt actaatacct cattgtttct   3720
tccaacttac tcctacacta catcctacat cttcttccta gtcttttatc tagaatatgc   3780
aacctcaaat aaaaatggtg gtgtcctcat tcattctcct ccttcctttt ttcccaagcc   3840
tgatcttcaa aaggttggtt aatttggcag ctgagttcct ccccaggcag agaatagacc   3900
aattttaggt gtattgggac tgagggagga tgtgtaaaga ttaacatcag taaagaaccg   3960
ctgtggagta attaagaact ttgttcttta taactggaga atataaccta accctaacat   4020
```

-continued

```
ccctcagcct ttactaaagt gtggcgtaaa tcacagtagt agcaaagaaa gtgactctgg   4080
atgtgttcct ggccagtacc tcccttatca tgaatgtaga ctctctcatc aagatttagg   4140
aatataaatc aaatcaaatg tgcccagcca agctatgtag taagggactt gaacaatatt   4200
aggcagaacc tataaaataa atcagggaat tagaaattat ttaaagtttt caaattgtaa   4260
attgccccgg tgtctttcag cctactgcca ttatttttgc tacaatacct acatttcaga   4320
ggagggccta ctgaaaattc catgcaagtg gaaaataatc ctcaagttat taatgagttt   4380
gaaaagcaat gagttcttaa gtctttgtga gtagagcaag atcctacaaa attcagaaat   4440
agtaaaaatg gattcatgct gatttgaaga gcatctgtgt gcataatata atgctgcatc   4500
tcttttaaaa gcagtctatt tttcttttta aatttgtccc catagatgct tttgaacatg   4560
aacatgctta tgttaccttt tccgaggttg ggaagagcca ggagctctca ggcagggccc   4620
cctccctcag ctgggcagga gctgctcagg aggagctagt tatagaggaa gcttagcgtt   4680
ggcattttca aaattcaagg tgataacgct ttcttcttcc tttctgtttt agaatagatt   4740
gctgtctgat ttgaaaaagg gaaatagatt tgatctcaaa tgaatctgtg cccagaagcc   4800
aggctcaggg tattcagaga tttgtatagt gccctcaaaa aataacaaaa ttttagcttt   4860
ccttttttct tcttttctcc atcaaattct tttttctcta gtttacaaat gacatggaaa   4920
aggaatttcc cctgagtttt gtatgccttt tttttttgg cttagactat agataggcgt   4980
gttgagctcc taagaaaata caaggaggaa ctctttgttg tgcagagcac tttatgagta   5040
gtttgtgtgg ataatatgtg actgcttccc tgacgagctt gtgaggctgt acttatgtct   5100
ttcctgtaag gcagcttcag tgccttctgt agtgtatata aggaaagatt acgccttctg   5160
aaaaatctca gagcaaccat aagattattt taaaatatgt agtatgactg atggactttt   5220
tcatcattaa attagtctag catctaaact tttaccactg aaataatatt gaccaaaaag   5280
caatttataa aaggtatttg tgaatagaaa atacaatgtg atcatttgta cttatgtgca   5340
ccttaaaaga ggaattctgt ctagctgtca aattctggtt ccttaacatc cagtccttga   5400
ttgtgattga gatctggtag gacgtgctgg ggcacgctag cagataaaat cccgtatact   5460
ttaggataga tgttacattt atgtcagtgt tggcaaagag cattgtgtag taataaagaa   5520
ttcaagactt cagcaatgtc aacctgaaac tttgtaaata tttcctagat tgttatttga   5580
tgcagtcaca gctctttatc acacaatgtt gtctttccct catcaggcaa ttttagaact   5640
gctgcacacc cctcctcaga tctcacctgc ccctcctgta cattcacctc tccagccttg   5700
tgcacacctc atttagcttt agtttgaaac acattgcagg gttcaggtga cctcttcaaa   5760
aactacctcc tcagaatgag gtaatgaata gttatttatt ttaaaatatg aaaagtcagg   5820
agctctagaa tatgaagatg atctaagatt ttaactttta tgtatacttg ttgagcactc   5880
tccttttgtc ctaaagggca ttatacattt aagcagtaat actgaaaaat gtagctcaga   5940
gtaactgaat gttgttgaaa gtggtgccag aatctgtttt aggggtacgt atcagaatct   6000
taatcttaaa tcggttacat gaaattaaat agttaatggt aacacttgac taacagatat   6060
aattttaatt ttcggtaggc ttttagcaag acagtaagta catcttcata atgagttagc   6120
cacagcttca tcacatgcac agattttcct gttgagagac tgcccagtta agagggtaga   6180
atgatgaacc atttttcagg attctcttct ttgtccaaac tggcattgtg agtgctagaa   6240
tatcagcact ttcaaactag tgattccaac tattaggcta ttaaaaagca aaacaaacca   6300
aacaaaccat agccagacat gggaagttta ctatgagtat aaacagcaaa tagcttacag   6360
gtcatacatt gaaatggtgt aggtaaggcg ttagaaaaat accttgacaa tttgccaaat   6420
```

```
gatcttactg tgccttcatg atgcaataaa aaaaaaaaaa atttagcata aatcagtgat   6480

ttgtgaagag agcagccacc ctggtctaac tcagctgtgt taatattttt tagcgtgcaa   6540

tttagactgc aaagataaat gcactaaaga gtttatagcc aaaatcacat ttaaaaaatg   6600

agagaaaaca caggtaaatt ttcagtgaac aaaattattt ttttaaagta cataatccct   6660

agtatagtca gatatattta tcacatagag caaataggtt gaaatcacaa ttcagtgaca   6720

tttctagaga aactttttct actcccatag gttcttcaaa gcatggaact tttatataac   6780

agaaatgtgt gacggtcatt ttaaattgct gtagtttggg gctgaagtac tgtgtgctgg   6840

gcagcaatca catgtattaa ctagtgagaa aggagaaatt aagatatagg acagaatttg   6900

attttcttgt tcccagatta ctgctgccaa cctagacact gagtttccag aggctgaaac   6960

gtaaacttgc agctcagcaa ctgttttgca aagttagtgg gactgtcctg cttatgctgt   7020

tcaaaaatgc tctgagggcc aggtggggcc tccaggggct cctctctgag gggacatcag   7080

actagctaac gacctggcgg gcggatgtga accggacaca ctccatggtg tgcttcttgt   7140

atcggtccct cgccaccctc aagaaaggct tcagcgggtt ctctagacgt ctccactaag   7200

gtgtgttact aacagccatg ggttgttgag cacccgagga gtgcaatagc atctctgcat   7260

gattgtatat tggcccgaag agaatgaagt ggccagtgta ctcatgttcc atgttgctag   7320

ctctggtaaa ctgaaaatac tggtaagatt tttgttttat cagtacacta gagagtaagc   7380

tttgttttgt tgtttttaga taatgttttc acttccattt ggaaagacat ttaaattgag   7440

tttcagtcct aaattttgcc agtcatggta attagcagtt tctatcaggt atttttaagg   7500

tagaagagga tagaaacata agttctaaaa gcttaaggta accgtggttt attttaaaat   7560

gtttaggggt ggttagtctc tacctcaaaa aaagtgagtg aatcttttat ttcagcattc   7620

acaagttcgg ctgttgtttt tgtaatacat tttttttta accttttgac ccccctttac   7680

ctaagtgtca atgtagtttt attaattact aagtcagttt cattaaaatg tttatttagc   7740

agttttgact aattgcaatg attaatatag ccagttgtgc atgaggacac agccagtgag   7800

tatatctggg tttttttgt gatgcttttt ttcttaagac ttctgtagat ttatgaagta   7860

ctcattgaaa acaactaaaa tacgtttatt cgtgttaata tggaaaaaaa aaaa         7914
```

<210> SEQ ID NO 108
<211> LENGTH: 766
<212> TYPE: PRT
<213> ORGANISM: Bos taurus

<400> SEQUENCE: 108

```
Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110
```

```
Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525
```

-continued

```
Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Ile Leu Ala Ser Ile Glu Leu Leu Ala Arg Ser Leu
705                 710                 715                 720

Pro Lys Ile His Arg Ser Ala Ser Glu Pro Ser Leu Asn Arg Ala Gly
                725                 730                 735

Phe Gln Thr Glu Asp Phe Ser Leu Tyr Ala Cys Ala Ser Pro Lys Thr
            740                 745                 750

Pro Ile Gln Ala Gly Gly Tyr Gly Glu Phe Ala Ala Phe Lys
        755                 760                 765
```

<210> SEQ ID NO 109
<211> LENGTH: 4670
<212> TYPE: DNA
<213> ORGANISM: Bos taurus

<400> SEQUENCE: 109

```
ggtgtgtcat agtgcagcag attgaatgca gaagatatga aaattcagat gtcttctgtt      60

aaggtgtgga atatcaaaca aatgattaag ttgacacagg agcatataga ggccctattg     120

gacaaatttg gtggggagca taatccacca tcaatatatc tggaggccta tgaagaatac     180

accagcaagc tagatgccct ccaacaaaga gaacaacagt tattggaatc cctggggaat     240

ggaactgatt tttctgtttc tagctctgca tcaacggaca ccgttacatc ttcttcctct     300

tctagccttt cagtgctgcc ttcatctctt tcagtttttc aaaatcccac agatgtgtca     360

cggagcaacc ccaagtcacc acaaaaacct atcgttagag tcttcctgcc caataaacag     420

aggacagtgg tacctgcacg gtgtggagtc acagtccggg acagcctgaa gaaggcactg     480

atgatgagag gtctaatccc agagtgctgt gctgtttaca gaattcagga tggggagaag     540

aaaccaattg gctgggacac tgatatttcc tggcttactg gagaggagtt gcatgtagaa     600

gtgttggaga atgttccact tacaacacac aactttgtac ggaaaacttt tttcacctta     660

gcattttgtg acttctgtag aaagctgctt ttccagggat tccgctgtca aacatgtggt     720

tataaatttc accagcgttg tagtacagag gttccactga tgtgtgttaa ttatgaccaa     780
```

-continued

```
ctagatttgc tgtttgtctc caagttcttt gaacaccacc caataccaca ggaggaggcc    840
tccttagcag agactaccct tccatgtggc tcatcccctt ctgcaccccc ctccgattct    900
attgggcccc caattctcac cagtccatct ccttcaaaat ccattccaat tccacagcct    960
ttccgaccag cagatgaaga tcatcgaaat cagtttggac aacgagaccg gtcctcatca   1020
gctccaaatg tgcatataaa cacaatagaa cccgtcaata ttgatgactt gattagagac   1080
caagggtttc gtagtgatgg aggatcaacc acaggtttat ccgccacacc ccctgcctca   1140
ttacctggct cactctctaa tgtgaaagca ttgcagaaat ctccaggacc tcagcgagaa   1200
agaaagtcct cttcatcctc agaagacagg aatcgaatga aaacgcttgg tagacgggat   1260
tcaagtgacg attgggagat tcctgatgga cagatcacag tgggacaaag aattggatca   1320
gggtcatttg ggacagtcta caagggaaag tggcatggtg atgtggcagt gaaaatgttg   1380
aatgtgacag cacccacacc tcagcagtta caggccttca aaaatgaagt aggagtactc   1440
aggaaaacgc gacatgtgaa tatcctcctc ttcatgggtt attcaacaaa gccacaactg   1500
gctattgtta cccagtggtg tgagggctcc agtttatatc atcatctcca catcattgag   1560
accaaattcg agatgatcaa acttatagat attgcacggc agactgcaca gggcatggat   1620
tacttacacg ccaagtcaat catccacaga gacctcaaga gtaataatat ttttcttcat   1680
gaagacctca cagtaaaaat aggtgatttt ggtctagcca cagtgaaatc tcgatggagt   1740
gggtcccatc agtttgaaca gttgtctgga tccattttgt ggatggcacc agaagtaatc   1800
agaatgcaag ataaaaaccc atatagcttt cagtcagatg tatatgcatt tgggattgtt   1860
ctgtatgaat tgatgaccgg acagttacct tattcaaata tcaacaacag ggaccagata   1920
atttttatgg tgggacgagg atatctgtct ccagatctca gtaaggtacg gagtaactgt   1980
ccaaaagcca tgaagagatt aatggcagag tgcctaaaaa agaaaagaga tgaaagacca   2040
ctctttcccc aagtaggaaa gactctccta agcaagagac aaaattcaga agttatcagg   2100
gaaaaagata agcagattct cgcctctatt gagctgctgg cccgctcatt gccaaaaatt   2160
caccgcagtg catcagaacc ctccttgaat cgggctggct tccaaacaga ggattttagt   2220
ctatatgctt gtgcttctcc aaaaacaccc attcaggcag ggggatatga agcagatttg   2280
gctcttacat caaataaaaa tagagtagaa gttgggattt agagatttcc tgacatgcaa   2340
gaaggaataa gcaagaaaaa aaggtttgtt ttccccaaat catatctatt gtcttttact   2400
tctatttttt cttaaatttt ttgtgatttc agagacatgt agagttttat tgatacctaa   2460
actatgagtt cttttttttt tttttttttc attattttga tttttttggc caagaggcat   2520
atgggatctt agcttgagaa agcaacaatt ttcttgatgt cattttgggt gagggcacat   2580
attgctgtga acagtgtggt gatagccacc agggaccaaa ctcacacccg ctgcattgaa   2640
aggtgaagtc ttaaacactg gaccagcaga gaaattccta ctctatgagt tctttttgtc   2700
atcccctccc cgcaccctcc acccccaacc taaagtctga tgatgaaatc aacaactatt   2760
ccattagaag cagtagattc tggtagcatg atctttagtt tgttagtaag attttgtgct   2820
ttgtggggtt gtgtcgtttt aaggctaata tttaagtttg tcaaatagaa tgctgttcag   2880
attgtaaaaa tgagtaataa acatctgaag ttttttttaa gttattttta acatggtata   2940
tacagttgag cttagagttt atcattttct gatattctct tacttagtag atgaattcta   3000
gccatttttt ataaagattt ctgttaagca aatcctgttt tcacatgggc ttcctttaag   3060
ggattttaga ttctgctgga tatggtgact gctcataaga ctgttgaaaa ttacttttaa   3120
gatgtattag aatacttctg aaaaaaaata gcaaccttaa aaccataagc aaaagtagta   3180
```

agggtgttta tacatttcta gagtccctgt ttaggtaata gcctcctatg attgtacttt 3240
aaatgttttg ctctccaagg ttttagtaac ttggcttttt ttctaatcag tgccaaactc 3300
ccccagtttt tttaacttta aatatgaggt aataaatctt ttacccttcc ttgatctttt 3360
gacttataat accttggtca gttgtttctt aaaaggaatc cttaaatgga aagagacaat 3420
atcactgtct gcagttctga ttagtagttt tattcagaat ggaaaaacag attattcatt 3480
tttgaaaatt gttcaggggt atgttcattg ttaggacctt ggactttgga gtcagtgcct 3540
agctatgcat tccaggtctg ccatttttctg gctgtgaaat tttggacaag ttacttaacc 3600
actttaaacc ccagctttaa gaagtaaatt aaccccagta aattaagaag taatagcagc 3660
cacttcgtag agttgttatg aggctcagat gcagtgcaaa tgtgtataaa gtattcaggg 3720
agtcacctgg tatactataa tagacactag aatagttgcc aatattatca gcatacaatc 3780
tgaggattct gtcagccaat cattagcaat ctgttgtttg ttgggacatg ccagtgttct 3840
ccagttgaaa tcagtagcaa tctaaaaatg gatagattat tcctcattta aatagtgtgt 3900
tcatataagt gattgcttgg atccttatca gaagttgctg ttactgaaaa atgataaggc 3960
tgactaaatt gtgatagttg tcagttacta accaactccc agaaatgaat aagaggaacc 4020
tatctctagt tcctagtaga aggtatggac aaaatagtag gtgaaaaata atgtcttgaa 4080
cccccaaatt aagtaagctt taaagagtac aatacctcaa agggtctttg cggtttaaaa 4140
tttgtatgct gagaatgatg ttcattgaca tgtgcctata tgtaattttt tgatagttta 4200
aaaggtgaaa tgaactacag atgggagagg tctgaatttt cttgccttca gtcaaatgtg 4260
taatgtggac atattatttg acctgtgaat tttatctttt aaaaaagatt aattcctgct 4320
tcttccttcc taatagttgc attataataa tgaaaatgag ttgataattt ggggggaaag 4380
tattctacaa atcaacctta ttattttacc attggtttct gagaaatttt gttcatttga 4440
accgtttata gcttgattag aatcatagca tgtaaaaccc aactgaggga ttatctgcag 4500
acttaatgta gtattatgta agttgtcttc tttcatttcg acctttttttg cttttgttgt 4560 tgctagatct gtagtatgta gctagtcacc tttcagcgag gtttcagcga ggcttttctg 4620
tgtctctagg ttatttgaga taactttttt aaaattagct cttgtcctcc 4670

<210> SEQ ID NO 110
<211> LENGTH: 761
<212> TYPE: PRT
<213> ORGANISM: Bos taurus

<400> SEQUENCE: 110

Met Lys Ile Gln Met Ser Ser Val Lys Val Trp Asn Ile Lys Gln Met
1 5 10 15

Ile Lys Leu Thr Gln Glu His Ile Glu Ala Leu Leu Asp Lys Phe Gly
20 25 30

Gly Glu His Asn Pro Pro Ser Ile Tyr Leu Glu Ala Tyr Glu Glu Tyr
35 40 45

Thr Ser Lys Leu Asp Ala Leu Gln Gln Arg Glu Gln Gln Leu Leu Glu
50 55 60

Ser Leu Gly Asn Gly Thr Asp Phe Ser Val Ser Ser Ser Ala Ser Thr
65 70 75 80

Asp Thr Val Thr Ser Ser Ser Ser Ser Ser Leu Ser Val Leu Pro Ser
85 90 95

Ser Leu Ser Val Phe Gln Asn Pro Thr Asp Val Ser Arg Ser Asn Pro
100 105 110

```
Lys Ser Pro Gln Lys Pro Ile Val Arg Val Phe Leu Pro Asn Lys Gln
        115                 120                 125

Arg Thr Val Val Pro Ala Arg Cys Gly Val Thr Val Arg Asp Ser Leu
    130                 135                 140

Lys Lys Ala Leu Met Met Arg Gly Leu Ile Pro Glu Cys Cys Ala Val
145                 150                 155                 160

Tyr Arg Ile Gln Asp Gly Glu Lys Lys Pro Ile Gly Trp Asp Thr Asp
                165                 170                 175

Ile Ser Trp Leu Thr Gly Glu Glu Leu His Val Glu Val Leu Glu Asn
            180                 185                 190

Val Pro Leu Thr Thr His Asn Phe Val Arg Lys Thr Phe Phe Thr Leu
        195                 200                 205

Ala Phe Cys Asp Phe Cys Arg Lys Leu Leu Phe Gln Gly Phe Arg Cys
    210                 215                 220

Gln Thr Cys Gly Tyr Lys Phe His Gln Arg Cys Ser Thr Glu Val Pro
225                 230                 235                 240

Leu Met Cys Val Asn Tyr Asp Gln Leu Asp Leu Leu Phe Val Ser Lys
                245                 250                 255

Phe Phe Glu His His Pro Ile Pro Gln Glu Glu Ala Ser Leu Ala Glu
            260                 265                 270

Thr Thr Leu Pro Cys Gly Ser Ser Pro Ser Ala Pro Pro Ser Asp Ser
        275                 280                 285

Ile Gly Pro Pro Ile Leu Thr Ser Pro Ser Pro Ser Lys Ser Ile Pro
    290                 295                 300

Ile Pro Gln Pro Phe Arg Pro Ala Asp Glu Asp His Arg Asn Gln Phe
305                 310                 315                 320

Gly Gln Arg Asp Arg Ser Ser Ser Ala Pro Asn Val His Ile Asn Thr
                325                 330                 335

Ile Glu Pro Val Asn Ile Asp Asp Leu Ile Arg Asp Gln Gly Phe Arg
            340                 345                 350

Ser Asp Gly Gly Ser Thr Thr Gly Leu Ser Ala Thr Pro Pro Ala Ser
        355                 360                 365

Leu Pro Gly Ser Leu Ser Asn Val Lys Ala Leu Gln Lys Ser Pro Gly
    370                 375                 380

Pro Gln Arg Glu Arg Lys Ser Ser Ser Ser Ser Glu Asp Arg Asn Arg
385                 390                 395                 400

Met Lys Thr Leu Gly Arg Arg Asp Ser Ser Asp Asp Trp Glu Ile Pro
                405                 410                 415

Asp Gly Gln Ile Thr Val Gly Gln Arg Ile Gly Ser Gly Ser Phe Gly
            420                 425                 430

Thr Val Tyr Lys Gly Lys Trp His Gly Asp Val Ala Val Lys Met Leu
        435                 440                 445

Asn Val Thr Ala Pro Thr Pro Gln Gln Leu Gln Ala Phe Lys Asn Glu
    450                 455                 460

Val Gly Val Leu Arg Lys Thr Arg His Val Asn Ile Leu Leu Phe Met
465                 470                 475                 480

Gly Tyr Ser Thr Lys Pro Gln Leu Ala Ile Val Thr Gln Trp Cys Glu
                485                 490                 495

Gly Ser Ser Leu Tyr His His Leu His Ile Ile Glu Thr Lys Phe Glu
            500                 505                 510

Met Ile Lys Leu Ile Asp Ile Ala Arg Gln Thr Ala Gln Gly Met Asp
        515                 520                 525
```

```
Tyr Leu His Ala Lys Ser Ile Ile His Arg Asp Leu Lys Ser Asn Asn
    530                 535                 540

Ile Phe Leu His Glu Asp Leu Thr Val Lys Ile Gly Asp Phe Gly Leu
545                 550                 555                 560

Ala Thr Val Lys Ser Arg Trp Ser Gly Ser His Gln Phe Glu Gln Leu
                565                 570                 575

Ser Gly Ser Ile Leu Trp Met Ala Pro Glu Val Ile Arg Met Gln Asp
            580                 585                 590

Lys Asn Pro Tyr Ser Phe Gln Ser Asp Val Tyr Ala Phe Gly Ile Val
        595                 600                 605

Leu Tyr Glu Leu Met Thr Gly Gln Leu Pro Tyr Ser Asn Ile Asn Asn
    610                 615                 620

Arg Asp Gln Ile Ile Phe Met Val Gly Arg Gly Tyr Leu Ser Pro Asp
625                 630                 635                 640

Leu Ser Lys Val Arg Ser Asn Cys Pro Lys Ala Met Lys Arg Leu Met
                645                 650                 655

Ala Glu Cys Leu Lys Lys Lys Arg Asp Glu Arg Pro Leu Phe Pro Gln
            660                 665                 670

Val Gly Lys Thr Leu Leu Ser Lys Arg Gln Asn Ser Glu Val Ile Arg
        675                 680                 685

Glu Lys Asp Lys Gln Ile Leu Ala Ser Ile Glu Leu Leu Ala Arg Ser
    690                 695                 700

Leu Pro Lys Ile His Arg Ser Ala Ser Glu Pro Ser Leu Asn Arg Ala
705                 710                 715                 720

Gly Phe Gln Thr Glu Asp Phe Ser Leu Tyr Ala Cys Ala Ser Pro Lys
                725                 730                 735

Thr Pro Ile Gln Ala Gly Gly Tyr Glu Ala Asp Leu Ala Leu Thr Ser
            740                 745                 750

Asn Lys Asn Arg Val Glu Val Gly Ile
        755                 760
```

<210> SEQ ID NO 111
<211> LENGTH: 4816
<212> TYPE: DNA
<213> ORGANISM: Bos taurus

<400> SEQUENCE: 111

```
ctcagctgcg ccgggtctca caagacggtt cccgaggtgg cccaggcgcc gtcccaccgc      60

cgacgccgcc cgggccgccc gggccgtccc tccccgctgc cccccgtcct ccgcctccgc     120

ctccccccgc cctcagcctc ccttcccccct ccccgcccag cagcggtcgc tcgggcccgg     180

ctctcggtta taagatggcg gcgctgagtg gcggcggcgg cggcggcggc ggtggcgcgg     240

agcagggcca ggctctgttc aacggggaca tggagcccga ggccggcgcc gcggcctctt     300

cggctgcgga ccccgccatt cccgaggagg tgtggaatat caaacaaatg attaagttga     360

cacaggagca tatagaggcc ctattggaca aatttggtgg ggagcataat ccaccatcaa     420

tatatctgga ggcctatgaa gaatacacca gcaagctaga tgccctccaa caaagagaac     480

aacagttatt ggaatccctg ggaatggaa ctgatttttc tgtttctagc tctgcatcaa     540

cggacaccgt tacatcttct tcctcttcta gcctttcagt gctgccttca tctctttcag     600

tttttcaaaa tcccacagat gtgtcacgga gcaaccccaa gtcaccacaa aaacctatcg     660

ttagagtctt cctgcccaat aaacagagga cagtggtacc tgcacggtgt ggagtcacag     720

tccgggacag cctgaagaag gcactgatga tgagaggtct aatcccagag tgctgtgctg     780
```

-continued

```
tttacagaat tcaggatggg gagaagaaac caattggctg ggacactgat atttcctggc    840
ttactggaga ggagttgcat gtagaagtgt tggagaatgt tccacttaca acacacaact    900
ttgtacggaa aacttttttc accttagcat tttgtgactt ctgtagaaag ctgcttttcc    960
agggattccg ctgtcaaaca tgtggttata aatttcacca gcgttgtagt acagaggttc   1020
cactgatgtg tgttaattat gaccaactag agcccccaat tctcaccagt ccatctcctt   1080
caaaatccat tccaattcca cagcctttcc gaccagcaga tgaagatcat cgaaatcagt   1140
ttggacaacg agaccggtcc tcatcagctc caaatgtgca tataaacaca atagaacccg   1200
tcaatattga tgacttgatt agagaccaag ggtttcgtag tgatggagga tcaaccacag   1260
gtttatccgc cacacccccct gcctcattac ctggctcact ctctaatgtg aaagcattgc   1320
agaaatctcc aggacctcag cgagaaagaa agtcctcttc atcctcagaa gacaggaatc   1380
gaatgaaaac gcttggtaga cgggattcaa gtgacgattg ggagattcct gatggacaga   1440
tcacagtggg acaaagaatt ggatcagggt catttgggac agtctacaag ggaaagtggc   1500
atggtgatgt ggcagtgaaa atgttgaatg tgacagcacc cacacctcag cagttacagg   1560
ccttcaaaaa tgaagtagga gtactcagga aaacgcgaca tgtgaatatc ctcctcttca   1620
tgggttattc aacaaagcca caactggcta ttgttaccca gtggtgtgag ggctccagtt   1680
tatatcatca tctccacatc attgagacca aattcgagat gatcaaactt atagatattg   1740
cacggcagac tgcacagggc atggattact tacacgccaa gtcaatcatc cacagagacc   1800
tcaagagtaa taatattttt cttcatgaag acctcacagt aaaaataggt gattttggtc   1860
tagccacagt gaaatctcga tggagtgggt cccatcagtt tgaacagttg tctggatcca   1920
ttttgtggat ggcaccagaa gtaatcagaa tgcaagataa aaacccatat agctttcagt   1980
cagatgtata tgcatttggg attgttctgt atgaattgat gaccggacag ttaccttatt   2040
caaatatcaa caacagggac cagataattt ttatggtggg acgaggatat ctgtctccag   2100
atctcagtaa ggtacggagt aactgtccaa aagccatgaa gagattaatg gcagagtgcc   2160
taaaaaagaa aagagatgaa agaccactct ttccccaagt aggaaagact ctcctaagca   2220
agagacaaaa ttcagaagtt atcagggaaa aagataagca gattctcgcc tctattgagc   2280
tgctggcccg ctcattgcca aaaattcacc gcagtgcatc agaaccctcc ttgaatcggg   2340
ctggcttcca aacagaggat tttagtctat atgcttgtgc ttctccaaaa acacccattc   2400
aggcaggggg atatgaagca gatttggctc ttacatcaaa taaaaataga gtagaagttg   2460
ggatttagag atttcctgac atgcaagaag gaataagcaa gaaaaaaagg tttgttttcc   2520
ccaaatcata tctattgtct tttacttcta ttttttctta aatttttttgt gatttcagag   2580
acatgtagag ttttattgat acctaaacta tgagttcttt tttttttttt tttttcatta   2640
ttttgatttt tttggccaag aggcatatgg gatcttagct tgagaaagca acaattttct   2700
tgatgtcatt ttgggtgagg gcacatattg ctgtgaacag tgtggtgata gccaccaggg   2760
accaaactca cacccgctgc attgaaaggt gaagtcttaa acactggacc agcagagaaa   2820
ttcctactct atgagttctt tttgtcatcc cctccccgca ccctccaccc ccaacctaaa   2880
gtctgatgat gaaatcaaca actattccat tagaagcagt agattctggt agcatgatct   2940
ttagtttgtt agtaagattt tgtgctttgt ggggttgtgt cgttttaagg ctaatattta   3000
agtttgtcaa atagaatgct gttcagattg taaaaatgag taataaacat ctgaagtttt   3060
ttttaagtta tttttaacat ggtatataca gttgagctta gagtttatca ttttctgata   3120
ttctcttact tagtagatga attctagcca ttttttataa agatttctgt taagcaaatc   3180
```

ctgttttcac atgggcttcc tttaagggat tttagattct gctggatatg gtgactgctc 3240
ataagactgt tgaaaattac ttttaagatg tattagaata cttctgaaaa aaaatagcaa 3300
ccttaaaacc ataagcaaaa gtagtaaggg tgtttataca tttctagagt ccctgtttag 3360
gtaatagcct cctatgattg tactttaaat gttttgctct ccaaggtttt agtaacttgg 3420 cttttttttct aatcagtgcc aaactccccc agttttttta actttaaata tgaggtaata 3480
aatcttttac ccttccttga tcttttgact tataatacct tggtcagttg tttcttaaaa 3540
ggaatcctta aatggaaaga gacaatatca ctgtctgcag ttctgattag tagttttatt 3600
cagaatggaa aaacagatta ttcatttttg aaaattgttc aggggtatgt tcattgttag 3660
gaccttggac tttggagtca gtgcctagct atgcattcca ggtctgccat tttctggctg 3720
tgaaattttg gacaagttac ttaaccactt taaaccccag ctttaagaag taaattaacc 3780
ccagtaaatt aagaagtaat agcagccact tcgtagagtt gttatgaggc tcagatgcag 3840
tgcaaatgtg tataaagtat tcagggagtc acctggtata ctataataga cactagaata 3900
gttgccaata ttatcagcat acaatctgag gattctgtca gccaatcatt agcaatctgt 3960
tgtttgttgg gacatgccag tgttctccag ttgaaatcag tagcaatcta aaaatggata 4020
gattattcct catttaaata gtgtgttcat ataagtgatt gcttggatcc ttatcagaag 4080
ttgctgttac tgaaaaatga taaggctgac taaattgtga tagttgtcag ttactaacca 4140
actcccagaa atgaataaga ggaacctatc tctagttcct agtagaaggt atggacaaaa 4200
tagtaggtga aaaataatgt cttgaacccc caaattaagt aagctttaaa gagtacaata 4260
cctcaaaggg tctttgcggt ttaaaatttg tatgctgaga atgatgttca ttgacatgtg 4320
cctatatgta attttttgat agtttaaaag gtgaaatgaa ctacagatgg gagaggtctg 4380
aattttcttg ccttcagtca aatgtgtaat gtggacatat tatttgacct gtgaatttta 4440
tcttttaaaa aagattaatt cctgcttctt ccttcctaat agttgcatta taataatgaa 4500
aatgagttga taatttgggg ggaaagtatt ctacaaatca accttattat tttaccattg 4560
gtttctgaga aattttgttc atttgaaccg tttatagctt gattagaatc atagcatgta 4620
aaacccaact gagggattat ctgcagactt aatgtagtat tatgtaagtt gtcttctttc 4680
atttcgacct tttttgcttt tgttgttgct agatctgtag tatgtagcta gtcacctttc 4740
agcgaggttt cagcgaggct tttctgtgtc tctaggttat ttgagataac ttttttaaaa 4800
ttagctcttg tcctcc 4816

<210> SEQ ID NO 112
<211> LENGTH: 757
<212> TYPE: PRT
<213> ORGANISM: Bos taurus

<400> SEQUENCE: 112

Met Ala Ala Leu Ser Gly Gly Gly Gly Gly Gly Gly Gly Gly Ala Glu
1 5 10 15

Gln Gly Gln Ala Leu Phe Asn Gly Asp Met Glu Pro Glu Ala Gly Ala
20 25 30

Ala Ala Ser Ser Ala Ala Asp Pro Ala Ile Pro Glu Glu Val Trp Asn
35 40 45

Ile Lys Gln Met Ile Lys Leu Thr Gln Glu His Ile Glu Ala Leu Leu
50 55 60

Asp Lys Phe Gly Gly Glu His Asn Pro Pro Ser Ile Tyr Leu Glu Ala
65 70 75 80

```
Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Glu Pro Pro
        275                 280                 285

Ile Leu Thr Ser Pro Ser Pro Ser Lys Ser Ile Pro Ile Pro Gln Pro
    290                 295                 300

Phe Arg Pro Ala Asp Glu Asp His Arg Asn Gln Phe Gly Gln Arg Asp
305                 310                 315                 320

Arg Ser Ser Ser Ala Pro Asn Val His Ile Asn Thr Ile Glu Pro Val
                325                 330                 335

Asn Ile Asp Asp Leu Ile Arg Asp Gln Gly Phe Arg Ser Asp Gly Gly
            340                 345                 350

Ser Thr Thr Gly Leu Ser Ala Thr Pro Pro Ala Ser Leu Pro Gly Ser
        355                 360                 365

Leu Ser Asn Val Lys Ala Leu Gln Lys Ser Pro Gly Pro Gln Arg Glu
    370                 375                 380

Arg Lys Ser Ser Ser Ser Ser Glu Asp Arg Asn Arg Met Lys Thr Leu
385                 390                 395                 400

Gly Arg Arg Asp Ser Ser Asp Asp Trp Glu Ile Pro Asp Gly Gln Ile
                405                 410                 415

Thr Val Gly Gln Arg Ile Gly Ser Gly Ser Phe Gly Thr Val Tyr Lys
            420                 425                 430

Gly Lys Trp His Gly Asp Val Ala Val Lys Met Leu Asn Val Thr Ala
        435                 440                 445

Pro Thr Pro Gln Gln Leu Gln Ala Phe Lys Asn Glu Val Gly Val Leu
    450                 455                 460

Arg Lys Thr Arg His Val Asn Ile Leu Leu Phe Met Gly Tyr Ser Thr
465                 470                 475                 480

Lys Pro Gln Leu Ala Ile Val Thr Gln Trp Cys Glu Gly Ser Ser Leu
                485                 490                 495
```

```
Tyr His His Leu His Ile Ile Glu Thr Lys Phe Glu Met Ile Lys Leu
            500                 505                 510

Ile Asp Ile Ala Arg Gln Thr Ala Gln Gly Met Asp Tyr Leu His Ala
        515                 520                 525

Lys Ser Ile Ile His Arg Asp Leu Lys Ser Asn Asn Ile Phe Leu His
    530                 535                 540

Glu Asp Leu Thr Val Lys Ile Gly Asp Phe Gly Leu Ala Thr Val Lys
545                 550                 555                 560

Ser Arg Trp Ser Gly Ser His Gln Phe Glu Gln Leu Ser Gly Ser Ile
                565                 570                 575

Leu Trp Met Ala Pro Glu Val Ile Arg Met Gln Asp Lys Asn Pro Tyr
            580                 585                 590

Ser Phe Gln Ser Asp Val Tyr Ala Phe Gly Ile Val Leu Tyr Glu Leu
        595                 600                 605

Met Thr Gly Gln Leu Pro Tyr Ser Asn Ile Asn Asn Arg Asp Gln Ile
    610                 615                 620

Ile Phe Met Val Gly Arg Gly Tyr Leu Ser Pro Asp Leu Ser Lys Val
625                 630                 635                 640

Arg Ser Asn Cys Pro Lys Ala Met Lys Arg Leu Met Ala Glu Cys Leu
                645                 650                 655

Lys Lys Lys Arg Asp Glu Arg Pro Leu Phe Pro Gln Val Gly Lys Thr
            660                 665                 670

Leu Leu Ser Lys Arg Gln Asn Ser Glu Val Ile Arg Glu Lys Asp Lys
        675                 680                 685

Gln Ile Leu Ala Ser Ile Glu Leu Leu Ala Arg Ser Leu Pro Lys Ile
    690                 695                 700

His Arg Ser Ala Ser Glu Pro Ser Leu Asn Arg Ala Gly Phe Gln Thr
705                 710                 715                 720

Glu Asp Phe Ser Leu Tyr Ala Cys Ala Ser Pro Lys Thr Pro Ile Gln
                725                 730                 735

Ala Gly Gly Tyr Glu Ala Asp Leu Ala Leu Thr Ser Asn Lys Asn Arg
            740                 745                 750

Val Glu Val Gly Ile
        755
```

<210> SEQ ID NO 113
<211> LENGTH: 2499
<212> TYPE: DNA
<213> ORGANISM: Bos taurus

<400> SEQUENCE: 113

```
ctcagctgcg ccgggtctca caagacggtt cccgaggtgg cccaggcgcc gtcccaccgc     60

cgacgccgcc cgggccgccc gggccgtccc tccccgctgc cccccgtcct ccgcctccgc    120

ctccccccgc cctcagcctc ccttccccct ccccgcccag cagcggtcgc tcgggcccgg    180

ctctcggtta taagatggcg gcgctgagtg gcggcggcgg cggcggcggc ggtggcgcgg    240

agcagggcca ggctctgttc aacggggaca tggagcccga ggccggcgcc gcggcctctt    300

cggctgcgga ccccgccatt cccgaggagg tgtggaatat caaacaaatg attaagttga    360

cacaggagca tatagaggcc ctattggaca aatttggtgg ggagcataat ccaccatcaa    420

tatatctgga ggcctatgaa gaatacacca gcaagctaga tgccctccaa caaagagaac    480

aacagttatt ggaatccctg gggaatggaa ctgatttttc tgtttctagc tctgcatcaa    540

cggacaccgt tacatcttct tcctcttcta gcctttcagt gctgccttca tctctttcag    600
```

-continued

```
tttttcaaaa tcccacagat gtgtcacgga gcaaccccaa gtcaccacaa aaacctatcg    660

ttagagtctt cctgcccaat aaacagagga cagtggtacc tgcacggtgt ggagtcacag    720

tccgggacag cctgaagaag gcactgatga tgagaggtct aatcccagag tgctgtgctg    780

tttacagaat tcaggatggg gagaagaaac caattggctg ggacactgat atttcctggc    840

ttactggaga ggagttgcat gtagaagtgt tggagaatgt tccacttaca acacacaact    900

ttgtacggaa aactttttc accttagcat tttgtgactt ctgtagaaag ctgcttttcc    960

agggattccg ctgtcaaaca tgtggttata aatttcacca gcgttgtagt acagaggttc   1020

cactgatgtg tgttaattat gaccaactag atttgctgtt tgtctccaag ttctttgaac   1080

accacccaat accacaggag gaggcctcct tagcagagac tacccttcca tgtggctcat   1140

ccccttctgc acccccctcc gattctattg ggcccccaat tctcaccagt ccatctcctt   1200

caaaatccat tccaattcca cagcctttcc gaccagcaga tgaagatcat cgaaatcagt   1260

ttggacaacg agaccggtcc tcatcagctc caaatgtgca tataaacaca atagaacccg   1320

tcaatattga tgacttgatt agagaccaag ggtttcgtag tgatggagga tcaaccacag   1380

gtttatccgc cacaccccct gcctcattac ctggctcact ctctaatgtg aaagcattgc   1440

agaaatctcc aggacctcag cgagaaagaa agtcctcttc atcctcagaa gacaggaatc   1500

gaatgaaaac gcttggtaga cgggattcaa gtgacgattg ggagattcct gatggacaga   1560

tcacagtggg acaaagaatt ggatcagggt catttgggac agtctacaag ggaaagtggc   1620

atggtgatgt ggcagtgaaa atgttgaatg tgacagcacc cacacctcag cagttacagg   1680

ccttcaaaaa tgaagtagga gtactcagga aaacgcgaca tgtgaatatc ctcctcttca   1740

tgggttattc aacaaagcca caactggcta ttgttaccca gtggtgtgag ggctccagtt   1800

tatatcatca tctccacatc attgagacca aattcgagat gatcaaactt atagatattg   1860

cacggcagac tgcacagggc atggattact tacacgccaa gtcaatcatc cacagagacc   1920

tcaagagtaa taatattttt cttcatgaag acctcacagt aaaaataggt gattttggtc   1980

tagccacagt gaaatctcga tggagtgggt cccatcagtt tgaacagttg tctggatcca   2040

ttttgtggat ggcaccagaa gtaatcagaa tgcaagataa aaacccatat agctttcagt   2100

cagatgtata tgcatttggg attgttctgt atgaattgat gaccggacag ttaccttatt   2160

caaatatcaa caacagggac cagataattt ttatggtggg acgaggatat ctgtctccag   2220

atctcagtaa ggtacggagt aactgtccaa aagccatgaa gagattaatg gcagagtgcc   2280

taaaaaagaa aagagatgaa agaccactct ttccccaagt aggaaagact ctcctaagca   2340

agagacaaaa ttcagaagtt atcagggaaa aagataagca ggaaaagtat gtttctttag   2400

tacattccag gcatttggga ttacagtaaa aacaatattc tcgcctctat tgagctgctg   2460

gcccgctcat tgccaaaaat tcaccgcagt gcatcagaa                          2499
```

<210> SEQ ID NO 114
<211> LENGTH: 744
<212> TYPE: PRT
<213> ORGANISM: Bos taurus

<400> SEQUENCE: 114

```
Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
```

```
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460
```

Gly Ser Phe Gly Thr Val Tyr Lys Gly Lys Trp His Gly Asp Val Ala
465 470 475 480

Val Lys Met Leu Asn Val Thr Ala Pro Thr Pro Gln Gln Leu Gln Ala
485 490 495

Phe Lys Asn Glu Val Gly Val Leu Arg Lys Thr Arg His Val Asn Ile
500 505 510

Leu Leu Phe Met Gly Tyr Ser Thr Lys Pro Gln Leu Ala Ile Val Thr
515 520 525

Gln Trp Cys Glu Gly Ser Ser Leu Tyr His His Leu His Ile Ile Glu
530 535 540

Thr Lys Phe Glu Met Ile Lys Leu Ile Asp Ile Ala Arg Gln Thr Ala
545 550 555 560

Gln Gly Met Asp Tyr Leu His Ala Lys Ser Ile Ile His Arg Asp Leu
565 570 575

Lys Ser Asn Asn Ile Phe Leu His Glu Asp Leu Thr Val Lys Ile Gly
580 585 590

Asp Phe Gly Leu Ala Thr Val Lys Ser Arg Trp Ser Gly Ser His Gln
595 600 605

Phe Glu Gln Leu Ser Gly Ser Ile Leu Trp Met Ala Pro Glu Val Ile
610 615 620

Arg Met Gln Asp Lys Asn Pro Tyr Ser Phe Gln Ser Asp Val Tyr Ala
625 630 635 640

Phe Gly Ile Val Leu Tyr Glu Leu Met Thr Gly Gln Leu Pro Tyr Ser
645 650 655

Asn Ile Asn Asn Arg Asp Gln Ile Ile Phe Met Val Gly Arg Gly Tyr
660 665 670

Leu Ser Pro Asp Leu Ser Lys Val Arg Ser Asn Cys Pro Lys Ala Met
675 680 685

Lys Arg Leu Met Ala Glu Cys Leu Lys Lys Lys Arg Asp Glu Arg Pro
690 695 700

Leu Phe Pro Gln Val Gly Lys Thr Leu Leu Ser Lys Arg Gln Asn Ser
705 710 715 720

Glu Val Ile Arg Glu Lys Asp Lys Gln Glu Lys Tyr Val Ser Leu Val
725 730 735

His Ser Arg His Leu Gly Leu Gln
740

<210> SEQ ID NO 115
<211> LENGTH: 2404
<212> TYPE: DNA
<213> ORGANISM: Bos taurus

<400> SEQUENCE: 115
ctcagctgcg ccgggtctca caagacggtt cccgaggtgg cccaggcgcc gtcccaccgc 60
cgacgccgcc cgggccgccc gggccgtccc tccccgctgc cccccgtcct ccgcctccgc 120
ctccccccgc cctcagcctc ccttccccct ccccgcccag cagcggtcgc tcgggcccgg 180
ctctcggtta taagatggcg gcgctgagtg gcggcggcgg cggcggcggc ggtggcgcgg 240
agcagggcca ggctctgttc aacggggaca tggagcccga ggccggcgcc gcggcctctt 300
cggctgcgga ccccgccatt cccgaggagg tgtggaatat caaacaaatg attaagttga 360
cacaggagca tatagaggcc ctattggaca aatttggtgg ggagcataat ccaccatcaa 420
tatatctgga ggcctatgaa gaatacacca gcaagctaga tgccctccaa caaagagaac 480

```
aacagttatt ggaatccctg gggaatggaa ctgatttttc tgtttctagc tctgcatcaa    540

cggacaccgt tacatcttct tcctcttcta gcctttcagt gctgccttca tctctttcag    600

tttttcaaaa tcccacagat gtgtcacgga gcaaccccaa gtcaccacaa aaacctatcg    660

ttagagtctt cctgcccaat aaacagagga cagtggtacc tgcacggtgt ggagtcacag    720

tccgggacag cctgaagaag gcactgatga tgagaggtct aatcccagag tgctgtgctg    780

tttacagaat tcaggatggg gagaagaaac caattggctg ggacactgat atttcctggc    840

ttactggaga ggagttgcat gtagaagtgt tggagaatgt tccacttaca acacacaact    900

ttgtacggaa aactttttc accttagcat tttgtgactt ctgtagaaag ctgcttttcc     960

agggattccg ctgtcaaaca tgtggttata aatttcacca gcgttgtagt acagaggttc   1020

cactgatgtg tgttaattat gaccaactag atttgctgtt tgtctccaag ttctttgaac   1080

accacccaat accacaggag gaggcctcct tagcagagac tacccttcca tgtggctcat   1140

ccccttctgc acccccctcc gattctattg ggcccccaat tctcaccagt ccatctcctt   1200

caaaatccat tccaattcca cagcctttcc gaccagcaga tgaagatcat cgaaatcagt   1260

ttggacaacg agaccggtcc tcatcagctc caaatgtgca tataaacaca atagaacccg   1320

tcaatattga tgacttgatt agagaccaag ggtttcgtag tgatggagga tcaaccacag   1380

gtttatccgc cacacccct gcctcattac ctggctcact ctctaatgtg aaagcattgc    1440

agaaatctcc aggacctcag cgagaaagaa agtcctcttc atcctcagaa gacaggaatc   1500

gaatgaaaac gcttggtaga cgggattcaa gtgacgattg ggagattcct gatggacaga   1560

tcacagtggg acaaagaatt ggatcagggt catttgggac agtctacaag ggaaagtggc   1620

atggtgatgt ggcagtgaaa atgttgaatg tgacagcacc cacacctcag cagttacagg   1680

ccttcaaaaa tgaagtagga gtactcagga aaacgcgaca tgtgaatatc ctcctcttca   1740

tgggttattc aacaaagcca caactggcta ttgttaccca gtggtgtgag ggctccagtt   1800

tatatcatca tctccacatc attgagacca aattcgagat gatcaaactt atagatattg   1860

cacggcagac tgcacagggc atggattact tacacgccaa gtcaatcatc cacagagacc   1920

tcaagagtaa taatattttt cttcatgaag acctcacagt aaaaataggt gattttggtc   1980

tagccacagt gaaatctcga tggagtgggt cccatcagtt tgaacagttg tctggatcca   2040

ttttgtggat ggcaccagaa gtaatcagaa tgcaagataa aaacccatat agctttcagt   2100

cagatgtata tgcatttggg attgttctgt atgaattgat gaccggacag ttaccttatt   2160

caaatatcaa caacagggac cagataattt ttatggtggg acgaggatat ctgtctccag   2220

atctcagtaa ggtacggagt aactgtccaa aagccatgaa gagattaatg gcagagtgcc   2280

taaaaaagaa aagagatgaa agaccactct ttccccaaga tctctcttcc caccatagac   2340

acaaaaattt cagatggcta caggtttaca tgtaaaaaac agaattataa caaatgattt   2400

ttat                                                                2404
```

<210> SEQ ID NO 116
<211> LENGTH: 726
<212> TYPE: PRT
<213> ORGANISM: Bos taurus

<400> SEQUENCE: 116

```
Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30
```

```
Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445
```

-continued

```
Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Asp Leu Ser Ser His His Arg His Lys Asn Phe Arg
705                 710                 715                 720

Trp Leu Gln Val Tyr Met
                725
```

<210> SEQ ID NO 117
<211> LENGTH: 2331
<212> TYPE: DNA
<213> ORGANISM: Bos taurus

<400> SEQUENCE: 117

```
ctcagctgcg ccgggtctca caagacggtt cccgaggtgg cccaggcgcc gtcccaccgc      60

cgacgccgcc cgggccgccc gggccgtccc tccccgctgc cccccgtcct ccgcctccgc     120

ctccccccgc cctcagcctc ccttccccct ccccgcccag cagcggtcgc tcgggcccgg     180

ctctcggtta taagatggcg gcgctgagtg gcggcggcgg cggcggcggc ggtggcgcgg     240

agcagggcca ggctctgttc aacggggaca tggagcccga ggccggcgcc gcggcctctt     300

cggctgcgga ccccgccatt cccgaggagg tgtggaatat caaacaaatg attaagttga     360

cacaggagca tatagaggcc ctattggaca aatttggtgg ggagcataat ccaccatcaa     420

tatatctgga ggcctatgaa gaatacacca gcaagctaga tgccctccaa caaagagaac     480

aacagttatt ggaatccctg ggaatggaa ctgatttttc tgtttctagc tctgcatcaa     540
```

```
cggacaccgt tacatcttct tcctcttcta gcctttcagt gctgccttca tctctttcag    600
tttttcaaaa tcccacagat gtgtcacgga gcaaccccaa gtcaccacaa aaacctatcg    660
ttagagtctt cctgcccaat aaacagagga cagtggtacc tgcacggtgt ggagtcacag    720
tccgggacag cctgaagaag gcactgatga tgagaggtct aatcccagag tgctgtgctg    780
tttacagaat tcaggatggg gagaagaaac caattggctg ggacactgat atttcctggc    840
ttactggaga ggagttgcat gtagaagtgt tggagaatgt tccacttaca acacacaact    900
ttgtacggaa aactttttc accttagcat tttgtgactt ctgtagaaag ctgcttttcc    960
agggattccg ctgtcaaaca tgtggttata aatttcacca gcgttgtagt acagaggttc   1020
cactgatgtg tgttaattat gaccaactag atttgctgtt tgtctccaag ttctttgaac   1080
accacccaat accacaggag gaggcctcct tagcagagac tacccttcca tgtggctcat   1140
ccccttctgc acccccctcc gattctattg ggcccccaat tctcaccagt ccatctcctt   1200
caaaatccat tccaattcca cagcctttcc gaccagcaga tgaagatcat cgaaatcagt   1260
ttggacaacg agaccggtcc tcatcagctc caaatgtgca tataaacaca atagaacccg   1320
tcaatattga tgacttgatt agagaccaag ggtttcgtag tgatggagga tcaaccacag   1380
gtttatccgc cacaccccct gcctcattac ctggctcact ctctaatgtg aaagcattgc   1440
agaaatctcc aggacctcag cgagaaagaa agtcctcttc atcctcagaa gacaggaatc   1500
gaatgaaaac gcttggtaga cgggattcaa gtgacgattg ggagattcct gatggacaga   1560
tcacagtggg acaaagaatt ggatcagggt catttgggac agtctacaag ggaaagtggc   1620
atggtgatgt ggcagtgaaa atgttgaatg tgacagcacc cacacctcag cagttacagg   1680
ccttcaaaaa tgaagtagga gtactcagga aaacgcgaca tgtgaatatc ctcctcttca   1740
tgggttattc aacaaagcca caactggcta ttgttaccca gtggtgtgag ggctccagtt   1800
tatatcatca tctccacatc attgagacca aattcgagat gatcaaactt atagatattg   1860
cacggcagac tgcacagggc atggattact tacacgccaa gtcaatcatc cacagagacc   1920
tcaagagtaa taatattttt cttcatgaag acctcacagt aaaaataggt gatttggtc    1980
tagccacagt gaaatctcga tggagtgggt cccatcagtt tgaacagttg tctggatcca   2040
ttttgtggat ggcaccagaa gtaatcagaa tgcaagataa aaacccatat agctttcagt   2100
cagatgtata tgcatttggg attgttctgt atgaattgat gaccggacag ttaccttatt   2160
caaatatcaa caacagggac caggtgcttt gtcctccatg ggagtgtaat aaatgctgtg   2220
caagggctta cttcccatga gagaagtgag tgaccaacag aaggataatt tttatggtgg   2280
gacgaggata tctgtctcca gatctcagta aggtacggag taactgtcca a            2331
```

<210> SEQ ID NO 118
<211> LENGTH: 681
<212> TYPE: PRT
<213> ORGANISM: Bos taurus

<400> SEQUENCE: 118

```
Met Ala Ala Leu Ser Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
```

```
            50                  55                  60
Asp Lys Phe Gly Gly Glu His Asn Pro Pro Ser Ile Tyr Leu Glu Ala
 65                  70                  75                  80

Tyr Glu Glu Tyr Thr Ser Lys Leu Asp Ala Leu Gln Gln Arg Glu Gln
                     85                  90                  95

Gln Leu Leu Glu Ser Leu Gly Asn Gly Thr Asp Phe Ser Val Ser Ser
                100                 105                 110

Ser Ala Ser Thr Asp Thr Val Thr Ser Ser Ser Ser Ser Ser Leu Ser
                115                 120                 125

Val Leu Pro Ser Ser Leu Ser Val Phe Gln Asn Pro Thr Asp Val Ser
130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
                180                 185                 190

Cys Cys Ala Val Tyr Arg Ile Gln Asp Gly Glu Lys Lys Pro Ile Gly
                195                 200                 205

Trp Asp Thr Asp Ile Ser Trp Leu Thr Gly Glu Glu Leu His Val Glu
210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
                260                 265                 270

Thr Glu Val Pro Leu Met Cys Val Asn Tyr Asp Gln Leu Asp Leu Leu
                275                 280                 285

Phe Val Ser Lys Phe Phe Glu His His Pro Ile Pro Gln Glu Glu Ala
                290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
                340                 345                 350

Arg Asn Gln Phe Gly Gln Arg Asp Arg Ser Ser Ser Ala Pro Asn Val
                355                 360                 365

His Ile Asn Thr Ile Glu Pro Val Asn Ile Asp Asp Leu Ile Arg Asp
                370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
                420                 425                 430

Asp Arg Asn Arg Met Lys Thr Leu Gly Arg Arg Asp Ser Ser Asp Asp
                435                 440                 445

Trp Glu Ile Pro Asp Gly Gln Ile Thr Val Gly Gln Arg Ile Gly Ser
                450                 455                 460

Gly Ser Phe Gly Thr Val Tyr Lys Gly Lys Trp His Gly Asp Val Ala
465                 470                 475                 480
```

```
Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Val Leu Cys Pro Pro Trp Glu Cys Asn
            660                 665                 670

Lys Cys Cys Ala Arg Ala Tyr Phe Pro
        675                 680
```

<210> SEQ ID NO 119
<211> LENGTH: 2319
<212> TYPE: DNA
<213> ORGANISM: Bos taurus

<400> SEQUENCE: 119

```
ctcagctgcg ccgggtctca caagacggtt cccgaggtgg cccaggcgcc gtcccaccgc     60

cgacgccgcc cgggccgccc gggccgtccc tccccgctgc cccccgtcct ccgcctccgc    120

ctccccccgc cctcagcctc ccttcccccct ccccgcccag cagcggtcgc tcgggcccgg    180

ctctcggtta taagatggcg gcgctgagtg gcggcggcgg cggcggcggc ggtggcgcgg    240

agcagggcca ggctctgttc aacggggaca tggagcccga ggccggcgcc gcggcctctt    300

cggctgcgga ccccgccatt cccgaggagg tgtggaatat caaacaaatg attaagttga    360

cacaggagca tatagaggcc ctattggaca aatttggtgg ggagcataat ccaccatcaa    420

tatatctgga ggcctatgaa gaatacacca gcaagctaga tgccctccaa caaagagaac    480

aacagttatt ggaatccctg gggaatggaa ctgatttttc tgtttctagc tctgcatcaa    540

cggacaccgt tacatcttct tcctcttcta gcctttcagt gctgccttca tctctttcag    600

tttttcaaaa tcccacagat gtgtcacgga gcaaccccaa gtcaccacaa aaacctatcg    660

ttagagtctt cctgcccaat aaacagagga cagtggtacc tgcacggtgt ggagtcacag    720

tccgggacag cctgaagaag gcactgatga tgagaggtct aatcccagag tgctgtgctg    780

tttacagaat tcaggatggg gagaagaaac caattggctg ggacactgat atttcctggc    840

ttactggaga ggagttgcat gtagaagtgt tggagaatgt tccacttaca acacacaact    900

ttgtacggaa aactttttc accttagcat tttgtgactt ctgtagaaag ctgcttttcc    960
```

agggattccg ctgtcaaaca tgtggttata aatttcacca gcgttgtagt acagaggttc 1020
cactgatgtg tgttaattat gaccaactag atttgctgtt tgtctccaag ttctttgaac 1080
accacccaat accacaggag gaggcctcct tagcagagac tacccttcca tgtggctcat 1140
ccccttctgc acccccctcc gattctattg ggcccccaat tctcaccagt ccatctcctt 1200
caaaatccat tccaattcca cagcctttcc gaccagcaga tgaagatcat cgaaatcagt 1260
ttggacaacg agaccggtcc tcatcagctc caaatgtgca tataaacaca atagaacccg 1320
tcaatattga tgacttgatt agagaccaag ggtttcgtag tgatggagga tcaaccacag 1380
gtttatccgc cacaccccct gcctcattac ctggctcact ctctaatgtg aaagcattgc 1440
agaaatctcc aggacctcag cgagaaagaa agtcctcttc atcctcagaa gacaggaatc 1500
gaatgaaaac gcttggtaga cgggattcaa gtgacgattg ggagattcct gatggacaga 1560
tcacagtggg acaaagaatt ggatcagggt catttgggac agtctacaag ggaaagtggc 1620
atggtgatgt ggcagtgaaa atgttgaatg tgacagcacc cacacctcag cagttacagg 1680
ccttcaaaaa tgaagtagga gtactcagga aaacgcgaca tgtgaatatc ctcctcttca 1740
tgggttattc aacaaagcca caactggcta ttgttaccca gtggtgtgag ggctccagtt 1800
tatatcatca tctccacatc attgagacca aattcgagat gatcaaactt atagatattg 1860
cacggcagac tgcacagggc atggattact tacacgccaa gtcaatcatc cacagagacc 1920
tcaagagtaa taatattttt cttcatgaag acctcacagt aaaaataggt gattttggtc 1980
tagccacagt gaaatctcga tggagtgggt cccatcagtt tgaacagttg tctggatcca 2040
ttttgtggat ggcaccagaa gtaatcagaa tgcaagataa aaacccatat agctttcagt 2100
cagatgtata tgcatttggg attgttctgt atgaattgat gaccggacag ttaccttatt 2160
caaatatcaa caacagggac caggtgcttt gtcctccatg ggagtgtaat aaatgctgtg 2220
caagggctta cttcccatga gagaagtgag tgaccaacag aaggtctgtg caaggaaaag 2280
agacaaagcc acggatcaga agcacatggc cataactga 2319

<210> SEQ ID NO 120
<211> LENGTH: 681
<212> TYPE: PRT
<213> ORGANISM: Bos taurus

<400> SEQUENCE: 120

Met Ala Ala Leu Ser Gly Gly Gly Gly Gly Gly Gly Gly Gly Ala Glu
1 5 10 15

Gln Gly Gln Ala Leu Phe Asn Gly Asp Met Glu Pro Glu Ala Gly Ala
20 25 30

Ala Ala Ser Ser Ala Ala Asp Pro Ala Ile Pro Glu Glu Val Trp Asn
35 40 45

Ile Lys Gln Met Ile Lys Leu Thr Gln Glu His Ile Glu Ala Leu Leu
50 55 60

Asp Lys Phe Gly Gly Glu His Asn Pro Pro Ser Ile Tyr Leu Glu Ala
65 70 75 80

Tyr Glu Glu Tyr Thr Ser Lys Leu Asp Ala Leu Gln Gln Arg Glu Gln
85 90 95

Gln Leu Leu Glu Ser Leu Gly Asn Gly Thr Asp Phe Ser Val Ser Ser
100 105 110

Ser Ala Ser Thr Asp Thr Val Thr Ser Ser Ser Ser Ser Ser Leu Ser
115 120 125

-continued

```
Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
```

```
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Val Leu Cys Pro Pro Trp Glu Cys Asn
            660                 665                 670

Lys Cys Cys Ala Arg Ala Tyr Phe Pro
        675                 680


<210> SEQ ID NO 121
<211> LENGTH: 2661
<212> TYPE: DNA
<213> ORGANISM: Bos taurus

<400> SEQUENCE: 121

tcagctgcgc cgggtctcac aagacggttc ccgaggtggc ccaggcgccg tcccaccgcc      60

gacgccgccc gggccgcccg ggccgtccct ccccgctgcc ccccgtcctc cgcctccgcc     120

tccccccgcc ctcagcctcc cttccccctc cccgcccagc agcggtcgct cgggcccggc     180

tctcggttat aagatggcgg cgctgagtgg cggcggcggc ggcggcggcg gtggcgcgga     240

gcagggccag gctctgttca acggggacat ggagcccgag gccggcgccg cggcctcttc     300

ggctgcggac cccgccattc ccgaggaggt gtggaatatc aaacaaatga ttaagttgac     360

acaggagcat atagaggccc tattggacaa atttggtggg gagcataatc caccatcaat     420

atatctggag gcctatgaag aatacaccag caagctagat gccctccaac aaagagaaca     480

acagttattg gaatccctgg ggaatggaac tgatttttct gtttctagct ctgcatcaac     540

ggacaccgtt acatcttctt cctcttctag cctttcagtg ctgccttcat ctctttcagt     600

tttcaaaat cccacagatg tgtcacggag caaccccaag tcaccacaaa aacctatcgt     660

tagagtcttc ctgcccaata aacagaggac agtggtacct gcacggtgtg gagtcacagt     720

ccgggacagc ctgaagaagg cactgatgat gagaggtcta atcccagagt gctgtgctgt     780

ttacagaatt caggatgggg agaagaaacc aattggctgg gacactgata tttcctggct     840

tactggagag gagttgcatg tagaagtgtt ggagaatgtt ccacttacaa cacacaactt     900

tgtacggaaa actttttca ccttagcatt ttgtgacttc tgtagaaagc tgcttttcca     960

gggattccgc tgtcaaacat gtggttataa atttcaccag cgttgtagta cagaggttcc    1020

actgatgtgt gttaattatg accaactaga tttgctgttt gtctccaagt tctttgaaca    1080

ccacccaata ccacaggagg aggcctcctt agcagagact acccttccat gtggctcatc    1140

cccttctgca cccccctccg attctattgg gcccccaatt ctcaccagtc catctccttc    1200

aaaatccatt ccaattccac agcctttccg accagcagat gaagatcatc gaaatcagtt    1260

tggacaacga gaccggtcct catcagctcc aaatgtgcat ataaacacaa tagaacccgt    1320

caatattgat gacttgatta gagaccaagg gtttcgtagt gatggaggat caaccacagg    1380
```

```
tttatccgcc acacccccctg cctcattacc tggctcactc tctaatgtga aagcattgca   1440
gaaatctcca ggacctcagc gagaaagaaa gtcctcttca tcctcagaag acaggaatcg   1500
aatgaaaacg cttggtagac gggattcaag tgacgattgg gagattcctg atggacagat   1560
cacagtggga caaagaattg gatcagggtc atttgggaca gtctacaagg gaaagtggca   1620
tggtgatgtg gcagtgaaaa tgttgaatgt gacagcaccc acacctcagc agttacaggc   1680
cttcaaaaat gaagtaggag tactcaggaa aacgcgacat gtgaatatcc tcctcttcat   1740
gggttattca acaaagccac aactggctat tgttacccag tggtgtgagg gctccagttt   1800
atatcatcat ctccacatca ttgagaccaa attcgagatg atcaaactta tagatattgc   1860
acggcagact gcacagggca tggattactt acacgccaag tcaatcatcc acagagacct   1920
caagagtaat aatatttttc ttcatgaaga cctcacagta aaaataggtg attttggtct   1980
agccacagtg aaatctcgat ggagtgggtc ccatcagttt gaacagttgt ctggatccat   2040
tttgtggatg gcaccagaag taatcagaat gcaagataaa aacccatata gctttcagtc   2100
agatgtatat gcatttggga ttgttctgta tgaattgatg accggacagt taccttattc   2160
aaatatcaac aacagggacc agtctgtgca aggaaaagag acaaagccac ggatcagaag   2220
cacatggcca taactgaaga ttttgtgaac tctcacaagg aaaaaatttg ctctttgaac   2280
aataagaagg aactcactaa aatgtaactg agaactgttc aacaggttga aagctgaaag   2340
atgccattgg aactgacaaa atgtttctta aacataaatg atgaaacagt gaaactacat   2400
aatatctcct ctggctgaaa cattcaagaa gtttaaaatg cttaagttaa aaataaaatc   2460
ctagtaaaca atggacttac tgtgcaacat agagaatatc ttacgataac ctgtaatgga   2520
aaagaatctg aaaaagaatg tatataactg aatcactttg ctgtaaacta gaatctgaca   2580
caacactgta aatcactaca cttttctgtt gcatgccaaa gattatttaa taacgtcatt   2640
aaaaaattat tttaataatt a                                              2661

<210> SEQ ID NO 122
<211> LENGTH: 679
<212> TYPE: PRT
<213> ORGANISM: Bos taurus

<400> SEQUENCE: 122

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Leu Ser
        115                 120                 125

Val Leu Pro Ser Ser Leu Ser Val Phe Gln Asn Pro Thr Asp Val Ser
    130                 135                 140
```

-continued

```
Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560
```

```
Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ser Val Gln Gly Lys Glu Thr Lys Pro
            660                 665                 670

Arg Ile Arg Ser Thr Trp Pro
        675
```

<210> SEQ ID NO 123
<211> LENGTH: 7434
<212> TYPE: DNA
<213> ORGANISM: Bos taurus

<400> SEQUENCE: 123

```
acaccgttac atcttcttcc tcttctagcc tttcagtgct gccttcatct ctttcagttt     60

ttcaaaatcc cacagatgtg tcacggagca accccaagtc accacaaaaa cctatcgtta    120

gagtcttcct gcccaataaa cagaggacag tggtacctgc acggtgtgga gtcacagtcc    180

gggacagcct gaagaaggca ctgatgatga gaggtctaat cccagagtgc tgtgctgttt    240

acagaattca ggatggggag aagaaaccaa ttggctggga cactgatatt tcctggctta    300

ctggagagga gttgcatgta gaagtgttgg agaatgttcc acttacaaca cacaactttg    360

tacggaaaac ttttttcacc ttagcatttt gtgacttctg tagaaagctg cttttccagg    420

gattccgctg tcaaacatgt ggttataaat ttcaccagcg ttgtagtaca gaggttccac    480

tgatgtgtgt taattatgac caactagatt tgctgtttgt ctccaagttc tttgaacacc    540

acccaatacc acaggaggag gcctccttag cagagactac ccttccatgt ggctcatccc    600

cttctgcacc cccctccgat tctattgggc ccccaattct caccagtcca tctccttcaa    660

aatccattcc aattccacag cctttccgac cagcagatga agatcatcga aatcagtttg    720

gacaacgaga ccggtcctca tcagctccaa atgtgcatat aaacacaata gaacccgtca    780

atattgatga cttgattaga gaccaagggt ttcgtagtga tggaggatca accacaggtt    840

tatccgccac acccccctgcc tcattacctg gctcactctc taatgtgaaa gcattgcaga    900

aatctccagg acctcagcga gaaagaaagt cctcttcatc ctcagaagac aggaatcgaa    960

tgaaaacgct tggtagacgg gattcaagtg acgattggga gattcctgat ggacagatca   1020

cagtgggaca aagaattgga tcagggtcat ttgggacagt ctacaaggga aagtggcatg   1080

gtgatgtggc agtgaaaatg ttgaatgtga cagcacccac acctcagcag ttacaggcct   1140

tcaaaaatga agtaggagta ctcaggaaaa cgcgacatgt gaatatcctc ctcttcatgg   1200

gttattcaac aaagccacaa ctggctattg ttacccagtg gtgtgagggc tccagtttat   1260

atcatcatct ccacatcatt gagaccaaat tcgagatgat caaacttata gatattgcac   1320

ggcagactgc acagggcatg gattacttac acgccaagtc aatcatccac agagacctca   1380

agagtaataa tatttttctt catgaagacc tcacagtaaa aataggtgat tttggtctag   1440
```

```
ccacagtgaa atctcgatgg agtgggtccc atcagtttga acagttgtct ggatccattt   1500
tgtggatggc accagaagta atcagaatgc aagataaaaa cccatatagc tttcagtcag   1560
atgtatatgc atttgggatt gttctgtatg aattgatgac cggacagtta ccttattcaa   1620
atatcaacaa cagggaccag ataattttta tggtgggacg aggatatctg tctccagatc   1680
tcagtaaggt acggagtaac tgtccaaaag ccatgaagag attaatggca gagtgcctaa   1740
aaaagaaaag agatgaaaga ccactctttc cccaagtagg aaagactctc ctaagcaaga   1800
gacaaaattc agaagttatc agggaaaaag ataagcagat tctcgcctct attgagctgc   1860
tggcccgctc attgccaaaa attcaccgca gtgcatcaga accctccttg aatcgggctg   1920
gcttccaaac agaggatttt agtctatatg cttgtgcttc tccaaaaaca cccattcagg   1980
caggggggata tggagaattt gcagccttca agtagccaca ccatcatgac agcatctact   2040
cttatttctt aagtcttgtg ttcgtacaat ttgttaacat caaaacacag ttctgttcct   2100
caactctttt taaagttaaa atttttcagt gcataagctg gtgtggaaca gaaggaaatt   2160
tcccatccaa caaaagaggg aagaatgttt taggaaccag aattctctgc tgccagtgtt   2220
tcttcttcaa cacaaatatc acaagtctgc ccactcccag gaagaaagag gagagaccct   2280
gagttctgac cttttgatgg tcaggcatga tggaaagaaa ctgctgctac agcttgggag   2340
atttgctctg ggaagtctgc cagtcaactt tgcccttcta accaccagat caatatgtgg   2400
ctgatcatct gatggggcag ttgcaatcac caagccttgt tctctttcct gttctgggat   2460
tgtgttgtgg aaccctttc cctagccacc accagttcat ttctgaggga tggaacaaaa   2520
atgcagcatg cccttcctgt gtggtgcatg ttcagtcctt gacaaatttt taccaaaatg   2580
aagctacttt atttaaaagg agggtgagag gtgaggaggt cactttgggt gtggcggaaa   2640
gggaatgctg catcttttttc ctgggctgct ggggctctgg ccttggcttg ccagccggaa   2700
gcgctggcac gcatcgcctt cttttcccat tgggtccagc aatgaagacg agtgtttggg   2760
gttttttttt tctccaccat gtagcaagtt ctcaggaaaa tacaattgat atcttcctcc   2820
taagctcttc caatcagtca ccaagtactt atgtggttac tttgtccagg gcacaaaatg   2880
cctgtatcta attaaaagcc tacaaaactg cttgataaca gttttgaatg tgagacattt   2940
atgtaattta aatgtaaggt acaagtttta atttctgagt ttcttctatt atatttttat   3000
taaaaaaaga aaataatttt cagattgaat tggagtaaaa taatattact tcccactaga   3060
attatatatc ctggaaaatt gtatttttgt tacataagca gcttttaaag aaagatcatt   3120
acccttttct ctacataaat atatggggag tcttagccta atgacaaata tttataattt   3180
ttaaattaat ggtacttgct ggatccatac taacatcttt actaatacct cattgtttct   3240
tccaacttac tcctacacta catcctacat cttcttccta gtcttttatc tagaatatgc   3300
aacctcaaat aaaaatggtg gtgtcctcat tcattctcct ccttcctttt ttcccaagcc   3360
tgatcttcaa aaggttggtt aatttggcag ctgagttcct ccccaggcag agaatagacc   3420
aattttaggt gtattgggac tgagggagga tgtgtaaaga ttaacatcag taaagaaccg   3480
ctgtggagta attaagaact ttgttcttta taactggaga atataaccta accctaacat   3540
ccctcagcct ttactaaagt gtggcgtaaa tcacagtagt agcaaagaaa gtgactctgg   3600
atgtgttcct ggccagtacc tcccttatca tgaatgtaga ctctctcatc aagatttagg   3660
aatataaatc aaatcaaatg tgcccagcca agctatgtag taagggactt gaacaatatt   3720
aggcagaacc tataaaataa atcagggaat tagaaattat ttaaagtttt caaattgtaa   3780
```

-continued

```
attgccccgg tgtctttcag cctactgcca ttatttttgc tacaatacct acatttcaga   3840
ggagggccta ctgaaaattc catgcaagtg gaaaataatc ctcaagttat taatgagttt   3900
gaaaagcaat gagttcttaa gtctttgtga gtagagcaag atcctacaaa attcagaaat   3960
agtaaaaatg gattcatgct gatttgaaga gcatctgtgt gcataatata atgctgcatc   4020
tcttttaaaa gcagtctatt tttcttttta aatttgtccc catagatgct tttgaacatg   4080
aacatgctta tgttaccttt tccgaggttg ggaagagcca ggagctctca ggcagggccc   4140
cctccctcag ctgggcagga gctgctcagg aggagctagt tatagaggaa gcttagcgtt   4200
ggcattttca aaattcaagg tgataacgct ttcttcttcc tttctgtttt agaatagatt   4260
gctgtctgat ttgaaaaagg gaaatagatt tgatctcaaa tgaatctgtg cccagaagcc   4320
aggctcaggg tattcagaga tttgtatagt gccctcaaaa aataacaaaa ttttagcttt   4380
ccttttttct tcttttctcc atcaaattct tttttctcta gtttacaaat gacatggaaa   4440
aggaatttcc cctgagtttt gtatgccttt tttttttgg cttagactat agataggcgt   4500
gttgagctcc taagaaaata caaggaggaa ctctttgttg tgcagagcac tttatgagta   4560
gtttgtgtgg ataatatgtg actgcttccc tgacgagctt gtgaggctgt acttatgtct   4620
ttcctgtaag gcagcttcag tgccttctgt agtgtatata aggaaagatt acgccttctg   4680
aaaaatctca gagcaaccat aagattattt taaaatatgt agtatgactg atggactttt   4740
tcatcattaa attagtctag catctaaact tttaccactg aaataatatt gaccaaaaag   4800
caatttataa aaggtatttg tgaatagaaa atacaatgtg atcatttgta cttatgtgca   4860
ccttaaaaga ggaattctgt ctagctgtca aattctggtt ccttaacatc cagtccttga   4920
ttgtgattga gatctggtag gacgtgctgg ggcacgctag cagataaaat cccgtatact   4980
ttaggataga tgttacattt atgtcagtgt tggcaaagag cattgtgtag taataaagaa   5040
ttcaagactt cagcaatgtc aacctgaaac tttgtaaata tttcctagat tgttatttga   5100
tgcagtcaca gctctttatc acacaatgtt gtctttccct catcaggcaa ttttagaact   5160
gctgcacacc cctcctcaga tctcacctgc ccctcctgta cattcacctc tccagccttg   5220
tgcacacctc atttagcttt agtttgaaac acattgcagg gttcaggtga cctcttcaaa   5280
aactacctcc tcagaatgag gtaatgaata gttatttatt ttaaaatatg aaaagtcagg   5340
agctctagaa tatgaagatg atctaagatt ttaactttta tgtatacttg ttgagcactc   5400
tccttttgtc ctaaagggca ttatacattt aagcagtaat actgaaaaat gtagctcaga   5460
gtaactgaat gttgttgaaa gtggtgccag aatctgtttt aggggtacgt atcagaatct   5520
taatcttaaa tcggttacat gaaattaaat agttaatggt aacacttgac taacagatat   5580
aattttaatt ttcggtaggc ttttagcaag acagtaagta catcttcata atgagttagc   5640
cacagcttca tcacatgcac agattttcct gttgagagac tgcccagtta agagggtaga   5700
atgatgaacc atttttcagg attctcttct ttgtccaaac tggcattgtg agtgctagaa   5760
tatcagcact ttcaaactag tgattccaac tattaggcta ttaaaaagca aaacaaacca   5820
aacaaaccat agccagacat gggaagttta ctatgagtat aaacagcaaa tagcttacag   5880
gtcatacatt gaaatggtgt aggtaaggcg ttagaaaaat accttgacaa tttgccaaat   5940
gatcttactg tgccttcatg atgcaataaa aaaaaaaaaa atttagcata aatcagtgat   6000
ttgtgaagag agcagccacc ctggtctaac tcagctgtgt taatattttt tagcgtgcaa   6060
tttagactgc aaagataaat gcactaaaga gtttatagcc aaaatcacat ttaaaaaatg   6120
agagaaaaca caggtaaatt ttcagtgaac aaaattattt ttttaaagta cataatccct   6180
```

agtatagtca gatatattta tcacatagag caaataggtt gaaatcacaa ttcagtgaca 6240
tttctagaga aactttttct actcccatag gttcttcaaa gcatggaact tttatataac 6300
agaaatgtgt gacggtcatt ttaaattgct gtagtttggg gctgaagtac tgtgtgctgg 6360
gcagcaatca catgtattaa ctagtgagaa aggagaaatt aagatatagg acagaatttg 6420 atttcttgt tcccagatta ctgctgccaa cctagacact gagtttccag aggctgaaac 6480
gtaaacttgc agctcagcaa ctgttttgca aagttagtgg gactgtcctg cttatgctgt 6540
tcaaaaatgc tctgagggcc aggtggggcc tccaggggct cctctctgag gggacatcag 6600
actagctaac gacctggcgg gcggatgtga accggacaca ctccatggtg tgcttcttgt 6660
atcggtccct cgccaccctc aagaaaggct tcagcgggtt ctctagacgt ctccactaag 6720
gtgtgttact aacagccatg ggttgttgag cacccgagga gtgcaatagc atctctgcat 6780
gattgtatat tggcccgaag agaatgaagt ggccagtgta ctcatgttcc atgttgctag 6840
ctctggtaaa ctgaaaatac tggtaagatt tttgttttat cagtacacta gagagtaagc 6900
tttgttttgt tgtttttaga taatgttttc acttccattt ggaaagacat ttaaattgag 6960
tttcagtcct aaattttgcc agtcatggta attagcagtt tctatcaggt atttttaagg 7020
tagaagagga tagaaacata agttctaaaa gcttaaggta accgtggttt attttaaaat 7080
gtttaggggt ggttagtctc tacctcaaaa aaagtgagtg aatcttttat ttcagcattc 7140
acaagttcgg ctgttgtttt tgtaatacat ttttttttta acctttttgac ccccctttac 7200 ctaagtgtca atgtagtttt attaattact aagtcagttt cattaaaatg tttatttagc 7260
agttttgact aattgcaatg attaatatag ccagttgtgc atgaggacac agccagtgag 7320
tatatctggg tttttttgt gatgcttttt ttcttaagac ttctgtagat ttatgaagta 7380
ctcattgaaa acaactaaaa tacgtttatt cgtgttaata tggaaaaaaa aaaa 7434

<210> SEQ ID NO 124
<211> LENGTH: 603
<212> TYPE: PRT
<213> ORGANISM: Bos taurus

<400> SEQUENCE: 124

Met Met Arg Gly Leu Ile Pro Glu Cys Cys Ala Val Tyr Arg Ile Gln
1 5 10 15

Asp Gly Glu Lys Lys Pro Ile Gly Trp Asp Thr Asp Ile Ser Trp Leu
20 25 30

Thr Gly Glu Glu Leu His Val Glu Val Leu Glu Asn Val Pro Leu Thr
35 40 45

Thr His Asn Phe Val Arg Lys Thr Phe Phe Thr Leu Ala Phe Cys Asp
50 55 60

Phe Cys Arg Lys Leu Leu Phe Gln Gly Phe Arg Cys Gln Thr Cys Gly
65 70 75 80

Tyr Lys Phe His Gln Arg Cys Ser Thr Glu Val Pro Leu Met Cys Val
85 90 95

Asn Tyr Asp Gln Leu Asp Leu Leu Phe Val Ser Lys Phe Phe Glu His
100 105 110

His Pro Ile Pro Gln Glu Glu Ala Ser Leu Ala Glu Thr Thr Leu Pro
115 120 125

Cys Gly Ser Ser Pro Ser Ala Pro Pro Ser Asp Ser Ile Gly Pro Pro
130 135 140

Ile Leu Thr Ser Pro Ser Pro Ser Lys Ser Ile Pro Ile Pro Gln Pro

```
145                 150                 155                 160

Phe Arg Pro Ala Asp Glu Asp His Arg Asn Gln Phe Gly Gln Arg Asp
                165                 170                 175

Arg Ser Ser Ser Ala Pro Asn Val His Ile Asn Thr Ile Glu Pro Val
            180                 185                 190

Asn Ile Asp Asp Leu Ile Arg Asp Gln Gly Phe Arg Ser Asp Gly Gly
        195                 200                 205

Ser Thr Thr Gly Leu Ser Ala Thr Pro Pro Ala Ser Leu Pro Gly Ser
    210                 215                 220

Leu Ser Asn Val Lys Ala Leu Gln Lys Ser Pro Gly Pro Gln Arg Glu
225                 230                 235                 240

Arg Lys Ser Ser Ser Ser Ser Glu Asp Arg Asn Arg Met Lys Thr Leu
                245                 250                 255

Gly Arg Arg Asp Ser Ser Asp Asp Trp Glu Ile Pro Asp Gly Gln Ile
            260                 265                 270

Thr Val Gly Gln Arg Ile Gly Ser Gly Ser Phe Gly Thr Val Tyr Lys
        275                 280                 285

Gly Lys Trp His Gly Asp Val Ala Val Lys Met Leu Asn Val Thr Ala
    290                 295                 300

Pro Thr Pro Gln Gln Leu Gln Ala Phe Lys Asn Glu Val Gly Val Leu
305                 310                 315                 320

Arg Lys Thr Arg His Val Asn Ile Leu Leu Phe Met Gly Tyr Ser Thr
                325                 330                 335

Lys Pro Gln Leu Ala Ile Val Thr Gln Trp Cys Glu Gly Ser Ser Leu
            340                 345                 350

Tyr His His Leu His Ile Ile Glu Thr Lys Phe Glu Met Ile Lys Leu
        355                 360                 365

Ile Asp Ile Ala Arg Gln Thr Ala Gln Gly Met Asp Tyr Leu His Ala
    370                 375                 380

Lys Ser Ile Ile His Arg Asp Leu Lys Ser Asn Asn Ile Phe Leu His
385                 390                 395                 400

Glu Asp Leu Thr Val Lys Ile Gly Asp Phe Gly Leu Ala Thr Val Lys
                405                 410                 415

Ser Arg Trp Ser Gly Ser His Gln Phe Glu Gln Leu Ser Gly Ser Ile
            420                 425                 430

Leu Trp Met Ala Pro Glu Val Ile Arg Met Gln Asp Lys Asn Pro Tyr
        435                 440                 445

Ser Phe Gln Ser Asp Val Tyr Ala Phe Gly Ile Val Leu Tyr Glu Leu
    450                 455                 460

Met Thr Gly Gln Leu Pro Tyr Ser Asn Ile Asn Asn Arg Asp Gln Ile
465                 470                 475                 480

Ile Phe Met Val Gly Arg Gly Tyr Leu Ser Pro Asp Leu Ser Lys Val
                485                 490                 495

Arg Ser Asn Cys Pro Lys Ala Met Lys Arg Leu Met Ala Glu Cys Leu
            500                 505                 510

Lys Lys Lys Arg Asp Glu Arg Pro Leu Phe Pro Gln Val Gly Lys Thr
        515                 520                 525

Leu Leu Ser Lys Arg Gln Asn Ser Glu Val Ile Arg Glu Lys Asp Lys
    530                 535                 540

Gln Ile Leu Ala Ser Ile Glu Leu Leu Ala Arg Ser Leu Pro Lys Ile
545                 550                 555                 560

His Arg Ser Ala Ser Glu Pro Ser Leu Asn Arg Ala Gly Phe Gln Thr
                565                 570                 575
```

```
Glu Asp Phe Ser Leu Tyr Ala Cys Ala Ser Pro Lys Thr Pro Ile Gln
            580                 585                 590

Ala Gly Gly Tyr Gly Glu Phe Ala Ala Phe Lys
        595                 600


<210> SEQ ID NO 125
<211> LENGTH: 2295
<212> TYPE: DNA
<213> ORGANISM: Equus caballus
<220> FEATURE:
<221> NAME/KEY: misc_feature
<222> LOCATION: (79)..(79)
<223> OTHER INFORMATION: n is a, c, g, or t

<400> SEQUENCE: 125

atgaagacgc tgagcggcgg cggcggcggc gcggagcagg gccaggctct gttcaacggg     60

gacatggaac ccggaggcnc cgcgccggcg cccgcggcct cgtcggccgc ggaccctgcc    120

attcccgagg aggtatggaa tatcaaacaa atgattaaat tgacacagga acatatagag    180

gccctattgg acaaatttgg tggggagcat aatccaccat caatatatct ggaggcctat    240

gaagaataca ccagcaagct agatgccctc caacaaagag aacaacagtt attggaatcc    300

ctggggaatg gaactgattt ttctgtttct agttctgcat caacggacac cgttacatct    360

tcttcctctt ctagcctttc agtgctacct tcatctcttt cagtttttca aaatcccaca    420

gatgtgtcac ggagcaaccc taagtcacca caaaaaccta tcgttagagt cttcctgccc    480

aacaaacaga ggacagtggt acctgcaagg tgtggcgtta cagtccggga cagtctaaag    540

aaagcactga tgatgagagg tctaatccca gagtgctgtg ctgtttacag aattcaggat    600

ggagagaaga aaccaattgg ctgggacact gatatttcct ggctcactgg agaggaattg    660

catgtagaag tgttggagaa tgttccactt acaacacaca actttgtacg gaaaactttt    720

ttcaccttag cattttgtga cttttgtcga aagctgcttt tccagggttt ccgctgtcaa    780

acatgtggtt ataaatttca ccagcgttgt agtacagagg ttccactgat gtgtgttaat    840

tatgaccaac ttgatttgct gtttgtctcc aagttctttg aacaccaccc agtatcacag    900

gaggaggcct ccttagcaga gactgccctt acatctggat catccccttc tgcacccccc    960

tccgattcca ttgggcccca aattctcacc agtccatctc cttcaaaatc cattccaatt   1020

ccacagcctt tccgaccagc agatgaagat catcgaaatc agtttggaca acgagaccgg   1080

tcctcatcag ctccaaatgt acatataaac acaatagaac ctgtcaatat tgatgacttg   1140

attagagacc aagggtttcg tagtgatgga ggatcaacca caggtttatc tgccaccccc   1200

cctgcctcat tacctggctc actcactaat gtgaaggcat tacagaaatc tccaggacct   1260

caacgggaaa ggaaatcatc ttcatcctca gaagacagga atcgaatgaa aactcttggt   1320

agacgggatt caagtgacga ttgggagatt cctgatgggc agatcacagt gggacaaaga   1380

attggatctg ggtcatttgg gacagtctac aagggaaagt ggcatggtga tgtggcagtg   1440

aaaatgttga atgtgacagc acccacacct cagcagttac aggccttcaa aaatgaagta   1500

ggagtactca ggaaaactcg acatgtgaat atcctactct tcatgggcta ttcaacaaag   1560

ccacaactgg ctattgttac ccagtggtgt gagggctcca gcttatatca ccatctccac   1620

atcattgaga ccaaatttga gatgatcaaa cttatagata ttgctcggca aactgcacag   1680

ggcatggatt acttacacgc caagtcaatc atccacagag acctcaagag taataatatt   1740

tttcttcatg aagacctcac agtaaaaata ggtgattttg gtctagccac agtgaaatct   1800
```

```
cgatggagtg ggtcccatca gtttgaacag ttgtctggat ccattttgtg gatggcacca   1860

gaagtaatca gaatgcaaga taaaaacccg tatagctttc aatcagatgt atatgccttt   1920

gggattgttc tgtatgaatt gatgactgga cagttacctt attcaaacat caacaacagg   1980

gaccagataa tttttatggt gggaagagga tatctatctc cagatctcag taaggtacgg   2040

agtaactgtc caaaagccat gaagagatta atggcagagt gcctaaaaaa gaaaagagac   2100

gagagaccac tcttcccccca aattctcgcc tctattgagc tgctggcccg ctcattgcca   2160

aaaattcacc gcagtgcatc agagccctcc ttgaatcggg ctggcttcca gacagaggat   2220

tttagtctat atgcttgtgc ttctccgaaa acacccatcc aggcaggggg atatggtgcg   2280

tttcctgtcc actga                                                    2295
```

<210> SEQ ID NO 126
<211> LENGTH: 764
<212> TYPE: PRT
<213> ORGANISM: Equus caballus
<220> FEATURE:
<221> NAME/KEY: misc_feature
<222> LOCATION: (27)..(27)
<223> OTHER INFORMATION: Xaa can be any naturally occurring amino acid

<400> SEQUENCE: 126

```
Met Lys Thr Leu Ser Gly Gly Gly Gly Gly Ala Glu Gln Gly Gln Ala
1               5                   10                  15

Leu Phe Asn Gly Asp Met Glu Pro Gly Gly Xaa Ala Pro Ala Pro Ala
            20                  25                  30

Ala Ser Ser Ala Ala Asp Pro Ala Ile Pro Glu Glu Val Trp Asn Ile
        35                  40                  45

Lys Gln Met Ile Lys Leu Thr Gln Glu His Ile Glu Ala Leu Leu Asp
    50                  55                  60

Lys Phe Gly Gly Glu His Asn Pro Pro Ser Ile Tyr Leu Glu Ala Tyr
65                  70                  75                  80

Glu Glu Tyr Thr Ser Lys Leu Asp Ala Leu Gln Gln Arg Glu Gln Gln
                85                  90                  95

Leu Leu Glu Ser Leu Gly Asn Gly Thr Asp Phe Ser Val Ser Ser Ser
            100                 105                 110

Ala Ser Thr Asp Thr Val Thr Ser Ser Ser Ser Ser Ser Leu Ser Val
        115                 120                 125

Leu Pro Ser Ser Leu Ser Val Phe Gln Asn Pro Thr Asp Val Ser Arg
    130                 135                 140

Ser Asn Pro Lys Ser Pro Gln Lys Pro Ile Val Arg Val Phe Leu Pro
145                 150                 155                 160

Asn Lys Gln Arg Thr Val Val Pro Ala Arg Cys Gly Val Thr Val Arg
                165                 170                 175

Asp Ser Leu Lys Lys Ala Leu Met Met Arg Gly Leu Ile Pro Glu Cys
            180                 185                 190

Cys Ala Val Tyr Arg Ile Gln Asp Gly Glu Lys Lys Pro Ile Gly Trp
        195                 200                 205

Asp Thr Asp Ile Ser Trp Leu Thr Gly Glu Glu Leu His Val Glu Val
    210                 215                 220

Leu Glu Asn Val Pro Leu Thr Thr His Asn Phe Val Arg Lys Thr Phe
225                 230                 235                 240

Phe Thr Leu Ala Phe Cys Asp Phe Cys Arg Lys Leu Leu Phe Gln Gly
                245                 250                 255

Phe Arg Cys Gln Thr Cys Gly Tyr Lys Phe His Gln Arg Cys Ser Thr
```

```
            260                 265                 270

Glu Val Pro Leu Met Cys Val Asn Tyr Asp Gln Leu Asp Leu Leu Phe
        275                 280                 285

Val Ser Lys Phe Phe Glu His His Pro Val Ser Gln Glu Glu Ala Ser
    290                 295                 300

Leu Ala Glu Thr Ala Leu Thr Ser Gly Ser Ser Pro Ser Ala Pro Pro
305                 310                 315                 320

Ser Asp Ser Ile Gly Pro Gln Ile Leu Thr Ser Pro Ser Pro Ser Lys
                325                 330                 335

Ser Ile Pro Ile Pro Gln Pro Phe Arg Pro Ala Asp Glu Asp His Arg
            340                 345                 350

Asn Gln Phe Gly Gln Arg Asp Arg Ser Ser Ser Ala Pro Asn Val His
        355                 360                 365

Ile Asn Thr Ile Glu Pro Val Asn Ile Asp Asp Leu Ile Arg Asp Gln
    370                 375                 380

Gly Phe Arg Ser Asp Gly Gly Ser Thr Thr Gly Leu Ser Ala Thr Pro
385                 390                 395                 400

Pro Ala Ser Leu Pro Gly Ser Leu Thr Asn Val Lys Ala Leu Gln Lys
                405                 410                 415

Ser Pro Gly Pro Gln Arg Glu Arg Lys Ser Ser Ser Ser Ser Glu Asp
            420                 425                 430

Arg Asn Arg Met Lys Thr Leu Gly Arg Arg Asp Ser Ser Asp Asp Trp
        435                 440                 445

Glu Ile Pro Asp Gly Gln Ile Thr Val Gly Gln Arg Ile Gly Ser Gly
    450                 455                 460

Ser Phe Gly Thr Val Tyr Lys Gly Lys Trp His Gly Asp Val Ala Val
465                 470                 475                 480

Lys Met Leu Asn Val Thr Ala Pro Thr Pro Gln Gln Leu Gln Ala Phe
                485                 490                 495

Lys Asn Glu Val Gly Val Leu Arg Lys Thr Arg His Val Asn Ile Leu
            500                 505                 510

Leu Phe Met Gly Tyr Ser Thr Lys Pro Gln Leu Ala Ile Val Thr Gln
        515                 520                 525

Trp Cys Glu Gly Ser Ser Leu Tyr His His Leu His Ile Ile Glu Thr
    530                 535                 540

Lys Phe Glu Met Ile Lys Leu Ile Asp Ile Ala Arg Gln Thr Ala Gln
545                 550                 555                 560

Gly Met Asp Tyr Leu His Ala Lys Ser Ile Ile His Arg Asp Leu Lys
                565                 570                 575

Ser Asn Asn Ile Phe Leu His Glu Asp Leu Thr Val Lys Ile Gly Asp
            580                 585                 590

Phe Gly Leu Ala Thr Val Lys Ser Arg Trp Ser Gly Ser His Gln Phe
        595                 600                 605

Glu Gln Leu Ser Gly Ser Ile Leu Trp Met Ala Pro Glu Val Ile Arg
    610                 615                 620

Met Gln Asp Lys Asn Pro Tyr Ser Phe Gln Ser Asp Val Tyr Ala Phe
625                 630                 635                 640

Gly Ile Val Leu Tyr Glu Leu Met Thr Gly Gln Leu Pro Tyr Ser Asn
                645                 650                 655

Ile Asn Asn Arg Asp Gln Ile Ile Phe Met Val Gly Arg Gly Tyr Leu
            660                 665                 670

Ser Pro Asp Leu Ser Lys Val Arg Ser Asn Cys Pro Lys Ala Met Lys
        675                 680                 685
```

```
Arg Leu Met Ala Glu Cys Leu Lys Lys Lys Arg Asp Glu Arg Pro Leu
    690                 695                 700

Phe Pro Gln Ile Leu Ala Ser Ile Glu Leu Leu Ala Arg Ser Leu Pro
705                 710                 715                 720

Lys Ile His Arg Ser Ala Ser Glu Pro Ser Leu Asn Arg Ala Gly Phe
                725                 730                 735

Gln Thr Glu Asp Phe Ser Leu Tyr Ala Cys Ala Ser Pro Lys Thr Pro
            740                 745                 750

Ile Gln Ala Gly Gly Tyr Gly Ala Phe Pro Val His
        755                 760


<210> SEQ ID NO 127
<211> LENGTH: 2678
<212> TYPE: DNA
<213> ORGANISM: Gallus gallus

<400> SEQUENCE: 127

tcccctccc tcgccccagc gcttcgatcc aagatggcgg cgctgagcag cggcagcagc      60

gccgaggggg cctcgctctt caacggggac atggagcccg agccgccgcc gcccgtgctg     120

ggcgcctgct acgccgggag cggcggcggc gacccggcca tcccggagga ggtgtggaat     180

atcaaacaga tgattaaatt aacacaagaa catatagaag cgctgttaga caagtttgga     240

ggagagcata acccaccatc aatatattta gaggcctatg aggagtacac cagcaaacta     300

gatgctctac agcagagaga acagcagtta ttggaatcca tgggaaatgg aactgatttc     360

tctgtttcca gttcagcttc aacggacaca gttgcatcat cttcctcctc tagcctctct     420

gtagcacctt catccctttc agtttatcaa aatcctactg atatgtcgcg gaataaccct     480

aagtctccac agaagcctat tgttagagtc ttcctgccca acaagcaaag gactgtggtt     540

ccggcaagat gtggggtgac agtccgagac agcctgaaga aagctctgat gatgagaggt     600

cttattccag aatgctgtgc tgtttacaga atacaggatg gagagaagaa gccaattggc     660

tgggacactg acatttcctg gctaaccgga gaggagttac acgtggaggt cttggagaat     720

gtgccactca caacacacaa ttttgtacga aaaacattct tcacgttagc gttctgcgac     780

ttctgtcgaa agctgctttt ccagggattc cgatgccaga catgtggcta caaatttcac     840

cagcgctgta gcacagaagt gccactgatg tgtgttaact acgaccaact cgatttgctg     900

tttgtctcca agttctttga acatcacccc atatcgcagg aggagaccac cttaggagag     960

accaccccgg catcgggatc gtacccctca gtgcccccat cagattctgt tggaccacca    1020

attctcccta gtccttctcc ttcaaaatcc attccaatcc cacagccctt ccgaccagca    1080

gatgaagacc atcggaatca gtttgggcaa cgcgaccgat cctcttcagc tcccaatgtt    1140

cacatcaata caattgagcc agtcaatatt gatgacttga ttagagacca gggtgtacga    1200

ggagagggag ccccctttgaa ccagctgatg cgctgtcttc ggaaatacca atcccggact    1260

cccagtcccc tccttcattc tgtccccagt gaaatagtgt ttgattttga gcctggccca    1320

gtgttcagag gttcaactgc aggtttgtct gcaacacctc ctgcatcttt gcctgggtca    1380

cttaccaatg tgaaagcatt acagaaatca ccaggccccc aacgggaaag gaaatcatcc    1440

tcatcctcag aagacagaaa taggatgaaa acccttggtc gacgagattc aagtgatgat    1500

tgggaaatac cagatgggca gatcacagtt ggacaaagga taggatctgg atcatttgga    1560

acagtctaca aaggaaagtg gcatggtgac gtggcagtga aaatgttgaa tgttacagca    1620

cccacacctc aacagttaca ggctttcaaa aatgaagtag gagtgctcag gaaaacacgg    1680
```

```
catgtgaata tcctactttt tatgggttat tcaacaaaac ctcagttggc tattgttaca   1740
cagtggtgtg aggggtccag cttatatcac catctgcaca taattgagac caagtttgaa   1800
atgatcaaac taattgatat tgcacgacag actgcacaag gcatggatta tttgcatgcc   1860
aagtcaatca tccacagaga cctcaagagt aataatattt ttcttcatga agacctcaca   1920
gtaaaaatag gtgacttcgg tctggctaca gtgaaatcac gatggagtgg atctcatcaa   1980
tttgaacagt tatctggatc aattctatgg atggcaccgg aagtgatcag gatgcaagac   2040
aaaaacccat atagctttca gtcagatgtg tatgcattcg ggattgtgct ttatgaactg   2100
atgactggac agttaccata ctcaaacatc aacaacaggg accagataat ttttatggtg   2160
ggacgaggat atctatctcc agacctcagt aaagtaagaa gtaactgtcc aaaagctatg   2220
aagagactaa tggcagaatg cttgaaaaag aaaagagatg agagacctct tttccacag    2280
attcttgcct ccattgagct tctggcccgg tcgttgccaa aaattcaccg cagtgcatct   2340
gagccgtcac taaaccgggc tggcttccag accgaggatt tcagtctgta tgcttgtgct   2400
tctccaaaaa cgcccatcca agcaggggga tacggtgggt ttccagtaca ctgaaaagaa   2460
atgtgaaagc gtgtgcctgt ttgctcatgt gctggtgtgt tcctgtgtgt gcaacgcata   2520
cgtacgttct cagttcctac cagcgacttt ttaaggttta ctgagggaat gaagactcat   2580
ttcctaacat ggggcattga acgtcctgag cacaagtcag tgctggtaag gaatgtcttg   2640
ggaacagctg gcaagaagaa ttagaaggta cttaaagg                           2678
```

```
<210> SEQ ID NO 128
<211> LENGTH: 806
<212> TYPE: PRT
<213> ORGANISM: Gallus gallus

<400> SEQUENCE: 128

Met Ala Ala Leu Ser Ser Gly Ser Ser Ala Glu Gly Ala Ser Leu Phe
1               5                   10                  15

Asn Gly Asp Met Glu Pro Glu Pro Pro Pro Pro Val Leu Gly Ala Cys
            20                  25                  30

Tyr Ala Gly Ser Gly Gly Gly Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Met Gly Asn Gly Thr Asp Phe Ser Val Ser
            100                 105                 110

Ser Ser Ala Ser Thr Asp Thr Val Ala Ser Ser Ser Ser Ser Ser Leu
        115                 120                 125

Ser Val Ala Pro Ser Ser Leu Ser Val Tyr Gln Asn Pro Thr Asp Met
    130                 135                 140

Ser Arg Asn Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190
```

```
Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Ser Gln Glu Glu
    290                 295                 300

Thr Thr Leu Gly Glu Thr Thr Pro Ala Ser Gly Ser Tyr Pro Ser Val
305                 310                 315                 320

Pro Pro Ser Asp Ser Val Gly Pro Pro Ile Leu Pro Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Val Arg Gly Glu Gly Ala Pro Leu Asn Gln Leu Met Arg
385                 390                 395                 400

Cys Leu Arg Lys Tyr Gln Ser Arg Thr Pro Ser Pro Leu Leu His Ser
                405                 410                 415

Val Pro Ser Glu Ile Val Phe Asp Phe Glu Pro Gly Pro Val Phe Arg
            420                 425                 430

Gly Ser Thr Ala Gly Leu Ser Ala Thr Pro Pro Ala Ser Leu Pro Gly
        435                 440                 445

Ser Leu Thr Asn Val Lys Ala Leu Gln Lys Ser Pro Gly Pro Gln Arg
    450                 455                 460

Glu Arg Lys Ser Ser Ser Ser Ser Glu Asp Arg Asn Arg Met Lys Thr
465                 470                 475                 480

Leu Gly Arg Arg Asp Ser Ser Asp Asp Trp Glu Ile Pro Asp Gly Gln
                485                 490                 495

Ile Thr Val Gly Gln Arg Ile Gly Ser Gly Ser Phe Gly Thr Val Tyr
            500                 505                 510

Lys Gly Lys Trp His Gly Asp Val Ala Val Lys Met Leu Asn Val Thr
        515                 520                 525

Ala Pro Thr Pro Gln Gln Leu Gln Ala Phe Lys Asn Glu Val Gly Val
    530                 535                 540

Leu Arg Lys Thr Arg His Val Asn Ile Leu Leu Phe Met Gly Tyr Ser
545                 550                 555                 560

Thr Lys Pro Gln Leu Ala Ile Val Thr Gln Trp Cys Glu Gly Ser Ser
                565                 570                 575

Leu Tyr His His Leu His Ile Ile Glu Thr Lys Phe Glu Met Ile Lys
            580                 585                 590

Leu Ile Asp Ile Ala Arg Gln Thr Ala Gln Gly Met Asp Tyr Leu His
        595                 600                 605

Ala Lys Ser Ile Ile His Arg Asp Leu Lys Ser Asn Asn Ile Phe Leu
```

-continued

```
    610                 615                 620

His Glu Asp Leu Thr Val Lys Ile Gly Asp Phe Gly Leu Ala Thr Val
625                 630                 635                 640

Lys Ser Arg Trp Ser Gly Ser His Gln Phe Glu Gln Leu Ser Gly Ser
                645                 650                 655

Ile Leu Trp Met Ala Pro Glu Val Ile Arg Met Gln Asp Lys Asn Pro
            660                 665                 670

Tyr Ser Phe Gln Ser Asp Val Tyr Ala Phe Gly Ile Val Leu Tyr Glu
        675                 680                 685

Leu Met Thr Gly Gln Leu Pro Tyr Ser Asn Ile Asn Asn Arg Asp Gln
    690                 695                 700

Ile Ile Phe Met Val Gly Arg Gly Tyr Leu Ser Pro Asp Leu Ser Lys
705                 710                 715                 720

Val Arg Ser Asn Cys Pro Lys Ala Met Lys Arg Leu Met Ala Glu Cys
                725                 730                 735

Leu Lys Lys Lys Arg Asp Glu Arg Pro Leu Phe Pro Gln Ile Leu Ala
            740                 745                 750

Ser Ile Glu Leu Leu Ala Arg Ser Leu Pro Lys Ile His Arg Ser Ala
        755                 760                 765

Ser Glu Pro Ser Leu Asn Arg Ala Gly Phe Gln Thr Glu Asp Phe Ser
    770                 775                 780

Leu Tyr Ala Cys Ala Ser Pro Lys Thr Pro Ile Gln Ala Gly Gly Tyr
785                 790                 795                 800

Gly Gly Phe Pro Val His
                805
```

CANCER TREATMENTS USING COMBINATIONS OF TYPE 2 MEK AND ERK INHIBITORS

CROSS REFERENCE TO RELATED APPLICATIONS

The present application is the National Stage of International Application No. PCT/US2014/071724, filed on Dec. 19, 2014, which claims benefit to U.S. Provisional Application Ser. No. 61/919,625, filed Dec. 20, 2013. The entire contents of the above applications are incorporated by reference as if recited in full herein.

FIELD OF INVENTION

The present invention provides, inter alia, methods, pharmaceutical compositions, and kits for treating or ameliorating the effects of a cancer in a subject using a first anti-cancer agent, which is BVD-523 or a pharmaceutically acceptable salt thereof and a second anti-cancer agent, which is a type 2 MEK inhibitor or a pharmaceutically acceptable salt thereof.

INCORPORATION BY REFERENCE OF SEQUENCE LISTING

This application contains references to amino acids and/or nucleic acid sequences that have been filed concurrently herewith as sequence listing text file "0375603.txt", file size of 474 KB, created on Dec. 19, 2014. The aforementioned sequence listing is hereby incorporated by reference in its entirety pursuant to 37 C.F.R. § 1.52(e)(5).

BACKGROUND OF THE INVENTION

Within cellular signaling networks, Ras and Raf play significant roles in the regulation of various biological processes, including cell growth, proliferation, differentiation, inflammatory responses, and programmed cell death. Notably, mutations in ras genes were the first genetic alterations identified in human cancer. Activating mutations of HRAS, NRAS, and KRAS ('RAS'), as well as BRAF are found frequently in several types of cancer.

A MEK inhibitor is an agent that inhibits the mitogen—activated protein kinase enzymes, MEK1 and/or MEK2. Depending on their target and effect, i.e. MEK1, MEK2 or both, MEK inhibitors may be classified as type 1 MEK inhibitors, type 2 MEK inhibitors or pan MEK inhibitors. MEK inhibitors are known to modulate, e.g., the MAPK pathway, which is often over-active in many cancers, and, therefore, have been used in cancer therapy. Unfortunately, many cancers become resistant to MEK inhibitor treatment over time.

Extracellular-signal-regulated kinases (ERKs) are protein kinases that are involved in cell cycle regulation, including the regulation of meiosis, mitosis, and postmitotic functions in differentiated cells. Disruption of the ERK pathway is common in cancers. However, to date, little progress has been made developing effective ERK inhibitors for the treatment of cancer.

As the understanding of the molecular basis of cancer grows, there is an increased emphasis on developing drugs that specifically target particular nodes in pathways that lead to cancer. In view of the deficiencies noted above, there is, inter alia, a need for effective molecularly targeted cancer treatments, including combination therapies. The present application is directed to meeting these and other needs.

SUMMARY OF THE INVENTION

One embodiment of the present invention is a method of treating or ameliorating the effects of a cancer in a subject in need thereof. The method comprises administering to the subject an effective amount of (i) a first anti-cancer agent, which is BVD-523 or a pharmaceutically acceptable salt thereof and (ii) a second anti-cancer agent, which is a type 2 MEK inhibitor or a pharmaceutically acceptable salt thereof, to treat or ameliorate the effects of the cancer.

Another embodiment of the present invention is a method of treating or ameliorating the effects of a cancer in a subject in need thereof. The method comprises administering to the subject an effective amount of (i) a first anti-cancer agent, which is BVD-523 or a pharmaceutically acceptable salt thereof and (ii) a second anti-cancer agent, which is trametinib or a pharmaceutically acceptable salt thereof, to treat or ameliorate the effects of the cancer.

A further embodiment of the present invention is a method of effecting cancer cell death. The method comprises contacting the cancer cell with an effective amount of (i) a first anti-cancer agent, which is BVD-523 or a pharmaceutically acceptable salt thereof and (ii) a second anti-cancer agent, which is a type 2 MEK inhibitor or a pharmaceutically acceptable salt thereof.

An additional embodiment of the present invention is a kit for treating or ameliorating the effects of a cancer in a subject in need thereof. The kit comprises an effective amount of (i) a first anti-cancer agent, which is BVD-523 or a pharmaceutically acceptable salt thereof and (ii) a second anti-cancer agent, which is a type 2 MEK inhibitor or a pharmaceutically acceptable salt thereof, packaged together with instructions for their use.

Another embodiment of the present invention is a pharmaceutical composition for treating or ameliorating the effects of cancer in a subject in need thereof. The pharmaceutical composition comprises a pharmaceutically acceptable diluent or carrier and an effective amount of (i) a first anti-cancer agent, which is BVD-523 or a pharmaceutically acceptable salt thereof and (ii) a second anti-cancer agent, which is a type 2 MEK inhibitor or a pharmaceutically acceptable salt thereof, wherein administration of the first and second anti-cancer agents provides a synergistic effect compared to administration of either anti-cancer agent alone.

A further embodiment of the present invention is a method of treating or ameliorating the effects of a cancer in a subject in need thereof. The method comprises administering to the subject an effective amount of (i) a first anti-cancer agent, which is BVD-523 or a pharmaceutically acceptable salt thereof and (ii) a second anti-cancer agent, which is a MEK inhibitor selected from the group consisting of antroquinonol (Golden Biotechnology), AS-1940477 (Astellas), AS-703988 (Merck KGaA), BI-847325 (Boehringer Ingelheim), E-6201 (Eisai), GDC-0623 (Hoffmann-La Roche), GDC-0973 (Hoffmann-La Roche), RG422 (Chugai Pharmaceutical Co.), RO4987655 (Hoffmann-La Roche), RO5126766 (Hoffmann-La Roche), SL327 (Sigma), WX-554 (Wilex), YopJ polypeptide (Mittal et al., 2010), pharmaceutically acceptable salts thereof, and combinations thereof, to treat or ameliorate the effects of the cancer.

An additional embodiment of the present invention is a method of effecting cancer cell death. The method comprises contacting the cancer cell with an effective amount of (i) a first anti-cancer agent, which is BVD-523 or a pharmaceutically acceptable salt thereof and (ii) a second anti-cancer agent, which is a MEK inhibitor selected from the group consisting of antroquinonol (Golden Biotechnology), AS-1940477 (Astellas), AS-703988 (Merck KGaA), BI-847325 (Boehringer Ingelheim), E-6201 (Eisai), GDC-0623 (Hoffmann-La Roche), GDC-0973, RG422, RO4987655, RO5126766, SL327, WX-554 (Wilex), YopJ polypeptide, pharmaceutically acceptable salts thereof, and combinations thereof.

Another embodiment of the present invention is a kit for treating or ameliorating the effects of a cancer in a subject in need thereof. The kit comprises an effective amount of (i) a first anti-cancer agent, which is BVD-523 or a pharmaceutically acceptable salt thereof and (ii) a second anti-cancer agent, which is a MEK inhibitor selected from the group consisting of antroquinonol (Golden Biotechnology), AS-1940477 (Astellas), AS-703988 (Merck KGaA), BI-847325 (Boehringer Ingelheim), E-6201 (Eisai), GDC-0623 (Hoffmann-La Roche), GDC-0973, RG422, RO4987655, RO5126766, SL327, WX-554 (Wilex), YopJ polypeptide, pharmaceutically acceptable salts thereof, and combinations thereof, packaged together with instructions for their use.

A further embodiment of the present invention is a pharmaceutical composition for treating or ameliorating the effects of a cancer in a subject in need thereof. The pharmaceutical composition comprises a pharmaceutically acceptable diluent or carrier and an effective amount of (i) a first anti-cancer agent, which is BVD-523 or a pharmaceutically acceptable salt thereof and (ii) a second anti-cancer agent, which is a MEK inhibitor selected from the group consisting of antroquinonol (Golden Biotechnology), AS-1940477 (Astellas), AS-703988 (Merck KGaA), BI-847325 (Boehringer Ingelheim), E-6201 (Eisai), GDC-0623 (Hoffmann-La Roche), GDC-0973, RG422, RO4987655, RO5126766, SL327, WX-554 (Wilex), YopJ polypeptide, pharmaceutically acceptable salts thereof, and combinations thereof, wherein administration of the first and second anti-cancer agents provides a synergistic effect compared to administration of either anti-cancer agent alone.

BRIEF DESCRIPTION OF THE DRAWINGS

FIGS. 2A-2C and 2G are normalized to control, whereas FIGS. 2D-2F and 2H show the raw data.

FIGS. 4A-4C and 4G are normalized to control, whereas FIGS. 4D-4F and 4H show the raw data.

FIGS. 5A-5C and 5G are normalized to control, whereas FIGS. 5D-5F and 5H show the raw data.

FIG. 10A is a dose matrix showing % inhibition of the trametinib/dabrafenib combination in A375 cells using the Alamar Blue cell viability assay. FIG. 10B is a dose matrix showing excess over Bliss for the trametinib/dabrafenib combination. FIGS. 10C and 10D show % viability relative to DMSO only treated controls for dabrafenib and trametinib single agent treatments in A375 cells using the Alamar Blue cell viability assay. FIG. 10E shows % viability relative to DMSO only treated controls for dabrafenib and trametinib combination treatments in A375 cells using the Alamar Blue cell viability assay.

FIG. 11A is a dose matrix showing % inhibition of the trametinib/dabrafenib combination in A375 cells using the CellTiter-Glo cell viability assay. FIG. 11B is a dose matrix showing excess over Bliss for the trametinib/dabrafenib combination. FIGS. 11C and 11D show % viability relative to DMSO only treated controls for dabrafenib and trametinib single agent treatments in A375 cells using the CellTiter-Glo cell viability assay. FIG. 11E shows % viability relative to DMSO only treated controls for dabrafenib and trametinib combination treatments in A375 cells using the CellTiter-Glo cell viability assay.

FIG. 12A is a dose matrix showing % inhibition of the BVD-523/dabrafenib combination in A375 cells using the Alamar Blue cell viability assay. FIG. 12B is a dose matrix showing excess over Bliss for the BVD-523/dabrafenib combination. FIGS. 12C and 12D show % viability relative to DMSO only treated controls for dabrafenib and BVD-523 single agent treatments in A375 cells using the Alamar Blue cell viability assay. FIG. 12E shows % viability relative to DMSO only treated controls for dabrafenib and BVD-523 combination treatments in A375 cells using the Alamar Blue cell viability assay.

FIG. 13A is a dose matrix showing % inhibition of the BVD-523/dabrafenib combination in A375 cells using the CellTiter-Glo cell viability assay. FIG. 13B is a dose matrix showing excess over Bliss for the BVD-523/dabrafenib combination. FIGS. 13C and 13D show % viability relative to DMSO only treated controls for dabrafenib and BVD-523 single agent treatments in A375 cells using the CellTiter-Glo cell viability assay. FIG. 13E shows % viability relative to DMSO only treated controls for dabrafenib and BVD-523 combination treatments in A375 cells using the CellTiter-Glo cell viability assay.

FIG. 14A is a dose matrix showing % inhibition of the trametinib/BVD-523 combination in A375 cells using the Alamar Blue cell viability assay. FIG. 14B is a dose matrix showing excess over Bliss for the trametinib/BVD-523 combination. FIGS. 14C and 14D show % viability relative to DMSO only treated controls for BVD-523 and trametinib single agent treatments in A375 cells using the Alamar Blue cell viability assay. FIG. 14E shows % viability relative to DMSO only treated controls for BVD-523 and trametinib combination treatments in A375 cells using the Alamar Blue cell viability assay.

FIGS. 16A and 16B show results from duplicate samples. Similarly, FIGS. 16C and 16D also show results from duplicate samples. In FIGS. 16A and 16B, pRSK1 had a relatively weak signal in A375 cells compared to other markers. A different pRSK1-5380 antibody from Cell Signaling (cat. #11989) was tested but did not give a detectable signal (data not shown). In FIGS. 16C and 16D, pCRAF-338 gave a minimal signal.

FIGS. 17A and 17B show results from duplicate samples. Similarly, FIGS. 17C and 17D also show results from duplicate samples. In FIGS. 17A-17B, pRSK1 levels appear to be very low in HCT116 cells, and in FIGS. 17C and 17D, pCRAF-338 signal was also very weak.

FIGS. 18A and 18B show results from duplicate samples. Similarly, FIGS. 18C and 18D also show results from duplicate samples. In FIGS. 18A and 18B, no band of a size corresponding to cleaved PARP (89 kDa) was apparent.

FIG. 23A shows a dose matrix showing inhibition (%) for the combination in parental A375 cells. FIG. 23B shows Loewe excess for the combination in 23A and FIG. 23C shows Bliss excess for the combination in 23A. FIG. 23D shows a dose matrix showing inhibition (%) for the combination in A375 NRAS (Q61K/+) cells. FIG. 23E shows Loewe excess for the combination in 23D and FIG. 23F shows Bliss excess for the combination in 23D. FIG. 23G-FIG. 23H show the results of single agent proliferation assays for the combination in 23A. FIG. 23I-FIG. 23J show the results of single agent proliferation assays for the combination in 23D.

FIG. 24A shows a dose matrix showing inhibition (%) for the combination in parental A375 cells. FIG. 24B shows Loewe excess for the combination in 24A and FIG. 24C shows Bliss excess for the combination in 24A. FIG. 24D shows a dose matrix showing inhibition (%) for the combination in A375 NRAS (Q61K/+) cells. FIG. 24E shows Loewe excess for the combination in 24D and FIG. 24F shows Bliss excess for the combination in 24D. FIG. 24G-FIG. 24H show the results of single agent proliferation assays for the combination in 24A. FIG. 24I-FIG. 24J show the results of single agent proliferation assays for the combination in 24D.

FIG. 25A shows a dose matrix showing inhibition (%) for the combination in parental A375 cells. FIG. 25B shows Loewe excess for the combination in 25A and FIG. 25C shows Bliss excess for the combination in 25A. FIG. 25D shows a dose matrix showing inhibition (%) for the combination in A375 NRAS (Q61K/+) cells. FIG. 25E shows Loewe excess for the combination in 25D and FIG. 25F shows Bliss excess for the combination in 25D. FIG. 25G-FIG. 25H show the results of single agent proliferation assays for the combination in 25A. FIG. 25I-FIG. 25J show the results of single agent proliferation assays for the combination in 25D.

FIG. 26A shows a dose matrix showing inhibition (%) for the combination in parental A375 cells. FIG. 26B shows Loewe excess for the combination in 26A and FIG. 26C shows Bliss excess for the combination in 26A. FIG. 26D shows a dose matrix showing inhibition (%) for the combination in A375 NRAS (Q61K/+) cells. FIG. 26E shows Loewe excess for the combination in 26D and FIG. 26F shows Bliss excess for the combination in 26D. FIG. 26G-FIG. 26H show the results of single agent proliferation assays for the combination in 26A. FIG. 26I-FIG. 26J show the results of single agent proliferation assays for the combination in 26D.

FIG. 27A shows a dose matrix showing inhibition (%) for the combination in parental A375 cells. FIG. 27B shows Loewe excess for the combination in 27A and FIG. 27C shows Bliss excess for the combination in 27A. FIG. 27D shows a dose matrix showing inhibition (%) for the combination in A375 NRAS (Q61K/+) cells. FIG. 27E shows Loewe excess for the combination in 27D and FIG. 27F shows Bliss excess for the combination in 27D. FIG. 27G-FIG. 27H show the results of single agent proliferation assays for the combination in 27A. FIG. 27I-FIG. 27J show the results of single agent proliferation assays for the combination in 27D.

FIG. 28A shows a dose matrix showing inhibition (%) for the combination in parental A375 cells. FIG. 28B shows Loewe excess for the combination in 28A and FIG. 28C shows Bliss excess for the combination in 28A. FIG. 28D shows a dose matrix showing inhibition (%) for the combination in A375 NRAS (Q61K/+) cells. FIG. 28E shows Loewe excess for the combination in 28D and FIG. 28F shows Bliss excess for the combination in 28D. FIG. 28G-FIG. 28H show the results of single agent proliferation assays for the combination in 28A. FIG. 28I-FIG. 28J show the results of single agent proliferation assays for the combination in 28D.

FIG. 29A shows a dose matrix showing inhibition (%) for the combination in parental HCT116 cells. FIG. 29B shows Loewe excess for the combination in 29A and FIG. 29C shows Bliss excess for the combination in 29A. FIG. 29D shows a dose matrix showing inhibition (%) for the combination in HCT116 KRAS KO (+/−) cells. FIG. 29E shows Loewe excess for the combination in 29D and FIG. 29F shows Bliss excess for the combination in 29D. FIG. 29G-FIG. 29H show the results of single agent proliferation assays for the combination in 29A. FIG. 29I-FIG. 29J show the results of single agent proliferation assays for the combination in 29D.

FIG. 30A shows a dose matrix showing inhibition (%) for the combination in parental HCT116 cells. FIG. 30B shows Loewe excess for the combination in 30A and FIG. 30C shows Bliss excess for the combination in 30A. FIG. 30D shows a dose matrix showing inhibition (%) for the combination in HCT116 KRAS KO (+/−) cells. FIG. 30E shows Loewe excess for the combination in 30D and FIG. 30F shows Bliss excess for the combination in 30D. FIG. 30G-FIG. 30H show the results of single agent proliferation assays for the combination in 30A. FIG. 30I-FIG. 30J show the results of single agent proliferation assays for the combination in 30D.

FIG. 31A shows a dose matrix showing inhibition (%) for the combination in parental HCT116 cells. FIG. 31B shows Loewe excess for the combination in 31A and FIG. 31C shows Bliss excess for the combination in 31A. FIG. 31D shows a dose matrix showing inhibition (%) for the combination in HCT116 KRAS KO (+/−) cells. FIG. 31E shows Loewe excess for the combination in 31D and FIG. 31F shows Bliss excess for the combination in 31D. FIG. 31G-FIG. 31H show the results of single agent proliferation assays for the combination in 31A. FIG. 31I-FIG. 31J show the results of single agent proliferation assays for the combination in 31D.

FIG. 32A shows a dose matrix showing inhibition (%) for the combination in parental HCT116 cells. FIG. 32B shows Loewe excess for the combination in 32A and FIG. 32C shows Bliss excess for the combination in 32A. FIG. 32D shows a dose matrix showing inhibition (%) for the combination in HCT116 KRAS KO (+/−) cells. FIG. 32E shows Loewe excess for the combination in 32D and FIG. 32F shows Bliss excess for the combination in 32D. FIG. 32G-FIG. 32H show the results of single agent proliferation assays for the combination in 32A. FIG. 32I-FIG. 32J show the results of single agent proliferation assays for the combination in 32D.

FIG. 33A shows a dose matrix showing inhibition (%) for the combination in parental RKO cells. FIG. 33B shows Loewe excess for the combination in 33A and FIG. 33C shows Bliss excess for the combination in 33A. FIG. 33D shows a dose matrix showing inhibition (%) for the combination in RKO BRAF V600E KO (+/−/−) cells. FIG. 33E shows Loewe excess for the combination in 33D and FIG. 33F shows Bliss excess for the combination in 33D. FIG. 33G-FIG. 33H show the results of single agent proliferation assays for the combination in 33A. FIG. 33I-FIG. 33J show the results of single agent proliferation assays for the combination in 33D.

FIG. 34A shows a dose matrix showing inhibition (%) for the combination in parental RKO cells. FIG. 34B shows Loewe excess for the combination in 34A and FIG. 34C shows Bliss excess for the combination in 34A. FIG. 34D shows a dose matrix showing inhibition (%) for the combination in RKO BRAF V600E KO (+/−/−) cells. FIG. 34E shows Loewe excess for the combination in 34D and FIG. 34F shows Bliss excess for the combination in 34D. FIG. 34G-FIG. 34H show the results of single agent proliferation assays for the combination in 34A. FIG. 34I-FIG. 34J show the results of single agent proliferation assays for the combination in 34D.

FIG. 35A shows a dose matrix showing inhibition (%) for the combination in parental RKO cells. FIG. 35B shows Loewe excess for the combination in 35A and FIG. 35C shows Bliss excess for the combination in 35A. FIG. 35D shows a dose matrix showing inhibition (%) for the combination in RKO BRAF V600E KO (+/−/−) cells.

FIG. 35E shows Loewe excess for the combination in 35D and FIG. 35F shows Bliss excess for the combination in 35D. FIG. 35G-FIG. 35H show the results of single agent proliferation assays for the combination in 35A. FIG. 35I-FIG. 35J show the results of single agent proliferation assays for the combination in 35D.

FIG. 36A shows a dose matrix showing inhibition (%) for the combination in parental RKO cells. FIG. 36B shows Loewe excess for the combination in 36A and FIG. 36C shows Bliss excess for the combination in 36A. FIG. 36D shows a dose matrix showing inhibition (%) for the combination in RKO BRAF V600E KO (+/−/−) cells. FIG. 36E shows Loewe excess for the combination in 36D and FIG. 36F shows Bliss excess for the combination in 36D. FIG. 36G-FIG. 36H show the results of single agent proliferation assays for the combination in 36A. FIG. 36I-FIG. 36J show the results of single agent proliferation assays for the combination in 36D.

FIG. 37A shows a dose matrix showing inhibition (%) for the combination. FIG. 37B shows Loewe excess for the combination in 37A and FIG. 37C shows Bliss excess for the combination in 37A. FIG. 37D-FIG. 37E show the results of single agent proliferation assays for the combination in 37A.

FIG. 38A shows a dose matrix showing inhibition (%) for the combination. FIG. 38B shows Loewe excess for the combination in 38A and FIG. 38C shows Bliss excess for the combination in 38A. FIG. 38D-FIG. 38E show the results of single agent proliferation assays for the combination in 38A.

FIG. 39A shows a dose matrix showing inhibition (%) for the combination. FIG. 39B shows Loewe excess for the combination in 39A and FIG. 39C shows Bliss excess for the combination in 39A. FIG. 39D-FIG. 39E show the results of single agent proliferation assays for the combination in 39A.

FIG. 40A shows a dose matrix showing inhibition (%) for the combination. FIG. 40B shows Loewe excess for the combination in 40A and FIG. 40C shows Bliss excess for the combination in 40A. FIG. 40D-FIG. 40E show the results of single agent proliferation assays for the combination in 40A.

FIG. 41A shows a dose matrix showing inhibition (%) for the combination. FIG. 41B shows Loewe excess for the combination in 41A and FIG. 41C shows Bliss excess for the combination in 41A. FIG. 41D-FIG. 41E show the results of single agent proliferation assays for the combination in 41A.

FIG. 42A shows a dose matrix showing inhibition (%) for the combination. FIG. 42B shows Loewe excess for the combination in 42A and FIG. 42C shows Bliss excess for the combination in 42A. FIG. 42D-FIG. 42E show the results of single agent proliferation assays for the combination in 42A.

FIG. 43A shows a dose matrix showing inhibition (%) for the combination. FIG. 43B-FIG. 43C show the results of single agent proliferation assays for the combination in 43A. FIG. 43D shows Loewe excess for the combination in 43A and FIG. 43E shows Bliss excess for the combination in 43A.

FIG. 44A shows a dose matrix showing inhibition (%) for the combination. FIG. 44B-FIG. 44C show the results of single agent proliferation assays for the combination in 44A. FIG. 44D shows Loewe excess for the combination in 44A and FIG. 44E shows Bliss excess for the combination in 44A.

FIG. 45A shows a dose matrix showing inhibition (%) for the combination. FIG. 45B-FIG. 45C show the results of single agent proliferation assays for the combination in 45A. FIG. 45D shows Loewe excess for the combination in 45A and FIG. 45E shows Bliss excess for the combination in 45A.

FIG. 46A shows a dose matrix showing inhibition (%) for the combination. FIG. 46B-FIG. 46C show the results of single agent proliferation assays for the combination in 46A. FIG. 46D shows Loewe excess for the combination in 46A and FIG. 46E shows Bliss excess for the combination in 46A.

FIG. 47A shows a dose matrix showing inhibition (%) for the combination. FIG. 47B-FIG. 47C show the results of single agent proliferation assays for the combination in 47A. FIG. 47D shows Loewe excess for the combination in 47A and FIG. 47E shows Bliss excess for the combination in 47A.

FIG. 48A shows a dose matrix showing inhibition (%) for the combination. FIG. 48B-FIG. 48C show the results of single agent proliferation assays for the combination in 48A. FIG. 48D shows Loewe excess for the combination in 48A and FIG. 48E shows Bliss excess for the combination in 48A.

FIG. 49A shows a dose matrix showing inhibition (%) for the combination. FIG. 49B-FIG. 49C show the results of single agent proliferation assays for the combination in 49A. FIG. 49D shows Loewe excess for the combination in 49A and FIG. 49E shows Bliss excess for the combination in 49A.

FIG. 50A shows a dose matrix showing inhibition (%) for the combination. FIG. 50B-FIG. 50C show the results of single agent proliferation assays for the combination in 50A. FIG. 50D shows Loewe excess for the combination in 50A and FIG. 50E shows Bliss excess for the combination in 50A.

FIG. 51A shows a dose matrix showing inhibition (%) for the combination. FIG. 51B-FIG. 51C show the results of single agent proliferation assays for the combination in 51A. FIG. 51D shows Loewe excess for the combination in 51A and FIG. 51E shows Bliss excess for the combination in 51A.

FIG. 52A shows a dose matrix showing inhibition (%) for the combination. FIG. 52B-FIG. 52C show the results of single agent proliferation assays for the combination in 52A. FIG. 52D shows Loewe excess for the combination in 52A and FIG. 52E shows Bliss excess for the combination in 52A.

FIG. 53A shows a dose matrix showing inhibition (%) for the combination. FIG. 53B-FIG. 53C show the results of single agent proliferation assays for the combination in 53A. FIG. 53D shows Loewe excess for the combination in 53A and FIG. 53E shows Bliss excess for the combination in 53A.

FIG. 54A shows a dose matrix showing inhibition (%) for the combination. FIG. 54B-FIG. 54C show the results of single agent proliferation assays for the combination in 54A. FIG. 54D shows Loewe excess for the combination in 54A and FIG. 54E shows Bliss excess for the combination in 54A.

FIG. 55A shows a dose matrix showing inhibition (%) for the combination. FIG. 55B-FIG. 55C show the results of single agent proliferation assays for the combination in 55A. FIG. 55D shows Loewe excess for the combination in 55A and FIG. 55E shows Bliss excess for the combination in 55A.

FIG. 56A shows a dose matrix showing inhibition (%) for the combination. FIG. 56B-FIG. 56C show the results of single agent proliferation assays for the combination in 56A. FIG. 56D shows Loewe excess for the combination in 56A and FIG. 56E shows Bliss excess for the combination in 56A.

FIG. 57A shows a dose matrix showing inhibition (%) for the combination. FIG. 57B-FIG. 57C show the results of single agent proliferation assays for the combination in 57A. FIG. 57D shows Loewe excess for the combination in 57A and FIG. 57E shows Bliss excess for the combination in 57A.

FIG. 58A shows a dose matrix showing inhibition (%) for the combination in A375 cells. FIG. 58B-FIG. 58C show the results of single agent proliferation assays for the combination in 58A. FIG. 58D shows Loewe excess for the combination in 58A and FIG. 58E shows Bliss excess for the combination in 58A.

DETAILED DESCRIPTION OF THE INVENTION

Figure 1:
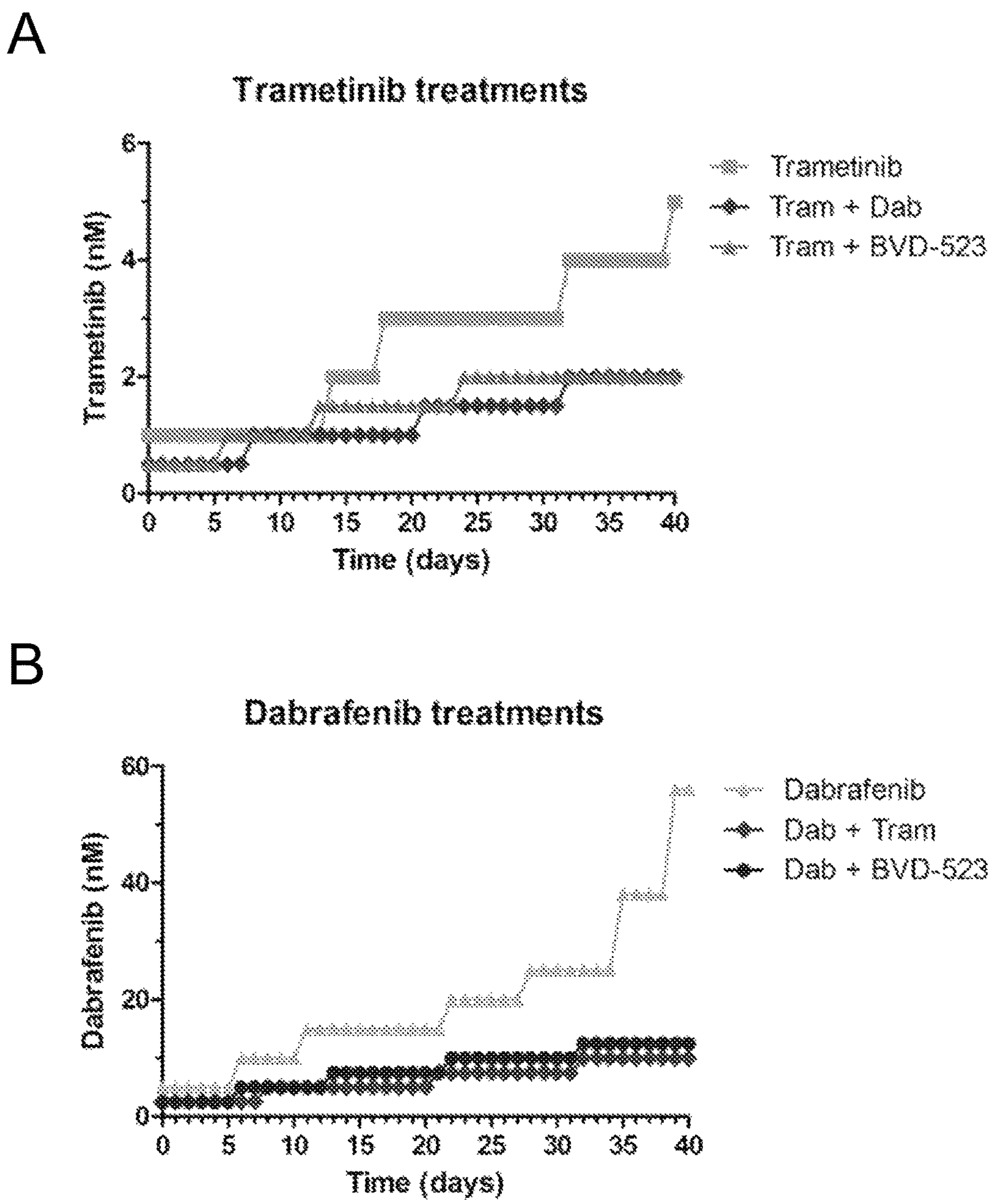
FIGS. 1A-C show the progress of a dose escalation study in a human malignant melanoma cell line (A375 cells) for month 1. Various treatments (trametinib (a type 2 MEK inhibitor), dabrafenib (a BRAF inhibitor), and BVD-523 (an ERK1/2 inhibior)) are as labeled.
Figure 2:
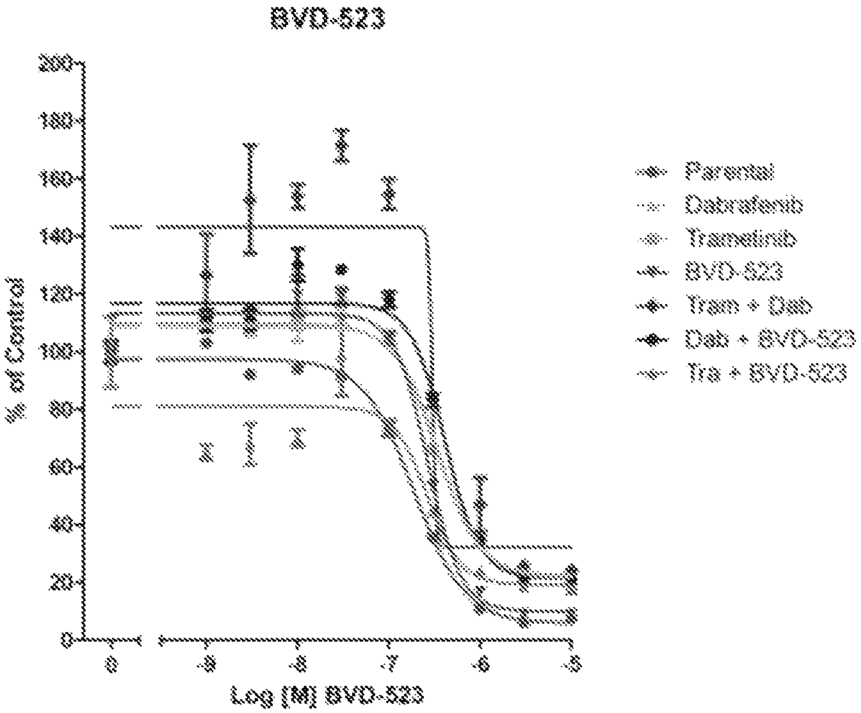
FIGS. 2A-H show the results of a proliferation assay that tracks changes in sensitivity to the escalated agent(s) at month 1. Various treatments (trametinib, dabrafenib, BVD-523, and pacitaxel) are as labeled on the top of the graph. The caption to the right of the graph shows the various types of cells generated from the dose escalation study. For example, "dabrafenib" refers to the cells that have been treated with the highest dose of dabrafenib from month 1 of the dose escalation study. Parental refers to the control cells that have not been treated with drugs.

One embodiment of the present invention is a method of treating or ameliorating the effects of a cancer in a subject in need thereof. The method comprises administering to the subject an effective amount of (i) a first anti-cancer agent, which is BVD-523 or a pharmaceutically acceptable salt thereof and (ii) a second anti-cancer agent, which is a type 2 MEK inhibitor or a pharmaceutically acceptable salt thereof, to treat or ameliorate the effects of the cancer.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

As used herein, the terms "ameliorate", "ameliorating" and grammatical variations thereof mean to decrease the severity of the symptoms of a disease in a subject.

In the present invention, cancers include both solid and hemotologic cancers. Non-limiting examples of solid cancers include adrenocortical carcinoma, anal cancer, bladder cancer, bone cancer (such as osteosarcoma), brain cancer, breast cancer, carcinoid cancer, carcinoma, cervical cancer, colon cancer, endometrial cancer, esophageal cancer, extrahepatic bile duct cancer, Ewing family of cancers, extracranial germ cell cancer, eye cancer, gallbladder cancer, gastric cancer, germ cell tumor, gestational trophoblastic tumor, head and neck cancer, hypopharyngeal cancer, islet cell carcinoma, kidney cancer, large intestine cancer, laryngeal cancer, leukemia, lip and oral cavity cancer, liver tumor/cancer, lung tumor/cancer, lymphoma, malignant mesothelioma, Merkel cell carcinoma, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell cancer, pancreatic cancer, paranasal sinus and nasal cavity cancer, parathyroid cancer, penile cancer, pituitary cancer, plasma cell neoplasm, prostate cancer, rhabdomyosarcoma, rectal cancer, renal cell cancer, transitional cell cancer of the renal pelvis and ureter, salivary gland cancer, Sezary syndrome, skin cancers (such as cutaneous t-cell lymphoma, Kaposi's sarcoma, mast cell tumor, and melanoma), small intestine cancer, soft tissue sarcoma, stomach cancer, testicular cancer, thymoma, thyroid cancer, urethral cancer, uterine cancer, vaginal cancer, vulvar cancer, and Wilms' tumor.

Examples of hematologic cancers include, but are not limited to, leukemias, such as adult/childhood acute lymphoblastic leukemia, adult/childhood acute myeloid leukemia, chronic lymphocytic leukemia, chronic myelogenous leukemia, and hairy cell leukemia, lymphomas, such as AIDS-related lymphoma, cutaneous T-cell lymphoma, adult/childhood Hodgkin lymphoma, mycosis fungoides, adult/childhood non-Hodgkin lymphoma, primary central nervous system lymphoma, Sézary syndrome, cutaneous T-cell lymphoma, and Waldenstrom macroglobulinemia, as well as other proliferative disorders such as chronic myeloproliferative disorders, Langerhans cell histiocytosis, multiple myeloma/plasma cell neoplasm, myelodysplastic syndromes, and myelodysplastic/myeloproliferative neoplasms.

A preferred set of cancers that may be treated according to the present invention include a cancer of the large intestine, breast cancer, pancreatic cancer, skin cancer, endometrial cancer, neuroblastoma, leukemia, lymphoma, liver cancer, lung cancer, testicular cancer, and thyroid cancer. Preferably, the cancer is melanoma.

As used herein, a "subject" is a mammal, preferably, a human. In addition to humans, categories of mammals within the scope of the present invention include, for example, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc.

In the present invention, BVD-523 corresponds to a compound according to formula (I):

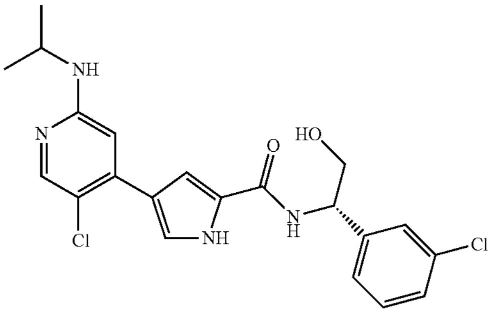 [SMILES: CC(C)Nc1cc(-c2c[nH]c(C(=O)N[C@H](CO)c3cccc(Cl)c3)c2)c(Cl)cn1]

and pharmaceutically acceptable salts thereof. BVD-523 may be synthesized according to the methods disclosed, e.g., in U.S. Pat. No. 7,354,939. Enantiomers and racemic mixtures of both enantiomers of BVD-523 are also contemplated within the scope of the present invention. BVD-523 is an ERK1/2 inhibitor with a mechanism of action that is believed to be, e.g., unique and distinct from certain other ERK1/2 inhibitors, such as SCH772984 and the pyrimidinal structure used by Hatzivassiliou et al. (2012). For example, other ERK1/2 inhibitors, such as SCH772984, inhibit autophosphorylation of ERK (Morris et al., 2013), whereas BVD-523 allows for the autophosphorylation of ERK while still inhibiting ERK. (See, e.g., FIG. 18).

As used herein, a "MEK inhibitor", such as a type 2 MEK inhibitor means those substances that (i) directly interact with MEK (i.e. MEK2), e.g. by binding to MEK (i.e. MEK2) and (ii) decrease the expression or the activity of MEK (i.e. MEK2). Therefore, inhibitors that act upstream of MEK (i.e. MEK2), such as RAS inhibitors and RAF inhibitors, are not MEK (i.e. MEK2) inhibitors according to the present invention. As noted above, MEK inhibitors may be classified into two types depending on whether the inhibitor competes with ATP. As used herein, "Type 1" MEK inhibitors mean those inhibitors that compete with ATP for binding to MEK. "Type 2" MEK inhibitors means those that do not compete with ATP for binding to MEK.

Non-limiting examples of type 2 MEK inhibitors according to the present invention include anthrax toxin, lethal factor portion of anthrax toxin, ARRY-142886 (6-(4-bromo-2-chloro-phenylamino)-7-fluoro-3-methyl-3H-benzoimidazole-5-carboxylic acid (2-hydroxy-ethoxy)-amide) (Array BioPharma), ARRY-438162 (Array BioPharma), AS-1940477 (Astellas), MEK162 (Array BioPharma), PD 098059 (2-(2'-amino-3'-methoxyphenyl)-oxanaphthalen-4-one), PD 184352 (CI-1040), PD-0325901 (Pfizer), pimasertib (Santhera Pharmaceuticals), refametinib (AstraZeneca), selumetinib (AZD6244) (AstraZeneca), TAK-733 (Takeda), trametinib (Japan Tobacco), U0126 (1,4-diamino-2,3-dicyano-1,4-bis(2-aminophenylthio)butadiene) (Sigma), RDEA119 (Ardea Biosciences/Bayer), pharmaceutically acceptable salts thereof, and combinations thereof. Preferably, the type 2 MEK inhibitor is trametinib or a pharmaceutically acceptable salt thereof.

In an additional aspect of this embodiment, the subject with cancer has a somatic RAS or BRAF mutation. As used herein, "somatic mutation" means a change occurring in any cell that is not destined to become a germ cell. The mutation may be, e.g., a substitution, deletion, insertion, or a fusion. Preferably, the RAS mutation is a mutation in H-RAS, N-RAS, or K-RAS. The following Tables 1, 2 and 3 show the SEQ ID Nos. of representative nucleic acid and amino acid sequences of wild type H-RAS, K-RAS, and N-RAS from various animals, respectively. These sequences may be used in methods for identifying subjects with a mutant RAS genotype (such as in the methods set forth below).

TABLE 1

| H-RAS sequences | | | |
|---|---|---|---|
| SEQ ID No. | polypeptide or nucleic acid sequence | Organism | Other Information |
| 1 | nucleic acid | human | isoform 1 |
| 2 | polypeptide | human | isoform 1 |
| 3 | nucleic acid | human | isoform 2 |
| 4 | polypeptide | human | isoform 2 |
| 5 | nucleic acid | human | isoform 3 |
| 6 | polypeptide | human | isoform 3 |
| 7 | nucleic acid | rat (*Rattus norvegicus*) | variant 1 |
| 8 | polypeptide | rat (*Rattus norvegicus*) | variant 1 |
| 9 | nucleic acid | rat (*Rattus norvegicus*) | variant 2 |
| 10 | polypeptide | rat (*Rattus norvegicus*) | variant 2 |
| 11 | nucleic acid | mouse, *Mus musculus* | |
| 12 | polypeptide | mouse, *Mus musculus* | |
| 13 | nucleic acid | guinea pig, *Cavia porcellus* | variant 1 |
| 14 | polypeptide | guinea pig, *Cavia porcellus* | variant 1 |
| 15 | nucleic acid | guinea pig, *Cavia porcellus* | variant 2 |
| 16 | polypeptide | guinea pig, *Cavia porcellus* | variant 2 |
| 17 | nucleic acid | guinea pig, *Cavia porcellus* | variant 3 |
| 18 | polypeptide | guinea pig, *Cavia porcellus* | variant 3 |
| 19 | nucleic acid | guinea pig, *Cavia porcellus* | variant 4 |
| 20 | polypeptide | guinea pig, *Cavia porcellus* | variant 4 |
| 21 | nucleic acid | dog, *Canis lupus familiaris* | variant 1 |
| 22 | polypeptide | dog, *Canis lupus familiaris* | variant 1 |
| 23 | nucleic acid | dog, *Canis lupus familiaris* | variant 2 |
| 24 | polypeptide | dog, *Canis lupus familiaris* | variant 2 |
| 25 | nucleic acid | cat, *Felis catus* | variant 1 |
| 26 | polypeptide | cat, *Felis catus* | variant 1 |
| 27 | nucleic acid | cat, *Felis catus* | variant 2 |
| 28 | polypeptide | cat, *Felis catus* | variant 2 |
| 29 | nucleic acid | cow, *Bos taurus* | variant 1 |
| 30 | polypeptide | cow, *Bos taurus* | variant 1 |
| 31 | nucleic acid | cow, *Bos taurus* | variant 2 |
| 32 | polypeptide | cow, *Bos taurus* | variant 2 |
| 33 | nucleic acid | cow, *Bos taurus* | variant X1 |
| 34 | polypeptide | cow, *Bos taurus* | variant X1 |
| 35 | nucleic acid | chicken, *Gallus gallus* | |
| 36 | polypeptide | chicken, *Gallus gallus* | |

TABLE 2

| K-RAS sequences | | | |
|---|---|---|---|
| SEQ ID No. | polypeptide or nucleic acid sequence | Organism | Other Information |
| 37 | nucleic acid | human | isoform a |
| 38 | polypeptide | human | isoform a |
| 39 | nucleic acid | human | isoform b |
| 40 | polypeptide | human | isoform b |

TABLE 2-continued

| K-RAS sequences | | | |
|---|---|---|---|
| SEQ ID No. | polypeptide or nucleic acid sequence | Organism | Other Information |
| 41 | nucleic acid | rat (*Rattus norvegicus*) | |
| 42 | polypeptide | rat (*Rattus norvegicus*) | |
| 43 | nucleic acid | mouse, *Mus musculus* | |
| 44 | polypeptide | mouse, *Mus musculus* | |
| 45 | nucleic acid | rabbit, *Oryctolagus cuniculus* | |
| 46 | polypeptide | rabbit, *Oryctolagus cuniculus* | |
| 47 | nucleic acid | guinea pig, *Cavia porcellus* | variant 1 |
| 48 | polypeptide | guinea pig, *Cavia porcellus* | variant 1 |
| 49 | nucleic acid | guinea pig, *Cavia porcellus* | variant 2 |
| 50 | polypeptide | guinea pig, *Cavia porcellus* | variant 2 |
| 51 | nucleic acid | dog, *Canis lupus familiaris* | variant 1 |
| 52 | polypeptide | dog, *Canis lupus familiaris* | variant 1 |
| 53 | nucleic acid | dog, *Canis lupus familiaris* | variant 2 |
| 54 | polypeptide | dog, *Canis lupus familiaris* | variant 2 |
| 55 | nucleic acid | cat, *Felis catus* | variant 1 |
| 56 | polypeptide | cat, *Felis catus* | variant 1 |
| 57 | nucleic acid | cat, *Felis catus* | variant 2 |
| 58 | polypeptide | cat, *Felis catus* | variant 2 |
| 59 | nucleic acid | cow, *Bos taurus* | |
| 60 | polypeptide | cow, *Bos taurus* | |
| 61 | nucleic acid | cow, *Bos taurus* | variant X2 |
| 62 | polypeptide | cow, *Bos taurus* | variant X2 |
| 63 | nucleic acid | cow, *Bos taurus* | variant X3 |
| 64 | polypeptide | cow, *Bos taurus* | variant X3 |
| 65 | nucleic acid | chicken, *Gallus gallus* | |
| 66 | polypeptide | chicken, *Gallus gallus* | |

TABLE 3

| N-RAS sequences | | | |
|---|---|---|---|
| SEQ ID No. | polypeptide or nucleic acid sequence | Organism | Other Information |
| 67 | nucleic acid | human | |
| 68 | polypeptide | human | |
| 69 | nucleic acid | rat (*Rattus norvegicus*) | |
| 70 | polypeptide | rat (*Rattus norvegicus*) | |
| 71 | nucleic acid | mouse, *Mus musculus* | |
| 72 | polypeptide | mouse, *Mus musculus* | |
| 73 | nucleic acid | guinea pig, *Cavia porcellus* | |
| 74 | polypeptide | guinea pig, *Cavia porcellus* | |
| 75 | nucleic acid | guinea pig, *Cavia porcellus* | variant X1 |
| 76 | polypeptide | guinea pig, *Cavia porcellus* | variant X1 |
| 77 | nucleic acid | dog, *Canis lupus familiaris* | |
| 78 | polypeptide | dog, *Canis lupus familiaris* | |

TABLE 3-continued

| N-RAS sequences | | | |
|---|---|---|---|
| SEQ ID No. | polypeptide or nucleic acid sequence | Organism | Other Information |
| 79 | nucleic acid | cat, *Felis catus* | |
| 80 | polypeptide | cat, *Felis catus* | |
| 81 | nucleic acid | cow, *Bos taurus* | |
| 82 | polypeptide | cow, *Bos taurus* | |
| 83 | nucleic acid | chicken, *Gallus gallus* | |
| 84 | polypeptide | chicken, *Gallus gallus* | |

The following Table 4 shows the SEQ ID Nos. of representative nucleic acid and amino acid sequences of wild type BRAF from various animals. These wild type sequences may be used in methods (such as the methods set forth below) for identifying subjects with a mutant BRAF genotype.

TABLE 4

| BRAF sequences | | | |
|---|---|---|---|
| SEQ ID NO | Nucleic acid or polypeptide | Organism | Other information |
| 85 | nucleic acid | human | |
| 86 | polypeptide | human | |
| 87 | nucleic acid | rat (*Rattus norvegicus*) | |
| 88 | polypeptide | rat (*Rattus norvegicus*) | |
| 89 | nucleic acid | mouse, *Mus musculus* | |
| 90 | polypeptide | mouse, *Mus musculus* | |
| 91 | nucleic acid | rabbit, *Oryctolagus cuniculus* | |
| 92 | polypeptide | rabbit, *Oryctolagus cuniculus* | |
| 93 | nucleic acid | guinea pig, *Cavia porcellus* | |
| 94 | polypeptide | guinea pig, *Cavia porcellus* | |
| 95 | nucleic acid | dog, *Canis lupus familiaris* | variant x1 |
| 96 | polypeptide | dog, *Canis lupus familiaris* | variant x1 |
| 97 | nucleic acid | dog, *Canis lupus familiaris* | variant x2 |
| 98 | polypeptide | dog, *Canis lupus familiaris* | variant x2 |
| 99 | nucleic acid | cat, *Felis catus* | |
| 100 | polypeptide | cat, *Felis catus* | |
| 101 | nucleic acid | cow, *Bos taurus* | variant X1 |
| 102 | polypeptide | cow, *Bos taurus* | variant X1 |
| 103 | nucleic acid | cow, *Bos taurus* | variant X2 |
| 104 | polypeptide | cow, *Bos taurus* | variant X2 |
| 105 | nucleic acid | cow, *Bos taurus* | variant X3 |
| 106 | polypeptide | cow, *Bos taurus* | variant X3 |
| 107 | nucleic acid | cow, *Bos taurus* | variant X4 |
| 108 | polypeptide | cow, *Bos taurus* | variant X4 |
| 109 | nucleic acid | cow, *Bos taurus* | variant X5 |
| 110 | polypeptide | cow, *Bos taurus* | variant X5 |
| 111 | nucleic acid | cow, *Bos taurus* | variant X6 |
| 112 | polypeptide | cow, *Bos taurus* | variant X6 |
| 113 | nucleic acid | cow, *Bos taurus* | variant X7 |
| 114 | polypeptide | cow, *Bos taurus* | variant X7 |
| 115 | nucleic acid | cow, *Bos taurus* | variant X8 |
| 116 | polypeptide | cow, *Bos taurus* | variant X8 |
| 117 | nucleic acid | cow, *Bos taurus* | variant X9 |
| 118 | polypeptide | cow, *Bos taurus* | variant X9 |
| 119 | nucleic acid | cow, *Bos taurus* | variant X10 |
| 120 | polypeptide | cow, *Bos taurus* | variant X10 |
| 121 | nucleic acid | cow, *Bos taurus* | variant X11 |
| 122 | polypeptide | cow, *Bos taurus* | variant X11 |
| 123 | nucleic acid | cow, *Bos taurus* | variant 2 |
| 124 | polypeptide | cow, *Bos taurus* | variant 2 |
| 125 | nucleic acid | horse, *Equus caballus* | |

TABLE 4-continued

| BRAF sequences | | | |
|---|---|---|---|
| SEQ ID NO | Nucleic acid or polypeptide | Organism | Other information |
| 126 | polypeptide | horse, *Equus caballus* | |
| 127 | nucleic acid | chicken, *Gallus gallus* | |
| 128 | polypeptide | chicken, *Gallus gallus* | |

Methods for identifying mutations in nucleic acids, such as the above identified RAS and BRAF genes, are known in the art. Nucleic acids may be obtained from biological samples. In the present invention, biological samples include, but are not limited to, blood, plasma, urine, skin, saliva, and biopsies. Biological samples are obtained from a subject by routine procedures and methods which are known in the art.

Non-limiting examples of methods for identifying mutations include PCR, sequencing, hybrid capture, in-solution capture, molecular inversion probes, fluorescent in situ hybridization (FISH) assay, and combinations thereof.

Various sequencing methods are known in the art. These include, but are not limited to, Sanger sequencing (also referred to as dideoxy sequencing) and various sequencing-by-synthesis (SBS) methods as disclosed in, e.g., Metzker 2005, sequencing by hybridization, by ligation (for example, WO 2005021786), by degradation (for example, U.S. Pat. Nos. 5,622,824 and 6,140,053) and nanopore sequencing (which is commercially available from Oxford Nanopore Technologies, UK). In deep sequencing techniques, a given nucleotide in the sequence is read more than once during the sequencing process. Deep sequencing techniques are disclosed in e.g., U.S. Patent Publication No. 20120264632 and International Patent Publication No. WO2012125848.

PCR-based methods for detecting mutations are known in the art and employ PCR amplification, where each target sequence in the sample has a corresponding pair of unique, sequence-specific primers. For example, the polymerase chain reaction-restriction fragment length polymorphism (PCR-RFLP) method allows for rapid detection of mutations after the genomic sequences are amplified by PCR. The mutation is discriminated by digestion with specific restriction endonucleases and is identified by electrophoresis. See, e.g., Ota et al., 2007. Mutations may also be detected using real time PCR. See, e.g., International Application publication No. WO2012046981.

Hybrid capture methods are known in the art and are disclosed in e.g., U.S. Patent Publication No. 20130203632 and U.S. Pat. Nos. 8,389,219 and 8,288,520. These methods are based on the selective hybridization of the target genomic regions to user-designed oligonucleotides. The hybridization can be to oligonucleotides immobilized on high or low density microarrays (on-array capture), or solution-phase hybridization to oligonucleotides modified with a ligand (e.g. biotin) which can subsequently be immobilized to a solid surface, such as a bead (in-solution capture).

Molecular Inversion Probe (MIP) techniques are known in the art and are disclosed in e.g., Absalan et al., 2008. This method uses MIP molecules, which are special "padlock" probes (Nilsson et al, 1994) for genotyping. A MIP molecule is a linear oligonucleotide that contains specific regions, universal sequences, restriction sites and a Tag (index) sequence (16-22 bp). A MIP hybridizes directly around the genetic marker/SNP of interest. The MIP method may also use a number of "padlock" probe sets that hybridize to genomic DNA in parallel (Hardenbol et al., 2003). In case of a perfect match, genomic homology regions are ligated by undergoing an inversion in configuration (as suggested by the name of the technique) and creating a circular molecule. After the first restriction, all molecules are amplified with universal primers. Amplicons are restricted again to ensure short fragments for hybridization on a microarray. Generated short fragments are labeled and, through a Tag sequence, hybridized to a cTag (complementary strand for index) on an array. After the formation of Tag-cTag duplex, a signal is detected.

In another aspect of this embodiment, the method further comprises administering to the subject at least one additional therapeutic agent effective for treating or ameliorating the effects of the cancer. The additional therapeutic agent may be selected from the group consisting of an antibody or fragment thereof, a cytotoxic agent, a toxin, a radionuclide, an immunomodulator, a photoactive therapeutic agent, a radiosensitizing agent, a hormone, an anti-angiogenesis agent, and combinations thereof.

As used herein, an "antibody" encompasses naturally occurring immunoglobulins as well as non-naturally occurring immunoglobulins, including, for example, single chain antibodies, chimeric antibodies (e.g., humanized murine antibodies), and heteroconjugate antibodies (e.g., bispecific antibodies). Fragments of antibodies include those that bind antigen, (e.g., Fab', $F(ab')_2$, Fab, Fv, and rlgG). See also, e.g., Pierce Catalog and Handbook, 1994-1995 (Pierce Chemical Co., Rockford, Ill.); Kuby, J., Immunology, 3rd Ed., W.H. Freeman & Co., New York (1998). The term antibody also includes bivalent or bispecific molecules, diabodies, triabodies, and tetrabodies. The term "antibody" further includes both polyclonal and monoclonal antibodies.

Examples of therapeutic antibodies that may be used in the present invention include rituximab (Rituxan), Cetuximab (Erbitux), bevacizumab (Avastin), and Ibritumomab (Zevalin).

Cytotoxic agents according to the present invention include DNA damaging agents, antimetabolites, anti-microtubule agents, antibiotic agents, etc. DNA damaging agents include alkylating agents, platinum-based agents, intercalating agents, and inhibitors of DNA replication. Non-limiting examples of DNA alkylating agents include cyclophosphamide, mechlorethamine, uramustine, melphalan, chlorambucil, ifosfamide, carmustine, lomustine, streptozocin, busulfan, temozolomide, pharmaceutically acceptable salts thereof, prodrugs, and combinations thereof. Non-limiting examples of platinum-based agents include cisplatin, carboplatin, oxaliplatin, nedaplatin, satraplatin, triplatin tetranitrate, pharmaceutically acceptable salts thereof, prodrugs, and combinations thereof. Non-limiting examples of intercalating agents include doxorubicin, daunorubicin, idarubicin, mitoxantrone, pharmaceutically acceptable salts thereof, prodrugs, and combinations thereof. Non-limiting examples of inhibitors of DNA replication include irinotecan, topotecan, amsacrine, etoposide, etoposide phosphate, teniposide, pharmaceutically acceptable salts thereof, prodrugs, and combinations thereof. Antimetabolites include folate antagonists such as methotrexate and premetrexed, purine antagonists such as 6-mercaptopurine, dacarbazine, and fludarabine, and pyrimidine antagonists such as 5-fluorouracil, arabinosylcytosine, capecitabine, gemcitabine, decitabine, pharmaceutically acceptable salts thereof, prodrugs, and combinations thereof. Anti-microtubule agents include without limitation vinca alkaloids, paclitaxel (Taxol®), docetaxel (Taxotere®), and ixabepilone (Ixempra®). Antibiotic agents include without limitation actinomycin, anthracyclines, valrubicin, epirubicin, bleomycin, plicamycin, mitomycin, pharmaceutically acceptable salts thereof, prodrugs, and combinations thereof.

Cytotoxic agents according to the present invention also include an inhibitor of the PI3K/Akt pathway. Non-limiting examples of an inhibitor of the PI3K/Akt pathway according to the present invention include A-674563 (CAS #552325-73-2), AGL 2263, AMG-319 (Amgen, Thousand Oaks, Calif.), AS-041164 (5-benzo[1,3]dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, Genentech (Roche Holdings Inc., South San Francisco, Calif.), BML-257 (CAS #32387-96-5), CAL-120 (Gilead Sciences, Foster City, Calif.), CAL-129 (Gilead Sciences), CAL-130 (Gilead Sciences), CAL-253 (Gilead Sciences), CAL-263 (Gilead Sciences), CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432 (Chroma Therapeutics, Ltd., Abingdon, UK), FPA 124 (CAS #902779-59-3), GS-1101 (CAL-101) (Gilead Sciences), GSK 690693 (CAS #937174-76-0), H-89 (CAS #127243-85-0), Honokiol, IC87114 (Gilead Science), IPI-145 (Intellikine Inc.), KAR-4139 (Karus Therapeutics, Chilworth, UK), KAR-4141 (Karus Therapeutics), KIN-1 (Karus Therapeutics), KT 5720 (CAS #108068-98-0), Miltefosine, MK-2206 dihydrochloride (CAS #1032350-13-2), ML-9 (CAS #105637-50-1), Naltrindole Hydrochloride, OXY-111A (NormOxys Inc., Brighton, Mass.), perifosine, PHT-427 (CAS #1191951-57-1), PI3 kinase delta inhibitor, Merck KGaA (Merck & Co., Whitehouse Station, N.J.), PI3 kinase delta inhibitors, Genentech (Roche Holdings Inc.), PI3 kinase delta inhibitors, Incozen (Incozen Therapeutics, Pvt. Ltd., Hyderabad, India), PI3 kinase delta inhibitors-2, Incozen (Incozen Therapeutics), PI3 kinase inhibitor, Roche-4 (Roche Holdings Inc.), PI3 kinase inhibitors, Roche (Roche Holdings Inc.), PI3 kinase inhibitors, Roche-5 (Roche Holdings Inc.), PI3-alpha/delta inhibitors, Pathway Therapeutics (Pathway Therapeutics Ltd., South San Francisco, Calif.), PI3-delta inhibitors, Cellzome (Cellzome AG, Heidelberg, Germany), PI3-delta inhibitors, Intellikine (Intellikine Inc., La Jolla, Calif.), PI3-delta inhibitors, Pathway Therapeutics-1 (Pathway Therapeutics Ltd.), PI3-delta inhibitors, Pathway Therapeutics-2 (Pathway Therapeutics Ltd.), PI3-delta/gamma inhibitors, Cellzome (Cellzome AG), PI3-delta/gamma inhibitors, Cellzome (Cellzome AG), PI3-delta/gamma inhibitors, Intellikine (Intellikine Inc.), PI3-delta/gamma inhibitors, Intellikine (Intellikine Inc.), PI3-delta/gamma inhibitors, Pathway Therapeutics (Pathway Therapeutics Ltd.), PI3-delta/gamma inhibitors, Pathway Therapeutics (Pathway Therapeutics Ltd.), PI3-gamma inhibitor Evotec (Evotec), PI3-gamma inhibitor, Cellzome (Cellzome AG), PI3-gamma inhibitors, Pathway Therapeutics (Pathway Therapeutics Ltd.), PI3K delta/gamma inhibitors, Intellikine-1 (Intellikine Inc.), PI3K delta/gamma inhibitors, Intellikine-1 (Intellikine Inc.), pictilisib (Roche Holdings Inc.), PIK-90 (CAS #677338-12-4), SC-103980 (Pfizer, New York, N.Y.), SF-1126 (Semafore Pharmaceuticals, Indianapolis, Ind.), SH-5, SH-6, Tetrahydro Curcumin, TG100-115 (Targegen Inc., San Diego, Calif.), Triciribine, X-339 (Xcovery, West Palm Beach, Fla.), XL-499 (Evotech, Hamburg, Germany), pharmaceutically acceptable salts thereof, and combinations thereof.

In the present invention, the term "toxin" means an antigenic poison or venom of plant or animal origin. An example is diphtheria toxin or portions thereof.

In the present invention, the term "radionuclide" means a radioactive substance administered to the patient, e.g., intravenously or orally, after which it penetrates via the patient's normal metabolism into the target organ or tissue, where it delivers local radiation for a short time. Examples of radionuclides include, but are not limited to, 1-125, At-211, Lu-177, Cu-67, I-131, Sm-153, Re-186, P-32, Re-188, In-114m, and Y-90.

In the present invention, the term "immunomodulator" means a substance that alters the immune response by augmenting or reducing the ability of the immune system to produce antibodies or sensitized cells that recognize and react with the antigen that initiated their production. Immunomodulators may be recombinant, synthetic, or natural preparations and include cytokines, corticosteroids, cytotoxic agents, thymosin, and immunoglobulins. Some immunomodulators are naturally present in the body, and certain of these are available in pharmacologic preparations. Examples of immunomodulators include, but are not limited to, granulocyte colony-stimulating factor (G-CSF), interferons, imiquimod and cellular membrane fractions from bacteria, IL-2, IL-7, IL-12, CCL3, CCL26, CXCL7, and synthetic cytosine phosphate-guanosine (CpG).

In the present invention, the term "photoactive therapeutic agent" means compounds and compositions that become active upon exposure to light. Certain examples of photoactive therapeutic agents are disclosed, e.g., in U.S. Patent Application Serial No. 2011/0152230 A1, "Photoactive Metal Nitrosyls For Blood Pressure Regulation And Cancer Therapy."

In the present invention, the term "radiosensitizing agent" means a compound that makes tumor cells more sensitive to radiation therapy. Examples of radiosensitizing agents include misonidazole, metronidazole, tirapazamine, and trans sodium crocetinate.

In the present invention, the term "hormone" means a substance released by cells in one part of a body that affects cells in another part of the body. Examples of hormones include, but are not limited to, prostaglandins, leukotrienes, prostacyclin, thromboxane, amylin, antimullerian hormone, adiponectin, adrenocorticotropic hormone, angiotensinogen, angiotensin, vasopressin, atriopeptin, brain natriuretic peptide, calcitonin, cholecystokinin, corticotropin-releasing hormone, encephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, somatomedin, leptin, liptropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostain, thrombopoietin, thyroid-stimulating hormone, testosterone, dehydroepiandrosterone, androstenedione, dihydrotestosterone, aldosterone, estradiol, estrone, estriol, cortisol, progesterone, calcitriol, and calcidiol.

Some compounds interfere with the activity of certain hormones or stop the production of certain hormones. These hormone-interfering compounds include, but are not limited to, tamoxifen (Nolvadex®), anastrozole (Arimidex®), letrozole (Femara®), and fulvestrant (Faslodex®). Such compounds are also within the meaning of hormone in the present invention.

As used herein, an "anti-angiogenesis" agent means a substance that reduces or inhibits the growth of new blood vessels, such as, e.g., an inhibitor of vascular endothelial growth factor (VEGF) and an inhibitor of endothelial cell migration. Anti-angiogenesis agents include without limitation 2-methoxyestradiol, angiostatin, bevacizumab, cartilage-derived angiogenesis inhibitory factor, endostatin, IFN-α, IL-12, itraconazole, linomide, platelet factor-4, prolactin, SU5416, suramin, tasquinimod, tecogalan, tetrathiomolybdate, thalidomide, thrombospondin, thrombospondin, TNP-470, ziv-aflibercept, pharmaceutically acceptable salts thereof, prodrugs, and combinations thereof.

In another aspect of this embodiment, administration of the first and second anti-cancer agents provides a synergistic effect compared to administration of either anti-cancer agent alone. As used herein, "synergistic" means more than additive. Synergistic effects may be measured by various assays known in the art, including but not limited to those disclosed herein, such as the excess over bliss assay.

Another embodiment of the present invention is a method of treating or ameliorating the effects of a cancer in a subject in need thereof. The method comprises administering to the subject an effective amount of (i) a first anti-cancer agent, which is BVD-523 or a pharmaceutically acceptable salt thereof and (ii) a second anti-cancer agent, which is trametinib or a pharmaceutically acceptable salt thereof, to treat or ameliorate the effects of the cancer.

Suitable and preferred subjects and various types of cancer are as disclosed herein. In this embodiment, the methods may be used to treat the cancers disclosed above, including those cancers with the mutational backgrounds identified above. Methods of identifying such mutations are also as set forth above.

In one aspect of this embodiment, the BVD-523 or a pharmaceutically acceptable salt thereof is administered in the form of a pharmaceutical composition further comprising a pharmaceutically acceptable carrier or diluent.

In a further aspect of this embodiment, the trametinib or a pharmaceutically acceptable salt thereof is administered in the form of a pharmaceutical composition further comprising a pharmaceutically acceptable carrier or diluent.

In an additional aspect of this embodiment, the method further comprises administering to the subject at least one additional therapeutic agent, preferably an inhibitor of the PI3K/Akt pathway, as disclosed herein.

In another aspect of this embodiment, administration of the first and second anti-cancer agents provides a synergistic effect compared to administration of either anti-cancer agent alone.

A further embodiment of the present invention is a method of effecting cancer cell death. The method comprises contacting the cancer cell with an effective amount of (i) a first anti-cancer agent, which is BVD-523 or a pharmaceutically acceptable salt thereof and (ii) a second anti-cancer agent, which is a type 2 MEK inhibitor or a pharmaceutically acceptable salt thereof.

Suitable and preferred type 2 MEK inhibitors are as disclosed herein. In this embodiment, effecting cancer cell death may be accomplished in cancer cells having various mutational backgrounds and/or that are characterized as disclosed above. Methods of identifying such mutations are also as set forth above.

In one aspect of this embodiment, the cancer cell is a mammalian cancer cell. Preferably, the mammalian cancer cell is obtained from a mammal selected from the group consisting of humans, primates, farm animals, and domestic animals. More preferably, the mammalian cancer cell is a human cancer cell.

The methods of this embodiment, which may be carried out in vitro or in vivo, may be used to effect cancer cell death, by e.g., killing cancer cells, in cells of the types of cancer disclosed herein.

In an additional aspect of this embodiment, the method further comprises contacting the cancer cell with at least one additional therapeutic agent, preferably an inhibitor of the PI3K/Akt pathway, as disclosed herein.

In another aspect of this embodiment, contacting the cancer cell with the first and second anti-cancer agents provides a synergistic effect compared to contacting the cancer cell with either anti-cancer agent alone. In this embodiment, "contacting" means bringing BVD-523 and the Type 2 MEK inhibitors, and optionally one or more additional therapeutic agents into close proximity to the cancer cells. This may be accomplished using conventional techniques of drug delivery to mammals or in the in vitro situation by, e.g., providing BVD-523 and the Type 2 MEK inhibitors, and optionally other therapeutic agents to a culture media in which the cancer cells are located.

An additional embodiment of the present invention is a kit for treating or ameliorating the effects of a cancer in a subject in need thereof. The kit comprises an effective amount of (i) a first anti-cancer agent, which is BVD-523 or a pharmaceutically acceptable salt thereof and (ii) a second anti-cancer agent, which is a type 2 MEK inhibitor or a pharmaceutically acceptable salt thereof, packaged together with instructions for their use.

The kits may also include suitable storage containers, e.g., ampules, vials, tubes, etc., for each anti-cancer agent of the present invention (which, e.g., may be in the form of pharmaceutical compositions) and other reagents, e.g., buffers, balanced salt solutions, etc., for use in administering the anti-cancer agents to subjects. The anti-cancer agents of the invention and other reagents may be present in the kits in any convenient form, such as, e.g., in a solution or in a powder form. The kits may further include a packaging container, optionally having one or more partitions for housing the pharmaceutical composition and other optional reagents.

In this embodiment, suitable and preferred type 2 MEK inhibitors and subjects are as set forth above. In this embodiment, the kit may be used to treat the cancers disclosed above, including those cancers with the mutational backgrounds identified herein. Methods of identifying such mutations are as set forth above.

In one aspect of this embodiment, the kit further comprises at least one additional therapeutic agent, preferably an inhibitor of the PI3K/Akt pathway, as disclosed herein.

In another aspect of this embodiment, administration of the first and second anti-cancer agents provides a synergistic effect compared to administration of either anti-cancer agent alone.

Another embodiment of the present invention is a pharmaceutical composition for treating or ameliorating the effects of a cancer in a subject in need thereof. The pharmaceutical composition comprises a pharmaceutically acceptable diluent or carrier and an effective amount of (i) a first anti-cancer agent, which is BVD-523 or a pharmaceutically acceptable salt thereof and (ii) a second anti-cancer agent, which is a type 2 MEK inhibitor or a pharmaceutically acceptable salt thereof, wherein administration of the first and second anti-cancer agents provides a synergistic effect compared to administration of either anti-cancer agent alone.

Suitable and preferred subjects and type 2 MEK inhibitors are as disclosed herein. The pharmaceutical compositions of the invention may be used to treat the cancers disclosed above, including those cancers with the mutational backgrounds identified herein. Methods of identifying such mutations are also as set forth above.

In a further aspect of this embodiment, the pharmaceutical composition further comprises at least one additional therapeutic agent, preferably an inhibitor of the PI3K/Akt pathway, as disclosed herein.

The pharmaceutical compositions according to the present invention may be in a unit dosage form comprising both anti-cancer agents. In another aspect of this embodiment, the first anti-cancer agent is in a first unit dosage form and the second anti-cancer agent is in a second unit dosage form, separate from the first.

The first and second anti-cancer agents may be co-administered to the subject, either simultaneously or at different times, as deemed most appropriate by a physician. If the first and second anti-cancer agents are administered at different times, for example, by serial administration, the first anti-cancer agent may be administered to the subject before the second anti-cancer agent. Alternatively, the second anti-cancer agent may be administered to the subject before the first anti-cancer agent.

A further embodiment of the present invention is a method of treating or ameliorating the effects of a cancer in a subject in need thereof. The method comprises administering to the subject an effective amount of (i) a first anti-cancer agent, which is BVD-523 or a pharmaceutically acceptable salt thereof and (ii) a second anti-cancer agent, which is a MEK inhibitor selected from the group consisting of antroquinonol (Golden Biotechnology), AS-1940477 (Astellas), AS-703988 (Merck KGaA), BI-847325 (Boehringer Ingelheim), E-6201 (Eisai), GDC-0623 (Hoffmann-La Roche), GDC-0973, RG422, RO4987655, RO5126766, SL327, WX-554 (Wilex), YopJ polypeptide, pharmaceutically acceptable salts thereof, and combinations thereof, to treat or ameliorate the effects of the cancer.

Suitable and preferred subjects are as disclosed herein. In this embodiment, the methods may be used to treat the cancers disclosed above, including those cancers with the mutational backgrounds identified above. Methods of identifying such mutations are also as set forth above.

In an additional aspect of this embodiment, the method further comprises administering to the subject at least one additional therapeutic agent, preferably an inhibitor of the PI3K/Akt pathway, as disclosed herein.

In another aspect of this embodiment, administration of the first and second anti-cancer agents provides a synergistic effect compared to administration of either anti-cancer agent alone.

An additional embodiment of the present invention is a method of effecting cancer cell death. The method comprises contacting the cancer cell with an effective amount of (i) a first anti-cancer agent, which is BVD-523 or a pharmaceutically acceptable salt thereof and (ii) a second anti-cancer agent, which is a MEK inhibitor selected from the group consisting of antroquinonol (Golden Biotechnology), AS-1940477 (Astellas), AS-703988 (Merck KGaA), BI-847325 (Boehringer Ingelheim), E-6201 (Eisai), GDC-0623 (Hoffmann-La Roche), GDC-0973, RG422, RO4987655, RO5126766, SL327, WX-554 (Wilex), YopJ polypeptide, pharmaceutically acceptable salts thereof, and combinations thereof.

In this embodiment, the methods may be used to effect cell death in any of the cancers disclosed above, including those cancers with the mutational backgrounds identified herein. Methods of identifying such mutations are also as set forth above.

In one aspect of this embodiment, the cancer cell is a mammalian cancer cell. Preferably, the mammalian cancer cell is obtained from a mammal selected from the group consisting of humans, primates, farm animals, and domestic animals. More preferably, the mammalian cancer cell is a human cancer cell.

In another aspect of this embodiment, the method further comprises contacting the cancer cell with at least one additional therapeutic agent, preferably an inhibitor of the PI3K/Akt pathway, as disclosed herein.

In a further aspect of this embodiment, contacting the cancer with the first and second anti-cancer agents provides a synergistic effect compared to contacting the cancer cell with either anti-cancer agent alone. In this embodiment, "contacting" means bringing BVD-523 and the MEK inhibitors, and optionally one or more additional therapeutic agents into close proximity to the cancer cells. This may be accomplished using conventional techniques of drug delivery to mammals or in the in vitro situation by, e.g., providing BVD-523 and the MEK inhibitors, and optionally other therapeutic agents to a culture media in which the cancer cells are located.

The methods of this embodiment, which may be carried out in vitro or in vivo, may be used to effect cancer cell death, by e.g., killing cancer cells, in cells of the types of cancer disclosed herein.

Another embodiment of the present invention is a kit for treating or ameliorating the effects of a cancer in a subject in need thereof. The kit comprises an effective amount of (i) a first anti-cancer agent, which is BVD-523 or a pharmaceutically acceptable salt thereof and (ii) a second anti-cancer agent, which is a MEK inhibitor selected from the group consisting of antroquinonol (Golden Biotechnology), AS-1940477 (Astellas), AS-703988 (Merck KGaA), BI-847325 (Boehringer Ingelheim), E-6201 (Eisai), GDC-0623 (Hoffmann-La Roche), GDC-0973, RG422, RO4987655, RO5126766, SL327, WX-554 (Wilex), YopJ polypeptide, pharmaceutically acceptable salts thereof, and combinations thereof, packaged together with instructions for their use.

Suitable and preferred subjects are as disclosed herein. In this embodiment, the kit may be used to treat the cancers disclosed above, including those cancers with the mutational backgrounds identified herein. Methods of identifying such mutations are also as set forth above.

In another aspect of this embodiment, the kit further comprises at least one additional therapeutic agent, preferably an inhibitor of the PI3K/Akt pathway, as disclosed herein.

In a further aspect of this embodiment, administration of the first and second anti-cancer agents provides a synergistic effect compared to administration of either anti-cancer agent alone.

A further embodiment of the present invention is a pharmaceutical composition for treating or ameliorating the effects of a cancer in a subject in need thereof. The pharmaceutical composition comprises a pharmaceutically acceptable diluent or carrier and an effective amount of (i) a first anti-cancer agent, which is BVD-523 or a pharmaceutically acceptable salt thereof and (ii) a second anti-cancer agent, which is a MEK inhibitor selected from the group consisting of antroquinonol (Golden Biotechnology), AS-1940477 (Astellas), AS-703988 (Merck KGaA), BI-847325 (Boehringer Ingelheim), E-6201 (Eisai), GDC-0623 (Hoffmann-La Roche), GDC-0973, RG422, RO4987655, RO5126766, SL327, WX-554 (Wilex), YopJ polypeptide, pharmaceutically acceptable salts thereof, and combinations thereof, wherein administration of the first and second anti-cancer agents provides a synergistic effect compared to administration of either anti-cancer agent alone.

Suitable and preferred subjects are as disclosed herein. In this embodiment, the pharmaceutical composition may be used to treat the cancers disclosed above, including those cancers with the mutational backgrounds identified herein. Methods of identifying such mutations are also as set forth above.

In another aspect of this embodiment, the pharmaceutical composition further comprises at least one additional therapeutic agent, preferably an inhibitor of the PI3K/Akt pathway, as disclosed herein.

The pharmaceutical compositions according to this embodiment may be in a unit dosage form comprising both anti-cancer agents. In another aspect of this embodiment, the first anti-cancer agent is in a first unit dosage form and the second anti-cancer agent is in a second unit dosage form, separate from the first.

The first and second anti-cancer agents may be co-administered to the subject, either simultaneously or at different times, as deemed most appropriate by a physician. If the first and second anti-cancer agents are administered at different times, for example, by serial administration, the first anti-cancer agent may be administered to the subject before the second anti-cancer agent. Alternatively, the second anti-cancer agent may be administered to the subject before the first anti-cancer agent.

In the present invention, an "effective amount" or a "therapeutically effective amount" of a compound or composition disclosed herein is an amount of such compound or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of a composition according to the invention will be that amount of the composition, which is the lowest dose effective to produce the desired effect. The effective dose of a compound or composition of the present invention may be administered as two, three, four, five, six or more sub-doses, administered separately at appropriate intervals throughout the day.

A suitable, non-limiting example of a dosage of an anti-cancer agent disclosed herein is from about 1 mg/kg to about 2400 mg/kg per day, such as from about 1 mg/kg to about 1200 mg/kg per day, 75 mg/kg per day to about 300 mg/kg per day, including from about 1 mg/kg to about 100 mg/kg per day. Other representative dosages of such agents include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, and 2300 mg/kg per day. The effective dose of an anti-cancer agent disclosed herein, e.g., BVD-523 and a MEK inhibitor, may be administered as two, three, four, five, six or more sub-doses, administered separately at appropriate intervals throughout the day.

The anti-cancer agents or the pharmaceutical compositions of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, the anti-cancer agents or the pharmaceutical compositions of the present invention may be administered in conjunction with other treatments. The anti-cancer agents or the pharmaceutical compositions of the present invention may be encapsulated or otherwise protected against gastric or other secretions, if desired.

The pharmaceutical compositions of the invention comprise one or more active ingredients, e.g. anti-cancer agents, in admixture with one or more pharmaceutically-acceptable diluents or carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy ($21^{st}$ Edition, Lippincott Williams and Wilkins, Philadelphia, Pa.).

Pharmaceutically acceptable diluents or carriers are well known in the art (see, e.g., Remington, The Science and Practice of Pharmacy ($21^{st}$ Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluent or carrier used in a pharmaceutical composition of the invention must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

The pharmaceutical compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable diluents or carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

The pharmaceutical compositions of the present invention for rectal or vaginal administration may be presented as a suppository, which may be prepared by mixing one or more active ingredient(s) with one or more suitable nonirritating diluents or carriers which are solid at room temperature, but liquid at body temperature and, therefore, will melt in the rectum or vaginal cavity and release the active compound. The pharmaceutical compositions of the present invention which are suitable for vaginal administration also include pessaries, tampons, creams, gels, pastes, foams or spray formulations containing such pharmaceutically-acceptable diluents or carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

The pharmaceutical compositions of the present invention suitable for parenteral administrations may comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These pharmaceutical compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid diluent or carrier, for example water for injection, immediately prior to use. Extemporaneous injection solutions and suspensions may be prepared from sterile powders, granules and tablets of the type described above.

Nucleic Acid

"Nucleic acid" or "oligonucleotide" or "polynucleotide" used herein mean at least two nucleotides covalently linked together. Many variants of a nucleic acid may be used for the same purpose as a given nucleic acid. Thus, a nucleic acid also encompasses substantially identical nucleic acids and complements thereof.

Nucleic acids may be single stranded or double stranded, or may contain portions of both double stranded and single stranded sequences. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be synthesized as a single stranded molecule or expressed in a cell (in vitro or in vivo) using a synthetic gene. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those disclosed in U.S. Pat. Nos. 5,235,033 and 5,034,506. Nucleic acids containing one or more non-naturally occurring or modified nucleotides are also included within the definition of nucleic acid.

A nucleic acid molecule is "complementary" to another nucleic acid molecule if it hybridizes with the second nucleic acid molecule, although some level of mismatch is permitted. Hybridization may be under conditions of low stringency, moderate stringency or high stringency. Suitable stringency conditions are, in general, determined by the length of the nucleic acid molecules, the degree of complementation, and other factors readily understood by those of skill in the art. In some embodiments, for example, for preliminary screening, low stringency conditions, such as a temperature of about 48 to about 55° C., in a buffer including about 5×SSC, about 0.1 to about 0.5% SDS, and about 0 to about 30% formamide. Moderate stringency hybridization conditions may be at a temperature of about 60° C. in a buffer including about 5× to about 6×SSC, about 0.1 to about 0.5% SDS, and about 40% formamide. High stringency hybridization conditions may be at a temperature of about 65° C. in a buffer including about 5× to about 6×SSC, about 0.1 to about 0.5% SDS, and about 50% formamide. In some embodiments, high stringency conditions are as described herein or are, for example, conditions that allow hybridization comparable with the hybridization that occurs using a DNA probe of at least 500 nucleotides in length, in a buffer containing 0.5 M $NaHP0_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C.

Hybridizations may be carried out over a period of about 20 to 30 minutes, or about 2 to 6 hours, or about 10 to 15 hours, or over 24 hours or more. High stringency hybridization is also relied upon for the success of numerous techniques routinely performed by molecular biologists, such as high stringency PCR, DNA sequencing, single strand conformational polymorphism analysis, and in situ hybridization. In contrast to northern and Southern hybridizations, these techniques are usually performed with relatively short probes (e.g., usually about 15 nucleotides or longer for PCR or sequencing and about 40 nucleotides or longer for in situ hybridization).

A probe or primer is a single-stranded DNA or RNA molecule (e.g., an oligonucleotide) of defined sequence that can base pair to a second DNA or RNA molecule that contains a complementary sequence (the target). The stability of the resulting hybrid molecule depends upon the extent of the base pairing that occurs, and is affected by parameters such as the degree of complementarity between the probe and target molecule, and the degree of stringency of the hybridization conditions. The degree of hybridization stringency is affected by parameters such as the temperature, salt concentration, and concentration of organic molecules, such as formamide, and is determined by methods that are known to those skilled in the art. Probes or primers specific for the nucleic acid sequences described herein, or portions thereof, may vary in length by any integer from at least 8 nucleotides to over 500 nucleotides, including any value in between, depending on the purpose for which, and conditions under which, the probe or primer is used. For example, a probe or primer may be 8, 10, 15, 20, or 25 nucleotides in length, or may be at least 30, 40, 50, or 60 nucleotides in length, or may be over 100, 200, 500, or 1000 nucleotides in length. Probes or primers specific for the nucleic acid molecules described herein may have greater than 55-75% sequence identity, or at least 75-85% sequence identity, or at least 85-99% sequence identity, or 100% sequence identity to the nucleic acid sequences described herein.

Probes or primers may be derived from a gene, chromosomal segment, or chromosome that is used as a reference, for example, in variance detection to determine whether a test sample of the same gene, chromosomal segment, or chromosome derived from a particular individual contains the identical sequence or a different sequence at one or more nucleotide positions. Probes may be derived from genomic DNA or cDNA, for example, by amplification, or from cloned DNA segments, and may contain either genomic DNA or cDNA sequences representing all or a portion of a single gene from a single individual. Probes or primers may be chemically synthesized.

Probes or primers can be detectably-labeled, either radioactively or nonradioactive, by methods that are known to those skilled in the art.

The present invention provides combinations shown to enhance the effects of ERK inhibitors. Herein, applicants have also shown that the combination of different ERK inhibitors is likewise synergistic. Therefore, it is contemplated that the effects of the combinations described herein can be further improved by the use of one or more additional ERK inhibitors. Accordingly, some embodiments of the present invention include one or more additional ERK inhibitors.

The following examples are provided to further illustrate the methods of the present invention. These examples are illustrative only and are not intended to limit the scope of the invention in any way.

EXAMPLES

Example 1

Materials and Methods

Cancer cell lines were maintained in cell culture under standard media and serum conditions. For dose escalation studies, A375 cells were split, grown to about 40-60% confluence, and then treated with the initial dose of the specified drug. Table 5 shows a summary of drug treatments that were escalated.

TABLE 5

Summary of Treatments Being Escalated

| Treatment | Inhibitor |
|---|---|
| 1 | Trametinib (MEKi) |
| 2 | Dabrafenib (BRAFi) |
| 3 | BVD-523 (ERKi) |
| 4 | Dabrafenib (BRAFi) + Trametinib (MEKi) |
| 5 | Dabrafenib (BRAFi) + BVD-523 (ERKi) |
| 6 | Trametinib (MEKi) + BVD-523 (ERKi) |

Figure 19:
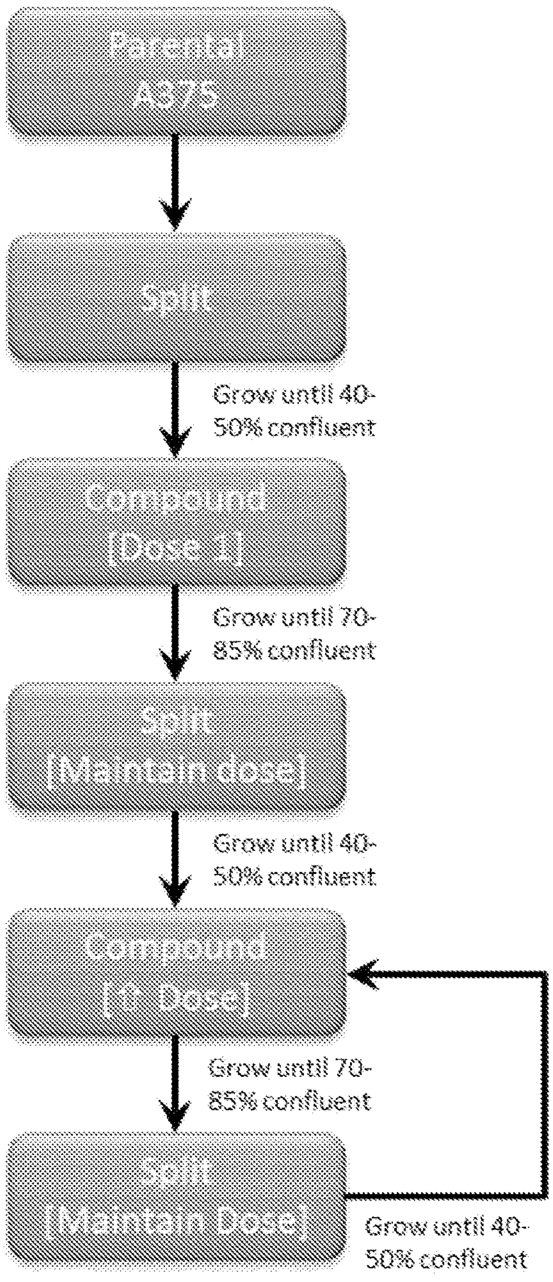
FIG. 19 is a flowchart showing the dose escalation protocol used herein.

Single agent dose escalations were performed based on Little et al., 2011 and is outlined in FIG. 19. Cells were then allowed to grow until 70-90% confluence and split. Split ratios were kept as "normal" as possible and reasonably consistent between treatments (e.g. a minimum of 50% of the normal split ratio of the parentals). Medium was refreshed every 3-4 days. When cells again reached about 40-60% confluence, the dose was escalated. In the event that the 40-60% window was missed, the cells were split again and dosed once they reached 40-60% confluence. Again, medium was refreshed every 3-4 days. The process was repeated as required (FIG. 19).

For single agent treatments, starting concentrations and dose increases were conducted by starting with the approximate $IC_{50}$, escalating in small increments or, gently, for the initial 4-5 doses, doubling the dose, increasing by the same increment for the next 4 doses, then moving to 1.5-fold increases in concentration for subsequent doses.

For combination treatments, starting concentrations and dose increases were conducted by starting with half of the approximate $IC_{50}$ of each compound (combination assay suggests this will result in about 40-70% inhibition range), escalating as per single agents (i.e. doing an initial doubling and then increasing by the same increment for the next 4 doses, then moving to 1.5-fold increases in concentration). Table 6 shows the projected dose increases using these schemes.

TABLE 6

Projected Dose Increases - Month 1

| | | | | Dab/Tram | | Dab/523 | | Tram/523 | |
|---|---|---|---|---|---|---|---|---|---|
| Dose | Tram (nM) | Dab (nM) | BVD-523 (μM) | Dab (nM) | Tram (nM) | Dab (nM) | 523 (μM) | Tram (nM) | 523 (μM) |
| 1 | 1 | 5 | 0.16 | 2.5 | 0.5 | 2.5 | 0.08 | 0.5 | 0.08 |
| 2 | 2 | 10 | 0.32 | 5 | 1 | 5 | 0.16 | 1 | 0.16 |
| 3 | 3 | 15 | 0.48 | 7.5 | 1.5 | 7.5 | 0.24 | 1.5 | 0.24 |
| 4 | 4 | 20 | 0.64 | 10 | 2 | 10 | 0.32 | 2 | 0.32 |
| 5 | 5 | 25 | 0.80 | 12.5 | 2.5 | 12.5 | 0.40 | 2.5 | 0.40 |
| 6 | 8 | 38 | 1.2 | 19 | 4 | 19 | 0.6 | 4 | 0.6 |
| 7 | 11 | 56 | 1.8 | 28 | 6 | 28 | 0.9 | 6 | 0.9 |
| 8 | 17 | 84 | 2.7 | 42 | 8 | 42 | 1.4 | 8 | 1.4 |
| 9 | 25 | 127 | 4.1 | 63 | 13 | 63 | 2.0 | 13 | 2.0 |
| 10 | 38 | 190 | 6.1 | 95 | 19 | 95 | 3.0 | 19 | 3.0 |
| 11 | 57 | 285 | 9.1 | 142 | 28 | 142 | 4.6 | 28 | 4.6 |
| 12 | 85 | 427 | 13.7 | 214 | 43 | 214 | 6.8 | 43 | 6.8 |
| 13 | 128 | 641 | 20.5 | 320 | 64 | 320 | 10.3 | 64 | 10.3 |
| 14 | 192 | 961 | 30.8 | 481 | 96 | 481 | 15.4 | 96 | 15.4 |
| 15 | 288 | 1442 | 46.1 | 721 | 144 | 721 | 23.1 | 144 | 23.1 |
| 16 | 432 | 2162 | 69.2 | 1081 | 216 | 1081 | 34.6 | 216 | 34.6 |
| 17 | 649 | 3244 | 103.8 | 1622 | 324 | 1622 | 51.9 | 324 | 51.9 |
| 18 | 973 | 4865 | 155.7 | 2433 | 487 | 2433 | 77.8 | 487 | 77.8 |
| 19 | 1460 | 7298 | 233.5 | 3649 | 730 | 3649 | 116.8 | 730 | 116.8 |
| 20 | 2189 | 10947 | 350.3 | 5474 | 1095 | 5474 | 175.2 | 1095 | 175.2 |

Clonal resistant cell populations were derived from resistant cell pools by limiting dilution.

Proliferation assays were used to track changes in sensitivity to the escalated agent(s) at appropriate time intervals (e.g. each month, although the timing is dependent on adequate cell numbers being available). For proliferation assays, cells were seeded in 96-well plates at 3000 cells per well in drug-free DMEM medium containing 10% FBS and allowed to adhere overnight prior to addition of compound or vehicle control. Compounds were prepared from DMSO stocks to give a final concentration range as shown in FIGS. 2A-H. The final DMSO concentration was constant at 0.1%. Test compounds were incubated with the cells for 96 hours at 37° C. and 5% $CO_2$ in a humidified atmosphere. Alamar Blue 10% (v/v) was then added and incubated for 4 hours and fluorescent product was detected using a BMG FLUOstar plate reader. The average media only background value was deducted and the data analyzed using a 4-parameter logistic equation in GraphPad Prism. Paclitaxel was used as a positive control.

Proliferation assays for month 1 were initiated at day 28 using cells growing in the concentrations of each agent indicated in Table 7.

TABLE 7

Initial Concentrations of Drugs Used in Proliferation Assays - Month 1

| Line | Dab | Tram | BVD-523 |
|---|---|---|---|
| Parental | — | — | — |
| Tram | — | 2 nM | — |
| Dab | 15 nM | — | — |
| BVD-523 | — | — | 0.48 μM |
| Tram + Dab | 5 nM | 1 nM | — |
| Dab + BVD-523 | 7.5 nM | — | 0.24 μM |
| Tram + BVD-523 | — | 1 nM | 0.16 μM |

Proliferation assays for month 2 were initiated at day 56 using cells growing in the concentrations of each agent indicated in Table 8.

TABLE 8

Initial Concentrations of Drugs Used in Proliferation Assays - Month 2

| Line | Dab | Tram | BVD-523 |
|---|---|---|---|
| Parental | — | — | — |
| Tram | — | 8 nM | — |
| Dab | 127 nM | — | — |
| BVD-523 | — | — | 0.8 μM |
| Tram + Dab | 10 nM | 2 nM | — |
| Dab + BVD-523 | 12.5 nM | — | 0.4 μM |
| Tram + BVD-523 | — | 2 nM | 0.32 μM |

At the end of the 3 month escalation period, cultures were maintained at the top concentration for 2 weeks prior to the final round of proliferation assays and potential single cell cloning. As the proliferation assays/single cell cloning required actively proliferating cells, for treatments where cells were proliferating very slowly at the top concentration or that were only recently escalated, a backup culture was also maintained at a lower concentration (Table 9). For the BVD-523 treatment, where cells appeared to have almost completely stopped growing and looked particularly fragile at the top concentration (1.8 μM), cultures were maintained at a lower concentration for the 2 week period.

TABLE 9

Details of Treatments Being Cultured at a Fixed Concentration for 2 Weeks

| Treatment | Inhibitor | Culture 1 | Backup Culture |
|---|---|---|---|
| 1 | Tram | 160 nM | 80 nM |
| 2 | Dab | 3.2 μM | — |
| 3 | BVD-523 | 1.2 μM | 0.8 μM |
| 4 | Dab + Tram | D: 160 nM<br>T: 30 nM | D: 80 nM<br>T: 16 nM |
| 5 | Dab + BVD-523 | D: 42 nM<br>523: 1.4 μM | D: 28 nM<br>523: 0.9 μM |
| 6 | Tram + BVD-523 | T: 4 nM<br>523: 0.6 μM | T: 2.5 nM<br>523: 0.4 μM |

Proliferation assays for month 3 used cells growing in the concentrations of each agent indicated in Table 10.

TABLE 10

Initial Concentrations of Drugs Used in Proliferation Assays - Month 3

| Line | Dab | Tram | BVD-523 |
|---|---|---|---|
| Parental | — | — | — |
| Tram | — | 160 nM | — |
| Dab | 3.2 μM | — | — |
| BVD-523 | — | — | 1.2 μM |
| Tram + Dab | 80 nM | 16 nM | — |
| Dab + BVD-523 | 28 nM | — | 0.9 μM |
| Tram + BVD-523 | — | 2.5 nM | 0.4 μM |

For combination studies, A375 cells (ATCC) were seeded into triplicate 96-well plates at a cell density of 3000 cells/well in DMEM plus 10% FBS and allowed to adhere overnight prior to addition of test compound or vehicle control. Combinations were tested using a 10×8 dose matrix with a final DMSO concentration of 0.2%. A 96 hour assay incubation period followed, with subsequent addition of Alamar Blue 10% (v/v) and 4 hours incubation prior to reading on a fluorescent plate reader. After reading Alamar Blue, the medium/Alamar Blue mix was flicked off and 100 μl of CellTiter-Glo/PBS (1:1) added and the plates processed as per the manufacturer's instructions (Promega). Media only background values were subtracted before the data was analysed. The Bliss additivity model was then applied.

In brief, predicted fractional inhibition values for combined inhibition were calculated using the equation $C_{bliss}$=A+B−(A×B) where A and B are the fractional inhibitions obtained by drug A alone or drug B alone at specific concentrations. $C_{bliss}$ is the fractional inhibition that would be expected if the combination of the two drugs were exactly additive. $C_{bliss}$ values are subtracted from the experimentally observed fractional inhibition values to give an 'excess over Bliss' value. Excess over Bliss values greater than 0 indicate synergy, whereas values less than 0 indicate antagonism. Excess over Bliss values are plotted as heat maps±SD.

The single and combination data are also presented as dose-response curves generated in GraphPad Prism (plotted using % viability relative to DMSO only treated controls).

For focused combination studies, the Alamar Blue viability assays were performed as described above for combination studies. Additionally, Caspase-Glo 3/7 assays were performed. In brief, HCT116 cells were seeded in triplicate in white 96-well plates at a cell density of 5000 cells/well in McCoy's 5A plus 10% FBS. A375 cells were seeded at a density of 5000 cells/well in DMEM plus 10% FBS. Cells were allowed to adhere overnight prior to addition of test compound or vehicle control. The final concentration of DMSO was 0.2%, and 800 nM staurosporine was included as a positive control. 24 and 48 hour assay incubation periods were used. Then, Caspase-Glo® 3/7 50% (v/v) was added, plates were mixed for 5 minutes on an orbital shaker and incubated for 1 hour at room temperature prior to reading on a luminescent plate reader. Media only background values were subtracted before the data was analysed.

Example 2

Dose Escalation and Proliferation Assays—Month 1

Dose Escalation Progress—Month 1

A375 cells were dose escalated using BVD-523, dabrafenib, and trametinib either as single agents or in combination. Doses were increased in small increments during the first month. Other than a marked reduction in growth rate, cells generally tolerated the escalations well and the doses were planned to be more aggressively escalated using larger increments in month 2. FIGS. 1A-C show month 1 progress for the dose escalation studies.

Proliferation Assay Results—Month 1

Proliferation assays were performed to assess the response of the escalated cells lines vs. parental cell line, to BVD-523, dabrafenib, and trametinib treatments.

FIGS. 2A-H show normalized and raw proliferation assay results from month 1 of the studies. Note that differences in max signals in DMSO controls between different treatments (FIGS. 2D-F, 2H) suggest differential growth rates between treatments. These differences may influence the responses of lines to inhibitors in the proliferation assays.

Table 11 shows $IC_{50}$ data for month 1 of the studies.

TABLE 11

$IC_{50}$ Data - Month 1

| | Cell Line, Relative $IC_{50}$ (nM) | | | | | | |
|---|---|---|---|---|---|---|---|
| Compound | Par * | Tram | Dab | BVD-523 | Dab/Tram | Dab/523 | Tram/523 |
| Dabrafenib | 6 | 29 | about 161 | 8 | 58 | 68 | 11 |
| Trametinib | 0.5 | 2.2 | 2.5 | 0.7 | 3.9 | 3.1 | 2.5 |
| BVD-523 | 189 | 335 | 350 | 268 | 300 | 412 | 263 |
| Paclitaxel | 2.2 | 3.0 | 3.3 | 3.4 | 3.5 | 3.4 | 3.4 |

* Par = Parental cell line

There were early hints that cells grown in the presence of escalating doses of dabrafenib or trametinib, either as single agents or in combinations, were exhibiting decreased responses to these two agents in proliferation assays.

In the early stages of month 2, the growth rate of cells in the dabrafenib only treatment notably increased relative to the early stages of month 1. This enabled an increased rate of progression and suggested that resistance was becoming apparent.

Example 3

Dose Escalation and Proliferation Assays—Month 2

Dose Escalation Progress—Month 2

Figure 3:
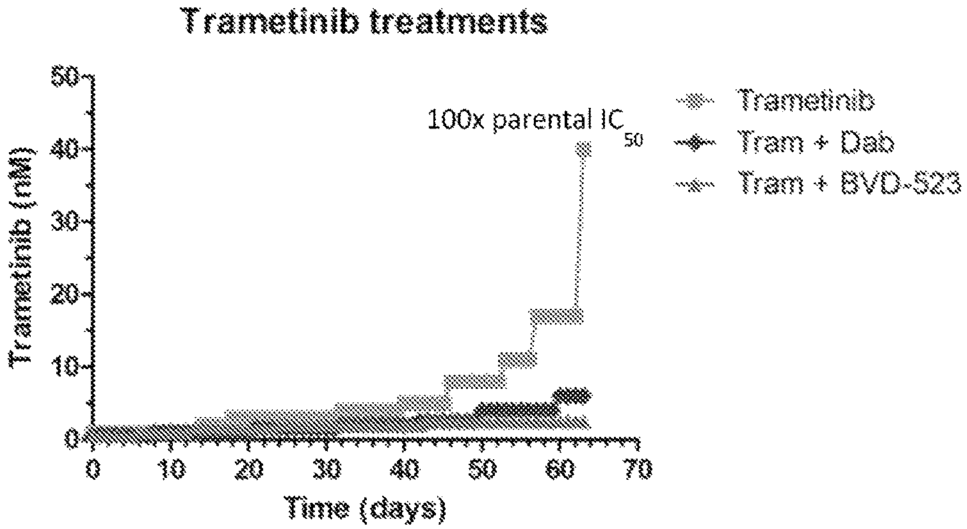
FIGS. 3A-3D show the progress of a dose escalation study in A375 cells for month 2. Various treatments (trametinib, dabrafenib, and BVD-523) are as labeled.
Figure 3:
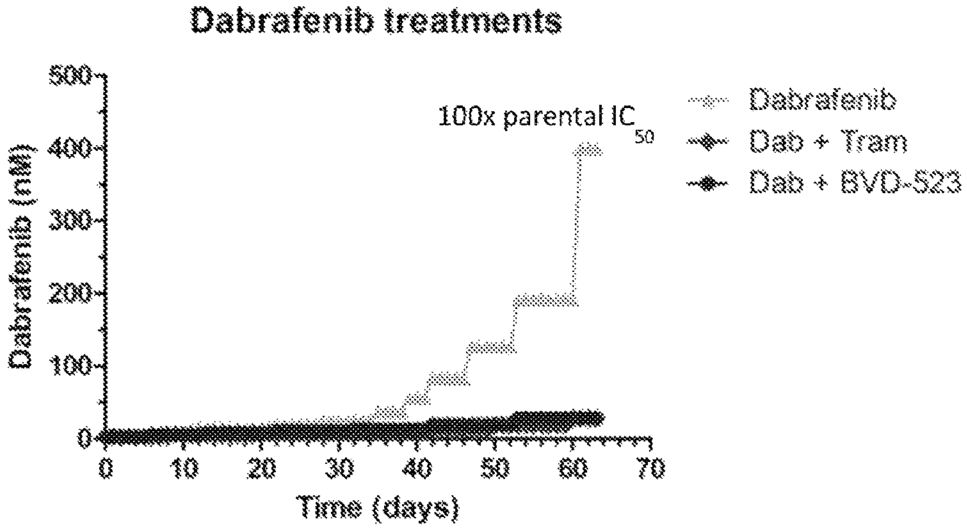
Figure 4:
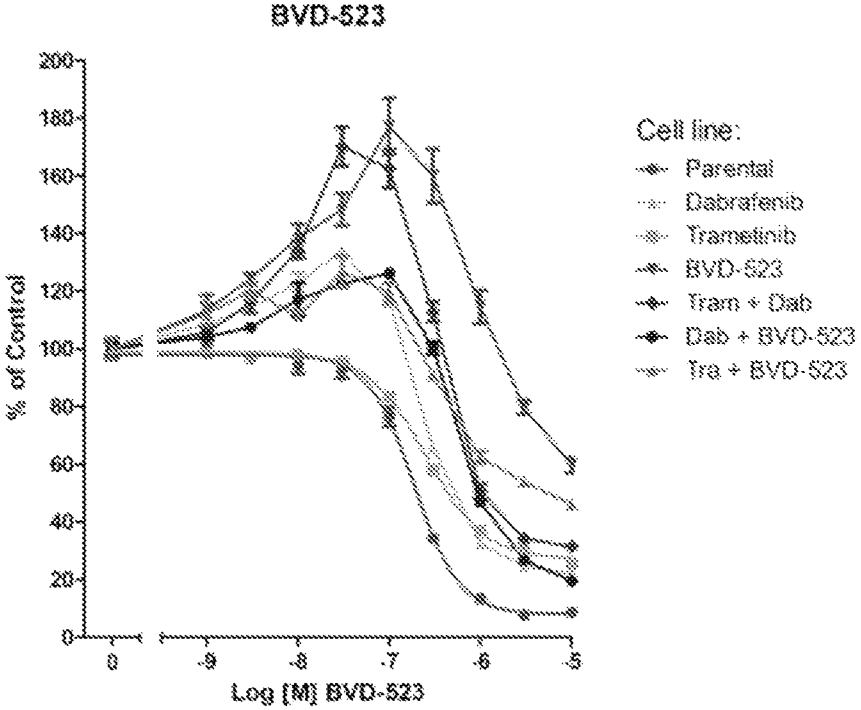
FIGS. 4A-H show the results of a proliferation assay that tracks changes in sensitivity to the escalated agent(s) at month 2. Various treatments (trametinib, dabrafenib, BVD-523, and pacitaxel) are as labeled on the top of the graph. The caption to the right of the graph shows the various types of cells generated from the dose escalation study. For example, "dabrafenib" refers to the cells that have been treated with the highest dose of dabrafenib from month 2 of the dose escalation study. Parental refers to the control cells that have not been treated with drugs.
Figure 5:
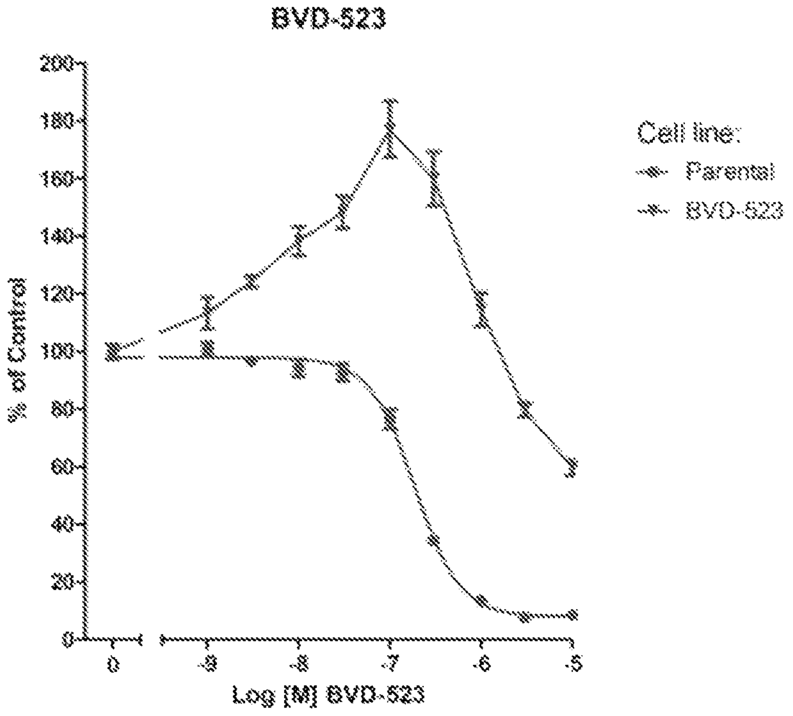
FIGS. 5A-H show only the parental and BVD-523 cell line data from FIG. 4. Various treatments (trametinib, dabrafenib, BVD-523, and pacitaxel) are as labeled.

The second month of studies saw most treatments move into a phase where doses were increased in greater increments (1.5-fold) compared to the initial gentle escalation phase. The single agent escalation of dabrafenib and trametinib was quickest, with cells growing in concentrations equivalent to 100× parental cell $IC_{50}$ (FIGS. 3A,B). The single agent escalation of BVD-523 progressed more slowly compared to dabrafenib and trametinib (FIG. 3C). See FIG. 3D for a comparison of the single agent escalations. BVD-523 escalated cells had a more "fragile" appearance and there was a greater number of floating cells compared to the dabrafenib and trametinib escalated populations.

The combined agent escalations progressed more slowly than the single agent treatments. The BVD-523/trametinib combination was particularly effective in preventing cells from progressing.

Proliferation Assay Results—Month 2

Proliferation assays on single agent escalated dabrafenib and trametinib cell populations revealed modest shifts in the dose response curves, suggesting that an additional period of escalation would be beneficial to further enrich for resistant cells. Interestingly, in the proliferations assay, there was evidence to suggest that cells exposed to BVD-523 grew less well upon inhibitor withdrawal, perhaps indicating a level of addiction.

FIGS. 4A-H show normalized and raw proliferation assay results from month 2 of the studies. Note that differences in max signals in DMSO controls between different treatments (FIGS. 4D-F, 4H) suggest differential growth rates between treatments. These differences may influence the responses of lines to inhibitors in the proliferation assays.

FIGS. 5A-H show normalized and raw proliferation assay results from month 2 of the studies with a focus on parental and BVD-523 line data only.

Table 12 shows $IC_{50}$ data for month 2 of the studies. Relative $IC_{50}$s were determined from 4-parameter curve fits in Prism.

TABLE 12

$IC_{50}$ Data - Month 2

| | Cell Line, Relative $IC_{50}$ (nM) | | | | | | |
|---|---|---|---|---|---|---|---|
| Compound | Par* | Tra | Dab | BVD-523 | Dab/Tram | Dab/523 | Tram/523 |
| Dabrafenib | 4.1 | 6.2 | 11.5 | 697 | 256 | 218 | 68 |
| Trametinib | 0.4 | 0.7 | 1.1 | 24.3 | 12.6 | 6.2 | 4.6 |
| BVD-523 | 187 | 252 | 284 | 1706 | 561 | 678 | 435 |
| Paclitaxel | 3.7 | 8.9 | 1.9 | 6.5 | 4.7 | 4.2 | 8.9 |

*Par = Parental cell line

Example 4

Dose Escalation and Proliferation Assays—Month 3

Dose Escalation Progress—Month 3

Figure 6:
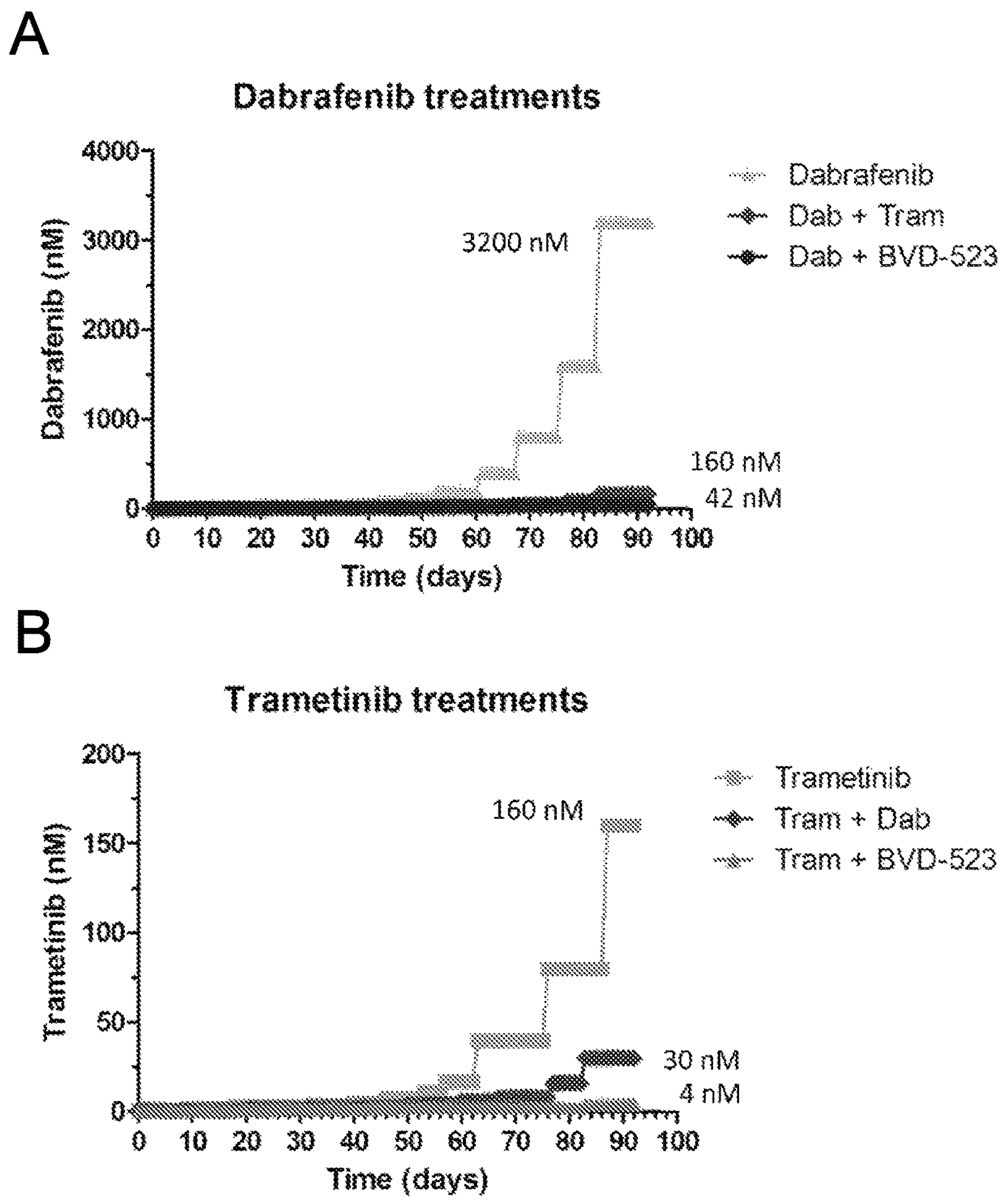
FIGS. 6A-D show the progress of the dose escalation study in a human malignant cell line (A375 cells) for month 3. Various treatments (trametinib, dabrafenib, and BVD-523) are as labeled.

FIGS. 6A-C show single and combination agent escalation for month 3 of the studies. FIG. 6D shows a comparison of single agent escalations.

Proliferation Assay Results—Month 3

Figure 7:
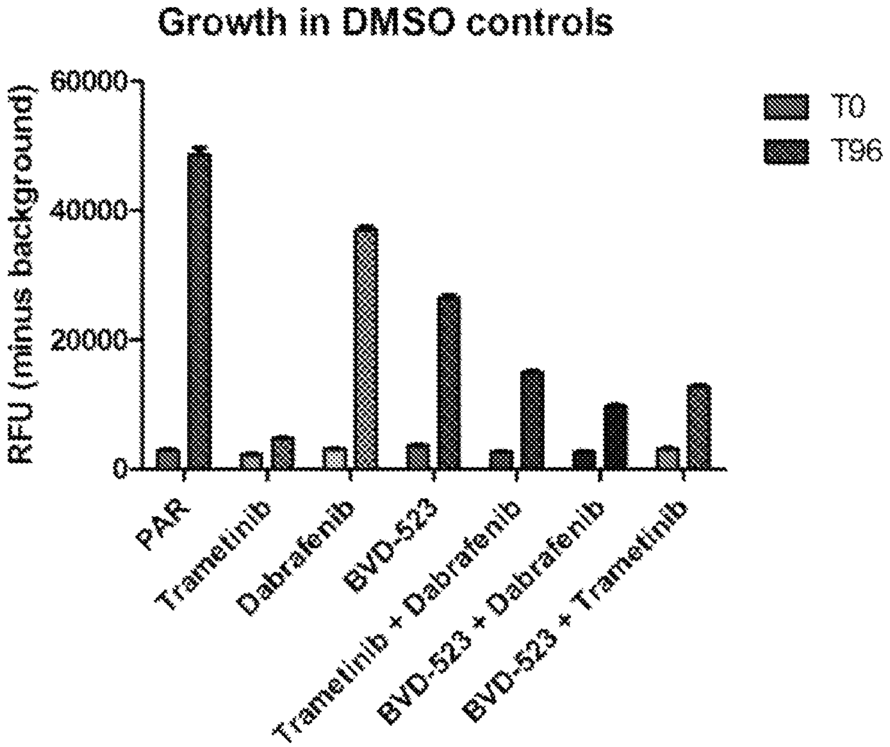
FIG. 7 is a histogram showing the results of a proliferation assay as applied to cells grown in the DMSO control wells from the dose escalation assay.
Figure 8:
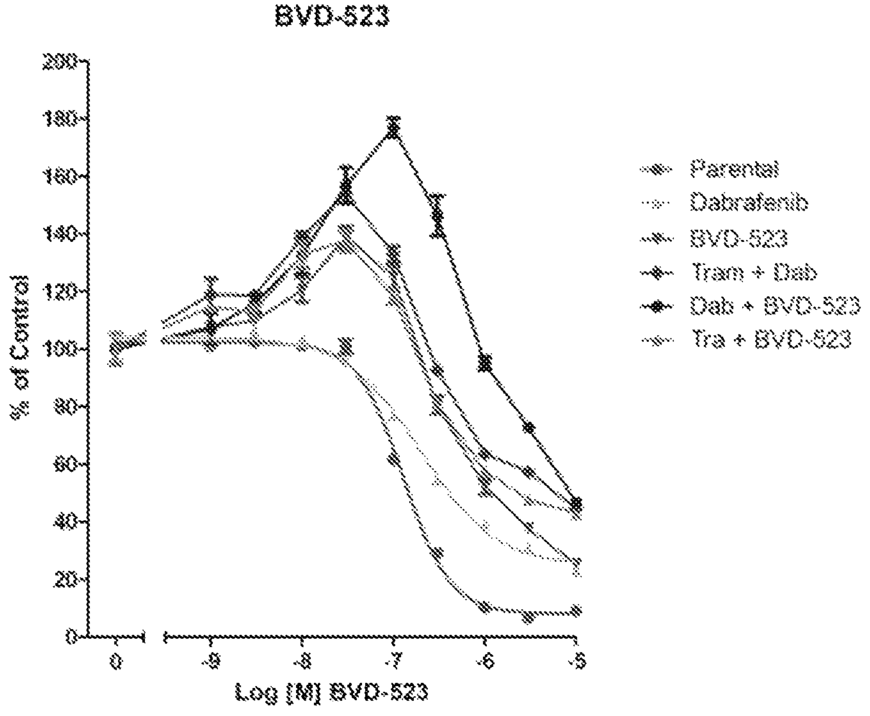
FIGS. 8A-D are a set of line graphs showing proliferation assays for month 3 of the study. Various treatments (trametinib, dabrafenib, BVD-523, and pacitaxel) are as labeled on the top of the graph. The caption to the right of the graph shows the various types of cells generated from the dose escalation study. For example, "dabrafenib" refers to the cells that have been treated with the highest dose of dabrafenib from month 3 of the dose escalation study. Parental refers to the control cells that have not been treated with drugs.
Figure 9:
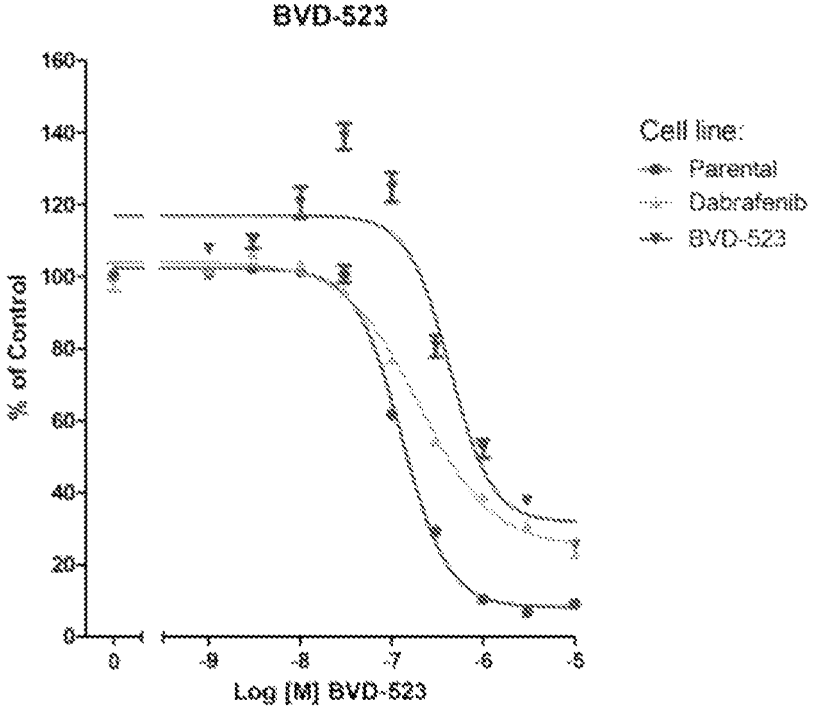
FIGS. 9A-D show only the parental, dabrafenib, and BVD-523 cell line data from FIG. 8.

FIG. 7 shows an assessment of growth during the proliferation assay in DMSO control wells. FIGS. 8A-D show results from month 3 of the studies. FIGS. 9A-D show results from month 3 of the studies with a focus on single treatment cell lines.

Table 13 shows $IC_{50}$ data for month 3 of the studies. Relative $IC_{50}$s were determined from 4-parameter curve fits in Prism. $IC_{50}$ values were not determined for the cell line escalated with trametinib due to a lack of growth during the assay (ND: not done).

TABLE 13

| IC$_{50}$ Data - Month 3 | | | | | | | |
|---|---|---|---|---|---|---|---|
| | Cell Line, Relative IC$_{50}$ (nM) | | | | | | |
| Compound | Par * | Tram | Dab | BVD-523 | Dab/Tram | Dab/523 | Tram/523 |
| Dabrafenib | 2.1 | ND | 2.5 | 18.4 | 17.9 | 337 | 73 |
| Trametinib | 0.2 | ND | 0.4 | 1.7 | 2.7 | 90 | 11.2 |
| BVD-523 | 129 | ND | 198 | 433 | 323 | 1151 | 296 |
| Paclitaxel | 1.9 | ND | 1.9 | 6.5 | 4.7 | 4.2 | 8.9 |

* Par = Parental cell line

Example 5

Combination Study Results

Figure 15:
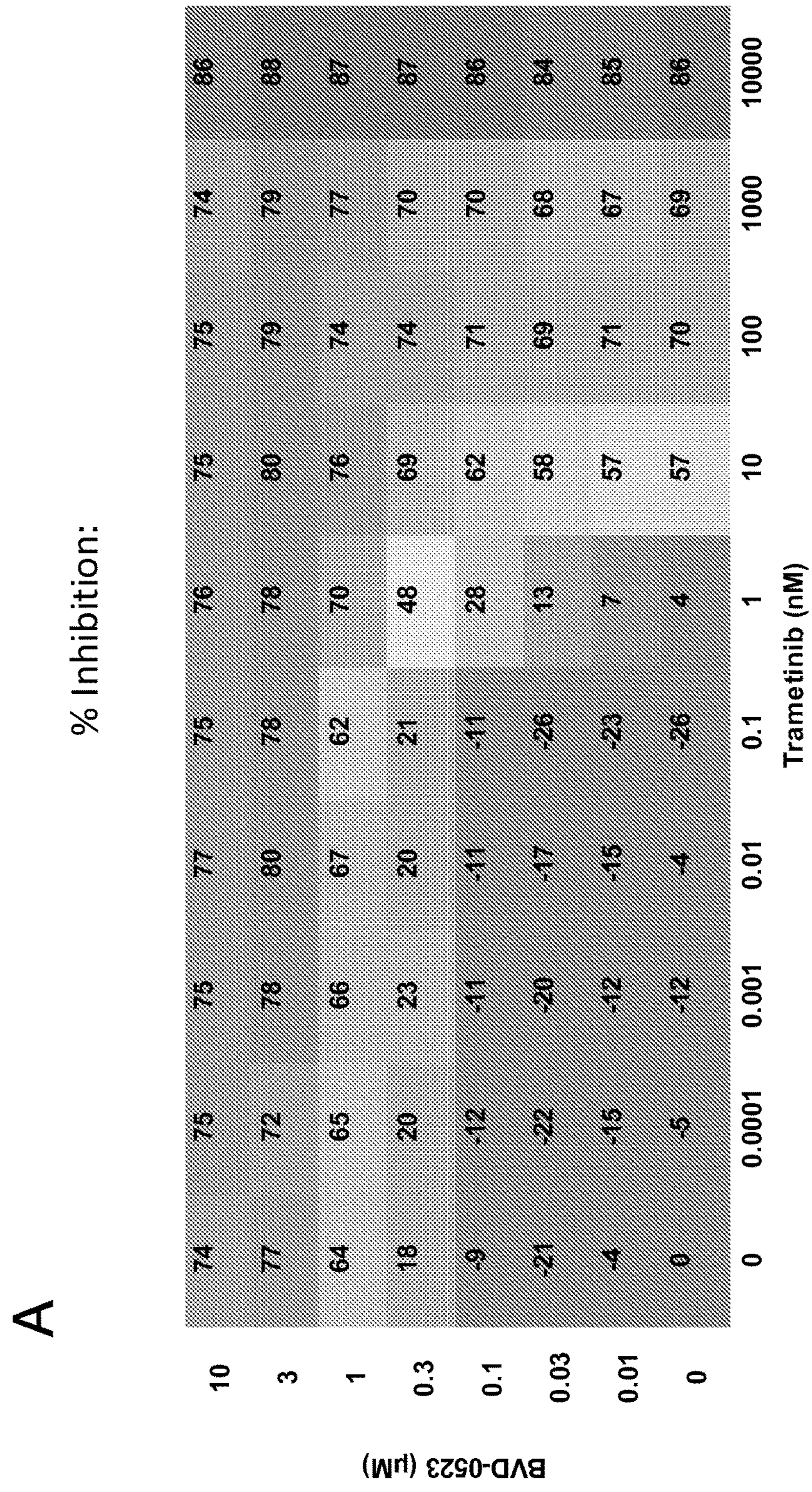
FIG. 15A is a dose matrix showing % inhibition of the trametinib/BVD-523 combination in A375 cells using the CellTiter-Glo cell viability assay.
FIG. 15B is a dose matrix showing excess over Bliss for the trametinib/BVD-523 combination.
FIGS. 15C and 15D show % viability relative to DMSO only treated controls for BVD-523 and trametinib single agent treatments in A375 cells using the CellTiter-Glo cell viability assay.
FIG. 15E shows % viability relative to DMSO only treated controls for BVD-523 and trametinib combination treatments in A375 cells using the CellTiter-Glo cell viability assay.

As expected, A375 cells, which carry a BRAF (V600E) mutation, were sensitive to dabrafenib. Single agent $IC_{50}$ values calculated using Alamar Blue (FIGS. 10, 12, 14) were generally slightly lower for Dabrafenib and BVD-523 compared to those derived using CellTiter-Glo (FIGS. 11, 13, 15). Published $IC_{50}$ values for Dabrafenib and Trametinib in a 72 hour CellTiter-Glo assay were 28±16 nM and 5±3 nM respectively (Greger et al., 2012; King et al., 2013)—the single agent results reported here are consistent with these values. There was some evidence for a window of synergy in all treatments. Variation between triplicates was low, however, there was some evidence of edge effects that likely explains the apparent enhanced growth observed in some treatments versus the no drug control (e.g. particularly apparent in the Trametinib/BVD-523 combination). This makes the interpretation of the Bliss analysis more challenging as in some treatments it may have resulted in the artefactual enhancement in the level of synergy.

The combination assays were repeated for A375 cells. Single agent BVD-523, Trametinib and Dabrafenib potencies were consistent with those reported in the previous studies.

HCT116 cells are human colorectal cancer cells with mutations in KRAS. Dabrafenib and Trametinib were antagonist at relevant on-target concentrations. In contrast, Trametinib exhibited synergy with AZ628 over a broad range of combinations, and with higher concentrations of Sorafenib. BVD-523 exhibited windows of synergy with both AZ628 and Sorafenib.

In A375 cells, trametinib exhibited pockets of synergy at lower concentrations of Dabrafenib and AZ628. BVD-523 exhibited a window of synergy with the lower concentrations of Sorafenib.

Example 6

BVD-523 Altered Markers of MAPK Kinase Activity and Effector Function

For Western blot studies, HCT116 cells ($5\times10^6$) were seeded into 10 cm dishes in McCoy's 5A plus 10% FBS. A375 cells ($2.5\times10^6$) were seeded into 10 cm dishes in DMEM plus 10% FBS. Cells were allowed to adhere overnight prior to addition of the indicated amount of test compound (BVD-523) or vehicle control. Cells were treated for either 4 or 24 hours before isolation of whole-cell protein lysates, as specified below. Cells were harvested by trypsinisation, pelleted and snap frozen. Lysates were prepared with RIPA (Radio-Immunoprecipitation Assay) buffer, clarified by centrifugation and quantitated by bicinchoninic acid assay (BCA) assay. 20-50 μg of protein was resolved by SDS-PAGE electrophoresis, blotted onto PVDF membrane and probed using the antibodies detailed in Table 14 (for the 4-hour treatment) and Table 15 (for the 24-hour treatment) below.

TABLE 14

| Antibody Details | | | | | | |
|---|---|---|---|---|---|---|
| Antigen | Size (kDa) | Supplier | Cat No | Dilution | Incubation/ Block Conditions | Secondary |
| pRSK1/2 pS380 | 90 | Cell Signaling | 9335 | 1:1000 | o/n 4° C. 5% BSA | anti-rabbit |
| pRSK1/2 pS380 | 90 | Cell Signaling | 11989 | 1:2000 | o/n 4° C. 5% BSA | anti-rabbit |
| pRSK-T359/S363 | 90 | Millipore | 04-419 | 1:40000 | o/n 4° C. 5% BSA | anti-rabbit |
| Total RSK | 90 | Cell Signaling | 9333 | 1:1000 | o/n 4° C. 5% BSA | anti-rabbit |
| pErk 1/2 | 42/44 | Cell Signaling | 9106S | 1:500 | o/n 4° C. 5% milk | anti-mouse |
| Total ERK | 42/44 | Cell Signaling | 9102 | 1:2000 | o/n 4° C. 5% milk | anti-rabbit |
| pMEK1/2 | 45 | Cell Signaling | 9154 | 1:1000 | o/n 4° C. 5% BSA | anti-rabbit |
| Total MEK | 45 | Cell Signaling | 9126 | 1:1000 | o/n 4° C. 5% BSA | anti-rabbit |
| pS6-pS235 | 32 | Cell Signaling | 2211S | 1:3000 | o/n 4° C. 5% milk | anti-rabbit |
| Total S6 | 32 | Cell Signaling | 2217 | 1:2000 | o/n 4° C. 5% milk | anti-rabbit |
| DUSP6 | 48 | Cell Signaling | 3058S | 1:1000 | o/n 4° C. 5% BSA | anti-rabbit |
| Total CRAF | 73 | BD Biosciences | 610152 | 1:2000 | o/n 4° C. 5% milk | anti-mouse |

TABLE 14-continued

| Antibody Details | | | | | | |
|---|---|---|---|---|---|---|
| Antigen | Size (kDa) | Supplier | Cat No | Dilution | Incubation/ Block Conditions | Secondary |
| pCRAF-Ser338 | 73 | Cell Signaling | 9427 | 1:1000 | o/n 4° C. 5% BSA | anti-rabbit |
| pRB (Ser780) | 105 | Cell Signaling | 9307 | 1:2000 | o/n 4° C. 5% BSA | anti-rabbit |
| β-Actin | 42 | Sigma | A5441 | 1:500,000 | o/n 4° C. 5% milk | anti-mouse |

TABLE 15

| Antibody details | | | | | | |
|---|---|---|---|---|---|---|
| Antigen | Size (kDa) | Supplier | Cat No | Dilution | Incubation/ Block Conditions | Secondary |
| pRB (Ser780) | 105 | Cell Signaling | 9307 | 1:2000 | o/n 4° C. 5% BSA | anti-rabbit |
| CCND1 | 34 | Abcam | ab6152 | 1:500 | o/n 4° C. 5% milk | anti-mouse |
| Bim-EL | 23 | Millipore | AB17003 | 1:1000 | o/n 4° C. 5% BSA | anti-rabbit |
| Bim-EL | 23 | Cell Signaling | 2933 | 1:1000 | o/n 4° C. 5% BSA | anti-rabbit |
| BCL-xL | 30 | Cell Signaling | 2762 | 1:2000 | o/n 4° C. 5% BSA | anti-rabbit |
| PARP | 116/89 | Cell Signaling | 9542 | 1:1000 | o/n 4° C. 5% milk | anti-rabbit |
| Cleaved Caspase 3 | 17, 19 | Cell Signaling | 9664X | 1:1000 | o/n 4° C. 5% milk | anti-rabbit |
| DUSP6 | 48 | Cell Signaling | 3058S | 1:1000 | o/n 4° C. 5% BSA | anti-rabbit |
| pRSK1/2 pS380 | 90 | Cell Signaling | 9335 | 1:1000 | o/n 4° C. 5% BSA | anti-rabbit |
| pRSK1/2 pS380 | 90 | Cell Signaling | 11989 | 1:2000 | o/n 4° C. 5% BSA | anti-rabbit |
| pRSK-T359/S363 | 90 | Millipore | 04-419 | 1:40000 | o/n 4° C. 5% BSA | anti-rabbit |
| Total RSK | 90 | Cell Signaling | 9333 | 1:1000 | o/n 4° C. 5% BSA | anti-rabbit |
| pErk 1/2 | 42/44 | Cell Signaling | 9106S | 1:500 | o/n 4° C. 5% milk | anti-mouse |
| Total ERK | 42/44 | Cell Signaling | 9102 | 1:2000 | o/n 4° C. 5% milk | anti-rabbit |
| B-Actin | 42 | Sigma | A5441 | 1:500,000 | o/n 4° C. 5% milk | anti-mouse |

Figure 16:
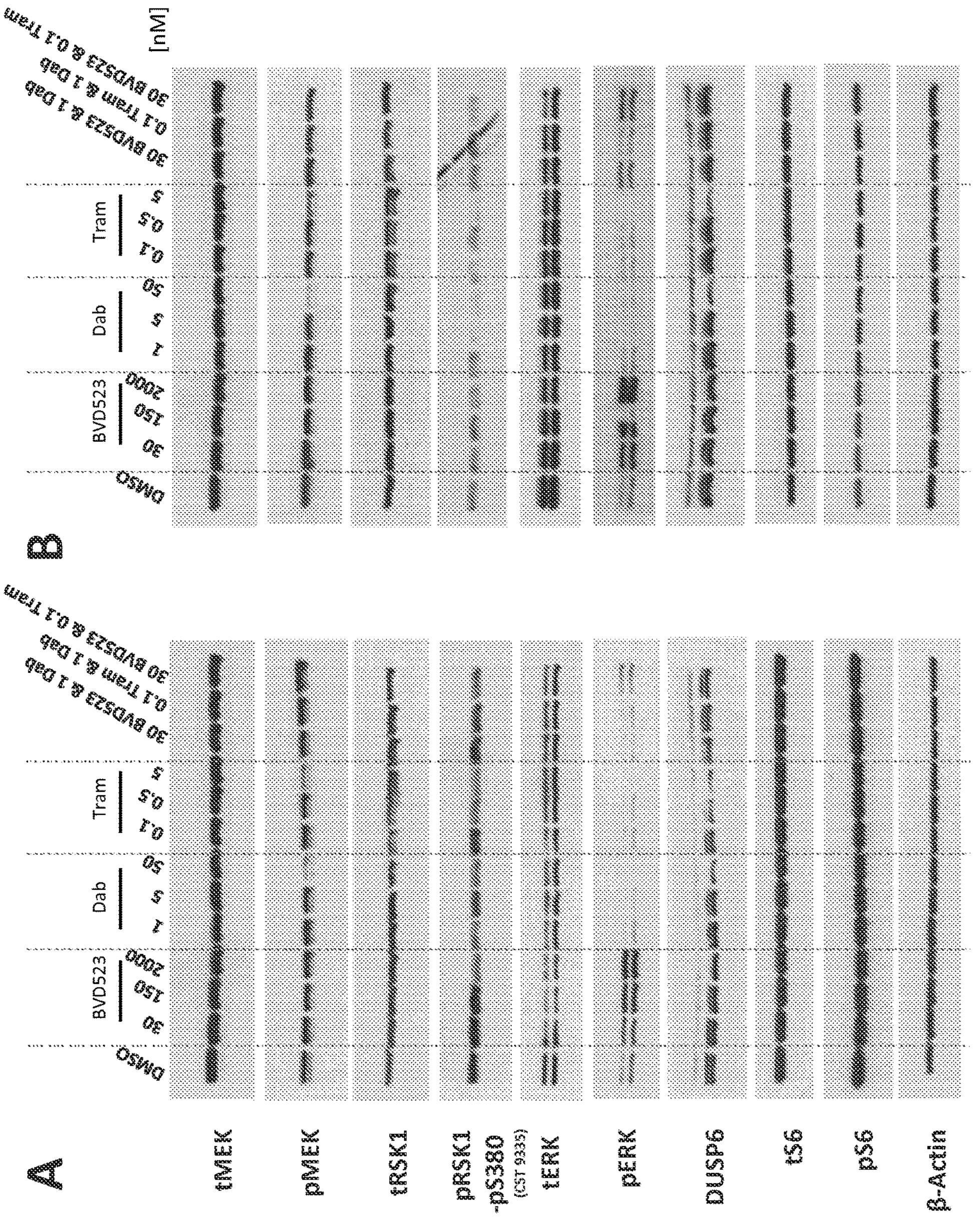
FIGS. 16A-D are a set of images showing Western blot analysis of MAPK signaling in A375 cells after a 4 hour treatment with various concentrations (in nM) of BVD-523, dabrafenib (Dab), and Trametinib (Tram). 40 μg of total protein was loaded in each lane except where indicated otherwise. In this experiment, duplicate samples were collected.
Figure 17:
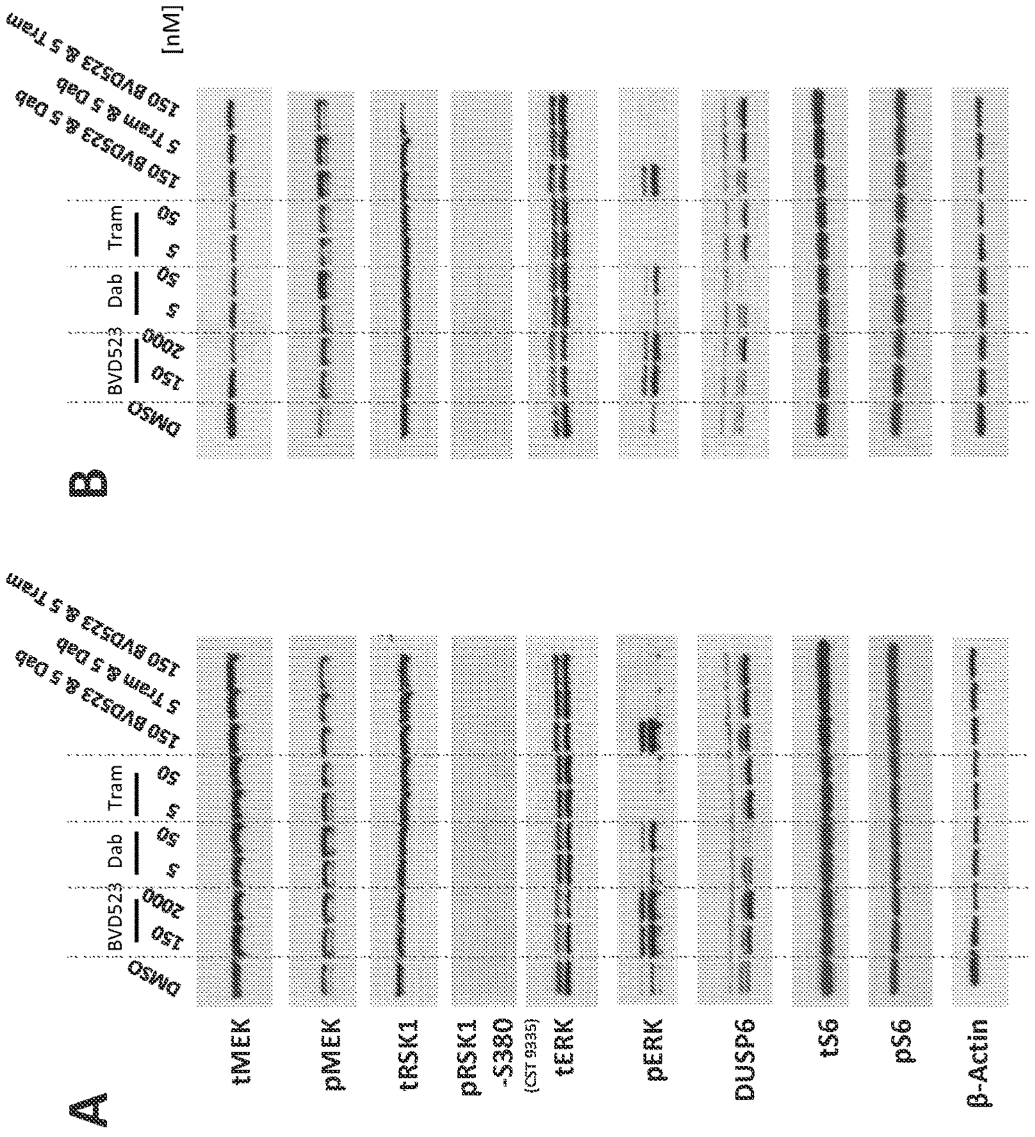
FIGS. 17A-D are a set of images showing Western blot analysis of MAPK signaling in a human colorectal carcinoma cell line (HCT116 cells) after a 4 hour treatment with various concentrations (in nM) of BVD-523, dabrafenib (Dab), and Trametinib (Tram). 40 μg of total protein was loaded in each lane except where indicated otherwise. In this experiment, duplicate samples were collected.
Figure 18:
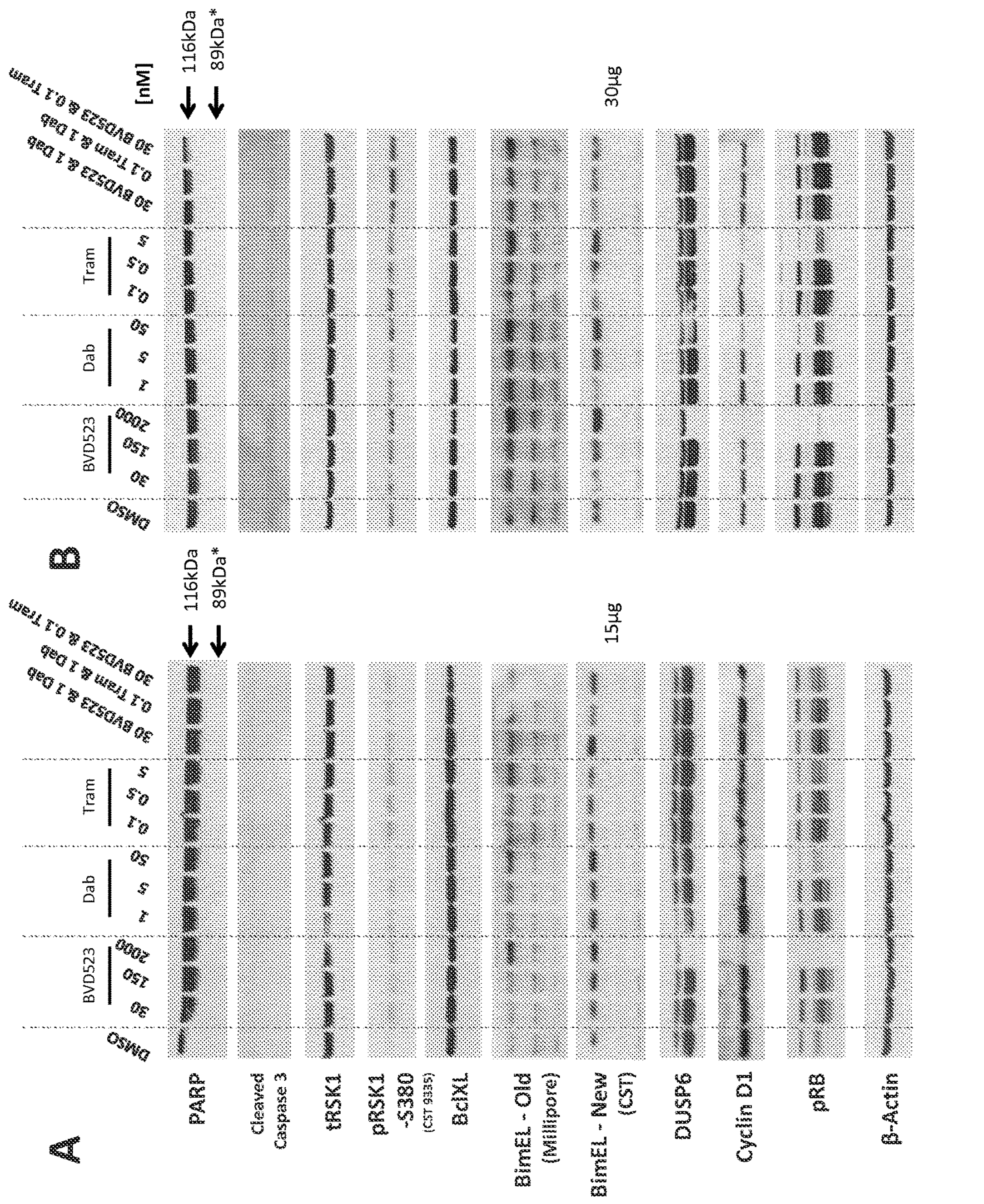
FIGS. 18A-D are a set of images showing Western blot analysis of cell cycle and apoptosis signalling in A375 melanoma cells after a 24 hour treatment with various concentrations (in nM) of BVD-523 ("BVD523"), trametinib ("Tram") and/or dabrafenib ("Dab") as labelled. 50 μg of total protein was loaded in each lane except where indicated otherwise. In this experiment, duplicate samples were collected.

FIGS. 16-18 show Western blot analyses of cells treated with BVD-523 at various concentrations for the following: 1) MAPK signaling components in A375 cells after 4 hours; 2) cell cycle and apoptosis signaling in A375 24 hours treatment with various amounts of BVD-523; and 3) MAPK signaling in HCT-116 cells treated for 4 hours. The results show that acute and prolonged treatment with BVD-523 in RAF and RAS mutant cancer cells in-vitro affects both substrate phosphorylation and effector targets of ERK kinases. The concentrations of BVD-523 required to induce these changes is typically in the low micromolar range.

Changes in several specific activity markers are noteworthy. First, the abundance of slowly migrating isoforms of ERK kinase increase following BVD-523 treatment; modest changes can be observed acutely, and increase following prolonged treatment. While this could indicate an increase in enzymatically active, phosphorylated forms of ERK, it remains noteworthy that multiple proteins subject to both direct and indirect regulation by ERK remain "off" following BVD-523 treatment. First, RSK1/2 proteins exhibit reduced phosphorylation at residues that are strictly dependent on ERK for protein modification (T359/5363). Second, BVD-523 treatment induces complex changes in the MAPK feedback phosphatase, DUSP6: slowly migrating protein isoforms are reduced following acute treatment, while total protein levels are greatly reduced following prolonged BVD-523 treatment. Both of these findings are consistent with reduced activity of ERK kinases, which control DUSP6 function through both post-translational and transcriptional mechanisms. Overall, despite increases in cellular forms of ERK that are typically thought to be active, it appears likely that cellular ERK enzyme activity is fully inhibited following either acute or prolonged treatment with BVD-523.

Consistent with these observations, effector genes that require MAPK pathway signaling are altered following treatment with BVD-523. The G1/S cell-cycle apparatus is regulated at both post-translational and transcriptional levels by MAPK signaling, and cyclin-D1 protein levels are greatly reduced following prolonged BVD-523 treatment. Similarly, gene expression and protein abundance of apoptosis effectors often require intact MAPK signaling, and total levels of Bim-EL increase following prolonged BVD-523 treatment. As noted above, however, PARP protein cleavage and increased apoptosis were not noted in the A375 cell background; this suggests that additional factors may influence whether changes in BVD-523/ERK-dependent effector signaling are translated into definitive events such as cell death and cell cycle arrest.

Consistent with the cellular activity of BVD-523, marker analysis suggests that ERK inhibition alters a variety of molecular signaling events in cancer cells, making them susceptible to both decreased cell proliferation and survival.

In sum, FIGS. 16-18 show that BVD-523 inhibits the MAPK signaling pathway and may be more favorable compared to RAF or MEK inhibition in this setting.

Finally, properties of BVD-523 may make this a preferred agent for use as an ERK inhibitor, compared to other agents with a similar activity. It is known that kinase inhibitor drugs display unique and specific interactions with their enzyme targets, and that drug efficacy is strongly influenced by both the mode of direct inhibition, as well as susceptibility to adaptive changes that occur following treatment. For example, inhibitors of ABL, KIT, EGFR and ALK kinases are effective only when their cognate target is found in active or inactive configurations. Likewise, certain of these inhibitors are uniquely sensitive to either secondary genetic mutation, or post-translational adaptive changes, of the protein target. Finally, RAF inhibitors show differential potency to RAF kinases present in certain protein complexes and/or subcellular localizations. In summary, as ERK kinases are similarly known to exist in diverse, variable, and complex biochemical states, it appears likely that BVD-523 may interact with and inhibit these targets in a fashion that is distinct and highly preferable to other agents.

Example 7

Cell Culture Studies of MEK and ERK Inhibitors

Single Agent Proliferation Assay

Cells were seeded in 96-well plates at the densities and media conditions indicated in Table 16 and allowed to adhere overnight prior to addition of compound or vehicle control. Compounds were prepared from DMSO stocks to give the desired final concentrations The final DMSO concentration was constant at 0.1%. Test compounds were incubated with the cells for 72 h at 37° C., 5% CO2 in a humidified atmosphere. CellTiter-Glo® reagent (Promega, Madison, Wis.) was added according to manufacturer's instructions and luminescence detected using the BMG FLUOstar plate reader (BMG Labtech, Ortenberg, Germany). The average media only background value was deducted and the data analysed using a 4-parameter logistic equation in GraphPad Prism (GraphPad Software, La Jolla, Calif.).

Combination Proliferation Assay

Cells were seeded in triplicate 96-well plates at the densities and media conditions indicated in Table 16 and allowed to adhere overnight prior to addition of compound or vehicle control. Compounds were prepared from DMSO stocks to give the desired final concentrations The final DMSO concentration was constant at 0.2%. Combinations were tested using a 10×8 dose matrix or a 10×6 dose matrix. Test compounds were incubated with the cells for 72 h at 37° C., 5% CO2 in a humidified atmosphere. CellTiter-Glo® reagent (Promega, Madison, Wis.) was added according to manufacturer's instructions and luminescence detected using the BMG FLUOstar plate reader (BMG Labtech, Ortenberg, Germany). The average media only background value was deducted and the data analysed.

Combination interactions across the dose matrix were determined by the Loewe Additivity and Bliss independence models using Chalice™ Combination Analysis Software (Horizon Discovery Group, Cambridge, Mass.) as outlined in the user manual (available at chalice.horizondiscovery-.com/chalice-portal/documentation/analyzer/home.jsp). Synergy is determined by comparing the experimentally observed level of inhibition at each combination point with the value expected for additivity, which is derived from the single-agent responses along the edges of the matrix. Potential synergistic interactions were identified by displaying the calculated excess inhibition over that predicted as being additive across the dose matrix as a heat map, and by reporting a quantitative 'Synergy Score' based on the Loewe model. The single agent data derived from the combination assay plates were presented as dose-response curves generated in GraphPad Prism (GraphPad Software, La Jolla, Calif.) (plotted using percentage viability relative to DMSO only treated controls).

TABLE 16

Cell Line Seeding Density and Growth Media

| Cell Line | Seeding Density (cells/well) | Media |
|---|---|---|
| HCT116 Parental | 1000 | McCoy's 5A + 10% FBS |
| HCT116 KRAS KO (+/−) | 2000 | McCoy's 5A + 10% FBS |
| RKO Parental | 2000 | McCoy's 5A + 10% FBS |
| RKO BRAF KO (+/−/−) | 2000 | McCoy's 5A + 10% FBS |
| A375 Parental | 2000 | DMEM + 10% FBS |
| A375 NRAS (Q61K/+/+) | 2000 | DMEM + 10% FBS |
| G-361 | 5000 | McCoy's 5A + 10% FBS |
| A549 | 750 | RPMI 1640 + 10% FBS |
| H2212 | 4000 | RPMI 1640 + 10% FBS |
| H1437 | 1500 | RPMI 1640 + 10% FBS |
| H226 | 750 | RPMI 1640 + 10% FBS |

Results

The aim of this study was to assess the effects on cell viability of combining ERK inhibitors with MEK inhibitors in a panel of isogenic and non-isogenic cancer cell lines (Table 17).

TABLE 17

Description of Cell Lines Studied

| Cell Line | Cancer Type | Description |
|---|---|---|
| HCT116 Parental | CRC | Heterozygous parental cells containing one mutant KRAS allele (G13D) and one wild type allele |
| HCT116 KRAS KO (+/−) | CRC | Knock out of mutant KRAS allele in heterozygous parental cells |
| RKO Parental | CRC | Triploid parental cells containing two mutant BRAF alleles (V600E) and one wild type allele |
| RKO BRAF KO (+/−/−) | CRC | Knock out of both mutant BRAF alleles (V600E) in triploid parental cells |
| A375 Parental | Melanoma | Hypotriploid parental line carrying BRAF (V600E) mutation |

TABLE 17-continued

| Description of Cell Lines Studied | | |
|---|---|---|
| Cell Line | Cancer Type | Description |
| A375 NRAS (Q61K/+/+) | Melanoma | Heterozygous knock-in of NRAS activating mutation (Q61K) |
| G-361 | Melanoma | BRAF (V600E) mutant |
| A549 | NSCLC | BRAF mutant |
| H2212 | NSCLC | BRAF mutant |
| H1437 | NSCLC | KRAS wild type |
| H226 | NSCLC | KRAS wild type |

Figure 20:
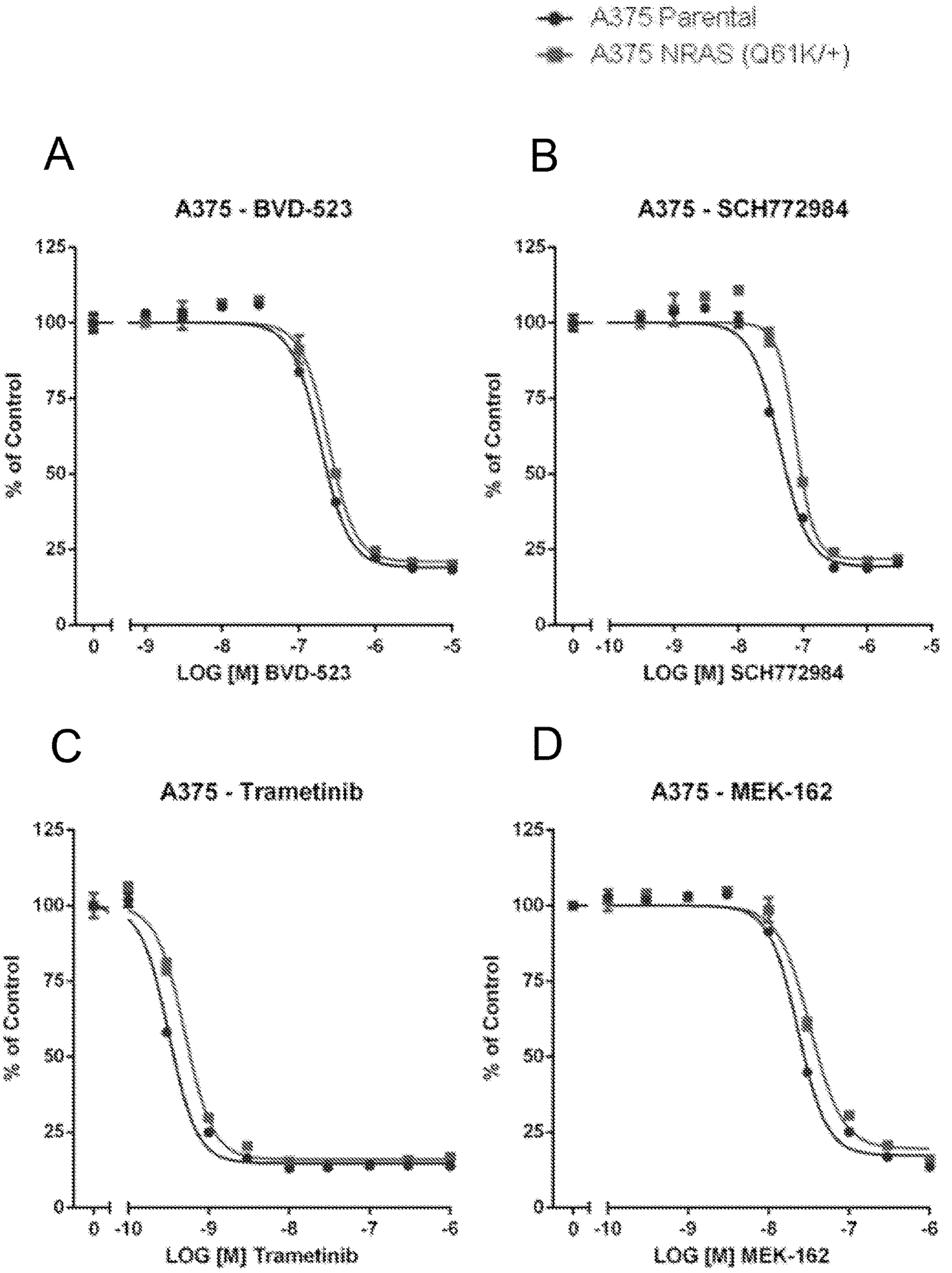
FIG. 20 shows the results of single agent proliferation assays in parental A375 and A375 NRAS (Q61K/+) cells. Proliferation results are shown for treatment with BVD-523 (FIG. 20A), SCH772984 (FIG. 20B), Trametinib (FIG. 20C), MEK-162 (FIG. 20D), GDC-0623 (FIG. 20E), GDC-0973 (FIG. 20F), and Paclitaxel (FIG. 20G).
Figure 21:
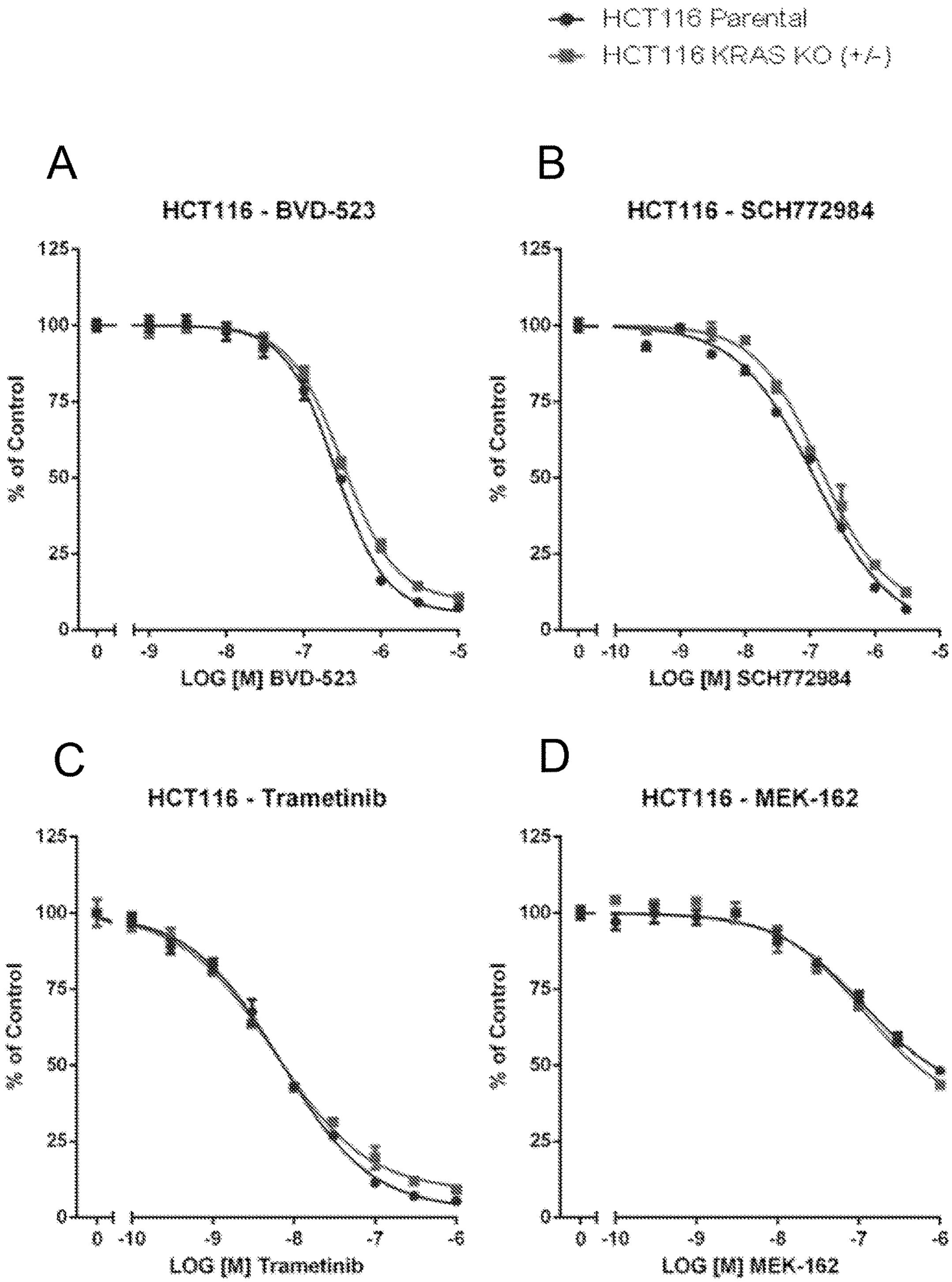
FIG. 21 shows the results of single agent proliferation assays in parental HCT116 and A375 KRAS KO (−/+) cells. Proliferation results are shown for treatment with BVD-523 (FIG. 21A), SCH772984 (FIG. 21B), Trametinib (FIG. 21C), MEK-162 (FIG. 21D), GDC-0623 (FIG. 21E), GDC-0973 (FIG. 21F), and Paclitaxel (FIG. 21G).

An initial round of single agent assays was performed in the A375 (FIG. 20), HCT116 (FIG. 21) and RKO-isogenic (FIG. 22) cell line pairs. $IC_{50}$ values are shown in Table 18. These revealed no differentials in response to ERK or MEK inhibition between the two cell lines within the A375 and HCT116 isogenic pair. This suggests that under the assay conditions tested 1) the knocked-in mutant NRAS allele does not drive resistance to MEK or ERK inhibition in A375 cells and 2) sensitivity of HCT116 to MEK/ERK inhibition is not coupled to the mutant KRAS allele.

TABLE 18

| Single Agent $IC_{50}$ Values | A375 | | HCT116 | | RKO | |
|---|---|---|---|---|---|---|
| Compound | Parental | NRAS (Q61K/+) | Parental | KRAS KO (+/−) | Parental | BRAF KO (+/−/−) |
| BVD-523 | 0.193 | 0.243 | 0.256 | 0.316 | 0.621 | 0.762 |
| SCH772984 | 0.043 | 0.079 | 0.116 | 0.141 | 0.126 | 0.125 |
| Trametinib | 0.0003 | 0.0005 | 0.007 | 0.006 | 0.008 | 0.003 |
| MEK-162 | 0.023 | 0.033 | 0.114 | 0.113 | 0.210 | 0.023 |
| GDC-0623 | 0.008 | 0.010 | 0.031 | 0.029 | 0.032 | 0.005 |
| GDC-0973 | 0.002 | 0.003 | 0.090 | 0.061 | 0.040 | 0.031 |
| Paclitaxel | 0.003 | 0.006 | 0.003 | 0.003 | 0.003 | 0.003 |

TABLE 19

| Bliss Volumes | A549 | H1437 | H2122 | H226 | HCT116 KRAS KO (+/−) | HCT116 Parental | RKO BRAF V600E KO (+/−/−) | RKO Parental | A375 NRAS (Q61K/+) | A375 Parental | G-361 |
|---|---|---|---|---|---|---|---|---|---|---|---|
| BVD-523 × GDC-0623 | nt | 0.29 | 0.633 | −0.505 | nt | nt | nt | nt | 0.014 | −0.963 | 4.02 |
| BVD-523 × MEK-162 | nt | nt | nt | nt | −0.221 | 1.09 | −0.781 | −0.748 | −0.117 | −0.488 | 1.29 |
| BVD-523 × Trametinib | −1.06 | −0.324 | 0.361 | 0.364 | 0.811 | 0.606 | −1.88 | −2.16 | 0.188 | −1.83 | 0.774 |
| SCH772984 × GDC-0623 | −0.0669 | 0.525 | 0.244 | −0.792 | nt | nt | nt | nt | 0.442 | −0.444 | 4.29 |
| SCH772984 × MEK-162 | nt | nt | nt | nt | 1.25 | 1.4 | −2.47 | 0.378 | −0.697 | −0.261 | 1.53 |
| SCH772984 × Trametinib | −0.436 | −1.44 | −0.0333 | −3.15 | 1.94 | 2.09 | −4.01 | −1.59 | 0.0516 | −0.256 | 2.42 |

TABLE 20

| Loewe Volumes | A549 | H1437 | H2122 | H226 | HCT116 KRAS KO (+/−) | HCT116 Parental | RKO BRAF V600E KO (+/−/−) | RKO Parental | A375 NRAS (Q61K/+) | A375 Parental | G-361 |
|---|---|---|---|---|---|---|---|---|---|---|---|
| BVD-523 × GDC-0623 | nt | 0.899 | 1.1 | 0.731 | nt | nt | nt | nt | −0.0852 | −0.217 | 4.39 |
| BVD-523 × MEK-162 | nt | nt | nt | nt | 1.3 | 1.93 | 3.08 | 0.596 | 1.18 | 0.821 | 1.94 |
| BVD-523 × Trametinib | 1.69 | 2.35 | 1.61 | 2.77 | 3.1 | 2.05 | 2.99 | 1.43 | 2.2 | 0.294 | 1.65 |
| SCH772984 × GDC-0623 | 0.846 | 1.52 | 1.1 | 1.22 | nt | nt | nt | nt | 0.0892 | 0.256 | 4.74 |
| SCH772984 × MEK-162 | nt | nt | nt | nt | 3.27 | 3.08 | 2.56 | 1.96 | 0.685 | 1.34 | 1.95 |
| SCH772984 × Trametinib | 2.4 | 2.4 | 2 | 2.1 | 4.94 | 4.23 | 2.52 | 2.71 | 2.1 | 1.95 | 2.72 |

TABLE 21

| Synergy Scores | A549 | H1437 | H2122 | H226 | HCT116 KRAS KO (+/−) | HCT116 Parental | RKO BRAF V600E KO (+/−/−) | RKO Parental | A375 NRAS (Q61K/+) | A375 Parental | G-361 |
|---|---|---|---|---|---|---|---|---|---|---|---|
| BVD-523 × GDC-0623 | nt | 0.562 | 0.483 | 0.578 | nt | nt | nt | nt | 0.465 | 0.498 | 2.5 |
| BVD-523 × MEK-162 | nt | nt | nt | nt | 1.68 | 2.28 | 2.53 | 0.777 | 1.43 | 1.49 | 1.88 |
| BVD-523 × Trametinib | 1.59 | 1.51 | 0.748 | 1.35 | 3.23 | 2.46 | 2.82 | 1.06 | 1.28 | 0.731 | 1.23 |
| SCH772984 × GDC-0623 | 0.897 | 0.695 | 0.546 | 0.679 | nt | nt | nt | nt | 0.695 | 0.673 | 2.74 |
| SCH772984 × MEK-162 | nt | nt | nt | nt | 3.2 | 3.4 | 2.06 | 1.26 | 1.22 | 1.54 | 2.08 |
| SCH772984 × Trametinib | 2 | 1.39 | 0.927 | 1.23 | 4.92 | 4.32 | 1.97 | 1.81 | 1.29 | 1.19 | 1.53 |

Figure 22:
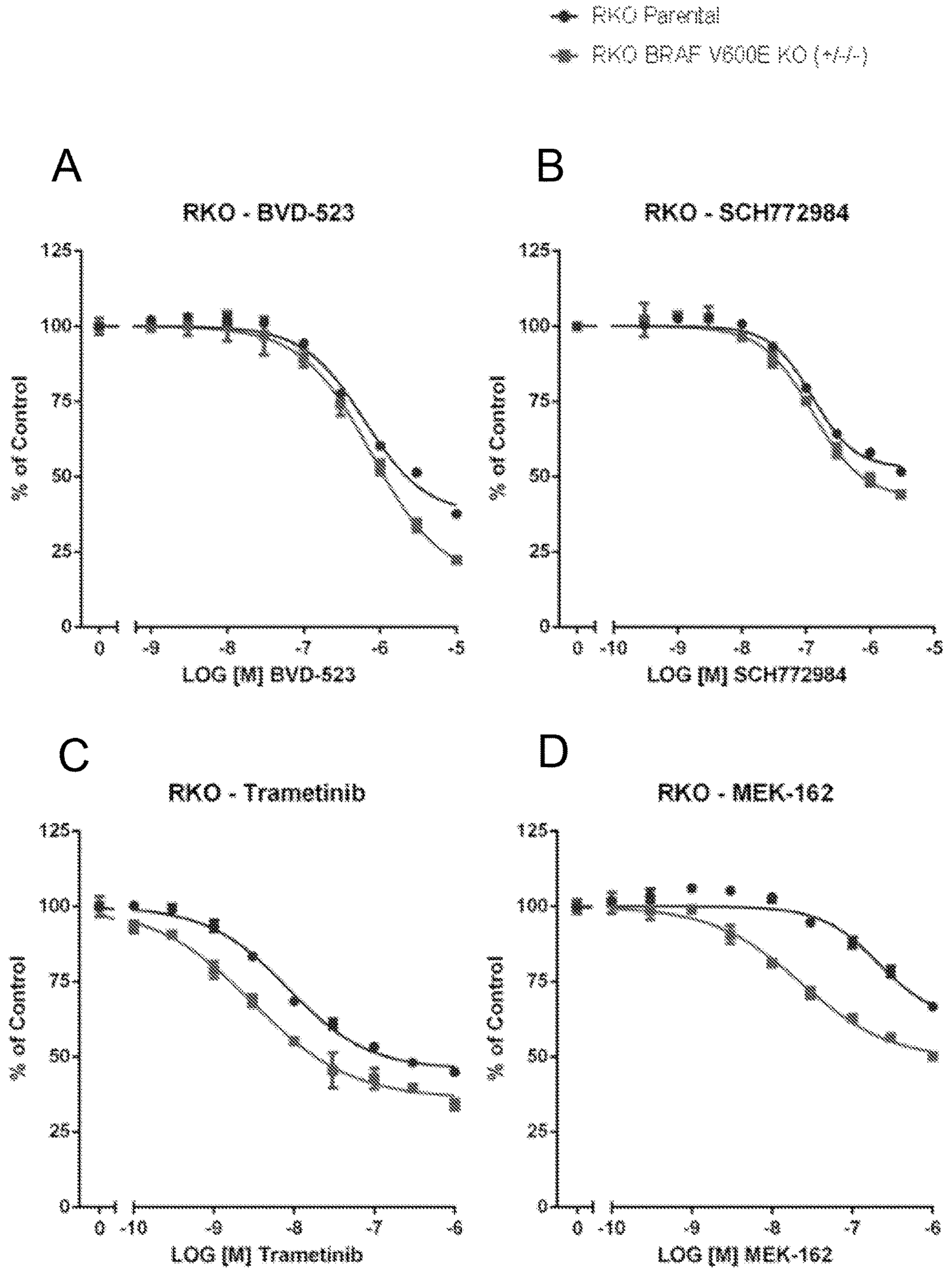
FIG. 22 shows the results of single agent proliferation assays in parental RKO and RKO BRAF V600E KO (+/−/−) cells. Proliferation results are shown for treatment with BVD-523 (FIG. 22A), SCH772984 (FIG. 22B), Trametinib (FIG. 22C), MEK-162 (FIG. 22D), GDC-0623 (FIG. 22E), GDC-0973 (FIG. 22F), and Paclitaxel (FIG. 22G).

Surprisingly, deletion of the mutant BRAF (V600E) alleles in RKO cells increased the sensitivity to several of the MEK inhibitors, but did not markedly alter the response to ERK inhibition (FIG. 22). This is consistent with the general observation that upstream modulations of the MAPK pathway that alter sensitivity to MEK inhibitors do not markedly affect sensitivity to ERK inhibition.

Combination interactions between two compounds were assessed across a matrix of concentrations using the Loewe Additivity and Bliss Independence Models with Chalice™ Bioinformatics Software (Horizon Discovery Group, Cambridge, Mass.). Chalice™ enables potential synergistic interactions to be identified by displaying the calculated excess inhibition over that predicted as being additive across the dose matrix as a heat map, and by reporting a quantitative 'Synergy Score' based on the Loewe model.

Figure 23:
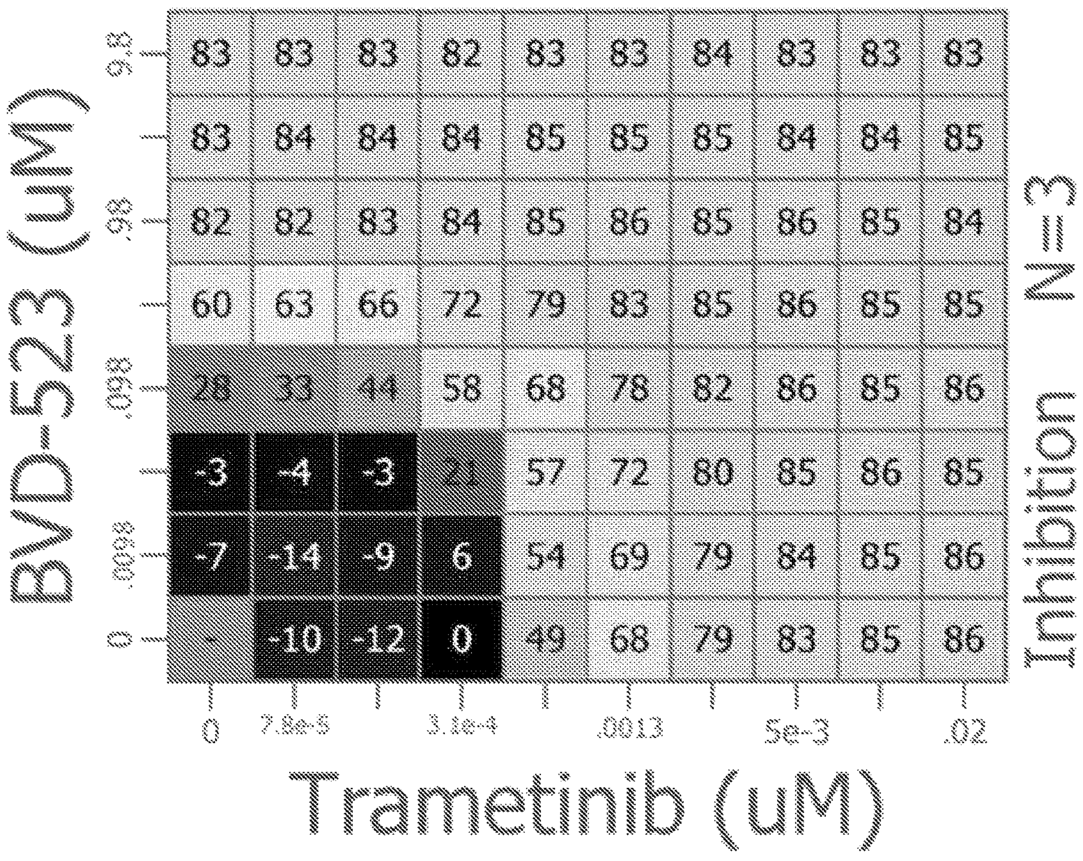
FIG. 23 shows the results of the combination of BVD-523 and Trametinib in parental A375 and A375 NRAS (Q61K/+) cells.
Figure 24:
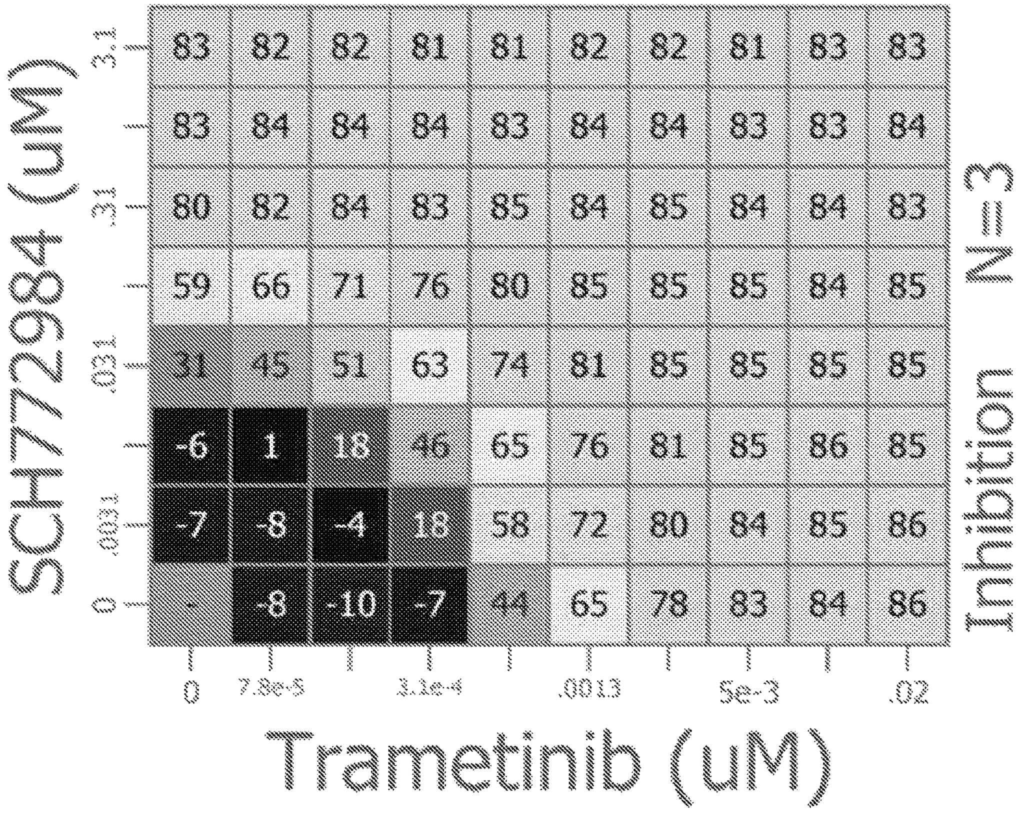
FIG. 24 shows the results of the combination of SCH772984 and Trametinib in parental A375 and A375 NRAS (Q61K/+) cells.
Figure 25:
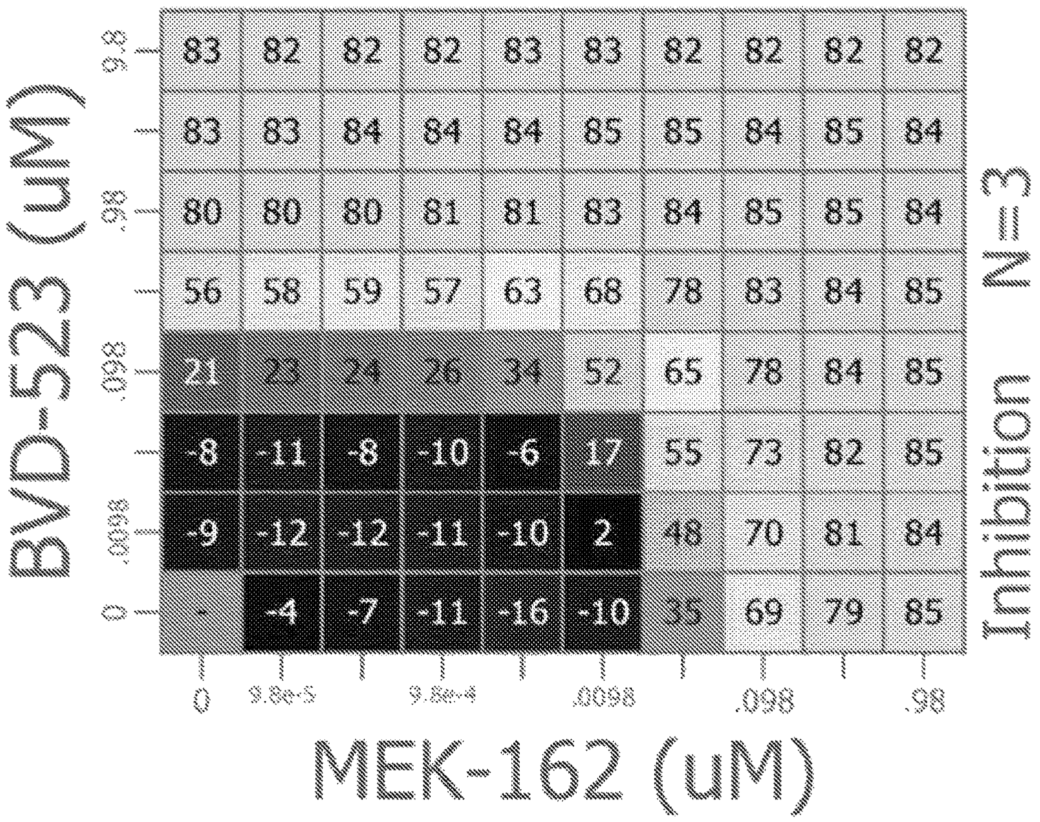
FIG. 25 shows the results of the combination of BVD-523 and MEK-162 in parental A375 and A375 NRAS (Q61K/+) cells.
Figure 26:
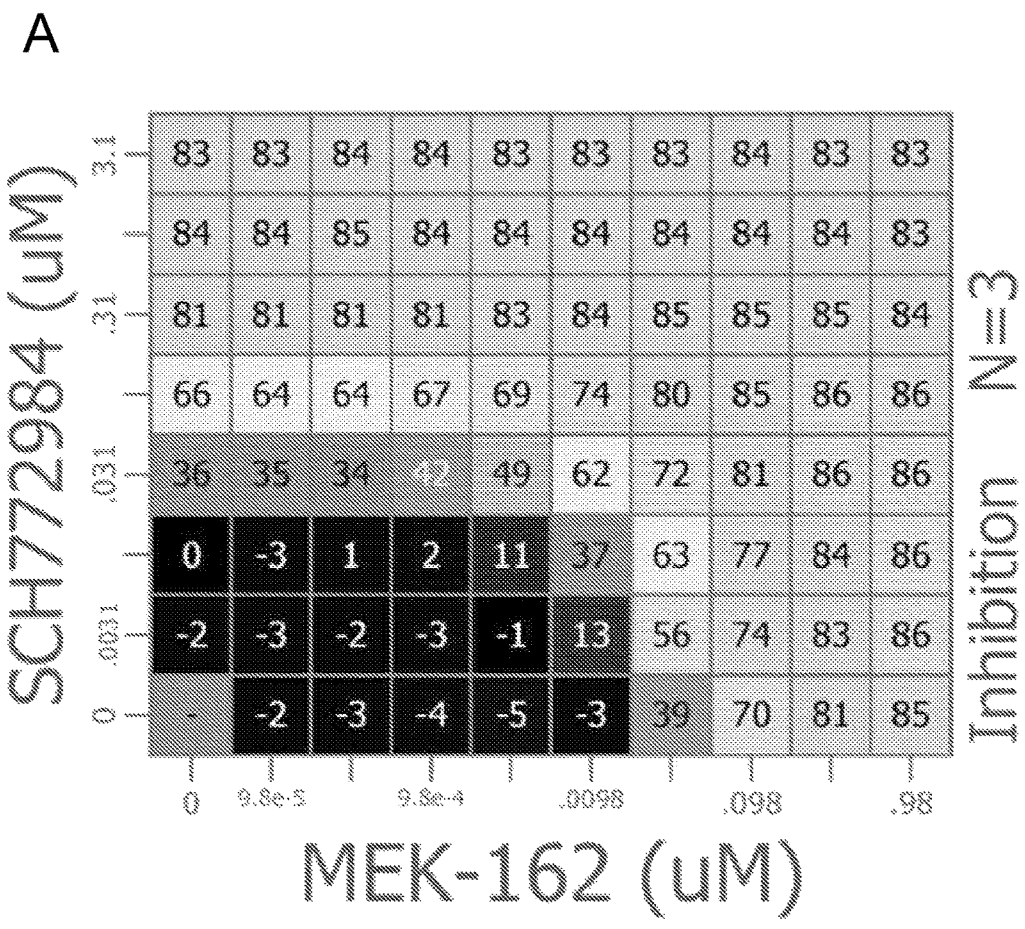
FIG. 26 shows the results of the combination of SCH772984 and MEK-162 in parental A375 and A375 NRAS (Q61K/+) cells.
Figure 27:
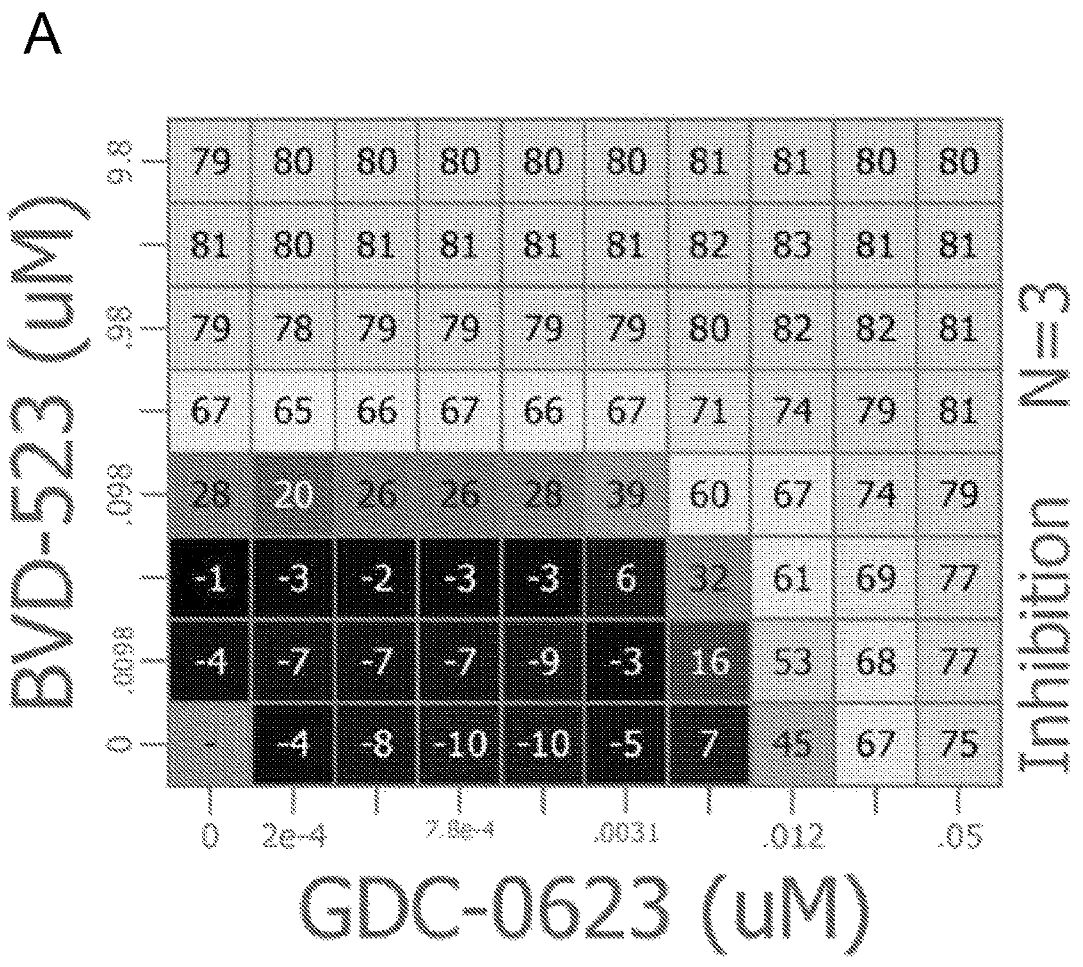
FIG. 27 shows the results of the combination of BVD-523 and GDC-0623 in parental A375 and A375 NRAS (Q61K/+) cells.
Figure 28:
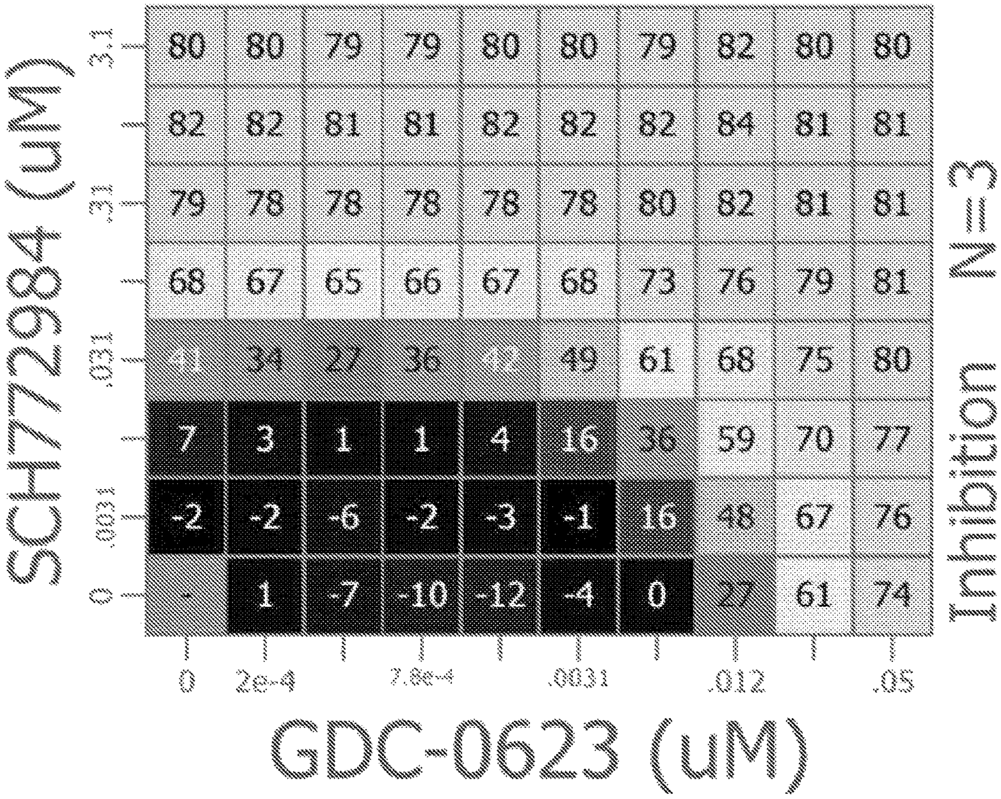
FIG. 28 shows the results of the combination of SCH772984 and GDC-0623 in parental A375 and A375 NRAS (Q61K/+) cells.
Figure 29:
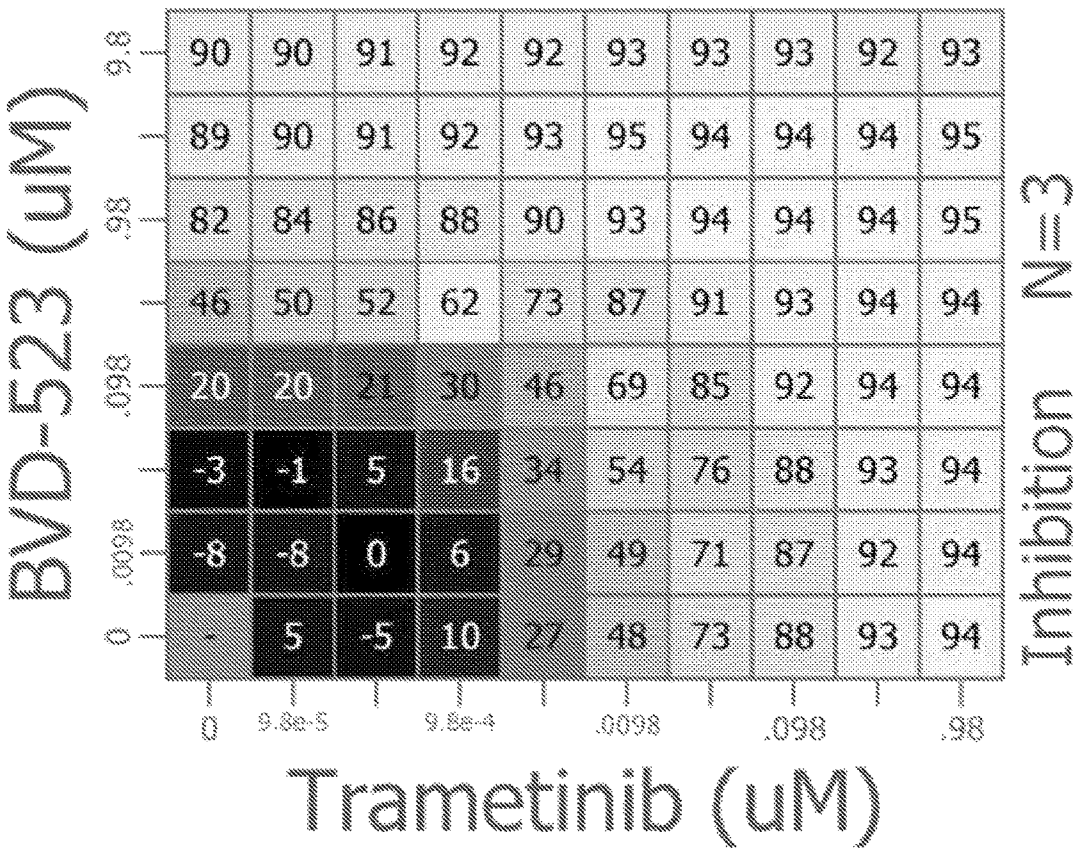
FIG. 29 shows the results of the combination of BVD-523 and Trametinib in parental HCT116 and HCT116 KRAS KO (+/−) cells.
Figure 30:
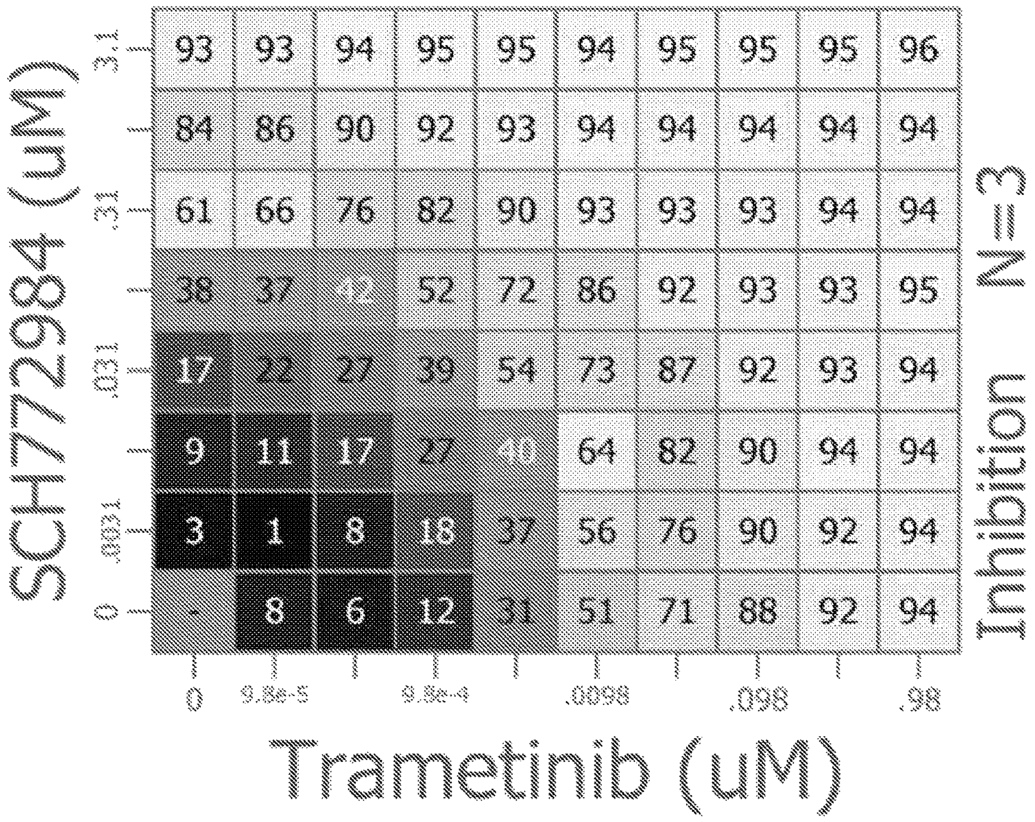
FIG. 30 shows the results of the combination of SCH772984 and Trametinib in parental HCT116 and HCT116 KRAS KO (+/−) cells.
Figure 31:
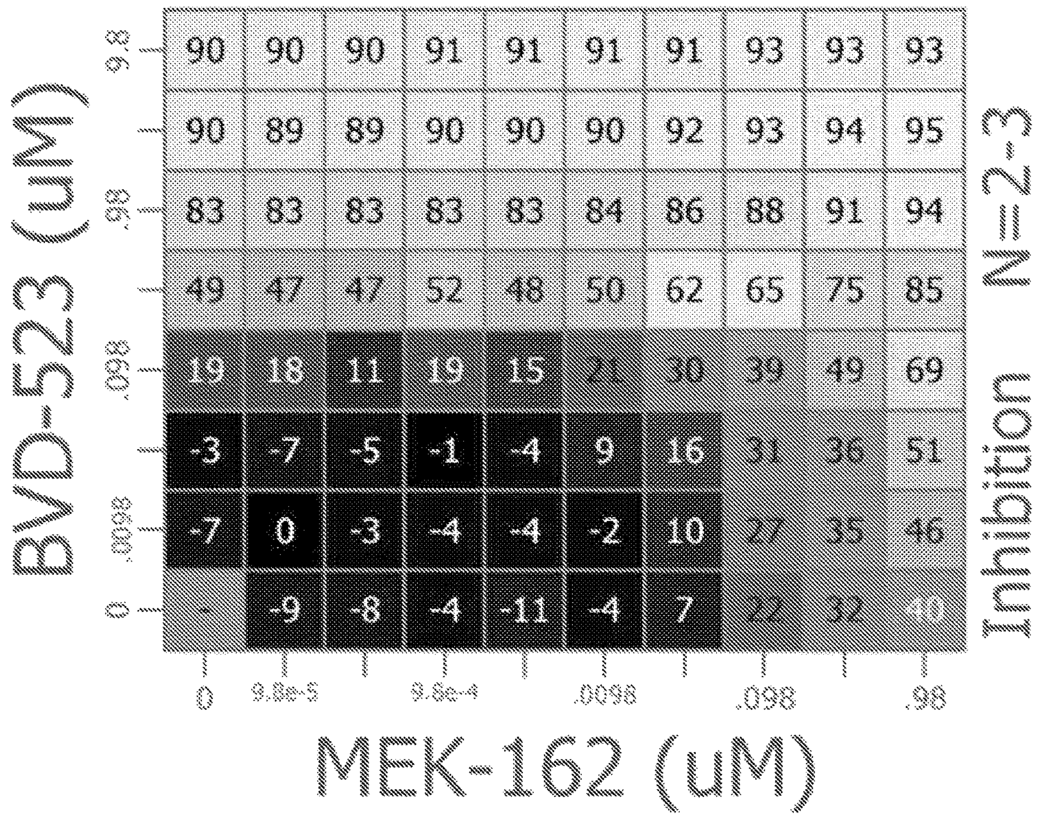
FIG. 31 shows the results of the combination of BVD-523 and MEK-162 in parental HCT116 and HCT116 KRAS KO (+/−) cells.
Figure 32:
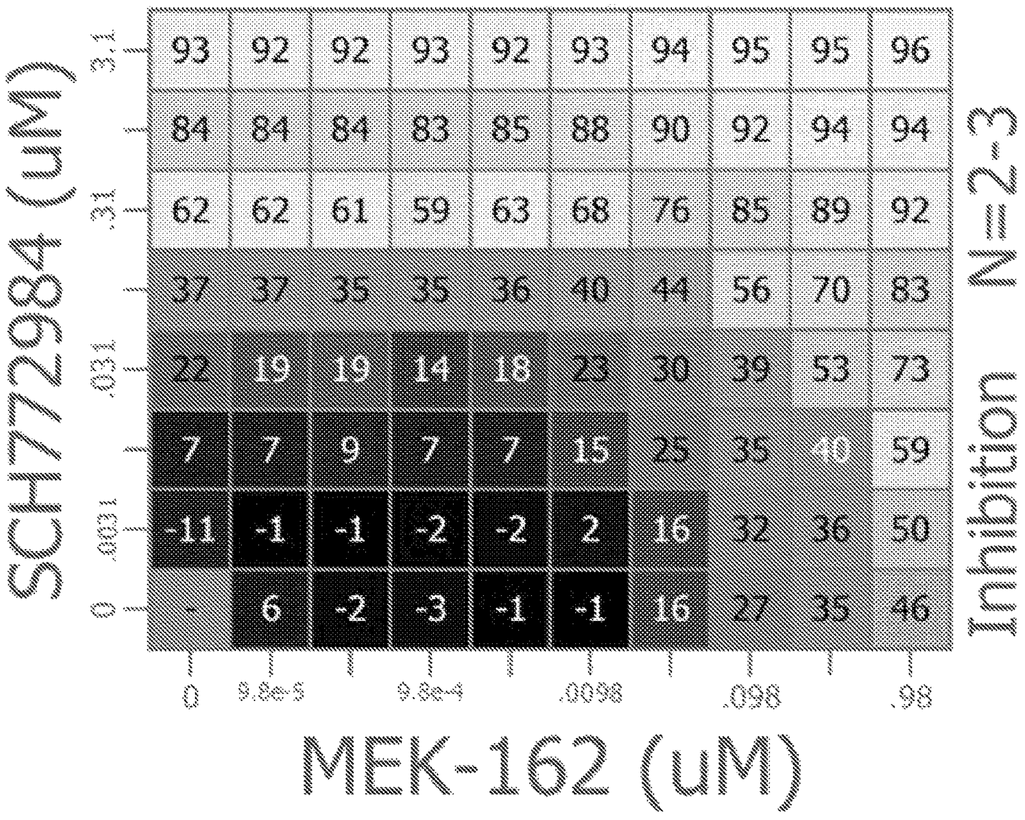
FIG. 32 shows the results of the combination of SCH772984 and MEK-162 in parental HCT116 and HCT116 KRAS KO (+/−) cells.
Figure 33:
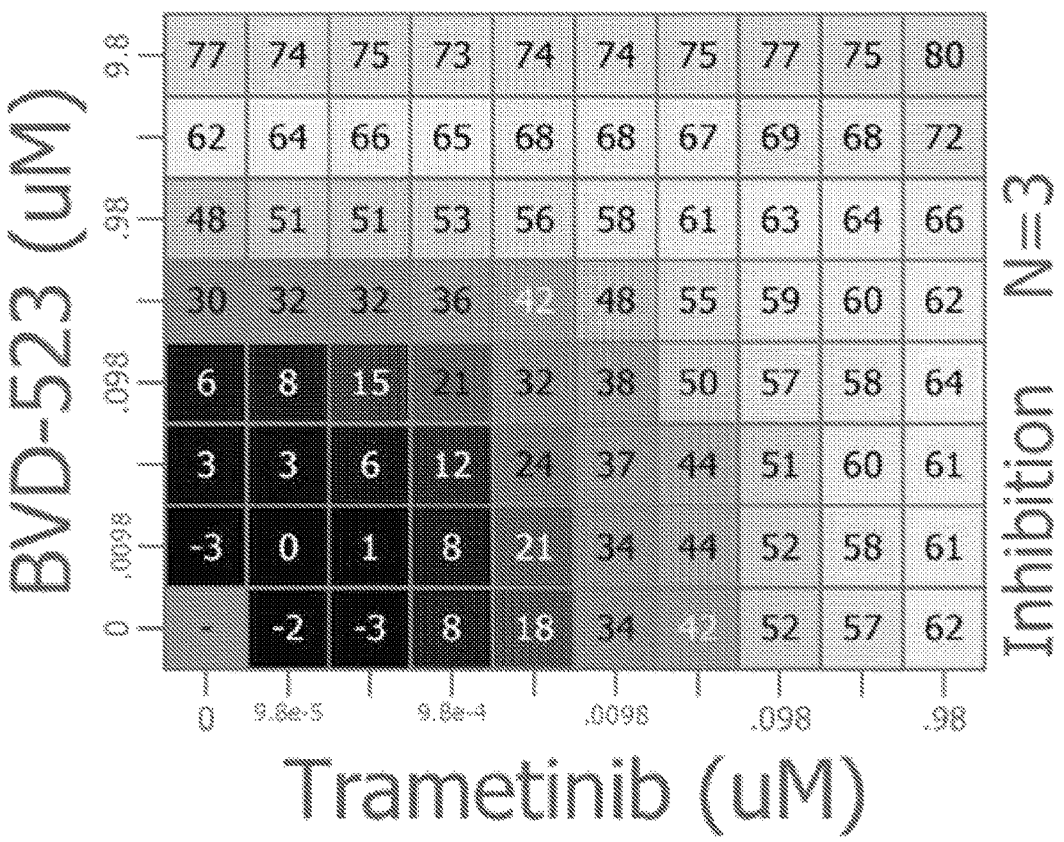
FIG. 33 shows the results of the combination of BVD-523 and Trametinib in parental RKO and RKO BRAF V600E KO (+/−/−) cells.
Figure 34:
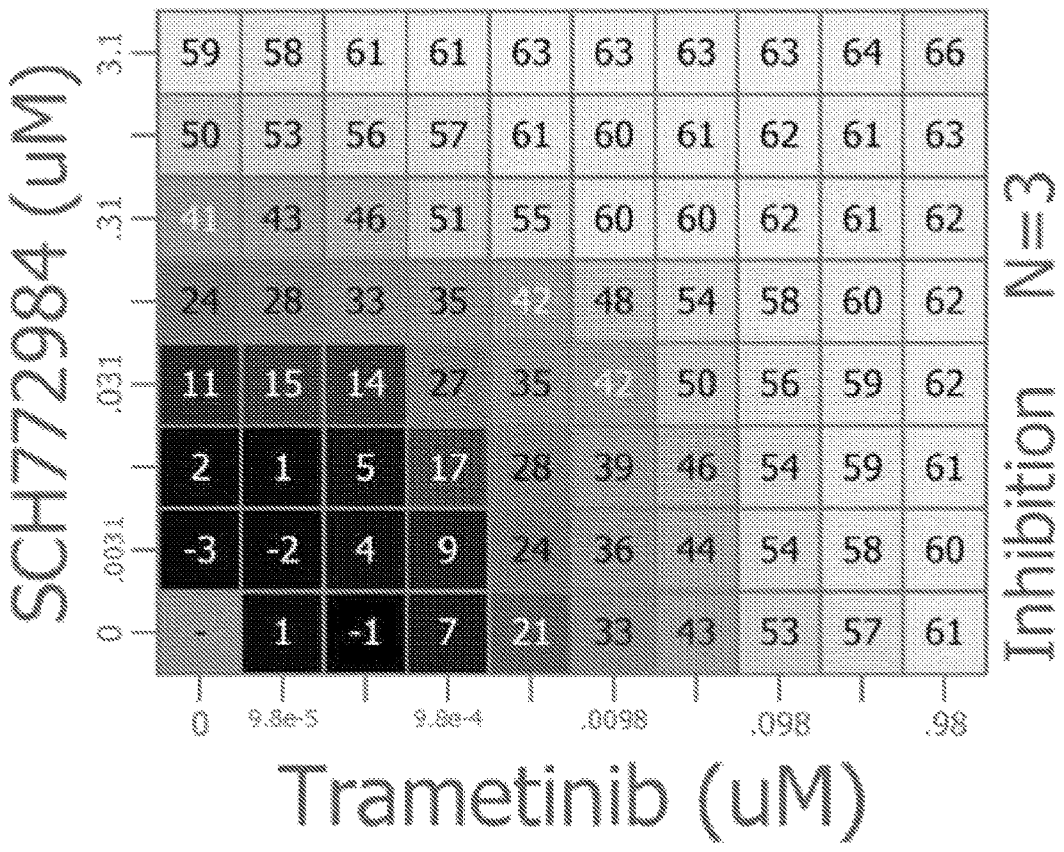
FIG. 34 shows the results of the combination of SCH772984 and Trametinib in parental RKO and RKO BRAF V600E KO (+/−/−) cells.
Figure 35:
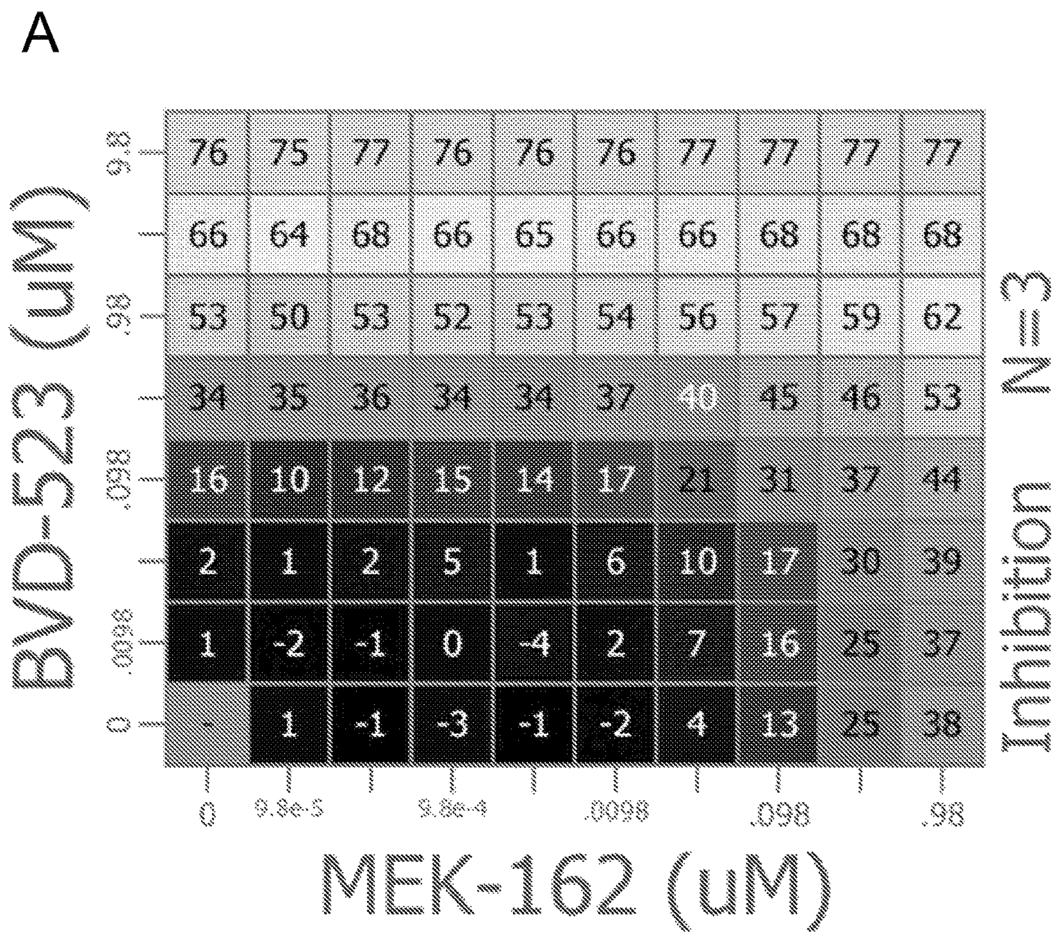
FIG. 35 shows the results of the combination of BVD-523 and MEK-162 in parental RKO and RKO BRAF V600E KO (+/−/−) cells.
Figure 36:
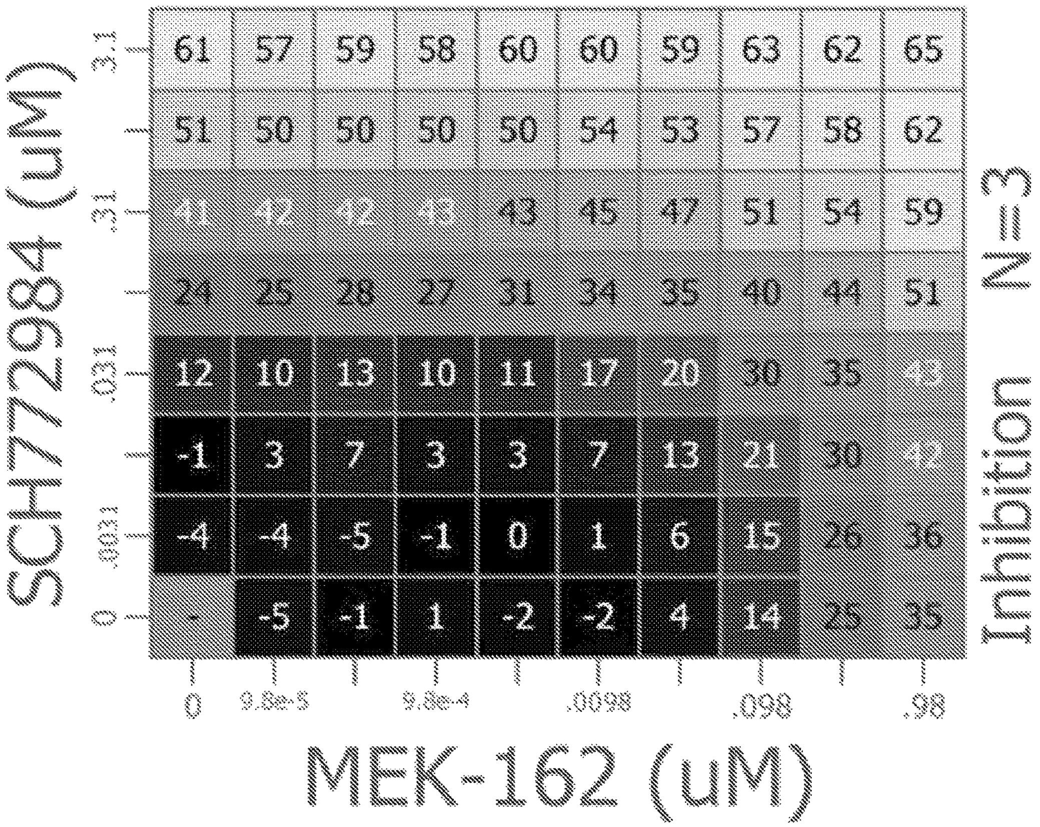
FIG. 36 shows the results of the combination of SCH772984 and MEK-162 in parental RKO and RKO BRAF V600E KO (+/−/−) cells.
Figure 37:
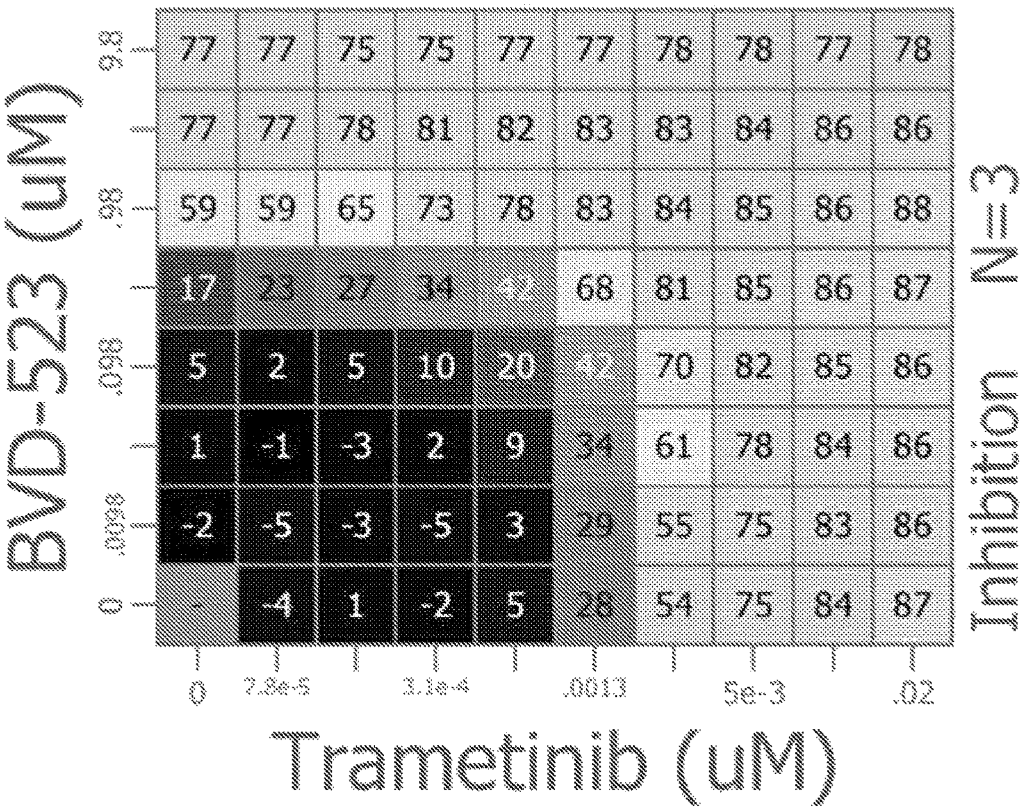
FIG. 37 shows the results of the combination of BVD-523 and Trametinib in G-361 cells.
Figure 38:
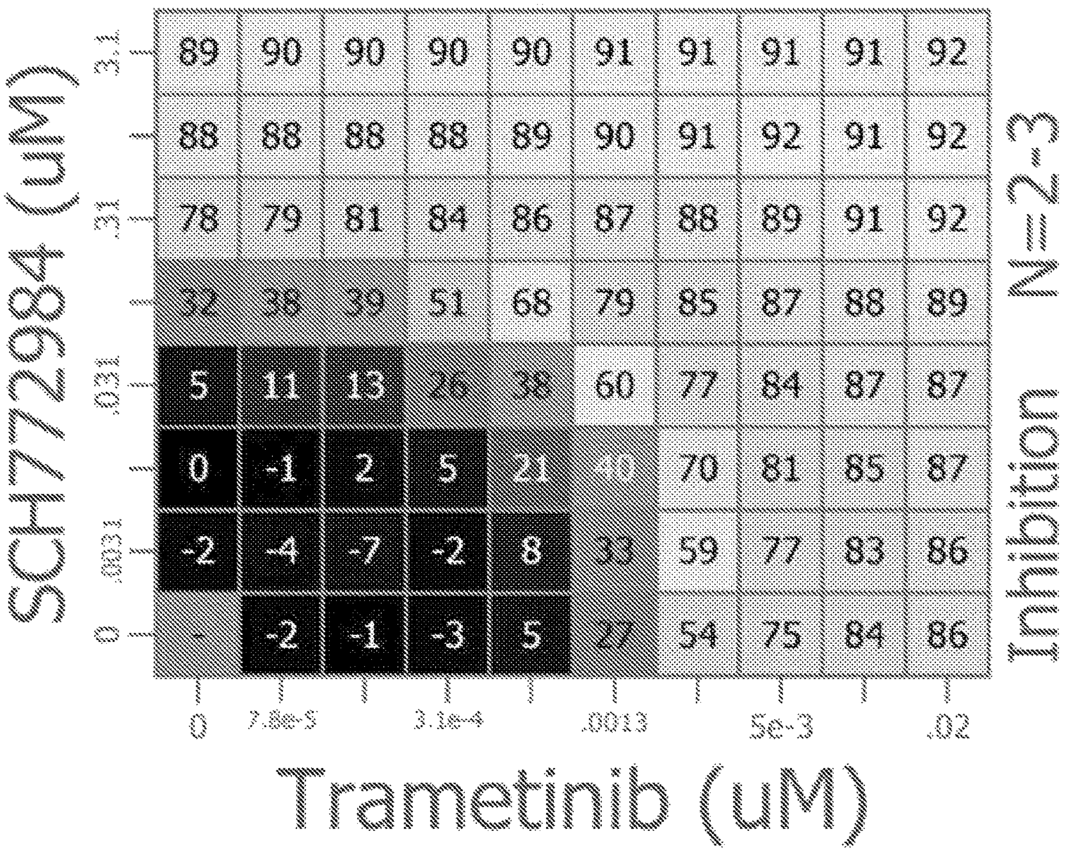
FIG. 38 shows the results of the combination of SCH772984 and Trametinib in G-361 cells.
Figure 39:
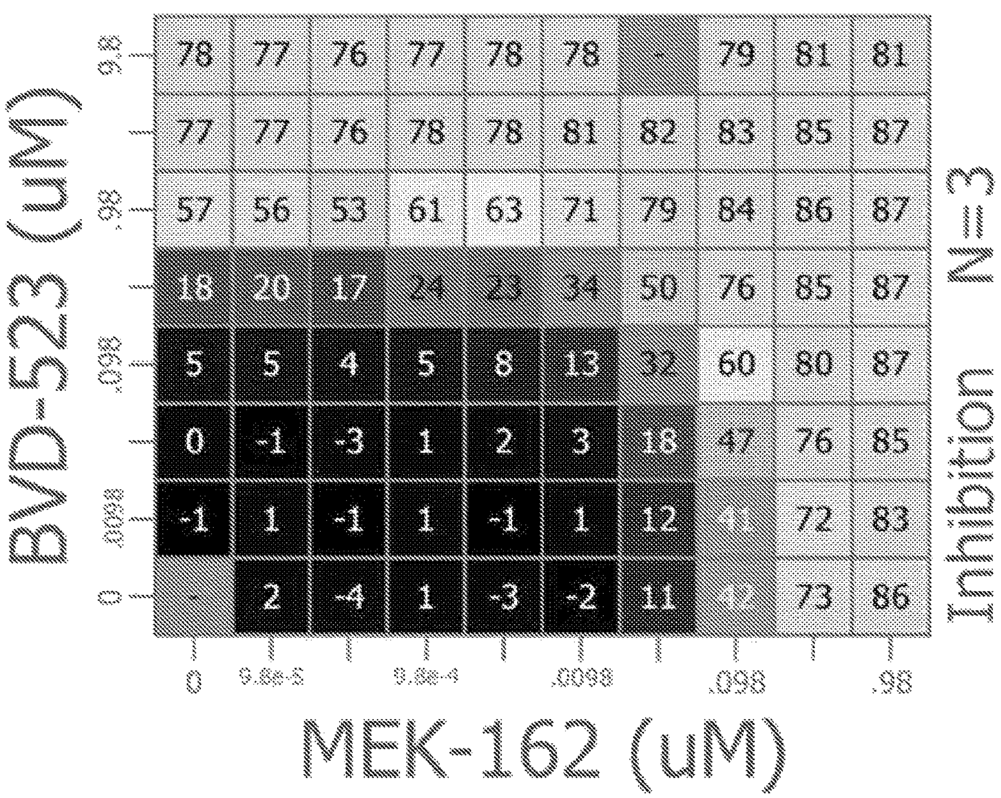
FIG. 39 shows the results of the combination of BVD-523 and MEK-162 in G-361 cells.
Figure 40:
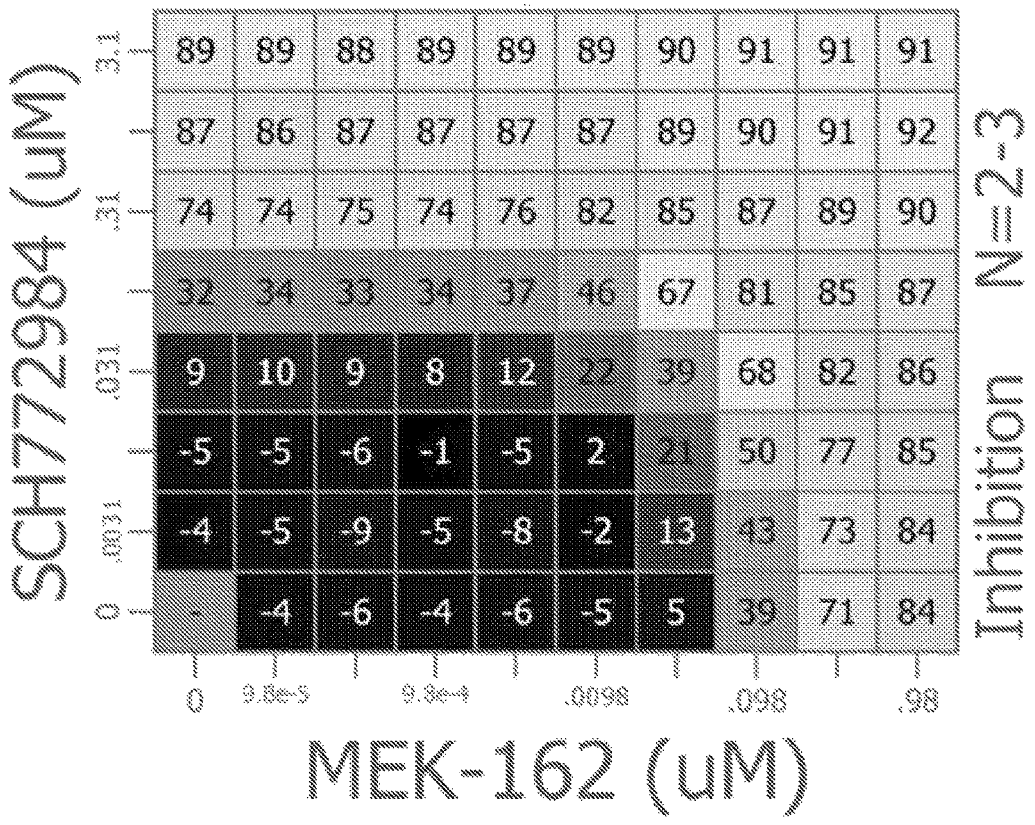
FIG. 40 shows the results of the combination of SCH772984 and MEK-162 in G-361 cells.
Figure 41:
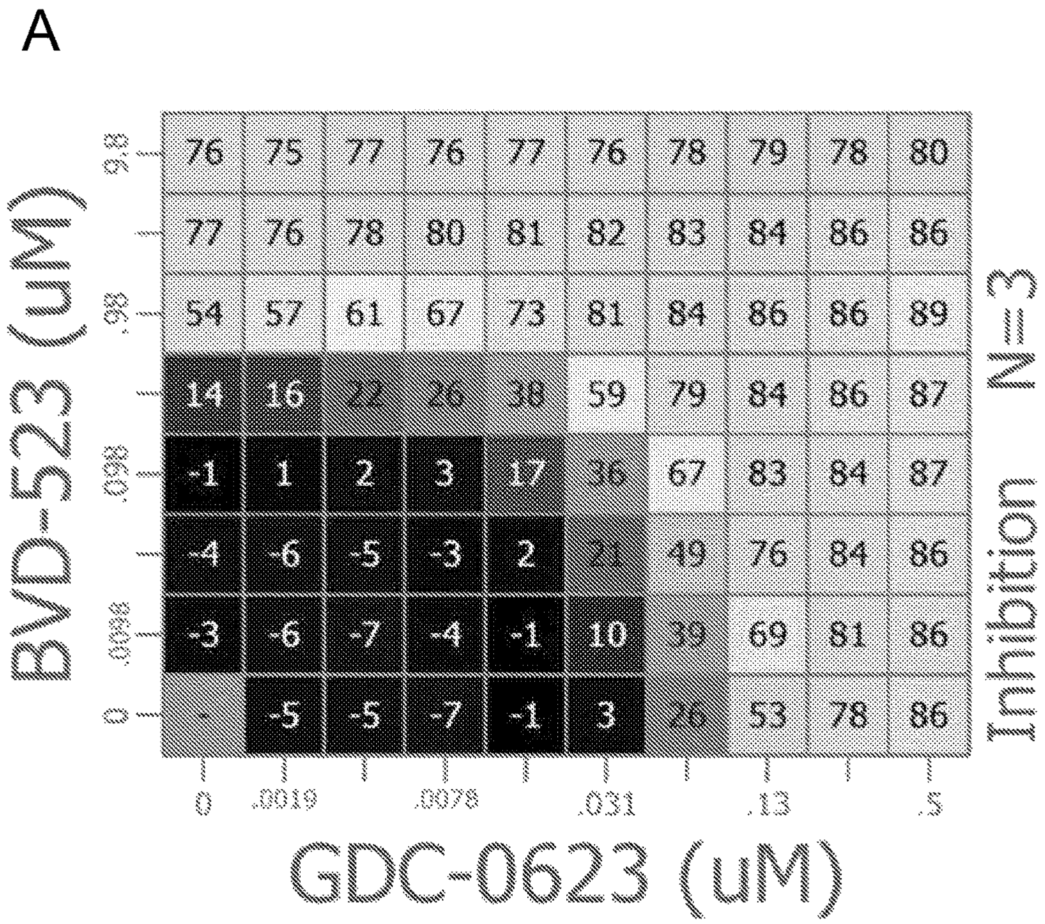
FIG. 41 shows the results of the combination of BVD-523 and GDC-0623 in G-361 cells.
Figure 42:
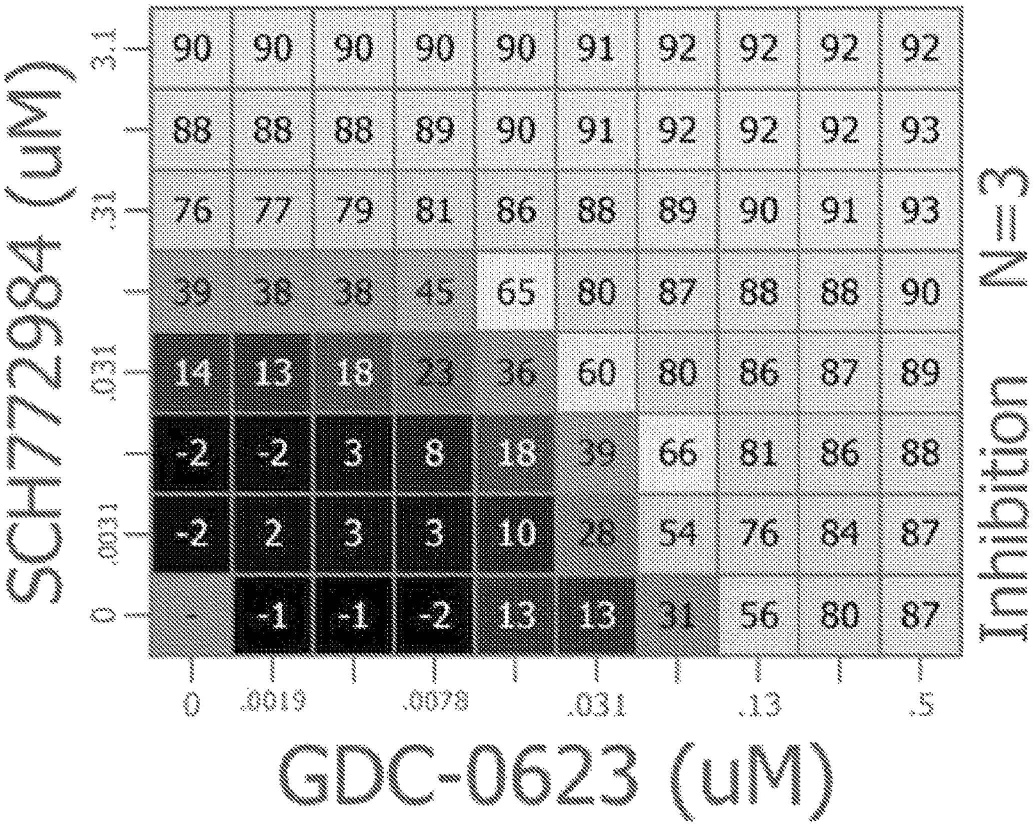
FIG. 42 shows the results of the combination of SCH772984 and GDC-0623 in G-361 cells.
Figure 43:
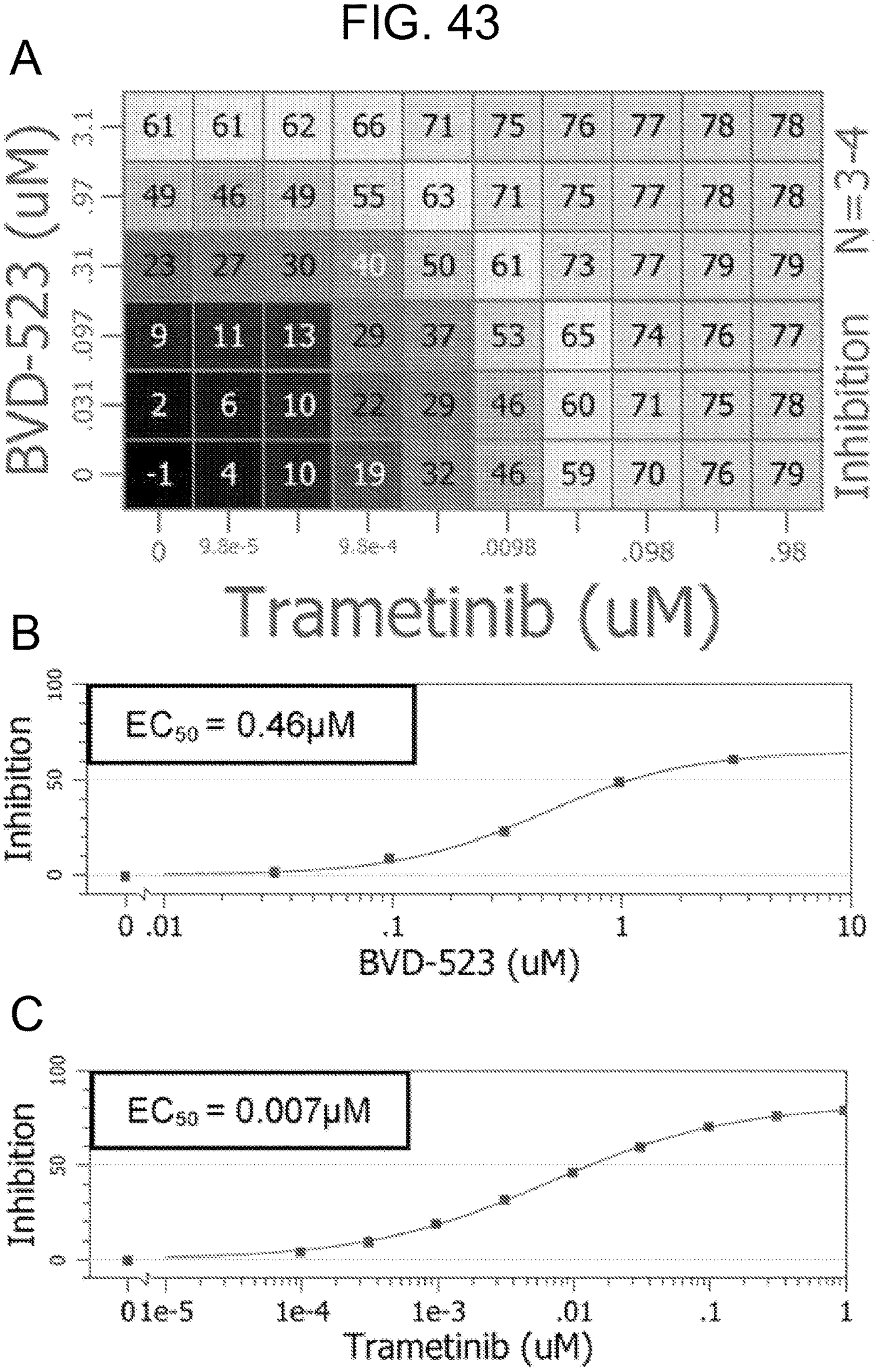
FIG. 43 shows the results of the combination of BVD-523 and Trametinib in A549 cells.
Figure 44:
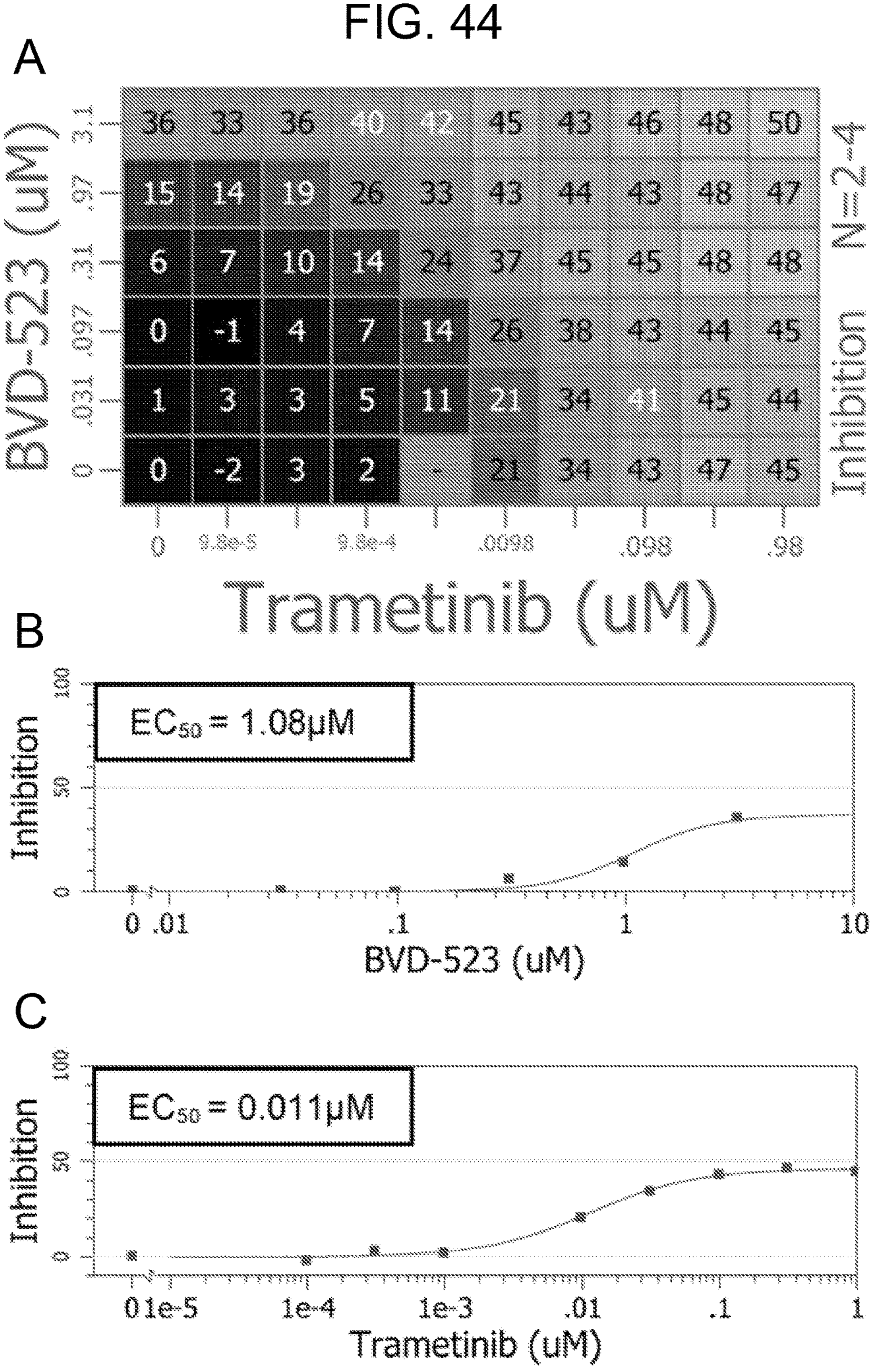
FIG. 44 shows the results of the combination of BVD-523 and Trametinib in H2122 cells.
Figure 45:
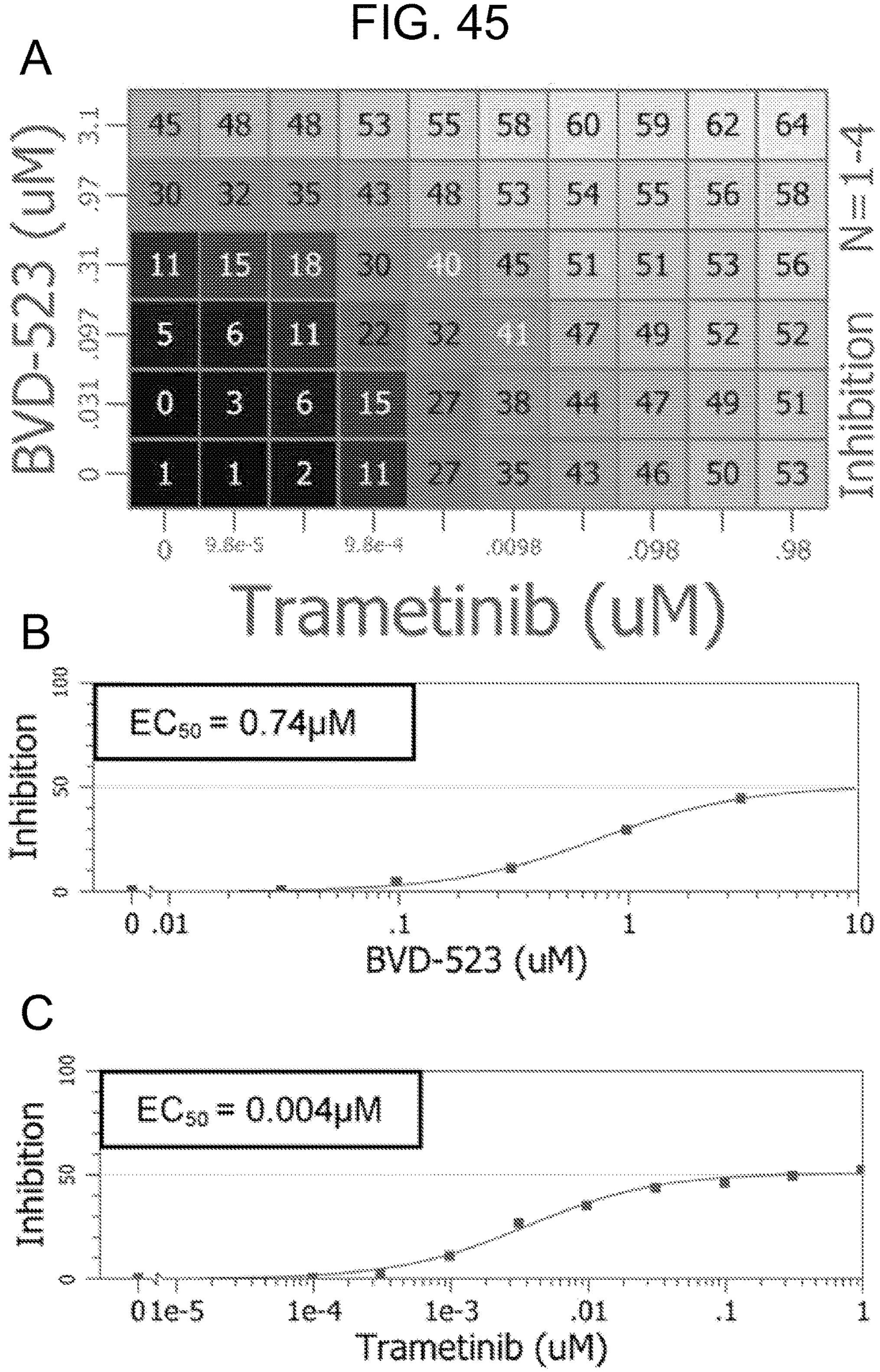
FIG. 45 shows the results of the combination of BVD-523 and Trametinib in H1437 cells.
Figure 46:
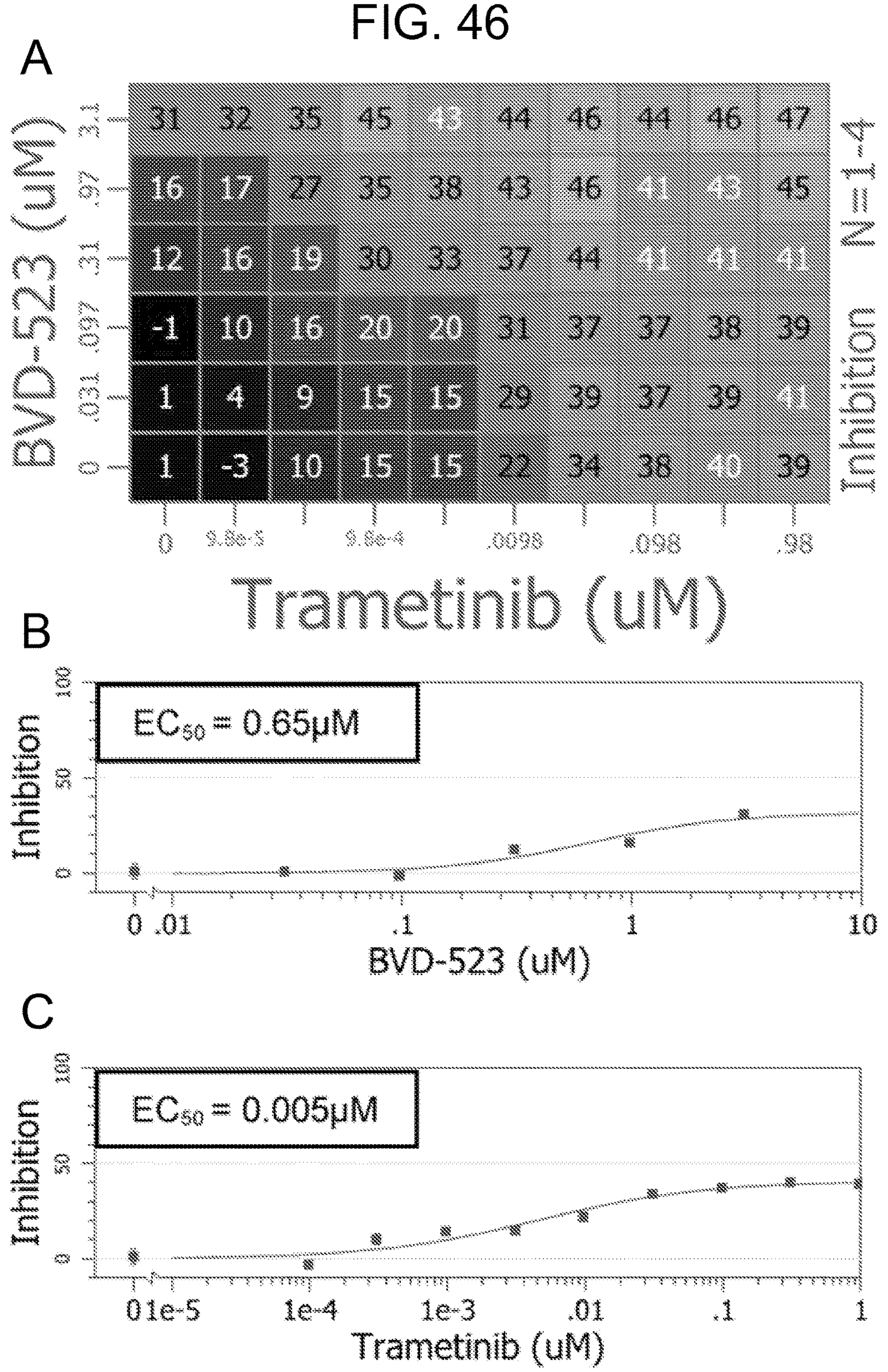
FIG. 46 shows the results of the combination of BVD-523 and Trametinib in H226 cells.
Figure 47:
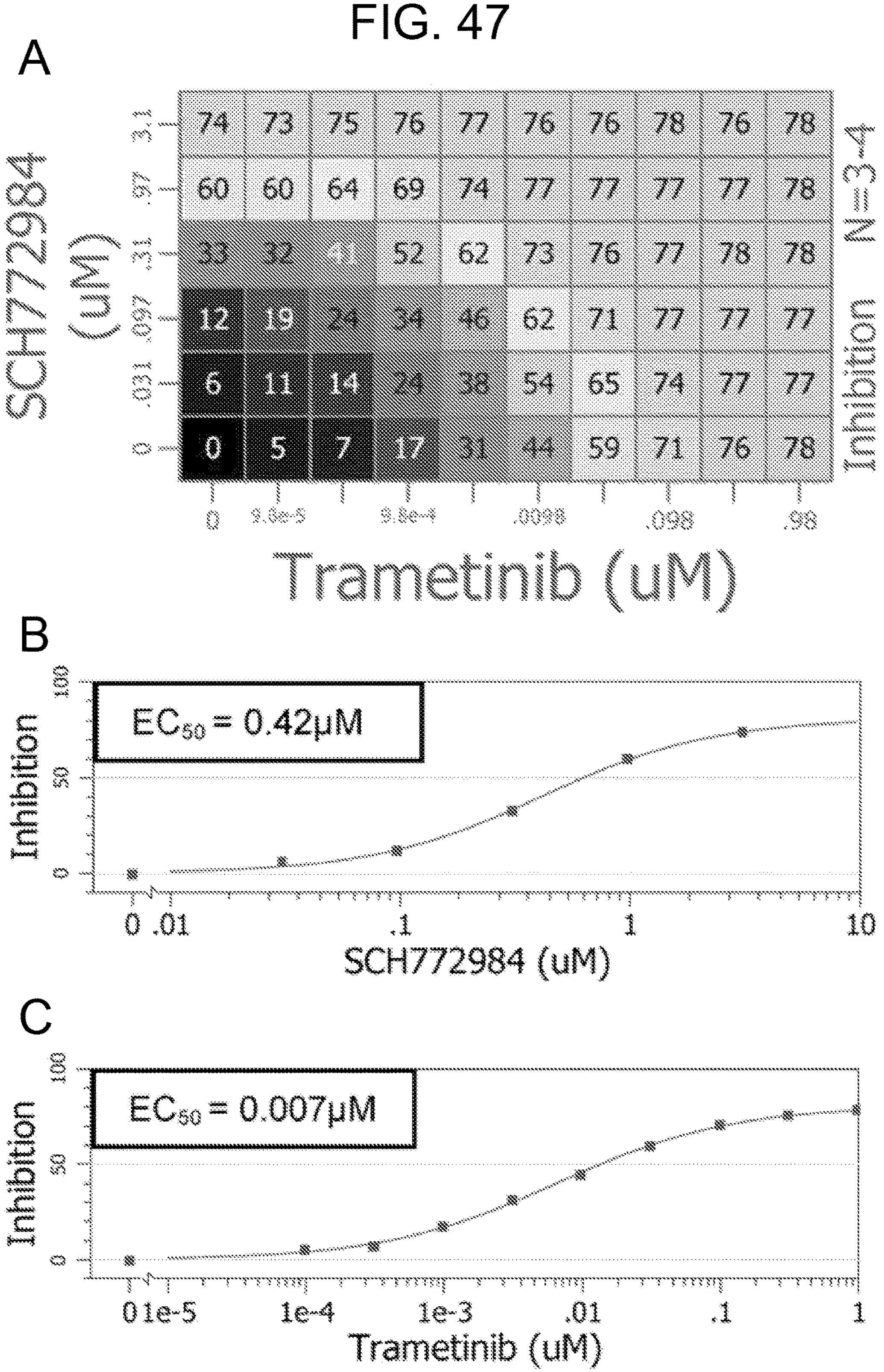
FIG. 47 shows the results of the combination of SCH772984 and Trametinib in A549 cells.
Figure 48:
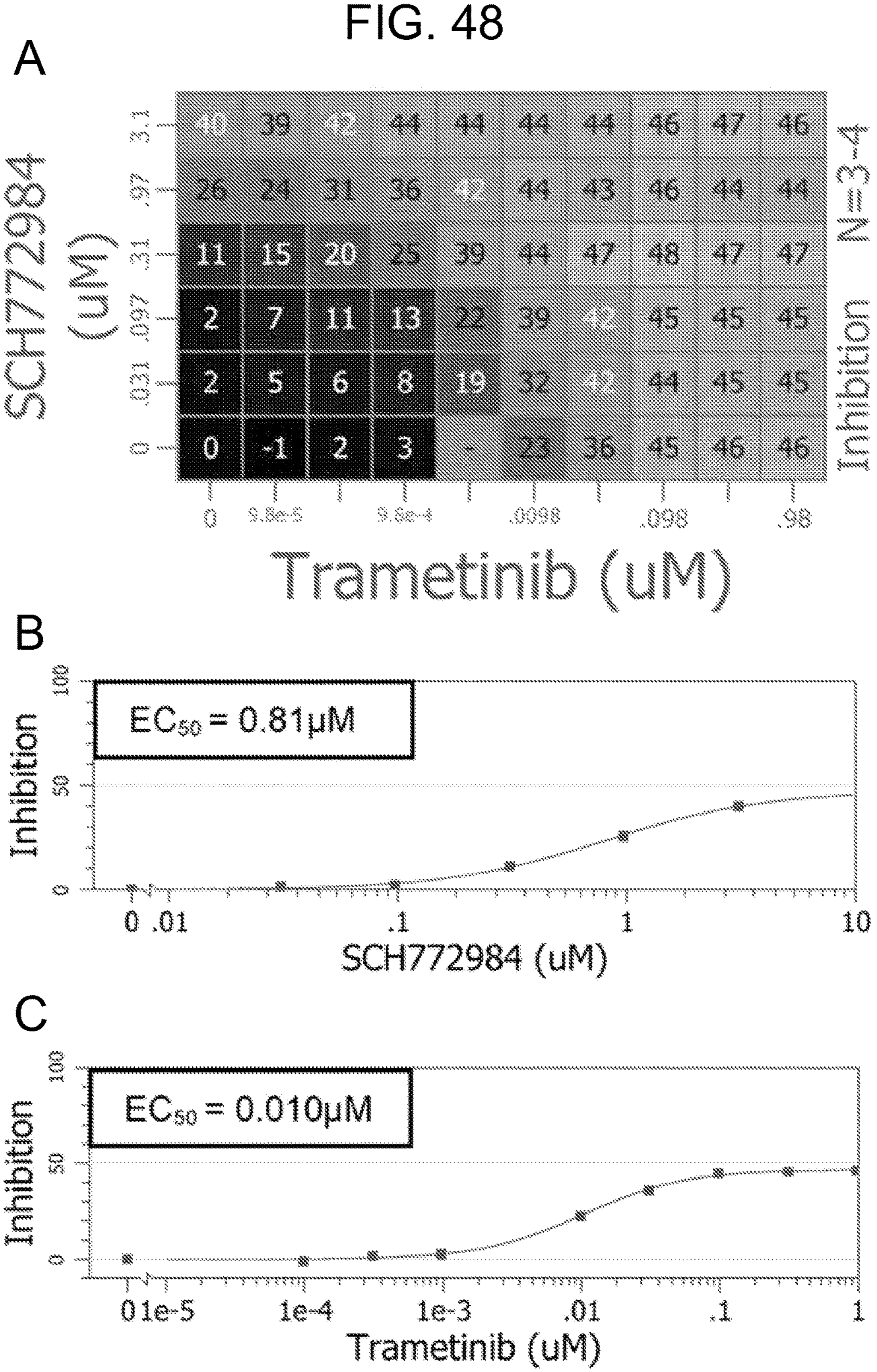
FIG. 48 shows the results of the combination of SCH772984 and Trametinib in H2122 cells.
Figure 49:
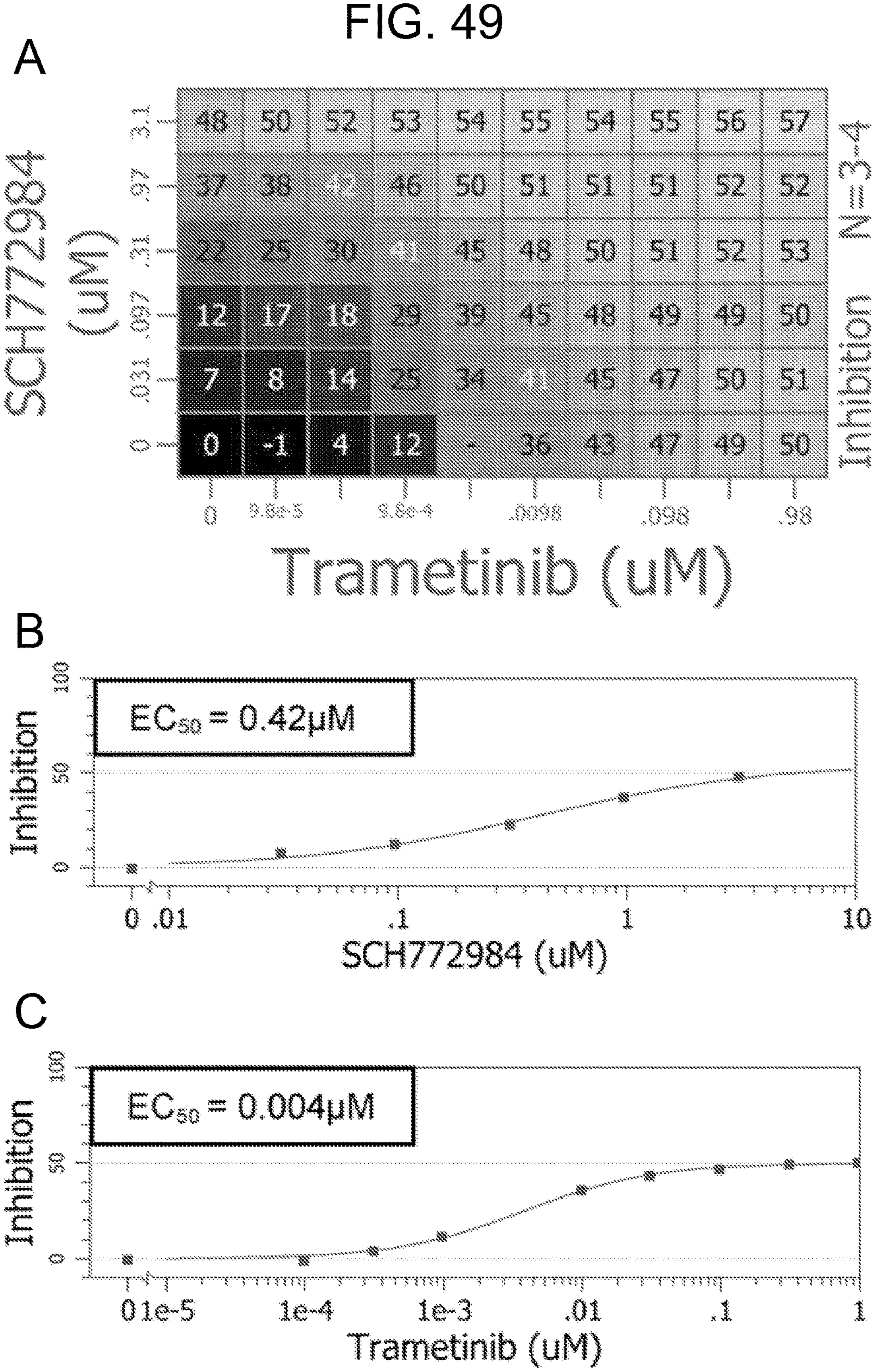
FIG. 49 shows the results of the combination of SCH772984 and Trametinib in H1437 cells.
Figure 50:
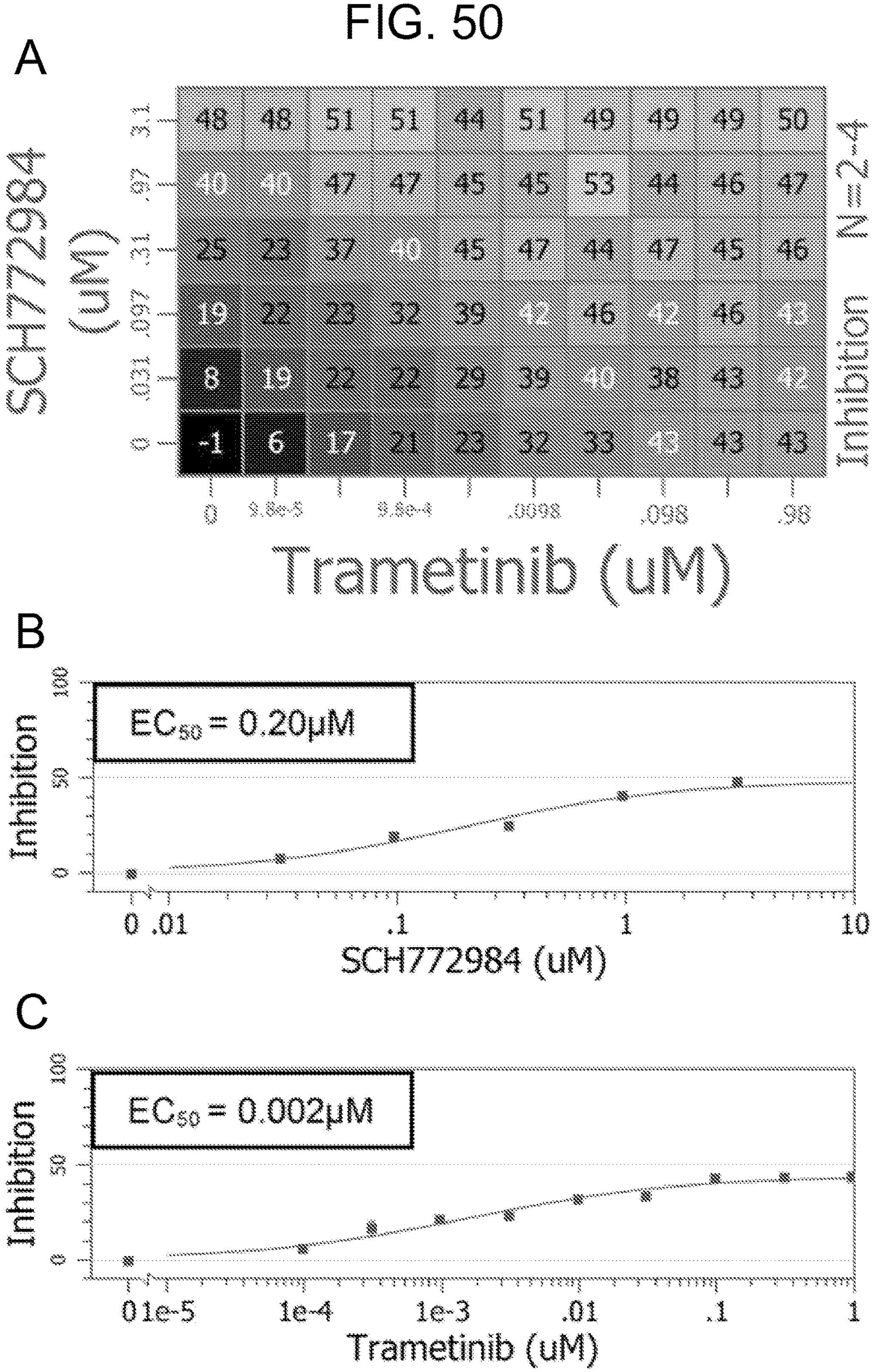
FIG. 50 shows the results of the combination of SCH772984 and Trametinib in H226 cells.
Figure 51:
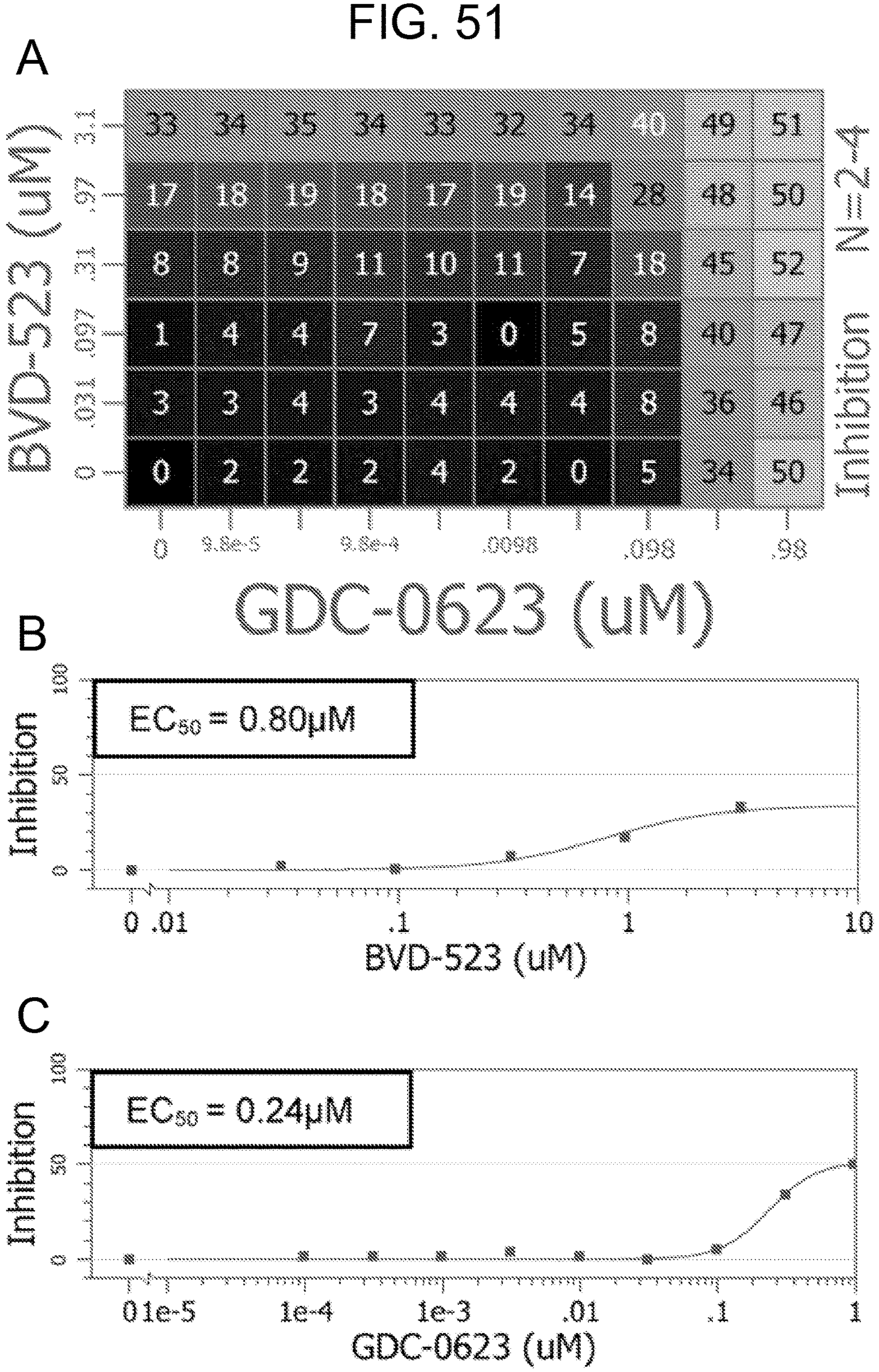
FIG. 51 shows the results of the combination of BVD-523 and GDC-0623 in H2122 cells.
Figure 52:
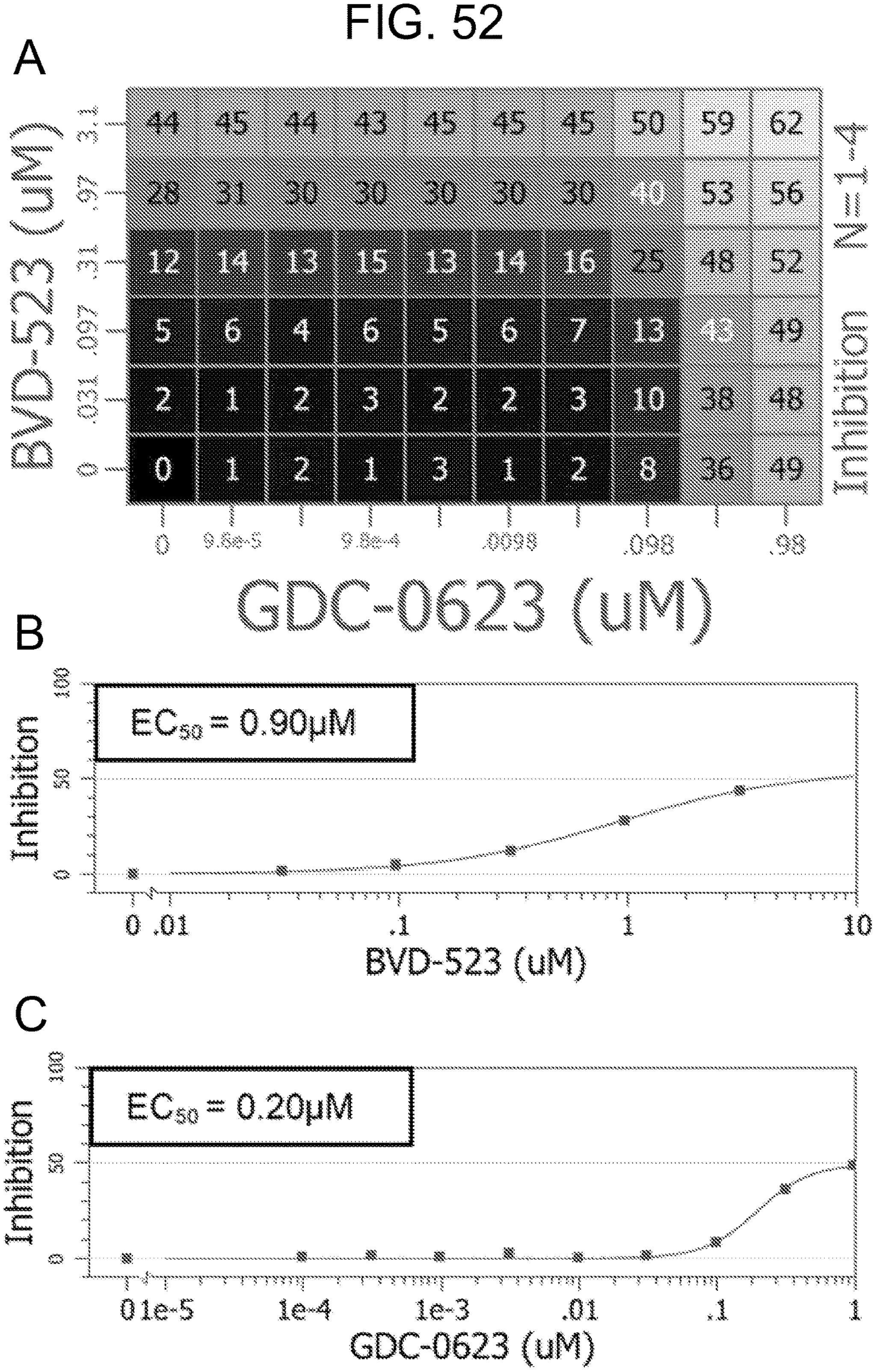
FIG. 52 shows the results of the combination of BVD-523 and GDC-0623 in H1437 cells.
Figure 53:
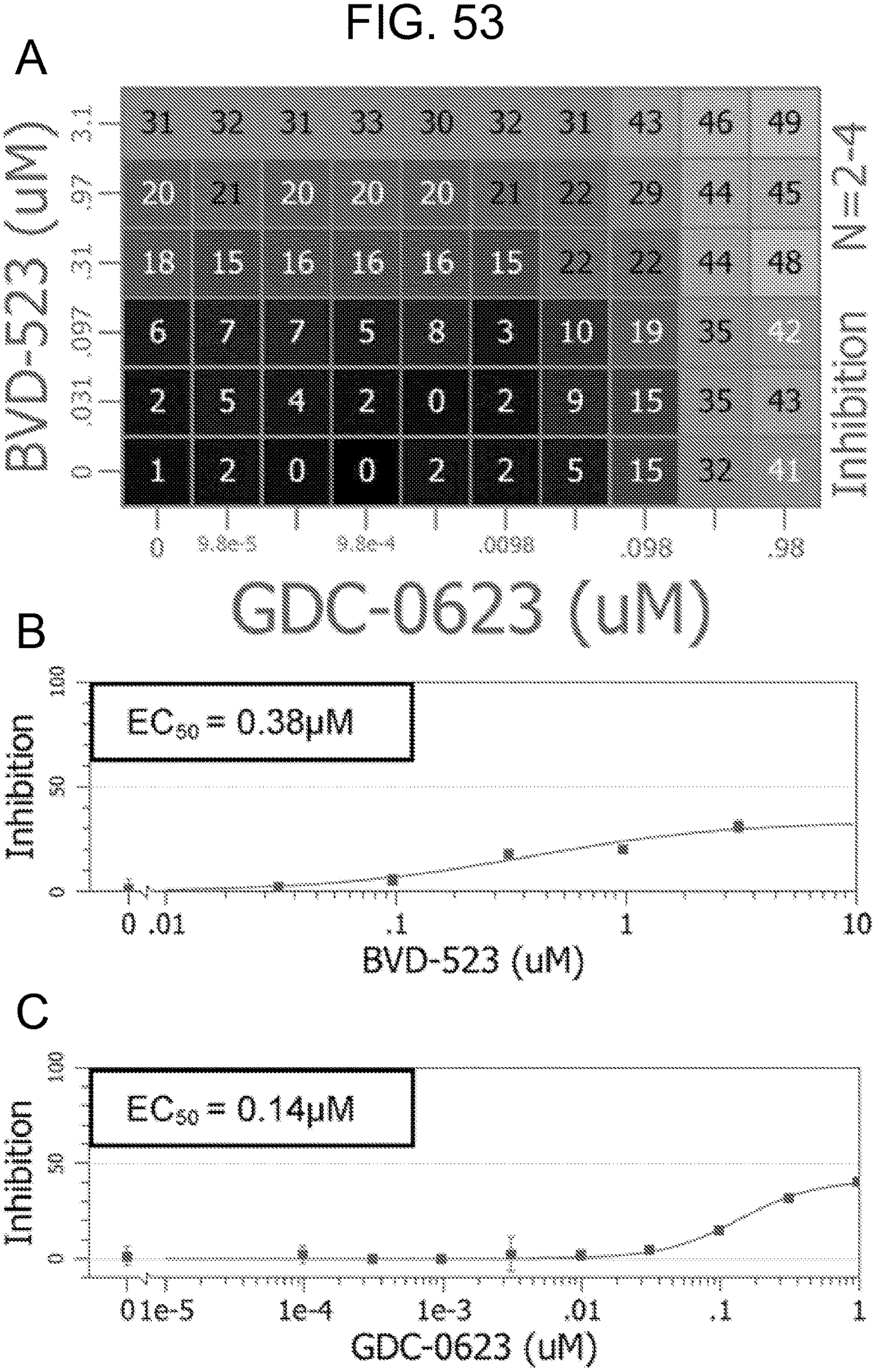
FIG. 53 shows the results of the combination of BVD-523 and GDC-0623 in H226 cells.
Figure 54:
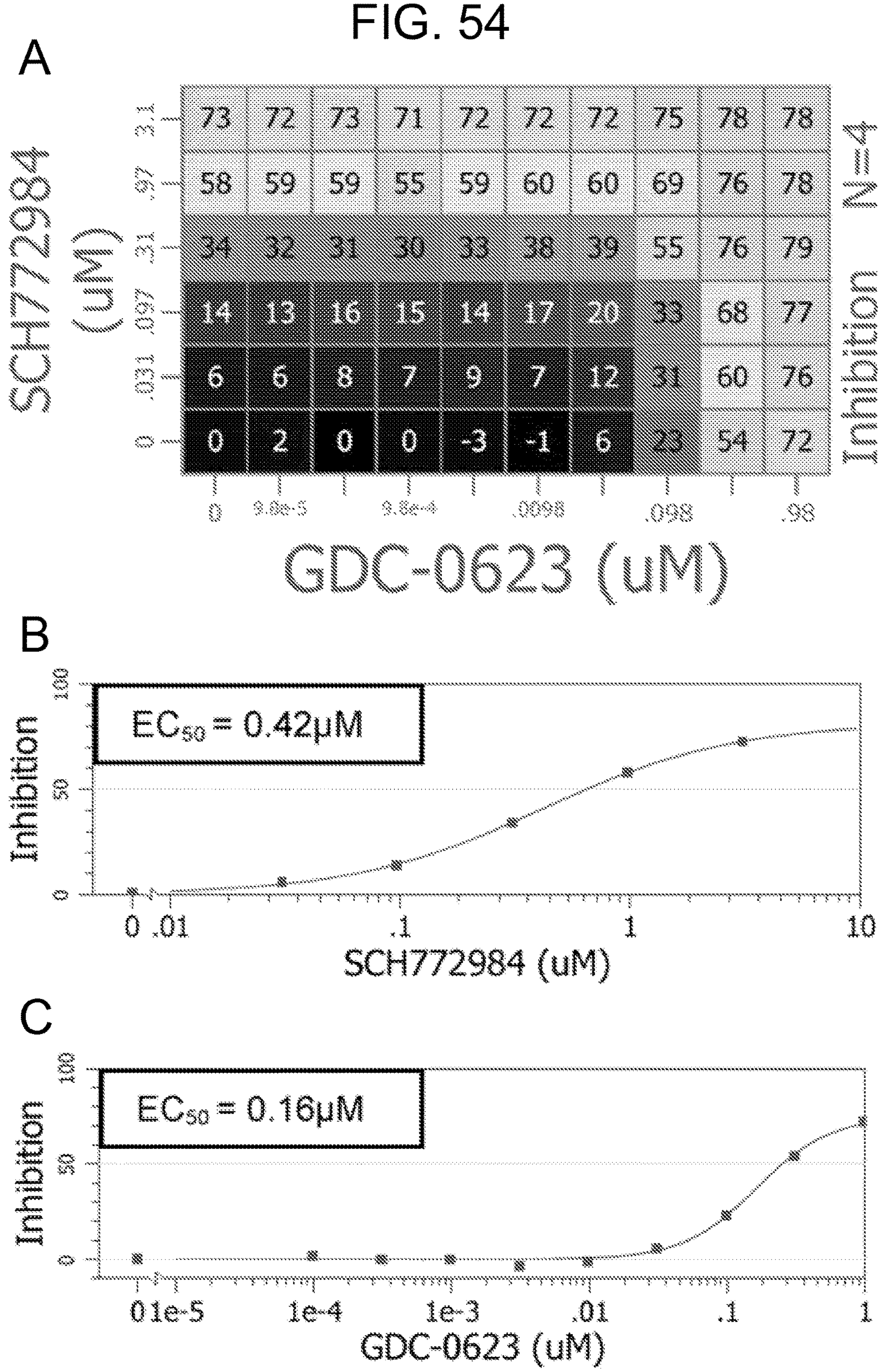
FIG. 54 shows the results of the combination of SCH772984 and GDC-0623 in A549 cells.
Figure 55:
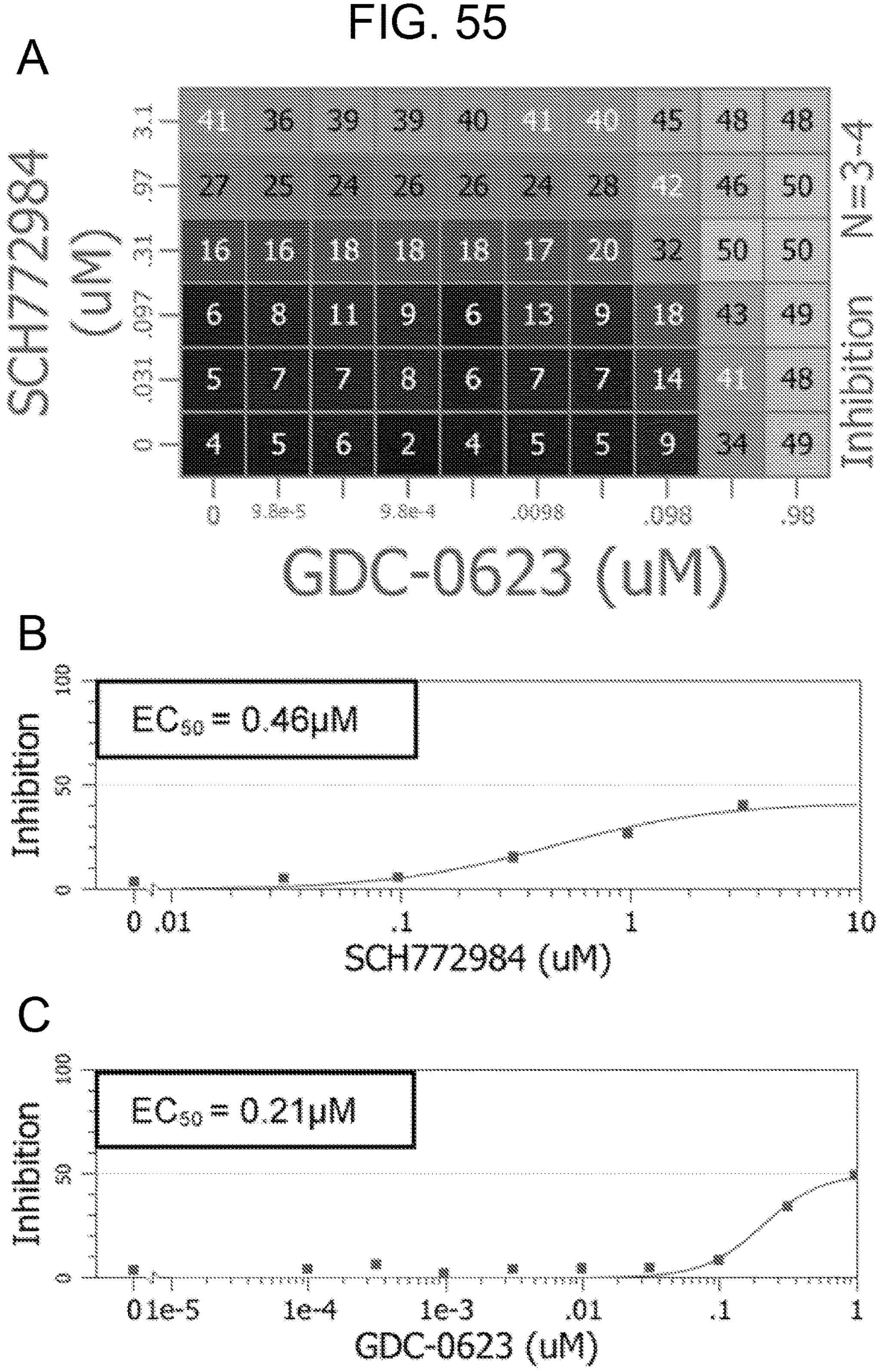
FIG. 55 shows the results of the combination of SCH772984 and GDC-0623 in H2122 cells.
Figure 56:
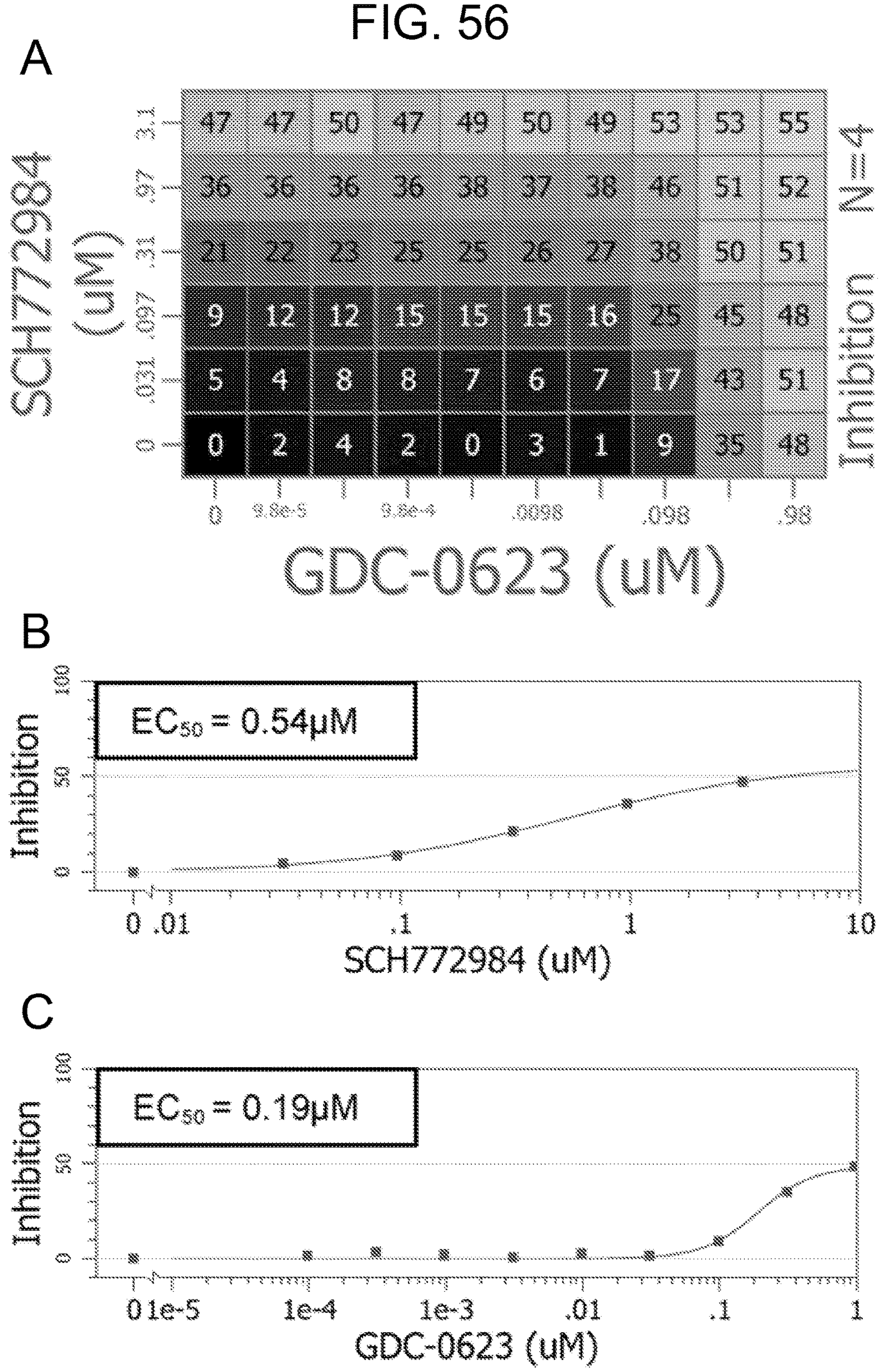
FIG. 56 shows the results of the combination of SCH772984 and GDC-0623 in H1437 cells.
Figure 57:
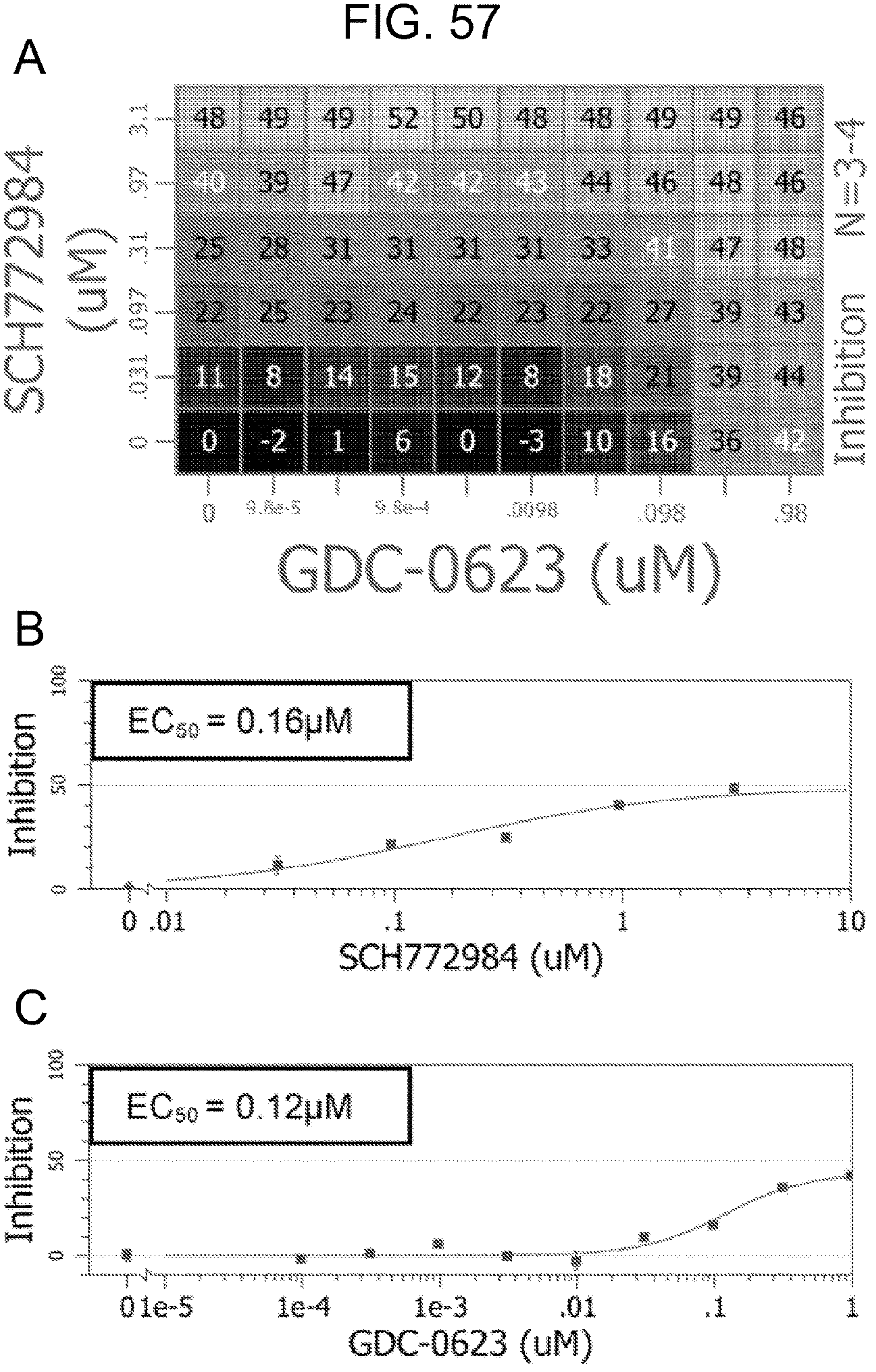
FIG. 57 shows the results of the combination of SCH772984 and GDC-0623 in H226 cells.

Visualization of the Bliss 'excess inhibition' heat maps for the A375 parental and NRAS mutant (Q61K) cell lines revealed a small window of synergy between BVD-523 and all three MEK inhibitors tested (FIG. 23, FIG. 25, FIG. 27). These observations were confirmed in a second BRAF mutant cell line G-361 (FIG. 37, FIG. 39, FIG. 41) and using a second benchmark ERK inhibitor SCH772984 (FIG. 24, FIG. 26, FIG. 28 and FIG. 38, FIG. 40, FIG. 42, respectively). Although not as strong, these windows of synergy were also mostly detected when the data was analyzed using the Loewe model.

In summary, these results suggest that interactions between BVD-523 and MEK inhibitors may potentially be synergistic in melanoma cell lines mutated for BRAF.

In contrast, when assessed using the Bliss model, interactions between BVD-523 or SCH772984 and MEK inhibitors in HCT116 (FIG. 29-FIG. 32) and the lung lines (FIG. 44-FIG. 57) appeared to be mostly additive. In the RKO cells (FIG. 33-FIG. 36) there were pockets of mild antagonism at higher concentrations. Excess scores were generally more positive, but still mainly additive, when the BVD-523 combinations were analyzed using the Loewe model. Similar results were also obtained for the SCH772984 combinations in these cell lines using the Bliss model, however, the Loewe model suggested the possible presence of regions of synergy in HCT116 and some of the lung lines that were not apparent from the Bliss model.

Synergistic interactions were scored in two ways. Excess activity over that predicted if a combination was additive can be calculated using a simple volume score, which calculates the volume between the measured and the predicted response surface. This volume score shows whether the overall response to a combination is synergistic (positive values), antagonistic (negative values) or additive (values~0). Table 19 shows Bliss volumes and Table 20 shows Loewe volumes; nt=not tested. Additionally, a 'Synergy Score', a positive-gated inhibition-weighted volume over Loewe additivity, is calculated and results are shown in Table 21; nt=not tested. This provides an additional prioritization favoring combinations whose synergy occurs at high effect levels, ignoring antagonistic portions of the response surface.

Example 8

Combination Interactions Between ERK Inhibitors

RAF mutant melanoma cell line A375 cells were cultured in DMEM with 10% FBS and seeded into triplicate 96-well plates at an initial density of 2000 cells per well. Combination interactions between ERK inhibitors BVD-523 and SCH772984 were analized after 72 hours as described above in Example 7. Viability was determined using CellTiter-Glo® reagent (Promega, Madison, Wis.) according to manufacturer's instructions and luminescence was detected using the BMG FLUOstar plate reader (BMG Labtech, Ortenberg, Germany).

Figure 58:
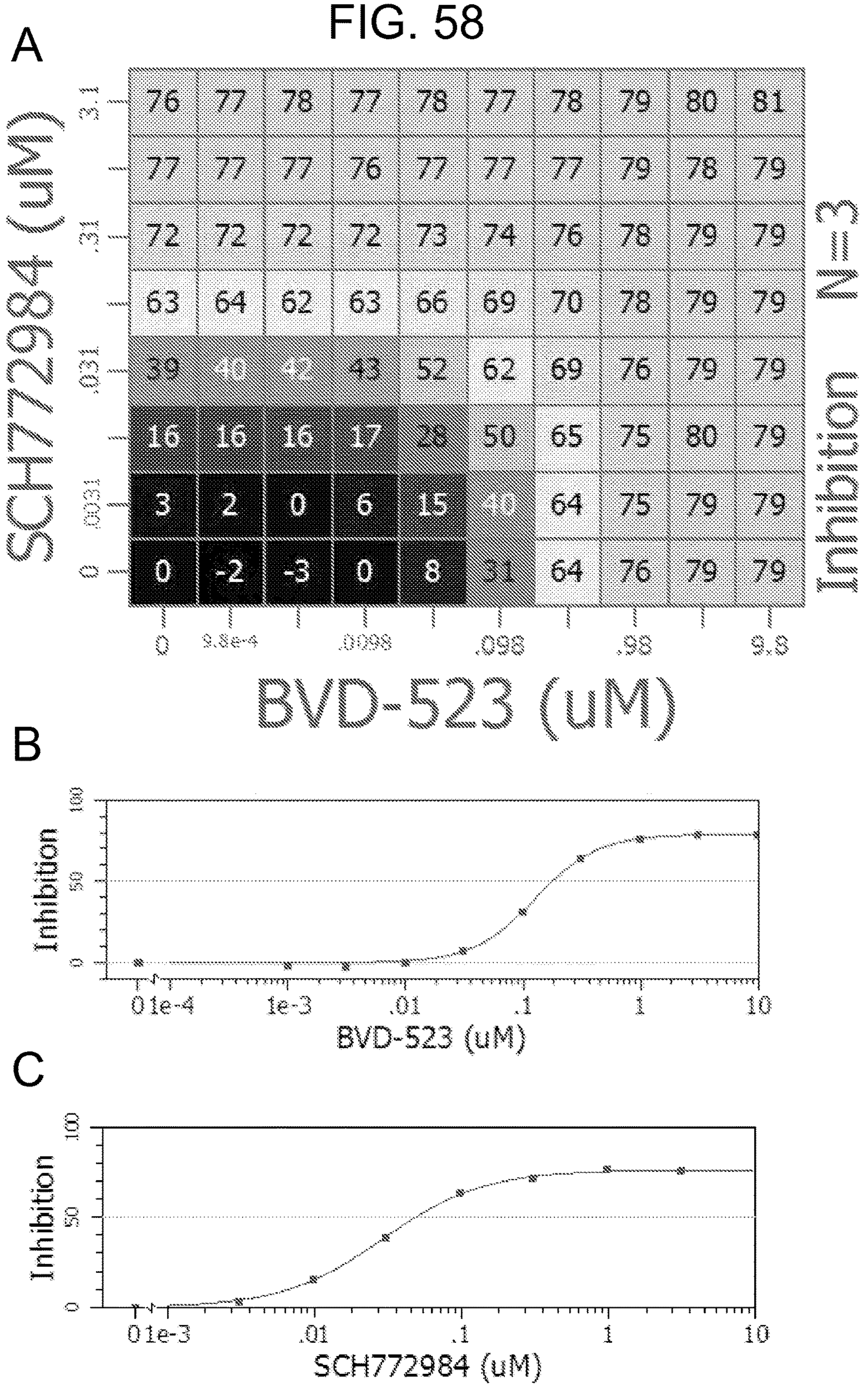
FIG. 58 shows the results of the combination of BVD-523 and SCH772984.

Visualization of the Loewe and Bliss 'excess inhibition' heat maps suggested that the combination of BVD-523 and SCH772984 was mainly additive with windows of potential synergy in mid-range doses (FIG. 58).

In summary, these results suggest that interactions between BVD-523 and SCH772984 are at least additive, and in some cases synergistic.

DOCUMENTS

ABSALAN, Farnaz; Mostafa Ronaghi (2008). Molecular Inversion Probe Assay. Methods in Molecular Biology 396. Humana Press. pp. 315-330.

GREGER, James G., et al. "Combinations of BRAF, MEK, and PI3K/mTOR inhibitors overcome acquired resistance to the BRAF inhibitor GSK2118436 dabrafenib, mediated by NRAS or MEK mutations." Molecular cancer therapeutics 11.4 (2012): 909-920.

HARDENBOL, P. et al. Multiplexed genotyping with sequence-tagged molecular inversion probes. Nat. Biotechnol. 2003, no. 21, pp. 673-678.

HATZIVASSILIOU, G. et al., "RAF inhibitors prime wild-type RAF to activate the MAPK pathway and enhance growth." Nature 464.7287 (2010): 431-435.

KING, Alastair J., et al. "Dabrafenib; preclinical characterization, increased efficacy when combined with trametinib, while BRAF/MEK tool combination reduced skin lesions." PloS one 8.7 (2013): e67583.

LITTLE, A. S. et al., Amplification of the Driving Oncogene, KRAS or BRAF, Underpins Acquired Resistance to MEK1/2 Inhibitors in Colorectal Cancer Cells. Sci. Signal. 4, ra17 (2011).

MANANDHAR S P, Hildebrandt E R, Schmidt W K. Small-molecule inhibitors of the Rce1p CaaX protease. J Biomol Screen. 2007; 12(7):983-993.

MAURER, T, Garrenton, L S, Oh, A, Pitts, K, Anderson, D J, Skelton, N J, Fauber, B P, Pan, B, Malek, S, Stokoe, D, Ludlam, M J C, Bowman, K K, Wu, J, Giannetti, A M, Starovasnik, M A, Mellman, I, Jackson, P K, Rudolph, J, Wang, W, Fang, G. Small-molecule ligands bind to a distinct pocket in Ras and inhibit SOS-mediated nucleotide exchange activity. PNAS. 2012; 109(14):5299-304.

METZKER, Emerging technologies in DNA sequencing Genome Res. 2005. 15: 1767-1776

MITTAL, Rohit et al. "The acetyltransferase activity of the bacterial toxin YopJ of Yersinia is activated by eukaryotic host cell inositol hexakisphosphate." Journal of Biological Chemistry 285.26 (2010): 19927-19934.

NILSSON, M. et al., Padlock probes: circularizing oligonucleotides for localized DNA detection. Science. 1994, no. 265, p. 2085-2088.

OTA et al., Single nucleotide polymorphism detection by polymerase chain reaction-restriction fragment length polymorphism. Nat Protoc. 2007; 2(11):2857-64.

PATGIRI, A, Yadav, K K, Arora, P S, Bar-Sagi, D. An orthosteric inhibitor of the Ras-Sos interaction. Nat Chem Biol. 2011; 7:585-587.

PORTER S B, Hildebrandt E R, Breevoort S R, Mokry D Z, Dore T M, Schmidt W K. Inhibition of the CaaX proteases Rce1p and Ste24p by peptidyl (acyloxy)methyl ketones. Biochim Biophys Acta.2007; 1773(6):853-862.

SHIMA, F, Yoshikawa, Y, Ye, M, Araki, M, Matsumoto, S, Liao, J, Hu, L, Sugimoto, T, Ijiri, Y, Takeda, A, Nishiyama, Y, Sato, C, Muraoka, S, Tamura, A, Osoda, T, Tsuda, K-I, Miyakawa, T, Fukunishi, H, Shimada, J, Kumasaka, Yamamoto, M, Kataoka, T. In silico discovery of small-molecule Ras inhibitors that display antitumor activity by blocking the Ras-effector interaction. PNAS. 2013; 110(20):8182-7.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method of treating or ameliorating the effects of a cancer in a subject in need thereof comprising administering to the subject an effective amount of (i) a first anti-cancer agent, which is BVD-523 or a pharmaceutically acceptable salt thereof and (ii) a second anti-cancer agent, which is a type 2 MEK inhibitor or a pharmaceutically acceptable salt thereof, to treat or ameliorate the effects of the cancer, wherein the type 2 MEK inhibitor is selected from the group consisting of GDC-0623, MEK162, trametinib, pharmaceutically acceptable salts thereof, and combinations thereof, and wherein administration of the first and second anti-cancer agents provides a synergistic effect compared to administration of either anti-cancer agent alone.

2. The method according to claim 1, wherein the subject is a mammal.

3. The method according to claim 2, wherein the mammal is selected from the group consisting of humans, primates, farm animals, and domestic animals.

4. The method according to claim 2, wherein the mammal is a human.

5. The method according to claim 1, wherein the subject with cancer has a somatic RAS or BRAF mutation.

6. The method according to claim 1, wherein the cancer is selected from the group consisting of a cancer of the large intestine, breast cancer, pancreatic cancer, skin cancer, endometrial cancer, neuroblastoma, leukemia, lymphoma, liver cancer, lung cancer, testicular cancer, and thyroid cancer.

7. The method according to claim 1, wherein the cancer is melanoma.

8. The method according to claim 1 further comprising administering to the subject at least one additional therapeutic agent selected from the group consisting of an antibody or fragment thereof, a cytotoxic agent, a drug, a toxin, a radionuclide, an immunomodulator, a photoactive therapeutic agent, a radiosensitizing agent, a hormone, an anti-angiogenesis agent, and combinations thereof.

9. The method according to claim 8, wherein the additional therapeutic agent is an inhibitor of the PI3K/Akt pathway.

10. The method according to claim 9, wherein the inhibitor of the PI3K/Akt pathway is selected from the group consisting of A-674563 (CAS #552325-73-2), AGL 2263, AMG-319, AS-041164 (5-benzo[1,3]dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, BML-257 (CAS #32387-96-5), CAL-120, CAL-129, CAL-130, CAL-253, CAL-263, CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432, FPA 124 (CAS #902779-59-3), GS-1101 (CAL-101), GSK 690693 (CAS #937174-76-0), H-89 (CAS #127243-85-0), Honokiol, IC87114, IPI-145, KAR-4139, KAR-4141, KIN-1, KT 5720 (CAS #108068-98-0), Miltefosine, MK-2206 dihydrochloride (CAS #1032350-13-2), ML-9 (CAS #105637-50-1), Naltrindole Hydrochloride, OXY-111A, perifosine, PHT-427 (CAS #1191951-57-1), pictilisib, PIK-90 (CAS #677338-12-4), SC-103980, SF-1126, SH-5, SH-6, Tetrahydro Curcumin, TG100-115, Triciribine, X-339, XL-499, pharmaceutically acceptable salts thereof, and combinations thereof.

11. A method of treating or ameliorating the effects of a cancer in a subject in need thereof comprising administering to the subject an effective amount of (i) a first anti-cancer agent, which is BVD-523 or a pharmaceutically acceptable salt thereof and (ii) a second anti-cancer agent, which is trametinib or a pharmaceutically acceptable salt thereof, to treat or ameliorate the effects of the cancer, wherein administration of the first and second anti-cancer agents provides a synergistic effect compared to administration of either anti-cancer agent alone.

12. The method according to claim 11, wherein the subject is a mammal.

13. The method according to claim 12, wherein the mammal is selected from the group consisting of humans, primates, farm animals, and domestic animals.

14. The method according to claim 12, wherein the mammal is a human.

15. The method according to claim 11, wherein the BVD-523 or a pharmaceutically acceptable salt thereof is administered in the form of a pharmaceutical composition further comprising a pharmaceutically acceptable carrier or diluent.

16. The method according to claim 11, wherein the trametinib or a pharmaceutically acceptable salt thereof is administered in the form of a pharmaceutical composition further comprising a pharmaceutically acceptable carrier or diluent.

17. The method according to claim 11, wherein the subject with cancer has a somatic RAS mutation or BRAF mutation.

18. The method according to claim 11, wherein the cancer is selected from the group consisting of a cancer of the large intestine, breast cancer, pancreatic cancer, skin cancer, endometrial cancer, neuroblastoma, leukemia, lymphoma, liver cancer, lung cancer, testicular cancer, and thyroid cancer.

19. The method according to claim 11, wherein the cancer is melanoma.

20. The method according to claim 11 further comprising administering to the subject at least one additional therapeutic agent selected from the group consisting of an antibody or fragment thereof, a cytotoxic agent, a drug, a toxin, a radionuclide, an immunomodulator, a photoactive therapeutic agent, a radiosensitizing agent, a hormone, an anti-angiogenesis agent, and combinations thereof.

21. The method according to claim 20, wherein the additional therapeutic agent is an inhibitor of the PI3K/Akt pathway.

22. The method according to claim 21, wherein the inhibitor of the PI3K/Akt pathway is selected from the group consisting of A-674563 (CAS #552325-73-2), AGL 2263, AMG-319, AS-041164 (5-benzo[1,3]dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, BML-257 (CAS #32387-96-5), CAL-120, CAL-129, CAL-130, CAL-253, CAL-263, CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432, FPA 124 (CAS #902779-59-3), GS-1101 (CAL-101), GSK 690693 (CAS #937174-76-0), H-89 (CAS #127243-85-0), Honokiol, IC87114, IPI-145, KAR-4139, KAR-4141, KIN-1, KT 5720 (CAS #108068-98-0), Miltefosine, MK-2206 dihydrochloride (CAS #1032350-13-2), ML-9 (CAS #105637-50-1), Naltrindole Hydrochloride, OXY-111A, perifosine, PHT-427 (CAS #1191951-57-1), pictilisib, PIK-90 (CAS #677338-12-4), SC-103980, SF-1126, SH-5, SH-6, Tetrahydro Curcumin, TG100-115, Triciribine, X-339, XL-499, pharmaceutically acceptable salts thereof, and combinations thereof.

23. A method of effecting cancer cell death comprising contacting the cancer cell with an effective amount of (i) a first anti-cancer agent, which is BVD-523 or a pharmaceutically acceptable salt thereof and (ii) a second anti-cancer agent, which is a type 2 MEK inhibitor or a pharmaceutically acceptable salt thereof, wherein the type 2 MEK inhibitor is selected from the group consisting of GDC-0623, MEK162, trametinib, pharmaceutically acceptable salts thereof, and combinations thereof, and wherein administration of the first and second anti-cancer agents provides a synergistic effect compared to administration of either anti-cancer agent alone.

24. The method according to claim 23, wherein the subject is a mammal.

25. The method according to claim 24, wherein the mammal is selected from the group consisting of humans, primates, farm animals, and domestic animals.

26. The method according to claim 24, wherein the mammal is a human.

27. The method according to claim 23, wherein the type 2 MEK inhibitor is trametinib or a pharmaceutically acceptable salt thereof.

28. The method according to claim 23, wherein the subject with cancer has a somatic RAS mutation or BRAF mutation.

29. The method according to claim 23, wherein the cancer is selected from the group consisting of a cancer of the large intestine, breast cancer, pancreatic cancer, skin cancer, endometrial cancer, neuroblastoma, leukemia, lymphoma, liver cancer, lung cancer, testicular cancer, and thyroid cancer.

30. The method according to claim 23, wherein the cancer is melanoma.

31. The method according to claim 23 further comprising administering to the subject at least one additional therapeutic agent selected from the group consisting of an antibody or fragment thereof, a cytotoxic agent, a drug, a toxin, a radionuclide, an immunomodulator, a photoactive therapeutic agent, a radiosensitizing agent, a hormone, an anti-angiogenesis agent, and combinations thereof.

32. The method according to claim 31, wherein the additional therapeutic agent is an inhibitor of the PI3K/Akt pathway.

33. The method according to claim 32, wherein the inhibitor of the PI3K/Akt pathway is selected from the group consisting of A-674563 (CAS #552325-73-2), AGL 2263, AMG-319, AS-041164 (5-benzo[1,3]dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, BML-257 (CAS #32387-96-5), CAL-120, CAL-129, CAL-130, CAL-253, CAL-263, CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432, FPA 124 (CAS #902779-59-3), GS-1101 (CAL-101), GSK 690693 (CAS #937174-76-0), H-89 (CAS #127243-85-0), Honokiol, IC87114, IPI-145, KAR-4139, KAR-4141, KIN-1, KT 5720 (CAS #108068-98-0), Miltefosine, MK-2206 dihydrochloride (CAS #1032350-13-2), ML-9 (CAS #105637-50-1), Naltrindole Hydrochloride, OXY-111A, perifosine, PHT-427 (CAS #1191951-57-1), pictilisib, PIK-90 (CAS #677338-12-4), SC-103980, SF-1126, SH-5, SH-6, Tetrahydro Curcumin, TG100-115, Triciribine, X-339, XL-499, pharmaceutically acceptable salts thereof, and combinations thereof.

* * * * *